(12) United States Patent
Umetani et al.

(10) Patent No.: US 12,114,658 B2
(45) Date of Patent: *Oct. 15, 2024

(54) COMPOUNDS HAVING A NITROGEN-CONTAINING UNSATURATED SIX-MEMBERED RING AND AGRICULTURAL AND HORTICULTURAL FUNGICIDES CONTAINING THE SAME AS ACTIVE INGREDIENTS

(71) Applicant: MITSUI CHEMICALS CROP & LIFE SOLUTIONS, INC., Tokyo (JP)

(72) Inventors: Hideki Umetani, Ritto (JP); Shun Okaya, Chiba (JP); Ryohei Naito, Kusatsu (JP); Takeshi Fukumoto, Chiba (JP)

(73) Assignee: MITSUI CHEMICALS CROP & LIFE SOLUTIONS, INC., Tokyo (JP)

( * ) Notice: Subject to any disclaimer, the term of this patent is extended or adjusted under 35 U.S.C. 154(b) by 831 days.

This patent is subject to a terminal disclaimer.

(21) Appl. No.: 17/252,349

(22) PCT Filed: Jul. 25, 2019

(86) PCT No.: PCT/JP2019/029138
§ 371 (c)(1),
(2) Date: Dec. 15, 2020

(87) PCT Pub. No.: WO2020/022412
PCT Pub. Date: Jan. 30, 2020

(65) Prior Publication Data
US 2021/0267202 A1    Sep. 2, 2021

(30) Foreign Application Priority Data

Jul. 25, 2018   (JP) ................. 2018-139462

(51) Int. Cl.
*A01N 43/50*   (2006.01)
*A01N 43/56*   (2006.01)
*C07D 401/04*   (2006.01)

(52) U.S. Cl.
CPC ............. *A01N 43/56* (2013.01); *A01N 43/50* (2013.01)

(58) Field of Classification Search
CPC ....... A01N 43/56; A01N 43/50; C07D 401/04
See application file for complete search history.

(56) References Cited

U.S. PATENT DOCUMENTS

| 6,200,982 | B1 | 3/2001 | Collins et al. |
| 11,178,870 | B2 * | 11/2021 | Umetani .................. A01P 3/00 |
| 2001/0018438 | A1 | 8/2001 | Collins et al. |
| 2017/0217890 | A1 | 8/2017 | Johns et al. |
| 2018/0279614 | A1 | 10/2018 | Umetani et al. |

FOREIGN PATENT DOCUMENTS

| EP | 0308020 A2 | 3/1989 |
| JP | H01128969 A | 5/1989 |
| JP | H02121970 A | 5/1990 |
| JP | 2011251945 A | 12/2011 |
| WO | 9855480 A1 | 12/1998 |
| WO | 2016012913 A1 | 1/2016 |
| WO | 2017061525 A1 | 4/2017 |

OTHER PUBLICATIONS

Klein et al. .Bioorganic & Medicinal Chemistry Letters 6.18 (1996): 2225-2230. (Year: 1996).*
Strange et al. Annu. Rev. Phytopathol. 2005. 43:83-116. (Year: 2005).*
Cropwatch. Obtained with date from Wayback Machine from URL:<https://web.archive.org/web/20191018181244/https://cropwatch.unl.edu/soybean-management/plant-disease>. (Year: 2019).*
International Search Report (PCT/ISA/210) with an English translation thereof, and Written Opinion (PCT/ISA/237) mailed on Oct. 15, 2019, by the Japan Patent Office as the International Searching Authority for International Application No. PCT/JP2019/029138.
Katritzky, Alan R., et al., "Synthesis and some transformations of 5-benzotriazolyl-3,4-dihydropyrid-2-ones", Journal of Heterocyclic Chemistry, 1996, vol. 333, pp. 2031-2036.

* cited by examiner

*Primary Examiner* — Mina Haghighatian
*Assistant Examiner* — Janice Y Silverman
(74) *Attorney, Agent, or Firm* — BUCHANAN, INGERSOLL & ROONEY PC

(57) ABSTRACT

An object of the present invention is to provide compounds represented by the formula (1) or salts thereof that are effective as agricultural and horticultural fungicides.

10 Claims, No Drawings

COMPOUNDS HAVING A NITROGEN-CONTAINING UNSATURATED SIX-MEMBERED RING AND AGRICULTURAL AND HORTICULTURAL FUNGICIDES CONTAINING THE SAME AS ACTIVE INGREDIENTS

TECHNICAL FIELD

The present invention relates to pyridone compounds and to agricultural chemicals containing the compounds as active ingredients.

BACKGROUND ART

The protection of agricultural and horticultural crops from diseases is important to ensure stable agricultural production, and various fungicides are used for this purpose. However, fungi become resistant to fungicides over years, and thus novel fungicides that are effective not only to drug-sensitive fungi but also to drug-resistant fungi are demanded.

Now, the prior arts regarding 1,3,5,6-substituted-2-pyridone compounds are known. For example, 1,3,5,6-substituted-2-pyridone compounds having an aryl group or a heteroaryl group at the 3-position are disclosed as GABA alpha 2/3 ligands (see, for example, WO 98/55480). Also, 1,3,5,6-substituted-2-pyridone compounds having a carboxyl group at the 3-position are disclosed as bacterial infection treatment agents (see, for example, EP Patent No. 0308020). Further, 1,3,5,6-substituted-2-pyridone compounds having a 4,4-dimethylpentanoate group introduced at the 1-position are disclosed as anti-HIV agents (see, for example, WO 2016/012913).

PRIOR ART LITERATURE

Patent Literature

Patent Literature 1: WO 98/55480
Patent Literature 2: EP Patent No. 0308020
Patent Literature 3: WO 2016/12913

SUMMARY OF INVENTION

Problem to be Solved by Invention

However, the compounds described in WO 98/55480, EP Patent No. 0308020 and WO 2016/12913 are used for pharmaceutical purposes, and thus belong to a technical field different from that of the agricultural and horticultural fungicides according to the present invention.

An object of the present invention is to provide novel compounds that are effective as agricultural and horticultural fungicides.

Solution to Problem

To achieve the above problem, the present inventors have extensively studied 1,3,5,6-substituted-2-pyridone compounds and 1,5,6-substituted-2-pyridone compounds. As a result, the present inventors have found that new compounds which have an azole group such as a pyrazole group and an imidazole group introduced at the 5-position in the 2-pyridone skeleton exhibit an excellent control activity against plant diseases, thus completing the present invention.

Specifically, the present invention is as follows.
[1] A compound represented by the formula (1), or a salt thereof:

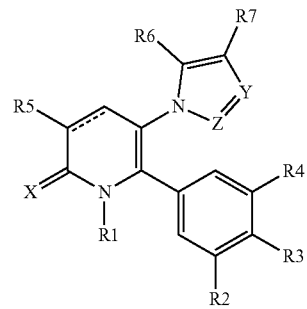

(1)

wherein R1 represents
  a hydroxy group,
  a cyano group,
  a C1-C6 alkyl group optionally substituted with substituent(s) A,
  a C1-C6 haloalkyl group,
  a C3-C8 cycloalkyl group optionally substituted with substituent(s) A,
  a C2-C6 alkenyl group optionally substituted with substituent(s) A,
  a C2-C6 haloalkenyl group,
  a C2-C6 alkynyl group optionally substituted with substituent(s) A,
  a C2-C6 haloalkynyl group,
  a C1-C6 alkoxy group optionally substituted with substituent(s) A,
  a C1-C6 haloalkoxy group,
  a C3-C8 cycloalkoxy group optionally substituted with substituent(s) A,
  a C2-C6 alkenyloxy group optionally substituted with substituent(s) A,
  a C2-C6 haloalkenyloxy group,
  a C3-C6 alkynyloxy group optionally substituted with substituent(s) A,
  a C3-C6 haloalkynyloxy group,
  an aralkyloxy group optionally substituted with 0 to 5 substituent(s) A, or
  RaRbN— (wherein Ra and Rb are independent of one another and each represent a hydrogen atom, a C1-C6 alkyl group optionally substituted with substituent(s) B, a C1-C6 haloalkyl group, or a C3-C8 cycloalkyl group, or Ra and Rb are taken together with the nitrogen atom to which they are bonded to form an aziridinyl group, an azetidinyl group, a pyrrolidinyl group, a piperidinyl group, a morpholyl group, a homopiperidinyl group, or an azocanyl group);
R2, R3 and R4 are independent of one another and each represent
  a hydrogen atom,
  a halogen atom,
  a hydroxy group,
  a cyano group,
  a nitro group,
  a C1-C6 alkyl group optionally substituted with substituent(s) C,
  a C1-C6 haloalkyl group,
  a C3-C8 cycloalkyl group optionally substituted with substituent(s) C, a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
RdC(=O)— (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)),
RdC(=O)O— (wherein Rd is the same as defined hereinabove),
Rc-L- (wherein Rc represents a C1-C6 alkyl group or a C1-C6 haloalkyl group, and L represents S, SO, or SO$_2$),
Rc-SO$_2$—O— (wherein Rc is the same as defined hereinabove),
RaRbN— (wherein Ra and Rb are the same as defined hereinabove), or
ReC(=O)N(Rf)— (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group);
R5 represents
a hydrogen atom,
a halogen atom,
a cyano group,
a nitro group,
a C1-C6 alkyl group optionally substituted with substituent(s) A,
a C1-C6 haloalkyl group,
a C3-C8 cycloalkyl group optionally substituted with substituent(s) A,
a C2-C6 alkenyl group optionally substituted with substituent(s) A,
a C2-C6 haloalkenyl group,
a C2-C6 alkynyl group optionally substituted with substituent(s) A,
a C2-C6 haloalkynyl group,
a C1-C6 alkoxy group optionally substituted with substituent(s) A,
a C1-C6 haloalkoxy group,
a C3-C8 cycloalkoxy group optionally substituted with substituent(s) A,
a C2-C6 alkenyloxy group optionally substituted with substituent(s) A,
a C2-C6 haloalkenyloxy group,
a C3-C6 alkynyloxy group optionally substituted with substituent(s) A,
a C3-C6 haloalkynyloxy group,
Rc-L- (wherein Rc and L are the same as defined hereinabove),
RaRbN— (wherein Ra and Rb are the same as defined hereinabove), or
RgC(=O)— (wherein Rg represents a hydrogen atom, a hydroxy group, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove));
X represents an oxygen atom or a sulfur atom;
Y represents R8-C or a nitrogen atom;
Z represents R9-C or a nitrogen atom;
R6, R7, R8 and R9 are independent of one another and each represent
a hydrogen atom,
a halogen atom,
a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
RdC(=O)— (wherein Rd is the same as defined hereinabove),
RdC(=O)O— (wherein Rd is the same as defined hereinabove),
Rc-L- (wherein Rc and L are the same as defined hereinabove),
RaRbN— (wherein Ra and Rb are the same as defined hereinabove), or
ReC(=O)N(Rf)— (wherein Re and Rf are the same as defined hereinabove), or
R6 and R7 are taken together to form a C2-C6 alkylene group, and, R8 and R9 represent those as defined hereinabove; and
the bond with a broken line represents a double bond or a single bond;
the substituent(s) A is at least one selected from the group consisting of a hydroxy group, a cyano group, a C3-C8 cycloalkyl group, a C1-C6 alkoxy group, a C1-C6 haloalkoxy group, a C3-C8 cycloalkoxy group, RaRbN— (wherein Ra and Rb are the same as defined hereinabove) and Rc-L- (wherein Rc and L are the same as defined hereinabove);

the substituent(s) B is at least one selected from the group consisting of a cyano group, a C1-C6 alkoxy group, a C1-C6 haloalkoxy group and a C3-C8 cycloalkoxy group; and the substituent(s) C is at least one selected from the group consisting of a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), RdC(=O)— (wherein Rd is the same as defined hereinabove) and a 3 to 6-membered ring group containing 1 to 2 oxygen atoms.

[2] The compound described in [1], or a salt thereof, wherein a hydroxyl group,

R1 represents a C1-C6 alkyl group optionally substituted with substituent(s) A, a C1-C6 haloalkyl group, a C2-C6 alkenyl group optionally substituted with substituent(s) A, a C2-C6 haloalkenyl group, a C2-C6 alkynyl group optionally substituted with substituent(s) A, a C1-C6 alkoxy group optionally substituted with substituent(s) A, a C1-C6 haloalkoxy group, a C2-C6 alkenyloxy group optionally substituted with substituent(s) A, a C3-C6 alkynyloxy group optionally substituted with substituent(s) A, an aralkyloxy group optionally substituted with 0 to 5 substituent(s) A, or RaRbN— (wherein Ra and Rb are independent of one another and each represent a hydrogen atom, a C1-C6 alkyl group optionally substituted with substituent(s) B, a C1-C6 haloalkyl group, or a C3-C8 cycloalkyl group, or Ra and Rb are taken together with the nitrogen atom to which they are bonded to form an aziridinyl group, an azetidinyl group, a pyrrolidinyl group, a piperidinyl group, a morpholyl group, a homopiperidinyl group, or an azocanyl group);

R2, R3 and R4 are independent of one another and each represent a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C3-C6 alkynyloxy group optionally substituted with substituent(s) C, RdC(=O)O— (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)), Rc-L- (wherein Rc represents a C1-C6 alkyl group or a CJ-C6 haloalkyl group, and L represents S, SO, or $SO_2$), Rc-$SO_2$—O— (wherein Rc is the same as defined hereinabove), RaRbN— (wherein Ra and Rb are the same as defined hereinabove), or ReC(=O)N(Rf)— (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group);

R5 represents a hydrogen atom, a halogen atom, a nitro group, a C1-C6 alkyl group optionally substituted with substituent(s) A, a C1-C6 haloalkyl group a C2-C6 alkenyl group optionally substituted with substituent(s) A, a C2-C6 alkynyl group optionally substituted with substituent(s) A, a C1-C6 alkoxy group optionally substituted with substituent(s) A, RaRbN— (wherein Ra and Rb are the same as defined hereinabove), or RgC(=O)— (wherein Rg represents a hydrogen atom, a hydroxy group, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove));

R6, R7, R8 and R9 are independent of one another and each represent a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C,
a C2-C6 alkenyloxy group optionally substituted with substituent(s) C,
a C3-C6 alkynyloxy group optionally substituted with substituent(s) C,
RdC(=O)— (wherein Rd is the same as defined hereinabove),
Rc-L- (wherein Rc and L are the same as defined hereinabove),
RaRbN— (wherein Ra and Rb are the same as defined hereinabove), or
ReC(=O)N(Rf)— (wherein Re and Rf are the same as defined hereinabove), or
R6 and R7 are taken together to form a C2-C6 alkylene group, and, R8 and R9 represent those as defined hereinabove.

[3] The compound described in [2], or a salt thereof, wherein
R1 represents
a hydroxyl group,
a C1-C6 alkyl group optionally substituted with substituent(s) A,
a C1-C6 haloalkyl group,
a C2-C6 alkenyl group optionally substituted with substituent(s) A,
a C1-C6 alkoxy group optionally substituted with substituent(s) A,
a C1-C6 haloalkoxy group,
a C2-C6 alkenyloxy group optionally substituted with substituent(s) A,
a C3-C6 alkynyloxy group optionally substituted with substituent(s) A,
an aralkyloxy group optionally substituted with 0 to 5 substituent(s) A, or
RaRbN— (wherein Ra and Rb are independent of one another and each represent a hydrogen atom, a C1-C6 alkyl group optionally substituted with substituent(s) B, a C1-C6 haloalkyl group, or a C3-C8 cycloalkyl group, or Ra and Rb are taken together with the nitrogen atom to which they are bonded to form an aziridinyl group, an azetidinyl group, a pyrrolidinyl group, a piperidinyl group, a morpholyl group, a homopiperidinyl group, or an azocanyl group);
R2, R3 and R4 are independent of one another and each represent
a hydrogen atom,
a halogen atom,
a hydroxy group,
a cyano group,
a nitro group,
a C1-C6 alkyl group optionally substituted with substituent(s) C,
a C3-C8 cycloalkyl group optionally substituted with substituent(s) C,
a C2-C6 alkynyl group optionally substituted with substituent(s) C,
a C1-C6 alkoxy group optionally substituted with substituent(s) C,
a C1-C6 haloalkoxy group,
a C3-C6 alkynyloxy group optionally substituted with substituent(s) C,
RdC(=O)O— (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) B, a C1-C6 haloalkyl group, or a C3-C8 cycloalkyl group, or Ra and Rb are taken together with the nitrogen atom to which they are bonded to form an aziridinyl group, an azetidinyl group, a pyrrolidinyl group, a piperidinyl group, a morpholyl group, a homopiperidinyl group, or an azocanyl group)),
Rc-SO$_2$—O— (wherein Rc represents a C1-C6 alkyl group or a C1-C6 haloalkyl group, and L represents S, SO, or SO$_2$),
RaRbN— (wherein Ra and Rb are the same as defined hereinabove), or
ReC(=O)N(Rf)— (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group);
R5 represents
a hydrogen atom,
a halogen atom,
a nitro group,
a C1-C6 alkyl group optionally substituted with substituent(s) A,
a C2-C6 alkenyl group optionally substituted with substituent(s) A,
a C1-C6 alkoxy group optionally substituted with substituent(s) A,
RaRbN— (wherein Ra and R b are the same as defined hereinabove), or
RgC(=O)— (wherein Rg represents a hydrogen atom, a hydroxy group, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove));
X represents an oxygen atom;
when Y is R8-C, Z represents a nitrogen atom, or, when Y is a nitrogen atom, Z represents R9-C;
R6, R7, R8 and R9 are independent of one another and each represent
a hydrogen atom,
a halogen atom,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 alkynyl group optionally substituted with substituent(s) C,
a C1-C6 alkoxy group optionally substituted with substituent(s) C,
RdC(=O)— (wherein Rd is the same as defined hereinabove), Rc-L- (wherein Rc and L are the same as defined hereinabove), or RaRbN— (wherein Ra and Rb are the same as defined hereinabove), or R6 and R7 are taken together to form a C2-C6 alkylene group, and R8 and R9 represent those as defined hereinabove.

[4] A compound represented by the formula (2), or a salt thereof:

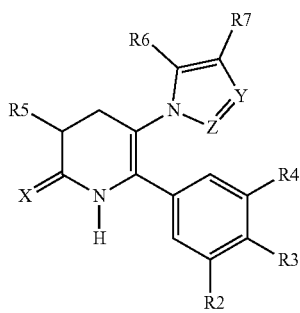

(2)

wherein

R2, R3 and R4 are independent of one another and each represent a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are independent of one another and each represent a hydrogen atom, a C1-C6 alkyl group optionally substituted with substituent(s) B, a C1-C6 haloalkyl group, or a C3-C8 cycloalkyl group, or Ra and Rb are taken together with the nitrogen atom to which they are bonded to form an aziridinyl group, an azetidinyl group, a pyrrolidinyl group, a piperidinyl group, a morpholyl group, a homopiperidinyl group, or an azocanyl group)), RdC(=O)O— (wherein Rd is the same as defined hereinabove), Rc-L- (wherein Rc represents a C1-C6 alkyl group or a C1-C6 haloalkyl group, and L represents S, SO, or $SO_2$), Rc-$SO_2$—O— (wherein Rc is the same as defined hereinabove), RaRbN— (wherein Ra and Rb are the same as defined hereinabove), or ReC(=O)N(Rf)— (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group);

R5 represents a hydrogen atom, a halogen atom, a cyano group, a nitro group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc and L are the same as defined hereinabove), RaRbN— (wherein Ra and Rb are the same as defined hereinabove), or RgC(=O)— (wherein Rg represents a hydrogen atom, a hydroxy group, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove));

X represents an oxygen atom or a sulfur atom;

Y represents R8-C or a nitrogen atom;

Z represents R9-C or a nitrogen atom;

R6, R7, R8 and R9 are independent of one another and each represent a hydrogen atom, a halogen atom, a hydroxy group,
a cyano group,
a nitro group,
a C1-C6 alkyl group optionally substituted with substituent(s) C,
a C1-C6 haloalkyl group,
a C3-C8 cycloalkyl group optionally substituted with substituent(s) C,
a C2-C6 alkenyl group optionally substituted with substituent(s) C,
a C2-C6 haloalkenyl group,
a C2-C6 alkynyl group optionally substituted with substituent(s) C,
a C2-C6 haloalkynyl group,
a C1-C6 alkoxy group optionally substituted with substituent(s) C,
a C1-C6 haloalkoxy group,
a C3-C8 cycloalkoxy group optionally substituted with substituent(s) C,
a C2-C6 alkenyloxy group optionally substituted with substituent(s) C,
a C2-C6 haloalkenyloxy group,
a C3-C6 alkynyloxy group optionally substituted with substituent(s) C,
a C3-C6 haloalkynyloxy group,
RdC(=O)— (wherein Rd is the same as defined hereinabove),
RdC(=O)O— (wherein Rd is the same as defined hereinabove),
Rc-L- (wherein Rc and L are the same as defined hereinabove),
RaRbN— (wherein Ra and Rb are the same as defined hereinabove), or
ReC(=O)N(Rf)— (wherein Re and Rf are the same as defined hereinabove), or
R6 and R7 are taken together to form a C2-C6 alkylene group, and, R8 and R9 represent those as defined hereinabove; and
the substituent(s) A is at least one selected from the group consisting of a hydroxy group, a cyano group, a C3-C8 cycloalkyl group, a C1-C6 alkoxy group, a C1-C6 haloalkoxy group, a C3-C8 cycloalkoxy group, RaRbN— (wherein Ra and Rb are the same as defined hereinabove) and Rc-L- (wherein Rc and L are the same as defined hereinabove);
the substituent(s) B is at least one selected from the group consisting of a cyano group, a C1-C6 alkoxy group, a C1-C6 haloalkoxy group and a C3-C8 cycloalkoxy group; and
the substituent(s) C is at least one selected from the group consisting of a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), RdC(=O)— (wherein Rd is the same as defined hereinabove) and a 3 to 6-membered ring group containing 1 to 2 oxygen atoms.
[5] The compound described in any one of [1] to [3], or salt thereof, wherein R1 is a hydroxyl group, a methyl group, an ethyl group, a propyl group, a 2-hydroxyethyl group, a 2-fluoroethyl group, a 2,2-difluoroethyl group, a 2,2,2-trifluoroethyl group, 1,1,2,2-tetrafluoroethyl group, an allyl group, a methoxy group, an ethoxy group, a monofluoromethoxy group, a difluoromethoxy group, an allyloxy group, a propargyloxy group, a benzyloxy group, an amino group or a methylamino group.
[6] The compound described in any one of [1] to [5], or a salt thereof, wherein R2, R3 and R4 are independent of one another and each represent a hydrogen atom, a fluorine atom, a chlorine atom, a bromine atom, a hydroxyl group, a cyano group, a nitro group, a methyl group, an ethyl group, a propyl group, a cyclopropyl group, an ethynyl group, a methoxy group, a methoxymethoxy group, an ethoxy group, a 2-methoxyethoxy group, a difluoromethoxy group, a trifluoromethoxy group, a 2,2-difluoroethoxy group, a 2,2,2-trifluoroethoxy group, a propargyloxy group, an acetyl oxy group, a methanesulfonyloxy group, an amino group, a methylamino group, a dimethylamino group, a morpholinyl group, a piperidin-1-yl group, an acetamide group, or a N-methylacetamide group.
[7] The compound described in any one of [1] to [5], or a salt thereof, wherein the partial structure Ph:

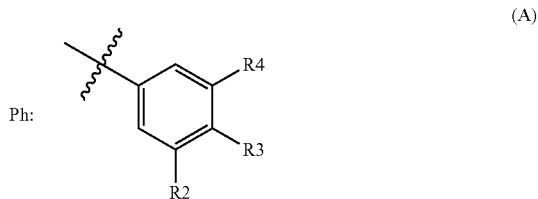

(A)

in the formula (1) is a phenyl group, a 3-fluorophenyl group, a 3-chlorophenyl group, a 3-bromophenyl group, a 4-fluorophenyl group, a 4-chlorophenyl group, a 4-bromophenyl group, a 3-chloro-4-fluorophenyl group, a 4-chloro-3-fluorophenyl group, a 3-bromo-4-fluorophenyl group, a 3,4-difluorophenyl group, a 3,5-difluorophenyl group, a 3,4-dichlorophenyl group, a 3,4,5-trifluorophenyl group, a 4-fluoro-3-methylphenyl group, a 4-fluoro-3-ethynylphenyl group, a 4-hydroxyphenyl group, a 4-cyanophenyl group, a 4-nitrophenyl group, a 4-methylphenyl group, a 4-ethylphenyl group, a 4-propylphenyl group, a 4-cyclopropylphenyl group, a 3-ethynylphenyl group, a 4-ethynylphenyl group, a 4-methoxyphenyl group, a 4-ethoxyphenyl group, a 4-(methoxymethoxy)phenyl group, a 4-(2-methoxyethoxy) phenyl group, a 4-difluoromethoxyphenyl group, a 4-trifluoromethoxyphenyl group, a 4-(2,2-difluoroethoxy)phenyl group, a 4-(2,2,2-trifluoroethoxy)phenyl group, a 4-propargylphenyl group, a 4-acetoxyphenyl group, a 4-methanesulfonyloxyphenyl group, a 4-aminophenyl group, a 4-(methylamino)phenyl group, a 4-(dimethylamino)phenyl group, a 4-(piperidin-1-yl)-phenyl group, a 4-morpholinophenyl group, a 4-(acetamido)phenyl group, or a 4-(N-methylacetamido)pheny group.
[8] The compound described in any one of [1] to [7], or salt thereof wherein R5 is a hydrogen atom, a chlorine atom, a bromine atom, an iodine atom, a nitro group, a methyl group, an ethyl group, a 1-hydroxyethyl group, a vinyl group, a methoxy group, an amino group, a methylamino group, a dimethylamino group, or an acetyl group.
[9] The compound described in any one of [1] to [2] and [4] to [8], or salt thereof,
wherein X is an oxygen atom.
[10] The compound described in any one of [1] to [9], or salt thereof, wherein Y is R8-C, and Z is a nitrogen atom.

[11] The compound described in any one of [1] to [9], or salt thereof, wherein Y is a nitrogen atom, and Z is R9-C.

[12] The compound described in any one of [1] to [11], or salt thereof, wherein R6, R7, R8 and R9 are independent of one onother and each represent a hydrogen atom, a fluorine atom, a chlorine atom, a bromine atom, a nitro group, a methyl group, an ethyl group, a propyl group, an isopropyl group, a t-butyl group, a hydroxymethyl group, a 1-hydroxyethyl group, a 1-hydroxypropyl group, a 2-hydroxypropan-2-yl group, a methoxymethyl group, a monochloromethyl group, a monobromomethyl group, a difluoromethyl group, a dibromomethyl group, a trifluoromethyl group, a chlorodifluoromethyl group, a bromodifluoromethyl group, a trichloromethyl group, a 1,1-difluoroethyl group, a 1,1,2,2-tetrafluoroethyl group, a pentafluoroethyl group, a cyclopropyl group, a vinyl group, an ethynyl group, a propargyl group, a 1-hydroxyprop-2-yn-1-yl group, a methoxy group, a formyl group, an acetyl group, a methoxycarbonyl group, an ethoxycarbonyl group, a methylthio group, a methanesulfinyl group, a methanesulfonyl group, or an amino group, or R6 and R7 are taken together to form a propylene group or a butylene group, and R8 and R9 are the same as defined hereinabove.

[13] The compound described in any one of [1] to [11], or salt thereof, wherein R6 is a hydrogen atom, a chlorine atom, a bromine atom, a methyl group, an ethyl group, an isopropyl group, a t-butyl group, a difluoromethyl group, a trifluoromethyl group, a chlorodifluoromethyl group, a bromodifluoromethyl group, a trichloromethyl group, a 1,1-difluoroethyl group, a 1,1,2,2-tetrafluoroethyl group, a pentafluoroethyl group, a cyclopropyl group, a methoxy group, a methoxycarbonyl group, a methylthio group, a methanesulfinyl group, or a methanesulfonyl group.

[14] The compound described in any one of [1] to [11] and [13], or salt thereof, wherein R7 is a hydrogen atom, a fluorine atom, a chlorine atom, a bromine atom, a nitro group, a methyl group, an ethyl group, a propyl group, an isopropyl group, a methoxymethyl group, a hydroxymethyl group, a 1-hydroxyethyl group, a 1-hydroxypropyl group, a 2-hydroxypropan-2-yl group, a monochloromethyl group, a monobromomethyl group, a difluoromethyl group, a dibromomethyl group, a vinyl group, an ethynyl group, a propargyl group, a 1-hydroxyprop-2-yn-1-yl group, a formyl group, an acetyl group, an ethoxycarbonyl group, or an amino group.

[15] The compound described in any one of [1] to [10], [13] and [14], or salt thereof, wherein R8 is a hydrogen atom, a chlorine atom, a bromine atom, a methyl group, an ethyl group, or a trifluoromethyl group.

[16] The compound described in any one of [1] to [9], [11], [13] to [15], or salt thereof, wherein R9 is a hydrogen atom or a chlorine atom.

[17] The compound described in any one of [1] to [12], [15] and [16], or salt thereof, wherein R6 and R7 are taken together to form a propylene group or a butylene group.

[18] The compound described in any one of [1] to [9], or salt thereof, wherein the partial structure Az:

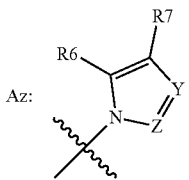

in the formula (1) is 1H-pyrazol-1-yl, 4-nitro-1H-pyrazol-1-yl,
3,5-diethyl-1H-pyrazol-1-yl, 3,5-dimethyl-1H-pyrazol-1-yl,
3-chloro-4-methyl-1H-pyrazol-1-yl, 3-bromo-4-methyl-1H-pyrazol-1-yl,
4-(ethoxycarbonyl)-1H-pyrazol-1-yl,
4-(ethoxycarbonyl)-5-(trifluoromethyl)-1H-pyrazol-1-yl,
4-(ethoxycarbonyl)-5-methyl-1H-pyrazol-1-yl,
4-(bromomethyl)-5-chloro-1H-pyrazol-1-yl, 4,5-dimethyl-1H-pyrazol-1-yl,
4-acetyl-5-chloro-1H-pyrazol-1-yl, 4-amino-1H-pyrazol-1-yl,
4-amino-5-chloro-1H-pyrazol-1-yl, 4-amino-5-bromo-1H-pyrazol-1-yl,
4-chloro-1H-pyrazol-1-yl, 4-fluoro-5-methyl-1H-pyrazol-1-yl,
4-bromo-3,5-dimethyl-1H-pyrazol-1-yl, 4-formyl-5-methyl-1H-pyrazol-1-yl,
4-methyl-1H-pyrazol-1-yl, 4-methyl-3-(trifluoromethyl)-1H-pyrazol-1-yl,
4-methyl-5-(1,1,2,2-tetrafluoroethyl)-1H-pyrazol-1-yl,
4-methyl-5-(trifluoromethyl)-1H-pyrazol-1-yl,
4-methyl-5-(pentafluoro)ethyl)-1H-pyrazol-1-yl,
4-methyl-5-(methanesulfinyl)-1H-pyrazol-1-yl,
4-methyl-5-(methanesulfonyl)-1H-pyrazol-1-yl,
4-methyl-5-(methylthio)-1H-pyrazol-1-yl,
5-(1,1-difluoroethyl)-4-methyl-1H-pyrazol-1-yl, 5-(t-butyl)-3-methyl-1H-pyrazol-1-yl,
5-(t-butyl)-4-methyl-1H-pyrazol-1-yl, 5-(ethoxycarbonyl)-4-methyl-1H-pyrazol-1-yl,
5-(chlorodifluoromethyl)-4-methyl-1H-pyrazol-1-yl,
5-(difluoromethyl)-4-methyl-1H-pyrazol-1-yl, 5-(trichloromethyl)-1H-pyrazol-1-yl,
5-(trifluoromethyl)-1H-pyrazol-1-yl,
5-(bromodifluoromethyl)-4-methyl-1H-pyrazol-1-yl, 5,6-dicyclocyclopenta[c]pyrazol-1(4H)-yl, 5-isopropyl-3-methyl-1H-pyrazol-1-yl, 5-isopropyl-4-methyl-1H-pyrazol-1-yl,
5-ethyl-3-methyl-1H-pyrazol-1-yl, 5-ethyl-4-methyl-1H-pyrazol-1-yl,
5-chloro-1H-pyrazol-1-yl, 5-chloro-4-(1-hydroxyethyl)-1H-pyrazole-1-yl,
5-chloro-4-(1-hydroxyprop-2-yn-1-yl)-1H-pyrazol-1-yl,
5-chloro-4-(1-hydroxypropyl)-H-pyrazol-1-yl,
5-chloro-4-(2-hydroxypropan-2-yl)-1H-pyrazol-1-yl,
5-chloro-4-(chloromethyl)-1H-pyrazole-1-yl,
5-chloro-4-(dibromomethyl)-1H-pyrazol-1-yl,
5-chloro-4-(difluoromethyl)-1H-pyrazol-1-yl,
5-chloro-4-(hydroxymethyl)-1H-pyrazol-1-yl,
5-chloro-4-(methoxymethyl)-1H-pyrazol-1-yl, 5-chloro-4-isopropyl-1H-pyrazol-1-yl,
5-chloro-4-ethynyl-1H-pyrazol-1-yl, 5-chloro-4-ethyl-1H-pyrazol-1-yl,
5-chloro-4-nitro-1H-pyrazol-1-yl, 5-chloro-4-vinyl-1H-pyrazol-1-yl,
5-chloro-4-propargyl-1H-pyrazol-1-yl, 5-chloro-4-propyl-1H-pyrazol-1-yl, 5-chloro-4-formyl-1H-pyrazol-1-yl, 5-chloro-4-methyl-1H-pyrazol-1-yl,
5-cyclopropyl-3-methyl-1H-pyrazol-1-yl, 5-cyclopropyl-4-methyl-1H-pyrazol-1-yl,
5-bromo-1H-pyrazol-1-yl, 5-bromo-4-nitro-1H-pyrazol-1-yl,
5-bromo-4-methyl-1H-pyrazol-1-yl, 5-methyl-1H-pyrazol-1-yl,
5-methoxy-1H-pyrazol-1-yl, 5-methoxy-4-methyl-1H-pyrazol-1-yl,
4,5,6,7-trahydro-1H-indazol-1-yl, 4,5-dichloro-1H-imidazol-1-yl,
4,5-dimethyl-1H-imidazol-1-yl, or 2,4,5-trichloro-1H-imidazol-1-yl.

[19] The compound described in any one of [1] to [3] and [5] to [18], or a salt thereof, wherein the bond with the broken line is a double bond.

[20] The compound described in any one of [1] to [3] and [5] to [18], or a salt thereof, wherein the bond with the broken line is a single bond.

[21] An agricultural and horticultural pest control agent comprising the compound described in any one of [1] to [3] and [5] to [20] or a salt thereof as an active ingredient.

[22] An agricultural and horticultural fungicide comprising the compound described in any one of [1] to [3] and [5] to [20] or a salt thereof as an active ingredient.

[23] A method for controlling a plant disease, including applying the agricultural and horticultural pest control agent described in [21] to a plant, a plant seed, or a soil for plant cultivation.

[24] A method for controlling a plant disease, including applying the agricultural and horticultural fungicide described in [22] to a plant, a plant seed, or a soil for plant cultivation.

Advantageous Effects of Invention

The novel compounds provided according to the present invention are effective as agricultural and horticultural fungicides.

DESCRIPTION OF EMBODIMENTS

Hereinbelow, embodiments of the present invention will be described in detail.

The terms used in the claims and the description have definitions generally used in the technical field unless otherwise mentioned.

The abbreviations in the specification are described below.

DMF: N,N-dimethylformamide, THF: tetrahydrofuran, Me: methyl group, Et: ethyl group, Pr propyl group, Bu: butyl group, Ac: acetyl group, Bn: benzyl group, i: iso, sec: secondary, t: tertiary, =: double bond, and ≡: triple bond. In the columns in the tables, Pr and Bu without prefix are normal.

Hereinbelow, the definitions of the terms used in the specification will be described.

The expression Cx-Cy means that the number of carbon atoms that are possessed ranges from x to y. Here, x and y are integers and are understood to disclose all individual integers between x and y inclusive. For example, C1-C6 means that the number of carbon atoms that are possessed is 1, 2, 3, 4, 5 or 6; C1-C5 means that the number of carbon atoms that are possessed is 1, 2, 3, 4 or 5; C2-C6 means that the number of carbon atoms that are possessed is 2, 3, 4, 5 or 6; C3-C8 means that the number of carbon atoms that are possessed is 3, 4, 5, 6, 7 or 8; and C3-C6 means that the number of carbon atoms that are possessed is 3, 4, 5 or 6.

The phrase "optionally substituted" means that the group, compound or the like may be substituted or unsubstituted. When this phrase is used without explicit indication of the number of substituents, the number of substituents is one.

The C1-C6 alkyl group may be linear or branched. Specific examples thereof include methyl group, ethyl group, propyl group, isopropyl group, butyl group, isobutyl group, sec-butyl group, t-butyl group, pentyl group, isopentyl group, 1-methylbutyl group, 2-methylbutyl group, neopentyl group, 1-ethylpropyl group, 1,2-dimethylpropyl group, hexyl group, 1-methylpentyl group, 2-methylpentyl group, 3-methylpentyl group, 4-methylpentyl group, 1,1-dimethylbutyl group, 2,2-dimethylbutyl group, 3,3-dimethylbutyl group, 1,2-dimethylbutyl group, 1,3-dimethylbutyl group, 2,3-dimethylbutyl group, 2-ethylbutyl group, 1-isopropylpropyl group, 1,1,2-trimethylpropyl group, 1,2,2-trimethylpropyl group, and the like.

Specific examples of the halogen atoms include fluorine atom, chlorine atom, bromine atom, iodine atom, and the like.

The C1-C6 haloalkyl group is a group resulting from the substitution of the above C1-C6 alkyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C1-C6 haloalkyl groups include monofluoromethyl group, difluoromethyl group, trifluoromethyl group, monochloromethyl group, dichloromethyl group, monobromomethyl group, dibromomethyl group, monoiodomethyl group, diiodomethyl group, chlorodifluoromethyl group, bromodifluoromethyl group, trichloromethyl group, 1-fluoroethyl group, 2-fluoroethyl group, 1,1-difluoroethyl group, 2,2-difluoroethyl group, 2,2,2-trifluoroethyl group, 1,1,2,2-tetrafluoroethyl group, pentafluoroethyl group, 2,2,2-trichloroethyl group, 3,3-difluoropropyl group, 3,3,3-trifluoropropyl group, heptafluoropropyl group, heptafluoroisopropyl group, 2,2,2-trifluoro-1-(trifluoromethyl)ethyl group, nonafluorobutyl group, nonafluoro-sec-butyl group, 3,3,4,4,5,5,5-heptafluoropentyl group, undecafluoropentyl group, tridecafluorohexyl group, and the like.

Specific examples of the C3-C8 cycloalkyl groups include cyclopropyl group, cyclobutyl group, cyclopentyl group, cyclohexyl group, cycloheptyl group, cyclooctyl group, and the like.

The C2-C6 alkenyl group is an unsaturated hydrocarbon group which has one, or two or more double bonds and is linear or branched. When the group has geometric isomeric forms, the group may be E-isomer, Z-isomer or a mixture containing E-isomer and Z-isomer in any proportions without limitation as long as the number of carbon atoms indicated is satisfied. Specific examples of the C2-C6 alkenyl groups include vinyl group, 1-propenyl group, allyl group, 1-butenyl group, 2-butenyl group, 3-butenyl group, 1-pentenyl group, 2-pentenyl group, 3-pentenyl group, 4-pentenyl group, 3-methyl-2-butenyl group, 1-hexenyl group, 2-hexenyl group, 3-hexenyl group, 4-hexenyl group, 5-hexenyl group, 4-methyl-3-pentenyl group, 3-methyl-2-pentenyl group, and the like.

The C2-C6 haloalkenyl group is a group resulting from the substitution of the above C2-C6 alkenyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkenyl groups include 2-fluorovinyl group, 2,2-difluorovinyl group, 2,2-dichlorovinyl group, 3-fluoroallyl group, 3,3-difluoroallyl group, 3,3-dichloroallyl group, 4,4-difluoro-3-butenyl group, 5,5-difluoro-4-pentenyl group, 6,6-difluoro-5-hexenyl group, and the like.

The C2-C6 alkynyl group is an unsaturated hydrocarbon group which has one, or two or more triple bonds and is linear or branched. Specific examples of the C2-C6 alkynyl groups include ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1,1-dimethyl-2-propynyl group, 1-hexynyl group, 2-hexynyl group, 3-hexynyl group, 4-hexynyl group, 5-hexynyl group, and the like.

The C2-C6 haloalkynyl group is a group resulting from the substitution of the above C2-C6 alkynyl group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkynyl groups include 2-fluoroethynyl group, 2-chloroethynyl group, 2-bromoethynyl group, 2-iodoethynyl group, 3,3-difluoro-1-propynyl group, 3-chloro-3,3-difluoro-1-propynyl group, 3-bromo-3,3-difluoro-1-propynyl group, 3,3,3-trifluoro-1-propynyl group, 4,4-difluoro-1-butynyl group, 4,4-difluoro-2-butynyl group, 4-chloro-4,4-difluoro-1-butynyl group, 4-chloro-4,4-difluoro-2-butynyl group, 4-bromo-4,4-difluoro-1-butynyl group, 4-bromo-4,4-difluoro-2-butynyl group, 4,4,4-trifluoro-1-butynyl group, 4,4,4-trifluoro-2-butynyl group, 5,5-difluoro-3-pentynyl group, 5-chloro-5,5-difluoro-3-pentynyl group, 5-bromo-5,5-difluoro-3-pentynyl group, 5,5,5-trifluoro-3-pentynyl group, 6,6-difluoro-4-hexynyl group, 6-chloro-6,6-difluoro-4-hexynyl group, 6-bromo-6,6-difluoro-4-hexynyl group, 6,6,6-trifluoro-4-hexynyl group, and the like.

The C1-C6 alkoxy group is a combination of the C1-C6 alkyl group described hereinabove and an oxygen atom as a bonding site. Specific examples of the C1-C6 alkoxy groups include methoxy group, ethoxy group, propyloxy group, isopropyloxy group, butoxy group, isobutoxy group, sec-butoxy group, t-butoxy group, pentyloxy group, isopentyloxy group, 1-methylbutoxy group, 2-methylbutoxy group, neopentyloxy group, 1-ethylpropyloxy group, 1,2-dimethylpropyloxy group, hexyloxy group, 1-methylpentyloxy group, 2-methylpentyloxy group, 3-methylpentyloxy group, 4-methylpentyloxy group, 1,1-dimethylbutoxy group, 2,2-dimethylbutoxy group, 3,3-dimethylbutoxy group, 1,2-dimethylbutoxy group, 1,3-dimethylbutoxy group, 2,3-dimethylbutoxy group, 2-ethylbutoxy group, 1-isopropylpropyloxy group, 1,1,2-trimethylpropyloxy group, 1,2,2-trimethylpropyloxy group, and the like.

The C1-C6 haloalkoxy group is a group resulting from the substitution of the above C1-C6 alkoxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C1-C6 haloalkoxy groups include monofluoromethoxy group, difluoromethoxy group, trifluoromethoxy group, chlorodifluoromethoxy group, bromodifluoromethoxy group, 2-fluoroethoxy group, 2,2-difluoroethoxy group, 2,2,2-trifluoroethoxy group, 1,1,2,2-tetrafluoroethoxy group, pentafluoroethoxy group, 2,2,2-trichloroethoxy group, 3,3-difluoropropyloxy group, 3,3,3-trifluoropropyloxy group, heptafluoropropyloxy group, heptafluoroisopropyloxy group, 2,2,2-trifluoro-1-(trifluoromethyl)-ethoxy group, nonafluorobutoxy group, nonafluoro-sec-butoxy group, 3,3,4,4,5,5,5-heptafluoropentyloxy group, undecafluoropentyloxy group, tridecafluorohexyloxy group, and the like.

The C3-C8 cycloalkoxy group is a combination of the C3-C8 cycloalkyl group described hereinabove and an oxygen atom as a bonding site. Specific examples of the C3-C8 cycloalkoxy groups include cyclopropyloxy group, cyclobutoxy group, cyclopentyloxy group, cyclohexyloxy group, cycloheptyloxy group, cyclooctyloxy group, and the like.

The C2-C6 alkenyloxy group is a combination of the C2-C6 alkenyl group described hereinabove and an oxygen atom as a bonding site. When the group has geometric isomeric forms, the group may be E-isomer, Z-isomer or a mixture containing E-isomer and Z-isomer in any proportions without limitation as long as the number of carbon atoms indicated is satisfied. Specific examples of the C2-C6 alkenyloxy groups include vinyloxy group, 1-propenyloxy group, allyloxy group, 1-butenyloxy group, 2-butenyloxy group, 3-butenyloxy group, 1-pentenyloxy group, 2-pentenyloxy group, 3-pentenyloxy group, 4-pentenyloxy group, 3-methyl-2-butenyloxy group, 1-hexenyloxy group, 2-hexenyloxy group, 3-hexenyloxy group, 4-hexenyloxy group, 5-hexenyloxy group, 3-methyl-2-pentenyloxy group, 4-methyl-3-pentenyloxy group, and the like.

The C2-C6 haloalkenyloxy group is a group resulting from the substitution of the above C2-C6 alkenyloxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C2-C6 haloalkenyloxy groups include 2-fluorovinyloxy group, 2,2-difluorovinyloxy group, 2,2-dichlorovinyloxy group, 3-fluoroallyloxy group, 3,3-difluoroallyloxy group, 3,3-dichloroallyloxy group, 4,4-difluoro-3-butenyloxy group, 5,5-difluoro-4-pentenyloxy group, 6,6-difluoro-5-hexenyloxy group, and the like.

The C3-C6 alkynyloxy group is a combination of any C3-C6 alkynyl group belonging to the C2-C6 alkynyl groups described hereinabove, and an oxygen atom as a bonding site. Specific examples of the C3-C6 alkynyloxy groups include propargyloxy group, 2-butynyloxy group, 3-butynyloxy group, 2-pentynyloxy group, 3-pentynyloxy group, 4-pentynyloxy group, 1,1-dimethyl-2-propynyloxy group, 2-hexynyloxy group, 3-hexynyloxy group, 4-hexynyloxy group, 5-hexynyloxy group, and the like.

The C3-C6 haloalkynyloxy group is a group resulting from the substitution of the above C3-C6 alkynyloxy group with one, or two or more halogen atoms in place of any hydrogen atom(s). When the group is substituted with two or more halogen atoms, the halogen atoms may be the same as or different from one another, and the number thereof is not particularly limited as long as such substitution is possible. Specific examples of the C3-C6 haloalkynyloxy groups include 1,1-difluoro-2-propynyloxy group, 4,4-difluoro-2-butynyloxy group, 4-chloro-4,4-difluoro-2-butynyloxy group, 4-bromo-4,4-difluoro-2-butynyloxy group, 4,4,4-trifluoro-2-butynyloxy group, 5,5-difluoro-3-pentynyloxy group, 5-chloro-5,5-difluoro-3-pentynyloxy group, 5-bromo-5,5-difluoro-3-pentynyloxy group, 5,5,5-trifluoro-3-pentynyloxy group, 6,6-difluoro-4-hexynyloxy group, 6-chloro-6,6-difluoro-4-hexynyloxy group, 6-bromo-6,6-difluoro-4-hexynyloxy group, 6,6,6-trifluoro-4-hexynyloxy group, and the like.

The aralkyloxy group represents a combination of an aralkyl group resulting from the substitution of a hydrogen atom in a C1-C3 alkyl group with an aryl group such as a phenyl group or a naphthyl group, and an oxygen atom as a bonding site. Specific examples of the aralkyloxy group include benzyloxy group, phenethyloxy group, phenylpropyloxy group, naphthalenyl methoxy group, naphthalenyl ethoxy group, naphthalenyl propoxy group, and the like.

Specific examples of the C2-C6 alkylene groups include ethylene group, propylene group, butylene group, pentylene group, hexylene group, and the like.

Specific examples of the 3 to 6-membered ring groups containing 1 to 2 oxygen atoms include 1,2-epoxyethanyl group, oxetanyl group, oxolanyl group, oxanyl group, 1,3-dioxolanyl group, 1,3-dioxanyl group, 1,4-dioxanyl group, and the like.

The C2-C6 alkoxyalkoxy group is a group resulting from the substitution of any C1-C5 alkoxy group belonging to the C1-C6 alkoxy groups described hereinabove with one, or two or more C1-C5 alkoxy groups in place of any hydrogen atom(s). This alkoxyalkoxy group is not particularly limited as long as the total number of carbon atoms is as indicated. Specific examples of the C2-C6 alkoxyalkoxy groups include methoxymethoxy group, ethoxymethoxy group, propyloxymethoxy group, isopropyloxymethoxy group, methoxyethoxy group, ethoxyethoxy group, propyloxyethoxy group, isopropyloxyethoxy group, methoxypropyloxy group, ethoxypropyloxy group, propyloxypropyloxy group, isopropyloxypropyloxy group, and the like.

The pyridone compounds of the present invention include those compounds represented by the following formula (1), or salts thereof (hereinafter referred to as the "compound(s) of the present invention").

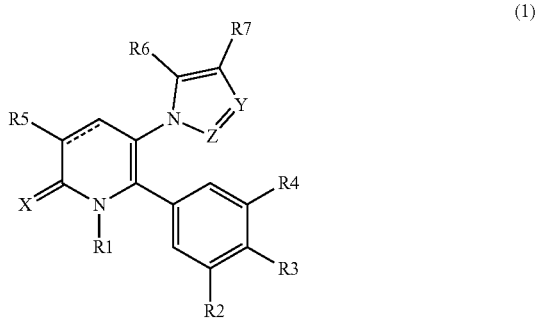
(1)

Hereinbelow, the formula (1) will be described.

In the formula (1), R1 represents a hydroxy group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, an aralkyloxy group optionally substituted with 0 to 5 substituent(s) A, or RaRbN— (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a morpholinyl group, a homopiperidinyl group or an azocanyl group).

In particular, R1 is preferably a hydroxyl group, a C1-C6 alkyl group optionally substituted with substituent(s) A, a C1-C6 haloalkyl group, a C2-C6 alkenyl group optionally substituted with substituent(s) A, a C2-C6 haloalkenyl group, a C2-C6 alkynyl group optionally substituted with substituent(s) A, a C1-C6 alkoxy group optionally substituted with substituent(s) A, a C1-C6 haloalkoxy group, a C2-C6 alkenyloxy group optionally substituted with substituent(s) A, a C3-C6 alkynyloxy group optionally substituted with substituent(s) A, an aralkyloxy group optionally substituted with 0 to 5 substituent(s) A, or RaRbN— (wherein Ra and Rb are the same as defined hereinabove), and R1 is particularly preferably a hydroxyl group, a C1-C6 alkyl group optionally substituted with substituent(s) A, a C1-C6 haloalkyl group, a C2-C6 alkenyl group optionally substituted with substituent(s) A, a C1-C6 alkoxy group optionally substituted with substituent(s) A, a C1-C6 haloalkoxy group, a C2-C6 alkenyloxy group optionally substituted with substituent(s) A, a C3-C6 alkynyloxy group optionally substituted with substituent(s) A, an aralkyloxy group optionally substituted with 0 to 5 substituent(s) A, or RaRbN— (wherein Ra and Rb are the same as defined hereinabove).

In the formula (1), R1 may represent a hydroxy group or a cyano group.

In the "C1-C6 alkyl group optionally substituted with substituent(s) A" represented by R1 in the formula (1), the C1-C6 alkyl group is the same as defined hereinabove, and is preferably a methyl group, an ethyl group, a propyl group or a butyl group, and more preferably a methyl group, an ethyl group or a propyl group. When this group has substituent(s) A, the C1-C6 alkyl group is optionally substituted with substituent(s) A in place of any hydrogen atom(s).

The "C1-C6 haloalkyl group" represented by R1 in the formula (1) is the same as defined hereinabove, and is preferably a 2-fluoroethyl group, a 2,2-difluoroethyl group, a 2,2,2-trifluoroethyl group, a 1,1,2,2-tetrafluoroethyl group, a pentafluoroethyl group, a 3,3-difluoropropyl group or a 3,3,3-trifluoropropyl group, and more preferably a 2-fluoroethyl group, a 2,2-difluoroethyl group, a 2,2,2-trifluoroethyl group, a 1,1,2,2-tetrafluoroethyl group or a pentafluoroethyl group.

In the "C3-C8 cycloalkyl group optionally substituted with substituent(s) A" represented by R1 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) A, the C3-C8 cycloalkyl group is appropriately substituted with substituent(s) A in place of any hydrogen atom(s).

In the "C2-C6 alkenyl group optionally substituted with substituent(s) A" represented by R1 in the formula (1), the C2-C6 alkenyl group is the same as defined hereinabove, and is preferably a vinyl group, a 1-propenyl group or an allyl group, and more preferably a vinyl group or an allyl group. When this group has substituent(s) A, the C2-C6 alkenyl group is optionally substituted with substituent(s) A in place of any hydrogen atom(s).

The "C2-C6 haloalkenyl group" represented by R1 in the formula (1) is the same as defined hereinabove, and is preferably a 2-fluorovinyl group, a 2,2-difluorovinyl group, a 3-fluoroallyl group or a 3,3-difluoroallyl group, and more preferably a 2-fluorovinyl group or a 2,2-difluorovinyl group.

In the "C2-C6 alkynyl group optionally substituted with substituent(s) A" represented by R1 in the formula (1), the C2-C6 alkynyl group is the same as defined hereinabove, and is preferably a propargyl group, a 2-butynyl group or a 3-butynyl group, and more preferably a propargyl group. When this group has substituent(s) A, the C2-C6 alkynyl group is optionally substituted with substituent(s) A in place of any hydrogen atom(s).

The "C2-C6 haloalkynyl group" represented by R1 in the formula (1) is the same as defined hereinabove, and is preferably a 4,4-difluoro-2-butynyl group, a 4-chloro-4,4-difluoro-2-butynyl group, a 4-bromo-4,4-difluoro-2-butynyl group or a 4,4,4-trifluoro-2-butynyl group, and more preferably a 4,4-difluoro-2-butynyl group or a 4,4,4-trifluoro-2-butynyl group.

In the "C1-C6 alkoxy group optionally substituted with substituent(s) A" represented by R1 in the formula (1), the C1-C6 alkoxy group is the same as defined hereinabove, and is preferably a methoxy group, an ethoxy group or a propyloxy group, and more preferably a methoxy group or an ethoxy group. When this group has substituent(s) A, the C1-C6 alkoxy group is optionally substituted with substituent(s) A in place of any hydrogen atom(s).

The "C1-C6 haloalkoxy group" represented by R1 in the formula (1) is the same as defined hereinabove, and is preferably a monofluoromethoxy group, a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a monofluoromethoxy group, a difluoromethoxy group or a trifluoromethoxy group.

In the "C3-C8 cycloalkoxy group optionally substituted with substituent(s) A" represented by R1 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) A, the C3-C8 cycloalkoxy group is optionally substituted with substituent(s) A in place of any hydrogen atom(s).

In the "C2-C6 alkenyloxy group optionally substituted with substituent(s) A" represented by R1 in the formula (1), the C2-C6 alkenyloxy group is the same as defined hereinabove, and is preferably a vinyloxy group, a 1-propenyloxy group or an allyloxy group, and more preferably a vinyloxy group or an allyloxy group. When this group has substituent(s) A, the C2-C6 alkenyloxy group is optionally substituted with substituent(s) A in place of any hydrogen atom(s).

The "C2-C6 haloalkenyloxy group" represented by R1 in the formula (1) is the same as defined hereinabove, and is preferably a 2-fluorovinyloxy group, a 2,2-difluorovinyloxy group, a 3-fluoroallyloxy group or a 3,3-difluoroallyloxy group, and more preferably a 2-fluorovinyloxy group or a 2,2-difluorovinyloxy group.

In the "C3-C6 alkynyloxy group optionally substituted with substituent(s) A" represented by R1 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) A, the C3-C6 alkynyloxy group is optionally substituted with substituent(s) A in place of any hydrogen atom(s).

The "C3-C6 haloalkynyloxy group" represented by R1 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

The aralkyloxy group of the "aralkyloxy group optionally substituted with 0 to substituent(s) A" represented by R1 in the formula (1) is the same as defined hereinabove, and is preferably a benzyloxy group, a phenethyloxy group or a phenylpropyloxy group, and more preferably a benzyloxy group or a phenethyloxy group. When this group has substituent(s) A, the aralkyloxy group is optionally substituted with substituent(s) A in place of any hydrogen atom(s). However, when there are two or more substituents A, each is independent.

In "RaRbN—" (wherein Ra and Rb are independent of one another and each represent a hydrogen atom, a C1-C6 alkyl group optionally substituted with substituent(s) B, a C1-C6 haloalkyl group or a C3-C8 cycloalkyl group, or Ra and Rb together with the nitrogen atom to which they are bonded form an aziridinyl group, an azetidinyl group, a pyrrolidinyl group, a piperidinyl group, a morpholinyl group, a homopiperidinyl group or an azocanyl group) represented by R1 in the formula (1), the terms are the same as defined hereinabove. When the "C1-C6 alkyl group optionally substituted with substituent(s) B" has substituent(s) B, the C1-C6 alkyl group is optionally substituted with substituent(s) B in place of any hydrogen atom(s). Ra and Rb are preferably a hydrogen atom, a C1-C6 alkyl group optionally substituted with substituent(s) B, or a C1-C6 haloalkyl group, and more preferably a hydrogen atom or a C1-C6 alkyl group optionally substituted with substituent(s) B. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably an amino group, a methylamino group or a dimethylamino group.

For example, in a preferred embodiment, R1 is a hydroxyl group, a methyl group, an ethyl group, a propyl group, a 2-hydroxyethyl group, a 2-fluoroethyl group, a 2,2-difluoroethyl group, a 2,2,2-trifluoroethyl group, 1,1,2,2-tetrafluoroethyl group, an allyl group, a methoxy group, an ethoxy group, a monofluoromethoxy group, a difluoromethoxy group, an allyloxy group, a propargyloxy group, a benzyloxy group, an amino group or a methylamino group.

R2, R3 and R4 in the formula (1) are independent of one another and each represent a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove)), RdC(=O)O— (wherein Rd is the same as defined hereinabove), Rc-L- (wherein Rc represents a C1-C6 alkyl group or a C1-C6 haloalkyl group, and L represents S, SO, or SO$_2$), Rc-SO$_2$—O— (wherein Rc is the same as defined hereinabove), RaRbN— (wherein Ra and Rb are the same as defined hereinabove), or ReC(=O)N (Rf)— (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group).

In particular, R2, R3 and R4 are preferably independent of one another and each represent a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C3-C6 alkynyloxy group optionally substituted with substituent(s) C, RdC(=O)O— (wherein Rd is the same as defined hereinabove), Rc-L-(wherein Rc and L are the same as defined hereinabove), Rc-SO$_2$—O— (wherein Rc is the same as defined hereinabove), RaRbN— (wherein Ra and Rb are the same as defined hereinabove), or ReC(=O)N(Rf)— (wherein Re and Rf are the same as defined hereinabove), and R2, R3 and R4 are particularly preferably independent of one another and each represent a hydrogen atom, a halogen atom, a hydroxy group, a cyano group, a nitro group, a C1-C6 alkyl group optionally substituted with substituent(s) C, a C3-C8 cycloalkyl group optionally substituted with substituent(s) C, a C2-C6 alkynyl group optionally substituted with substituent(s) C, a C1-C6 alkoxy group optionally substituted with substituent(s) C, a C1-C6 haloalkoxy group, a C3-C6 alkynyloxy group optionally substituted with substituent(s) C, RdC(=O)O— (wherein Rd is the same as defined hereinabove), Rc-SO$_2$—O— (wherein Rc and L are the same as defined hereinabove), RaRbN— (wherein Ra and Rb are the same as defined hereinabove), or ReC(=O)N(Rf)— (wherein Re and Rf are the same as defined hereinabove).

In the formula (1), R2 may represent a hydrogen atom, a hydroxy group, a cyano group or a nitro group.

The halogen atom represented by R2 in the formula (1) is the same as defined hereinabove, and is preferably a fluorine atom, a chlorine atom, a bromine atom or an iodine atom.

In the "C1-C6 alkyl group optionally substituted with substituent(s) C" represented by R2 in the formula (1), the C1-C6 alkyl group is the same as defined hereinabove, and is preferably a methyl group, an ethyl group, a propyl group, an isopropyl group, a butyl group or an isobutyl group, and more preferably a methyl group, an ethyl group, a propyl group or an isopropyl group. When this group has substituent(s) C, the C1-C6 alkyl group is optionally substituted with substituent(s) C in place of any hydrogen atom(s).

The "C1-C6 haloalkyl group" represented by R2 in the formula (1) is the same as defined hereinabove, and is preferably a difluoromethyl group, a trifluoromethyl group, a 2,2-difluoroethyl group or a 2,2,2-trifluoroethyl group, and more preferably a difluoromethyl group or a trifluoromethyl group.

In the "C3-C8 cycloalkyl group optionally substituted with substituent(s) C" represented by R2 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R2 in the formula (1), the C2-C6 alkenyl group is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When this group has substituent(s) C, the C2-C6 alkenyl group is optionally substituted with substituent(s) C in place of any hydrogen atom(s).

The "C2-C6 haloalkenyl group" represented by R2 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) C" represented by R2 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) C, the C2-C6 alkynyl group is optionally substituted with substituent(s) C in place of any hydrogen atom(s).

The "C2-C6 haloalkynyl group" represented by R2 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) C" represented by R2 in the formula (1), the C1-C6 alkoxy group is the same as defined hereinabove, and is preferably a methoxy group, an ethoxy group, a propyloxy group, an isopropyloxy group, a butoxy group, an isobutoxy group or a pentyloxy group, and more preferably a methoxy group, an ethoxy group, a propyloxy group or an isopropyloxy group. When this group has substituent(s) C, the C1-C6 alkoxy group is optionally substituted with substituent(s) C in place of any hydrogen atom(s).

The "C1-C6 haloalkoxy group" represented by R2 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) C" represented by R2 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R2 in the formula (1), the C2-C6 alkenyloxy group is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When this group has substituent(s) C, the C2-C6 alkenyloxy group is optionally substituted with substituent(s) C in place of any hydrogen atom(s).

The "C2-C6 haloalkenyloxy group" represented by R2 in the formula (1) is the same as defined hereinabove, and is preferably a 2-fluorovinyloxy group, a 2,2-dfluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) C" represented by R2 in the formula (1), the C3-C6 alkynyloxy group is the same as defined hereinabove, and is preferably a propargyloxy group, a 2-butynyloxy group or a 3-butynyloxy group, and more preferably a propargyloxy group or a 2-butynyloxy group. When this group has substituent(s) C, the C3-C6 alkynyloxy group is optionally substituted with substituent(s) C in place of any hydrogen atom(s).

The "C3-C6 haloalkynyloxy group" represented by R2 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In "RdC(=O)—" (wherein Rd represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group or RaRbN— (wherein Ra and Rb are the same as defined hereinabove)) represented by R2 in the formula (1), the terms are the same as defined hereinabove. Where the "C1-C6 alkyl group optionally substituted with substituent(s) B" has substituent(s) B, the C1-C6 alkyl group is optionally optionally substituted with substituent(s) B in place of any hydrogen atom(s). Rd is preferably a C1-C6 alkyl group optionally substituted with substituent(s) B, or a C1-C6 alkoxy group, and more preferably a C1-C6 alkyl group optionally substituted with substituent(s) B. "RdC(=O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group or a piperidinylcarbonyl group, and more preferably an acetyl group, a methoxyacetyl group, a cyanoacetyl group, a propionyl group, a methoxycarbonyl group or an ethoxycarbonyl group.

In "RdC(=O)O—" represented by R2 in the formula (1), Rd is the same as defined hereinabove. Rd is preferably a C1-C6 alkyl group optionally substituted with substituent(s) B, or a C1-C6 alkoxy group, and more preferably a C1-C6 alkyl group optionally substituted with substituent(s) B. "RdC(=O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, and more preferably an acetyloxy group, a methoxyacetyloxy group, a cyanoacetyloxy group or a propionyloxy group.

In "Rc-L-" (wherein Rc represents a C1-C6 alkyl group or a C1-C6 haloalkyl group and L represents S, SO or $SO_2$) represented by R2 in the formula (1), the terms are the same as defined hereinabove. "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "Rc-SO$_2$—O—" represented by R2 in the formula (1), Rc is the same as defined hereinabove. Rc is preferably a C1-C6 alkyl group. "Rc-SO$_2$—O—" is preferably a methanesulfonyloxy group, an ethanesulfonyloxy group, or a trifluoromethanesulfonyloxy group, and more preferably a methanesulfonyloxy group, or an ethanesulfonyloxy group.

In "RaRbN—" represented by R2 in the formula (1), Ra and Rb are the same as defined hereinabove. Ra and Rb represent preferably a hydrogen atom, a C1-C6 alkyl group optionally substituted with substituent(s) B, or a C1-C6 haloalkyl group, or Ra and Rb are taken together with the nitrogen atom to which they are bonded to form a pyrrolidinyl group, a piperidinyl group, or a morpholyl group, and Ra and Rb represent more preferably a hydrogen atom, or a C1-C6 alkyl group optionally substituted with substituent(s) B, or Ra and Rb are taken together with the nitrogen atom to which they are bonded to form a pyrrolidinyl group, a piperidinyl group, or a morpholyl group. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl) methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, a piperidinyl group, or a morpholyl group, and more preferably an amino group, a methylamino group, an ethylamino group, a dimethylamino group, an ethylmethylamino group, a diethylamino group, a pyrrolidinyl group, a piperidinyl group, or a morpholyl group.

In "ReC(=O)N(Rf)—" (wherein Re represents a hydrogen atom, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are the same as defined hereinabove), and Rf represents a hydrogen atom, a C1-C6 alkyl group optionally substituted with substituent(s) B, a C1-C6 haloalkyl group, or a C3-C8 cycloalkyl group) represented by R2 in the formula (1), the terms are the same as defined hereinabove. Further, when the "C1-C6 alkyl group optionally substituted with substituent(s) B" represented by Re and Rf has substituent(s) B, the C1-C6 alkyl group is optionally substituted with substituent(s) B in place of any hydrogen atom(s). Re is preferably a hydrogen atom, a C1-C6 alkyl group optionally substituted with substituent(s) B, a C1-C6 haloalkyl group, a C1-C6 alkoxy group, or a C1-C6 haloalkoxy group, and more preferably a C1-C6 alkyl group optionally substituted with substituent(s) B. Specific examples of Re include preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy group, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl) methylamino group, a (cyanomethyl)methylamino group, a (2-cyanoethyl)methylamino group, a 2,2-difluoroethylamino group, a 2,2,2-trifluoroethylamino group, cyclopropylamino group, a (cyclopropyl)methylamino group, a pyrrolidinyl group, or a piperidinyl group, and more preferably a methyl group, or an ethyl group. Also, Rf is preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. Specific examples of Rf include preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group, or a cyclopropyl group, and more preferably a hydrogen atom, a methyl group, or an ethyl group.

In the formula (1), R3 is defined the same as R2.

In the formula (1), R4 is defined the same as R2.

R2, R3 and R4 in the formula (1) are independent of one another and may be the same as or different from one another without limitation.

For example, in a preferred embodiment, R2, R3 and R4 are independent of one another and each represent a hydrogen atom, a fluorine atom, a chlorine atom, a bromine atom, a hydroxyl group, a cyano group, a nitro group, a methyl group, an ethyl group, a propyl group, a cyclopropyl group, an ethynyl group, a methoxy group, a methoxymethoxy group, an ethoxy group, a 2-methoxyethoxy group, a difluoromethoxy group, a trifluoromethoxy group, a 2,2-difluoroethoxy group, a 2,2,2-trifluoroethoxy group, a propargyloxy group, an acetyl oxy group, a methanesulfonyloxy group, an amino group, a methylamino group, a dimethylamino group, a morpholinyl group, a piperidin-1-yl group, an acetamide group, or a N-methylacetamide group.

For example, in a preferred embodiment, the partial structure Ph:

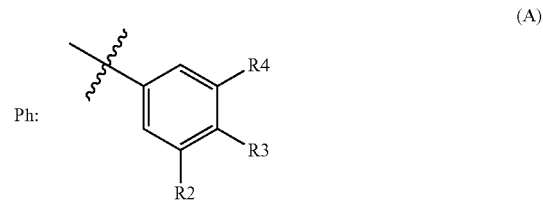

(A)

in the formula (1) is a phenyl group, a 3-fluorophenyl group, a 3-chlorophenyl group, a 3-bromophenyl group, a 4-fluorophenyl group, a 4-chlorophenyl group, a 4-bromophenyl group, a 3-chloro-4-fluorophenyl group, a 4-chloro-3-fluorophenyl group, a 3-bromo-4-fluorophenyl group, a 3,4-difluorophenyl group, a 3,5-difluorophenyl group, a 3,4-dichlorophenyl group, a 3,4,5-trifluorophenyl group, a 4-fluoro-3-methylphenyl group, a 4-fluoro-3-ethynylphenyl group, a 4-hydroxyphenyl group, a 4-cyanophenyl group, a 4-nitrophenyl group, a 4-methylphenyl group, a 4-ethylphenyl group, a 4-propylphenyl group, a 4-cyclopropylphenyl group, a 3-ethynylphenyl group, a 4-ethynylphenyl group, a 4-methoxyphenyl group, a 4-ethoxyphenyl group, a 4-(methoxymethoxy)phenyl group, a 4-(2-methoxyethoxy)phenyl group, a 4-difluoromethoxyphenyl group, a 4-trifluoromethoxyphenyl group, a 4-(2,2-difluoroethoxy)phenyl group, a 4-(2,2,2-trifluoroethoxy)phenyl group, a 4-propargylphenyl group, a 4-acetoxyphenyl group, a 4-methanesulfonyloxyphenyl group, a 4-aminophenyl group, a 4-(methylamino)phenyl group, a 4-(dimethylamino)phenyl group, a 4-(piperidin-1-yl)-phenyl group, a 4-morpholinophenyl group, a 4-(acetamido)phenyl group, or a 4-(N-methylacetamido)pheny group.

R5 in the formula (1) represents a hydrogen atom, a halogen atom, a cyano group, a nitro group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc and L are the same as defined hereinabove), RaRbN— (wherein Ra and Rb are the same as defined hereinabove) or RgC(=O)— (wherein Rg represents a hydrogen atom, a hydroxy group, a C1-C6 alkyl group optionally substituted with substituent(s) B, a C1-C6 haloalkyl group, a C3-C8 cycloalkyl group or a C1-C6 alkoxy group, a C1 to C6 haloalkoxy group, a C3 to C8 cycloalkoxy group, or RaRbN— (wherein, Ra and Rb are as defined above)).

In particular, R5 is preferably a hydrogen atom, a halogen atom, a nitro group, a C1-C6 alkyl group optionally substituted with substituent(s) A, a C1-C6 haloalkyl group, a C2-C6 alkenyl group optionally substituted with substituent(s) A, a C2-C6 alkynyl group optionally substituted with substituent(s) A, a C1-C6 alkoxy group optionally substituted with substituent(s) A, RaRbN— (wherein Ra and Rb are the same as defined hereinabove) or RgC(=O)— (wherein Rg is the same as defined hereinabove), and R5 is particularly preferably a hydrogen atom, a halogen atom, a nitro group, a C1-C6 alkyl group optionally substituted with substituent(s) A, a C2-C6 alkenyl group optionally substituted with substituent(s) A, a C1-C6 alkoxy group optionally substituted with substituent(s) A, RaRbN— (wherein Ra and Rb are the same as defined hereinabove) or RgC(=O)— (wherein Rg is the same as defined hereinabove).

In the formula (1), R5 may represent a hydrogen atom, a cyano group or a nitro group.

The halogen atom represented by R5 in the formula (1) is the same as defined hereinabove, and is preferably a fluorine atom, a chlorine atom, a bromine atom or an iodine atom.

In the "C1-C6 alkyl group optionally substituted with substituent(s) A" represented by R5 in the formula (1), the C1-C6 alkyl group is the same as defined hereinabove, and is preferably a methyl group, an ethyl group, a propyl group, an isopropyl group, a butyl group or an isobutyl group, and more preferably a methyl group or an ethyl group. When this group has substituent(s) A, the C1-C6 alkyl group is optionally substituted with substituent(s) A in place of any hydrogen atom(s).

The "C1-C6 haloalkyl group" represented by R5 in the formula (1) is the same as defined hereinabove, and is preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and more preferably a difluoromethyl group or a trifluoromethyl group.

In the "C3-C8 cycloalkyl group optionally substituted with substituent(s) A" represented by R5 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) A, the C3-C8 cycloalkyl group is optionally substituted with substituent(s) A in place of any hydrogen atom(s).

In the "C2-C6 alkenyl group optionally substituted with substituent(s) A" represented by R5 in the formula (1), the C2-C6 alkenyl group is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When this group has substituent(s) A, the C2-C6 alkenyl group is optionally substituted with substituent(s) A in place of any hydrogen atom(s).

The "C2-C6 haloalkenyl group" represented by R5 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) A" represented by R5 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) A, the C2-C6 alkynyl group is optionally substituted with substituent(s) A in place of any hydrogen atom(s).

The "C2-C6 haloalkynyl group" represented by R5 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) A" represented by R5 in the formula (1), the C1-C6 alkoxy group is the same as defined hereinabove, and is preferably a methoxy group, an ethoxy group, a propyloxy group, an isopropyloxy group, a butoxy group or an isobutoxy group, and more preferably a methoxy group or an ethoxy group. When this group has substituent(s) A, the C1-C6 alkoxy group is optionally substituted with substituent(s) A in place of any hydrogen atom(s).

The "C1-C6 haloalkoxy group" represented by R5 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) A" represented by R5 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) A, the C3-C8 cycloalkoxy group is optionally substituted with substituent(s) A in place of any hydrogen atom(s).

In the "C2-C6 alkenyloxy group optionally substituted with substituent(s) A" represented by R5 in the formula (1), the C2-C6 alkenyloxy group is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When this group has substituent(s) A, the C2-C6 alkenyloxy group is optionally substituted with substituent(s) A in place of any hydrogen atom(s).

The "C2-C6 haloalkenyloxy group" represented by R5 in the formula (1) is the same as defined hereinabove, and may be a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) A" represented by R5 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) A, the C3-C6 alkynyloxy group is optionally substituted with substituent(s) A in place of any hydrogen atom(s).

The "C3-C6 haloalkynyloxy group" represented by R5 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In "Rc-L-" represented by R5 in the formula (1), Rc and L are the same as defined hereinabove. "Rc-L-" is preferably a methylthio group, a methanesulfinyl group, an ethylthio group, an ethanesulfinyl group, an ethanesulfonyl group, a methanesulfonyl group, a trifluoromethylthio group, a trifluoromethanesulfinyl group or a trifluoromethanesulfonyl group, and more preferably a methylthio group, a methanesulfinyl group or a methanesulfonyl group.

In "RaRbN—" represented by R5 in the formula (1), Ra and Rb are the same as defined hereinabove. Ra and Rb are preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. "RaRbN—" is preferably an amino group, a methylamino group, an ethylamino group, a (methoxymethyl)amino group, a (2-methoxyethyl)amino group, a (cyanomethyl) amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group or a piperidinyl group, and more preferably an amino group, a methylamino group, a dimethylamino group, an ethylmethylamino group or a diethylamino group.

In "RgC(=O)—" (wherein Rg represents a hydrogen atom, a hydroxy group, a C1-C6 alkyl group optionally substituted with substituent(s) B, a C1-C6 haloalkyl group, a C3-C8 cycloalkyl group, a C1-C6 alkoxy group, a C1-C6 haloalkoxy group, a C3-C8 cycloalkoxy group, or RaRbN— (wherein Ra and Rb are as defined hereinabove)) represented by R5 in the formula (1), the terms are the same as defined hereinabove. Further, when the "C1-C6 alkyl group optionally substituted with substituent(s) B" has substituent(s) B, the C1-C6 alkyl group is optionally substituted with substituent(s) B in place of any hydrogen atom(s). Rg is preferably a C1-C6 alkyl group optionally substituted with substituent(s) B, or a C1-C6 alkoxy group, and more preferably a C1-C6 alkyl group optionally substituted with substituent(s) B, "RgC(=O)—" is preferably a formyl group, a hydroxycarbonyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, or a piperidinylcarbonyl group, and more preferably an acetyl group, a methoxyacetyl group, a cyanoacetyl group, or a propionyl group.

For example, in a preferred embodiment, R5 is a hydrogen atom, a chlorine atom, a bromine atom, an iodine atom, a nitro group, a methyl group, an ethyl group, a 1-hydroxyethyl group, a vinyl group, a methoxy group, an amino group, a methylamino group, a dimethylamino group, or an acetyl group.

X in the formula (1) represents an oxygen atom or a sulfur atom. Preferred X is an oxygen atom.

Y represents R8-C or a nitrogen atom, and Z represents R9-C or a nitrogen atom.

In particular, when Y is R8-C, Z represents a nitrogen atom, or, when Y is a nitrogen atom, Z is preferably a combination represented by R9-C.

When Y is R8-C and Z is R9-C, the compound is represented by the formula (1-a):

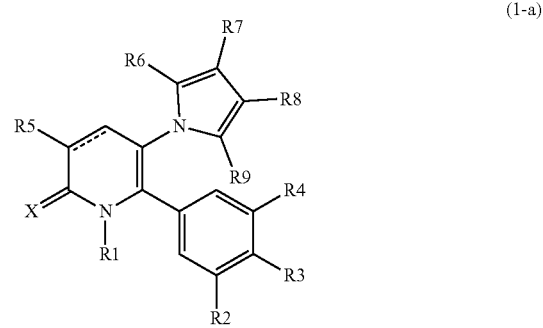

(1-a)

wherein R1, R2, R3, R4, R5, R6, R7, R8, R9, X and the broken line are the same as defined in the formula (1), or a salt thereof.

When Y is R8-C and Z is a nitrogen atom, the compound is represented by the formula (1-b):

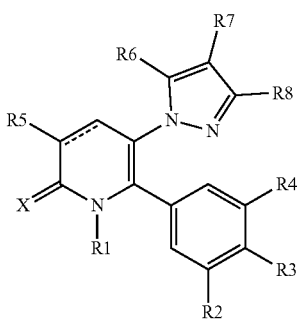

(1-b)

wherein R1, R2, R3, R4, R5, R6, R7, R8, X and the broken line are the same as defined in the formula (1), or a salt thereof.

When Y is a nitrogen atom and Z is R9-C, the compound is represented by the formula (1-c):

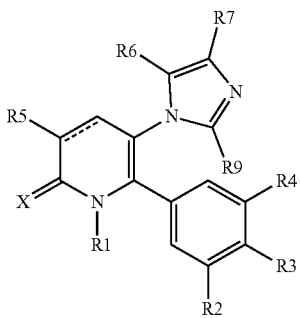

(1-c)

wherein R1, R2, R3, R4, R5, R6, R7, R9, X and the broken line are the same as defined in the formula (1), or a salt thereof.

When Y and Z are a nitrogen atom, the compound is represented by the formula (1-d):

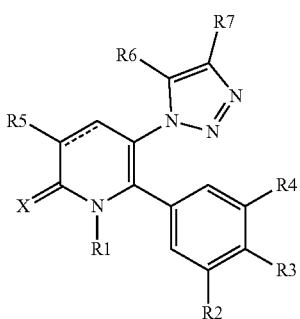

(1-d)

wherein R1, R2, R3, R4, R5, R6, R7, X and the broken line are the same as defined in the formula (1), or a salt thereof.

R6 in the formula (1) represents a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alky- nyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove).

In particular, R6 is preferably a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RdC(=O)— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), R6 is particularly preferably a hydrogen atom, a halogen atom, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, RdC(=O)— (wherein Rd is the same as defined hereinabove), Rc-L-(wherein Rc and L are the same as defined hereinabove), or RaRbN— (wherein Ra and Rb are the same as defined hereinabove), and R6 is more preferably a hydrogen atom, a halogen atom, a C1-C6 alkyl group optionally substituted with substituent(s) C, a C1-C6 haloalkyl group, a C3-C8 cycloalkyl group optionally substituted with substituent(s) C, a C1-C6 alkoxy group optionally substituted with substituent(s) C, RdC(=O)— (wherein Rd is the same as defined hereinabove), or Rc-L- (wherein Rc and L are the same as defined hereinabove).

R6 in the formula (1) includes a hydrogen atom, a hydroxy group, cyano group, and a nitro group. The halogen atom presented by R6 in the formula (1) is the same as defined hereinabove, and is preferably a fluorine atom, a chlorine atom, a bromine atom, or an iodine atom.

In the "C1-C6 alkyl group optionally substituted with substituent(s) C" represented by R6 in the formula (1), the C1-C6 alkyl group is the same as defined hereinabove, and is preferably a methyl group, an ethyl group, a propyl group, an isopropyl group, a butyl group, an isobutyl group, a sec-butyl group, a t-butyl group, or a pentyl group, and more preferably a methyl group, an ethyl group, a propyl group, an isopropyl group, a butyl group, an isobutyl group, a sec-butyl group, or a t-butyl group. When this group has substituent(s) C, the C1-C6 alkyl group is optionally substituted with substituent(s) C in place of any hydrogen atom(s).

The "C1-C6 haloalkyl group" represented by R6 in the formula (1) is the same as defined hereinabove, and is preferably a monofluoromethyl group, a monochloromethyl group, a monobromomethyl group, a difluoromethyl group, a dibromomethyl group, a trifluoromethyl group, a chlorodifluoromethyl group, a bromodifluoromethyl group, a trichloromethyl group, a 1,1-difluoroethyl group, a 2,2-difluoroethyl group, a 2,2,2-trifluoroethyl group, a 1,1,2,2-tetrafluoroethyl group, a pentafluoroethyl group, a 3,3-difluoropropyl group, or a 3,3,3-trifluoropropyl group, and more preferably a difluoromethyl group, a trifluoromethyl group, a chlorodifluoromethyl group, a bromodifluoromethyl group, a trichloromethyl group a 1,1-difluoroethyl group, a 1,1,2,2-tetrafluoroethyl group, or a pentafluoroethyl group.

In the "C3-C8 cycloalkyl group optionally substituted with substituent(s) C" represented by R6 in the formula (1), the C3-C8 cycloalkyl group is the same as defined hereinabove, and is preferably a cyclopropyl group, a cyclobutyl group, a cyclopentyl group, or a cyclohexyl group, and more preferably a cyclopropyl group, or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R6 in the formula (1), the C2-C6 alkenyl group is the same as defined hereinabove, and is preferably a vinyl group, a 1-propenyl group, or an allyl group, and more preferably a vinyl group. When this group has substituent(s) C, the C2-C6 alkenyl group is optionally substituted with substituent(s) C in place of any hydrogen atom(s).

The "C2-C6 haloalkenyl group" represented by R6 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group, or a 3,3-dichloroallyl group, and more preferably a 2-fluorovinyl group, or a 2,2-difluorovinyl group.

In the "C2-C6 alkynyl group optionally substituted with substituent(s) C" represented by R6 in the formula (1), the C2-C6 alkynyl group is the same as defined hereinabove, and is preferably an ethynyl group, a 1-propynyl group, a propargyl group, a 1-butynyl group, a 2-butynyl group, or a 3-butynyl group, and more preferably an ethynyl group, a 1-propynyl group, or a propargyl group. When this group has substituent(s) C, the C2-C6 alkynyl group is optionally substituted with substituent(s) C in place of any hydrogen atom(s).

The "C2-C6 haloalkynyl group" represented by R6 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group, or a 4,4,4-trifluoro-2-butynyl group, and more preferably a 3,3-difluoro-1-propynyl group, or a 3,3,3-trifluoro-1-propynyl group.

In the "C1-C6 alkoxy group optionally substituted with substituent(s) C" represented by R6 in the formula (1), the C1-C6 alkoxy group is the same as defined hereinabove, and is preferably a methoxy group, an ethoxy group, a propyloxy group, or an isopropyloxy group, and more preferably a methoxy group, or an ethoxy group. When this group has substituent(s) C, the C1-C6 alkoxy group is optionally substituted with substituent(s) C in place of any hydrogen atom(s).

The "C1-C6 haloalkoxy group" represented by R6 in the formula (1) is the same as defined hereinabove, and preferably a difluoromethoxy group, a trifluoromethoxy group, a 2,2-difluoroethoxy group, a 2,2,2-trifluoroethoxy group, a 3,3-difluoropropyloxy group, or a 3,3,3-trifluoropropyloxy group, and more preferably a difluoromethoxy group, a trifluoromethoxy group, a 2,2-difluoroethoxy group, or a 2,2,2-trifluoroethoxy group.

In the "C3-C8 cycloalkoxy group optionally substituted with substituent(s) C" represented by R6 in the formula (1), the C3-C8 cycloalkoxy group is the same as defined hereinabove, and is preferably a cyclopropyloxy group, a cyclobutoxy group, a cyclopentyloxy group, or a cyclohexyloxy group, and more preferably a cyclopropyloxy group, or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R6 in the formula (1), the C2-C6 alkenyloxy group is the same as defined hereinabove, and is preferably a vinyloxy group, a 1-propenyloxy group, or an allyloxy group, and more preferably a vinyloxy group. When this group has substituent(s) C, the C2-C6 alkenyloxy group is optionally substituted with substituent(s) C in place of any hydrogen atom(s).

The "C2-C6 haloalkenyloxy group" represented by R6 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group, or a 3,3-dichloroallyloxy group, and more preferably a 2-fluorovinyloxy group, or a 2,2-difluorovinyloxy group.

In the "C3-C6 alkynyloxy group optionally substituted with substituent(s) C" represented by R6 in the formula (1), the C3-C6 alkynyloxy group is the same as defined hereinabove, and is preferably a propargyloxy group, a 2-butynyloxy group, or a 3-butynyloxy group, and more preferably a propargyloxy group. When this group has substituent(s) C, the C3-C6 alkynyloxy group is optionally substituted with substituent(s) C in place of any hydrogen atom(s).

The "C3-C6 haloalkynyloxy group" represented by R6 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group, or a 4,4,4-trifluoro-2-butynyloxy group, and more preferably a 4,4-difluoro-2-butynyloxy group, or a 4,4,4-trifluoro-2-butynyloxy group.

In "RdC(=O)—" represented by R6 in the formula (1), Rd is the same as defined hereinabove. Rd is preferably a C1-C6 alkyl group optionally substituted with substituent(s) B, a C1-C6 alkoxy group or a C1-C6 haloalkoxy group, and more preferably a C1-C6 alkoxy group. "RdC(=O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, or a piperidinylcarbonyl group, and more preferably a methoxycarbonyl group, an ethoxycarbonyl group, a 2,2-difluoroethoxycarbonyl group, or a 2,2,2-trifluoroethoxycarbonyl group.

In "RdC(=O)O—" represented by R6 in the formula (1), Rd is the same as defined hereinabove. "RdC(=O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group or a piperidinylcarbonyloxy group, and more preferably an acetyloxy group, a methoxyacetyloxy group, a cyanoacetyloxy group, a propionyloxy group, a methoxycarbonyloxy group or an ethoxycarbonyloxy group.

In "Rc-L-" represented by R6 in the formula (1), Rc and L are the same as defined hereinabove. "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group or a trifluoromethanesulfonyl group, and more preferably a methylthio group, a methanesulfinyl group or a methanesulfonyl group.

Ra and Rb in "RaRbN—" represented by R6 in the formula (1) are the same as defined hereinabove. Ra and Rb are preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably an amino group, a methylamino group, or a dimethylamino group.

Re and Rf in "ReC(=O)N(Rf)—" represented by R6 in the formula (1) are the same as defined hereinabove. Specific examples of Re include preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy group, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl) amino group, a (2-cyanoethyl) amino group, a dimethylamino group, an ethylmethylamino group, an diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably a methyl group, or an ethyl group. Specific examples of Rf include preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group, or a cyclopropyl group, and more preferably a hydrogen atom, a methyl group, or an ethyl group.

R7 in the formula (1) represents a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent (s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove).

In particular, R7 is preferably a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RdC(=O)— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), R7 is particularly preferably a hydrogen atom, a halogen atom, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, RdC(=O)— (wherein Rd is the same as defined hereinabove), Rc-L-(wherein Rc and L are the same as defined hereinabove), or RaRbN—

(wherein Ra and Rb are the same as defined hereinabove), and R7 is more preferably a hydrogen atom, a halogen atom, a nitro group, a C1-C6 alkyl group optionally substituted with substituent(s) C, a C1-C6 haloalkyl group, a C2-C6 alkenyl group optionally substituted with substituent(s) C, a C2-C6 alkynyl group optionally substituted with substituent(s) C, RdC(=O)— (wherein Rd is the same as defined hereinabove), or RaRbN— (wherein Ra and Rb are the same as defined hereinabove).

R7 in the formula (1) includes a hydrogen atom, a hydroxy group, a cyano group, and a nitro group.

The halogen atom represented by R7 in the formula (1) is the same as defined hereinabove, and is preferably a fluorine atom, a chlorine atom, a bromine atom, or an iodine atom.

In the "C1-C6 alkyl group optionally substituted with substituent(s) C" represented by R7 in the formula (1), the C1-C6 alkyl group is the same as defined hereinabove, and is preferably a methyl group, an ethyl group, a propyl group, an isopropyl group, a butyl group, an isobutyl group, a sec-butyl group, a t-butyl group, or a pentyl group, and more preferably a methyl group, an ethyl group, a propyl group, an isopropyl group, or a butyl group. When this group has substituent(s) C, the C1-C6 alkyl group is optionally substituted with substituent(s) B in place of any hydrogen atom(s).

The "C1-C6 haloalkyl group" represented by R7 in the formula (1) is the same as defined hereinabove, and is preferably a monofluoromethyl group, a monochloromethyl group, a monobromomethyl group, a difluoromethyl group, a dibromomethyl group, a trifluoromethyl group, a 2,2-difluoroethyl group, a 2,2,2-trifluoroethyl group, a 3,3-difluoropropyl group, or a 3,3,3-trifluoropropyl group, and more preferably a monofluoromethyl group, a monochloromethyl group, a monobromomethyl group, a difluoromethyl group, a dibromomethyl group, or a trifluoromethyl group.

In the "C3-C8 cycloalkyl group optionally substituted with substituent(s) C" represented by R7 in the formula (1), the C3-C8 cycloalkyl group is the same as defined hereinabove, and is preferably a cyclopropyl group, a cyclobutyl group, a cyclopentyl group or a cyclohexyl group, and more preferably a cyclopropyl group or a cyclobutyl group. When this group has substituent(s) C, the C3-C8 cycloalkyl group is optionallyoptionally substituted with substituent(s) C in place of any hydrogen atom(s).

In the "C2-C6 alkenyl group optionally substituted with substituent(s) C" represented by R7 in the formula (1), the C2-C6 alkenyl group is the same as defined hereinabove, and is preferably a vinyl group, a 1-propenyl group, or an allyl group, and more preferably a vinyl group. When this group has substituent(s) C, the C2-C6 alkenyl group is optionally substituted with substituent(s) C in place of any hydrogen atom(s).

The "C2-C6 haloalkenyl group" represented by R7 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

In the "C2-C6 alkynyl group optionally substituted with substituent(s) C" represented by R7 in the formula (1), the C2-C6 alkynyl group is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When this group has substituent(s) C, the C2-C6 alkynyl group is optionally substituted with substituent(s) C in place of any hydrogen atom(s).

The "C2-C6 haloalkynyl group" represented by R7 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

In the "C1-C6 alkoxy group optionally substituted with substituent(s) C" represented by R7 in the formula (1), the C1-C6 alkoxy group is the same as defined hereinabove, and is preferably a methoxy group, an ethoxy group, a propyloxy group, or an isopropyloxy group, and more preferably a methoxy group, or an ethoxy group. When this group has substituent(s) C, the C1-C6 alkoxy group is optionally substituted with substituent(s) C in place of any hydrogen atom(s).

The "C1-C6 haloalkoxy group" represented by R7 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

In the "C3-C8 cycloalkoxy group optionally substituted with substituent(s) C" represented by R7 in the formula (1), the C3-C8 cycloalkoxy group is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R7 in the formula (1), the C2-C6 alkenyloxy group is the same as defined hereinabove, and is preferably a vinyloxy group, a 1-propenyloxy group, or an allyloxy group, and more preferably a vinyloxy group. When this group has substituent(s) C, the C2-C6 alkenyloxy group is optionally substituted with substituent(s) C in place of any hydrogen atom(s).

The "C2-C6 haloalkenyloxy group" represented by R7 in the formula (1) is the same as defined hereinabove, and is preferably a 2-fluorovinyloxy group, a 22-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

In the "C3-C6 alkynyloxy group optionally substituted with substituent(s) C" represented by R7 in the formula (1), the C3-C6 alkynyloxy group is the same as defined hereinabove, and is preferably a propargyloxy group, a 2-butynyloxy group or a 3-butynyloxy group, and more preferably a propargyloxy group. When this group has substituent(s) C, the C3-C6 alkynyloxy group is optionally substituted with substituent(s) C in place of any hydrogen atom(s).

The "C3-C6 haloalkynyloxy group" represented by R7 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

In "RdC(=O)—" represented by R7 in the formula (1), Rd is the same as defined hereinabove. Rd is preferably a hydrogen atom, a C1-C6 alkyl group optionally substituted with substituent(s) B, a C1-C6 haloalkyl group, a C1-C6 alkoxy group, or a C1-C6 haloalkoxy group, and more preferably a hydrogen atom, a C1-C6 alkyl group optionally substituted with substituent(s) B, or a C1-C6 haloalkoxy group. "RdC(=O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, or a piperidinylcarbonyl group, and more preferably a formyl group, an acetyl group, a propionyl group, a methoxycarbonyl group, or an ethoxycarbonyl group.

In "RdC(=O)O—" represented by R7 in the formula (1), Rd is the same as defined hereinabove. "RdC(=O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group, or a piperidinylcarbonyloxy group, and more preferably an acetyloxy group, a methoxyacetyloxy group, a cyanoacetyloxy group, a propionyloxy group, a methoxycarbonyloxy group, or an ethoxycarbonyloxy group.

In "Rc-L-" represented by R7 in the formula (1), Rc and L are the same as defined hereinabove. "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group, or a trifluoromethanesulfonyl group, and more preferably a methylthio group, a methanesulfinyl group, or a methanesulfonyl group.

In "RaRbN—" represented by R7 in the formula (1), Ra and Rb are the same as defined hereinabove. Ra and Rb are preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. Specific examples of "RaRbN—" include preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably an amino group, a methylamino group, or a dimethylamino group.

In "ReC(=O)N(Rf)—" represented by R7 in the formula (1), Re and Rf are the same as defined hereinabove. Specific examples of Re include preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy group, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably a methyl group, or an ethyl group. Specific examples of Rf include preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group, or a cyclopropyl group, and more preferably a hydrogen atom, a methyl group, or an ethyl group.

R8 in the formula (1) represents a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove).

In particular, R8 is preferably a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RdC(=O)— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), R8 is particularly preferably a hydrogen atom, a halogen atom, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, RdC(=O)— (wherein Rd is the same as defined hereinabove), Rc-L-(wherein Rc and L are the same as defined hereinabove), or RaRbN— (wherein Ra and Rb are the same as defined hereinabove), and R8 is more preferably a hydrogen atom, a halogen atom, a C1-C6 alkyl group optionally substituted with substituent(s) C, or a C1-C6 haloalkyl group.

R8 in the formula (1) includes a hydrogen atom, a hydroxy group, a cyano group, and a nitro group.

The halogen atom represented by R8 in the formula (1) is the same as defined hereinabove, and is preferably a fluorine atom, a chlorine atom, a bromine atom, or an iodine atom.

In the "C1-C6 alkyl group optionally substituted with substituent(s) C" represented by R8 in the formula (1), the C1-C6 alkyl group is the same as defined hereinabove, and is preferably a methyl group, an ethyl group, a propyl group, an isopropyl group, or a butyl group, and more preferably a methyl group, or an ethyl group. When this group has substituent(s) C, the C1-C6 alkyl group is optionally substituted with substituent(s) B in place of any hydrogen atom(s).

The "C1-C6 haloalkyl group" represented by R8 in the formula (1) is the same as defined hereinabove, and is preferably a difluoromethyl group, a dibromomethyl group, a trifluoromethyl group, a 2,2-difluoroethyl group, a 2,2,2-trifluoroethyl group, a 3,3-difluoropropyl group, or a 3,3,3-trifluoropropyl group, and more preferably a difluoromethyl group, or a trifluoromethyl group.

In the "C3-C8 cycloalkyl group optionally substituted with substituent(s) C" represented by R8 in the formula (1), the C3-C8 cycloalkyl group is the same as defined hereinabove, and is preferably a cyclopropyl group, a cyclobutyl group, a cyclopentyl group, or a cyclohexyl group, and more preferably a cyclopropyl group, or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R8 in the formula (1), the C2-C6 alkenyl group is the same as defined hereinabove, and is preferably a vinyl group, a 1-propenyl group, or an allyl group, and more preferably a vinyl group. When this group has substituent(s) C, the C2-C6 alkenyl group is optionally substituted with substituent(s) C in place of any hydrogen atom(s).

The "C2-C6 haloalkenyl group" represented by R8 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group, or a 3,3-dichloroallyl group, and more preferably a 2-fluorovinyl group, or a 2,2-difluorovinyl group.

In the "C2-C6 alkynyl group optionally substituted with substituent(s) C" represented by R8 in the formula (1), the C2-C6 alkynyl group is the same as defined hereinabove, and is preferably an ethynyl group, a 1-propynyl group, a propargyl group, a 1-butynyl group, a 2-butynyl group, or a 3-butynyl group, and more preferably an ethynyl group, a 1-propynyl group, or a propargyl group. When this group has substituent(s) C, the C2-C6 alkynyl group is optionally substituted with substituent(s) C in place of any hydrogen atom(s).

The "C2-C6 haloalkynyl group" represented by R8 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group, or a 4,4,4-trifluoro-2-butynyl group, and more preferably a 3,3-difluoro-1-propynyl group, or a 3,3,3-trifluoro-1-propynyl group.

In the "C1-C6 alkoxy group optionally substituted with substituent(s) C" represented by R8 in the formula (1), the C1-C6 alkoxy group is the same as defined hereinabove, and is preferably a methoxy group, an ethoxy group, a propyloxy group, or an isopropyloxy group, and more preferably a methoxy group, or an ethoxy group. When this group has substituent(s) C, the C1-C6 alkoxy group is optionally substituted with substituent(s) C in place of any hydrogen atom(s).

The "C1-C6 haloalkoxy group" represented by R8 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group, or a 3,3,3-trifluoropropyloxy group, and more preferably a difluoromethoxy group, a trifluoromethoxy group, a 2,2-difluoroethoxy group, or a 2,2,2-trifluoroethoxy group.

In the "C3-C8 cycloalkoxy group optionally substituted with substituent(s) C" represented by R8 in the formula (1), the C3-C8 cycloalkoxy group is the same as defined hereinabove, and is preferably a cyclopropyloxy group, a cyclobutoxy group, a cyclopentyloxy group, or a cyclohexyloxy group, and more preferably a cyclopropyloxy group, or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R8 in the formula (1), the C2-C6 alkenyloxy group is the same as defined hereinabove, and is preferably a vinyloxy group, a 1-propenyloxy group, or an allyloxy group, and more preferably a vinyloxy group. When this group has substituent(s) C, the C2-C6 alkenyloxy group is optionally substituted with substituent(s) C in place of any hydrogen atom(s).

The "C2-C6 haloalkenyloxy group" represented by R8 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group, or a 3,3-dichloroallyloxy group, and more preferably a 2-fluorovinyloxy group, or a 2,2-difluorovinyloxy group.

In the "C3-C6 alkynyloxy group optionally substituted with substituent(s) C" represented by R8 in the formula (1), the C3-C6 alkynyloxy group is the same as defined hereinabove, and is preferably a propargyloxy group, a 2-butynyloxy group, or a 3-butynyloxy group, and more preferably a propargyloxy group. When this group has substituent(s) C, the C3-C6 alkynyloxy group is optionally substituted with substituent(s) C in place of any hydrogen atom(s).

The "C3-C6 haloalkynyloxy group" represented by R8 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group, or a 4,4,4-trifluoro-2-butynyloxy group, and more preferably a 4,4-difluoro-2-butynyloxy group, or a 4,4,4-trifluoro-2-butynyloxy group.

In "RdC(=O)—" represented by R8 in the formula (1), Rd is the same as defined hereinabove. Rd is preferably a hydrogen atom, a C1-C6 alkyl group optionally substituted with substituent(s) B, a C1-C6 haloalkyl group, or a C1-C6 alkoxy group, and more preferably a hydrogen atom, a C1-C6 alkyl group optionally substituted with substituent(s) B, or a C1-C6 alkoxy group. "RdC(=O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 2,2-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, or a piperidinylcarbonyl group, and more preferably a formyl group, an acetyl group, a methoxyacetyl group, a cyanoacetyl group, a propionyl group, a methoxycarbonyloxy group, or an ethoxycarbonyloxy group.

In "RdC(=O)O—" represented by R8 in the formula (1), Rd is the same as defined hereinabove. "RdC(=O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group, or a piperidinylcarbonyloxy group, and more preferably an acetyloxy group, a methoxyacetyloxy group, a cyanoacetyloxy group, a propionyloxy group, a methoxycarbonyloxy group, or an ethoxycarbonyloxy group.

In "Rc-L-" represented by R8 in the formula (1), Rc and L are the same as defined hereinabove. "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group, or a trifluoromethanesulfonyl group, and more preferably a methylthio group, a methanesulfinyl group, or a methanesulfonyl group.

In "RaRbN—" represented by R8 in the formula (1), Ra and Rb are the same as defined hereinabove. Ra and Rb is preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably an amino group, a methylamino group, or a dimethylamino group.

In "ReC(=O)N(Rf)—" represented by R8 in the formula (1), Re and Rf are the same as defined hereinabove. Specific examples of Re include preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy group, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably a methyl group, or an ethyl group. Specific examples of Rf include preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group, or a cyclopropyl group, and more preferably a hydrogen atom, a methyl group, or an ethyl group.

R9 in the formula (1) represents a hydrogen atom, a halogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove).

In particular, R9 is preferably a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RdC(=O)— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), R9 is particularly preferably a hydrogen atom, a halogen atom, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, RdC(=O)— (wherein Rd is the same as defined hereinabove), Rc-L-(wherein Rc and L are the same as defined hereinabove), or RaRbN— (wherein Ra and Rb are the same as defined hereinabove), and R9 is more preferably a hydrogen atom, or a halogen atom.

R9 in the formula (1) includes a hydrogen atom, a hydroxy group, a cyano group, and a nitro group.

The halogen atom represented by R9 in the formula (1) is the same as defined hereinabove, and is preferably a fluorine atom, a chlorine atom, a bromine atom, or an iodine atom.

In the "C1-C6 alkyl group optionally substituted with substituent(s) C" represented by R9 in the formula (1), the C1-C6 alkyl group is the same as defined hereinabove, and is preferably a methyl group, an ethyl group, a propyl group, an isopropyl group, or a butyl group, and more preferably a methyl group, or an ethyl group. When this group has substituent(s) C, the C1-C6 alkyl group is optionally substituted with substituent(s) B in place of any hydrogen atom(s).

The "C1-C6 haloalkyl group" represented by R9 in the formula (1) is the same as defined hereinabove, and is preferably a difluoromethyl group, a dibromomethyl group, a trifluoromethyl group, a 2,2-difluoroethyl group, a 2,2,2-trifluoroethyl group, a 3,3-difluoropropyl group, or a 3,3,3-trifluoropropyl group, and more preferably a difluoromethyl group, a trifluoromethyl group, or a trichloromethyl group.

In the "C3-C8 cycloalkyl group optionally substituted with substituent(s) C" represented by R9 in the formula (1), the C3-C8 cycloalkyl group is the same as defined hereinabove, and is preferably a cyclopropyl group, a cyclobutyl group, a cyclopentyl group, or a cyclohexyl group, and more preferably a cyclopropyl group, or a cyclobutyl group. When this group has substituent(s) C, the C3-C8 cycloalkyl group is optionally substituted with substituent(s) C in place of any hydrogen atom(s).

In the "C2-C6 alkenyl group optionally substituted with substituent(s) C" represented by R9 in the formula (1), the C2-C6 alkenyl group is the same as defined hereinabove, and is preferably a vinyl group, a 1-propenyl group, or an allyl group, and more preferably a vinyl group. When this group has substituent(s) C, the C2-C6 alkenyl group is optionally substituted with substituent(s) C in place of any hydrogen atom(s).

The "C2-C6 haloalkenyl group" represented by R9 in the formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group, or a 3,3-dichloroallyl group, and more preferably a 2-fluorovinyl group, or a 2,2-difluorovinyl group.

In the "C2-C6 alkynyl group optionally substituted with substituent(s) C" represented by R9 in the formula (1), the C2-C6 alkynyl group is the same as defined hereinabove, and is preferably an ethynyl group, a 1-propynyl group, a propargyl group, a 1-butynyl group, a 2-butynyl group, or a 3-butynyl group, and more preferably an ethynyl group, a 1-propynyl group, or a propargyl group. When this group has substituent(s) C, the C2-C6 alkynyl group is optionally substituted with substituent(s) C in place of any hydrogen atom(s).

The "C2-C6 haloalkynyl group" represented by R9 in the formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group, or a 4,4,4-trifluoro-2-butynyl group, and more preferably a 3,3-difluoro-1-propynyl group, or a 3,3,3-trifluoro-1-propynyl group.

In the "C1-C6 alkoxy group optionally substituted with substituent(s) C" represented by R9 in the formula (1), the C1-C6 alkoxy group is the same as defined hereinabove, and is preferably a methoxy group, an ethoxy group, a propyloxy group, or an isopropyloxy group, and more preferably a methoxy group, or an ethoxy group. When this group has substituent(s) C, the C1-C6 alkoxy group is optionally substituted with substituent(s) C in place of any hydrogen atom(s).

The "C1-C6 haloalkoxy group" represented by R9 in the formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group, or a 3,3,3-trifluoropropyloxy group, and more preferably a difluoromethoxy group, a trifluoromethoxy group, a 2,2-difluoroethoxy group, or a 2,2,2-trifluoroethoxy group.

In the "C3-C8 cycloalkoxy group optionally substituted with substituent(s) C" represented by R9 in the formula (1), the C3-C8 cycloalkoxy group is the same as defined hereinabove, and is preferably a cyclopropyloxy group, a cyclobutoxy group, a cyclopentyloxy group, or a cyclohexyloxy group, and more preferably a cyclopropyloxy group, or a cyclobutoxy group. When this group has substituent(s) C, the C3-C8 cycloalkoxy group is optionally substituted with substituent(s) C in place of any hydrogen atom(s).

In the "C2-C6 alkenyloxy group optionally substituted with substituent(s) C" represented by R9 in the formula (1), the C2-C6 alkenyloxy group is the same as defined hereinabove, and is preferably a vinyloxy group, a 1-propenyloxy group, or an allyloxy group, and more preferably a vinyloxy group. When this group has substituent(s) C, the C2-C6 alkenyloxy group is optionally substituted with substituent(s) C in place of any hydrogen atom(s).

The "C2-C6 haloalkenyloxy group" represented by R9 in the formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group, or a 3,3-dichloroallyloxy group, and more preferably a 2-fluorovinyloxy group, or a 2,2-difluorovinyloxy group.

In the "C3-C6 alkynyloxy group optionally substituted with substituent(s) C" represented by R9 in the formula (1), the C3-C6 alkynyloxy group is the same as defined hereinabove, and is preferably a propargyloxy group, a 2-butynyloxy group, or a 3-butynyloxy group, and more preferably a propargyloxy group. When this group has substituent(s) C, the C3-C6 alkynyloxy group is optionally substituted with substituent(s) C in place of any hydrogen atom(s).

The "C3-C6 haloalkynyloxy group" represented by R9 in the formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group, or a 4,4,4-trifluoro-2-butynyloxy group, and more preferably a 4,4-difluoro-2-butynyloxy group, or a 4,4,4-trifluoro-2-butynyloxy group.

In "RdC(=O)—" represented by R9 in the formula (1), Rd is the same as defined hereinabove. Rd is preferably a hydrogen atom, a C1-C6 alkyl group optionally substituted with substituent(s) B, or a C1-C6 haloalkyl group, or a C1-C6 alkoxy group, and more preferably a hydrogen atom, a C1-C6 alkyl group optionally substituted with substituent(s) B, or a C1-C6 alkoxy group. "RdC(=O)—" is preferably a formyl group, an acetyl group, a methoxyacetyl group, a cyanoacetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a 3,3,3-trifluoropropyloxycarbonyl group, a cyclopropyloxycarbonyl group, an aminocarbonyl group, a methylaminocarbonyl group, an ethylaminocarbonyl group, a (methoxymethyl)aminocarbonyl group, a (2-methoxyethyl)aminocarbonyl group, a (cyanomethyl)aminocarbonyl group, a (2-cyanoethyl)aminocarbonyl group, a dimethylaminocarbonyl group, an ethylmethylaminocarbonyl group, a diethylaminocarbonyl group, a (methoxymethyl)methylaminocarbonyl group, a (2-methoxyethyl)methylaminocarbonyl group, a (cyanomethyl)methylaminocarbonyl group, a (2-cyanoethyl)methylaminocarbonyl group, a 22-difluoroethylaminocarbonyl group, a 2,2,2-trifluoroethylaminocarbonyl group, a cyclopropylaminocarbonyl group, a (cyclopropyl)methylaminocarbonyl group, a pyrrolidinylcarbonyl group, or a piperidinylcarbonyl group, and more preferably a formyl group, an acetyl group, a methoxyacetyl group, a cyanoacetyl group, a propionyl group, a methoxycarbonyloxy group, or an ethoxycarbonyloxy group.

In "RdC(=O)O—" represented by R9 in the formula (1), Rd is the same as defined hereinabove. "RdC(=O)O—" is preferably a formyloxy group, an acetyloxy group, a methoxyacetyloxy group, a cyanoacetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a 3,3,3-trifluoropropyloxycarbonyloxy group, a cyclopropyloxycarbonyloxy group, an aminocarbonyloxy group, a methylaminocarbonyloxy group, an ethylaminocarbonyloxy group, a (methoxymethyl)aminocarbonyloxy group, a (2-methoxyethyl)aminocarbonyloxy group, a (cyanomethyl)aminocarbonyloxy group, a (2-cyanoethyl)aminocarbonyloxy group, a dimethylaminocarbonyloxy group, an ethylmethylaminocarbonyloxy group, a diethylaminocarbonyloxy group, a (methoxymethyl)methylaminocarbonyloxy group, a (2-methoxyethyl)methylaminocarbonyloxy group, a (cyanomethyl)methylaminocarbonyloxy group, a (2-cyanoethyl)methylaminocarbonyloxy group, a 2,2-difluoroethylaminocarbonyloxy group, a 2,2,2-trifluoroethylaminocarbonyloxy group, a cyclopropylaminocarbonyloxy group, a (cyclopropyl)methylaminocarbonyloxy group, a pyrrolidinylcarbonyloxy group, or a piperidinylcarbonyloxy group, and more preferably an acetyloxy group, a methoxyacetyloxy group, a cyanoacetyloxy group, a propionyloxy group, a methoxycarbonyloxy group, or an ethoxycarbonyloxy group.

In "Rc-L-" represented by R9 in the formula (1), Rc and L are the same as defined hereinabove. "Rc-L-" is preferably a methylthio group, a methanesulfinyl group, a methanesulfonyl group, an ethylthio group, an ethanesulfinyl group, an ethanesulfonyl group, a trifluoromethylthio group, a trifluoromethanesulfinyl group, or a trifluoromethanesulfonyl group, and more preferably a methylthio group, a methanesulfinyl group, or a methanesulfonyl group.

In "RaRbN—" represented by R9 in the formula (1), Ra and Rb are the same as defined hereinabove. Ra and Rb is preferably a hydrogen atom, a C1-C6 alkyl group optionally substituted with substituent(s) B, or a C1-C6 haloalkyl group, and more preferably a hydrogen atom, or a C1-C6 alkyl group optionally substituted with substituent(s) B. "RaRbN—" is preferably an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, a pyrrolidinyl group, or a piperidinyl group, and more preferably an amino group, a methylamino group, or a dimethylamino group.

In the "ReC(=O)N(Rf)—" represented by R9 in the formula (1), Re and Rf are the same as defined hereinabove. Specific examples of Re include preferably a hydrogen atom, a methyl group, a methoxymethyl group, a cyanomethyl group, an ethyl group, a difluoromethyl group, a trifluoromethyl group, a cyclopropyl group, a methoxy group, an ethoxy group, a 2,2-difluoroethoxy group, a 2,2,2-trifluoroethoxy group, a cyclopropyloxy group, an amino group, a methylamino group, an ethylamino group, a (methoxymethyl)amino group, a (2-methoxyethyl)amino group, a (cyanomethyl)amino group, a (2-cyanoethyl)amino group, a dimethylamino group, an ethylmethylamino group, a diethylamino group, a (methoxymethyl)methylamino group, a (2-methoxyethyl)methylamino group, a (cyanomethyl)methylamino group, a (2-cyanoethyl)methylamino group, a 2,2-difluoroethylamino group, a 2,2,2-trifluoroethylamino group, a cyclopropylamino group, a (cyclopropyl)methylamino group, pyrrolidinyl group, or a piperidinyl group, and more preferably a methyl group, or an ethyl group. Specific examples of Rf include preferably a hydrogen atom, a methyl group, a methoxymethyl group, an ethoxymethyl group, a cyanomethyl group, an ethyl group, a 2-methoxyethyl group, a 2-ethoxyethyl group, a 2-cyanoethyl group, a propyl group, a 2,2-difluoroethyl group, a 2,2,2-trifluoroethyl group, or a cyclopropyl group, and more preferably a hydrogen atom, a methyl group, or an ethyl group.

In "R6 and R7 are taken together to form a C2-C6 alkylene group, and, R8 and R9 represent those as defined hereinabove" in the formula (1), the C2-C6 alkylene group is the same as defined hereinabove, and is preferably an ethylene group, a propylene group, a butylene group, or a pentylene group, and more preferably a propylene group, or a butylene group. For example, when the C2-C6 alkylene group formed by taking together R6 and R7 is a propylene group, the compound is represented by the formula (1-e):

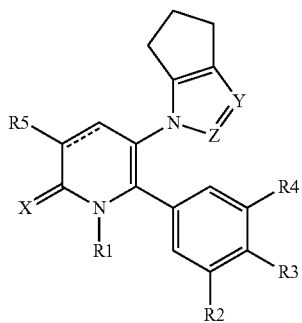

(1-e)

wherein R1, R2, R3, R4, R5, X, Y, Z and the broken line are the same as defined in the formula (1), or a salt thereof.

R6, R7, R8 and R9 in the formula (1) are independent of one another and may be the same as or different from one another without limitation.

For example, in a preferred embodiment, R6, R7, R8 and R9 are independent of one onother and each represent a hydrogen atom, a fluorine atom, a chlorine atom, a bromine atom, a nitro group, a methyl group, an ethyl group, a propyl group, an isopropyl group, a t-butyl group, a hydroxymethyl group, a 1-hydroxyethyl group, a 1-hydroxypropyl group, a 2-hydroxypropan-2-yl group, a methoxymethyl group, a monochloromethyl group, a monobromomethyl group, a difluoromethyl group, a dibromomethyl group, a trifluoromethyl group, a chlorodifluoromethyl group, a bromodifluoromethyl group, a trichloromethyl group, a 1,1-difluoroethyl group, a 1,1,2,2-tetrafluoroethyl group, a pentafluoroethyl group, a cyclopropyl group, a vinyl group, an ethynyl group, a propargyl group, a 1-hydroxyprop-2-yn-1-yl group, a methoxy group, a formyl group, an acetyl group, a methoxycarbonyl group, an ethoxycarbonyl group, a methylthio group, a methanesulfinyl group, a methanesulfonyl group, or an amino group, or R6 and R7 are taken together to form a propylene group or a butylene group, and R8 and R9 are the same as defined hereinabove.

For example, in a preferred embodiment, R6 is a hydrogen atom, a chlorine atom, a bromine atom, a methyl group, an ethyl group, an isopropyl group, a t-butyl group, a difluoromethyl group, a trifluoromethyl group, a chlorodifluoromethyl group, a bromodifluoromethyl group, a trichloromethyl group, a 1,1-difluoroethyl group, a 1,1,2,2-tetrafluoroethyl group, a pentafluoroethyl group, a cyclopropyl group, a methoxy group, a methoxycarbonyl group, a methylthio group, a methanesulfinyl group, or a methanesulfonyl group.

For example, in a preferred embodiment, R7 is a hydrogen atom, a fluorine atom, a chlorine atom, a bromine atom, a nitro group, a methyl group, an ethyl group, a propyl group, an isopropyl group, a methoxymethyl group, a hydroxymethyl group, a 1-hydroxyethyl group, a 1-hydroxypropyl group, a 2-hydroxypropan-2-yl group, a monochloromethyl group, a monobromomethyl group, a difluoromethyl group, a dibromomethyl group, a vinyl group, an ethynyl group, a propargyl group, a 1-hydroxyprop-2-yn-1-yl group, a formyl group, an acetyl group, an ethoxycarbonyl group, or an amino group.

For example, in a preferred embodiment, R8 is a hydrogen atom, a chlorine atom, a bromine atom, a methyl group, an ethyl group, or a trifluoromethyl group.

For example, in a preferred embodiment, R9 is a hydrogen atom or a chlorine atom.

For example, in a preferred embodiment, R6 and R7 are taken together to form a propylene group or a butylene group.

For example, in a preferred embodiment, the partial structure Az:

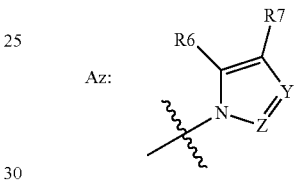

in the formula (1) is 1H-pyrazol-1-yl, 4-nitro-1H-pyrazol-1-yl,
3,5-diethyl-1H-pyrazol-1-yl, 3,5-dimethyl-1H-pyrazol-1-yl,
3-chloro-4-methyl-1H-pyrazol-1-yl, 3-bromo-4-methyl-1H-pyrazol-1-yl,
4-(ethoxycarbonyl)-1H-pyrazol-1-yl,
4-(ethoxycarbonyl)-5-(trifluoromethyl)-1H-pyrazol-1-yl,
4-(ethoxycarbonyl)-5-methyl-1H-pyrazol-1-yl,
4-(bromomethyl)-5-chloro-1H-pyrazol-1-yl, 4,5-dimethyl-1H-pyrazol-1-yl,
4-acetyl-5-chloro-1H-pyrazol-1-yl, 4-amino-1H-pyrazol-1-yl,
4-amino-5-chloro-1H-pyrazol-1-yl, 4-amino-5-bromo-1H-pyrazol-1-yl,
4-chloro-1H-pyrazol-1-yl, 4-fluoro-5-methyl-1H-pyrazol-1-yl,
4-bromo-3,5-dimethyl-1H-pyrazol-1-yl, 4-formyl-5-methyl-1H-pyrazol-1-yl,
4-methyl-1H-pyrazol-1-yl, 4-methyl-3-(trifluoromethyl)-1H-pyrazol-1-yl, 4-methyl-5-(1,1,2,2-tetrafluoroethyl)-1H-pyrazol-1-yl,
4-methyl-5-(trifluoromethyl)-1H-pyrazol-1-yl,
4-methyl-5-(pentafluoro)ethyl)-1H-pyrazol-1-yl,
4-methyl-5-(methanesulfinyl)-1H-pyrazol-1-yl,
4-methyl-5-(methanesulfonyl)-1H-pyrazol-1-yl,
4-methyl-5-(methylthio)-1H-pyrazol-1-yl,
5-(1,1-difluoroethyl)-4-methyl-1H-pyrazol-1-yl, 5-(t-butyl)-3-methyl-1H-pyrazol-1-yl,
5-(t-butyl)-4-methyl-1H-pyrazol-1-yl, 5-(ethoxycarbonyl)-4-methyl-1H-pyrazol-1-yl,
5-(chlorodifluoromethyl)-4-methyl-1H-pyrazol-1-yl,
5-(difluoromethyl)-4-methyl-1H-pyrazol-1-yl, 5-(trichloromethyl)-1H-pyrazol-1-yl,
5-(trifluoromethyl)-1H-pyrazol-1-yl,
5-(bromodifluoromethyl)-4-methyl-1H-pyrazol-1-yl, 5,6-dicyclocyclopenta[c]pyrazol-1

(4H)-yl, 5-isopropyl-3-methyl-1H-pyrazol-1-yl, 5-isopropyl-4-methyl-1H-pyrazol-1-yl, 5-ethyl-3-methyl-1H-pyrazol-1-yl, 5-ethyl-4-methyl-1H-pyrazol-1-yl, 5-chloro-1H-pyrazol-1-yl, 5-chloro-4-(1-hydroxyethyl)-1H-pyrazole-1-yl, 5-chloro-4-(1-hydroxyprop-2-yn-1-yl)-1H-pyrazol-1-yl, 5-chloro-4-(1-hydroxypropyl)-H-pyrazol-1-yl, 5-chloro-4-(2-hydroxypropan-2-yl)-1H-pyrazol-1-yl, 5-chloro-4-(chloromethyl)-1H-pyrazole-1-yl, 5-chloro-4-(dibromomethyl)-1H-pyrazol-1-yl, 5-chloro-4-(difluoromethyl)-1H-pyrazol-1-yl, 5-chloro-4-(hydroxymethyl)-1H-pyrazol-1-yl, 5-chloro-4-(methoxymethyl)-1H-pyrazol-1-yl, 5-chloro-4-isopropyl-1H-pyrazol-1-yl, 5-chloro-4-ethynyl-1H-pyrazol-1-yl, 5-chloro-4-ethyl-1H-pyrazol-1-yl, 5-chloro-4-nitro-1H-pyrazol-1-yl, 5-chloro-4-vinyl-1H-pyrazol-1-yl, 5-chloro-4-propargyl-1H-pyrazol-1-yl, 5-chloro-4-propyl-1H-pyrazol-1-yl, 5-chloro-4-formyl-1H-pyrazol-1-yl, 5-chloro-4-methyl-1H-pyrazol-1-yl, 5-cyclopropyl-3-methyl-1H-pyrazol-1-yl, 5-cyclopropyl-4-methyl-1H-pyrazol-1-yl, 5-bromo-1H-pyrazol-1-yl, 5-bromo-4-nitro-1H-pyrazol-1-yl, 5-bromo-4-methyl-1H-pyrazol-1-yl, 5-methyl-1H-pyrazol-1-yl, 5-methoxy-1H-pyrazol-1-yl, 5-methoxy-4-methyl-11H-pyrazol-1-yl, 4,5,6,7-trahydro-1H-indazol-1-yl, 4,5-dichloro-1H-imidazol-1-yl, 4,5-dimethyl-1H-imidazol-1-yl, or 2,4,5-trichloro-1H-imidazol-1-yl.

In Formula (1), when the bond with a broken line is a double bond, the compound is represented by the formula (1a):

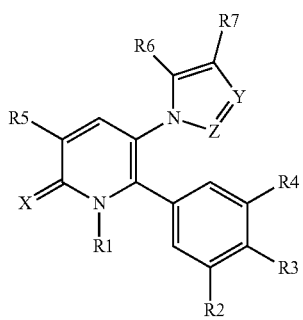

(1a)

wherein R1, R2, R3, R4, R5, R6, R7, X, Y and Z are the same as defined in the formula (1), or a salt thereof.

In Formula (1), when the bond with a broken line is a single bond, the compound is represented by the formula (1b):

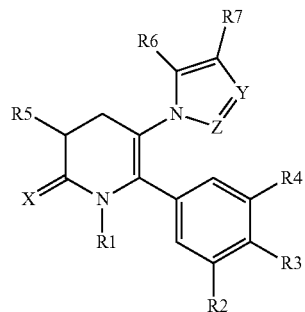

(1b)

wherein R1, R2, R3, R4, R5, R6, R7, X, Y and Z are the same as defined in the formula (1), or a salt thereof.

When R5 in the formula (1b) is a substituent other than hydrogen, the compound is R-isomer, S-isomer, or a mixture containing R-isomer and S-isomer in any proportions.

The compound represented by the formula (1) may have one or two chiral axes. In such a case, the compound may be any single isomer or a mixture of isomers in any proportions without limitation.

The compound represented by the formula (1) may have a chiral atom. In such a case, the compound may be any single isomer or a mixture of isomers in any proportions without limitation.

The compound represented by the formula (1) may have geometric isomeric forms. In such a case, the compound may be any single isomer or a mixture of isomers in any proportions without limitation.

The compound represented by the formula (1) may form a salt with, for example, an acid such as hydrochloric acid, sulfuric acid, acetic acid, fumaric acid or maleic acid, or a metal such as sodium, potassium or calcium. The form of the salt is not particularly limited as long as the salt may be used as an agricultural and horticultural fungicide.

The "substituent(s) A" in the formula (1) is at least one selected from the group consisting of hydroxy group, cyano group, C3-C8 cycloalkyl groups, C1-C6 alkoxy groups, C1-C6 haloalkoxy groups, C3-C8 cycloalkoxy groups, RaRbN— (wherein Ra and Rb are the same as defined hereinabove) and Rc-L- (wherein Rc and L are the same as defined hereinabove).

In particular, the substituent(s) A is preferably a hydroxy group, a cyano group, a C1-C6 alkoxy group or Rc-L- (wherein Rc and L are the same as defined hereinabove), and the substituent(s) A is particularly preferably a hydroxy group or a C1-C6 alkoxy group.

The terms used in association with the substituent(s) A are the same as defined hereinabove.

Specifically, some preferred examples of the substituents A are hydroxy group; cyano group; C3-C8 cycloalkyl groups such as cyclopropyl group, cyclobutyl group, cyclopentyl group and cyclohexyl group; C1-C6 alkoxy groups such as methoxy group, ethoxy group, propyloxy group and isopropyloxy group; C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group; C3-C8 cycloalkoxy groups such as cyclopropyloxy group, cyclobutoxy group, cyclopentyloxy group and cyclohexyloxy group; RaRbN— (wherein Ra and Rb are as defined hereinabove) such as amino group, methylamino group, ethylamino group, (methoxymethyl)amino group, (2-methoxyethyl)amino group, (cyanomethyl)amino group, (2-cyanoethyl)amino group, dimethylamino group, ethylmethylamino group, diethylamino group, (methoxymethyl)methylamino group, (2-methoxyethyl)methylamino group, (cyanomethyl)methylamino group, (2-cyanoethyl)methylamino group, 2,2-difluoroethylamino group, 2,2,2-trifluoroethylamino group, cyclopropylamino group, (cyclopropyl)methylamino group, pyrrolidinyl group and piperidinyl group; Rc-L- (wherein Rc and L are the same as defined hereinabove) such as methylthio group, methanesulfinyl group, methanesulfonyl group, ethylthio group, ethanesulfinyl group, ethanesulfonyl group, trifluoromethylthio group, trifluoromethanesulfinyl group and trifluoromethanesulfonyl group; and the like.

Specifically, more preferred examples of the substituents A are hydroxy group; cyano group; C3-C8 cycloalkyl groups such as cyclopropyl group and cyclobutyl group; C1-C6 alkoxy groups such as methoxy group and ethoxy group; C1-C6 haloalkoxy groups such as difluoromethoxy group, trifluoromethoxy group, 2,2-difluoroethoxy group and 2,2,2-trifluoroethoxy group; C3-C8 cycloalkoxy groups such as cyclopropyloxy group and cyclobutoxy group; RaRbN— (wherein Ra and Rb are the same as defined hereinabove) such as dimethylamino group, ethylmethylamino group and diethylamino group; Rc-L- (wherein Rc and L are the same as defined hereinabove) such as methylthio group, methanesulfinyl group and methanesulfonyl group; and the like.

The "substituent(s) B" in the formula (1) is at least one selected from the group consisting of cyano group, C1-C6 alkoxy groups, C1-C6 haloalkoxy groups and C3-C8 cycloalkoxy groups.

In particular, the substituent(s) B is preferably a cyano group or a C1-C6 alkoxy group.

The terms used in association with the substituent(s) B are the same as defined hereinabove.

Specifically, some preferred examples of the substituents B are cyano group; C1-C6 alkoxy groups such as methoxy group, ethoxy group, propyloxy group and isopropyloxy group; C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group; C3-C8 cycloalkoxy groups such as cyclopropyloxy group, cyclobutoxy group, cyclopentyloxy group and cyclohexyloxy group; and the like.

Specifically, more preferred examples of the substituents B are cyano group; C1-C6 alkoxy groups such as methoxy group and ethoxy group; C1-C6 haloalkoxy groups such as difluoromethoxy group, trifluoromethoxy group, 2,2-difluoroethoxy group and 2,2,2-trifluoroethoxy group; C3-C8 cycloalkoxy groups such as cyclopropyloxy group and cyclobutoxy group; and the like.

The "substituent(s) C" in the formula (1) represents at least one selected from the group consisting of a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, RaRbN— (wherein Ra and Rb are the same as defined hereinabove), Rc-L- (wherein Rc and L are the same as defined hereinabove), RdC(=O)— (wherein Rd is the same as defined hereinabove) and a 3 to 6-membered ring group containing 1 to 2 oxygen atoms.

In particular, the substituent(s) C is preferably a hydroxy group, a cyano group, a C3-C8 cycloalkyl group, a C1-C6 alkoxy group, a C1-C6 haloalkoxy group, or Rc-L-(wherein Rc and L are the same as defined hereinabove), and the substituent(s) C is particularly preferably a hydroxy group, or a C1-C6 alkoxy group.

The terms used in association with the substituent(s) C are the same as defined hereinabove.

Specifically, some preferred examples of the substituents C are hydroxy group; cyano group; C3-C8 cycloalkyl groups such as cyclopropyl group, cyclobutyl group, cyclopentyl group and cyclohexyl group; C1-C6 alkoxy groups such as methoxy group, ethoxy group, propyloxy group, isopropyloxy group, butoxy group, isobutoxy group and t-butoxy group; C1-C6 haloalkoxy groups such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group; C3-C8 cycloalkoxy groups such as cyclopropyloxy group, cyclobutoxy group, cyclopentyloxy group and cyclohexyloxy group; C2-C6 alkoxyalkoxy groups such as methoxymethoxy group, ethoxymethoxy group, methoxyethoxy group, ethoxyethoxy group and methoxypropyloxy group; RaRbN— (wherein Ra and Rb are the same as defined hereinabove) such as amino group, methylamino group, ethylamino group, (methoxymethyl)amino group, (2-methoxyethyl)amino group, (cyanomethyl)amino group, (2-cyanoethyl)amino group, dimethylamino group, ethylmethylamino group, diethylamino group, (methoxymethyl)methylamino group, (2-methoxyethyl)methylamino group, (cyanomethyl)methylamino group, (2-cyanoethyl)methylamino group, 2,2-difluoroethylamino group, 2,2,2-trifluoroethylamino group, cyclopropylamino group, (cyclopropyl)methylamino group, pyrrolidinyl group, piperidinyl group and morpholinyl group; Rc-L- (wherein Rc and L are the same as defined hereinabove) such as methylthio group, methanesulfinyl group, methanesulfonyl group, trifluoromethylthio group, trifluoromethanesulfinyl group and trifluoromethanesulfonyl group; RdC(=O)— (wherein Rd is the same as defined hereinabove) such as formyl group, acetyl group, methoxyacetyl group, cyanoacetyl group, propionyl group, difluoroacetyl group, trifluoroacetyl group, cyclopropanecarbonyl group, methoxycarbonyl group, ethoxycarbonyl group, 2,2-difluoroethoxycarbonyl group, 2,2,2-trifluoroethoxycarbonyl group, 3,3,3-trifluoropropyloxycarbonyl group, cyclopropyloxycarbonyl group, aminocarbonyl group, methylaminocarbonyl group, ethylaminocarbonyl group, (methoxymethyl)aminocarbonyl group, (2-methoxyethyl)aminocarbonyl group, (cyanomethyl)aminocarbonyl group, (2-cyanoethyl)aminocarbonyl group, dimethylaminocarbonyl group, ethylmethylaminocarbonyl group, diethylaminocarbonyl group, (methoxymethyl)methylaminocarbonyl group, (2-methoxyethyl)methylaminocarbonyl group, (cyanomethyl)methylaminocarbonyl group, (2-cyanoethyl)methylaminocarbonyl group, 2,2-difluoroethylaminocarbonyl group, 2,2,2-trifluoroethylaminocarbonyl group, cyclopropylaminocarbonyl group, (cyclopropyl)methylaminocarbonyl group, pyrrolidinylcarbonyl group and piperidinylcarbonyl group; 3 to 6-membered ring groups containing 1 to 2 oxygen atoms such as oxolanyl group, oxanyl group, 1,3-dioxolanyl group and 1,3-dioxanyl group; and the like.

Specifically, more preferred examples of the substituents C are hydroxy group; cyano group; C3-C8 cycloalkyl groups such as cyclopropyl group and cyclobutyl group; C1-C6 alkoxy groups such as methoxy group and ethoxy group; C1-C6 haloalkoxy groups such as difluoromethoxy group, trifluoromethoxy group, 2,2-difluoroethoxy group and 2,2,2-trifluoroethoxy group; C3-C8 cycloalkoxy groups such as cyclopropyloxy group and cyclobutoxy group; C2-C6 alkoxyalkoxy groups such as methoxymethoxy group, ethoxymethoxy group, methoxyethoxy group and ethoxyethoxy group; RaRbN— (wherein Ra and Rb are the same as defined hereinabove) such as dimethylamino group, ethylmethylamino group and diethylamino group; Rc-L- (wherein Rc and L are the same as defined hereinabove) such as methylthio group, methanesulfinyl group and methanesulfonyl group; RdC(=O)— (wherein Rd is the same as defined hereinabove) such as acetyl group, methoxyacetyl group, cyanoacetyl group, difluoroacetyl group, trifluoroacetyl group, methoxycarbonyl group, ethoxycarbonyl group, aminocarbonyl group, dimethylaminocarbonyl group, ethylmethylaminocarbonyl group and diethylaminocarbonyl group; 3 to 6-membered ring groups containing 1 to 2 oxygen atoms such as 1,3-dioxolanyl group and 1,3-dioxanyl group; and the like.

All the compounds resulting from any combination of preferred embodiments of R1, R2, R3, R4, R5, R6, R7, R8, R9, X, Y, Z, the broken line, the substituents A, the substituents B and the substituents C described hereinabove are incorporated herein as the compounds of the formula (1) according to the present invention.

The present invention also includes a compound represented by the following formula (2) or a salt thereof:

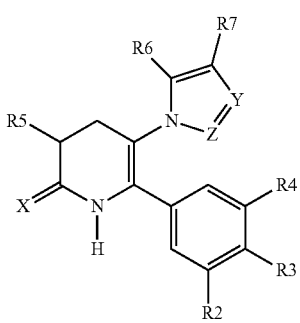

(2)

wherein R2, R3, R4, R5, R6, R7, R8, R9, X, Y and Z are the same as defined hereinabove.

The compound represented by the formula (2) may be a useful intermediate for the production of a compound of the formula (1) of the present invention.

Next, some specific compounds of the present invention are represented by combinations of the structures shown in Table 1, substituents (R2, R3 and R4) on the phenyl shown in Table 2, and azolyl groups (R6, R7, Y and Z) shown in Table 3. Further, the bond with a broken line shown in Table 1 represents a double bond or a single bond, X represents an oxygen atom or a sulfur atom, Ph represents one partial structure illustrated below:

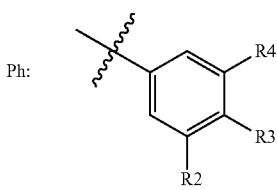

and Az represents one partial structure illustrated below:

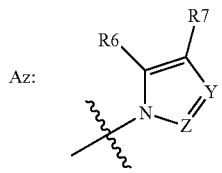

Those compounds are only illustrative and the scope of the invention is not limited to such compounds.

TABLE 1

P-1

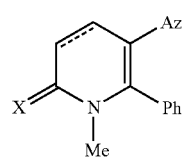

P-2

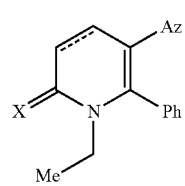

P-3

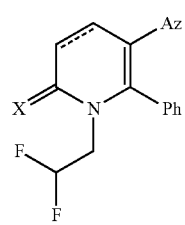

P-4

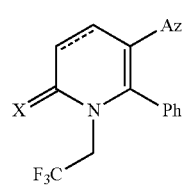

P-5

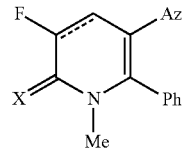

P-6

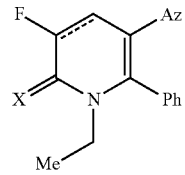

TABLE 1-continued
P-7
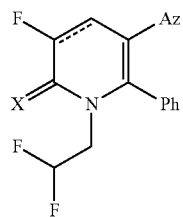
P-8
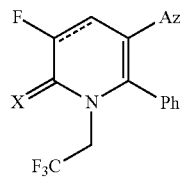
P-9
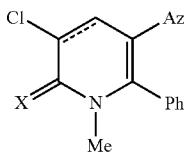
P-10
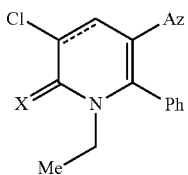
P-11
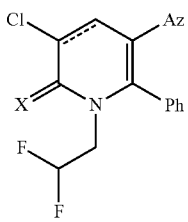
P-12
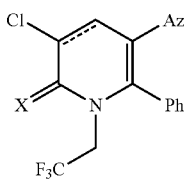
P-13
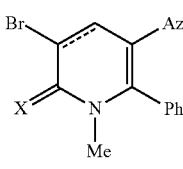
TABLE 1-continued
P-14
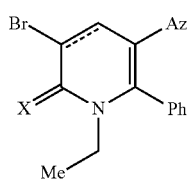
P-15
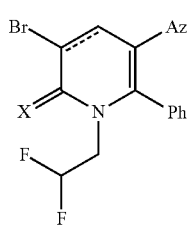
P-16
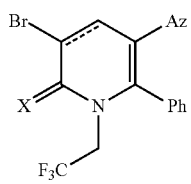
P-17
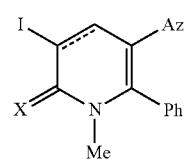
P-18
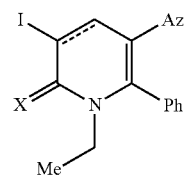
P-19
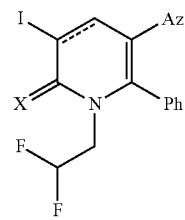

TABLE 1-continued
P-20
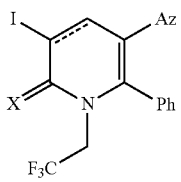
P-21
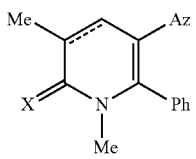
P-22
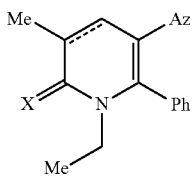
P-23
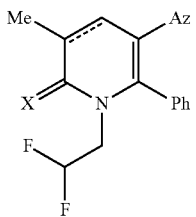
P-24
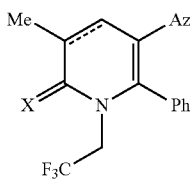
P-25
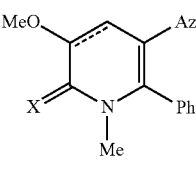
P-26
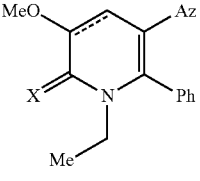
TABLE 1-continued
P-27
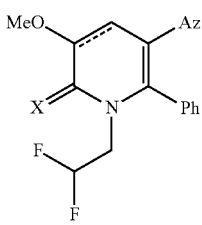
P-28
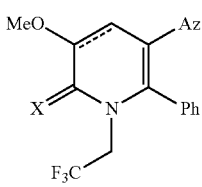
P-29
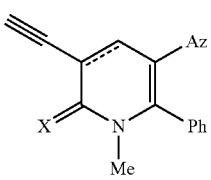
P-30
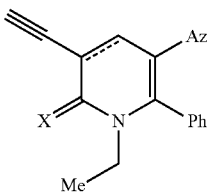
P-31
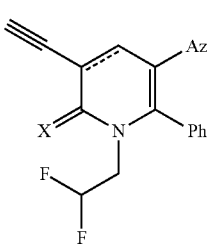
P-32
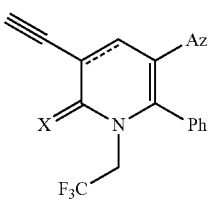

TABLE 1-continued
P-33
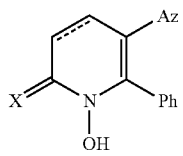
P-34
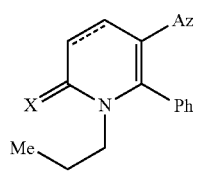
P-35
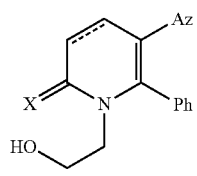
P-36
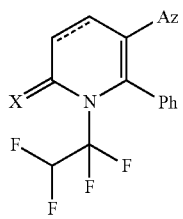
P-37
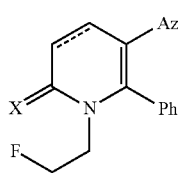
P-38
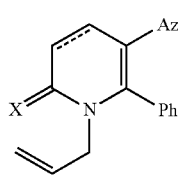
P-39
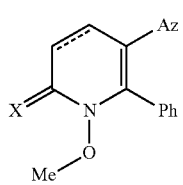
TABLE 1-continued
P-40
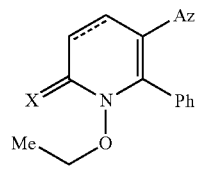
P-41
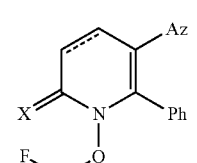
P-42
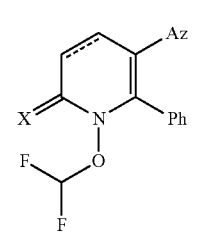
P-43
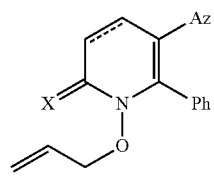
P-44
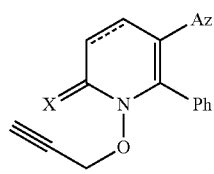
P-45
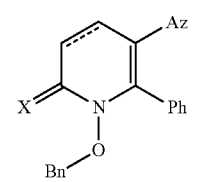
P-46
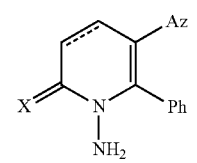

TABLE 1-continued
P-47
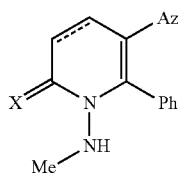
P-48
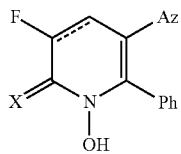
P-49
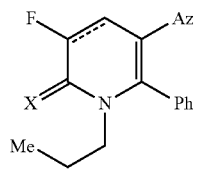
P-50
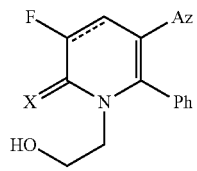
P-51
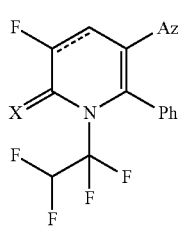
P-52
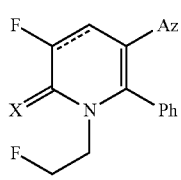
P-53
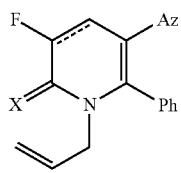
TABLE 1-continued
P-54
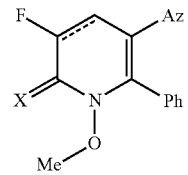
P-55
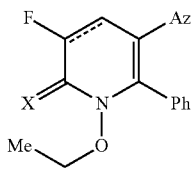
P-56
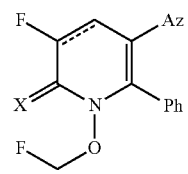
P-57
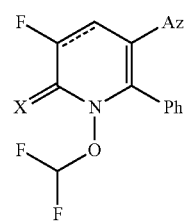
P-58
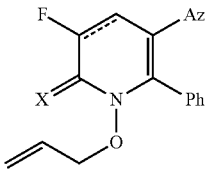
P-59
P-60
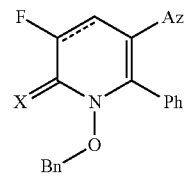

TABLE 1-continued
P-61
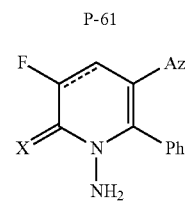
P-62
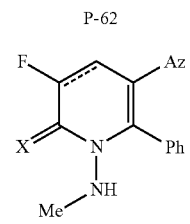
P-63
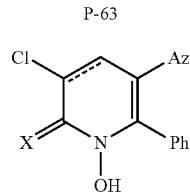
P-64
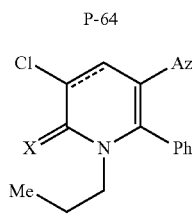
P-65
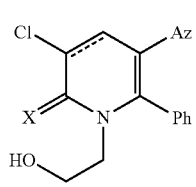
P-66
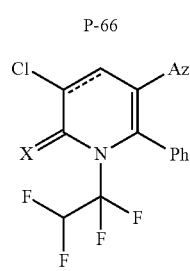
P-67
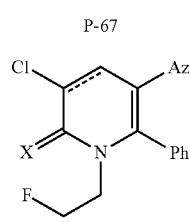
TABLE 1-continued
P-68
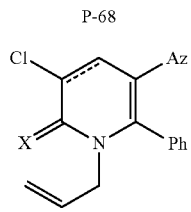
P-69
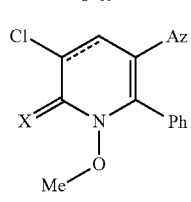
P-70
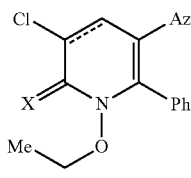
P-71
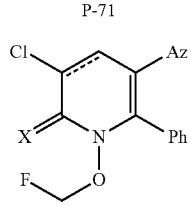
P-72
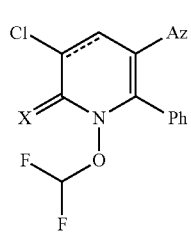
P-73
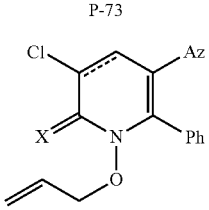
P-74
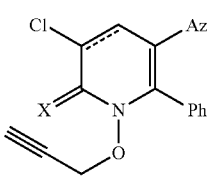

TABLE 1-continued

P-75

P-76

P-77

P-78

P-79

P-80

P-81

P-82

P-83

P-84

P-85

P-86

P-87

P-88

TABLE 1-continued

P-89, P-90, P-91, P-92, P-93, P-94, P-95, P-96, P-97, P-98, P-99, P-100, P-101, P-102

TABLE 1-continued
P-103
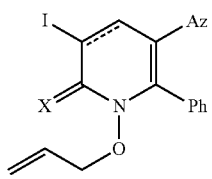
P-104
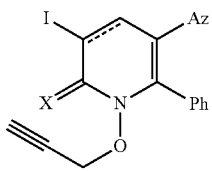
P-105
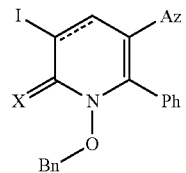
P-106
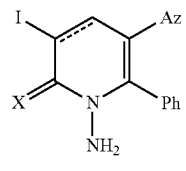
P-107
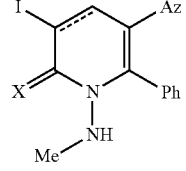
P-108
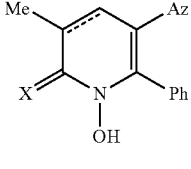
P-109
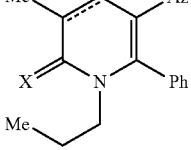
TABLE 1-continued
P-110
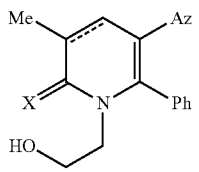
P-111
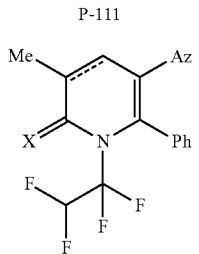
P-112
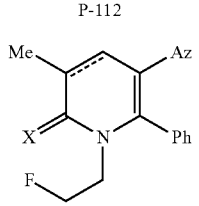
P-113
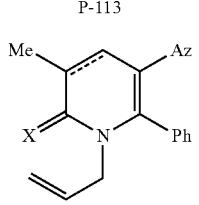
P-114
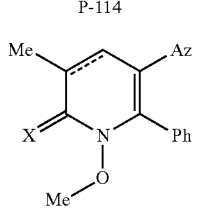
P-115
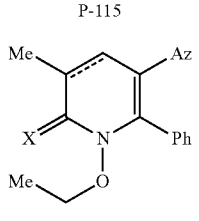
P-116
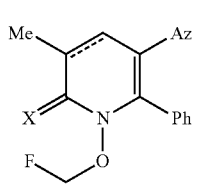

TABLE 1-continued

P-117

P-118

P-119

P-120

P-121

P-122

P-123

P-124

P-125

P-126

P-127

P-128

P-129

P-130

TABLE 1-continued
P-131
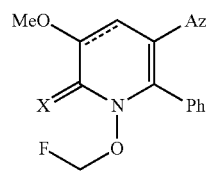
P-132
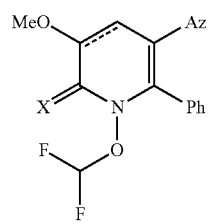
P-133
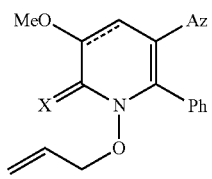
P-134
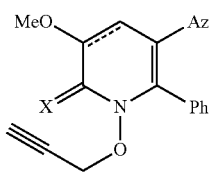
P-135
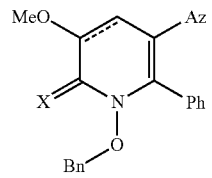
P-136
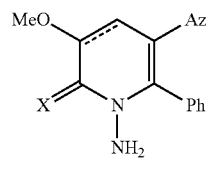
P-137
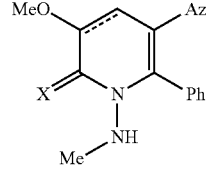
TABLE 1-continued
P-138
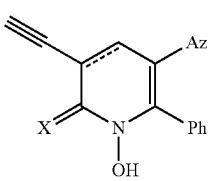
P-139
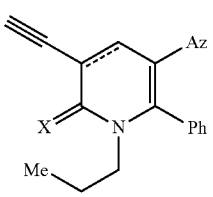
P-140
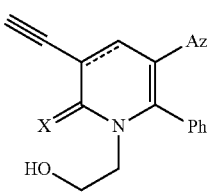
P-141
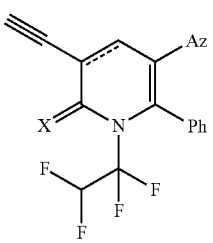
P-142
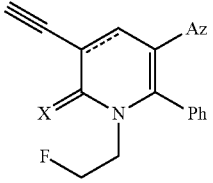
P-143
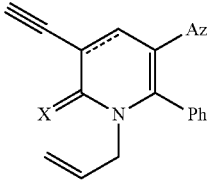

TABLE 1-continued
P-144
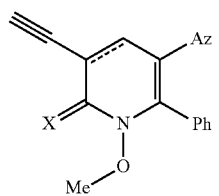
P-145
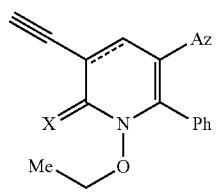
P-146
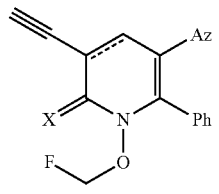
P-147
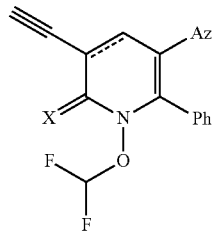
P-148
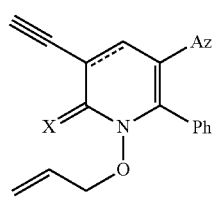
P-149
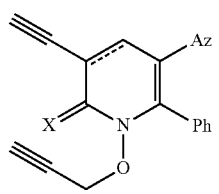
TABLE 1-continued
P-150
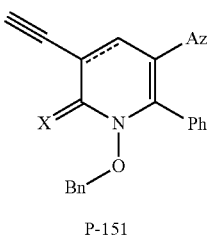
P-151
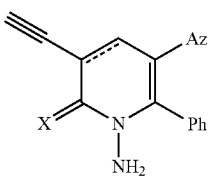
P-152
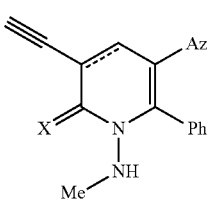
P-153
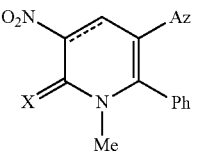
P-154
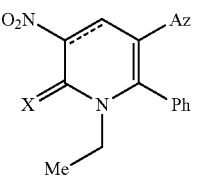
P-155
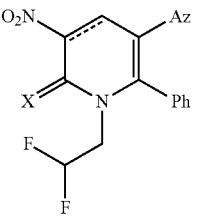
P-156
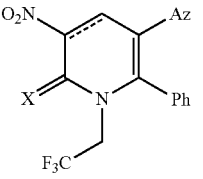

TABLE 1-continued

P-157, P-158, P-159, P-160, P-161, P-162, P-163, P-164, P-165, P-166, P-167, P-168, P-169, P-170

TABLE 1-continued
P-171
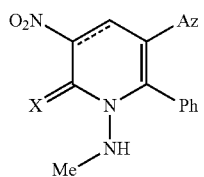
P-172
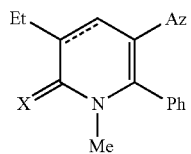
P-173
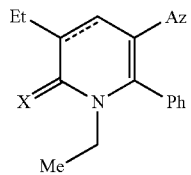
P-174
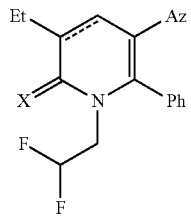
P-175
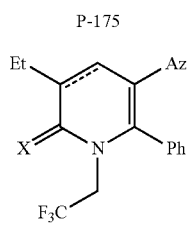
P-176
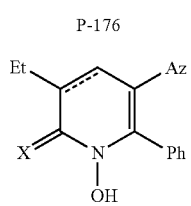
P-177
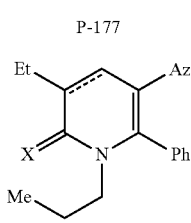
TABLE 1-continued
P-178
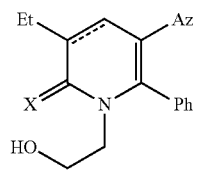
P-179
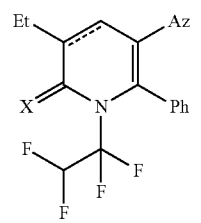
P-180
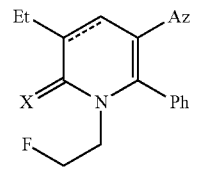
P-181
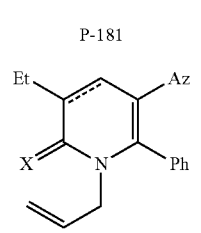
P-182
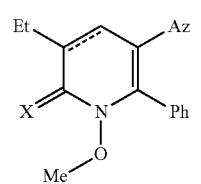
P-183
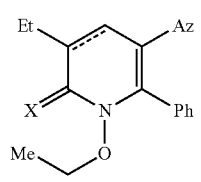
P-184
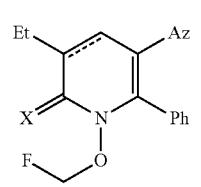

TABLE 1-continued
P-185
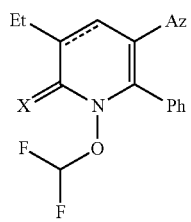
P-186
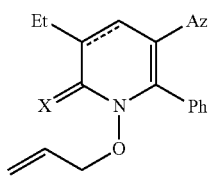
P-187
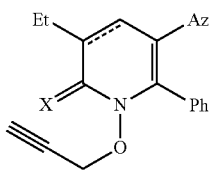
P-188
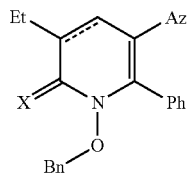
P-189
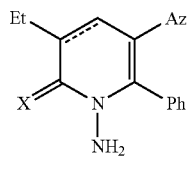
P-190
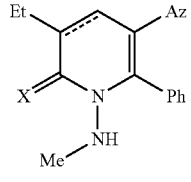
P-191
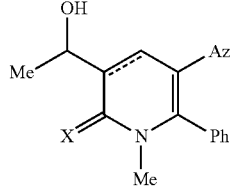
TABLE 1-continued
P-192
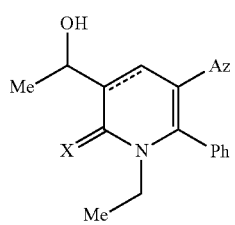
P-193
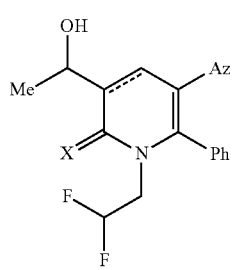
P-194
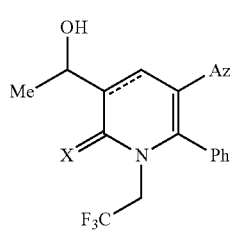
P-195
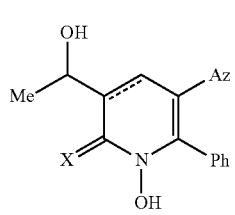
P-196
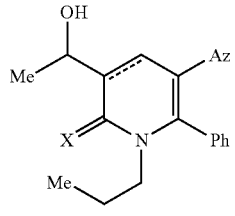
P-197
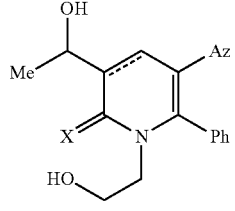

TABLE 1-continued
P-198
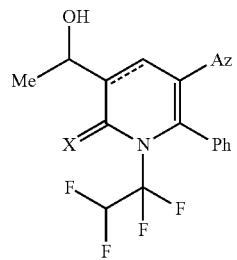
P-199
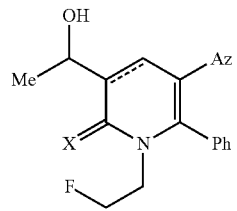
P-200
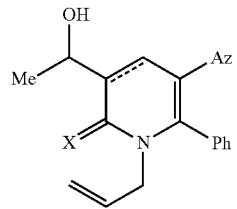
P-201
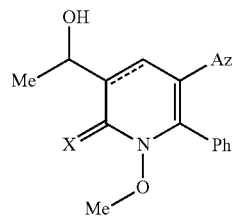
P-202
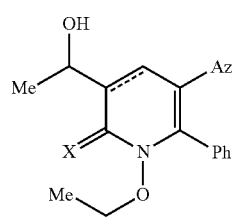
P-203
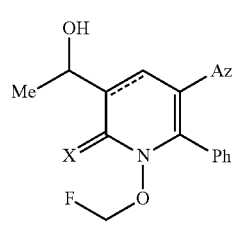
TABLE 1-continued
P-204
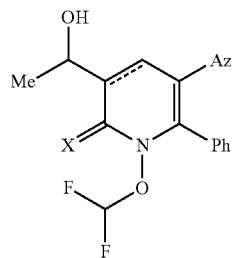
P-205
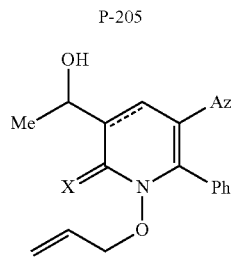
P-206
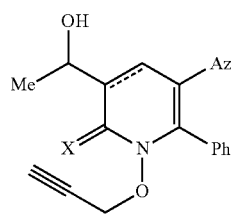
P-207
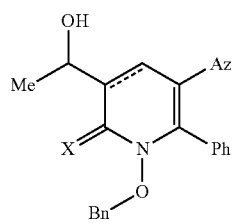
P-208
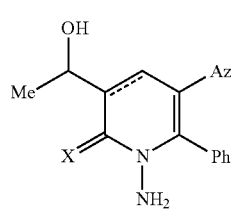
P-209
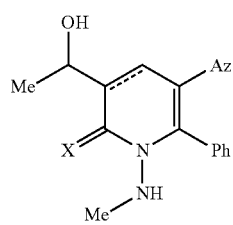

TABLE 1-continued
P-210
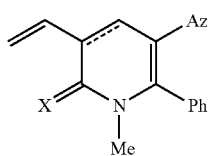
P-211
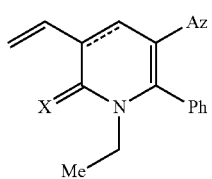
P-212
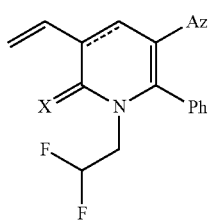
P-213
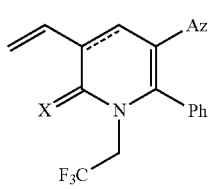
P-214
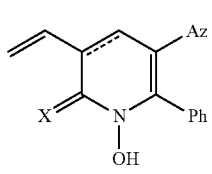
P-215
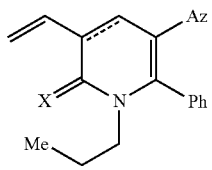
P-216
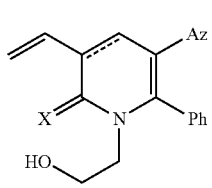
TABLE 1-continued
P-217
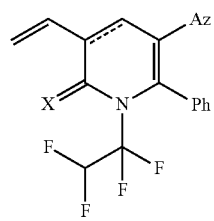
P-218
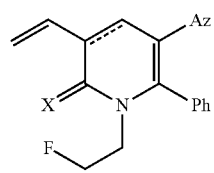
P-219
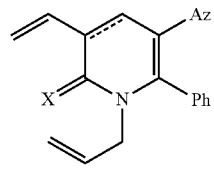
P-220
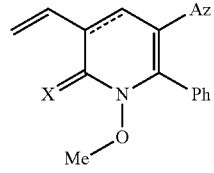
P-221
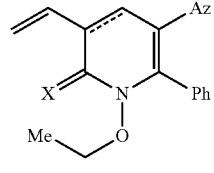
P-222
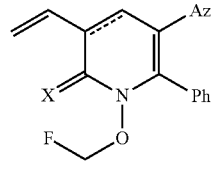
P-223
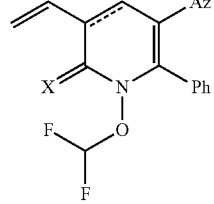

TABLE 1-continued
P-224
P-225
P-226
P-227
P-228
P-229
P-230
TABLE 1-continued
P-231 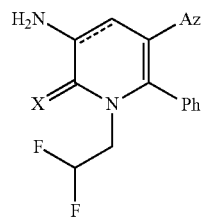
P-232 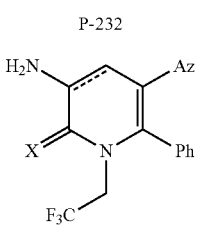
P-233 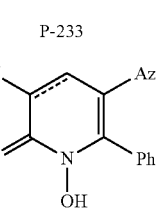
P-234 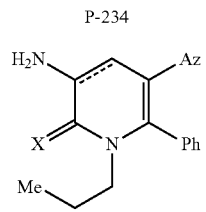
P-235 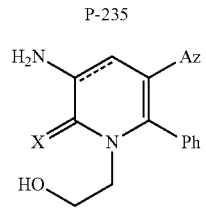
P-236 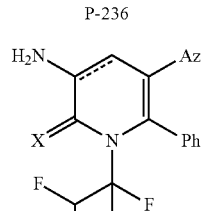
P-237 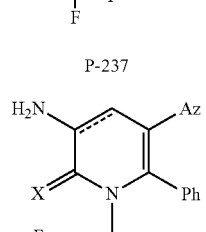

TABLE 1-continued
P-238
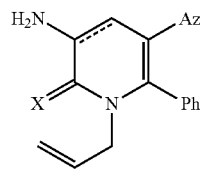
P-239
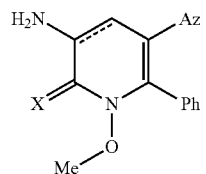
P-240
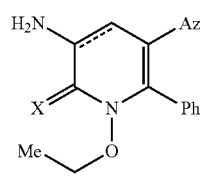
P-241
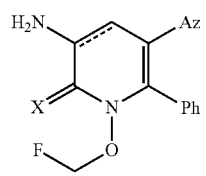
P-242
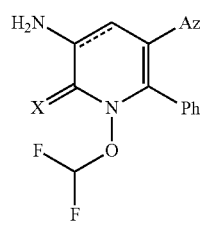
P-243
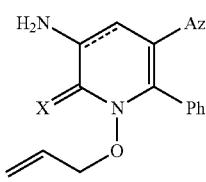
P-244
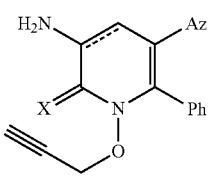
TABLE 1-continued
P-245
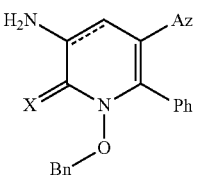
P-246
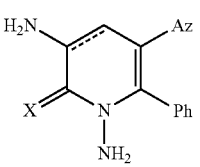
P-247
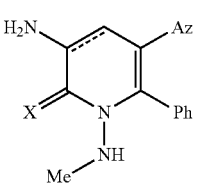
P-248
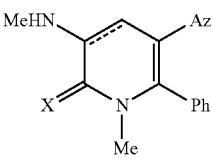
P-249
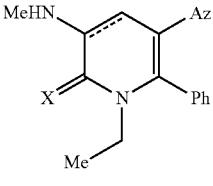
P-250
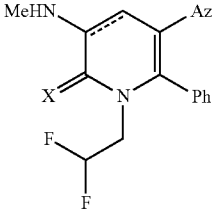
P-251
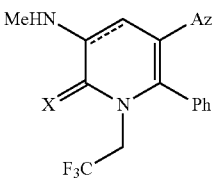

TABLE 1-continued
P-252
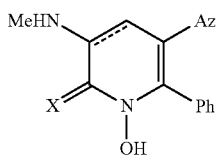
P-253
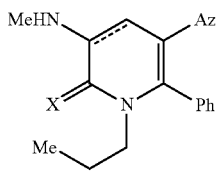
P-254
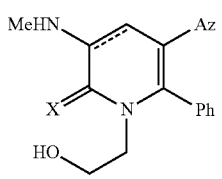
P-255
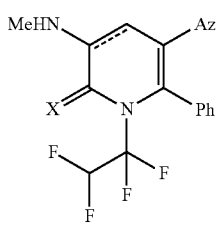
P-256
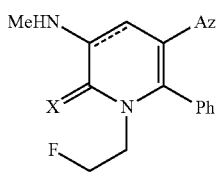
P-257
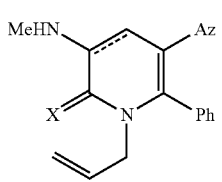
P-258
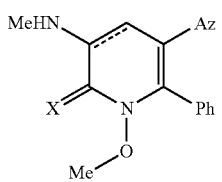
TABLE 1-continued
P-259
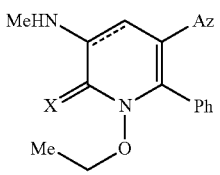
P-260
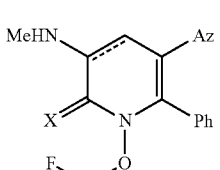
P-261
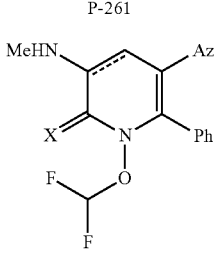
P-262
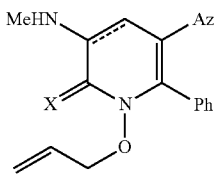
P-263
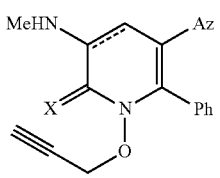
P-264
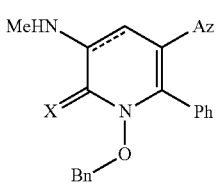
P-265
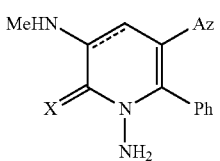

TABLE 1-continued
P-266
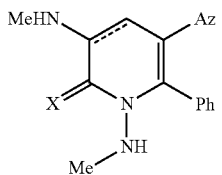
P-267
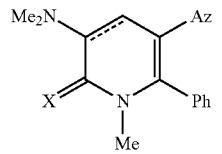
P-268
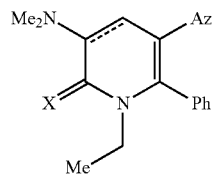
P-269
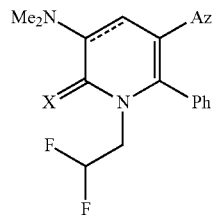
P-270
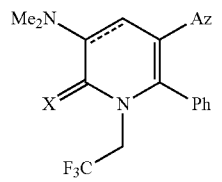
P-271
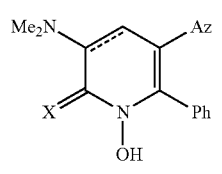
P-272
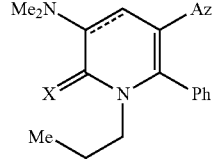
TABLE 1-continued
P-273
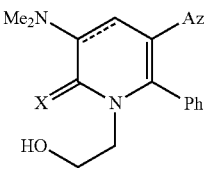
P-274
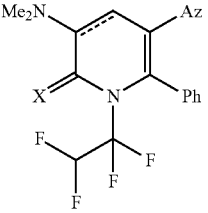
P-275
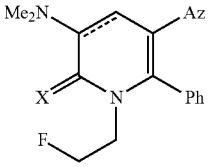
P-276
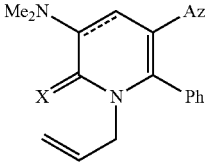
P-277
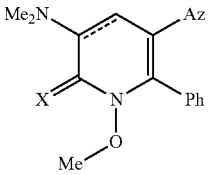
P-278
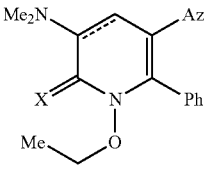
P-279
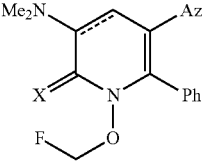

TABLE 1-continued

P-280, P-281, P-282, P-283, P-284, P-285, P-286, P-287, P-288, P-289, P-290, P-291, P-292, P-293

TABLE 1-continued
P-294
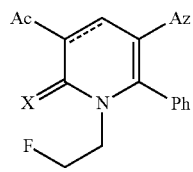
P-295
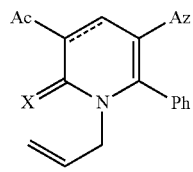
P-296
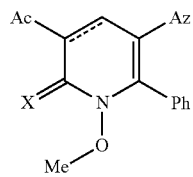
P-297
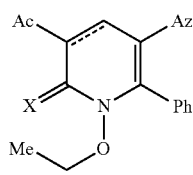
P-298
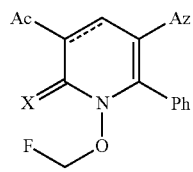
P-299
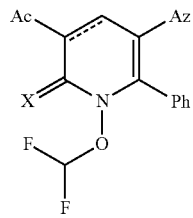
P-300
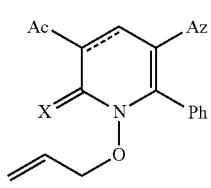
TABLE 1-continued
P-301
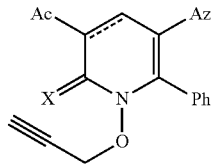
P-302
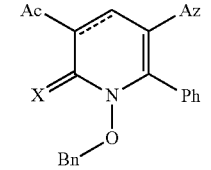
P-303
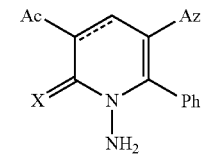
P-304
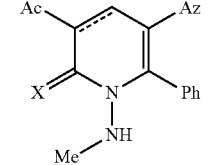
TABLE 2
| No. | R2 | R3 | R4 |
|---|---|---|---|
| Ph-001 | H | H | H |
| Ph-002 | H | F | H |
| Ph-003 | H | Cl | H |
| Ph-004 | H | Br | H |
| Ph-005 | H | I | H |
| Ph-006 | H | HO— | H |
| Ph-007 | H | N≡C— | H |
| Ph-008 | H | O2N— | H |
| Ph-009 | H | Me | H |
| Ph-010 | H | Et | H |
| Ph-011 | H | Pr | H |
| Ph-012 | H | iPr | H |
| Ph-013 | H | MeOCH2O— | H |
| Ph-014 | H | EtOCH2O— | H |
| Ph-015 | H | MeOCH2CH2O— | H |
| Ph-016 | H | EtOCH2CH2O— | H |
| Ph-017 | H | cPr | H |
| Ph-018 | H | cBu | H |
| Ph-019 | H | MeO— | H |
| Ph-020 | H | EtO— | H |
| Ph-021 | H | Pro— | H |
| Ph-022 | H | iPrO— | H |
| Ph-023 | H | F2CHO— | H |
| Ph-024 | H | F3CO— | H |
| Ph-025 | H | F2CHCH2O— | H |
| Ph-026 | H | F3CCH2O— | H |
| Ph-027 | H | HC≡CCH2O— | H |
| Ph-028 | H | MeC≡CCH2O— | H |
| Ph-029 | H | AcO— | H |
| Ph-030 | H | MeSO2O— | H |

TABLE 2-continued

| No. | R2 | R3 | R4 |
|---|---|---|---|
| Ph-031 | H | EtSO2O— | H |
| Ph-032 | H | H2N— | H |
| Ph-033 | H | MeNH— | H |
| Ph-034 | H | EtNH— | H |
| Ph-035 | H | Me2N— | H |
| Ph-036 | H | Et2N— | H |
| Ph-037 | H | Et(Me)N— | H |
| Ph-038 | H | pyrrolidin-1-yl | H |
| Ph-039 | H | piperidin-1-yl | H |
| Ph-040 | H | morpholino | H |
| Ph-041 | H | AcNH— | H |
| Ph-042 | H | Ac(Me)N— | H |
| Ph-043 | H | Ac(Et)N— | H |
| Ph-044 | H | H | F |
| Ph-045 | H | H | Cl |
| Ph-046 | H | H | Br |
| Ph-047 | H | H | I |
| Ph-048 | H | H | HO— |
| Ph-049 | H | H | N≡C— |
| Ph-050 | H | H | O2N— |
| Ph-051 | H | H | Me |
| Ph-052 | H | H | Et |
| Ph-053 | H | H | Pr |
| Ph-054 | H | H | iPr |
| Ph-055 | H | H | MeOCH2O— |
| Ph-056 | H | H | EtOCH2O— |
| Ph-057 | H | H | MeOCH2CH2O— |
| Ph-058 | H | H | EtOCH2CH2O— |
| Ph-059 | H | H | cPr |
| Ph-060 | H | H | cBu |
| Ph-061 | H | H | MeO— |
| Ph-062 | H | H | EtO— |
| Ph-063 | H | H | Pro— |
| Ph-064 | H | H | iPrO— |
| Ph-065 | H | H | F2CHO— |
| Ph-066 | H | H | F3CO— |
| Ph-067 | H | H | F2CHCH2O— |
| Ph-068 | H | H | F3CCH2O— |
| Ph-069 | H | H | HC≡CCH2O— |
| Ph-070 | H | H | MeC≡CCH2O— |
| Ph-071 | H | H | AcO— |
| Ph-072 | H | H | MeSO2O— |
| Ph-073 | H | H | EtSO2O— |
| Ph-074 | H | H | H2N— |
| Ph-075 | H | H | MeNH— |
| Ph-076 | H | H | EtNH— |
| Ph-077 | H | H | Me2N— |
| Ph-078 | H | H | Et2N— |
| Ph-079 | H | H | Et(Me)N— |
| Ph-080 | H | H | pyrrolidin-1-yl |
| Ph-081 | H | H | piperidin-1-yl |
| Ph-082 | H | H | morpholino |
| Ph-083 | H | H | AcNH— |
| Ph-084 | H | H | Ac(Me)N— |
| Ph-085 | H | H | Ac(Et)N— |
| Ph-086 | H | F | F |
| Ph-087 | H | Cl | Cl |
| Ph-088 | H | Br | Br |
| Ph-089 | H | I | I |
| Ph-090 | F | H | F |
| Ph-091 | Cl | H | Cl |
| Ph-092 | Br | H | Br |
| Ph-093 | I | H | I |
| Ph-094 | F | F | F |
| Ph-095 | Cl | Cl | Cl |
| Ph-096 | Br | Br | Br |
| Ph-097 | I | I | I |
| Ph-098 | H | HC≡C— | H |
| Ph-099 | H | H | HC≡C— |
| Ph-100 | H | Cl | F |
| Ph-101 | H | Br | F |
| Ph-102 | H | I | F |
| Ph-103 | H | HC≡C— | F |
| Ph-104 | H | Me | F |
| Ph-105 | H | Et | F |
| Ph-106 | H | F | Cl |
| Ph-107 | H | Br | Cl |
| Ph-108 | H | I | Cl |
| Ph-109 | H | HC≡C— | Cl |
| Ph-110 | H | Me | Cl |
| Ph-111 | H | Et | Cl |
| Ph-112 | H | F | Br |
| Ph-113 | H | Cl | Br |
| Ph-114 | H | I | Br |
| Ph-115 | H | HC≡C— | Br |
| Ph-116 | H | Me | Br |
| Ph-117 | H | Et | Br |
| Ph-118 | H | F | I |
| Ph-119 | H | Cl | I |
| Ph-120 | H | Br | I |
| Ph-121 | H | HC≡C— | I |
| Ph-122 | H | Me | I |
| Ph-123 | H | Et | I |
| Ph-124 | H | F | HC≡C— |
| Ph-125 | H | Cl | HC≡C— |
| Ph-126 | H | Br | HC≡C— |
| Ph-127 | H | I | HC≡C— |
| Ph-128 | H | Me | HC≡C— |
| Ph-129 | H | Et | HC≡C— |
| Ph-130 | H | F | Me |
| Ph-131 | H | Cl | Me |
| Ph-132 | H | Br | Me |
| Ph-133 | H | I | Me |
| Ph-134 | H | HC≡C— | Me |
| Ph-135 | H | Me | Me |
| Ph-136 | H | Et | Me |
| Ph-137 | H | F | Et |
| Ph-138 | H | Cl | Et |
| Ph-139 | H | Br | Et |
| Ph-140 | H | I | Et |
| Ph-141 | H | HC≡C— | Et |
| Ph-142 | H | Me | Et |
| Ph-143 | H | Et | Et |

TABLE 3

|  | R6 | R7 | Y | Z |
|---|---|---|---|---|
| AZ-0001 | H | H | H—C | N |
| AZ-0002 | O2N— | H | H—C | N |
| AZ-0003 | F | H | H—C | N |
| AZ-0004 | Cl | H | H—C | N |
| AZ-0005 | Br | H | H—C | N |
| AZ-0006 | I | H | H—C | N |
| AZ-0007 | Me | H | H—C | N |
| AZ-0008 | Et | H | H—C | N |
| AZ-0009 | Pr | H | H—C | N |
| AZ-0010 | iPr | H | H—C | N |
| AZ-0011 | Bu | H | H—C | N |
| AZ-0012 | secBu | H | H—C | N |
| AZ-0013 | iBu | H | H—C | N |

TABLE 3-continued

|  | R6 | R7 | Y | Z |
|---|---|---|---|---|
| AZ-0014 | tBu | H | H—C | N |
| AZ-0015 | HOCH2— | H | H—C | N |
| AZ-0016 | MeOCH2— | H | H—C | N |
| AZ-0017 | F2CH— | H | H—C | N |
| AZ-0018 | F3C— | H | H—C | N |
| AZ-0019 | Cl3C— | H | H—C | N |
| AZ-0020 | H2C=CH— | H | H—C | N |
| AZ-0021 | HC≡C— | H | H—C | N |
| AZ-0022 | MeC≡C— | H | H—C | N |
| AZ-0023 | MeO— | H | H—C | N |
| AZ-0024 | EtO— | H | H—C | N |
| AZ-0025 | HC(=O)— | H | H—C | N |
| AZ-0026 | H | O2N— | H—C | N |
| AZ-0027 | H | F | H—C | N |
| AZ-0028 | H | Cl | H—C | N |
| AZ-0029 | H | Br | H—C | N |
| AZ-0030 | H | — | H—C | N |
| AZ-0031 | H | Me | H—C | N |
| AZ-0032 | H | Et | H—C | N |
| AZ-0033 | H | Pr | H—C | N |
| AZ-0034 | H | iPr | H—C | N |
| AZ-0035 | H | Bu | H—C | N |
| AZ-0036 | H | secBu | H—C | N |
| AZ-0037 | H | iBu | H—C | N |
| AZ-0038 | H | tBu | H—C | N |
| AZ-0039 | H | HOCH2— | H—C | N |
| AZ-0040 | H | MeOCH2— | H—C | N |
| AZ-0041 | H | F2CH— | H—C | N |
| AZ-0042 | H | F3C— | H—C | N |
| AZ-0043 | H | Cl3C— | H—C | N |
| AZ-0044 | H | H2C=CH— | H—C | N |
| AZ-0045 | H | HC≡C— | H—C | N |
| AZ-0046 | H | MeC≡C— | H—C | N |
| AZ-0047 | H | MeO— | H—C | N |
| AZ-0048 | H | EtO— | H—C | N |
| AZ-0049 | H | HC(=O)— | H—C | N |
| AZ-0050 | H | H | O2N—C | N |
| AZ-0051 | H | H | F—C | N |
| AZ-0052 | H | H | Cl—C | N |
| AZ-0053 | H | H | Br—C | N |
| AZ-0054 | H | H | I—C | N |
| AZ-0055 | H | H | Me—C | N |
| AZ-0056 | H | H | Et—C | N |
| AZ-0057 | H | H | Pr—C | N |
| AZ-0058 | H | H | iPr—C | N |
| AZ-0059 | H | H | Bu—C | N |
| AZ-0060 | H | H | secBu—C | N |
| AZ-0061 | H | H | iBu—C | N |
| AZ-0062 | H | H | tBu—C | N |
| AZ-0063 | H | H | HOCH2—C | N |
| AZ-0064 | H | H | MeOCH2—C | N |
| AZ-0065 | H | H | F2CH—C | N |
| AZ-0066 | H | H | F3C—C | N |
| AZ-0067 | H | H | Cl3C—C | N |
| AZ-0068 | H | H | H2C=CH—C | N |
| AZ-0069 | H | H | HC≡C—C | N |
| AZ-0070 | H | H | MeC≡C—C | N |
| AZ-0071 | H | H | MeO—C | N |
| AZ-0072 | H | H | EtO—C | N |
| AZ-0073 | H | H | HC(=O)—C | N |
| AZ-0074 | F | O2N— | H—C | N |
| AZ-0075 | Cl | O2N— | H—C | N |
| AZ-0076 | Br | O2N— | H—C | N |
| AZ-0077 | I | O2N— | H—C | N |
| AZ-0078 | Me | O2N— | H—C | N |
| AZ-0079 | Et | O2N— | H—C | N |
| AZ-0080 | Pr | O2N— | H—C | N |
| AZ-0081 | iPr | O2N— | H—C | N |
| AZ-0082 | Bu | O2N— | H—C | N |
| AZ-0083 | secBu | O2N— | H—C | N |
| AZ-0084 | iBu | O2N— | H—C | N |
| AZ-0085 | tBL | O2N— | H—C | N |
| AZ-0086 | HOCH2— | O2N— | H—C | N |
| AZ-0087 | MeOCH2— | O2N— | H—C | N |
| AZ-0088 | F2CH— | O2N— | H—C | N |
| AZ-0089 | F3C— | O2N— | H—C | N |
| AZ-0090 | Cl3C— | O2N— | H—C | N |
| AZ-0091 | H2C=CH— | O2N— | H—C | N |

TABLE 3-continued

|  | R6 | R7 | Y | Z |
|---|---|---|---|---|
| AZ-0092 | HC≡C— | O2N— | H—C | N |
| AZ-0093 | MeC≡C— | O2N— | H—C | N |
| AZ-0094 | MeO— | O2N— | H—C | N |
| AZ-0095 | EtO— | O2N— | H—C | N |
| AZ-0096 | HC(=O)— | O2N— | H—C | N |
| AZ-0097 | F | F | H—C | N |
| AZ-0098 | Cl | F | H—C | N |
| AZ-0099 | Br | F | H—C | N |
| AZ-0100 | I | F | H—C | N |
| AZ-0101 | Me | F | H—C | N |
| AZ-0102 | Et | F | H—C | N |
| AZ-0103 | Pr | F | H—C | N |
| AZ-0104 | iPr | F | H—C | N |
| AZ-0105 | Bu | F | H—C | N |
| AZ-0106 | secBu | F | H—C | N |
| AZ-0107 | iBu | F | H—C | N |
| AZ-0108 | tBu | F | H—C | N |
| AZ-0109 | HOCH2— | F | H—C | N |
| AZ-0110 | MeOCH2— | F | H—C | N |
| AZ-0111 | F2CH— | F | H—C | N |
| AZ-0112 | F3C— | F | H—C | N |
| AZ-0113 | Cl3C— | F | H—C | N |
| AZ-0114 | H2C=CH— | F | H—C | N |
| AZ-0115 | HC≡C— | F | H—C | N |
| AZ-0116 | MeC≡C— | F | H—C | N |
| AZ-0117 | MeO— | F | H—C | N |
| AZ-0118 | EtO— | F | H—C | N |
| AZ-0119 | HC(=O)— | F | H—C | N |
| AZ-0120 | F | Cl | H—C | N |
| AZ-0121 | Cl | Cl | H—C | N |
| AZ-0122 | Br | Cl | H—C | N |
| AZ-0123 | I | Cl | H—C | N |
| AZ-0124 | Me | Cl | H—C | N |
| AZ-0125 | Et | Cl | H—C | N |
| AZ-0126 | Pr | Cl | H—C | N |
| AZ-0127 | iPr | Cl | H—C | N |
| AZ-0128 | Bu | Cl | H—C | N |
| AZ-0129 | secBu | Cl | H—C | N |
| AZ-0130 | iBu | Cl | H—C | N |
| AZ-0131 | tBu | Cl | H—C | N |
| AZ-0132 | HOCH2— | Cl | H—C | N |
| AZ-0133 | MeOCH2— | Cl | H—C | N |
| AZ-0134 | F2CH— | Cl | H—C | N |
| AZ-0135 | F3C— | Cl | H—C | N |
| AZ-0136 | Cl3C— | Cl | H—C | N |
| AZ-0137 | H2C=CH— | Cl | H—C | N |
| AZ-0138 | HC≡C— | Cl | H—C | N |
| AZ-0139 | MeC≡C— | Cl | H—C | N |
| AZ-0140 | MeO— | Cl | H—C | N |
| AZ-0141 | EtO— | Cl | H—C | N |
| AZ-0142 | HC(=O)— | Cl | H—C | N |
| AZ-0143 | F | Br | H—C | N |
| AZ-0144 | Cl | Br | H—C | N |
| AZ-0145 | Br | Br | H—C | N |
| AZ-0146 | I | Br | H—C | N |
| AZ-0147 | Me | Br | H—C | N |
| AZ-0148 | Et | Br | H—C | N |
| AZ-0149 | Pr | Br | H—C | N |
| AZ-0150 | iPr | Br | H—C | N |
| AZ-0151 | Bu | Br | H—C | N |
| AZ-0152 | secBu | Br | H—C | N |
| AZ-0153 | iBu | Br | H—C | N |
| AZ-0154 | tBu | Br | H—C | N |
| AZ-0155 | HOCH2— | Br | H—C | N |
| AZ-0156 | MeOCH2— | Br | H—C | N |
| AZ-0157 | F2CH— | Br | H—C | N |
| AZ-0158 | F3C— | Br | H—C | N |
| AZ-0159 | Cl3C— | Br | H—C | N |
| AZ-0160 | H2C=CH— | Br | H—C | N |
| AZ-0161 | HC≡C— | Br | H—C | N |
| AZ-0162 | MeC≡C— | Br | H—C | N |
| AZ-0163 | MeO— | Br | H—C | N |
| AZ-0164 | EtO— | Br | H—C | N |
| AZ-0165 | HC(=O)— | Br | H—C | N |
| AZ-0166 | F | I | H—C | N |
| AZ-0167 | Cl | I | H—C | N |
| AZ-0168 | Br | I | H—C | N |
| AZ-0169 | I | I | H—C | N |

TABLE 3-continued

|  | R6 | R7 | Y | Z |
|---|---|---|---|---|
| AZ-0170 | Me | I | H—C | N |
| AZ-0171 | Et | I | H—C | N |
| AZ-0172 | Pr | I | H—C | N |
| AZ-0173 | iPr | I | H—C | N |
| AZ-0174 | Bu | I | H—C | N |
| AZ-0175 | secBu | I | H—C | N |
| AZ-0176 | iBu | I | H—C | N |
| AZ-0177 | tBu | I | H—C | N |
| AZ-0178 | HOCH2— | I | H—C | N |
| AZ-0179 | MeOCH2— | I | H—C | N |
| AZ-0180 | F2CH— | I | H—C | N |
| AZ-0181 | F3C— | I | H—C | N |
| AZ-0182 | Cl3C— | I | H—C | N |
| AZ-0183 | H2C=CH— | I | H—C | N |
| AZ-0184 | HC≡C— | I | H—C | N |
| AZ-0185 | MeC≡C— | I | H—C | N |
| AZ-0186 | MeO— | I | H—C | N |
| AZ-0187 | EtO— | I | H—C | N |
| AZ-0188 | HC(=O)— | I | H—C | N |
| AZ-0189 | F | Me | H—C | N |
| AZ-0190 | Cl | Me | H—C | N |
| AZ-0191 | Br | Me | H—C | N |
| AZ-0192 | I | Me | H—C | N |
| AZ-0193 | Me | Me | H—C | N |
| AZ-0194 | Et | Me | H—C | N |
| AZ-0195 | Pr | Me | H—C | N |
| AZ-0196 | iPr | Me | H—C | N |
| AZ-0197 | Bu | Me | H—C | N |
| AZ-0198 | secBu | Me | H—C | N |
| AZ-0199 | iBu | Me | H—C | N |
| AZ-0200 | tBu | Me | H—C | N |
| AZ-0201 | HOCH2— | Me | H—C | N |
| AZ-0202 | MeOCH2— | Me | H—C | N |
| AZ-0203 | F2CH— | Me | H—C | N |
| AZ-0204 | F3C— | Me | H—C | N |
| AZ-0205 | Cl3C— | Me | H—C | N |
| AZ-0206 | H2C=CH— | Me | H—C | N |
| AZ-0207 | HC≡C— | Me | H—C | N |
| AZ-0208 | MeC≡C— | Me | H—C | N |
| AZ-0209 | MeO— | Me | H—C | N |
| AZ-0210 | EtO— | Me | H—C | N |
| AZ-0211 | HC(=O)— | Me | H—C | N |
| AZ-0212 | H | Me | F—C | N |
| AZ-0213 | H | Me | Cl—C | N |
| AZ-0214 | H | Me | Br—C | N |
| AZ-0215 | H | Me | I—C | N |
| AZ-0216 | H | Me | Me—C | N |
| AZ-0217 | H | Me | Et—C | N |
| AZ-0218 | H | Me | Pr—C | N |
| AZ-0219 | H | Me | iPr—C | N |
| AZ-0220 | H | Me | Bu—C | N |
| AZ-0221 | H | Me | secBu—C | N |
| AZ-0222 | H | Me | iBu—C | N |
| AZ-0223 | H | Me | tBu—C | N |
| AZ-0224 | H | Me | HOCH2—C | N |
| AZ-0225 | H | Me | MeOCH2—C | N |
| AZ-0226 | H | Me | F2CH—C | N |
| AZ-0227 | H | Me | F3C—C | N |
| AZ-0228 | H | Me | Cl3C—C | N |
| AZ-0229 | H | Me | H2C=CH—C | N |
| AZ-0230 | H | Me | HC≡C—C | N |
| AZ-0231 | H | Me | MeC≡C—C | N |
| AZ-0232 | H | Me | MeO—C | N |
| AZ-0233 | H | Me | EtO—C | N |
| AZ-0234 | H | Me | HC(=O)—C | N |
| AZ-0235 | F | HOCH2— | H—C | N |
| AZ-0236 | Cl | HOCH2— | H—C | N |
| AZ-0237 | Br | HOCH2— | H—C | N |
| AZ-0238 | I | HOCH2— | H—C | N |
| AZ-0239 | Me | HOCH2— | H—C | N |
| AZ-0240 | Et | HOCH2— | H—C | N |
| AZ-0241 | Pr | HOCH2— | H—C | N |
| AZ-0242 | iPr | HOCH2— | H—C | N |
| AZ-0243 | Bu | HOCH2— | H—C | N |
| AZ-0244 | secBu | HOCH2— | H—C | N |
| AZ-0245 | iBu | HOCH2— | H—C | N |
| AZ-0246 | tBu | HOCH2— | H—C | N |
| AZ-0247 | HOCH2— | HOCH2— | H—C | N |

TABLE 3-continued

|  | R6 | R7 | Y | Z |
|---|---|---|---|---|
| AZ-0248 | MeOCH2— | HOCH2— | H—C | N |
| AZ-0249 | F2CH— | HOCH2— | H—C | N |
| AZ-0250 | F3C— | HOCH2— | H—C | N |
| AZ-0251 | Cl3C— | HOCH2— | H—C | N |
| AZ-0252 | H2C=CH— | HOCH2— | H—C | N |
| AZ-0253 | HC≡C— | HOCH2— | H—C | N |
| AZ-0254 | MeC≡C— | HOCH2— | H—C | N |
| AZ-0255 | MeO— | HOCH2— | H—C | N |
| AZ-0256 | EtO— | HOCH2— | H—C | N |
| AZ-0257 | HC(=O)— | HOCH2— | H—C | N |
| AZ-0258 | F | MeOCH2— | H—C | N |
| AZ-0259 | Cl | MeOCH2— | H—C | N |
| AZ-0260 | Br | MeOCH2— | H—C | N |
| AZ-0261 | I | MeOCH2— | H—C | N |
| AZ-0262 | Me | MeOCH2— | H—C | N |
| AZ-0263 | Et | MeOCH2— | H—C | N |
| AZ-0264 | Pr | MeOCH2— | H—C | N |
| AZ-0265 | iPr | MeOCH2— | H—C | N |
| AZ-0266 | Bu | MeOCH2— | H—C | N |
| AZ-0267 | secBu | MeOCH2— | H—C | N |
| AZ-0268 | iBu | MeOCH2— | H—C | N |
| AZ-0269 | tBu | MeOCH2— | H—C | N |
| AZ-0270 | HOCH2— | MeOCH2— | H—C | N |
| AZ-0271 | MeOCH2— | MeOCH2— | H—C | N |
| AZ-0272 | F2CH— | MeOCH2— | H—C | N |
| AZ-0273 | F3C— | MeOCH2— | H—C | N |
| AZ-0274 | Cl3C— | MeOCH2— | H—C | N |
| AZ-0275 | H2C=CH— | MeOCH2— | H—C | N |
| AZ-0276 | HC≡C— | MeOCH2— | H—C | N |
| AZ-0277 | MeC≡C— | MeOCH2— | H—C | N |
| AZ-0278 | MeO— | MeOCH2— | H—C | N |
| AZ-0279 | EtO— | MeOCH2— | H—C | N |
| AZ-0280 | HC(=O)— | MeOCH2— | H—C | N |
| AZ-0281 | F | Et | H—C | N |
| AZ-0282 | Cl | Et | H—C | N |
| AZ-0283 | Br | Et | H—C | N |
| AZ-0284 | I | Et | H—C | N |
| AZ-0285 | Me | Et | H—C | N |
| AZ-0286 | Et | Et | H—C | N |
| AZ-0287 | Pr | Et | H—C | N |
| AZ-0288 | iPr | Et | H—C | N |
| AZ-0289 | Bu | Et | H—C | N |
| AZ-0290 | secBu | Et | H—C | N |
| AZ-0291 | iBu | Et | H—C | N |
| AZ-0292 | tBu | Et | H—C | N |
| AZ-0293 | HOCH2— | Et | H—C | N |
| AZ-0294 | MeOCH2— | Et | H—C | N |
| AZ-0295 | F2CH— | Et | H—C | N |
| AZ-0296 | F3C— | Et | H—C | N |
| AZ-0297 | Cl3C— | Et | H—C | N |
| AZ-0298 | H2C=CH— | Et | H—C | N |
| AZ-0299 | HC≡C— | Et | H—C | N |
| AZ-0300 | MeC≡C— | Et | H—C | N |
| AZ-0301 | MeO— | Et | H—C | N |
| AZ-0302 | EtO— | Et | H—C | N |
| AZ-0303 | HC(=O)— | Et | H—C | N |
| AZ-0304 | H | Et | F—C | N |
| AZ-0305 | H | Et | Cl—C | N |
| AZ-0306 | H | Et | Br—C | N |
| AZ-0307 | H | Et | I—C | N |
| AZ-0308 | H | Et | Me—C | N |
| AZ-0309 | H | Et | Et—C | N |
| AZ-0310 | H | Et | Pr—C | N |
| AZ-0311 | H | Et | iPr—C | N |
| AZ-0312 | H | Et | Bu—C | N |
| AZ-0313 | H | Et | secBu—C | N |
| AZ-0314 | H | Et | iBu—C | N |
| AZ-0315 | H | Et | tBu—C | N |
| AZ-0316 | H | Et | HOCH2—C | N |
| AZ-0317 | H | Et | MeOCH2—C | N |
| AZ-0318 | H | Et | F2CH—C | N |
| AZ-0319 | H | Et | F3C—C | N |
| AZ-0320 | H | Et | Cl3C—C | N |
| AZ-0321 | H | Et | H2C=CH—C | N |
| AZ-0322 | H | Et | HC≡C—C | N |
| AZ-0323 | H | Et | MeC≡C—C | N |
| AZ-0324 | H | Et | MeO—C | N |
| AZ-0325 | H | Et | EtO—C | N |

TABLE 3-continued

|  | R6 | R7 | Y | Z |
|---|---|---|---|---|
| AZ-0326 | H | Et | HC(=O)—C | N |
| AZ-0327 | F | F2CH— | H—C | N |
| AZ-0328 | Cl | F2CH— | H—C | N |
| AZ-0329 | Br | F2CH— | H—C | N |
| AZ-0330 | I | F2CH— | H—C | N |
| AZ-0331 | Me | F2CH— | H—C | N |
| AZ-0332 | Et | F2CH— | H—C | N |
| AZ-0333 | Pr | F2CH— | H—C | N |
| AZ-0334 | iPr | F2CH— | H—C | N |
| AZ-0335 | Bu | F2CH— | H—C | N |
| AZ-0336 | secBu | F2CH— | H—C | N |
| AZ-0337 | iBu | F2CH— | H—C | N |
| AZ-0338 | tBu | F2CH— | H—C | N |
| AZ-0339 | HOCH2— | F2CH— | H—C | N |
| AZ-0340 | MeOCH2— | F2CH— | H—C | N |
| AZ-0341 | F2CH— | F2CH— | H—C | N |
| AZ-0342 | F3C— | F2CH— | H—C | N |
| AZ-0343 | Cl3C— | F2CH— | H—C | N |
| AZ-0344 | H2C=CH— | F2CH— | H—C | N |
| AZ-0345 | HC≡C— | F2CH— | H—C | N |
| AZ-0346 | MeC≡C— | F2CH— | H—C | N |
| AZ-0347 | MeO— | F2CH— | H—C | N |
| AZ-0348 | EtO— | F2CH— | H—C | N |
| AZ-0349 | HC(=O)— | F2CH— | H—C | N |
| AZ-0350 | F | F3C— | H—C | N |
| AZ-0351 | Cl | F3C— | H—C | N |
| AZ-0352 | Br | F3C— | H—C | N |
| AZ-0353 | I | F3C— | H—C | N |
| AZ-0354 | Me | F3C— | H—C | N |
| AZ-0355 | Et | F3C— | H—C | N |
| AZ-0356 | Pr | F3C— | H—C | N |
| AZ-0357 | iPr | F3C— | H—C | N |
| AZ-0358 | Bu | F3C— | H—C | N |
| AZ-0359 | secBu | F3C— | H—C | N |
| AZ-0360 | iBu | F3C— | H—C | N |
| AZ-0361 | tBu | F3C— | H—C | N |
| AZ-0362 | HOCH2— | F3C— | H—C | N |
| AZ-0363 | MeOCH2— | F3C— | H—C | N |
| AZ-0364 | F2CH— | F3C— | H—C | N |
| AZ-0365 | F3C— | F3C— | H—C | N |
| AZ-0366 | Cl3C— | F3C— | H—C | N |
| AZ-0367 | H2C=CH— | F3C— | H—C | N |
| AZ-0368 | HC≡C— | F3C— | H—C | N |
| AZ-0369 | MeC≡C— | F3C— | H—C | N |
| AZ-0370 | MeO— | F3C— | H—C | N |
| AZ-0371 | EtO— | F3C— | H—C | N |
| AZ-0372 | HC(=O)— | F3C— | H—C | N |
| AZ-0373 | F | H2C=CH— | H—C | N |
| AZ-0374 | Cl | H2C=CH— | H—C | N |
| AZ-0375 | Br | H2C=CH— | H—C | N |
| AZ-0376 | I | H2C=CH— | H—C | N |
| AZ-0377 | Me | H2C=CH— | H—C | N |
| AZ-0378 | Et | H2C=CH— | H—C | N |
| AZ-0379 | Pr | H2C=CH— | H—C | N |
| AZ-0380 | iPr | H2C=CH— | H—C | N |
| AZ-0381 | Bu | H2C=CH— | H—C | N |
| AZ-0382 | secBu | H2C=CH— | H—C | N |
| AZ-0383 | iBu | H2C=CH— | H—C | N |
| AZ-0384 | tBu | H2C=CH— | H—C | N |
| AZ-0385 | HOCH2— | H2C=CH— | H—C | N |
| AZ-0386 | MeOCH2— | H2C=CH— | H—C | N |
| AZ-0387 | F2CH— | H2C=CH— | H—C | N |
| AZ-0388 | F3C— | H2C=CH— | H—C | N |
| AZ-0389 | Cl3C— | H2C=CH— | H—C | N |
| AZ-0390 | H2C=CH— | H2C=CH— | H—C | N |
| AZ-0391 | HC≡C— | H2C=CH— | H—C | N |
| AZ-0392 | MeC≡C— | H2C=CH— | H—C | N |
| AZ-0393 | MeO— | H2C=CH— | H—C | N |
| AZ-0394 | EtO— | H2C=CH— | H—C | N |
| AZ-0395 | HC(=O)— | H2C=CH— | H—C | N |
| AZ-0396 | F | HC≡C— | H—C | N |
| AZ-0397 | Cl | HC≡C— | H—C | N |
| AZ-0398 | Br | HC≡C— | H—C | N |
| AZ-0399 | I | HC≡C— | H—C | N |
| AZ-0400 | Me | HC≡C— | H—C | N |
| AZ-0401 | Et | HC≡C— | H—C | N |
| AZ-0402 | Pr | HC≡C— | H—C | N |
| AZ-0403 | iPr | HC≡C— | H—C | N |

TABLE 3-continued

|  | R6 | R7 | Y | Z |
|---|---|---|---|---|
| AZ-0404 | Bu | HC≡C— | H—C | N |
| AZ-0405 | secBu | HC≡C— | H—C | N |
| AZ-0406 | iBu | HC≡C— | H—C | N |
| AZ-0407 | tBu | HC≡C— | H—C | N |
| AZ-0408 | HOCH2— | HC≡C— | H—C | N |
| AZ-0409 | MeOCH2— | HC≡C— | H—C | N |
| AZ-0410 | F2CH— | HC≡C— | H—C | N |
| AZ-0411 | F3C— | HC≡C— | H—C | N |
| AZ-0412 | Cl3C— | HC≡C— | H—C | N |
| AZ-0413 | H2C=CH— | HC≡C— | H—C | N |
| AZ-0414 | HC≡C— | HC≡C— | H—C | N |
| AZ-0415 | MeC≡C— | HC≡C— | H—C | N |
| AZ-0416 | MeO— | HC≡C— | H—C | N |
| AZ-0417 | EtO— | HC≡C— | H—C | N |
| AZ-0418 | HC(=O)— | HC≡C— | H—C | N |
| AZ-0419 | F | MeC≡C— | H—C | N |
| AZ-0420 | Cl | MeC≡C— | H—C | N |
| AZ-0421 | Br | MeC≡C— | H—C | N |
| AZ-0422 | I | MeC≡C— | H—C | N |
| AZ-0423 | Me | MeC≡C— | H—C | N |
| AZ-0424 | Et | MeC≡C— | H—C | N |
| AZ-0425 | Pr | MeC≡C— | H—C | N |
| AZ-0426 | iPr | MeC≡C— | H—C | N |
| AZ-0427 | Bu | MeC≡C— | H—C | N |
| AZ-0428 | secBu | MeC≡C— | H—C | N |
| AZ-0429 | iBu | MeC≡C— | H—C | N |
| AZ-0430 | tBu | MeC≡C— | H—C | N |
| AZ-0431 | HOCH2— | MeC≡C— | H—C | N |
| AZ-0432 | MeOCH2— | MeC≡C— | H—C | N |
| AZ-0433 | F2CH— | MeC≡C— | H—C | N |
| AZ-0434 | F3C— | MeC≡C— | H—C | N |
| AZ-0435 | Cl3C— | MeC≡C— | H—C | N |
| AZ-0436 | H2C=CH— | MeC≡C— | H—C | N |
| AZ-0437 | HC≡C— | MeC≡C— | H—C | N |
| AZ-0438 | MeC≡C— | MeC≡C— | H—C | N |
| AZ-0439 | MeO— | MeC≡C— | H—C | N |
| AZ-0440 | EtO— | MeC≡C— | H—C | N |
| AZ-0441 | HC(=O)— | MeC≡C— | H—C | N |
| AZ-0442 | F | HC(=O)— | H—C | N |
| AZ-0443 | Cl | HC(=O)— | H—C | N |
| AZ-0444 | Br | HC(=O)— | H—C | N |
| AZ-0445 | I | HC(=O)— | H—C | N |
| AZ-0446 | Me | HC(=O)— | H—C | N |
| AZ-0447 | Et | HC(=O)— | H—C | N |
| AZ-0448 | Pr | HC(=O)— | H—C | N |
| AZ-0449 | iPr | HC(=O)— | H—C | N |
| AZ-0450 | Bu | HC(=O)— | H—C | N |
| AZ-0451 | secBu | HC(=O)— | H—C | N |
| AZ-0452 | iBu | HC(=O)— | H—C | N |
| AZ-0453 | tBu | HC(=O)— | H—C | N |
| AZ-0454 | HOCH2— | HC(=O)— | H—C | N |
| AZ-0455 | MeOCH2— | HC(=O)— | H—C | N |
| AZ-0456 | F2CH— | HC(=O)— | H—C | N |
| AZ-0457 | F3C— | HC(=O)— | H—C | N |
| AZ-0458 | Cl3C— | HC(=O)— | H—C | N |
| AZ-0459 | H2C=CH— | HC(=O)— | H—C | N |
| AZ-0460 | HC≡C— | HC(=O)— | H—C | N |
| AZ-0461 | MeC≡C— | HC(=O)— | H—C | N |
| AZ-0462 | MeO— | HC(=O)— | H—C | N |
| AZ-0463 | EtO— | HC(=O)— | H—C | N |
| AZ-0464 | HC(=O)— | HC(=O)— | H—C | N |
| AZ-0465 | F | H2N— | H—C | N |
| AZ-0466 | Cl | H2N— | H—C | N |
| AZ-0467 | Br | H2N— | H—C | N |
| AZ-0468 | I | H2N— | H—C | N |
| AZ-0469 | Me | H2N— | H—C | N |
| AZ-0470 | Et | H2N— | H—C | N |
| AZ-0471 | Pr | H2N— | H—C | N |
| AZ-0472 | iPr | H2N— | H—C | N |
| AZ-0473 | Bu | H2N— | H—C | N |
| AZ-0474 | secBu | H2N— | H—C | N |
| AZ-0475 | iBu | H2N— | H—C | N |
| AZ-0476 | tBu | H2N— | H—C | N |
| AZ-0477 | HOCH2— | H2N— | H—C | N |
| AZ-0478 | MeOCH2— | H2N— | H—C | N |
| AZ-0479 | F2CH— | H2N— | H—C | N |
| AZ-0480 | F3C— | H2N— | H—C | N |
| AZ-0481 | Cl3C— | H2N— | H—C | N |

TABLE 3-continued

|  | R6 | R7 | Y | Z |
|---|---|---|---|---|
| AZ-0482 | H2C=CH— | H2N— | H—C | N |
| AZ-0483 | HC≡C— | H2N— | H—C | N |
| AZ-0484 | MeC≡C— | H2N— | H—C | N |
| AZ-0485 | MeO— | H2N— | H—C | N |
| AZ-0486 | EtO— | H2N— | H—C | N |
| AZ-0487 | HC(=O)— | H2N— | H—C | N |
| AZ-0488 | Me | H | Me—C | N |
| AZ-0489 | Me | F | Me—C | N |
| AZ-0490 | Me | Cl | Me—C | N |
| AZ-0491 | Me | Br | Me—C | N |
| AZ-0492 | Me | I | Me—C | N |
| AZ-0493 | Me | Me | Me—C | N |
| AZ-0494 | Me | Et | Me—C | N |
| AZ-0495 | Me | Pr | Me—C | N |
| AZ-0496 | Me | iPr | Me—C | N |
| AZ-0497 | Me | Bu | Me—C | N |
| AZ-0498 | Me | secBu | Me—C | N |
| AZ-0499 | Me | iBu | Me—C | N |
| AZ-0500 | Me | tBu | Me—C | N |
| AZ-0501 | Me | HOCH2— | Me—C | N |
| AZ-0502 | Me | MeOCH2— | Me—C | N |
| AZ-0503 | Me | F2CH— | Me—C | N |
| AZ-0504 | Me | F3C— | Me—C | N |
| AZ-0505 | Me | Cl3C— | Me—C | N |
| AZ-0506 | Me | H2C=CH— | Me—C | N |
| AZ-0507 | Me | HC≡C— | Me—C | N |
| AZ-0508 | Me | MeC≡C— | Me—C | N |
| AZ-0509 | Me | MeO— | Me—C | N |
| AZ-0510 | Me | EtO— | Me—C | N |
| AZ-0511 | Me | O2N— | Me—C | N |
| AZ-0512 | Me | HC(=O)— | Me—C | N |
| AZ-0513 | F3C— | H | F3C—C | N |
| AZ-0514 | F3C— | F | F3C—C | N |
| AZ-0515 | F3C— | Cl | F3C—C | N |
| AZ-0516 | F3C— | Br | F3C—C | N |
| AZ-0517 | F3C— | I | F3C—C | N |
| AZ-0518 | F3C— | Me | F3C—C | N |
| AZ-0519 | F3C— | Et | F3C—C | N |
| AZ-0520 | F3C— | Pr | F3C—C | N |
| AZ-0521 | F3C— | iPr | F3C—C | N |
| AZ-0522 | F3C— | Bu | F3C—C | N |
| AZ-0523 | F3C— | secBu | F3C—C | N |
| AZ-0524 | F3C— | iBu | F3C—C | N |
| AZ-0525 | F3C— | tBu | F3C—C | N |
| AZ-0526 | F3C— | HOCH2— | F3C—C | N |
| AZ-0527 | F3C— | MeOCH2— | F3C—C | N |
| AZ-0528 | F3C— | F2CH— | F3C—C | N |
| AZ-0529 | F3C— | F3C— | F3C—C | N |
| AZ-0530 | F3C— | Cl3C— | F3C—C | N |
| AZ-0531 | F3C— | H2C=CH— | F3C—C | N |
| AZ-0532 | F3C— | HC≡C— | F3C—C | N |
| AZ-0533 | F3C— | MeC≡C— | F3C—C | N |
| AZ-0534 | F3C— | MeO— | F3C—C | N |
| AZ-0535 | F3C— | EtO— | F3C—C | N |
| AZ-0536 | F3C— | O2N— | F3C—C | N |
| AZ-0537 | F3C— | HC(=O)— | F3C—C | N |
| AZ-0538 | F2CH— | H | F2CH—C | N |
| AZ-0539 | F2CH— | F | F2CH—C | N |
| AZ-0540 | F2CH— | Cl | F2CH—C | N |
| AZ-0541 | F2CH— | Br | F2CH—C | N |
| AZ-0542 | F2CH— | I | F2CH—C | N |
| AZ-0543 | F2CH— | Me | F2CH—C | N |
| AZ-0544 | F2CH— | Et | F2CH—C | N |
| AZ-0545 | F2CH— | Pr | F2CH—C | N |
| AZ-0546 | F2CH— | iPr | F2CH—C | N |
| AZ-0547 | F2CH— | Bu | F2CH—C | N |
| AZ-0548 | F2CH— | secBu | F2CH—C | N |
| AZ-0549 | F2CH— | iBu | F2CH—C | N |
| AZ-0550 | F2CH— | tBu | F2CH—C | N |
| AZ-0551 | F2CH— | HOCH2— | F2CH—C | N |
| AZ-0552 | F2CH— | MeOCH2— | F2CH—C | N |
| AZ-0553 | F2CH— | F2CH— | F2CH—C | N |
| AZ-0554 | F2CH— | F3C— | F2CH—C | N |
| AZ-0555 | F2CH— | Cl3C— | F2CH—C | N |
| AZ-0556 | F2CH— | H2C=CH— | F2CH—C | N |
| AZ-0557 | F2CH— | HC≡C— | F2CH—C | N |
| AZ-0558 | F2CH— | MeC≡C— | F2CH—C | N |
| AZ-0559 | F2CH— | MeO— | F2CH—C | N |

TABLE 3-continued

|  | R6 | R7 | Y | Z |
|---|---|---|---|---|
| AZ-0560 | F2CH— | EtO— | F2CH—C | N |
| AZ-0561 | F2CH— | O2N— | F2CH—C | N |
| AZ-0562 | F2CH— | HC(=O)— | F2CH—C | N |
| AZ-0563 | H | H | N | H—C |
| AZ-0564 | F | H | N | H—C |
| AZ-0565 | Cl | H | N | H—C |
| AZ-0566 | Br | H | N | H—C |
| AZ-0567 | I | H | N | H—C |
| AZ-0568 | Me | H | N | H—C |
| AZ-0569 | Et | H | N | H—C |
| AZ-0570 | Pr | H | N | H—C |
| AZ-0571 | iPr | H | N | H—C |
| AZ-0572 | Bu | H | N | H—C |
| AZ-0573 | secBu | H | N | H—C |
| AZ-0574 | iBu | H | N | H—C |
| AZ-0575 | tBu | H | N | H—C |
| AZ-0576 | HOCH2— | H | N | H—C |
| AZ-0577 | MeOCH2— | H | N | H—C |
| AZ-0578 | F2CH— | H | N | H—C |
| AZ-0579 | F3C— | H | N | H—C |
| AZ-0580 | Cl3C— | H | N | H—C |
| AZ-0581 | H2C=CH— | H | N | H—C |
| AZ-0582 | HC≡C— | H | N | H—C |
| AZ-0583 | MeC≡C— | H | N | H—C |
| AZ-0584 | MeO— | H | N | H—C |
| AZ-0585 | EtO— | H | N | H—C |
| AZ-0586 | O2N— | H | N | H—C |
| AZ-0587 | HC(=O)— | H | N | H—C |
| AZ-0588 | H | F | N | H—C |
| AZ-0589 | H | Cl | N | H—C |
| AZ-0590 | H | Br | N | H—C |
| AZ-0591 | H | E | N | H—C |
| AZ-0592 | H | Me | N | H—C |
| AZ-0593 | H | Et | N | H—C |
| AZ-0594 | H | Pr | N | H—C |
| AZ-0595 | H | iPr | N | H—C |
| AZ-0596 | H | Bu | N | H—C |
| AZ-0597 | H | secBu | N | H—C |
| AZ-0598 | H | iBu | N | H—C |
| AZ-0599 | H | tBu | N | H—C |
| AZ-0600 | H | HOCH2— | N | H—C |
| AZ-0601 | H | MeOCH2— | N | H—C |
| AZ-0602 | H | F2CH— | N | H—C |
| AZ-0603 | H | F3C— | N | H—C |
| AZ-0604 | H | Cl3C— | N | H—C |
| AZ-0605 | H | H2C=CH— | N | H—C |
| AZ-0606 | H | HC≡C— | N | H—C |
| AZ-0607 | H | MeC≡C— | N | H—C |
| AZ-0608 | H | MeO— | N | H—C |
| AZ-0609 | H | EtO— | N | H—C |
| AZ-0610 | H | O2N— | N | H—C |
| AZ-0611 | H | HC(=O)— | N | H—C |
| AZ-0612 | H | H | N | F—C |
| AZ-0613 | H | H | N | Cl—C |
| AZ-0614 | H | H | N | Br—C |
| AZ-0615 | H | H | N | I—C |
| AZ-0616 | H | H | N | Me—C |
| AZ-0617 | H | H | N | Et—C |
| AZ-0618 | H | H | N | Pr—C |
| AZ-0619 | H | H | N | iPr—C |
| AZ-0620 | H | H | N | Bu—C |
| AZ-0621 | H | H | N | secBu—C |
| AZ-0622 | H | H | N | iBu—C |
| AZ-0623 | H | H | N | tBu—C |
| AZ-0624 | H | H | N | HOCH2—C |
| AZ-0625 | H | H | N | MeOCH2—C |
| AZ-0626 | H | H | N | F2CH—C |
| AZ-0627 | H | H | N | F3C—C |
| AZ-0628 | H | H | N | Cl3C—C |
| AZ-0629 | H | H | N | H2C=CH—C |
| AZ-0630 | H | H | N | HC≡C—C |
| AZ-0631 | H | H | N | MeC≡C—C |
| AZ-0632 | H | H | N | MeO—C |
| AZ-0633 | H | H | N | EtO—C |
| AZ-0634 | H | H | N | O2N—C |
| AZ-0635 | H | H | N | HC(=O)—C |
| AZ-0636 | F | F | N | H—C |
| AZ-0637 | Cl | Cl | N | H—C |

TABLE 3-continued

|  | R6 | R7 | Y | Z |
|---|---|---|---|---|
| AZ-0638 | Br | Br | N | H—C |
| AZ-0639 | I | I | N | H—C |
| AZ-0640 | Me | Me | N | H—C |
| AZ-0641 | F | F | N | F—C |
| AZ-0642 | Cl | Cl | N | Cl—C |
| AZ-0643 | Me | Me | N | Me—C |
| AZ-0644 | H | H | H—C | H—C |
| AZ-0645 | F | H | H—C | H—C |
| AZ-0646 | Cl | H | H—C | H—C |
| AZ-0647 | Br | H | H—C | H—C |
| AZ-0648 | I | H | H—C | H—C |
| AZ-0649 | Me | H | H—C | H—C |
| AZ-0650 | F | H | H—C | F—C |
| AZ-0651 | Cl | H | H—C | Cl—C |
| AZ-0652 | Br | H | H—C | Br—C |
| AZ-0653 | I | H | H—C | I—C |
| AZ-0654 | Me | H | H—C | Me—C |
| AZ-0655 | H | H | N | N |
| AZ-0656 | F | H | N | N |
| AZ-0657 | Cl | H | N | N |
| AZ-0658 | Br | H | N | N |
| AZ-0659 | I | H | N | N |
| AZ-0660 | Me | H | N | N |
| AZ-0661 | F | F | N | N |
| AZ-0662 | Cl | Cl | N | N |
| AZ-0663 | Me | Me | N | N |
| AZ-0664 | —(CH2)2— |  | H—C | H—C |
| AZ-0665 | —(CH2)3— |  | H—C | H—C |
| AZ-0666 | —(CH2)4— |  | H—C | H—C |
| AZ-0667 | —(CH2)5— |  | H—C | H—C |
| AZ-0668 | —(CH2)6— |  | H—C | H—C |
| AZ-0669 | —(CH2)2— |  | H—C | N |
| AZ-0670 | —(CH2)3— |  | H—C | N |
| AZ-0671 | —(CH2)4— |  | H—C | N |
| AZ-0672 | —(CH2)5— |  | H—C | N |
| AZ-0673 | —(CH2)6— |  | H—C | N |
| AZ-0674 | —(CH2)2— |  | N | H—C |
| AZ-0675 | —(CH2)3— |  | N | H—C |
| AZ-0676 | —(CH2)4— |  | N | H—C |
| AZ-0677 | —(CH2)5— |  | N | H—C |
| AZ-0678 | —(CH2)6— |  | N | H—C |
| AZ-0679 | —(CH2)2— |  | N | N |
| AZ-0680 | —(CH2)3— |  | N | N |
| AZ-0681 | —(CH2)4— |  | N | N |
| AZ-0682 | —(CH2)5— |  | N | N |
| AZ-0683 | —(CH2)6— |  | N | N |
| AZ-0684 | Me | H | Et—C | N |
| AZ-0685 | Et | H | Et—C | N |
| AZ-0686 | MeCH(OH)— | H | H—C | N |
| AZ-0687 | EtCH(OH)— | H | H—C | N |
| AZ-0688 | Me2C(OH)— | H | H—C | N |
| AZ-0689 | F3CCF2— | H | H—C | N |
| AZ-0690 | F2CHCF2— | H | H—C | N |
| AZ-0691 | ClCF2— | H | H—C | N |
| AZ-0692 | MeCF2— | H | H—C | N |
| AZ-0693 | BrCF2— | H | H—C | N |
| AZ-0694 | BrCH2— | H | H—C | N |
| AZ-0695 | Br2CH— | H | H—C | N |
| AZ-0696 | cPr | H | H—C | N |
| AZ-0697 | HC≡CCH2— | H | H—C | N |
| AZ-0698 | HC≡CCH(OH)— | H | H—C | N |
| AZ-0699 | Ac | H | H—C | N |
| AZ-0700 | MeOC(=O)— | H | H—C | N |
| AZ-0701 | EtOC(=O)— | H | H—C | N |
| AZ-0702 | MeS— | H | H—C | N |
| AZ-0703 | MeS(O)— | H | H—C | N |
| AZ-0704 | MeSO2— | H | H—C | N |
| AZ-0705 | H2N— | H | H—C | N |
| AZ-0706 | H | MeCH(OH)— | H—C | N |
| AZ-0707 | H | EtCH(OH)— | H—C | N |
| AZ-0708 | H | Me2C(OH)— | H—C | N |
| AZ-0709 | H | F3CCF2— | H—C | N |
| AZ-0710 | H | F2CHCF2— | H—C | N |
| AZ-0711 | H | ClCF2— | H—C | N |
| AZ-0712 | H | MeCF2— | H—C | N |
| AZ-0713 | H | BrCF2— | H—C | N |
| AZ-0714 | H | BrCH2— | H—C | N |
| AZ-0715 | H | Br2CH— | H—C | N |

TABLE 3-continued

|  | R6 | R7 | Y | Z |
|---|---|---|---|---|
| AZ-0716 | H | cPr | H—C | N |
| AZ-0717 | H | HC≡CCH2— | H—C | N |
| AZ-0718 | H | HC≡CCH(OH)— | H—C | N |
| AZ-0719 | H | Ac | H—C | N |
| AZ-0720 | H | MeOC(=O)— | H—C | N |
| AZ-0721 | H | EtOC(=O)— | H—C | N |
| AZ-0722 | H | MeS— | H—C | N |
| AZ-0723 | H | MeS(O)— | H—C | N |
| AZ-0724 | H | MeSO2— | H—C | N |
| AZ-0725 | H | H2N— | H—C | N |
| AZ-0726 | H | H | MeCH(OH)—C | N |
| AZ-0727 | H | H | EtCH(OH)—C | N |
| AZ-0728 | H | H | Me2C(OH)—C | N |
| AZ-0729 | H | H | F3CCF2—C | N |
| AZ-0730 | H | H | F2CHCF2—C | N |
| AZ-0731 | H | H | ClCF2—C | N |
| AZ-0732 | H | H | MeCF2—C | N |
| AZ-0733 | H | H | BrCF2—C | N |
| AZ-0734 | H | H | BrCH2—C | N |
| AZ-0735 | H | H | Br2CH—C | N |
| AZ-0736 | H | H | cPr—C | N |
| AZ-0737 | H | H | HC≡CCH2—C | N |
| AZ-0738 | H | H | HC≡CCH(OH)—C | N |
| AZ-0739 | H | H | Ac—C | N |
| AZ-0740 | H | H | MeOC(=O)—C | N |
| AZ-0741 | H | H | EtOC(=O)—C | N |
| AZ-0742 | H | H | MeS—C | N |
| AZ-0743 | H | H | MeS(O)—C | N |
| AZ-0744 | H | H | MeSO2—C | N |
| AZ-0745 | H | H | H2N—C | N |
| AZ-0746 | MeCH(OH)— | O2N— | H—C | N |
| AZ-0747 | EtCH(OH)— | O2N— | H—C | N |
| AZ-0748 | Me2C(OH)— | O2N— | H—C | N |
| AZ-0749 | F3CCF2— | O2N— | H—C | N |
| AZ-0750 | F2CHCF2— | O2N— | H—C | N |
| AZ-0751 | ClCF2— | O2N— | H—C | N |
| AZ-0752 | MeCF2— | O2N— | H—C | N |
| AZ-0753 | BrCF2— | O2N— | H—C | N |
| AZ-0754 | BrCH2— | O2N— | H—C | N |
| AZ-0755 | ClCH2— | O2N— | H—C | N |
| AZ-0756 | Br2CH— | O2N— | H—C | N |
| AZ-0757 | cPr | O2N— | H—C | N |
| AZ-0758 | HC≡CCH2— | O2N— | H—C | N |
| AZ-0759 | HC≡CCH(OH)— | O2N— | H—C | N |
| AZ-0760 | Ac | O2N— | H—C | N |
| AZ-0761 | MeOC(=O)— | O2N— | H—C | N |
| AZ-0762 | EtOC(=O)— | O2N— | H—C | N |
| AZ-0763 | MeS— | O2N— | H—C | N |
| AZ-0764 | MeS(O)— | O2N— | H—C | N |
| AZ-0765 | MeSO2— | O2N— | H—C | N |
| AZ-0766 | H2N— | O2N— | H—C | N |
| AZ-0767 | MeCH(OH)— | F | H—C | N |
| AZ-0768 | EtCH(OH)— | F | H—C | N |
| AZ-0769 | Me2C(OH)— | F | H—C | N |
| AZ-0770 | F3CCF2— | F | H—C | N |
| AZ-0771 | F2CHCF2— | F | H—C | N |
| AZ-0772 | ClCF2— | F | H—C | N |
| AZ-0773 | MeCF2— | F | H—C | N |
| AZ-0774 | BrCF2— | F | H—C | N |
| AZ-0775 | BrCH2— | F | H—C | N |
| AZ-0776 | ClCH2— | F | H—C | N |
| AZ-0777 | Br2CH— | F | H—C | N |
| AZ-0778 | cPr | F | H—C | N |
| AZ-0779 | HC≡CCH2— | F | H—C | N |
| AZ-0780 | HC≡CCH(OH)— | F | H—C | N |
| AZ-0781 | Ac | F | H—C | N |
| AZ-0782 | MeOC(=O)— | F | H—C | N |
| AZ-0783 | EtOC(=O)— | F | H—C | N |
| AZ-0784 | MeS— | F | H—C | N |
| AZ-0785 | MeS(O)— | F | H—C | N |
| AZ-0786 | MeSO2— | F | H—C | N |
| AZ-0787 | H2N— | F | H—C | N |
| AZ-0788 | MeCH(OH)— | Cl | H—C | N |
| AZ-0789 | EtCH(OH)— | Cl | H—C | N |
| AZ-0790 | Me2C(OH)— | Cl | H—C | N |
| AZ-0791 | F3CCF2— | Cl | H—C | N |
| AZ-0792 | F2CHCF2— | Cl | H—C | N |
| AZ-0793 | ClCF2— | Cl | H—C | N |

TABLE 3-continued

|  | R6 | R7 | Y | Z |
|---|---|---|---|---|
| AZ-0794 | MeCF2— | Cl | H—C | N |
| AZ-0795 | BrCF2— | Cl | H—C | N |
| AZ-0796 | BrCH2— | Cl | H—C | N |
| AZ-0797 | ClCH2— | Cl | H—C | N |
| AZ-0798 | Br2CH— | Cl | H—C | N |
| AZ-0799 | cPr | Cl | H—C | N |
| AZ-0800 | HC≡CCH2— | Cl | H—C | N |
| AZ-0801 | HC≡CCH(OH)— | Cl | H—C | N |
| AZ-0802 | Ac | Cl | H—C | N |
| AZ-0803 | MeOC(=O)— | Cl | H—C | N |
| AZ-0804 | EtOC(=O)— | Cl | H—C | N |
| AZ-0805 | MeS— | Cl | H—C | N |
| AZ-0806 | MeS(O)— | Cl | H—C | N |
| AZ-0807 | MeSO2— | Cl | H—C | N |
| AZ-0808 | H2N— | Cl | H—C | N |
| AZ-0809 | MeCH(OH)— | Br | H—C | N |
| AZ-0810 | EtCH(OH)— | Br | H—C | N |
| AZ-0811 | Me2C(OH)— | Br | H—C | N |
| AZ-0812 | F3CCF2— | Br | H—C | N |
| AZ-0813 | F2CHCF2— | Br | H—C | N |
| AZ-0814 | ClCF2— | Br | H—C | N |
| AZ-0815 | MeCF2— | Br | H—C | N |
| AZ-0816 | BrCF2— | Br | H—C | N |
| AZ-0817 | BrCH2— | Br | H—C | N |
| AZ-0818 | ClCH2— | Br | H—C | N |
| AZ-0819 | Br2CH— | Br | H—C | N |
| AZ-0820 | cPr | Br | H—C | N |
| AZ-0821 | HC≡CCH2— | Br | H—C | N |
| AZ-0822 | HC≡CCH(OH)— | Br | H—C | N |
| AZ-0823 | Ac | Br | H—C | N |
| AZ-0824 | MeOC(=O)— | Br | H—C | N |
| AZ-0825 | EtOC(=O)— | Br | H—C | N |
| AZ-0826 | MeS— | Br | H—C | N |
| AZ-0827 | MeS(O)— | Br | H—C | N |
| AZ-0828 | MeSO2— | Br | H—C | N |
| AZ-0829 | H2N— | Br | H—C | N |
| AZ-0830 | MeCH(OH)— | I | H—C | N |
| AZ-0831 | EtCH(OH)— | I | H—C | N |
| AZ-0832 | Me2C(OH)— | I | H—C | N |
| AZ-0833 | F3CCF2— | I | H—C | N |
| AZ-0834 | F2CHCF2— | I | H—C | N |
| AZ-0835 | ClCF2— | I | H—C | N |
| AZ-0836 | MeCF2— | I | H—C | N |
| AZ-0837 | BrCF2— | I | H—C | N |
| AZ-0838 | BrCH2— | I | H—C | N |
| AZ-0839 | ClCH2— | I | H—C | N |
| AZ-0840 | Br2CH— | I | H—C | N |
| AZ-0841 | cPr | I | H—C | N |
| AZ-0842 | HC≡CCH2— | I | H—C | N |
| AZ-0843 | HC≡CCH(OH)— | I | H—C | N |
| AZ-0844 | Ac | I | H—C | N |
| AZ-0845 | MeOC(=O)— | I | H—C | N |
| AZ-0846 | EtOC(=O)— | I | H—C | N |
| AZ-0847 | MeS— | I | H—C | N |
| AZ-0848 | MeS(O)— | I | H—C | N |
| AZ-0849 | MeSO2— | I | H—C | N |
| AZ-0850 | H2N— | I | H—C | N |
| AZ-0851 | MeCH(OH)— | Me | H—C | N |
| AZ-0852 | EtCH(OH)— | Me | H—C | N |
| AZ-0853 | Me2C(OH)— | Me | H—C | N |
| AZ-0854 | F3CCF2— | Me | H—C | N |
| AZ-0855 | F2CHCF2— | Me | H—C | N |
| AZ-0856 | ClCF2— | Me | H—C | N |
| AZ-0857 | MeCF2— | Me | H—C | N |
| AZ-0858 | BrCF2— | Me | H—C | N |
| AZ-0859 | BrCH2— | Me | H—C | N |
| AZ-0860 | ClCH2— | Me | H—C | N |
| AZ-0861 | Br2CH— | Me | H—C | N |
| AZ-0862 | cPr | Me | H—C | N |
| AZ-0863 | HC≡CCH2— | Me | H—C | N |
| AZ-0864 | HC≡CCH(OH)— | Me | H—C | N |
| AZ-0865 | Ac | Me | H—C | N |
| AZ-0866 | MeOC(=O)— | Me | H—C | N |
| AZ-0867 | EtOC(=O)— | Me | H—C | N |
| AZ-0868 | MeS— | Me | H—C | N |
| AZ-0869 | MeS(O)— | Me | H—C | N |
| AZ-0870 | MeSO2— | Me | H—C | N |
| AZ-0871 | H2N— | Me | H—C | N |

TABLE 3-continued

|  | R6 | R7 | Y | Z |
|---|---|---|---|---|
| AZ-0872 | H | Me | MeCH(OH)—C | N |
| AZ-0873 | H | Me | EtCH(OH)—C | N |
| AZ-0874 | H | Me | Me2C(OH)—C | N |
| AZ-0875 | H | Me | F3CCF2—C | N |
| AZ-0876 | H | Me | F2CHCF2—C | N |
| AZ-0877 | H | Me | ClCF2—C | N |
| AZ-0878 | H | Me | MeCF2—C | N |
| AZ-0879 | H | Me | BrCF2—C | N |
| AZ-0880 | H | Me | BrCH2—C | N |
| AZ-0881 | H | Me | ClCH2—C | N |
| AZ-0882 | H | Me | Br2CH—C | N |
| AZ-0883 | H | Me | cPr—C | N |
| AZ-0884 | H | Me | HC≡CCH2—C | N |
| AZ-0885 | H | Me | HC≡CCH(OH)—C | N |
| AZ-0886 | H | Me | Ac—C | N |
| AZ-0887 | H | Me | MeOC(=O)—C | N |
| AZ-0888 | H | Me | EtOC(=O)—C | N |
| AZ-0889 | H | Me | MeS—C | N |
| AZ-0890 | H | Me | MeS(O)—C | N |
| AZ-0891 | H | Me | MeSO2—C | N |
| AZ-0892 | H | Me | H2N—C | N |
| AZ-0893 | MeCH(OH)— | HOCH2— | H—C | N |
| AZ-0894 | EtCH(OH)— | HOCH2— | H—C | N |
| AZ-0895 | Me2C(OH)— | HOCH2— | H—C | N |
| AZ-0896 | F3CCF2— | HOCH2— | H—C | N |
| AZ-0897 | F2CHCF2— | HOCH2— | H—C | N |
| AZ-0898 | ClCF2— | HOCH2— | H—C | N |
| AZ-0899 | MeCF2— | HOCH2— | H—C | N |
| AZ-0900 | BrCF2— | HOCH2— | H—C | N |
| AZ-0901 | BrCH2— | HOCH2— | H—C | N |
| AZ-0902 | ClCH2— | HOCH2— | H—C | N |
| AZ-0903 | Br2CH— | HOCH2— | H—C | N |
| AZ-0904 | cPr | HOCH2— | H—C | N |
| AZ-0905 | HC≡CCH2— | HOCH2— | H—C | N |
| AZ-0906 | HC≡CCH(OH)— | HOCH2— | H—C | N |
| AZ-0907 | Ac | HOCH2— | H—C | N |
| AZ-0908 | MeOC(=O)— | HOCH2— | H—C | N |
| AZ-0909 | EtOC(=O)— | HOCH2— | H—C | N |
| AZ-0910 | MeS— | HOCH2— | H—C | N |
| AZ-0911 | MeS(O)— | HOCH2— | H—C | N |
| AZ-0912 | MeSO2— | HOCH2— | H—C | N |
| AZ-0913 | H2N— | HOCH2— | H—C | N |
| AZ-0914 | MeCH(OH)— | MeOCH2— | H—C | N |
| AZ-0915 | EtCH(OH)— | MeOCH2— | H—C | N |
| AZ-0916 | Me2C(OH)— | MeOCH2— | H—C | N |
| AZ-0917 | F3CCF2— | MeOCH2— | H—C | N |
| AZ-0918 | F2CHCF2— | MeOCH2— | H—C | N |
| AZ-0919 | ClCF2— | MeOCH2— | H—C | N |
| AZ-0920 | MeCF2— | MeOCH2— | H—C | N |
| AZ-0921 | BrCF2— | MeOCH2— | H—C | N |
| AZ-0922 | BrCH2— | MeOCH2— | H—C | N |
| AZ-0923 | ClCH2— | MeOCH2— | H—C | N |
| AZ-0924 | Br2CH— | MeOCH2— | H—C | N |
| AZ-0925 | cPr | MeOCH2— | H—C | N |
| AZ-0926 | HC≡CCH2— | MeOCH2— | H—C | N |
| AZ-0927 | HC≡CCH(OH)— | MeOCH2— | H—C | N |
| AZ-0928 | Ac | MeOCH2— | H—C | N |
| AZ-0929 | MeOC(=O)— | MeOCH2— | H—C | N |
| AZ-0930 | EtOC(=O)— | MeOCH2— | H—C | N |
| AZ-0931 | MeS— | MeOCH2— | H—C | N |
| AZ-0932 | MeS(O)— | MeOCH2— | H—C | N |
| AZ-0933 | MeSO2— | MeOCH2— | H—C | N |
| AZ-0934 | H2N— | MeOCH2— | H—C | N |
| AZ-0935 | MeCH(OH)— | Et | H—C | N |
| AZ-0936 | EtCH(OH)— | Et | H—C | N |
| AZ-0937 | Me2C(OH)— | Et | H—C | N |
| AZ-0938 | F3CCF2— | Et | H—C | N |
| AZ-0939 | F2CHCF2— | Et | H—C | N |
| AZ-0940 | ClCF2— | Et | H—C | N |
| AZ-0941 | MeCF2— | Et | H—C | N |
| AZ-0942 | BrCF2— | Et | H—C | N |
| AZ-0943 | BrCH2— | Et | H—C | N |
| AZ-0944 | ClCH2— | Et | H—C | N |
| AZ-0945 | Br2CH— | Et | H—C | N |
| AZ-0946 | cPr | Et | H—C | N |
| AZ-0947 | HC≡CCH2— | Et | H—C | N |
| AZ-0948 | HC≡CCH(OH)— | Et | H—C | N |
| AZ-0949 | Ac | Et | H—C | N |

TABLE 3-continued

|  | R6 | R7 | Y | Z |
|---|---|---|---|---|
| AZ-0950 | MeOC(=O)— | Et | H—C | N |
| AZ-0951 | EtOC(=O)— | Et | H—C | N |
| AZ-0952 | MeS— | Et | H—C | N |
| AZ-0953 | MeS(O)— | Et | H—C | N |
| AZ-0954 | MeSO2— | Et | H—C | N |
| AZ-0955 | H2N— | Et | H—C | N |
| AZ-0956 | H | Et | MeCH(OH)—C | N |
| AZ-0957 | H | Et | EtCH(OH)—C | N |
| AZ-0958 | H | Et | Me2C(OH)—C | N |
| AZ-0959 | H | Et | F3CCF2—C | N |
| AZ-0960 | H | Et | F2CHCF2—C | N |
| AZ-0961 | H | Et | ClCF2—C | N |
| AZ-0962 | H | Et | MeCF2—C | N |
| AZ-0963 | H | Et | BrCF2—C | N |
| AZ-0964 | H | Et | BrCH2—C | N |
| AZ-0965 | H | Et | ClCH2—C | N |
| AZ-0966 | H | Et | Br2CH—C | N |
| AZ-0967 | H | Et | cPr—C | N |
| AZ-0968 | H | Et | HC≡CCH2—C | N |
| AZ-0969 | H | Et | HC≡CCH(OH)—C | N |
| AZ-0970 | H | Et | Ac—C | N |
| AZ-0971 | H | Et | MeOC(=O)—C | N |
| AZ-0972 | H | Et | EtOC(=O)—C | N |
| AZ-0973 | H | Et | MeS—C | N |
| AZ-0974 | H | Et | MeS(O)—C | N |
| AZ-0975 | H | Et | MeSO2—C | N |
| AZ-0976 | H | Et | H2N—C | N |
| AZ-0977 | MeCH(OH)— | F2CH— | H—C | N |
| AZ-0978 | EtCH(OH)— | F2CH— | H—C | N |
| AZ-0979 | Me2C(OH)— | F2CH— | H—C | N |
| AZ-0980 | F3CCF2— | F2CH— | H—C | N |
| AZ-0981 | F2CHCF2— | F2CH— | H—C | N |
| AZ-0982 | ClCF2— | F2CH— | H—C | N |
| AZ-0983 | MeCF2— | F2CH— | H—C | N |
| AZ-0984 | BrCF2— | F2CH— | H—C | N |
| AZ-0985 | BrCH2— | F2CH— | H—C | N |
| AZ-0986 | ClCH2— | F2CH— | H—C | N |
| AZ-0987 | Br2CH— | F2CH— | H—C | N |
| AZ-0988 | cPr | F2CH— | H—C | N |
| AZ-0989 | HC≡CCH2— | F2CH— | H—C | N |
| AZ-0990 | HC≡CCH(OH)— | F2CH— | H—C | N |
| AZ-0991 | Ac | F2CH— | H—C | N |
| AZ-0992 | MeOC(=O)— | F2CH— | H—C | N |
| AZ-0993 | EtOC(=O)— | F2CH— | H—C | N |
| AZ-0994 | MeS— | F2CH— | H—C | N |
| AZ-0995 | MeS(O)— | F2CH— | H—C | N |
| AZ-0996 | MeSO2— | F2CH— | H—C | N |
| AZ-0997 | H2N— | F2CH— | H—C | N |
| AZ-0998 | MeCH(OH)— | F3C— | H—C | N |
| AZ-0999 | EtCH(OH)— | F3C— | H—C | N |
| AZ-1000 | Me2C(OH)— | F3C— | H—C | N |
| AZ-1001 | F3CCF2— | F3C— | H—C | N |
| AZ-1002 | F2CHCF2— | F3C— | H—C | N |
| AZ-1003 | ClCF2— | F3C— | H—C | N |
| AZ-1004 | MeCF2— | F3C— | H—C | N |
| AZ-1005 | BrCF2— | F3C— | H—C | N |
| AZ-1006 | BrCH2— | F3C— | H—C | N |
| AZ-1007 | ClCH2— | F3C— | H—C | N |
| AZ-1008 | Br2CH— | F3C— | H—C | N |
| AZ-1009 | cPr | F3C— | H—C | N |
| AZ-1010 | HC≡CCH2— | F3C— | H—C | N |
| AZ-1011 | HC≡CCH(OH)— | F3C— | H—C | N |
| AZ-1012 | Ac | F3C— | H—C | N |
| AZ-1013 | MeOC(=O)— | F3C— | H—C | N |
| AZ-1014 | EtOC(=O)— | F3C— | H—C | N |
| AZ-1015 | MeS— | F3C— | H—C | N |
| AZ-1016 | MeS(O)— | F3C— | H—C | N |
| AZ-1017 | MeSO2— | F3C— | H—C | N |
| AZ-1018 | H2N— | F3C— | H—C | N |
| AZ-1019 | MeCH(OH)— | H2C=CH— | H—C | N |
| AZ-1020 | EtCH(OH)— | H2C=CH— | H—C | N |
| AZ-1021 | Me2C(OH)— | H2C=CH— | H—C | N |
| AZ-1022 | F3CCF2— | H2C=CH— | H—C | N |
| AZ-1023 | F2CHCF2— | H2C=CH— | H—C | N |
| AZ-1024 | ClCF2— | H2C=CH— | H—C | N |
| AZ-1025 | MeCF2— | H2C=CH— | H—C | N |
| AZ-1026 | BrCF2— | H2C=CH— | H—C | N |
| AZ-1027 | BrCH2— | H2C=CH— | H—C | N |

TABLE 3-continued

|  | R6 | R7 | Y | Z |
|---|---|---|---|---|
| AZ-1028 | ClCH2— | H2C=CH— | H—C | N |
| AZ-1029 | Br2CH— | H2C=CH— | H—C | N |
| AZ-1030 | cPr | H2C=CH— | H—C | N |
| AZ-1031 | HC≡CCH2— | H2C=CH— | H—C | N |
| AZ-1032 | HC≡CCH(OH)— | H2C=CH— | H—C | N |
| AZ-1033 | Ac | H2C=CH— | H—C | N |
| AZ-1034 | MeOC(=O)— | H2C=CH— | H—C | N |
| AZ-1035 | EtOC(=O)— | H2C=CH— | H—C | N |
| AZ-1036 | MeS— | H2C=CH— | H—C | N |
| AZ-1037 | MeS(O)— | H2C=CH— | H—C | N |
| AZ-1038 | MeSO2— | H2C=CH— | H—C | N |
| AZ-1039 | H2N— | H2C=CH— | H—C | N |
| AZ-1040 | MeCH(OH)— | HC≡C— | H—C | N |
| AZ-1041 | EtCH(OH)— | HC≡C— | H—C | N |
| AZ-1042 | Me2C(OH)— | HC≡C— | H—C | N |
| AZ-1043 | F3CCF2— | HC≡C— | H—C | N |
| AZ-1044 | F2CHCF2— | HC≡C— | H—C | N |
| AZ-1045 | ClCF2— | HC≡C— | H—C | N |
| AZ-1046 | MeCF2— | HC≡C— | H—C | N |
| AZ-1047 | BrCF2— | HC≡C— | H—C | N |
| AZ-1048 | BrCH2— | HC≡C— | H—C | N |
| AZ-1049 | ClCH2— | HC≡C— | H—C | N |
| AZ-1050 | Br2CH— | HC≡C— | H—C | N |
| AZ-1051 | cPr | HC≡C— | H—C | N |
| AZ-1052 | HC≡CCH2— | HC≡C— | H—C | N |
| AZ-1053 | HC≡CCH(OH)— | HC≡C— | H—C | N |
| AZ-1054 | Ac | HC≡C— | H—C | N |
| AZ-1055 | MeOC(=O)— | HC≡C— | H—C | N |
| AZ-1056 | EtOC(=O)— | HC≡C— | H—C | N |
| AZ-1057 | MeS— | HC≡C— | H—C | N |
| AZ-1058 | MeS(O)— | HC≡C— | H—C | N |
| AZ-1059 | MeSO2— | HC≡C— | H—C | N |
| AZ-1060 | H2N— | HC≡C— | H—C | N |
| AZ-1061 | MeCH(OH)— | MeC≡C— | H—C | N |
| AZ-1062 | EtCH(OH)— | MeC≡C— | H—C | N |
| AZ-1063 | Me2C(OH)— | MeC≡C— | H—C | N |
| AZ-1064 | F3CCF2— | MeC≡C— | H—C | N |
| AZ-1065 | F2CHCF2— | MeC≡C— | H—C | N |
| AZ-1066 | ClCF2— | MeC≡C— | H—C | N |
| AZ-1067 | MeCF2— | MeC≡C— | H—C | N |
| AZ-1068 | BrCF2— | MeC≡C— | H—C | N |
| AZ-1069 | BrCH2— | MeC≡C— | H—C | N |
| AZ-1070 | ClCH2— | MeC≡C— | H—C | N |
| AZ-1071 | Br2CH— | MeC≡C— | H—C | N |
| AZ-1072 | cPr | MeC≡C— | H—C | N |
| AZ-1073 | HC≡CCH2— | MeC≡C— | H—C | N |
| AZ-1074 | HC≡CCH(OH)— | MeC≡C— | H—C | N |
| AZ-1075 | Ac | MeC≡C— | H—C | N |
| AZ-1076 | MeOC(=O)— | MeC≡C— | H—C | N |
| AZ-1077 | EtOC(=O)— | MeC≡C— | H—C | N |
| AZ-1078 | MeS— | MeC≡C— | H—C | N |
| AZ-1079 | MeS(O)— | MeC≡C— | H—C | N |
| AZ-1080 | MeSO2— | MeC≡C— | H—C | N |
| AZ-1081 | H2N— | MeC≡C— | H—C | N |
| AZ-1082 | MeCH(OH)— | HC(=O)— | H—C | N |
| AZ-1083 | EtCH(OH)— | HC(=O)— | H—C | N |
| AZ-1084 | Me2C(OH)— | HC(=O)— | H—C | N |
| AZ-1085 | F3CCF2— | HC(=O)— | H—C | N |
| AZ-1086 | F2CHCF2— | HC(=O)— | H—C | N |
| AZ-1087 | ClCF2— | HC(=O)— | H—C | N |
| AZ-1088 | MeCF2— | HC(=O)— | H—C | N |
| AZ-1089 | BrCF2— | HC(=O)— | H—C | N |
| AZ-1090 | BrCH2— | HC(=O)— | H—C | N |
| AZ-1091 | ClCH2— | HC(=O)— | H—C | N |
| AZ-1092 | Br2CH— | HC(=O)— | H—C | N |
| AZ-1093 | cPr | HC(=O)— | H—C | N |
| AZ-1094 | HC≡CCH2— | HC(=O)— | H—C | N |
| AZ-1095 | HC≡CCH(OH)— | HC(=O)— | H—C | N |
| AZ-1096 | Ac | HC(=O)— | H—C | N |
| AZ-1097 | MeOC(=O)— | HC(=O)— | H—C | N |
| AZ-1098 | EtOC(=O)— | HC(=O)— | H—C | N |
| AZ-1099 | MeS— | HC(=O)— | H—C | N |
| AZ-1100 | MeS(O)— | HC(=O)— | H—C | N |
| AZ-1101 | MeSO2— | HC(=O)— | H—C | N |
| AZ-1102 | H2N— | HC(=O)— | H—C | N |
| AZ-1103 | MeCH(OH)— | H2N— | H—C | N |
| AZ-1104 | EtCH(OH)— | H2N— | H—C | N |
| AZ-1105 | Me2C(OH)— | H2N— | H—C | N |

TABLE 3-continued

|  | R6 | R7 | Y | Z |
|---|---|---|---|---|
| AZ-1106 | F3CCF2— | H2N— | H—C | N |
| AZ-1107 | F2CHCF2— | H2N— | H—C | N |
| AZ-1108 | ClCF2— | H2N— | H—C | N |
| AZ-1109 | MeCF2— | H2N— | H—C | N |
| AZ-1110 | BrCF2— | H2N— | H—C | N |
| AZ-1111 | BrCH2— | H2N— | H—C | N |
| AZ-1112 | ClCH2— | H2N— | H—C | N |
| AZ-1113 | Br2CH— | H2N— | H—C | N |
| AZ-1114 | cPr | H2N— | H—C | N |
| AZ-1115 | HC≡CCH2— | H2N— | H—C | N |
| AZ-1116 | HC≡CCH(OH)— | H2N— | H—C | N |
| AZ-1117 | Ac | H2N— | H—C | N |
| AZ-1118 | MeOC(=O)— | H2N— | H—C | N |
| AZ-1119 | EtOC(=O)— | H2N— | H—C | N |
| AZ-1120 | MeS— | H2N— | H—C | N |
| AZ-1121 | MeS(O)— | H2N— | H—C | N |
| AZ-1122 | MeSO2— | H2N— | H—C | N |
| AZ-1123 | H2N— | H2N— | H—C | N |
| AZ-1124 | O2N— | MeCH(OH)— | H—C | N |
| AZ-1125 | F | MeCH(OH)— | H—C | N |
| AZ-1126 | Cl | MeCH(OH)— | H—C | N |
| AZ-1127 | Br | MeCH(OH)— | H—C | N |
| AZ-1128 | I | MeCH(OH)— | H—C | N |
| AZ-1129 | Me | MeCH(OH)— | H—C | N |
| AZ-1130 | Et | MeCH(OH)— | H—C | N |
| AZ-1131 | Pr | MeCH(OH)— | H—C | N |
| AZ-1132 | iPr | MeCH(OH)— | H—C | N |
| AZ-1133 | Bu | MeCH(OH)— | H—C | N |
| AZ-1134 | secBu | MeCH(OH)— | H—C | N |
| AZ-1135 | iBu | MeCH(OH)— | H—C | N |
| AZ-1136 | tBu | MeCH(OH)— | H—C | N |
| AZ-1137 | HOCH2— | MeCH(OH)— | H—C | N |
| AZ-1138 | MeOCH2— | MeCH(OH)— | H—C | N |
| AZ-1139 | F2CH— | MeCH(OH)— | H—C | N |
| AZ-1140 | F3C— | MeCH(OH)— | H—C | N |
| AZ-1141 | Cl3C— | MeCH(OH)— | H—C | N |
| AZ-1142 | H2C=CH— | MeCH(OH)— | H—C | N |
| AZ-1143 | HC≡C— | MeCH(OH)— | H—C | N |
| AZ-1144 | MeC≡C— | MeCH(OH)— | H—C | N |
| AZ-1145 | MeO— | MeCH(OH)— | H—C | N |
| AZ-1146 | EtO— | MeCH(OH)— | H—C | N |
| AZ-1147 | HC(=O)— | MeCH(OH)— | H—C | N |
| AZ-1148 | MeCH(OH)— | MeCH(OH)— | H—C | N |
| AZ-1149 | EtCH(OH)— | MeCH(OH)— | H—C | N |
| AZ-1150 | Me2C(OH)— | MeCH(OH)— | H—C | N |
| AZ-1151 | F3CCF2— | MeCH(OH)— | H—C | N |
| AZ-1152 | F2CHCF2— | MeCH(OH)— | H—C | N |
| AZ-1153 | ClCF2— | MeCH(OH)— | H—C | N |
| AZ-1154 | MeCF2— | MeCH(OH)— | H—C | N |
| AZ-1155 | BrCF2— | MeCH(OH)— | H—C | N |
| AZ-1156 | BrCH2— | MeCH(OH)— | H—C | N |
| AZ-1157 | ClCH2— | MeCH(OH)— | H—C | N |
| AZ-1158 | Br2CH— | MeCH(OH)— | H—C | N |
| AZ-1159 | cPr | MeCH(OH)— | H—C | N |
| AZ-1160 | HC≡CCH2— | MeCH(OH)— | H—C | N |
| AZ-1161 | HC≡CCH(OH)— | MeCH(OH)— | H—C | N |
| AZ-1162 | Ac | MeCH(OH)— | H—C | N |
| AZ-1163 | MeOC(=O)— | MeCH(OH)— | H—C | N |
| AZ-1164 | EtOC(=O)— | MeCH(OH)— | H—C | N |
| AZ-1165 | MeS— | MeCH(OH)— | H—C | N |
| AZ-1166 | MeS(O)— | MeCH(OH)— | H—C | N |
| AZ-1167 | MeSO2— | MeCH(OH)— | H—C | N |
| AZ-1168 | H2N— | MeCH(OH)— | H—C | N |
| AZ-1169 | O2N— | EtCH(OH)— | H—C | N |
| AZ-1170 | F | EtCH(OH)— | H—C | N |
| AZ-1171 | Cl | EtCH(OH)— | H—C | N |
| AZ-1172 | Br | EtCH(OH)— | H—C | N |
| AZ-1173 | I | EtCH(OH)— | H—C | N |
| AZ-1174 | Me | EtCH(OH)— | H—C | N |
| AZ-1175 | Et | EtCH(OH)— | H—C | N |
| AZ-1176 | Pr | EtCH(OH)— | H—C | N |
| AZ-1177 | iPr | EtCH(OH)— | H—C | N |
| AZ-1178 | Bu | EtCH(OH)— | H—C | N |
| AZ-1179 | secBu | EtCH(OH)— | H—C | N |
| AZ-1180 | iBu | EtCH(OH)— | H—C | N |
| AZ-1181 | tBu | EtCH(OH)— | H—C | N |
| AZ-1182 | HOCH2— | EtCH(OH)— | H—C | N |
| AZ-1183 | MeOCH2— | EtCH(OH)— | H—C | N |

TABLE 3-continued

| | R6 | R7 | Y | Z |
|---|---|---|---|---|
| AZ-1184 | F2CH— | EtCH(OH)— | H—C | N |
| AZ-1185 | F3C— | EtCH(OH)— | H—C | N |
| AZ-1186 | Cl3C— | EtCH(OH)— | H—C | N |
| AZ-1187 | H2C=CH— | EtCH(OH)— | H—C | N |
| AZ-1188 | HC≡C— | EtCH(OH)— | H—C | N |
| AZ-1189 | MeC≡C— | EtCH(OH)— | H—C | N |
| AZ-1190 | MeO— | EtCH(OH)— | H—C | N |
| AZ-1191 | EtO— | EtCH(OH)— | H—C | N |
| AZ-1192 | HC(=O)— | EtCH(OH)— | H—C | N |
| AZ-1193 | MeCH(OH)— | EtCH(OH)— | H—C | N |
| AZ-1194 | EtCH(OH)— | EtCH(OH)— | H—C | N |
| AZ-1195 | Me2C(OH)— | EtCH(OH)— | H—C | N |
| AZ-1196 | F3CCF2— | EtCH(OH)— | H—C | N |
| AZ-1197 | F2CHCF2— | EtCH(OH)— | H—C | N |
| AZ-1198 | ClCF2— | EtCH(OH)— | H—C | N |
| AZ-1199 | MeCF2— | EtCH(OH)— | H—C | N |
| AZ-1200 | BrCF2— | EtCH(OH)— | H—C | N |
| AZ-1201 | BrCH2— | EtCH(OH)— | H—C | N |
| AZ-1202 | ClCH2— | EtCH(OH)— | H—C | N |
| AZ-1203 | Br2CH— | EtCH(OH)— | H—C | N |
| AZ-1204 | cPr | EtCH(OH)— | H—C | N |
| AZ-1205 | HC=CCH2— | EtCH(OH)— | H—C | N |
| AZ-1206 | HC≡CCH(OH)— | EtCH(OH)— | H—C | N |
| AZ-1207 | Ac | EtCH(OH)— | H—C | N |
| AZ-1208 | MeOC(=O)— | EtCH(OH)— | H—C | N |
| AZ-1209 | EtOC(=O)— | EtCH(OH)— | H—C | N |
| AZ-1210 | MeS— | EtCH(OH)— | H—C | N |
| AZ-1211 | MeS(O)— | EtCH(OH)— | H—C | N |
| AZ-1212 | MeSO2— | EtCH(OH)— | H—C | N |
| AZ-1213 | H2N— | EtCH(OH)— | H—C | N |
| AZ-1214 | O2N— | Me2C(OH)— | H—C | N |
| AZ-1215 | F | Me2C(OH)— | H—C | N |
| AZ-1216 | Cl | Me2C(OH)— | H—C | N |
| AZ-1217 | Br | Me2C(OH)— | H—C | N |
| AZ-1218 | I | Me2C(OH)— | H—C | N |
| AZ-1219 | Me | Me2C(OH)— | H—C | N |
| AZ-1220 | Et | Me2C(OH)— | H—C | N |
| AZ-1221 | Pr | Me2C(OH)— | H—C | N |
| AZ-1222 | iPr | Me2C(OH)— | H—C | N |
| AZ-1223 | Bu | Me2C(OH)— | H—C | N |
| AZ-1224 | secBu | Me2C(OH)— | H—C | N |
| AZ-1225 | iBu | Me2C(OH)— | H—C | N |
| AZ-1226 | tBu | Me2C(OH)— | H—C | N |
| AZ-1227 | HOCH2— | Me2C(OH)— | H—C | N |
| AZ-1228 | MeOCH2— | Me2C(OH)— | H—C | N |
| AZ-1229 | F2CH— | Me2C(OH)— | H—C | N |
| AZ-1230 | F3C— | Me2C(OH)— | H—C | N |
| AZ-1231 | Cl3C— | Me2C(OH)— | H—C | N |
| AZ-1232 | H2C=CH— | Me2C(OH)— | H—C | N |
| AZ-1233 | HC≡C— | Me2C(OH)— | H—C | N |
| AZ-1234 | MeC≡C— | Me2C(OH)— | H—C | N |
| AZ-1235 | MeO— | Me2C(OH)— | H—C | N |
| AZ-1236 | EtO— | Me2C(OH)— | H—C | N |
| AZ-1237 | HC(=O)— | Me2C(OH)— | H—C | N |
| AZ-1238 | MeCH(OH)— | Me2C(OH)— | H—C | N |
| AZ-1239 | EtCH(OH)— | Me2C(OH)— | H—C | N |
| AZ-1240 | Me2C(OH)— | Me2C(OH)— | H—C | N |
| AZ-1241 | F3CCF2— | Me2C(OH)— | H—C | N |
| AZ-1242 | F2CHCF2— | Me2C(OH)— | H—C | N |
| AZ-1243 | ClCF2— | Me2C(OH)— | H—C | N |
| AZ-1244 | MeCF2— | Me2C(OH)— | H—C | N |
| AZ-1245 | BrCF2— | Me2C(OH)— | H—C | N |
| AZ-1246 | BrCH2— | Me2C(OH)— | H—C | N |
| AZ-1247 | ClCH2— | Me2C(OH)— | H—C | N |
| AZ-1248 | Br2CH— | Me2C(OH)— | H—C | N |
| AZ-1249 | cPr | Me2C(OH)— | H—C | N |
| AZ-1250 | HC=CCH2— | Me2C(OH)— | H—C | N |
| AZ-1251 | HC≡CCH(OH)— | Me2C(OH)— | H—C | N |
| AZ-1252 | Ac | Me2C(OH)— | H—C | N |
| AZ-1253 | MeOC(=O)— | Me2C(OH)— | H—C | N |
| AZ-1254 | EtOC(=O)— | Me2C(OH)— | H—C | N |
| AZ-1255 | MeS— | Me2C(OH)— | H—C | N |
| AZ-1256 | MeS(O)— | Me2C(OH)— | H—C | N |
| AZ-1257 | MeSO2— | Me2C(OH)— | H—C | N |
| AZ-1258 | H2N— | Me2C(OH)— | H—C | N |
| AZ-1259 | O2N— | F2CHCF2— | H—C | N |
| AZ-1260 | F | F2CHCF2— | H—C | N |
| AZ-1261 | Cl | F2CHCF2— | H—C | N |

TABLE 3-continued

|  | R6 | R7 | Y | Z |
|---|---|---|---|---|
| AZ-1262 | Br | F2CHCF2— | H—C | N |
| AZ-1263 | I | F2CHCF2— | H—C | N |
| AZ-1264 | Me | F2CHCF2— | H—C | N |
| AZ-1265 | Et | F2CHCF2— | H—C | N |
| AZ-1266 | Pr | F2CHCF2— | H—C | N |
| AZ-1267 | iPr | F2CHCF2— | H—C | N |
| AZ-1268 | Bu | F2CHCF2— | H—C | N |
| AZ-1269 | secBu | F2CHCF2— | H—C | N |
| AZ-1270 | iBu | F2CHCF2— | H—C | N |
| AZ-1271 | tBu | F2CHCF2— | H—C | N |
| AZ-1272 | HOCH2— | F2CHCF2— | H—C | N |
| AZ-1273 | MeOCH2— | F2CHCF2— | H—C | N |
| AZ-1274 | F2CH— | F2CHCF2— | H—C | N |
| AZ-1275 | F3C— | F2CHCF2— | H—C | N |
| AZ-1276 | Cl3C— | F2CHCF2— | H—C | N |
| AZ-1277 | H2C=CH— | F2CHCF2— | H—C | N |
| AZ-1278 | HC≡C— | F2CHCF2— | H—C | N |
| AZ-1279 | MeC≡C— | F2CHCF2— | H—C | N |
| AZ-1280 | MeO— | F2CHCF2— | H—C | N |
| AZ-1281 | EtO— | F2CHCF2— | H—C | N |
| AZ-1282 | HC(=O)— | F2CHCF2— | H—C | N |
| AZ-1283 | MeCH(OH)— | F2CHCF2— | H—C | N |
| AZ-1284 | EtCH(OH)— | F2CHCF2— | H—C | N |
| AZ-1285 | Me2C(OH)— | F2CHCF2— | H—C | N |
| AZ-1286 | F3CCF2— | F2CHCF2— | H—C | N |
| AZ-1287 | F2CHCF2— | F2CHCF2— | H—C | N |
| AZ-1288 | ClCF2— | F2CHCF2— | H—C | N |
| AZ-1289 | MeCF2— | F2CHCF2— | H—C | N |
| AZ-1290 | BrCF2— | F2CHCF2— | H—C | N |
| AZ-1291 | BrCH2— | F2CHCF2— | H—C | N |
| AZ-1292 | ClCH2— | F2CHCF2— | H—C | N |
| AZ-1293 | Br2CH— | F2CHCF2— | H—C | N |
| AZ-1294 | cPr | F2CHCF2— | H—C | N |
| AZ-1295 | HC≡CCH2— | F2CHCF2— | H—C | N |
| AZ-1296 | HC≡CCH(OH)— | F2CHCF2— | H—C | N |
| AZ-1297 | Ac | F2CHCF2— | H—C | N |
| AZ-1298 | MeOC(=O)— | F2CHCF2— | H—C | N |
| AZ-1299 | EtOC(=O)— | F2CHCF2— | H—C | N |
| AZ-1300 | MeS— | F2CHCF2— | H—C | N |
| AZ-1301 | MeS(O)— | F2CHCF2— | H—C | N |
| AZ-1302 | MeSO2— | F2CHCF2— | H—C | N |
| AZ-1303 | H2N— | F2CHCF2— | H—C | N |
| AZ-1304 | O2N— | ClCF2— | H—C | N |
| AZ-1305 | F | ClCF2— | H—C | N |
| AZ-1306 | Cl | ClCF2— | H—C | N |
| AZ-1307 | Br | ClCF2— | H—C | N |
| AZ-1308 | I | ClCF2— | H—C | N |
| AZ-1309 | Me | ClCF2— | H—C | N |
| AZ-1310 | Et | ClCF2— | H—C | N |
| AZ-1311 | Pr | ClCF2— | H—C | N |
| AZ-1312 | iPr | ClCF2— | H—C | N |
| AZ-1313 | Bu | ClCF2— | H—C | N |
| AZ-1314 | secBu | ClCF2— | H—C | N |
| AZ-1315 | iBu | ClCF2— | H—C | N |
| AZ-1316 | tBu | ClCF2— | H—C | N |
| AZ-1317 | HOCH2— | ClCF2— | H—C | N |
| AZ-1318 | MeOCH2— | ClCF2— | H—C | N |
| AZ-1319 | F2CH— | ClCF2— | H—C | N |
| AZ-1320 | F3C— | ClCF2— | H—C | N |
| AZ-1321 | Cl3C— | ClCF2— | H—C | N |
| AZ-1322 | H2C=CH— | ClCF2— | H—C | N |
| AZ-1323 | HC≡C— | ClCF2— | H—C | N |
| AZ-1324 | MeC≡C— | ClCF2— | H—C | N |
| AZ-1325 | MeO— | ClCF2— | H—C | N |
| AZ-1326 | EtO— | ClCF2— | H—C | N |
| AZ-1327 | HC(=O)— | ClCF2— | H—C | N |
| AZ-1328 | MeCH(OH)— | ClCF2— | H—C | N |
| AZ-1329 | EtCH(OH)— | ClCF2— | H—C | N |
| AZ-1330 | Me2C(OH)— | ClCF2— | H—C | N |
| AZ-1331 | F3CCF2— | ClCF2— | H—C | N |
| AZ-1332 | F2CHCF2— | ClCF2— | H—C | N |
| AZ-1333 | ClCF2— | ClCF2— | H—C | N |
| AZ-1334 | MeCF2— | ClCF2— | H—C | N |
| AZ-1335 | BrCF2— | ClCF2— | H—C | N |
| AZ-1336 | BrCH2— | ClCF2— | H—C | N |
| AZ-1337 | ClCH2— | ClCF2— | H—C | N |
| AZ-1338 | Br2CH— | ClCF2— | H—C | N |
| AZ-1339 | cPr | ClCF2— | H—C | N |

TABLE 3-continued

| | R6 | R7 | Y | Z |
|---|---|---|---|---|
| AZ-1340 | HC≡CCH2— | ClCF2— | H—C | N |
| AZ-1341 | HC≡CCH(OH)— | ClCF2— | H—C | N |
| AZ-1342 | Ac | ClCF2— | H—C | N |
| AZ-1343 | MeOC(=O)— | ClCF2— | H—C | N |
| AZ-1344 | EtOC(=O)— | ClCF2— | H—C | N |
| AZ-1345 | MeS— | ClCF2— | H—C | N |
| AZ-1346 | MeS(O)— | ClCF2— | H—C | N |
| AZ-1347 | MeSO2— | ClCF2— | H—C | N |
| AZ-1348 | H2N— | ClCF2— | H—C | N |
| AZ-1349 | O2N— | MeCF2— | H—C | N |
| AZ-1350 | F | MeCF2— | H—C | N |
| AZ-1351 | Cl | MeCF2— | H—C | N |
| AZ-1352 | Br | MeCF2— | H—C | N |
| AZ-1353 | I | MeCF2— | H—C | N |
| AZ-1354 | Me | MeCF2— | H—C | N |
| AZ-1355 | Et | MeCF2— | H—C | N |
| AZ-1356 | Pr | MeCF2— | H—C | N |
| AZ-1357 | iPr | MeCF2— | H—C | N |
| AZ-1358 | Bu | MeCF2— | H—C | N |
| AZ-1359 | secBu | MeCF2— | H—C | N |
| AZ-1360 | iBu | MeCF2— | H—C | N |
| AZ-1361 | tBu | MeCF2— | H—C | N |
| AZ-1362 | HOCH2— | MeCF2— | H—C | N |
| AZ-1363 | MeOCH2— | MeCF2— | H—C | N |
| AZ-1364 | F2CH— | MeCF2— | H—C | N |
| AZ-1365 | F3C— | MeCF2— | H—C | N |
| AZ-1366 | Cl3C— | MeCF2— | H—C | N |
| AZ-1367 | H2C=CH— | MeCF2— | H—C | N |
| AZ-1368 | HC≡C— | MeCF2— | H—C | N |
| AZ-1369 | MeC≡C— | MeCF2— | H—C | N |
| AZ-1370 | MeO— | MeCF2— | H—C | N |
| AZ-1371 | EtO— | MeCF2— | H—C | N |
| AZ-1372 | HC(=O)— | MeCF2— | H—C | N |
| AZ-1373 | MeCH(OH)— | MeCF2— | H—C | N |
| AZ-1374 | EtCH(OH)— | MeCF2— | H—C | N |
| AZ-1375 | Me2C(OH)— | MeCF2— | H—C | N |
| AZ-1376 | F3CCF2— | MeCF2— | H—C | N |
| AZ-1377 | F2CHCF2— | MeCF2— | H—C | N |
| AZ-1378 | ClCF2— | MeCF2— | H—C | N |
| AZ-1379 | MeCF2— | MeCF2— | H—C | N |
| AZ-1380 | BrCF2— | MeCF2— | H—C | N |
| AZ-1381 | BrCH2— | MeCF2— | H—C | N |
| AZ-1382 | ClCH2— | MeCF2— | H—C | N |
| AZ-1383 | Br2CH— | MeCF2— | H—C | N |
| AZ-1384 | cPr | MeCF2— | H—C | N |
| AZ-1385 | HC≡CCH2— | MeCF2— | H—C | N |
| AZ-1386 | HC≡CCH(OH)— | MeCF2— | H—C | N |
| AZ-1387 | Ac | MeCF2— | H—C | N |
| AZ-1388 | MeOC(=O)— | MeCF2— | H—C | N |
| AZ-1389 | EtOC(=O)— | MeCF2— | H—C | N |
| AZ-1390 | MeS— | MeCF2— | H—C | N |
| AZ-1391 | MeS(O)— | MeCF2— | H—C | N |
| AZ-1392 | MeSO2— | MeCF2— | H—C | N |
| AZ-1393 | H2N— | MeCF2— | H—C | N |
| AZ-1394 | O2N— | BrCF2— | H—C | N |
| AZ-1395 | F | BrCF2— | H—C | N |
| AZ-1396 | Cl | BrCF2— | H—C | N |
| AZ-1397 | Br | BrCF2— | H—C | N |
| AZ-1398 | I | BrCF2— | H—C | N |
| AZ-1399 | Me | BrCF2— | H—C | N |
| AZ-1400 | Et | BrCF2— | H—C | N |
| AZ-1401 | Pr | BrCF2— | H—C | N |
| AZ-1402 | iPr | BrCF2— | H—C | N |
| AZ-1403 | Bu | BrCF2— | H—C | N |
| AZ-1404 | secBu | BrCF2— | H—C | N |
| AZ-1405 | iBu | BrCF2— | H—C | N |
| AZ-1406 | tBu | BrCF2— | H—C | N |
| AZ-1407 | HOCH2— | BrCF2— | H—C | N |
| AZ-1408 | MeOCH2— | BrCF2— | H—C | N |
| AZ-1409 | F2CH— | BrCF2— | H—C | N |
| AZ-1410 | F3C— | BrCF2— | H—C | N |
| AZ-1411 | Cl3C— | BrCF2— | H—C | N |
| AZ-1412 | H2C=CH— | BrCF2— | H—C | N |
| AZ-1413 | HC≡C— | BrCF2— | H—C | N |
| AZ-1414 | MeC≡C— | BrCF2— | H—C | N |
| AZ-1415 | MeO— | BrCF2— | H—C | N |
| AZ-1416 | EtO— | BrCF2— | H—C | N |
| AZ-1417 | HC(=O)— | BrCF2— | H—C | N |

TABLE 3-continued

|  | R6 | R7 | Y | Z |
|---|---|---|---|---|
| AZ-1418 | MeCH(OH)— | BrCF2— | H—C | N |
| AZ-1419 | EtCH(OH)— | BrCF2— | H—C | N |
| AZ-1420 | Me2C(OH)— | BrCF2— | H—C | N |
| AZ-1421 | F3CCF2— | BrCF2— | H—C | N |
| AZ-1422 | F2CHCF2— | BrCF2— | H—C | N |
| AZ-1423 | ClCF2— | BrCF2— | H—C | N |
| AZ-1424 | MeCF2— | BrCF2— | H—C | N |
| AZ-1425 | BrCF2— | BrCF2— | H—C | N |
| AZ-1426 | BrCH2— | BrCF2— | H—C | N |
| AZ-1427 | ClCH2— | BrCF2— | H—C | N |
| AZ-1428 | Br2CH— | BrCF2— | H—C | N |
| AZ-1429 | cPr | BrCF2— | H—C | N |
| AZ-1430 | HC≡CCH2— | BrCF2— | H—C | N |
| AZ-1431 | HC≡CCH(OH)— | BrCF2— | H—C | N |
| AZ-1432 | Ac | BrCF2— | H—C | N |
| AZ-1433 | MeOC(=O)— | BrCF2— | H—C | N |
| AZ-1434 | EtOC(=O)— | BrCF2— | H—C | N |
| AZ-1435 | MeS— | BrCF2— | H—C | N |
| AZ-1436 | MeS(O)— | BrCF2— | H—C | N |
| AZ-1437 | MeSO2— | BrCF2— | H—C | N |
| AZ-1438 | H2N— | BrCF2— | H—C | N |
| AZ-1439 | O2N— | BrCH2— | H—C | N |
| AZ-1440 | F | BrCH2— | H—C | N |
| AZ-1441 | Cl | BrCH2— | H—C | N |
| AZ-1442 | Br | BrCH2— | H—C | N |
| AZ-1443 | I | BrCH2— | H—C | N |
| AZ-1444 | Me | BrCH2— | H—C | N |
| AZ-1445 | Et | BrCH2— | H—C | N |
| AZ-1446 | Pr | BrCH2— | H—C | N |
| AZ-1447 | iPr | BrCH2— | H—C | N |
| AZ-1448 | Bu | BrCH2— | H—C | N |
| AZ-1449 | secBu | BrCH2— | H—C | N |
| AZ-1450 | iBu | BrCH2— | H—C | N |
| AZ-1451 | tBu | BrCH2— | H—C | N |
| AZ-1452 | HOCH2— | BrCH2— | H—C | N |
| AZ-1453 | MeOCH2— | BrCH2— | H—C | N |
| AZ-1454 | F2CH— | BrCH2— | H—C | N |
| AZ-1455 | F3C— | BrCH2— | H—C | N |
| AZ-1456 | Cl3C— | BrCH2— | H—C | N |
| AZ-1457 | H2C=CH— | BrCH2— | H—C | N |
| AZ-1458 | HC≡C— | BrCH2— | H—C | N |
| AZ-1459 | MeC≡C— | BrCH2— | H—C | N |
| AZ-1460 | MeO— | BrCH2— | H—C | N |
| AZ-1461 | EtO— | BrCH2— | H—C | N |
| AZ-1462 | HC(=O)— | BrCH2— | H—C | N |
| AZ-1463 | MeCH(OH)— | BrCH2— | H—C | N |
| AZ-1464 | EtCH(OH)— | BrCH2— | H—C | N |
| AZ-1465 | Me2C(OH)— | BrCH2— | H—C | N |
| AZ-1466 | F3CCF2— | BrCH2— | H—C | N |
| AZ-1467 | F2CHCF2— | BrCH2— | H—C | N |
| AZ-1468 | ClCF2— | BrCH2— | H—C | N |
| AZ-1469 | MeCF2— | BrCH2— | H—C | N |
| AZ-1470 | BrCF2— | BrCH2— | H—C | N |
| AZ-1471 | BrCH2— | BrCH2— | H—C | N |
| AZ-1472 | ClCH2— | BrCH2— | H—C | N |
| AZ-1473 | Br2CH— | BrCH2— | H—C | N |
| AZ-1474 | cPr | BrCH2— | H—C | N |
| AZ-1475 | HC≡CCH2— | BrCH2— | H—C | N |
| AZ-1476 | HC≡CCH(OH)— | BrCH2— | H—C | N |
| AZ-1477 | Ac | BrCH2— | H—C | N |
| AZ-1478 | MeOC(=O)— | BrCH2— | H—C | N |
| AZ-1479 | EtOC(=O)— | BrCH2— | H—C | N |
| AZ-1480 | MeS— | BrCH2— | H—C | N |
| AZ-1481 | MeS(O)— | BrCH2— | H—C | N |
| AZ-1482 | MeSO2— | BrCH2— | H—C | N |
| AZ-1483 | H2N— | BrCH2— | H—C | N |
| AZ-1484 | O2N— | Br2CH— | H—C | N |
| AZ-1485 | F | Br2CH— | H—C | N |
| AZ-1486 | Cl | Br2CH— | H—C | N |
| AZ-1487 | Br | Br2CH— | H—C | N |
| AZ-1488 | I | Br2CH— | H—C | N |
| AZ-1489 | Me | Br2CH— | H—C | N |
| AZ-1490 | Et | Br2CH— | H—C | N |
| AZ-1491 | Pr | Br2CH— | H—C | N |
| AZ-1492 | iPr | Br2CH— | H—C | N |
| AZ-1493 | Bu | Br2CH— | H—C | N |
| AZ-1494 | secBu | Br2CH— | H—C | N |
| AZ-1495 | iBu | Br2CH— | H—C | N |

TABLE 3-continued

|  | R6 | R7 | Y | Z |
|---|---|---|---|---|
| AZ-1496 | tBu | Br2CH— | H—C | N |
| AZ-1497 | HOCH2— | Br2CH— | H—C | N |
| AZ-1498 | MeOCH2— | Br2CH— | H—C | N |
| AZ-1499 | F2CH— | Br2CH— | H—C | N |
| AZ-1500 | F3C— | Br2CH— | H—C | N |
| AZ-1501 | Cl3C— | Br2CH— | H—C | N |
| AZ-1502 | H2C=CH— | Br2CH— | H—C | N |
| AZ-1503 | HC≡C— | Br2CH— | H—C | N |
| AZ-1504 | MeC≡C— | Br2CH— | H—C | N |
| AZ-1505 | MeO— | Br2CH— | H—C | N |
| AZ-1506 | EtO— | Br2CH— | H—C | N |
| AZ-1507 | HC(=O)— | Br2CH— | H—C | N |
| AZ-1508 | MeCH(OH)— | Br2CH— | H—C | N |
| AZ-1509 | EtCH(OH)— | Br2CH— | H—C | N |
| AZ-1510 | Me2C(OH)— | Br2CH— | H—C | N |
| AZ-1511 | F3CCF2— | Br2CH— | H—C | N |
| AZ-1512 | F2CHCF2— | Br2CH— | H—C | N |
| AZ-1513 | ClCF2— | Br2CH— | H—C | N |
| AZ-1514 | MeCF2— | Br2CH— | H—C | N |
| AZ-1515 | BrCF2— | Br2CH— | H—C | N |
| AZ-1516 | BrCH2— | Br2CH— | H—C | N |
| AZ-1517 | ClCH2— | Br2CH— | H—C | N |
| AZ-1518 | Br2CH— | Br2CH— | H—C | N |
| AZ-1519 | cPr | Br2CH— | H—C | N |
| AZ-1520 | HC≡CCH2— | Br2CH— | H—C | N |
| AZ-1521 | HC≡CCH(OH)— | Br2CH— | H—C | N |
| AZ-1522 | Ac | Br2CH— | H—C | N |
| AZ-1523 | MeOC(=O)— | Br2CH— | H—C | N |
| AZ-1524 | EtOC(=O)— | Br2CH— | H—C | N |
| AZ-1525 | MeS— | Br2CH— | H—C | N |
| AZ-1526 | MeS(O)— | Br2CH— | H—C | N |
| AZ-1527 | MeSO2— | Br2CH— | H—C | N |
| AZ-1528 | H2N— | Br2CH— | H—C | N |
| AZ-1529 | O2N— | cPr | H—C | N |
| AZ-1530 | F | cPr | H—C | N |
| AZ-1531 | Cl | cPr | H—C | N |
| AZ-1532 | Br | cPr | H—C | N |
| AZ-1533 | I | cPr | H—C | N |
| AZ-1534 | Me | cPr | H—C | N |
| AZ-1535 | Et | cPr | H—C | N |
| AZ-1536 | Pr | cPr | H—C | N |
| AZ-1537 | iPr | cPr | H—C | N |
| AZ-1538 | Bu | cPr | H—C | N |
| AZ-1539 | secBu | cPr | H—C | N |
| AZ-1540 | iBu | cPr | H—C | N |
| AZ-1541 | tBu | cPr | H—C | N |
| AZ-1542 | HOCH2— | cPr | H—C | N |
| AZ-1543 | MeOCH2— | cPr | H—C | N |
| AZ-1544 | F2CH— | cPr | H—C | N |
| AZ-1545 | F3C— | cPr | H—C | N |
| AZ-1546 | Cl3C— | cPr | H—C | N |
| AZ-1547 | H2C=CH— | cPr | H—C | N |
| AZ-1548 | HC≡C— | cPr | H—C | N |
| AZ-1549 | MeC≡C— | cPr | H—C | N |
| AZ-1550 | MeO— | cPr | H—C | N |
| AZ-1551 | EtO— | cPr | H—C | N |
| AZ-1552 | HC(=O)— | cPr | H—C | N |
| AZ-1553 | MeCH(OH)— | cPr | H—C | N |
| AZ-1554 | EtCH(OH)— | cPr | H—C | N |
| AZ-1555 | Me2C(OH)— | cPr | H—C | N |
| AZ-1556 | F3CCF2— | cPr | H—C | N |
| AZ-1557 | F2CHCF2— | cPr | H—C | N |
| AZ-1558 | ClCF2— | cPr | H—C | N |
| AZ-1559 | MeCF2— | cPr | H—C | N |
| AZ-1560 | BrCF2— | cPr | H—C | N |
| AZ-1561 | BrCH2— | cPr | H—C | N |
| AZ-1562 | ClCH2— | cPr | H—C | N |
| AZ-1563 | Br2CH— | cPr | H—C | N |
| AZ-1564 | cPr | cPr | H—C | N |
| AZ-1565 | HC≡CCH2— | cPr | H—C | N |
| AZ-1566 | HC≡CCH(OH)— | cPr | H—C | N |
| AZ-1567 | Ac | cPr | H—C | N |
| AZ-1568 | MeOC(=O)— | cPr | H—C | N |
| AZ-1569 | EtOC(=O)— | cPr | H—C | N |
| AZ-1570 | MeS— | cPr | H—C | N |
| AZ-1571 | MeS(O)— | cPr | H—C | N |
| AZ-1572 | MeSO2— | cPr | H—C | N |
| AZ-1573 | H2N— | cPr | H—C | N |

TABLE 3-continued

|  | R6 | R7 | Y | Z |
|---|---|---|---|---|
| AZ-1574 | O2N— | HC≡CCH2— | H—C | N |
| AZ-1575 | F | HC≡CCH2— | H—C | N |
| AZ-1576 | Cl | HC≡CCH2— | H—C | N |
| AZ-1577 | Br | HC≡CCH2— | H—C | N |
| AZ-1578 | I | HC≡CCH2— | H—C | N |
| AZ-1579 | Me | HC≡CCH2— | H—C | N |
| AZ-1580 | Et | HC≡CCH2— | H—C | N |
| AZ-1581 | Pr | HC≡CCH2— | H—C | N |
| AZ-1582 | iPr | HC≡CCH2— | H—C | N |
| AZ-1583 | Bu | HC≡CCH2— | H—C | N |
| AZ-1584 | secBu | HC≡CCH2— | H—C | N |
| AZ-1585 | iBu | HC≡CCH2— | H—C | N |
| AZ-1586 | tBu | HC≡CCH2— | H—C | N |
| AZ-1587 | HOCH2— | HC≡CCH2— | H—C | N |
| AZ-1588 | MeOCH2— | HC≡CCH2— | H—C | N |
| AZ-1589 | F2CH— | HC≡CCH2— | H—C | N |
| AZ-1590 | F3C— | HC≡CCH2— | H—C | N |
| AZ-1591 | Cl3C— | HC≡CCH2— | H—C | N |
| AZ-1592 | H2C=CH— | HC≡CCH2— | H—C | N |
| AZ-1593 | HC≡C— | HC≡CCH2— | H—C | N |
| AZ-1594 | MeC≡C— | HC≡CCH2— | H—C | N |
| AZ-1595 | MeO— | HC≡CCH2— | H—C | N |
| AZ-1596 | EtO— | HC≡CCH2— | H—C | N |
| AZ-1597 | HC(=O)— | HC≡CCH2— | H—C | N |
| AZ-1598 | MeCH(OH)— | HC≡CCH2— | H—C | N |
| AZ-1599 | EtCH(OH)— | HC≡CCH2— | H—C | N |
| AZ-1600 | Me2C(OH)— | HC≡CCH2— | H—C | N |
| AZ-1601 | F3CCF2— | HC≡CCH2— | H—C | N |
| AZ-1602 | F2CHCF2— | HC≡CCH2— | H—C | N |
| AZ-1603 | ClCF2— | HC≡CCH2— | H—C | N |
| AZ-1604 | MeCF2— | HC≡CCH2— | H—C | N |
| AZ-1605 | BrCF2— | HC≡CCH2— | H—C | N |
| AZ-1606 | BrCH2— | HC≡CCH2— | H—C | N |
| AZ-1607 | ClCH2— | HC≡CCH2— | H—C | N |
| AZ-1608 | Br2CH— | HC≡CCH2— | H—C | N |
| AZ-1609 | cPr | HC≡CCH2— | H—C | N |
| AZ-1610 | HC≡CCH2— | HC≡CCH2— | H—C | N |
| AZ-1611 | HC≡CCH(OH)— | HC≡CCH2— | H—C | N |
| AZ-1612 | Ac | HC≡CCH2— | H—C | N |
| AZ-1613 | MeOC(=O)— | HC≡CCH2— | H—C | N |
| AZ-1614 | EtOC(=O)— | HC≡CCH2— | H—C | N |
| AZ-1615 | MeS— | HC≡CCH2— | H—C | N |
| AZ-1616 | MeS(O)— | HC≡CCH2— | H—C | N |
| AZ-1617 | MeSO2— | HC≡CCH2— | H—C | N |
| AZ-1618 | H2N— | HC≡CCH2— | H—C | N |
| AZ-1619 | O2N— | HC≡CCH(OH)— | H—C | N |
| AZ-1620 | F | HC≡CCH(OH)— | H—C | N |
| AZ-1621 | Cl | HC≡CCH(OH)— | H—C | N |
| AZ-1622 | Br | HC≡CCH(OH)— | H—C | N |
| AZ-1623 | I | HC≡CCH(OH)— | H—C | N |
| AZ-1624 | Me | HC≡CCH(OH)— | H—C | N |
| AZ-1625 | Et | HC≡CCH(OH)— | H—C | N |
| AZ-1626 | Pr | HC≡CCH(OH)— | H—C | N |
| AZ-1627 | iPr | HC≡CCH(OH)— | H—C | N |
| AZ-1628 | Bu | HC≡CCH(OH)— | H—C | N |
| AZ-1629 | secBu | HC≡CCH(OH)— | H—C | N |
| AZ-1630 | iBu | HC≡CCH(OH)— | H—C | N |
| AZ-1631 | tBu | HC≡CCH(OH)— | H—C | N |
| AZ-1632 | HOCH2— | HC≡CCH(OH)— | H—C | N |
| AZ-1633 | MeOCH2— | HC≡CCH(OH)— | H—C | N |
| AZ-1634 | F2CH— | HC≡CCH(OH)— | H—C | N |
| AZ-1635 | F3C— | HC≡CCH(OH)— | H—C | N |
| AZ-1636 | Cl3C— | HC≡CCH(OH)— | H—C | N |
| AZ-1637 | H2C=CH— | HC≡CCH(OH)— | H—C | N |
| AZ-1638 | HC≡C— | HC≡CCH(OH)— | H—C | N |
| AZ-1639 | MeC≡C— | HC≡CCH(OH)— | H—C | N |
| AZ-1640 | MeO— | HC≡CCH(OH)— | H—C | N |
| AZ-1641 | EtO— | HC≡CCH(OH)— | H—C | N |
| AZ-1642 | HC(=O)— | HC≡CCH(OH)— | H—C | N |
| AZ-1643 | MeCH(OH)— | HC≡CCH(OH)— | H—C | N |
| AZ-1644 | EtCH(OH)— | HC≡CCH(OH)— | H—C | N |
| AZ-1645 | Me2C(OH)— | HC≡CCH(OH)— | H—C | N |
| AZ-1646 | F3CCF2— | HC≡CCH(OH)— | H—C | N |
| AZ-1647 | F2CHCF2— | HC≡CCH(OH)— | H—C | N |
| AZ-1648 | ClCF2— | HC≡CCH(OH)— | H—C | N |
| AZ-1649 | MeCF2— | HC≡CCH(OH)— | H—C | N |
| AZ-1650 | BrCF2— | HC≡CCH(OH)— | H—C | N |
| AZ-1651 | BrCH2— | HC≡CCH(OH)— | H—C | N |

TABLE 3-continued

| | R6 | R7 | Y | Z |
|---|---|---|---|---|
| AZ-1652 | ClCH2— | HC≡CCH(OH)— | H—C | N |
| AZ-1653 | Br2CH— | HC≡CCH(OH)— | H—C | N |
| AZ-1654 | cPr | HC≡CCH(OH)— | H—C | N |
| AZ-1655 | HC≡CCH2— | HC≡CCH(OH)— | H—C | N |
| AZ-1656 | HC≡CCH(OH)— | HC≡CCH(OH)— | H—C | N |
| AZ-1657 | Ac | HC≡CCH(OH)— | H—C | N |
| AZ-1658 | MeOC(=O)— | HC≡CCH(OH)— | H—C | N |
| AZ-1659 | EtOC(=O)— | HC≡CCH(OH)— | H—C | N |
| AZ-1660 | MeS— | HC≡CCH(OH)— | H—C | N |
| AZ-1661 | MeS(O)— | HC≡CCH(OH)— | H—C | N |
| AZ-1662 | MeSO2— | HC≡CCH(OH)— | H—C | N |
| AZ-1663 | H2N— | HC≡CCH(OH)— | H—C | N |
| AZ-1664 | O2N— | Ac | H—C | N |
| AZ-1665 | F | Ac | H—C | N |
| AZ-1666 | Cl | Ac | H—C | N |
| AZ-1667 | Br | Ac | H—C | N |
| AZ-1668 | I | Ac | H—C | N |
| AZ-1669 | Me | Ac | H—C | N |
| AZ-1670 | Et | Ac | H—C | N |
| AZ-1671 | Pr | Ac | H—C | N |
| AZ-1672 | iPr | Ac | H—C | N |
| AZ-1673 | Bu | Ac | H—C | N |
| AZ-1674 | secBu | Ac | H—C | N |
| AZ-1675 | iBu | Ac | H—C | N |
| AZ-1676 | tBu | Ac | H—C | N |
| AZ-1677 | HOCH2— | Ac | H—C | N |
| AZ-1678 | MeOCH2— | Ac | H—C | N |
| AZ-1679 | F2CH— | Ac | H—C | N |
| AZ-1680 | F3C— | Ac | H—C | N |
| AZ-1681 | Cl3C— | Ac | H—C | N |
| AZ-1682 | H2C=CH— | Ac | H—C | N |
| AZ-1683 | HC≡C— | Ac | H—C | N |
| AZ-1684 | MeC≡C— | Ac | H—C | N |
| AZ-1685 | MeO— | Ac | H—C | N |
| AZ-1686 | EtO— | Ac | H—C | N |
| AZ-1687 | HC(=O)— | Ac | H—C | N |
| AZ-1688 | MeCH(OH)— | Ac | H—C | N |
| AZ-1689 | EtCH(OH)— | Ac | H—C | N |
| AZ-1690 | Me2C(OH)— | Ac | H—C | N |
| AZ-1691 | F3CCF2— | Ac | H—C | N |
| AZ-1692 | F2CHCF2— | Ac | H—C | N |
| AZ-1693 | ClCF2— | Ac | H—C | N |
| AZ-1694 | MeCF2— | Ac | H—C | N |
| AZ-1695 | BrCF2— | Ac | H—C | N |
| AZ-1696 | BrCH2— | Ac | H—C | N |
| AZ-1697 | ClCH2— | Ac | H—C | N |
| AZ-1698 | Br2CH— | Ac | H—C | N |
| AZ-1699 | cPr | Ac | H—C | N |
| AZ-1700 | HC≡CCH2— | Ac | H—C | N |
| AZ-1701 | HC≡CCH(OH)— | Ac | H—C | N |
| AZ-1702 | Ac | Ac | H—C | N |
| AZ-1703 | MeOC(=O)— | Ac | H—C | N |
| AZ-1704 | EtOC(=O)— | Ac | H—C | N |
| AZ-1705 | MeS— | Ac | H—C | N |
| AZ-1706 | MeS(O)— | Ac | H—C | N |
| AZ-1707 | MeSO2— | Ac | H—C | N |
| AZ-1708 | H2N— | Ac | H—C | N |
| AZ-1709 | O2N— | MeOC(=O)— | H—C | N |
| AZ-1710 | F | MeOC(=O)— | H—C | N |
| AZ-1711 | Cl | MeOC(=O)— | H—C | N |
| AZ-1712 | Br | MeOC(=O)— | H—C | N |
| AZ-1713 | I | MeOC(=O)— | H—C | N |
| AZ-1714 | Me | MeOC(=O)— | H—C | N |
| AZ-1715 | Et | MeOC(=O)— | H—C | N |
| AZ-1716 | Pr | MeOC(=O)— | H—C | N |
| AZ-1717 | iPr | MeOC(=O)— | H—C | N |
| AZ-1718 | Bu | MeOC(=O)— | H—C | N |
| AZ-1719 | secBu | MeOC(=O)— | H—C | N |
| AZ-1720 | iBu | MeOC(=O)— | H—C | N |
| AZ-1721 | tBu | MeOC(=O)— | H—C | N |
| AZ-1722 | HOCH2— | MeOC(=O)— | H—C | N |
| AZ-1723 | MeOCH2— | MeOC(=O)— | H—C | N |
| AZ-1724 | F2CH— | MeOC(=O)— | H—C | N |
| AZ-1725 | F3C— | MeOC(=O)— | H—C | N |
| AZ-1726 | Cl3C— | MeOC(=O)— | H—C | N |
| AZ-1727 | H2C=CH— | MeOC(=O)— | H—C | N |
| AZ-1728 | HC≡C— | MeOC(=O)— | H—C | N |
| AZ-1729 | MeC≡C— | MeOC(=O)— | H—C | N |

TABLE 3-continued

|  | R6 | R7 | Y | Z |
|---|---|---|---|---|
| AZ-1730 | MeO— | MeOC(=O)— | H—C | N |
| AZ-1731 | EtO— | MeOC(=O)— | H—C | N |
| AZ-1732 | HC(=O)— | MeOC(=O)— | H—C | N |
| AZ-1733 | MeCH(OH)— | MeOC(=O)— | H—C | N |
| AZ-1734 | EtCH(OH)— | MeOC(=O)— | H—C | N |
| AZ-1735 | Me2C(OH)— | MeOC(=O)— | H—C | N |
| AZ-1736 | F3CCF2— | MeOC(=O)— | H—C | N |
| AZ-1737 | F2CHCF2— | MeOC(=O)— | H—C | N |
| AZ-1738 | ClCF2— | MeOC(=O)— | H—C | N |
| AZ-1739 | MeCF2— | MeOC(=O)— | H—C | N |
| AZ-1740 | BrCF2— | MeOC(=O)— | H—C | N |
| AZ-1741 | BrCH2— | MeOC(=O)— | H—C | N |
| AZ-1742 | ClCH2— | MeOC(=O)— | H—C | N |
| AZ-1743 | Br2CH— | MeOC(=O)— | H—C | N |
| AZ-1744 | cPr | MeOC(=O)— | H—C | N |
| AZ-1745 | HC=CCH2— | MeOC(=O)— | H—C | N |
| AZ-1746 | HC≡CCH(OH)— | MeOC(=O)— | H—C | N |
| AZ-1747 | Ac | MeOC(=O)— | H—C | N |
| AZ-1748 | MeOC(=O)— | MeOC(=O)— | H—C | N |
| AZ-1749 | EtOC(=O)— | MeOC(=O)— | H—C | N |
| AZ-1750 | MeS— | MeOC(=O)— | H—C | N |
| AZ-1751 | MeS(O)— | MeOC(=O)— | H—C | N |
| AZ-1752 | MeSO2— | MeOC(=O)— | H—C | N |
| AZ-1753 | H2N— | MeOC(=O)— | H—C | N |
| AZ-1754 | O2N— | EtOC(=O)— | H—C | N |
| AZ-1755 | F | EtOC(=O)— | H—C | N |
| AZ-1756 | Cl | EtOC(=O)— | H—C | N |
| AZ-1757 | Br | EtOC(=O)— | H—C | N |
| AZ-1758 | I | EtOC(=O)— | H—C | N |
| AZ-1759 | Me | EtOC(=O)— | H—C | N |
| AZ-1760 | Et | EtOC(=O)— | H—C | N |
| AZ-1761 | Pr | EtOC(=O)— | H—C | N |
| AZ-1762 | iPr | EtOC(=O)— | H—C | N |
| AZ-1763 | Bu | EtOC(=O)— | H—C | N |
| AZ-1764 | secBu | EtOC(=O)— | H—C | N |
| AZ-1765 | iBu | EtOC(=O)— | H—C | N |
| AZ-1766 | tBu | EtOC(=O)— | H—C | N |
| AZ-1767 | HOCH2— | EtOC(=O)— | H—C | N |
| AZ-1768 | MeOCH2— | EtOC(=O)— | H—C | N |
| AZ-1769 | F2CH— | EtOC(=O)— | H—C | N |
| AZ-1770 | F3C— | EtOC(=O)— | H—C | N |
| AZ-1771 | Cl3C— | EtOC(=O)— | H—C | N |
| AZ-1772 | H2C=CH— | EtOC(=O)— | H—C | N |
| AZ-1773 | HC≡C— | EtOC(=O)— | H—C | N |
| AZ-1774 | MeC≡C— | EtOC(=O)— | H—C | N |
| AZ-1775 | MeO— | EtOC(=O)— | H—C | N |
| AZ-1776 | EtO— | EtOC(=O)— | H—C | N |
| AZ-1777 | HC(=O)— | EtOC(=O)— | H—C | N |
| AZ-1778 | MeCH(OH)— | EtOC(=O)— | H—C | N |
| AZ-1779 | EtCH(OH)— | EtOC(=O)— | H—C | N |
| AZ-1780 | Me2C(OH)— | EtOC(=O)— | H—C | N |
| AZ-1781 | F3CCF2— | EtOC(=O)— | H—C | N |
| AZ-1782 | F2CHCF2— | EtOC(=O)— | H—C | N |
| AZ-1783 | ClCF2— | EtOC(=O)— | H—C | N |
| AZ-1784 | MeCF2— | EtOC(=O)— | H—C | N |
| AZ-1785 | BrCF2— | EtOC(=O)— | H—C | N |
| AZ-1786 | BrCH2— | EtOC(=O)— | H—C | N |
| AZ-1787 | ClCH2— | EtOC(=O)— | H—C | N |
| AZ-1788 | Br2CH— | EtOC(=O)— | H—C | N |
| AZ-1789 | cPr | EtOC(=O)— | H—C | N |
| AZ-1790 | HC=CCH2— | EtOC(=O)— | H—C | N |
| AZ-1791 | HC≡CCH(OH)— | EtOC(=O)— | H—C | N |
| AZ-1792 | Ac | EtOC(=O)— | H—C | N |
| AZ-1793 | MeOC(=O)— | EtOC(=O)— | H—C | N |
| AZ-1794 | EtOC(=O)— | EtOC(=O)— | H—C | N |
| AZ-1795 | MeS— | EtOC(=O)— | H—C | N |
| AZ-1796 | MeS(O)— | EtOC(=O)— | H—C | N |
| AZ-1797 | MeSO2— | EtOC(=O)— | H—C | N |
| AZ-1798 | H2N— | EtOC(=O)— | H—C | N |
| AZ-1799 | O2N— | MeS— | H—C | N |
| AZ-1800 | F | MeS— | H—C | N |
| AZ-1801 | Cl | MeS— | H—C | N |
| AZ-1802 | Br | MeS— | H—C | N |
| AZ-1803 | I | MeS— | H—C | N |
| AZ-1804 | Me | MeS— | H—C | N |
| AZ-1805 | Et | MeS— | H—C | N |
| AZ-1806 | Pr | MeS— | H—C | N |
| AZ-1807 | iPr | MeS— | H—C | N |

TABLE 3-continued

| | R6 | R7 | Y | Z |
|---|---|---|---|---|
| AZ-1808 | Bu | MeS— | H—C | N |
| AZ-1809 | secBu | MeS— | H—C | N |
| AZ-1810 | iBu | MeS— | H—C | N |
| AZ-1811 | tBL | MeS— | H—C | N |
| AZ-1812 | HOCH2— | MeS— | H—C | N |
| AZ-1813 | MeOCH2— | MeS— | H—C | N |
| AZ-1814 | F2CH— | MeS— | H—C | N |
| AZ-1815 | F3C— | MeS— | H—C | N |
| AZ-1816 | Cl3C— | MeS— | H—C | N |
| AZ-1817 | H2C=CH— | MeS— | H—C | N |
| AZ-1818 | HC≡C— | MeS— | H—C | N |
| AZ-1819 | MeC≡C— | MeS— | H—C | N |
| AZ-1820 | MeO— | MeS— | H—C | N |
| AZ-1821 | EtO— | MeS— | H—C | N |
| AZ-1822 | HC(=O)— | MeS— | H—C | N |
| AZ-1823 | MeCH(OH)— | MeS— | H—C | N |
| AZ-1824 | EtCH(OH)— | MeS— | H—C | N |
| AZ-1825 | Me2C(OH)— | MeS— | H—C | N |
| AZ-1826 | F3CCF2— | MeS— | H—C | N |
| AZ-1827 | F2CHCF2— | MeS— | H—C | N |
| AZ-1828 | ClCF2— | MeS— | H—C | N |
| AZ-1829 | MeCF2— | MeS— | H—C | N |
| AZ-1830 | BrCF2— | MeS— | H—C | N |
| AZ-1831 | BrCH2— | MeS— | H—C | N |
| AZ-1832 | ClCH2— | MeS— | H—C | N |
| AZ-1833 | Br2CH— | MeS— | H—C | N |
| AZ-1834 | cPr | MeS— | H—C | N |
| AZ-1835 | HC≡CCH2— | MeS— | H—C | N |
| AZ-1836 | HC≡CCH(OH)— | MeS— | H—C | N |
| AZ-1837 | Ac | MeS— | H—C | N |
| AZ-1838 | MeOC(=O)— | MeS— | H—C | N |
| AZ-1839 | EtOC(=O)— | MeS— | H—C | N |
| AZ-1840 | MeS— | MeS— | H—C | N |
| AZ-1841 | MeS(O)— | MeS— | H—C | N |
| AZ-1842 | MeSO2— | MeS— | H—C | N |
| AZ-1843 | H2N— | MeS— | H—C | N |
| AZ-1844 | O2N— | MeS(O)— | H—C | N |
| AZ-1845 | F | MeS(O)— | H—C | N |
| AZ-1846 | Cl | MeS(O)— | H—C | N |
| AZ-1847 | Br | MeS(O)— | H—C | N |
| AZ-1848 | I | MeS(O)— | H—C | N |
| AZ-1849 | Me | MeS(O)— | H—C | N |
| AZ-1850 | Et | MeS(O)— | H—C | N |
| AZ-1851 | Pr | MeS(O)— | H—C | N |
| AZ-1852 | iPr | MeS(O)— | H—C | N |
| AZ-1853 | Bu | MeS(O)— | H—C | N |
| AZ-1854 | secBu | MeS(O)— | H—C | N |
| AZ-1855 | iBu | MeS(O)— | H—C | N |
| AZ-1856 | tBu | MeS(O)— | H—C | N |
| AZ-1857 | HOCH2— | MeS(O)— | H—C | N |
| AZ-1858 | MeOCH2— | MeS(O)— | H—C | N |
| AZ-1859 | F2CH— | MeS(O)— | H—C | N |
| AZ-1860 | F3C— | MeS(O)— | H—C | N |
| AZ-1861 | Cl3C— | MeS(O)— | H—C | N |
| AZ-1862 | H2C=CH— | MeS(O)— | H—C | N |
| AZ-1863 | HC≡C— | MeS(O)— | H—C | N |
| AZ-1864 | MeC≡C— | MeS(O)— | H—C | N |
| AZ-1865 | MeO— | MeS(O)— | H—C | N |
| AZ-1866 | EtO— | MeS(O)— | H—C | N |
| AZ-1867 | HC(=O)— | MeS(O)— | H—C | N |
| AZ-1868 | MeCH(OH)— | MeS(O)— | H—C | N |
| AZ-1869 | EtCH(OH)— | MeS(O)— | H—C | N |
| AZ-1870 | Me2C(OH)— | MeS(O)— | H—C | N |
| AZ-1871 | F3CCF2— | MeS(O)— | H—C | N |
| AZ-1872 | F2CHCF2— | MeS(O)— | H—C | N |
| AZ-1873 | ClCF2— | MeS(O)— | H—C | N |
| AZ-1874 | MeCF2— | MeS(O)— | H—C | N |
| AZ-1875 | BrCF2— | MeS(O)— | H—C | N |
| AZ-1876 | BrCH2— | MeS(O)— | H—C | N |
| AZ-1877 | ClCH2— | MeS(O)— | H—C | N |
| AZ-1878 | Br2CH— | MeS(O)— | H—C | N |
| AZ-1879 | cPr | MeS(O)— | H—C | N |
| AZ-1880 | HC≡CCH2— | MeS(O)— | H—C | N |
| AZ-1881 | HC≡CCH(OH)— | MeS(O)— | H—C | N |
| AZ-1882 | Ac | MeS(O)— | H—C | N |
| AZ-1883 | MeOC(=O)— | MeS(O)— | H—C | N |
| AZ-1884 | EtOC(=O)— | MeS(O)— | H—C | N |
| AZ-1885 | MeS— | MeS(O)— | H—C | N |

TABLE 3-continued

| | R6 | R7 | Y | Z |
|---|---|---|---|---|
| AZ-1886 | MeS(O)— | MeS(O)— | H—C | N |
| AZ-1887 | MeSO2— | MeS(O)— | H—C | N |
| AZ-1888 | H2N— | MeS(O)— | H—C | N |
| AZ-1889 | O2N— | MeSO2— | H—C | N |
| AZ-1890 | F | MeSO2— | H—C | N |
| AZ-1891 | Cl | MeSO2— | H—C | N |
| AZ-1892 | Br | MeSO2— | H—C | N |
| AZ-1893 | I | MeSO2— | H—C | N |
| AZ-1894 | Me | MeSO2— | H—C | N |
| AZ-1895 | Et | MeSO2— | H—C | N |
| AZ-1896 | Pr | MeSO2— | H—C | N |
| AZ-1897 | iPr | MeSO2— | H—C | N |
| AZ-1898 | Bu | MeSO2— | H—C | N |
| AZ-1899 | secBu | MeSO2— | H—C | N |
| AZ-1900 | iBu | MeSO2— | H—C | N |
| AZ-1901 | tBu | MeSO2— | H—C | N |
| AZ-1902 | HOCH2— | MeSO2— | H—C | N |
| AZ-1903 | MeOCH2— | MeSO2— | H—C | N |
| AZ-1904 | F2CH— | MeSO2— | H—C | N |
| AZ-1905 | F3C— | MeSO2— | H—C | N |
| AZ-1906 | Cl3C— | MeSO2— | H—C | N |
| AZ-1907 | H2C=CH— | MeSO2— | H—C | N |
| AZ-1908 | HC≡C— | MeSO2— | H—C | N |
| AZ-1909 | MeC≡C— | MeSO2— | H—C | N |
| AZ-1910 | MeO— | MeSO2— | H—C | N |
| AZ-1911 | EtO— | MeSO2— | H—C | N |
| AZ-1912 | HC(=O)— | MeSO2— | H—C | N |
| AZ-1913 | MeCH(OH)— | MeSO2— | H—C | N |
| AZ-1914 | EtCH(OH)— | MeSO2— | H—C | N |
| AZ-1915 | Me2C(OH)— | MeSO2— | H—C | N |
| AZ-1916 | F3CCF2— | MeSO2— | H—C | N |
| AZ-1917 | F2CHCF2— | MeSO2— | H—C | N |
| AZ-1918 | ClCF2— | MeSO2— | H—C | N |
| AZ-1919 | MeCF2— | MeSO2— | H—C | N |
| AZ-1920 | BrCF2— | MeSO2— | H—C | N |
| AZ-1921 | BrCH2— | MeSO2— | H—C | N |
| AZ-1922 | ClCH2— | MeSO2— | H—C | N |
| AZ-1923 | Br2CH— | MeSO2— | H—C | N |
| AZ-1924 | cPr | MeSO2— | H—C | N |
| AZ-1925 | HC≡CCH2— | MeSO2— | H—C | N |
| AZ-1926 | HC≡CCH(OH)— | MeSO2— | H—C | N |
| AZ-1927 | Ac | MeSO2— | H—C | N |
| AZ-1928 | MeOC(=O)— | MeSO2— | H—C | N |
| AZ-1929 | EtOC(=O)— | MeSO2— | H—C | N |
| AZ-1930 | MeS— | MeSO2— | H—C | N |
| AZ-1931 | MeS(O)— | MeSO2— | H—C | N |
| AZ-1932 | MeSO2— | MeSO2— | H—C | N |
| AZ-1933 | H2N— | MeSO2— | H—C | N |
| AZ-1934 | tBu | Pr | H—C | N |
| AZ-1935 | tBu | iPr | H—C | N |
| AZ-1936 | tBu | Bu | H—C | N |
| AZ-1937 | tBu | secBu | H—C | N |
| AZ-1938 | tBu | iBu | H—C | N |
| AZ-1939 | tBu | tBu | H—C | N |
| AZ-1940 | tBu | Cl3C— | H—C | N |
| AZ-1941 | tBu | MeO— | H—C | N |
| AZ-1942 | tBu | EtO— | H—C | N |
| AZ-1943 | tBu | H | Me—C | N |
| AZ-1944 | tBu | H | Et—C | N |
| AZ-1945 | iPr | Pr | H—C | N |
| AZ-1946 | iPr | iPr | H—C | N |
| AZ-1947 | iPr | Bu | H—C | N |
| AZ-1948 | iPr | secBu | H—C | N |
| AZ-1949 | iPr | iBu | H—C | N |
| AZ-1950 | iPr | tBu | H—C | N |
| AZ-1951 | iPr | Cl3C— | H—C | N |
| AZ-1952 | iPr | MeO— | H—C | N |
| AZ-1953 | iPr | EtO— | H—C | N |
| AZ-1954 | iPr | H | Me—C | N |
| AZ-1955 | iPr | H | Et—C | N |
| AZ-1956 | Et | H | Me—C | N |
| AZ-1957 | ClCH2— | H | H—C | N |
| AZ-1958 | H | ClCH2— | H—C | N |
| AZ-1959 | H | H | ClCH2—C | N |
| AZ-1960 | O2N— | ClCH2— | H—C | N |
| AZ-1961 | F | ClCH2— | H—C | N |
| AZ-1962 | Cl | ClCH2— | H—C | N |
| AZ-1963 | Br | ClCH2— | H—C | N |

TABLE 3-continued

|  | R6 | R7 | Y | Z |
|---|---|---|---|---|
| AZ-1964 | I | ClCH2— | H—C | N |
| AZ-1965 | Me | ClCH2— | H—C | N |
| AZ-1966 | Et | ClCH2— | H—C | N |
| AZ-1967 | Pr | ClCH2— | H—C | N |
| AZ-1968 | iPr | ClCH2— | H—C | N |
| AZ-1969 | Bu | ClCH2— | H—C | N |
| AZ-1970 | secBu | ClCH2— | H—C | N |
| AZ-1971 | iBu | ClCH2— | H—C | N |
| AZ-1972 | tBu | ClCH2— | H—C | N |
| AZ-1973 | HOCH2— | ClCH2— | H—C | N |
| AZ-1974 | MeOCH2— | ClCH2— | H—C | N |
| AZ-1975 | F2CH— | ClCH2— | H—C | N |
| AZ-1976 | F3C— | ClCH2— | H—C | N |
| AZ-1977 | Cl3C— | ClCH2— | H—C | N |
| AZ-1978 | H2C=CH— | ClCH2— | H—C | N |
| AZ-1979 | HC≡C— | ClCH2— | H—C | N |
| AZ-1980 | MeC≡C— | ClCH2— | H—C | N |
| AZ-1981 | MeO— | ClCH2— | H—C | N |
| AZ-1982 | EtO— | ClCH2— | H—C | N |
| AZ-1983 | HC(=O)— | ClCH2— | H—C | N |
| AZ-1984 | MeCH(OH)— | ClCH2— | H—C | N |
| AZ-1985 | EtCH(OH)— | ClCH2— | H—C | N |
| AZ-1986 | Me2C(OH)— | ClCH2— | H—C | N |
| AZ-1987 | F3CCF2— | ClCH2— | H—C | N |
| AZ-1988 | F2CHCF2— | ClCH2— | H—C | N |
| AZ-1989 | ClCF2— | ClCH2— | H—C | N |
| AZ-1990 | MeCF2— | ClCH2— | H—C | N |
| AZ-1991 | BrCF2— | ClCH2— | H—C | N |
| AZ-1992 | BrCH2— | ClCH2— | H—C | N |
| AZ-1993 | ClCH2— | ClCH2— | H—C | N |
| AZ-1994 | Br2CH— | ClCH2— | H—C | N |
| AZ-1995 | cPr | ClCH2— | H—C | N |
| AZ-1996 | HC≡CCH2— | ClCH2— | H—C | N |
| AZ-1997 | HC≡CCH(OH)— | ClCH2— | H—C | N |
| AZ-1998 | Ac | ClCH2— | H—C | N |
| AZ-1999 | MeOC(=O)— | ClCH2— | H—C | N |
| AZ-2000 | EtOC(=O)— | ClCH2— | H—C | N |
| AZ-2001 | MeS— | ClCH2— | H—C | N |
| AZ-2002 | MeS(O)— | ClCH2— | H—C | N |
| AZ-2003 | MeSO2— | ClCH2— | H—C | N |
| AZ-2004 | H2N— | ClCH2— | H—C | N |
| AZ-2005 | ClCH2— | Pr | H—C | N |
| AZ-2006 | ClCH2— | iPr | H—C | N |
| AZ-2007 | ClCH2— | Bu | H—C | N |
| AZ-2008 | ClCH2— | secBu | H—C | N |
| AZ-2009 | ClCH2— | iBu | H—C | N |
| AZ-2010 | ClCH2— | tBu | H—C | N |
| AZ-2011 | ClCH2— | Cl3C— | H—C | N |
| AZ-2012 | ClCH2— | MeO— | H—C | N |
| AZ-2013 | ClCH2— | EtO— | H—C | N |
| AZ-2014 | ClCH2— | F3CCF2— | H—C | N |
| AZ-2015 | O2N— | iPr | H—C | N |
| AZ-2016 | F | iPr | H—C | N |
| AZ-2017 | Cl | iPr | H—C | N |
| AZ-2018 | Br | iPr | H—C | N |
| AZ-2019 | I | iPr | H—C | N |
| AZ-2020 | Me | iPr | H—C | N |
| AZ-2021 | Et | iPr | H—C | N |
| AZ-2022 | Pr | iPr | H—C | N |
| AZ-2023 | Bu | iPr | H—C | N |
| AZ-2024 | secBu | iPr | H—C | N |
| AZ-2025 | iBu | iPr | H—C | N |
| AZ-2026 | HOCH2— | iPr | H—C | N |
| AZ-2027 | MeCH(OH)— | iPr | H—C | N |
| AZ-2028 | EtCH(OH)— | iPr | H—C | N |
| AZ-2029 | Me2C(OH)— | iPr | H—C | N |
| AZ-2030 | MeOCH2— | iPr | H—C | N |
| AZ-2031 | F2CH— | iPr | H—C | N |
| AZ-2032 | F3C— | iPr | H—C | N |
| AZ-2033 | Cl3C— | iPr | H—C | N |
| AZ-2034 | F2CHCF2— | iPr | H—C | N |
| AZ-2035 | ClCF2— | iPr | H—C | N |
| AZ-2036 | MeCF2— | iPr | H—C | N |
| AZ-2037 | BrCF2— | iPr | H—C | N |
| AZ-2038 | BrCH2— | iPr | H—C | N |
| AZ-2039 | Br2CH— | iPr | H—C | N |
| AZ-2040 | cPr | iPr | H—C | N |
| AZ-2041 | H2C=CH— | iPr | H—C | N |

TABLE 3-continued

|  | R6 | R7 | Y | Z |
|---|---|---|---|---|
| AZ-2042 | HC≡C— | iPr | H—C | N |
| AZ-2043 | MeC≡C— | iPr | H—C | N |
| AZ-2044 | HC≡CCH2— | iPr | H—C | N |
| AZ-2045 | HC≡CCH(OH)— | iPr | H—C | N |
| AZ-2046 | MeO— | iPr | H—C | N |
| AZ-2047 | EtO— | iPr | H—C | N |
| AZ-2048 | HC(=O)— | iPr | H—C | N |
| AZ-2049 | Ac | iPr | H—C | N |
| AZ-2050 | MeOC(=O)— | iPr | H—C | N |
| AZ-2051 | EtOC(=O)— | iPr | H—C | N |
| AZ-2052 | MeS— | iPr | H—C | N |
| AZ-2053 | MeS(O)— | iPr | H—C | N |
| AZ-2054 | MeSO2— | iPr | H—C | N |
| AZ-2055 | H2N— | iPr | H—C | N |
| AZ-2056 | Me | Pr | H—C | N |
| AZ-2057 | Me | Bu | H—C | N |
| AZ-2058 | Me | secBu | H—C | N |
| AZ-2059 | Me | iBu | H—C | N |
| AZ-2060 | Me | tBu | H—C | N |
| AZ-2061 | Ac | Pr | H—C | N |
| AZ-2062 | Ac | Bu | H—C | N |
| AZ-2063 | Ac | secBu | H—C | N |
| AZ-2064 | Ac | iBu | H—C | N |
| AZ-2065 | Ac | tBu | H—C | N |
| AZ-2066 | Ac | Cl3C— | H—C | N |
| AZ-2067 | Ac | MeO— | H—C | N |
| AZ-2068 | Ac | EtO— | H—C | N |
| AZ-2069 | Ac | F3CCF2— | H—C | N |
| AZ-2070 | O2N— | Br | H—C | N |
| AZ-2071 | Br | Pr | H—C | N |
| AZ-2072 | Br | Bu | H—C | N |
| AZ-2073 | Br | secBu | H—C | N |
| AZ-2074 | Br | iBu | H—C | N |
| AZ-2075 | Br | tBu | H—C | N |
| AZ-2076 | Br | Cl3C— | H—C | N |
| AZ-2077 | Br | MeO— | H—C | N |
| AZ-2078 | Br | EtO— | H—C | N |
| AZ-2079 | Br | F3CCF2— | H—C | N |
| AZ-2080 | Br2CH— | Pr | H—C | N |
| AZ-2081 | Br2CH— | Bu | H—C | N |
| AZ-2082 | Br2CH— | secBu | H—C | N |
| AZ-2083 | Br2CH— | iBu | H—C | N |
| AZ-2084 | Br2CH— | tBu | H—C | N |
| AZ-2085 | Br2CH— | Cl3C— | H—C | N |
| AZ-2086 | Br2CH— | MeO— | H—C | N |
| AZ-2087 | Br2CH— | EtO— | H—C | N |
| AZ-2088 | Br2CH— | F3CCF2— | H—C | N |
| AZ-2089 | BrCF2— | Pr | H—C | N |
| AZ-2090 | BrCF2— | Bu | H—C | N |
| AZ-2091 | BrCF2— | secBu | H—C | N |
| AZ-2092 | BrCF2— | iBu | H—C | N |
| AZ-2093 | BrCF2— | tBu | H—C | N |
| AZ-2094 | BrCF2— | Cl3C— | H—C | N |
| AZ-2095 | BrCF2— | MeO— | H—C | N |
| AZ-2096 | BrCF2— | EtO— | H—C | N |
| AZ-2097 | BrCF2— | F3CCF2— | H—C | N |
| AZ-2098 | BrCH2— | Pr | H—C | N |
| AZ-2099 | BrCH2— | Bu | H—C | N |
| AZ-2100 | BrCH2— | secBu | H—C | N |
| AZ-2101 | BrCH2— | iBu | H—C | N |
| AZ-2102 | BrCH2— | tBu | H—C | N |
| AZ-2103 | BrCH2— | Cl3C— | H—C | N |
| AZ-2104 | BrCH2— | MeO— | H—C | N |
| AZ-2105 | BrCH2— | EtO— | H—C | N |
| AZ-2106 | BrCH2— | F3CCF2— | H—C | N |
| AZ-2107 | O2N— | Cl | H—C | N |
| AZ-2108 | Cl | Pr | H—C | N |
| AZ-2109 | Cl | Bu | H—C | N |
| AZ-2110 | Cl | secBu | H—C | N |
| AZ-2111 | Cl | iBu | H—C | N |
| AZ-2112 | Cl | tBu | H—C | N |
| AZ-2113 | Cl | Cl3C— | H—C | N |
| AZ-2114 | Cl | MeO— | H—C | N |
| AZ-2115 | Cl | EtO— | H—C | N |
| AZ-2116 | Cl | F3CCF2— | H—C | N |
| AZ-2117 | O2N— | Cl3C— | H—C | N |
| AZ-2118 | F | Cl3C— | H—C | N |
| AZ-2119 | I | Cl3C— | H—C | N |

TABLE 3-continued

|  | R6 | R7 | Y | Z |
|---|---|---|---|---|
| AZ-2120 | Me | Cl3C— | H—C | N |
| AZ-2121 | Et | Cl3C— | H—C | N |
| AZ-2122 | Pr | Cl3C— | H—C | N |
| AZ-2123 | Bu | Cl3C— | H—C | N |
| AZ-2124 | secBu | Cl3C— | H—C | N |
| AZ-2125 | iBu | Cl3C— | H—C | N |
| AZ-2126 | HOCH2— | Cl3C— | H—C | N |
| AZ-2127 | MeCH(OH)— | Cl3C— | H—C | N |
| AZ-2128 | EtCH(OH)— | Cl3C— | H—C | N |
| AZ-2129 | Me2C(OH)— | Cl3C— | H—C | N |
| AZ-2130 | MeOCH2— | Cl3C— | H—C | N |
| AZ-2131 | F2CH— | Cl3C— | H—C | N |
| AZ-2132 | F3C— | Cl3C— | H—C | N |
| AZ-2133 | Cl3C— | Cl3C— | H—C | N |
| AZ-2134 | F2CHCF2— | Cl3C— | H—C | N |
| AZ-2135 | ClCF2— | Cl3C— | H—C | N |
| AZ-2136 | MeCF2— | Cl3C— | H—C | N |
| AZ-2137 | cPr | Cl3C— | H—C | N |
| AZ-2138 | H2C=CH— | Cl3C— | H—C | N |
| AZ-2139 | HC≡C— | Cl3C— | H—C | N |
| AZ-2140 | MeC≡C— | Cl3C— | H—C | N |
| AZ-2141 | HC≡CCH2— | Cl3C— | H—C | N |
| AZ-2142 | HC≡CCH(OH)— | Cl3C— | H—C | N |
| AZ-2143 | MeO— | Cl3C— | H—C | N |
| AZ-2144 | EtO— | Cl3C— | H—C | N |
| AZ-2145 | HC(=O)— | Cl3C— | H—C | N |
| AZ-2146 | MeOC(=O)— | Cl3C— | H—C | N |
| AZ-2147 | EtOC(=O)— | Cl3C— | H—C | N |
| AZ-2148 | MeS— | Cl3C— | H—C | N |
| AZ-2149 | MeS(O)— | Cl3C— | H—C | N |
| AZ-2150 | MeSO2— | Cl3C— | H—C | N |
| AZ-2151 | H2N— | Cl3C— | H—C | N |
| AZ-2152 | F3CCF2— | Cl3C— | H—C | N |
| AZ-2153 | Cl3C— | Pr | H—C | N |
| AZ-2154 | Cl3C— | Bu | H—C | N |
| AZ-2155 | Cl3C— | secBu | H—C | N |
| AZ-2156 | Cl3C— | iBu | H—C | N |
| AZ-2157 | Cl3C— | tBu | H—C | N |
| AZ-2158 | Cl3C— | MeO— | H—C | N |
| AZ-2159 | Cl3C— | EtO— | H—C | N |
| AZ-2160 | Cl3C— | F3CCF2— | H—C | N |
| AZ-2161 | ClCF2— | Pr | H—C | N |
| AZ-2162 | ClCF2— | Bu | H—C | N |
| AZ-2163 | ClCF2— | secBu | H—C | N |
| AZ-2164 | ClCF2— | iBu | H—C | N |
| AZ-2165 | ClCF2— | tBu | H—C | N |
| AZ-2166 | ClCF2— | MeO— | H—C | N |
| AZ-2167 | ClCF2— | EtO— | H—C | N |
| AZ-2168 | ClCF2— | F3CCF2— | H—C | N |
| AZ-2169 | cPr | Pr | H—C | N |
| AZ-2170 | cPr | Bu | H—C | N |
| AZ-2171 | cPr | secBu | H—C | N |
| AZ-2172 | cPr | iBu | H—C | N |
| AZ-2173 | cPr | tBu | H—C | N |
| AZ-2174 | cPr | MeO— | H—C | N |
| AZ-2175 | cPr | EtO— | H—C | N |
| AZ-2176 | cPr | F3CCF2— | H—C | N |
| AZ-2177 | O2N— | Et | H—C | N |
| AZ-2178 | Et | Pr | H—C | N |
| AZ-2179 | Et | Bu | H—C | N |
| AZ-2180 | Et | secBu | H—C | N |
| AZ-2181 | Et | iBu | H—C | N |
| AZ-2182 | Et | tBu | H—C | N |
| AZ-2183 | Et | MeO— | H—C | N |
| AZ-2184 | Et | EtO— | H—C | N |
| AZ-2185 | Et | F3CCF2— | H—C | N |
| AZ-2186 | EtCH(OH)— | Pr | H—C | N |
| AZ-2187 | EtCH(OH)— | Bu | H—C | N |
| AZ-2188 | EtCH(OH)— | secBu | H—C | N |
| AZ-2189 | EtCH(OH)— | iBu | H—C | N |
| AZ-2190 | EtCH(OH)— | tBu | H—C | N |
| AZ-2191 | EtCH(OH)— | MeO— | H—C | N |
| AZ-2192 | EtCH(OH)— | EtO— | H—C | N |
| AZ-2193 | EtCH(OH)— | F3CCF2— | H—C | N |
| AZ-2194 | EtOC(=O)— | Pr | H—C | N |
| AZ-2195 | EtOC(=O)— | Bu | H—C | N |
| AZ-2196 | EtOC(=O)— | secBu | H—C | N |
| AZ-2197 | EtOC(=O)— | iBu | H—C | N |

TABLE 3-continued

|  | R6 | R7 | Y | Z |
|---|---|---|---|---|
| AZ-2198 | EtOC(=O)— | tBu | H—C | N |
| AZ-2199 | EtOC(=O)— | MeO— | H—C | N |
| AZ-2200 | EtOC(=O)— | EtO— | H—C | N |
| AZ-2201 | EtOC(=O)— | F3CCF2— | H—C | N |
| AZ-2202 | F | Pr | H—C | N |
| AZ-2203 | F | Bu | H—C | N |
| AZ-2204 | F | secBu | H—C | N |
| AZ-2205 | F | iBu | H—C | N |
| AZ-2206 | F | tBu | H—C | N |
| AZ-2207 | F | MeO— | H—C | N |
| AZ-2208 | F | EtO— | H—C | N |
| AZ-2209 | F | F3CCF2— | H—C | N |
| AZ-2210 | F2CH— | Pr | H—C | N |
| AZ-2211 | F2CH— | Bu | H—C | N |
| AZ-2212 | F2CH— | secBu | H—C | N |
| AZ-2213 | F2CH— | iBu | H—C | N |
| AZ-2214 | F2CH— | tBu | H—C | N |
| AZ-2215 | F2CH— | MeO— | H—C | N |
| AZ-2216 | F2CH— | EtO— | H—C | N |
| AZ-2217 | F2CH— | F3CCF2— | H—C | N |
| AZ-2218 | F2CHCF2— | Pr | H—C | N |
| AZ-2219 | F2CHCF2— | Bu | H—C | N |
| AZ-2220 | F2CHCF2— | secBu | H—C | N |
| AZ-2221 | F2CHCF2— | iBu | H—C | N |
| AZ-2222 | F2CHCF2— | tBu | H—C | N |
| AZ-2223 | F2CHCF2— | MeO— | H—C | N |
| AZ-2224 | F2CHCF2— | EtO— | H—C | N |
| AZ-2225 | F2CHCF2— | F3CCF2— | H—C | N |
| AZ-2226 | F3C— | Pr | H—C | N |
| AZ-2227 | F3C— | Bu | H—C | N |
| AZ-2228 | F3C— | secBu | H—C | N |
| AZ-2229 | F3C— | iBu | H—C | N |
| AZ-2230 | F3C— | tBu | H—C | N |
| AZ-2231 | F3C— | MeO— | H—C | N |
| AZ-2232 | F3C— | EtO— | H—C | N |
| AZ-2233 | F3C— | F3CCF2— | H—C | N |
| AZ-2234 | F3CCF2— | iPr | H—C | N |
| AZ-2235 | F3CCF2— | Pr | H—C | N |
| AZ-2236 | F3CCF2— | Bu | H—C | N |
| AZ-2237 | F3CCF2— | secBu | H—C | N |
| AZ-2238 | F3CCF2— | iBu | H—C | N |
| AZ-2239 | F3CCF2— | tBu | H—C | N |
| AZ-2240 | F3CCF2— | MeO— | H—C | N |
| AZ-2241 | F3CCF2— | EtO— | H—C | N |
| AZ-2242 | F3CCF2— | F3CCF2— | H—C | N |
| AZ-2243 | F3CCF2— | iPr | H—C | N |
| AZ-2244 | F3CCF2— | Pr | H—C | N |
| AZ-2245 | F3CCF2— | Bu | H—C | N |
| AZ-2246 | F3CCF2— | secBu | H—C | N |
| AZ-2247 | F3CCF2— | iBu | H—C | N |
| AZ-2248 | F3CCF2— | tBu | H—C | N |
| AZ-2249 | F3CCF2— | MeO— | H—C | N |
| AZ-2250 | F3CCF2— | EtO— | H—C | N |
| AZ-2251 | F3CCF2— | F3CCF2— | H—C | N |
| AZ-2252 | H2C=CH— | Pr | H—C | N |
| AZ-2253 | H2C=CH— | Bu | H—C | N |
| AZ-2254 | H2C=CH— | secBu | H—C | N |
| AZ-2255 | H2C=CH— | iBu | H—C | N |
| AZ-2256 | H2C=CH— | tBu | H—C | N |
| AZ-2257 | H2C=CH— | MeO— | H—C | N |
| AZ-2258 | H2C=CH— | EtO— | H—C | N |
| AZ-2259 | H2C=CH— | F3CCF2— | H—C | N |
| AZ-2260 | H2N— | Pr | H—C | N |
| AZ-2261 | H2N— | Bu | H—C | N |
| AZ-2262 | H2N— | secBu | H—C | N |
| AZ-2263 | H2N— | iBu | H—C | N |
| AZ-2264 | H2N— | tBu | H—C | N |
| AZ-2265 | H2N— | MeO— | H—C | N |
| AZ-2266 | H2N— | EtO— | H—C | N |
| AZ-2267 | H2N— | F3CCF2— | H—C | N |
| AZ-2268 | HC(=O)— | Pr | H—C | N |
| AZ-2269 | HC(=O)— | Bu | H—C | N |
| AZ-2270 | HC(=O)— | secBu | H—C | N |
| AZ-2271 | HC(=O)— | iBu | H—C | N |
| AZ-2272 | HC(=O)— | tBu | H—C | N |
| AZ-2273 | HC(=O)— | MeO— | H—C | N |
| AZ-2274 | HC(=O)— | EtO— | H—C | N |
| AZ-2275 | HC(=O)— | F3CCF2— | H—C | N |

TABLE 3-continued

| | R6 | R7 | Y | Z |
|---|---|---|---|---|
| AZ-2276 | HC≡C— | Pr | H—C | N |
| AZ-2277 | HC≡C— | Bu | H—C | N |
| AZ-2278 | HC≡C— | secBu | H—C | N |
| AZ-2279 | HC≡C— | iBu | H—C | N |
| AZ-2280 | HC≡C— | tBu | H—C | N |
| AZ-2281 | HC≡C— | MeO— | H—C | N |
| AZ-2282 | HC≡C— | EtO— | H—C | N |
| AZ-2283 | HC≡C— | F3CCF2— | H—C | N |
| AZ-2284 | HC≡CCH(OH)— | Pr | H—C | N |
| AZ-2285 | HC≡CCH(OH)— | Bu | H—C | N |
| AZ-2286 | HC≡CCH(OH)— | secBu | H—C | N |
| AZ-2287 | HC≡CCH(OH)— | iBu | H—C | N |
| AZ-2288 | HC≡CCH(OH)— | tBu | H—C | N |
| AZ-2289 | HC≡CCH(OH)— | MeO— | H—C | N |
| AZ-2290 | HC≡CCH(OH)— | EtO— | H—C | N |
| AZ-2291 | HC≡CCH(OH)— | F3CCF2— | H—C | N |
| AZ-2292 | HC≡CCH2— | Pr | H—C | N |
| AZ-2293 | HC≡CCH2— | Bu | H—C | N |
| AZ-2294 | HC≡CCH2— | secBu | H—C | N |
| AZ-2295 | HC≡CCH2— | iBu | H—C | N |
| AZ-2296 | HC≡CCH2— | tBu | H—C | N |
| AZ-2297 | HC≡CCH2— | MeO— | H—C | N |
| AZ-2298 | HC≡CCH2— | EtO— | H—C | N |
| AZ-2299 | HC≡CCH2— | F3CCF2— | H—C | N |
| AZ-2300 | HOCH2— | Pr | H—C | N |
| AZ-2301 | HOCH2— | Bu | H—C | N |
| AZ-2302 | HOCH2— | secBu | H—C | N |
| AZ-2303 | HOCH2— | iBu | H—C | N |
| AZ-2304 | HOCH2— | tBu | H—C | N |
| AZ-2305 | HOCH2— | MeO— | H—C | N |
| AZ-2306 | HOCH2— | EtO— | H—C | N |
| AZ-2307 | HOCH2— | F3CCF2— | H—C | N |
| AZ-2308 | iBu | Pr | H—C | N |
| AZ-2309 | iBu | Bu | H—C | N |
| AZ-2310 | iBu | secBu | H—C | N |
| AZ-2311 | iBu | iBu | H—C | N |
| AZ-2312 | iBu | tBu | H—C | N |
| AZ-2313 | iBu | MeO— | H—C | N |
| AZ-2314 | iBu | EtO— | H—C | N |
| AZ-2315 | iBu | F3CCF2— | H—C | N |
| AZ-2316 | iPr | F3CCF2— | H—C | N |
| AZ-2317 | Me | MeO— | H—C | N |
| AZ-2318 | Me | EtO— | H—C | N |
| AZ-2319 | Me | F3CCF2— | H—C | N |
| AZ-2320 | Me2C(OH)— | Pr | H—C | N |
| AZ-2321 | Me2C(OH)— | Bu | H—C | N |
| AZ-2322 | Me2C(OH)— | secBu | H—C | N |
| AZ-2323 | Me2C(OH)— | iBu | H—C | N |
| AZ-2324 | Me2C(OH)— | tBu | H—C | N |
| AZ-2325 | Me2C(OH)— | MeO— | H—C | N |
| AZ-2326 | Me2C(OH)— | EtO— | H—C | N |
| AZ-2327 | Me2C(OH)— | F3CCF2— | H—C | N |
| AZ-2328 | MeC≡C— | Pr | H—C | N |
| AZ-2329 | MeC≡C— | Bu | H—C | N |
| AZ-2330 | MeC≡C— | secBu | H—C | N |
| AZ-2331 | MeC≡C— | iBu | H—C | N |
| AZ-2332 | MeC≡C— | tBu | H—C | N |
| AZ-2333 | MeC≡C— | MeO— | H—C | N |
| AZ-2334 | MeC≡C— | EtO— | H—C | N |
| AZ-2335 | MeC≡C— | F3CCF2— | H—C | N |
| AZ-2336 | MeCF2— | Pr | H—C | N |
| AZ-2337 | MeCF2— | Bu | H—C | N |
| AZ-2338 | MeCF2— | secBu | H—C | N |
| AZ-2339 | MeCF2— | iBu | H—C | N |
| AZ-2340 | MeCF2— | tBu | H—C | N |
| AZ-2341 | MeCF2— | MeO— | H—C | N |
| AZ-2342 | MeCF2— | EtO— | H—C | N |
| AZ-2343 | MeCF2— | F3CCF2— | H—C | N |
| AZ-2344 | MeCH(OH)— | Pr | H—C | N |
| AZ-2345 | MeCH(OH)— | Bu | H—C | N |
| AZ-2346 | MeCH(OH)— | secBu | H—C | N |
| AZ-2347 | MeCH(OH)— | iBu | H—C | N |
| AZ-2348 | MeCH(OH)— | tBu | H—C | N |
| AZ-2349 | MeCH(OH)— | MeO— | H—C | N |
| AZ-2350 | MeCH(OH)— | EtO— | H—C | N |
| AZ-2351 | MeCH(OH)— | F3CCF2— | H—C | N |
| AZ-2352 | MeO— | Pr | H—C | N |
| AZ-2353 | MeO— | Bu | H—C | N |

TABLE 3-continued

| | R6 | R7 | Y | Z |
|---|---|---|---|---|
| AZ-2354 | MeO— | secBu | H—C | N |
| AZ-2355 | MeO— | iBu | H—C | N |
| AZ-2356 | MeO— | tBu | H—C | N |
| AZ-2357 | MeO— | MeO— | H—C | N |
| AZ-2358 | MeO— | EtO— | H—C | N |
| AZ-2359 | MeO— | F3CCF2— | H—C | N |
| AZ-2360 | MeOC(=O)— | Pr | H—C | N |
| AZ-2361 | MeOC(=O)— | Bu | H—C | N |
| AZ-2362 | MeOC(=O)— | secBu | H—C | N |
| AZ-2363 | MeOC(=O)— | iBu | H—C | N |
| AZ-2364 | MeOC(=O)— | tBu | H—C | N |
| AZ-2365 | MeOC(=O)— | MeO— | H—C | N |
| AZ-2366 | MeOC(=O)— | EtO— | H—C | N |
| AZ-2367 | MeOC(=O)— | F3CCF2— | H—C | N |
| AZ-2368 | MeOCH2— | Pr | H—C | N |
| AZ-2369 | MeOCH2— | Bu | H—C | N |
| AZ-2370 | MeOCH2— | secBu | H—C | N |
| AZ-2371 | MeOCH2— | iBu | H—C | N |
| AZ-2372 | MeOCH2— | tBu | H—C | N |
| AZ-2373 | MeOCH2— | MeO— | H—C | N |
| AZ-2374 | MeOCH2— | EtO— | H—C | N |
| AZ-2375 | MeOCH2— | F3CCF2— | H—C | N |
| AZ-2376 | MeS— | Pr | H—C | N |
| AZ-2377 | MeS— | Bu | H—C | N |
| AZ-2378 | MeS— | secBu | H—C | N |
| AZ-2379 | MeS— | iBu | H—C | N |
| AZ-2380 | MeS— | tBu | H—C | N |
| AZ-2381 | MeS— | MeO— | H—C | N |
| AZ-2382 | MeS— | EtO— | H—C | N |
| AZ-2383 | MeS— | F3CCF2— | H—C | N |
| AZ-2384 | MeS(O)— | Pr | H—C | N |
| AZ-2385 | MeS(O)— | Bu | H—C | N |
| AZ-2386 | MeS(O)— | secBu | H—C | N |
| AZ-2387 | MeS(O)— | iBu | H—C | N |
| AZ-2388 | MeS(O)— | tBu | H—C | N |
| AZ-2389 | MeS(O)— | MeO— | H—C | N |
| AZ-2390 | MeS(O)— | EtO— | H—C | N |
| AZ-2391 | MeS(O)— | F3CCF2— | H—C | N |
| AZ-2392 | MeSO2— | Pr | H—C | N |
| AZ-2393 | MeSO2— | Bu | H—C | N |
| AZ-2394 | MeSO2— | secBu | H—C | N |
| AZ-2395 | MeSO2— | iBu | H—C | N |
| AZ-2396 | MeSO2— | tBu | H—C | N |
| AZ-2397 | MeSO2— | MeO— | H—C | N |
| AZ-2398 | MeSO2— | EtO— | H—C | N |
| AZ-2399 | MeSO2— | F3CCF2— | H—C | N |
| AZ-2400 | Pr | Pr | H—C | N |
| AZ-2401 | Pr | Bu | H—C | N |
| AZ-2402 | Pr | secBu | H—C | N |
| AZ-2403 | Pr | iBu | H—C | N |
| AZ-2404 | Pr | tBu | H—C | N |
| AZ-2405 | Pr | MeO— | H—C | N |
| AZ-2406 | Pr | EtO— | H—C | N |
| AZ-2407 | Pr | F3CCF2— | H—C | N |
| AZ-2408 | tBu | F3CCF2— | H—C | N |
| AZ-2409 | O2N— | F2CH— | H—C | N |
| AZ-2410 | O2N— | F3C— | H—C | N |
| AZ-2411 | O2N— | F3CCF2— | H—C | N |
| AZ-2412 | I | F3CCF2— | H—C | N |
| AZ-2413 | Bu | F3CCF2— | H—C | N |
| AZ-2414 | secBu | F3CCF2— | H—C | N |
| AZ-2415 | HC≡CCH2— | F3CCF2— | H—C | N |
| AZ-2416 | EtO— | F3CCF2— | H—C | N |
| AZ-2417 | O2N— | H2C=CH— | H—C | N |
| AZ-2418 | O2N— | H2N— | H—C | N |
| AZ-2419 | O2N— | HC(=O)— | H—C | N |
| AZ-2420 | O2N— | HC≡C— | H—C | N |
| AZ-2421 | O2N— | HOCH2— | H—C | N |
| AZ-2422 | O2N— | I | H—C | N |
| AZ-2423 | O2N— | iBu | H—C | N |
| AZ-2424 | I | iBu | H—C | N |
| AZ-2425 | Bu | iBu | H—C | N |
| AZ-2426 | secBu | iBu | H—C | N |
| AZ-2427 | HC≡CCH2— | iBu | H—C | N |
| AZ-2428 | EtO— | iBu | H—C | N |
| AZ-2429 | O2N— | Me | H—C | N |
| AZ-2430 | O2N— | MeC≡C— | H—C | N |
| AZ-2431 | O2N— | MeO— | H—C | N |

TABLE 3-continued

| | R6 | R7 | Y | Z |
|---|---|---|---|---|
| AZ-2432 | I | MeO— | H—C | N |
| AZ-2433 | Bu | MeO— | H—C | N |
| AZ-2434 | secBu | MeO— | H—C | N |
| AZ-2435 | HC≡CCH2— | MeO— | H—C | N |
| AZ-2436 | EtO— | MeO— | H—C | N |
| AZ-2437 | O2N— | MeOCH2— | H—C | N |
| AZ-2438 | O2N— | Pr | H—C | N |
| AZ-2439 | I | Pr | H—C | N |
| AZ-2440 | Bu | Pr | H—C | N |
| AZ-2441 | secBu | Pr | H—C | N |
| AZ-2442 | EtO— | Pr | H—C | N |
| AZ-2443 | O2N— | tBu | H—C | N |
| AZ-2444 | I | tBu | H—C | N |
| AZ-2445 | Bu | tBu | H—C | N |
| AZ-2446 | secBu | tBu | H—C | N |
| AZ-2447 | HC≡CCH2— | tBu | H—C | N |
| AZ-2448 | EtO— | tBu | H—C | N |
| AZ-2449 | O2N— | secBu | H—C | N |
| AZ-2450 | I | secBu | H—C | N |
| AZ-2451 | Bu | secBu | H—C | N |
| AZ-2452 | secBu | secBu | H—C | N |
| AZ-2453 | HC≡CCH2— | secBu | H—C | N |
| AZ-2454 | EtO— | secBu | H—C | N |
| AZ-2455 | Bu | Bu | H—C | N |
| AZ-2456 | Bu | EtO— | H—C | N |
| AZ-2457 | EtO— | Bu | H—C | N |
| AZ-2458 | EtO— | EtO— | H—C | N |
| AZ-2459 | I | Bu | H—C | N |
| AZ-2460 | I | EtO— | H—C | N |
| AZ-2461 | secBu | Bu | H—C | N |
| AZ-2462 | secBu | EtO— | H—C | N |
| AZ-2463 | Cl | H | Cl—C | N |
| AZ-2464 | Cl | Me | Cl—C | N |
| AZ-2465 | Cl | Et | Cl—C | N |
| AZ-2466 | Br | H | Br—C | N |
| AZ-2467 | Br | Me | Br—C | N |
| AZ-2468 | Br | Et | Br—C | N |
| AZ-2469 | Br | H | Cl—C | N |
| AZ-2470 | Br | Me | Cl—C | N |
| AZ-2471 | Br | Et | Cl—C | N |
| AZ-2472 | Cl | H | Br—C | N |
| AZ-2473 | Cl | Me | Br—C | N |
| AZ-2474 | Cl | Et | Br—C | N |

Hereinbelow, examples of the processes for producing the compounds represented by the formula (1) or the compounds represented by the formula (2) will be described. The processes for producing the compounds of the present invention are not limited to Production Process A to Production Process A1.

Production Process A

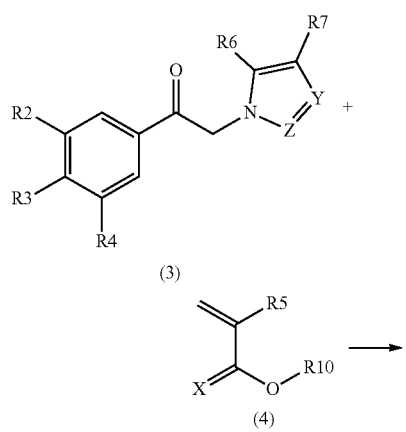

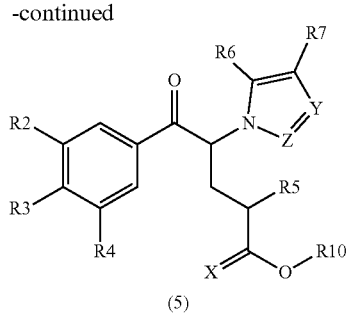

wherein R10 represents a hydrogen atom, or a C1-C6 alkyl group, and R2, R3, R4, R5, R6, R7, X, Y and Z are the same as defined hereinabove.

Production Process A is a process for synthesizing an intermediate for production represented by the formula (5), the process comprising reacting a compound represented by the formula (3) with a compound represented by the formula (4) in the presence of abase in a solvent.

The compound represented by the formula (3) used in the reaction may be synthesized in accordance with a known method or reference example.

The compound represented by the formula (4) used in the reaction may be purchased from the market or may be produced by a known method.

The amount of the compound represented by the formula (4) used in the reaction is at least 1 equivalent amount relative to the compound represented by the formula (3) and is not particularly limited as long as the target reaction takes place, but is usually 1 equivalent amount to 3 equivalent amounts.

Examples of the bases used in the reaction include inorganic bases such as sodium carbonate, potassium carbonate, cesium carbonate and tripotassium phosphate, metal alkoxides such as sodium methoxide, sodium ethoxide, sodium t-butoxide and potassium t-butoxide, organic bases such as triethylamine, tributylamine, 1,8-diazabicyclo[5.4.0]-7-undecene and 1,4-diazabicyclo[2.2.2]octane, and the like.

The amount of the base used in the reaction is at least a catalytic amount and is not particularly limited as long as the target reaction takes place, but is usually 0.01 equivalent amount to 3 equivalent amounts relative to the compound represented by the formula (3).

Examples of the solvents used in the reaction include ether solvents such as diethyl ether, diisopropyl ether, methyl-t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (3).

The temperature at which the reaction is performed is not particularly limited as long as the target reaction takes place, but is usually from −50° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (5) obtained above may be dehydrated with a desiccant such as sodium sulfate or magnesium sulfate. This drying process may be omitted.

The reaction mixture including the compound represented by the formula (5) obtained above may be distilled under reduced pressure to remove the solvent while avoiding the decomposition of the compound.

After the distillation, the reaction mixture including the compound represented by the formula (5) may be purified by, for example, washing, reprecipitation, recrystallization or column chromatography using an appropriate solvent. The purification process may be selected appropriately in accordance with the desired purity.

Production Process B

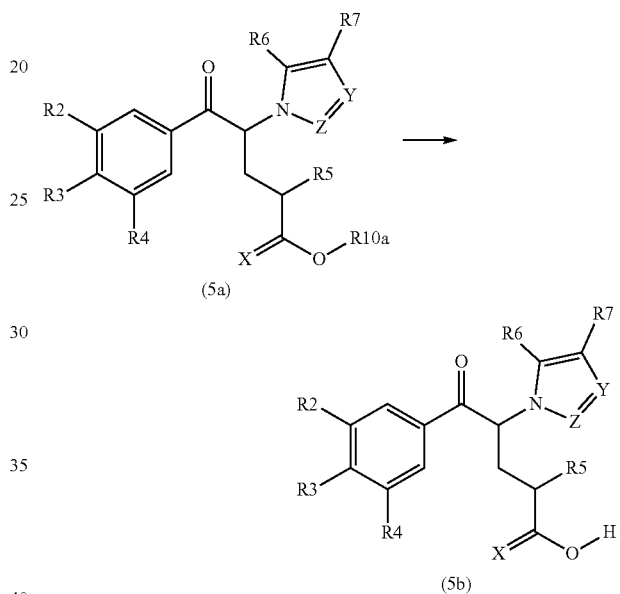

wherein R10a represents a C1-C6 alkyl group, and R2, R3, R4, R5, R6, R7, X, Y and Z are the same as defined hereinabove.

Production Process B is a process for producing an intermediate for production represented by the formula (5b), which belongs to the compounds represented by the formula (5), the process comprising reacting a compound represented by the formula (5a) under acidic or basic conditions in a solvent.

First, the reaction under acidic conditions will be described below.

Examples of the acids used in the reaction include inorganic acids such as hydrochloric acid, hydrobromic acid and phosphoric acid, and organic acids such as acetic acid, methanesulfonic acid, p-toluenesulfonic acid and trifluoroacetic acid. The acids are not particularly limited as long as the target reaction takes place.

The amount of the acid used in the reaction is at least a catalytic amount and is not particularly limited as long as the target reaction takes place, but is usually at least 0.01 equivalent amount relative to the compound represented by the formula (5a). Also, when the acid used is liquid, the acid may also serve as a solvent.

The solvent used in the reaction is not particularly limited as long as the target reaction takes place, and examples thereof include aqueous solvents, acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (5a).

The temperature at which the reaction is performed is not particularly limited as long as the target reaction takes place, but is usually 0° C. to 180° C. or is not more than the boiling point of the solvent.

Next, the reaction under basic conditions will be described below.

Examples of the bases used in the reaction include inorganic bases such as lithium hydroxide, sodium hydroxide and potassium hydroxide and is not particularly limited as long as the target reaction takes place.

The amount of the base used in the reaction is at least 1 equivalent amount relative to the compound represented by the formula (5a) and is not particularly limited as long as the target reaction takes place, but is usually 1 equivalent amount to 30 equivalent amounts.

The solvent used in the reaction is not particularly limited as long as the target reaction takes place, and examples thereof include aqueous solvents, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (5a).

The temperature at which the reaction is performed is not particularly limited as long as the target reaction takes place, but is usually from −20° C. to 180° C. or is not more than the boiling point of the solvent.

The post treatment after the reaction may be performed by a common method irrespective of whether the reaction conditions are acidic or basic. Water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (5b) obtained above may be dehydrated with a desiccant such as sodium sulfate or magnesium sulfate. This drying process may be omitted.

The reaction mixture including the compound represented by the formula (5b) obtained above may be distilled under reduced pressure to remove the solvent while avoiding the decomposition of the compound.

After the distillation, the reaction mixture including the compound represented by the formula (5b) may be purified by, for example, washing, reprecipitation, recrystallization or column chromatography using an appropriate solvent. The purification process may be selected appropriately in accordance with the desired purity.

The compound represented by the formula (5b) also comprises an isomer represented by the formula (5b'):

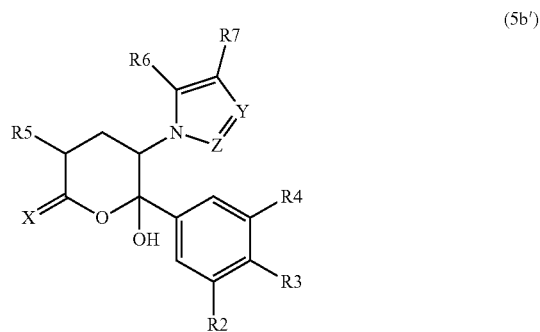

(5b')

wherein R2, R3, R4, R5, R6, R7, X, Y and Z are the same as defined hereinabove.

The compound represented by the Formula (5b') may be handled similarly to the compound represented by the formula (5b), and may be applied to Production Process C. Also, the compound represented by the Formula (5b') has an asymmetric carbon, and may be a single isomer or a mixture of isomers in an appropriate ratio. Further, a mixture of the compound represented by the formula (5b) and the compound represented by the formula (5b') may be used, and each of these compounds may be a single isomer or a mixture of isomers in an appropriate ratio.

Production Process C

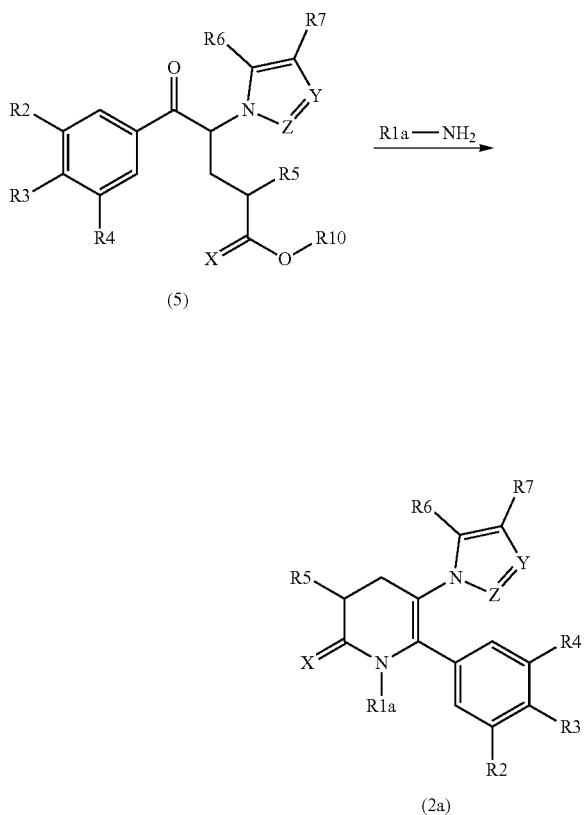

wherein R1a represents a hydrogen atom, a hydroxy group, a cyano group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, or RaRbN— (wherein Ra and Rb are the same as defined hereinabove), and R2, R3, R4, R5, R6, R7, R10, X, Y and Z are the same as defined hereinabove.

Production Process C is a process of obtaining a compound represented by the formula (2a) including an inventive compound and an intermediate for production of the present invention, the process comprising reacting a compound represented by the formula (5) with R1a-NH$_2$ in the presence of an acid.

R1a-NH$_2$ used in the reaction may be purchased from the market or may be produced by a known method. R1a-NH$_2$ may be in the form of a salt with an acidic compound such as hydrochloric acid and acetic acid and is not particularly limited as long as the target reaction takes place.

R1a-NH$_2$ used in the reaction is at least 1 equivalent amount relative to the compound represented by the formula (5) and is not particularly limited as long as the target reaction takes place, but is usually 1 equivalent amount to 200 equivalent amounts.

Examples of the acids used in the reaction include inorganic acids such as hydrochloric acid and sulfuric acid, and organic acids such as acetic acid, methanesulfonic acid and p-toluenesulfonic acid and is not particularly limited as long as the target reaction takes place, but acetic acid is preferable. Also, the use of an acid is not indispensable when the R1a-NH$_2$ is used as a salt with an acidic compound.

The amount of the acid used in the reaction is at least 1 equivalent amount relative to R1a-NH$_2$ and is not particularly limited as long as the target reaction takes place, but is usually 1 equivalent amount to 200 equivalent amounts. Also, when the acid used is liquid, the acid may also serve as a solvent.

The reaction may involve a solvent, but not indispensable.

The solvent used in the reaction is not particularly limited as long as the target reaction takes place, and examples thereof include acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be mixed in any proportions. As the solvents, among others, acidic solvents are preferable, and acetic acid is more preferable.

The amount of the solvent used in the reaction is not particularly limited as long as the target reaction takes place, but is usually 3 to 200 times the weight of the compound represented by the formula (5).

The temperature at which the reaction is performed is not particularly limited as long as the target reaction takes place, but is usually from 50° C. to 180° C. or is not more than the boiling point of the solvent.

As post-treatment, water or an appropriate aqueous solution may be added to the reaction mixture to perform separation. The aqueous solution that is used here may be, for example, an acidic aqueous solution such as hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (2a) obtained above may be dehydrated with a desiccant such as sodium sulfate or magnesium sulfate. This drying process may be omitted.

The reaction mixture including the compound represented by the formula (2a) obtained above may be distilled under reduced pressure to remove the solvent while avoiding the decomposition of the compound.

After the distillation, the reaction mixture including the compound represented by the formula (2a) may be purified by, for example, washing, reprecipitation, recrystallization or column chromatography using an appropriate solvent. The purification process may be selected appropriately in accordance with the desired purity.

A compound produced by Production Process C that is represented by the formula (2a) in which R1a is a hydrogen atom, namely, a compound represented by the formula (2), may be a useful intermediate for the production of a compound of the formula (1) of the present invention.

Specific examples of the intermediate for production represented by the formula (2) are represented by combinations of the structures shown in Table 4, substituents (R2, R3 and R4) on the phenyl shown in Table 2, azolyl groups (R6, R7, Y and Z) shown in Table 3, and X that is an oxygen atom or a sulfur atom. Those compounds are only illustrative and the scope of the invention is not limited to such compounds Production Process D

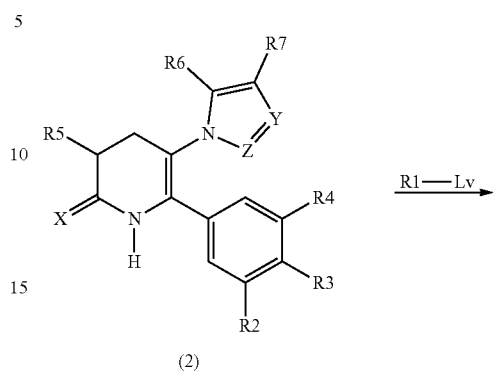

TABLE 4

| I-1 | I-2 | I-3 | I-4 |
|---|---|---|---|
| | F | Cl | Br |

| I-5 | I-6 | I-7 | I-8 |
|---|---|---|---|
| I | Me | MeO | ≡ |

| O$_2$N | Et | OH/Me | vinyl |

| H$_2$N | MeHN | Me$_2$N | Ac |

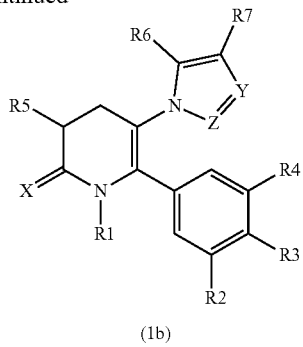

(1b)

wherein Lv represents a leaving group such as a methanesulfonyl group, a trifluoromethanesulfonyl group, a p-toluenesulfonyl group and a halogen atom, and R1, R2, R3, R4, R5, R6, R7, X, Y and Z are the same as defined hereinabove.

Production Process D is a process of obtaining a compound represented by the formula (1b), the process comprising reacting an intermediate for production represented by the formula (2) with R1-Lv in the presence of a base in a solvent.

R1-Lv used in the reaction may be purchased from the market or may be produced by a known method.

The amount of R1-Lv used in the reaction is at least 1 equivalent amount relative to the compound represented by the formula (2) and is not particularly limited as long as the target reaction takes place, but is usually 1 equivalent amount to 10 equivalent amounts.

Examples of the bases used in the reaction include inorganic bases such as sodium hydroxide, potassium hydroxide, sodium carbonate, potassium carbonate, cesium carbonate and sodium hydride and is not particularly limited as long as the target reaction takes place.

The amount of the base used in the reaction is at least 1 equivalent amount relative to the compound represented by the formula (2) and is not particularly limited as long as the target reaction takes place, but is usually 1 equivalent amount to 10 equivalent amounts.

The solvent used in the reaction is not particularly limited as long as the target reaction takes place, and examples thereof include ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (2).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1b) may be dehydrated with a desiccant such as sodium sulfate or magnesium sulfate. This drying process may be omitted.

The reaction mixture including the compound of the formula (1b) may be distilled under reduced pressure to remove the solvent while avoiding the decomposition of the compound.

After the distillation, the reaction mixture including the compound of the formula (1b) may be purified by, for example, washing, reprecipitation, recrystallization or column chromatography using an appropriate solvent. The purification process may be selected appropriately in accordance with the desired purity.

Production Process E

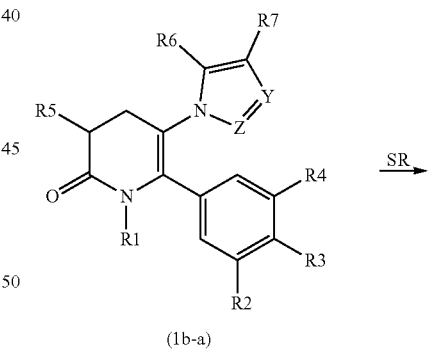

(1b-a)

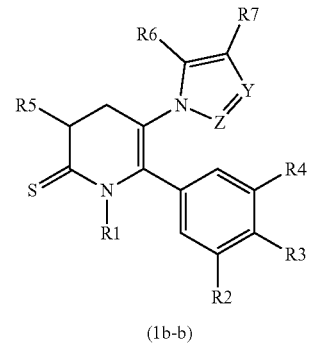

(1b-b)

wherein SR represents a sulfurizing agent, and R1, R2, R3, R4, R5, R6, Y and Z are the same as defined hereinabove.

Production Process E is a method for producing a compound of the formula (1b-b) which belongs to the compounds represented by the formula (1b). This production process includes reacting a compound of the formula (1b-a) with a sulfurizing reagent (SR) in a solvent.

Examples of the sulfurizing reagents used in the reaction include Lawesson's reagent (2,4-bis(4-methoxyphenyl)-1,3-dithia-2,4-diphosphetane-2,4-disulfide), and the like.

The amount of the sulfurizing reagent used in the reaction is at least 0.5 equivalent amounts relative to the compound of the formula (1b-a) and is not particularly limited as long as the above equivalent amount is satisfied and also the target reaction takes place. The amount is usually 1 equivalent amount to 10 equivalent amounts.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b-a).

The temperature at which the reaction is performed is not particularly limited as long as the target reaction takes place, but is usually from 50° C. to 180° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1b-b) may be dehydrated with a desiccant such as sodium sulfate or magnesium sulfate. This drying process may be omitted.

The reaction mixture including the compound of the formula (1b-b) may be distilled under reduced pressure to remove the solvent while avoiding the decomposition of the compound.

After the distillation, the reaction mixture including the compound of the formula (1b-b) may be purified by, for example, washing, reprecipitation, recrystallization or column chromatography using an appropriate solvent. The purification process may be selected appropriately in accordance with the desired purity.

Production Process F

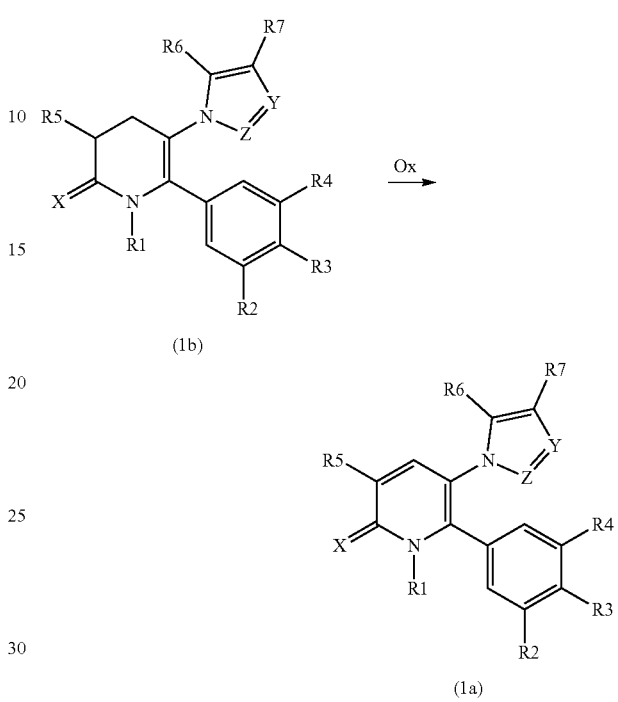

wherein Ox represents an oxidizer, and R1, R2, R3, R4, R5, R6, R7, X, Y and Z are the same as defined hereinabove.

Production Process F is a process of obtaining a compound represented by the formula (1a), the process comprising reacting a compound represented by the formula (1b) with an oxidizing agent (Ox) in a solvent.

Examples of the oxidizers that can be used in the reaction include a combination of metal oxides, benzoquinones, radical initiators, halogenating reagents, and the like.

Hereinbelow, the process will be described assuming that a metal oxide is used as the oxidizing agent.

Examples of the metal oxides used in the reaction include manganese dioxide, and the like.

The amount of the oxidizer used in the reaction is at least 1 equivalent amount relative to the compound of the formula (1b) and is not particularly limited as long as the above equivalent amount is satisfied and also the target reaction takes place. The amount is usually 1 equivalent amount to 200 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 0° C. to 150° C. or is not more than the boiling point of the solvent.

As post-treatment, insoluble metals may be removed by filtration. Further, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

Hereinbelow, the process using a benzoquinone as the oxidizer will be described.

Examples of benzoquinones used in the reaction include 2,3-dichloro-5,6-dicyano-p-benzoquinone, and the like.

The amount of the oxidizer used in the reaction is at least 1 equivalent amount relative to the compound of the formula (1b) and is not particularly limited as long as the above equivalent amount is satisfied and also the target reaction takes place. The amount is usually 1 equivalent amount to 20 equivalent amounts.

The solvent used in the reaction is not particularly limited as long as the target reaction takes place. Examples of the solvents include benzene-based solvents such as benzene, toluene, xylene, mesitylene, chlorobenzene and dichlorobenzene, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. In this reaction, the separation operations may be omitted.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

Hereinbelow, the process using a combination of a radical initiator and a halogenating agent as the oxidizer will be described.

Examples of the radical initiators used in the reaction include azobisisobutyronitrile, 2,2'-azobis(4-methoxy-2,4-dimethylvaleronitrile), benzoyl peroxide, and the like.

The amount of radical initiator used in the reaction is at least 0.01 equivalent amount relative to the compound represented by the formula (1b) and is not particularly limited as long as the target reaction takes place, but is usually 0.01 equivalent amount to 1 equivalent amount.

Examples of the halogenating reagents used in the reaction include N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, and the like.

The amount of the halogenating reagent used in the reaction is at least 1.0 equivalent amount relative to the compound represented by the formula (1b) and is not particularly limited as long as the target reaction takes place, but is usually 1 equivalent amount to 3 equivalent amounts. However, the amount of the halogenating reagent containing hydantoin is at least 0.5 equivalent amount and is not particularly limited as long as the target reaction takes place, but is usually 0.5 equivalent amount to 1.5 equivalent amounts.

The solvent used in the reaction is not particularly limited as long as the target reaction takes place. Examples of the solvents include halogenated benzene-based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1b).

The temperature at which the reaction is performed is not particularly limited as long as the target reaction takes place, but is usually from 20° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane and chloroform, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1a) may be dehydrated with a desiccant such as sodium sulfate or magnesium sulfate. This drying process may be omitted.

The reaction mixture including the compound of the formula (1a) may be distilled under reduced pressure to remove the solvent while avoiding the decomposition of the compound.

After the distillation, the reaction mixture including the compound of the formula (1a) may be purified by, for example, washing, reprecipitation, recrystallization or column chromatography using an appropriate solvent. The purification process may be selected appropriately in accordance with the desired purity.

Production Process G

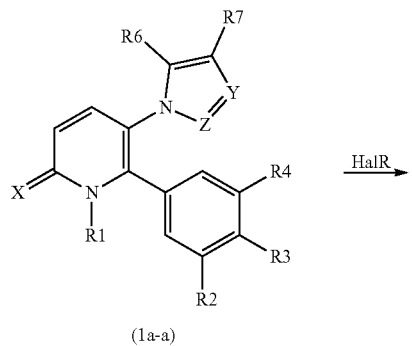

(1a-a)

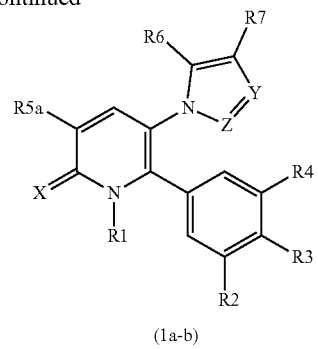

(1a-b)

wherein R5a represents a halogen atom, HalR represents a halogenating reagent, and R1, R2, R3, R4, R6, R7, X, Y and Z are the same as defined hereinabove.

Production Process G is a method for obtaining a compound of the formula (1a-b), which belongs to the compound represented by the formula (1a), in which R5a is a halogen atom. This production process includes reacting a compound of the formula (1a-a) with a halogenating reagent (HalR) in a solvent.

Examples of the halogenating reagents used in the reaction include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine, and the like.

The amount of the halogenating reagent used in the reaction is at least 1 equivalent amount relative to the compound of the formula (1a-a), and is not particularly limited as long as the above equivalent amount is satisfied and also the target reaction takes place. The amount is usually 1 equivalent amount to 10 equivalent amounts. Where the halogenating reagent contains hydantoin, the amount thereof is at least 0.5 equivalent amounts, and, although not particularly limited as long as the above equivalent amount is satisfied and also the target reaction takes place, is usually 1 equivalent amount to 5 equivalent amounts.

When the halogenating reagent used in the reaction is an iodizing agent, an acid may be added, with examples including inorganic acids such as hydrochloric acid and sulfuric acid, organic acids such as acetic acid, trifluoroacetic acid, methanesulfonic acid and trifluoromethanesulfonic acid, and the like.

The amount of the acid used when the halogenating reagent in the reaction is an iodizing agent is at least 0.01 equivalent amount relative to the compound of the formula (1a-a), and is not particularly limited as long as the above equivalent amount is satisfied and also the target reaction takes place. The amount is usually 0.1 equivalent amount to 3 equivalent amounts.

The solvent used in the reaction is not particularly limited as long as the target reaction takes place. Examples of the solvents include acidic solvents such as sulfuric acid, acetic acid, trifluoroacetic acid, methanesulfonic acid and trifluoromethanesulfonic acid, ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-a).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1a-b) may be dehydrated with a desiccant such as sodium sulfate or magnesium sulfate. This drying process may be omitted.

The reaction mixture including the compound of the formula (1a-b) may be distilled under reduced pressure to remove the solvent while avoiding the decomposition of the compound.

After the distillation, the reaction mixture including the compound of the formula (1a-b) may be purified by, for example, washing, reprecipitation, recrystallization or column chromatography using an appropriate solvent. The purification process may be selected appropriately in accordance with the desired purity.

Production Process H

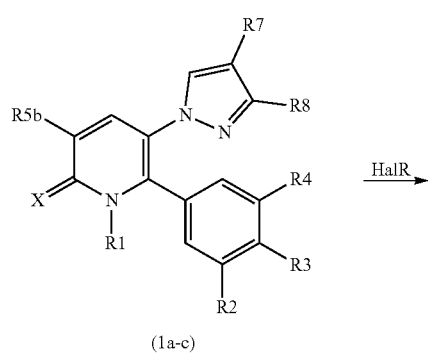

(1a-c)

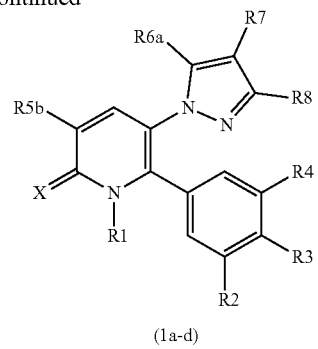

(1a-d)

wherein R5b represents a halogen atom, a cyano group, a nitro group, a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C2-C6 alkynyl group optionally substituted with substituent(s) A, a C2-C6 haloalkynyl group, a C1-C6 alkoxy group optionally substituted with substituent(s) A, a C1-C6 haloalkoxy group, a C3-C8 cycloalkoxy group optionally substituted with substituent(s) A, a C2-C6 alkenyloxy group optionally substituted with substituent(s) A, a C2-C6 haloalkenyloxy group, a C3-C6 alkynyloxy group optionally substituted with substituent(s) A, a C3-C6 haloalkynyloxy group, Rc-L- (wherein Rc and L are the same as defined hereinabove), RaRbN— (wherein Ra and Rb are the same as defined hereinabove), or RgC(=O)— (wherein Rg is the same as defined hereinabove), R6a represents a halogen atom, and R1, R2, R3, R4, R7, R8, X and HalR are the same as defined hereinabove.

Production Process H is a production process of obtaining a compound represented by the formula (1a-d), which belongs to the compounds represented by the formula (1a), in which R6a is a halogen atom, the process comprising reacting a compound represented by the formula (1a-c) with a halogenating reagent (HalR) in a solvent.

Examples of the halogenating reagents used in the reaction include Selectfluor (N-fluoro-N'-triethylenediamine bis (tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

The amount of the halogenating reagent used in the reaction is at least 1 equivalent amount relative to the compound represented by the formula (1a-c) and is not particularly limited as long as the target reaction takes place, but is usually 1 equivalent amount to 10 equivalent amounts. However, the amount of the halogenating reagent containing hydantoin is at least 0.5 equivalent amount and is not particularly limited as long as the target reaction takes place, but is usually 1 equivalent amount to 5 equivalent amounts.

When the halogenating reagent used in the reaction is an iodinating agent, the reaction may involve an acid, for example, inorganic acids such as hydrochloric acid and sulfuric acid, and organic acids such as acetic acid, trifluoroacetic acid, methanesulfonic acid and trifluoromethanesulfonic acid.

The amount of the acid, which is added when the halogenating reagent used in the reaction is an iodinating agent, is at least 0.01 equivalent amount relative to the compound represented by the formula (1a-c) and is not particularly limited as long as the target reaction takes place, but is usually 0.1 equivalent amount to 3 equivalent amounts.

To allow the reaction to proceed efficiently, a halogenotrialkylsilane such as chlorotrimethylsilane and bromotrimethylsilane may be added. In this case, the halogenotrialkylsilane may be selected such that the halogen atom thereof is identical to that of the halogenating reagent used. Specifically, the halogenating reagents used include chlorotrialkylsilanes for chlorinating and bromotrialkylsilanes for brominating. However, the addition of the halogenotrialkylsilane is not indispensable.

The amount of the halogenotrialkylsilane used in the reaction usually 1 equivalent amount to 20 equivalent amounts.

The solvent used in the reaction is not particularly limited as long as the target reaction takes place, and examples thereof include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1a-c).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1a-d) obtained above may be dehydrated with a desiccant such as sodium sulfate or magnesium sulfate. This drying process may be omitted.

The reaction mixture including the compound represented by the formula (1a-d) obtained above may be distilled under reduced pressure to remove the solvent while avoiding the decomposition of the compound.

After the distillation, the reaction mixture including the compound represented by the formula (1a-d) may be purified by, for example, washing, reprecipitation, recrystallization or column chromatography using an appropriate solvent. The purification process may be selected appropriately in accordance with the desired purity.

Production Process G may involve halogenated ethanes as the halogenating reagents. Hereinbelow, an alternative process will be described assuming that the halogenated ethanes are used.

Examples of the halogenating reagents used in the reaction include halogenated ethanes such as hexachloroethane and 1,2-dibromo-1,1,2,2-tetrachloroethane.

The amount of the halogenating reagent used in the reaction is at least 1 equivalent amount relative to the compound represented by the formula (1a-c) and is not particularly limited as long as the target reaction takes place, but is usually 1 equivalent amount to 10 equivalent amounts.

To perform the reaction, a base is needed.

Examples of the bases used in the reaction include metal hydrides such as sodium hydride, organolithiums such as methyllithium, butyllithium, sec-butyllithium, t-butyllithium and hexyllithium, and metal amides such as lithium diisopropylamide, hexamethyldisilazane lithium, hexamethyldisilazane sodium and hexamethyldisilazane potassium.

The amount of the base used in the reaction is at least 1 equivalent amount relative to the compound represented by the formula (1a-c) and is not particularly limited as long as the target reaction takes place, but is usually 1 equivalent amount to equivalent amounts.

The solvent used in the reaction is not particularly limited as long as the target reaction takes place, and examples thereof include ether solvents such as diethyl ether, diisopropyl ether, methyl-t-butyl ether, dimethoxyethane, tetrahydrofuran and dioxane, benzene-based solvents such as benzene, toluene, xylene, mesitylene, chlorobenzene and dichlorobenzene, hydrocarbon solvents such as hexane, heptane, cyclohexane and methylcyclohexane, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1a-c).

The temperature at which the reaction is performed is not particularly limited as long as the target reaction takes place, but is usually from −80° C. to 100° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1a-d) obtained above may be dehydrated with a desiccant such as sodium sulfate or magnesium sulfate. This drying process may be omitted.

The reaction mixture including the compound represented by the formula (1a-d) obtained above may be distilled under reduced pressure to remove the solvent while avoiding the decomposition of the compound.

After the distillation, the reaction mixture including the compound represented by the formula (1a-d) may be purified by, for example, washing, reprecipitation, recrystallization or column chromatography using an appropriate solvent. The purification process may be selected appropriately in accordance with the desired purity.

Production Process I

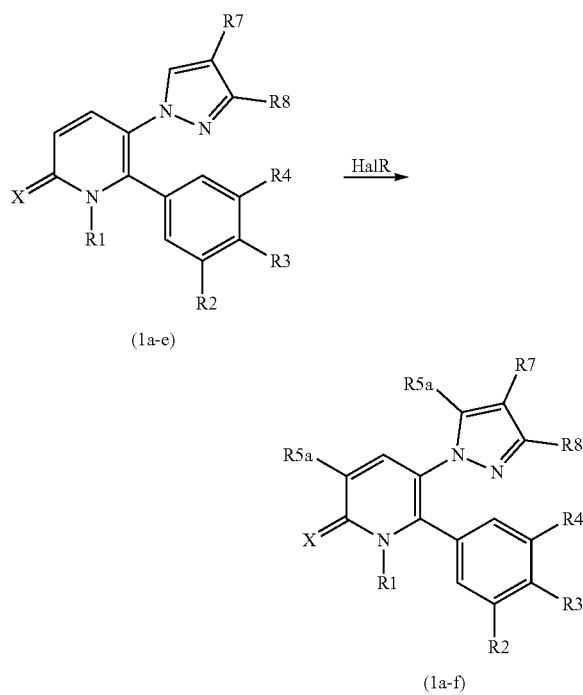

wherein R1, R2, R3, R4, R5a, R7, R8, X and HalR are the same as defined hereinabove.

Production Process I is a production process of obtaining a compound represented by the formula (1a-f), which belongs to the compounds represented by the formula (1a), in which R5a is a halogen atom, the process comprising reacting a compound represented by the formula (1a-e) with a halogenating reagent (HalR) in a solvent.

Examples of the halogenating reagents used in the reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

The amount of the halogenating reagent used in the reaction is at least 2 equivalents relative to the compound represented by the formula (1a-e) and is not particularly limited as long as the target reaction takes place, but is usually 2 equivalent amounts to 10 equivalent amounts. However, the amount of the halogenating reagent containing hydantoin is at least 1 equivalent amount and is not particularly limited as long as the target reaction takes place, but is usually 1 equivalent amount to 5 equivalent amounts.

When the halogenating reagent used in the reaction is an iodinating agent, the reaction may involve an acid, for example, inorganic acids such as hydrochloric acid and sulfuric acid, and organic acids such as acetic acid, trifluoroacetic acid, methanesulfonic acid, trifluoromethanesulfonic acid.

The amount of the acid, which is added when the halogenating reagent used in the reaction is an iodinating agent, is at least 0.01 equivalent amount relative to the compound represented by the formula (1a-e) and is not particularly limited as long as the target reaction takes place, but is usually 0.1 equivalent amount to 3 equivalent amounts.

To allow the reaction to proceed efficiently, a halogenotrialkylsilane such as chlorotrimethylsilane and bromotrimethylsilane may be added. In this case, the halogenotrialkylsilane may be selected such that the halogen atom thereof is identical to that of the halogenating reagent used. Specifically, the halogenating reagents used include chlorotrialkylsilanes for chlorinating and bromotrialkylsilanes for brominating. however, the addition of the halogenotrialkylsilane is not indispensable.

The amount of the halogenotrialkylsilane used in the reaction usually 1 equivalent amount to 20 equivalent amounts.

The solvent used in the reaction is not particularly limited as long as the target reaction takes place, and examples thereof include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1a-e).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1a-f) obtained above may be dehydrated with a desiccant such as sodium sulfate or magnesium sulfate. This drying process may be omitted.

The reaction mixture including the compound represented by the formula (1a-f) obtained above may be distilled under reduced pressure to remove the solvent while avoiding the decomposition of the compound.

After the distillation, the reaction mixture including the compound represented by the formula (1a-f) may be purified by, for example, washing, reprecipitation, recrystallization or column chromatography using an appropriate solvent. The purification process may be selected appropriately in accordance with the desired purity.

Production Process J

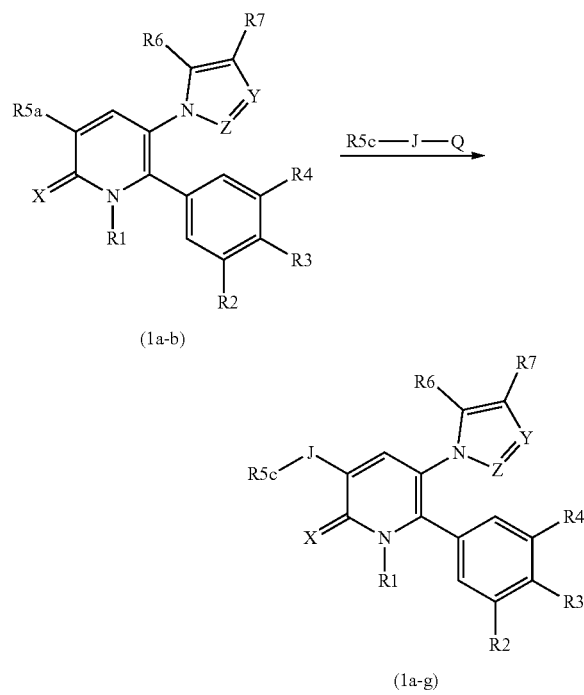

(1a-b)

(1a-g)

wherein J represents an oxygen atom or a sulfur atom, when J is an oxygen atom, R5c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A, or a C3-C6 haloalkynyl group, when J is an sulfur atom, R5c represents a C1-C6 alkyl group or a C1-C6 haloalkyl group, Q represents a hydrogen atom or a metal, and R1, R2, R3, R4, R5a, R6, R7, X, Y and Z are the same as defined hereinabove.

Production Process J is a process for synthesizing a compound represented by the formula (1a-g), which belongs to the compounds represented by the formula (1a), in which J represents an oxygen atom or a sulfur atom, when J is an oxygen atom, R5c represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, a C2-C6 haloalkenyl group, a C3-C6 alkynyl group optionally substituted with substituent(s) A, or a C3-C6 haloalkynyl group, when J is an sulfur atom, R5c represents a C1-C6 alkyl group or a C1-C6 haloalkyl group, the process comprising obtaining the compound by coupling reaction that reacts a compound represented by the formula (1a-b) with R5c-J-Q in the presence of a transition metal in a solvent.

In the compound represented by the formula (1a-b), R5a is preferably a chlorine atom, a bromine atom, or an iodine atom.

R5c-J-Q used in the reaction may be purchased from the market or may be produced by a known method. Q is preferably a hydrogen atom, or an alkali metal such as sodium and potassium.

The amount of R5c-J-Q used in the reaction is at least 1 equivalent amount relative to the compound represented by the formula (1a-b) and is not particularly limited as long as the target reaction takes place. When Q is a hydrogen atom, the reagent may be used also as a solvent.

The transition metal used in the reaction may have a ligand, and examples thereof include palladium materials such as palladium acetate, [1,1'-bis(diphenylphosphino)ferrocene]palladium dichloride, tris(dibenzylideneacetone)dipalladium, tetrakis(triphenylphosphine)palladium, bis(triphenylphosphine)palladium dichloride.

The amount of transition metal used in the reaction is 0.001 equivalent amount to 1 equivalent amount relative to the compound represented by the formula (1a-b) and is not particularly limited as long as the target reaction takes place.

To allow the reaction to proceed efficiently, a phosphine ligand such as triphenylphosphine, 1,1'-bis(diphenylphosphino)ferrocene, 2-dicyclohexylphosphino-2'4'6'-triisopropylbiphenyl and 2-di-t-butylphosphino-2'4'6'-triisopropylbiphenyl may be added.

The amount of the phosphine ligand used in the reaction is 0.001 equivalent amount to 1 equivalent amount relative to the compound represented by the formula (1a-b) and is not particularly limited as long as the target reaction takes place.

Examples of the bases used in the reaction include inorganic bases such as sodium carbonate, potassium carbonate and cesium carbonate, organic bases such as triethylamine, tributylamine, diisopropylethylamine, and the like. However, when Q is an alkali metal, a base is not indispensable.

The amount of the base used in the reaction is at least 1 equivalent amount relative to the compound represented by the formula (1a-b) and is not particularly limited as long as the target reaction takes place, but is usually 1 equivalent amount to 50 equivalent amounts.

The solvent used in the reaction is not particularly limited as long as the target reaction takes place, and examples thereof include alcohol solvents represented by R5c-J-H (wherein R5c is the same as defined hereinabove, J is an oxygen atom), ether solvents such as diethyl ether, diisopropyl ether, methyl-t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 30° C. to 200° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield. Also, insolubles may be removed by filtration, but this operation is not indispensable.

The reaction mixture including the compound represented by the formula (1a-g) obtained above may be dehydrated with a desiccant such as sodium sulfate or magnesium sulfate. This drying process may be omitted.

The reaction mixture including the compound represented by the formula (1a-g) obtained above may be distilled under reduced pressure to remove the solvent while avoiding the decomposition of the compound.

After the distillation, the reaction mixture including the compound represented by the formula (1a-g) may be purified by, for example, washing, reprecipitation, recrystallization or column chromatography using an appropriate solvent. The purification process may be selected appropriately in accordance with the desired purity.

Production Process K

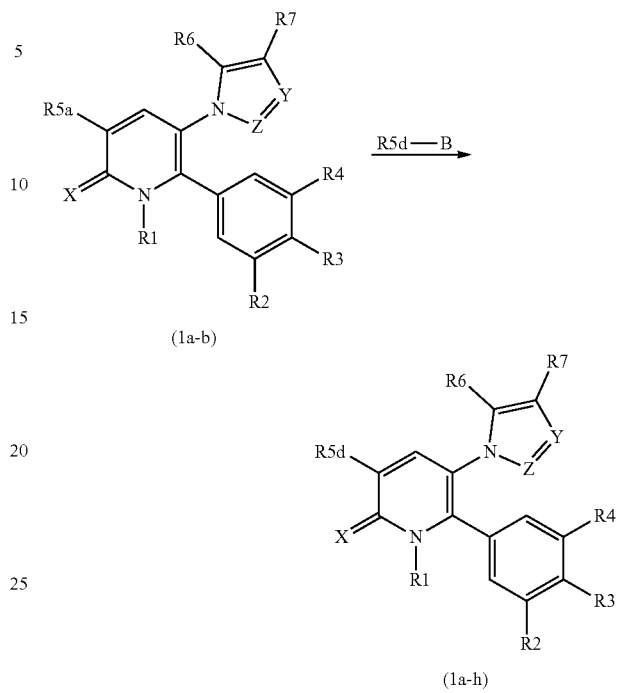

(1a-b)

(1a-h)

wherein R5d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, or a C2-C6 haloalkenyl group, R5d-B represents an organoboronic acid, and R1, R2, R3, R4, R5a, R6, R7, X, Y and Z are the same as defined hereinabove.

Production Process K is a method for synthesizing a compound of the formula (1a-h), which belongs to the compounds represented by the formula (1a), in which R5d represents a C1-C6 alkyl group optionally substituted with substituent(s) A, a C1-C6 haloalkyl group, a C3-C8 cycloalkyl group optionally substituted with substituent(s) A, a C2-C6 alkenyl group optionally substituted with substituent(s) A, or a C2-C6 haloalkenyl group. This production process includes reacting a compound of the formula (1a-b) with an organoboronic acid (R5d-B) by the Suzuki-Miyaura coupling reaction in the presence of a transition metal and a base in a solvent.

In the formula (1a-b), R5a is preferably a chlorine atom, a bromine atom or an iodine atom.

R5d-B used in the reaction is an organoboronic acid such as an organic boronic acid or an organic boronate ester, and may be purchased from the market or may be produced by a known method.

The amount of R5d-B used in the reaction is at least 1 equivalent amount relative to the compound of the formula (1a-b), and is not particularly limited as long as the above equivalent amount is satisfied and also the target reaction takes place. The amount is usually 1 equivalent amount to 10 equivalent amounts.

The transition metal used in the reaction may be, for example, palladium, nickel or ruthenium, and may have a ligand. Palladiums are preferable, with examples including palladium acetate, [1,1'-bis(diphenylphosphino)ferrocene] palladium dichloride, tris(dibenzylideneacetone)dipalladium, tetrakis(triphenylphosphine)palladium, bis(triphenylphosphine)palladium dichloride, and the like.

The amount of the transition metal used in the reaction is 0.001 equivalent amount to 1 equivalent amount relative to the compound of the formula (1a-b), but is not particularly limited thereto as long as the target reaction takes place.

To allow the reaction to proceed efficiently, a phosphine ligand such as triphenylphosphine or tricyclohexylphosphine may be added.

The amount of the phosphine ligand used in the reaction is 0.001 equivalent amount to 1 equivalent amount relative to the compound of the formula (1a-b), and is not particularly limited as long as the above equivalent amount is satisfied and also the target reaction takes place.

Examples of the bases used in the reaction include inorganic bases such as sodium carbonate, potassium carbonate, cesium carbonate and tripotassium phosphate, metal alkoxides such as sodium methoxide, sodium ethoxide, sodium t-butoxide and potassium t-butoxide, and the like.

The amount of the base used in the reaction is at least 1 equivalent amount relative to the compound of the formula (1a-b) and is not particularly limited as long as the above equivalent amount is satisfied and also the target reaction takes place. The amount is usually 1 equivalent amount to 50 equivalent amounts.

The solvent used in the reaction is not particularly limited as long as the target reaction takes place. Examples of the solvents include water solvent, ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 30° C. to 200° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. Further, insolubles may be removed by filtration, but this operation is not indispensable.

The reaction mixture including the compound of the formula (1a-h) may be dehydrated with a desiccant such as sodium sulfate or magnesium sulfate. This drying process may be omitted.

The reaction mixture including the compound of the formula (1a-h) may be distilled under reduced pressure to remove the solvent while avoiding the decomposition of the compound.

After the distillation, the reaction mixture including the compound of the formula (1a-h) may be purified by, for example, washing, reprecipitation, recrystallization or column chromatography using an appropriate solvent. The purification process may be selected appropriately in accordance with the desired purity.

Production Process L

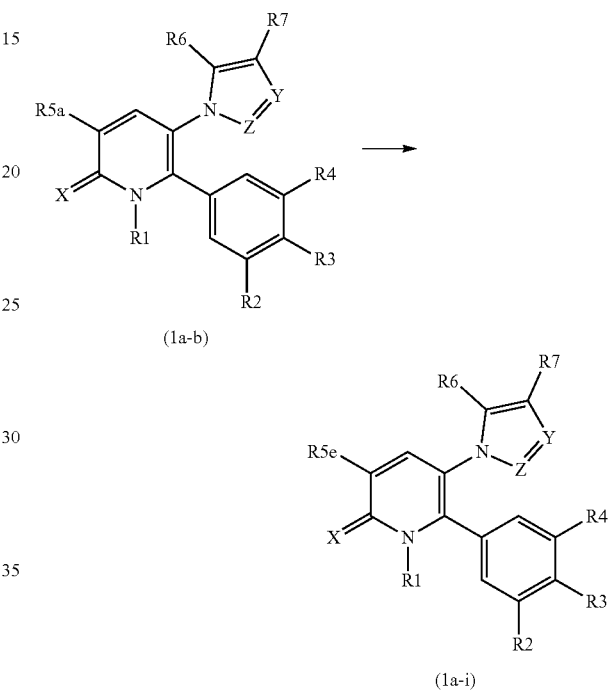

wherein R5e represents a C2-C6 alkynyl group optionally substituted with substituent(s) A, or a C2-C6 haloalkynyl group, and R1, R2, R3, R4, R5a, R6, R7, X, Y and Z are the same as defined hereinabove.

Production Process L is a method for synthesizing a compound of the formula (1a-i), which belongs to the compounds represented by the formula (1a), in which R5e represents a C2-C6 alkynyl group optionally substituted with substituent(s) A, or a C2-C6 haloalkynyl group. This production process includes reacting a compound of the formula (1a-b) with an alkyne-terminated compound by the Sonogashira coupling reaction in the presence of transition metals and a base in a solvent.

In the formula (1a-b), R5a is preferably a chlorine atom, a bromine atom or an iodine atom.

The alkyne-terminated compound used in the reaction may be purchased from the market or may be produced by a known method. Trimethylsilylacetylene is also usable as the alkyne-terminated compound. In this case, a trimethylsilylethynyl group is introduced into the compound of the formula (1a-b), and the compound is desilylated later. The desilylation may be performed with reference to non patent literature such as Journal of the American Chemical Society, vol. 131, No. 2, pp. 634-643 (2009) and Journal of Organometallic Chemistry, vol. 696, No. 25, pp. 4039-4045 (2011).

The amount of the alkyne-terminated compound used in the reaction is at least 1 equivalent amount relative to the compound of the formula (1a-b) and is not particularly limited as long as the above equivalent amount is satisfied and also the target reaction takes place. The amount is usually 1 equivalent amount to 10 equivalent amounts.

The transition metals used in the reaction may have a ligand. Examples thereof include palladiums such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride, and the like. Coppers such as copper chloride, copper bromide and copper iodide are used concurrently.

The amounts of the transition metals used in the reaction are such that the amounts of the palladium and the copper are each at least 0.001 equivalent amount relative to the compound of the formula (1a-b), and are not particularly limited as long as the above equivalent amounts are satisfied and also the target reaction takes place. The amounts are preferably both 0.001 equivalent amount to 1 equivalent amount.

Examples of the bases used in the reaction include organic amines such as triethylamine, tributylamine, isopropylamine, diethylamine, diisopropylamine and diisopropylethylamine, inorganic bases such as sodium carbonate, potassium carbonate and cesium carbonate, and the like.

The amount of the base used in the reaction is at least 1 equivalent amount relative to the compound of the formula (1a-b) and is not particularly limited as long as the above equivalent amount is satisfied and also the target reaction takes place. The amount is usually 1 equivalent amount to 50 equivalent amounts. A liquid organic base may also serve as a solvent.

To allow the reaction to proceed efficiently, a phosphine ligand such as tri-t-butylphosphine or 2-dicyclohexylphosphino-2',4',6'-triisopropylbiphenyl may be added, although the use of such a ligand is not indispensable.

The amount of the phosphine ligand used in the reaction is 0.001 equivalent amount to 1 equivalent amount relative to the compound of the formula (1a-b), but is not particularly limited thereto as long as the target reaction takes place.

The solvent used in the reaction is not particularly limited as long as the target reaction takes place. Examples of the solvents include ether solvents such as diethyl ether, diisopropyl ether, methyl t-butyl ether, dimethoxyethane, tetrahydrofuran and dioxane, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, organic amine solvents such as triethylamine, tributylamine, isopropylamine, diethylamine, diisopropylamine and diisopropylethylamine, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1a-b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield. Further, insolubles may be removed by filtration, but this operation is not indispensable.

The reaction mixture including the compound of the formula (1a-i) may be dehydrated with a desiccant such as sodium sulfate or magnesium sulfate. This drying process may be omitted.

The reaction mixture including the compound of the formula (1a-i) may be distilled under reduced pressure to remove the solvent while avoiding the decomposition of the compound.

After the distillation, the reaction mixture including the compound of the formula (1a-i) may be purified by, for example, washing, reprecipitation, recrystallization or column chromatography using an appropriate solvent. The purification process may be selected appropriately in accordance with the desired purity.

Production Process M

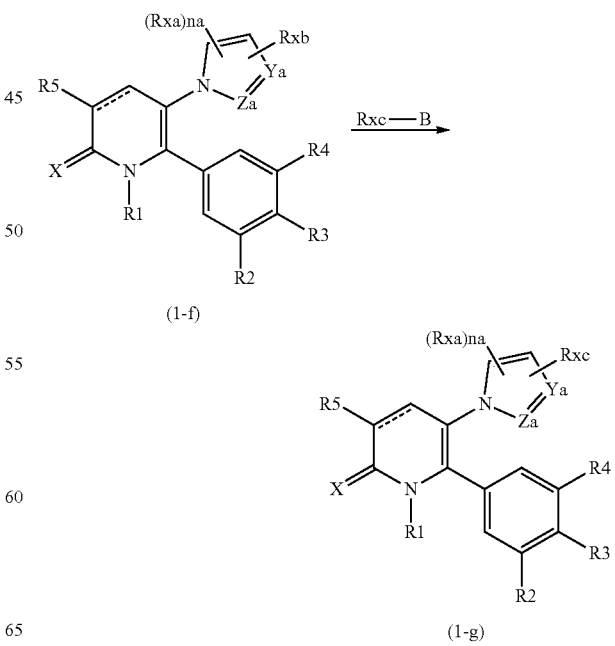

wherein Rxa represents a hydrogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), Rxb represents a halogen atom, Rxc represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, or a C2-C6 haloalkenyl group, Ya represents Rxa-C, Rxb-C (in this case, Rxb-C is a substrate state before the reaction is performed. When Rxb-C is selected, Rxb is not selected at the position of R6, R7 and R9 in the compound represented by the formula (1)), or a nitrogen atom, Za represents Rxa-C, Rxb-C (in this case, Rxb-C is a substrate state before the reaction is performed. When Rxb-C is selected, Rxb is not selected at the position of R6, R7 and R8 in the compound represented by the formula (1)), or a nitrogen atom, na represents an integer of 1 to 3 (provided that na is 2 or more, 2 or more Rxas are independent of one another and each represent a substituent, and they may be same or different), and R1, R2, R3, R4, R5, X and the broken line are the same as defined hereinabove. Rxa, Rxb and Rxc in the compound represented by the formula (1-f) and Formula (1-g) are substituted at any appropriate position of R6, R7, R8 or R9 in the compound represented by the formula (1).

Production Process M is a process for synthesizing a compound represented by the formula (1-g), which belongs to the compounds represented by the formula (1), in which Rxc is a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent (s) C, or a C2-C6 haloalkenyl group, the process comprising obtaining the compound by Suzuki-Miyaura coupling reaction that reacts a compound represented by the formula (1-f) with an organoboronic acid (Rxc-B) in the presence of a transition metal and a base in a solvent.

In the compound represented by the formula (1-g), Rxb is preferably a chlorine atom, a bromine atom, or an iodine atom.

Rxc-B used in the reaction represents an organoboronic acid such as an organoboronic acid or an organoboronate ester and may be purchased from the market or may be produced by a known method.

Production Process M may be performed in accordance with Production Process K while replacing the compound represented by the formula (1a-b) and R5d-B in Production Process K by the compound represented by the formula (1-f) and Rxc-B, respectively.

Production Process N

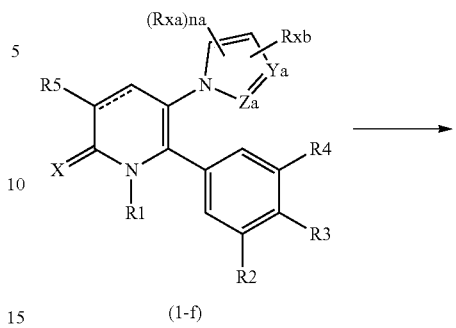

(1-f)

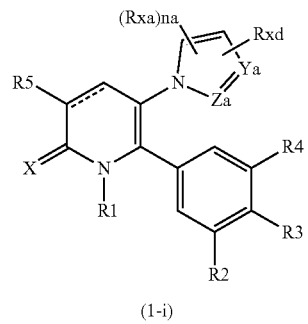

(1-i)

wherein Rxd represents a C2-C6 alkynyl group optionally substituted with substituent(s) C, or a C2-C6 haloalkynyl group, and R1, R2, R3, R4, R5, Rxa, Rxb, X, Ya, Za, the broken line and na are the same as defined hereinabove. Rxa, Rxb and Rxd in the compound represented by the formula (1-f) and Formula (1-i) are substituted at any appropriate position of R6, R7, R8 or R9 in the compound represented by the formula (1).

Production Process N is a process for synthesizing a compound represented by the formula (1-i), which belongs to the compounds represented by the formula (1), in which Rxd is a C2-C6 alkynyl group optionally substituted with substituent(s) C, or a C2-C6 haloalkynyl group, the process comprising obtaining the compound by Sonogashira coupling reaction that reacts a compound represented by the formula (1-f) with an alkyne-terminated compound in the presence of a transition metal and a base in a solvent.

In the compound represented by the formula (1-f), Rxb is preferably a chlorine atom, a bromine atom, or an iodine atom.

The alkyne-terminated compound used in the reaction may be purchased from the market or may be produced by a known method.

Production Process N may be performed in accordance with Production Process L while replacing the compound represented by the formula (1a-b) in Production Process L by the compound represented by the formula (1-f).

Production Process O

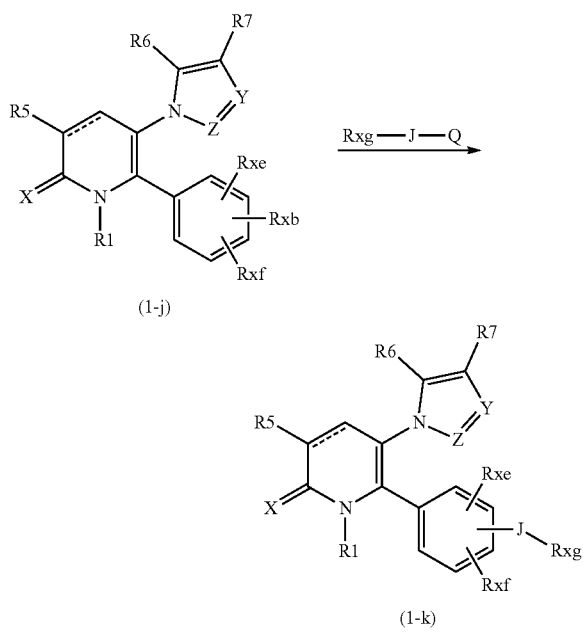

(1-j)

(1-k)

wherein Rxe and Rxf are independent of one another and each represent a hydrogen atom, a hydroxy group, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), Rc-SO$_2$—O— (wherein Rc is the same as defined hereinabove), RaRbN— (wherein Ra and Rb are the same as defined hereinabove), or ReC(=O)N(Rf)— (wherein Re and Rf are the same as defined hereinabove), when J is an oxygen atom, Rxg represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, or a C3-C6 haloalkynyl group, when J is an sulfur atom, Rxg represents a C1-C6 alkyl group or a C1-C6 haloalkyl group, and R1, R5, R6, R7, Rxb, J, X, Y, Z and the broken line are the same as defined hereinabove. Rxb, Rxe, Rxf and Rxg-J- in the compound represented by the formula (1-j) and Formula (1-k) are substituted at any appropriate position of R2, R3 or R4 in the compound represented by the formula (1).

Production Process O is a process for synthesizing a compound represented by the formula (1-k), which belongs to the compounds represented by the formula (1), in which J represents an oxygen atom or a sulfur atom, when J is an oxygen atom, Rxg represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, or a C3-C6 haloalkynyl group, and when J is an sulfur atom, Rxg represents a C1-C6 alkyl group or a C1-C6 haloalkyl group, the process comprising obtaining the compound by coupling reaction that reacts a compound represented by the formula (1-j) with Rxg-J-Q in the presence of a transition metal in a solvent.

In the compound represented by the formula (1-j), Rxb is preferably a chlorine atom, a bromine atom, or an iodine atom.

Rxg-J-Q used in the reaction may be purchased from the market or may be produced by a known method.

Production Process O may be performed in accordance with Production Process J while replacing the compound represented by the formula (1a-b) and R5c-J-Q in Production Process J by the compound represented by the formula (1-j) and Rxg-J-Q, respectively.

Production Process P

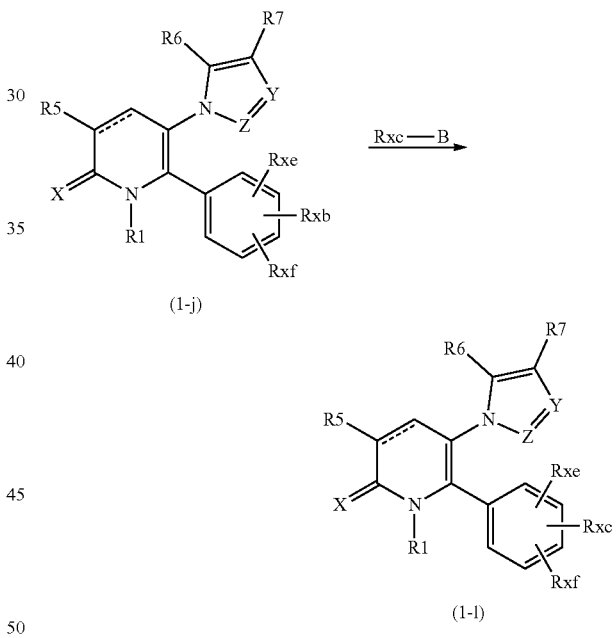

(1-j)

(1-l)

wherein R1, R5, R6, R7, Rxb, Rxc, Rxe, Rxf X, Y, Z and the broken line are the same as defined hereinabove. Rxb, Rxc, Rxe and Rxf in the compound represented by the formula (1-j) and Formula (1-l) are substituted at any appropriate position of R2, R3 or R4 in the compound represented by the formula (1).

Production Process P is a process for synthesizing a compound represented by the formula (1-l), which belongs to the compounds represented by the formula (1), in which Rxc is a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, or a C2-C6 haloalkenyl group, the process comprising obtaining the compound by Suzuki-Miyaura coupling reaction that reacts a compound represented by the formula (1-j) with an organoboronic acid (Rxc-B) in the presence of a transition metal and a base in a solvent.

In the compound represented by the formula (1-j), Rxb is preferably a chlorine atom, a bromine atom, or an iodine atom.

Rxc-B used in the reaction represents an organoboronic acid such as an organoboronic acid or an organoboronate ester and may be purchased from the market or may be produced by a known method.

Production Process P may be performed in accordance with Production Process K while replacing the compound represented by the formula (1a-b) and R5d-B in Production Process K by the compound represented by the formula (1-j) and Rxc-B, respectively.

Production Process Q

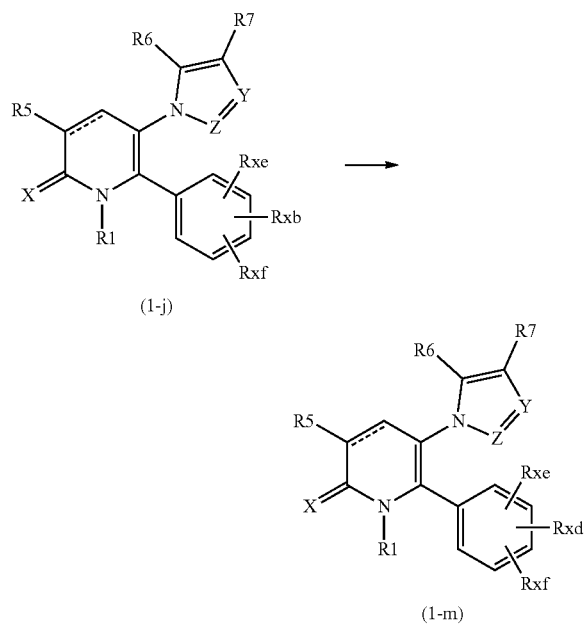

wherein R1, R5, R6, R7, Rxb, Rxe, Rxf, Rxd, X, Y, Z and the broken line are the same as defined hereinabove. Rxb, Rxd, Rxe and Rxf in the compound represented by the formula (1-j) and Formula (1-m) are substituted at any appropriate position of R2, R3 or R4 in the compound represented by the formula (1).

Production Process Q is a process for synthesizing a compound represented by the formula (1-m), which belongs to the compounds represented by the formula (1), in which Rxd is a C2-C6 alkynyl group optionally substituted with substituent(s) C, or a C2-C6 haloalkynyl group, the processes comprising obtaining the compound by Sonogashira coupling reaction that reacts a compound represented by the formula (1-j) with an alkyne-terminated compound in the presence of a transition metal and a base in a solvent.

In the compound represented by the formula (1-j), Rxb is preferably a chlorine atom, a bromine atom, or an iodine atom.

The alkyne-terminated compound used in the reaction may be purchased from the market or may be produced by a known method.

Production Process Q may be performed in accordance with Production Process L while replacing the compound represented by the formula (1a-b) in Production Process L by the compound represented by the formula (1-j).

Production Process R

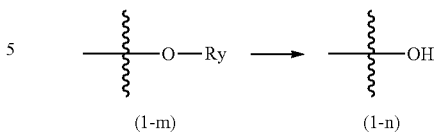

wherein Ry represents a C1-C6 alkyl group.

Production Process R is a process for synthesizing a compound represented by the formula (1-n) having a hydroxy group at any appropriate position of R1, R2, R3, R4, R5, R7, R8 and R9 in the compound represented by the formula (1), the process comprising reacting a compound represented by the formula (1-m) with an alkylthiol in the precence of halogenated aluminum in a solvent.

Examples of the halogenated aluminums used in the reaction include aluminum chloride, for example.

The amount of the halogenated aluminum used in the reaction is at least 1 equivalent amount relative to the compound represented by the formula (1-m) and is not particularly limited as long as the target reaction takes place, but is usually 1 equivalent amount to 10 equivalent amounts.

Examples of the alkylthiols used in the reaction include methanethiol, ethanethiol, 1-propanethiol, 1-butanethiol, 1-octanethiol, 1-decanethiol, and the like.

The amount of alkylthiol the used in the reaction is at least 1 equivalent amount relative to the compound represented by the formula (1-m) and is not particularly limited as long as the target reaction takes place, but is usually 1 equivalent amount to 10 equivalent amounts.

The solvent used in the reaction is not particularly limited as long as the target reaction takes place, and examples thereof include benzene-based solvents such as benzene, toluene, xylene, mesitylene, chlorobenzene and dichlorobenzene, halogen solvents such as dichloromethane, dichloroethane, chloroform and carbon tetrachloride, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-m).

The temperature at which the reaction is performed is not particularly limited as long as the target reaction takes place, but is usually from −10° C. to 200° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1-n) may be dehydrated with a desiccant such as sodium sulfate or magnesium sulfate. This drying process may be omitted.

The reaction mixture including the compound of the formula (1-n) may be distilled under reduced pressure to remove the solvent while avoiding the decomposition of the compound.

After the distillation, the reaction mixture including the compound of the formula (1-n) may be purified by, for example, washing, reprecipitation, recrystallization or column chromatography using an appropriate solvent. The purification process may be selected appropriately in accordance with the desired purity.

The compound represented by the formula (1-m) may be converted into a compound represented by the formula (1-n) using an acid. Hereinbelow, an alternative process will be described.

Production Process R is a process for synthesizing a compound represented by the formula (1-n) having a hydroxy group at any appropriate position of R1, R2, R3, R4, R5, R7, R8 and R9, which belongs to the compounds represented by the formula (1), the process comprising reacting a compound represented by the formula (1-m) with an acid in a solvent.

Examples of the acids used in the reaction include boron halides such as boron trichloride and boron tribromide, and the like.

The amount of the acid used in the reaction is at least 1 equivalent amount relative to the compound represented by the formula (1-m) and is not particularly limited as long as the target reaction takes place, but is usually 1 equivalent amount to 10 equivalent amounts.

The solvent used in the reaction is not particularly limited as long as the target reaction takes place, and examples thereof include benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-m).

The temperature at which the reaction is performed is not particularly limited as long as the target reaction takes place, but is usually from −80° C. to 100° C. or is not more than the boiling point of the solvent.

Similarly, the process described above using the alkylthiol and halogenated aluminum may be used as post-treatment.
Production Process S

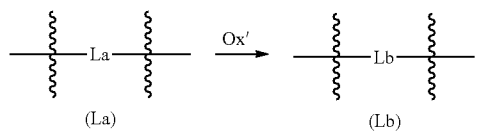

(La)    (Lb)

wherein La represents S, Lb represents SO or $SO_2$, and Ox' represents an oxidizing agent.

Production Process S is a process for synthesizing a compound represented by the formula (Lb) in which Lb in R1, R2, R3, R4, R5, R6, R7, R8 and R9 in the compound represented by the formula (1) is SO or $SO_2$, the process comprising reacting a compound represented by the formula (La) in which La in R1, R2, R3, R4, R5, R6, R7, R8 and R9 in the compound represented by the formula (1) is S with an oxidizing agent (Ox') in a solvent.

The oxidizer used in the reaction may be a peroxide such as hydrogen peroxide solution or m-chloroperbenzoic acid. Transition metals such as sodium tungstate may be added.

When the target product is SO, the amount of the oxidizer used in the reaction is usually 1.0 equivalent amount to 1.2 equivalent amounts relative to the compound having the formula (La). When the target product is $SO_2$, the amount is usually 2 equivalent amounts to 10 equivalent amounts relative to the compound having the formula (La). When a transition metal is added, the amount thereof is usually 0.001 equivalent amount to 1 equivalent amount.

The solvent used in the reaction is not particularly limited as long as the target reaction takes place. Examples of the solvents include water solvent, acidic solvents such as acetic acid, benzene-based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, and the like. The solvents may be used singly, or two or more may be used in combination in any ratio.

The amount of the solvent used in the reaction is not particularly limited as long as the target reaction takes place, but is usually 3 to 200 times the weight of the compound having the formula (La).

The temperature at which the reaction is performed is not particularly limited as long as the target reaction takes place, but is usually from −10° C. to 120° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be used in combination in any ratio. The number of separation operations is not particularly limited and may be determined in accordance with the desired purity or yield.

The reaction mixture including the compound with the formula (Lb) may be dehydrated with a desiccant such as sodium sulfate or magnesium sulfate. This drying process may be omitted.

The reaction mixture including the compound with the formula (Lb) may be distilled under reduced pressure to remove the solvent while avoiding the decomposition of the compound.

After the distillation, the reaction mixture including the compound with the formula (Lb) may be purified by, for example, washing, reprecipitation, recrystallization or column chromatography using an appropriate solvent. The purification process may be selected appropriately in accordance with the desired purity.

Production Process T

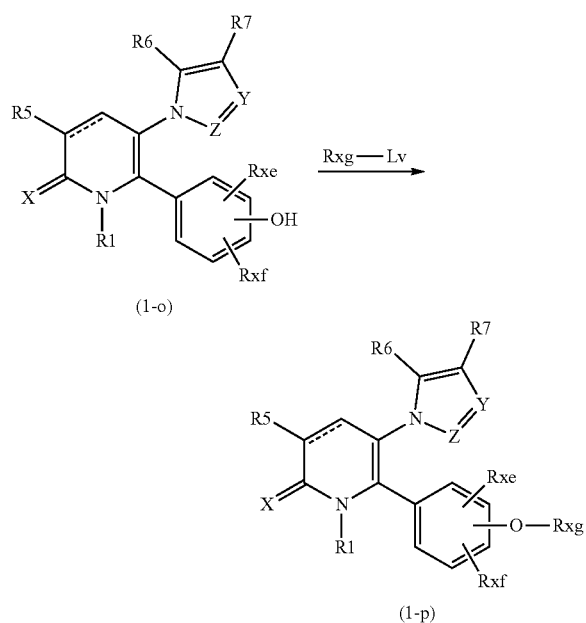

wherein Rxg represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, RdC(=O)—, or Rc-SO$_2$—O— (wherein Rc is the same as defined hereinabove), and R1, R5, R6, R7, Rxe, Rxf, X, Y, Z, Lv and the broken line are the same as defined hereinabove. The hydroxy group, Rxe, Rxf and Rxg-O— in the compound represented by the formula (1-o) and Formula (1-p) are substituted at any appropriate position of R2, R3 or R4 in the compound represented by the formula (1).

Production Process T is a process for synthesizing a compound represented by the formula (1-p), which belongs to the compounds represented by the formula (1), in which Rxg represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, or RdC(=O)—, the process comprising reacting a compound represented by the formula (1-o) with Rxg-Lv in the presence of a base in a solvent.

Rxg-Lv used in the reaction may be purchased from the market or may be produced by a known method.

The amount of Rxg-Lv used in the reaction is at least 1 equivalent amount relative to the compound represented by the formula (1-o) and is not particularly limited as long as the target reaction takes place, but is usually 1 equivalent amount to 10 equivalent amounts.

Examples of the bases used in the reaction include inorganic bases such as sodium carbonate, potassium carbonate, cesium carbonate, sodium hydride, and organic bases such as triethylamine, tributylamine, diisopropylethylamine, pyridine, 4-dimethylaminopyridine, collidine and lutidine and is not particularly limited as long as the target reaction takes place.

The amount of the base used in the reaction is at least 1 equivalent amount relative to the compound represented by the formula (1-o) and is not particularly limited as long as the target reaction takes place, but is usually 1 equivalent amount to 10 equivalent amounts.

The solvent used in the reaction is not particularly limited as long as the target reaction takes place. Examples of the solvents used in the reaction include ether solvents such as diethyl ether, diisopropyl ether, methyl t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. The solvents may be used singly, or two or more may be used in combination in any ratio.

The amount of the solvent used in the reaction is not particularly limited as long as the target reaction takes place, but is usually 3 to 200 times the weight of the compound represented by the formula (1-o).

The temperature at which the reaction is performed is not particularly limited as long as the target reaction takes place, but is usually from −80° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution in which a salt containing a sulfur atom such as sodium thiosulfate or sodium sulfite is dissolved, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl t-butyl ether, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions. The number of separation operations is not particularly limited and may be determined in accordance with the desired purity or yield.

The reaction mixture including the compound of the formula (1-p) may be dehydrated with a desiccant such as sodium sulfate or magnesium sulfate. This drying process may be omitted.

The reaction mixture including the compound of the formula (1-p) may be distilled under reduced pressure to remove the solvent while avoiding the decomposition of the compound.

After the distillation, the reaction mixture including the compound of the formula (1-p) may be purified by, for example, washing, reprecipitation, recrystallization or column chromatography using an appropriate solvent. The purification process may be selected appropriately in accordance with the desired purity.

Production Process U

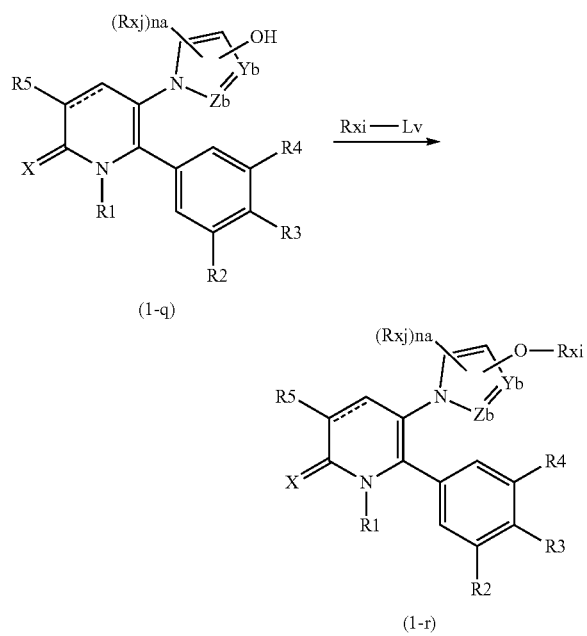

wherein Rxj represents a hydrogen atom, a halogen atom, a cyano group, a nitro group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 alkynyl group optionally substituted with substituent(s) C, a C1-C6 alkoxy group optionally substituted with substituent(s) C, a C2-C6 alkenyloxy group optionally substituted with substituent(s) C, a C3-C6 alkynyloxy group optionally substituted with substituent(s) C, RdC(=O)— (wherein Rd is the same as defined hereinabove), RaRbN— (wherein Ra and Rb are the same as defined hereinabove), or ReC(=O)N(Rf)— (wherein Re and Rf are the same as defined hereinabove), Rxi represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, or RdC(=O)—, Yb represents Rxj-C, HO—C(in this case, HO—C is a substrate state before the reaction is performed. When HO—C is selected, a hydroxy group is not selected at the position of R6, R7 and R9 in the compound represented by the formula (1)), or a nitrogen atom, Zb represents Rxj-C, HO—C(in this case, HO—C is a substrate state before the reaction is performed. When HO—C is selected, a hydroxy group is not selected at the position of R6, R7 and R8 in the compound represented by the formula (1)), or a nitrogen atom, and R1, R2, R3, R4, R5, na, X, Lv, the broken line and na are the same as defined hereinabove. The hydroxy group, Rxa and Rxi-O— in the compound represented by the formula (1-q) and Formula (1-r) are substituted at any appropriate position of R6, R7, R8 or R9 in the compound represented by the formula (1).

Production Process U is a process for synthesizing a compound represented by the formula (1-r), which belongs to the compounds represented by the formula (1), in which Rxi represents a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C3-C6 alkynyl group optionally substituted with substituent(s) C, a C3-C6 haloalkynyl group, or RdC(=O)—, the process comprising reacting a compound represented by the formula (1-q) with Rxi-Lv in the presence of a base in a solvent.

Rxi-Lv used in the reaction may be purchased from the market or may be produced by a known method.

Production Process U may be performed in accordance with Production Process T while replacing the compound represented by the formula (1-o) and Rxg-Lv in Production Process T by the compound represented by the formula (1-q) and Rxi-Lv, respectively.

Production Process V

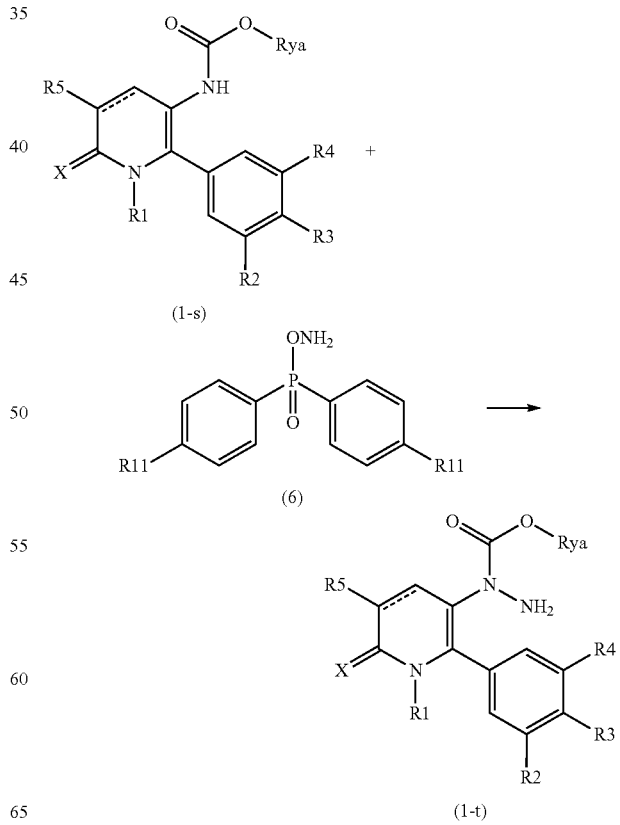

wherein R11 represents a hydrogen atom or a methoxy group, Rya represents a C1-C6 alkyl group or a benzyl group, and R1, R2, R3, R4, R5, X and the broken line are the same as defined hereinabove.

Production Process V is a process for synthesizing an intermediate for production represented by the formula (1-t), the process comprising reacting a compound represented by the formula (1-s) with a compound represented by the formula (6) in the presence of a base in a solvent.

The compound represented by the formula (1-s) used in the reaction may be synthesized in accordance with a reference example.

The compound represented by the formula (6) used in the reaction may be purchased from the market or may be produced by a known method.

The amount of the compound represented by the formula (6) used in the reaction is at least 1 equivalent amount relative to the compound represented by the formula (1-s) and is not particularly limited as long as the target reaction takes place, but is usually 1 equivalent amount to 20 equivalent amounts.

Examples of the bases used in the reaction include metal hydrides such as sodium hydride, inorganic bases such as sodium carbonate, potassium carbonate and cesium carbonate, metal alkoxides such as sodium methoxide, sodium ethoxide, sodium t-butoxide, potassium t-butoxide, and metal amides such as lithium diisopropylamide, hexamethyldisilazane lithium, hexamethyldisilazane sodium and hexamethyldisilazane potassium.

The amount of the base used in the reaction is at least 1 equivalent amount relative to the compound represented by the formula (1-s) and is not particularly limited as long as the target reaction takes place, but is usually 1 equivalent amount to 20 equivalent amounts.

The solvent used in the reaction is not particularly limited as long as the target reaction takes place, and examples thereof include ether solvents such as diethyl ether, diisopropyl ether, methyl-t-butyl ether, dimethoxyethane, tetrahydrofran and dioxane, amide solvents such as N-methylpyrrolidone, N,N-dimethylformamide and N,N-dimethylacetamide, urea solvents such as 1,3-dimethyl-2-imidazolidinone, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-s).

The temperature at which the reaction is performed is not particularly limited as long as the target reaction takes place, but is usually from −80° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1-t) obtained above may be dehydrated with a desiccant such as sodium sulfate or magnesium sulfate. This drying process may be omitted.

The reaction mixture including the compound represented by the formula (1-t) obtained above may be distilled under reduced pressure to remove the solvent while avoiding the decomposition of the compound.

After the distillation, the reaction mixture including the compound represented by the formula (1-t) may be purified by, for example, washing, reprecipitation, recrystallization or column chromatography using an appropriate solvent. The purification process may be selected appropriately in accordance with the desired purity.

Production Process W

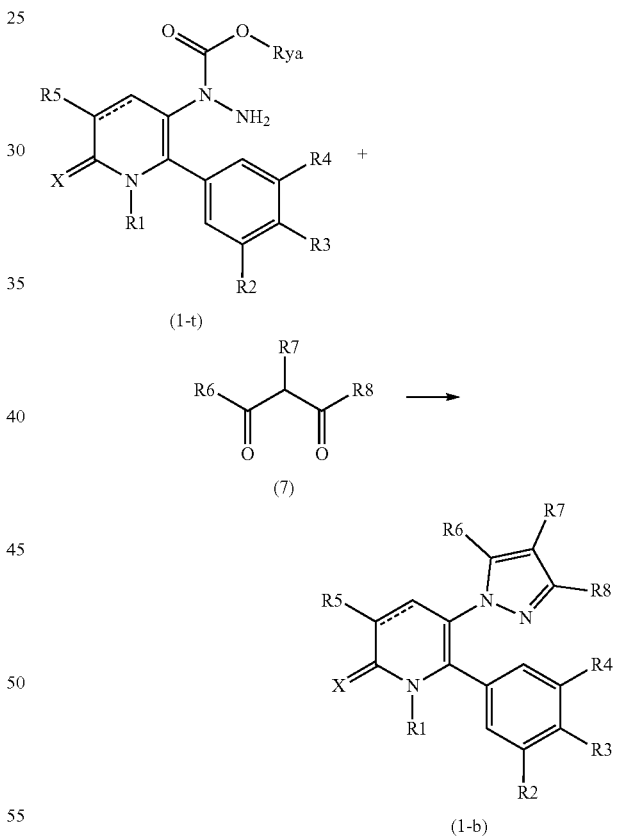

wherein R1, R2, R3, R4, R5, R6, R7, R8, Rya, X and the broken line are the same as defined hereinabove.

Production Process W is a process for synthesizing a compound represented by the formula (1-b), which belongs to the compounds represented by the formula (1), the process comprising reacting a compound represented by the formula (1-t) with a compound represented by the formula (7) in the presence of an acid in a solvent.

In the compound represented by the formula (1-t), Rya is preferably a t-butoxy group. The compound represented by the formula (7) used in the reaction may be purchased from the market or may be produced by a known method. Also, the compound represented by the formula (7) includes the reaction equivalents represented by the following formulae:

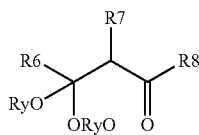
(7-a)

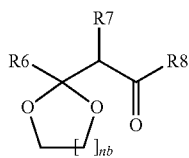
(7-b)

wherein nb represents an integer of 1 to 4, and R6, R7, R8 and Ry are the same as defined hereinabove. Further, when R8 represents a hydrogen atom, the compound represented by the formula (7) includes the compounds represented by the following formulae:

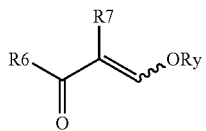
(7-c)

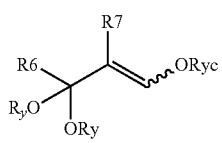
(7-d)

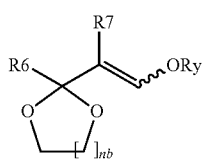
(7-e)

wherein Ryc represents a C1-C6 alkyl group, and R6, R7, R8, Ry and nb are the same as defined hereinabove. The broken line represents geometric isomerism, the group may be either the E-isomer or the Z-isomer, or may be a mixture of the E-isomer and the Z-isomer in an appropriate ratio.

The amount of the compound represented by the formula (7) used in the reaction is at least 1 equivalent amount relative to the compound represented by the formula (1-t) and is not particularly limited as long as the target reaction takes place, but is usually 1 equivalent amount to 10 equivalent amounts.

Examples of the acids used in the reaction include inorganic acids such as hydrochloric acid and sulfuric acid, and organic acids such as acetic acid, methanesulfonic acid and p-toluenesulfonic acid, and are not particularly limited as long as the target reaction takes place.

The amount of the acid used in the reaction is at least a catalytic amount relative to the compound represented by the formula (1-t) and is not particularly limited as long as the target reaction takes place, but is usually 1 equivalent amount to 20 equivalent amounts.

The solvent used in the reaction is not particularly limited as long as the target reaction takes place, and examples thereof include ether solvents such as diethyl ether, diisopropyl ether, methyl-t-butyl ether, dimethoxyethane, tetrahydrofuran and dioxane, alcohol solvents such as methanol, ethanol and isopropanol, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-t).

The temperature at which the reaction is performed is not particularly limited as long as the target reaction takes place, but is usually from −80° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1-b) obtained above may be dehydrated with a desiccant such as sodium sulfate or magnesium sulfate. This drying process may be omitted.

The reaction mixture including the compound represented by the formula (1-b) obtained above may be distilled under reduced pressure to remove the solvent while avoiding the decomposition of the compound.

After the distillation, the reaction mixture including the compound represented by the formula (1-b) may be purified by, for example, washing, reprecipitation, recrystallization or column chromatography using an appropriate solvent. The purification process may be selected appropriately in accordance with the desired purity.

Production Process X

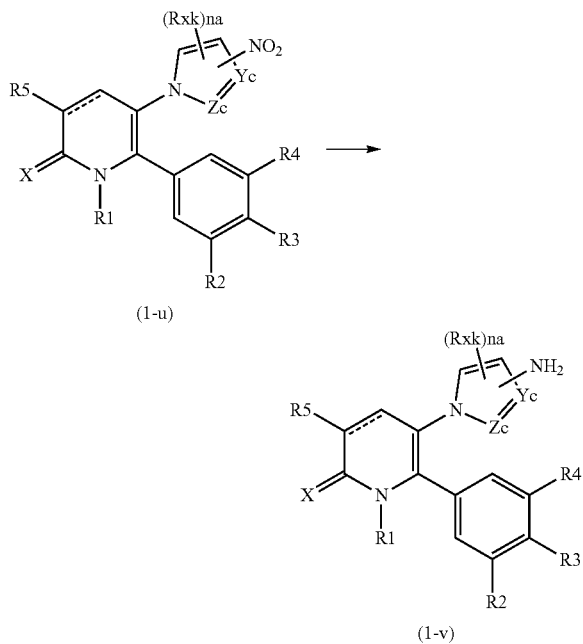

wherein Rxk represents a hydrogen atom, a halogen atom, a hydroxy group, a cyano group, a C1-C6 alkyl group optionally substituted with substituent(s) C, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)— (wherein Rd is the same as defined hereinabove), RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), Yc represents Rxk-C, $O_2N$—C(in this case, $O_2N$—C is a substrate state before the reaction is performed. When $O_2N$—C is selected, a nitro group is not selected at the position of R6, R7 and R9 in the compound represented by the formula (1)), or a nitrogen atom, Zc represents Rxk-C, $O_2N$—C(in this case, $O_2N$—C is a substrate state before the reaction is performed. When $O_2N$—C is selected, a nitro group is not selected at the position of R6, R7 and R8 in the compound represented by the formula (1)), or a nitrogen atom, and R1, R2, R3, R4, R5, X, the broken line and na are the same as defined hereinabove. Rxk, the nitro group and the amino group in the compound represented by the formula (1-u) and Formula (1-v) are substituted at any appropriate position of R6, R7, R8 or R9 in the compound represented by the formula (1).

Production Process X is a process for synthesizing a compound represented by the formula (1-v) having an amino group, which belongs to the compounds represented by the formula (1), the process comprising reacting a compound represented by the formula (1-u) with a reducing agent in a solvent.

Examples of the reducing agents used in the reaction include a combination of hydrogen with palladium, and a combination of an acid with tin, and the like and is not particularly limited as long as the target reaction takes place. Here, a combination of an acid with iron will be described.

The amount of the iron used in the reaction is at least 3 equivalent amounts relative to the compound represented by the formula (1-u) and is not particularly limited as long as the target reaction takes place, but is usually 3 equivalent amounts to 50 equivalent amounts.

Examples of the acids used in the reaction include inorganic acids such as hydrochloric acid and ammonium chloride. The amount of the acid used in the reaction is at least a catalytic amount relative to the compound represented by the formula (1-u) and is not particularly limited as long as the target reaction takes place, but is usually 1 equivalent amount to 20 equivalent amounts.

The solvent used in the reaction is not particularly limited as long as the target reaction takes place, and examples thereof include aqueous solvents, alcohol solvents such as methanol, ethanol and isopropanol, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-u).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield. Also, insolubles may be removed by filtration, but this operation is not indispensable.

The reaction mixture including the compound represented by the formula (1-v) obtained above may be dehydrated with a desiccant such as sodium sulfate or magnesium sulfate. This drying process may be omitted.

The reaction mixture including the compound represented by the formula (1-v) obtained above may be distilled under reduced pressure to remove the solvent while avoiding the decomposition of the compound.

After the distillation, the reaction mixture including the compound represented by the formula (1-v) may be purified by, for example, washing, reprecipitation, recrystallization or column chromatography using an appropriate solvent. The purification process may be selected appropriately in accordance with the desired purity.

Production Process Y

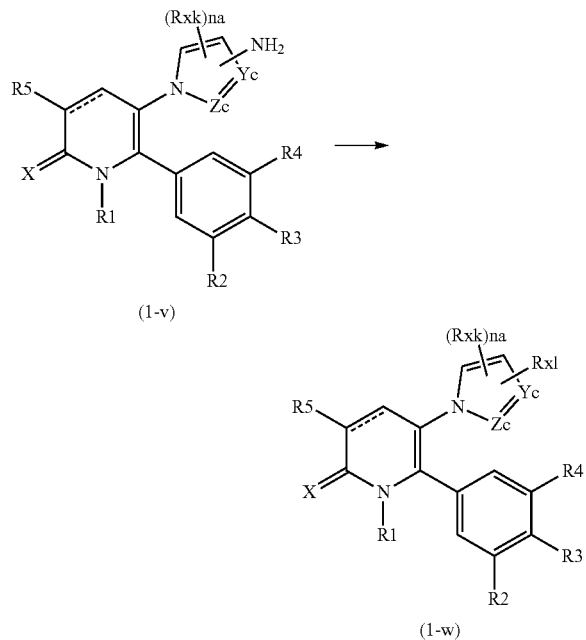

(1-v)

(1-w)

wherein Rxl represents a hydrogen atom, a halogen atom, a hydroxy group or a cyano group, and R1, R2, R3, R4, R5, Rxk, X, Yc, Zc, the broken line and na are the same as defined hereinabove. Rxk, Rxl and the amino group in the compound represented by in the formula (1-v) and Formula (1-w) are substituted at any appropriate position of R6, R7, R8 or R9 in the compound represented by the formula (1).

Production Process Y is a process for synthesizing a compound represented by the formula (1-w), which belongs to the compounds represented by the formula (1), the process comprising reacting a compound represented by the formula (1-v) with a nitrite in a solvent followed by Sandmeyer reaction that reacts the resulting product with a nucleophilic reagent.

Examples of the nitrites used in the reaction include metal nitrites such as sodium nitrite, nitrite esters such as isoamyl nitrite and t-butyl nitrite, and the like.

The amount of the nitrite used in the reaction is at least 1 equivalent amount relative to the compound represented by the formula (1-v) and is not particularly limited as long as the target reaction takes place, but is usually 1 equivalent amount to 10 equivalent amounts.

The nucleophile used in the reaction may be selected appropriately depending on a substituent to be introduced, and as the nucleophile, hypophosphorous acid is used when the substituent is a hydrogen atom, copper chloride is used when the substituent is a chlorine atom, copper bromide is used when the substituent is a bromine atom, copper iodide is used when the substituent is an iodine atom, water is used when the substituent is a hydroxy group, and copper cyanide is used when the substituent is a cyano group, for example.

The amount of the nucleophile used in the reaction is at least 1 equivalent amount relative to the compound represented by the formula (1-v) and is not particularly limited as long as the target reaction takes place.

The solvent used in the reaction is not particularly limited as long as the target reaction takes place, and examples thereof include aqueous solvents, ether solvents such as diethyl ether, diisopropyl ether, methyl-t-butyl ether, dimethoxyethane, tetrahydrofuran and dioxane, alcohol solvents such as methanol, ethanol and isopropanol, benzene-based solvents such as benzene, toluene, xylene, mesitylene, chlorobenzene and dichlorobenzene, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-v).

The temperature at which the reaction is performed is not particularly limited as long as the target reaction takes place, but is usually from −20° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield. Also, insolubles may be removed by filtration, but this operation is not indispensable.

The reaction mixture including the compound represented by the formula (1-w) obtained above may be dehydrated with a desiccant such as sodium sulfate or magnesium sulfate. This drying process may be omitted.

The reaction mixture including the compound represented by the formula (1-w) obtained above may be distilled under reduced pressure to remove the solvent while avoiding the decomposition of the compound.

After the distillation, the reaction mixture including the compound represented by the formula (1-w) may be purified by, for example, washing, reprecipitation, recrystallization or column chromatography using an appropriate solvent. The purification process may be selected appropriately in accordance with the desired purity.

Production Process Z

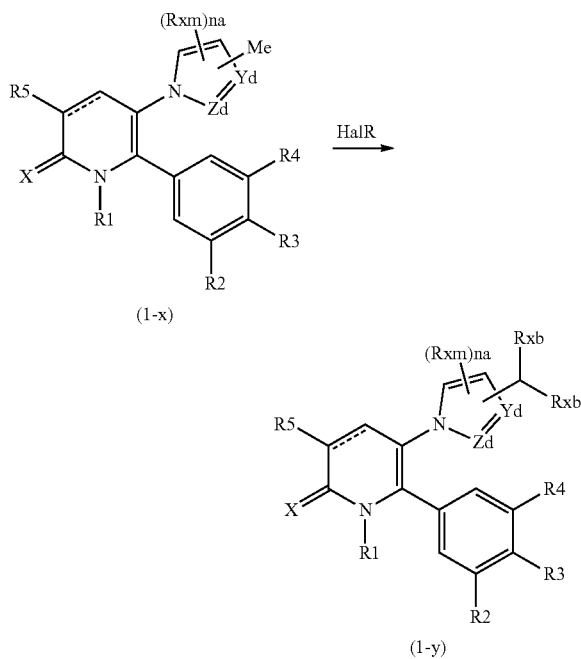

wherein Rxm represents a hydrogen atom, a halogen atom, a hydroxy group, a cyano group, a nitro group, a C1-C6 haloalkyl group, a C3-C8 cycloalkyl group optionally substituted with substituent(s) C, a C2-C6 alkenyl group optionally substituted with substituent(s) C, a C2-C6 haloalkenyl group, a C2-C6 alkynyl group optionally substituted with substituent(s) C, a C2-C6 haloalkynyl group, a C1-C6 alkoxy group optionally substituted with substituent(s) C, a C1-C6 haloalkoxy group, a C3-C8 cycloalkoxy group optionally substituted with substituent(s) C, a C2-C6 alkenyloxy group optionally substituted with substituent(s) C, a C2-C6 haloalkenyloxy group, a C3-C6 alkynyloxy group optionally substituted with substituent(s) C, a C3-C6 haloalkynyloxy group, RdC(=O)O— (wherein Rd is the same as defined hereinabove), Rc-L- (wherein Rc and L are the same as defined hereinabove), RaRbN— (wherein Ra and Rb are the same as defined hereinabove), or ReC(=O)N(Rf)— (wherein Re and Rf are the same as defined hereinabove), Yd represents Rxm-C, Me-C (in this case, Me-C is a substrate state before the reaction is performed. When Me-C is selected, a methyl group is not selected at the position of R6, R7 and R9 in the compound represented by the formula (1)), or a nitrogen atom, Zd represents Rxm-C, Me-C (in this case, Me-C is a substrate state before the reaction is performed. when Me-C is selected, a methyl group is not selected at the position of R6, R7, R8 in the compound represented by the formula (1)), or a nitrogen atom, and R1, R2, R3, R4, R5, X, HalR, the broken line and na are the same as defined hereinabove. Rxm, the methyl group and (Rxb)₂C— in the compound represented by the formula (1-x) and Formula (1-y) are substituted at any appropriate position of R6, R7, R8 or R9 in the compound represented by the formula (1).

Production Process Z is a process of obtaining a compound represented by the formula (1-y), which belongs to the compounds represented by the formula (1), in which Rxb is a halogen atom, the process comprising reacting a compound represented by the formula (1-x) using a radical initiator and a halogenating reagent (HalR) in a solvent.

In the formula (1-y), Rxb is preferably a chlorine atom, a bromine atom, or an iodine atom.

Examples of the radical initiators used in the reaction include azobisisobutyronitrile, 2,2'-azobis(4-methoxy-2,4-dimethylvaleronitrile), benzoyl peroxide, and the like.

The amount of radical initiator used in the reaction is not particularly limited as long as the target reaction takes place, but is usually 0.01 equivalent amount to 1.0 equivalent amount relative to the compound represented by the formula (1-x).

Examples of the halogenating reagents used in the reaction include N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, and the like.

The amount of the halogenating reagent used in the reaction is at least 2 equivalent amounts relative to the compound represented by the formula (1-x) and is not particularly limited as long as the target reaction takes place, but is usually 2 equivalent amounts to 2.8 equivalent amounts. However, the amount of the halogenating reagent containing hydantoin is at least 1 equivalent amount and is not particularly limited as long as the target reaction takes place, but is usually 1 equivalent amount to 1.4 equivalent amounts.

The solvent used in the reaction is not particularly limited as long as the target reaction takes place, and examples thereof include halogenated benzene-based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-x).

The temperature at which the reaction is performed is not particularly limited as long as the target reaction takes place, but is usually from 20° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane and chloroform, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1-y) obtained above may be dehydrated with a desiccant such as sodium sulfate or magnesium sulfate. This drying process may be omitted.

The reaction mixture including the compound represented by the formula (1-y) obtained above may be distilled under reduced pressure to remove the solvent while avoiding the decomposition of the compound.

After the distillation, the reaction mixture including the compound represented by the formula (1-y) may be purified by, for example, washing, reprecipitation, recrystallization or column chromatography using an appropriate solvent. The purification process may be selected appropriately in accordance with the desired purity.

Production Process AA

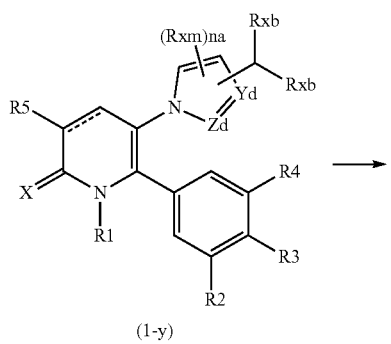

(1-y)

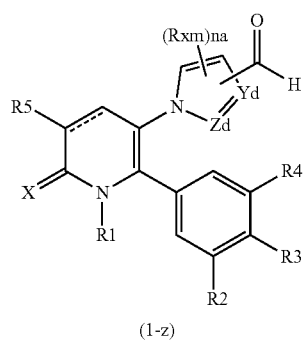

(1-z)

wherein R1, R2, R3, R4, R5, Rxb, Rxm, X, Yd, Zd, the broken line and na are the same as defined hereinabove. Rxm, the formyl group and (Rxb)$_2$C— in the compound represented by the formula (1-y) and Formula (1-z) are substituted at any appropriate position of R6, R7, R8 or R9 in the compound represented by the formula (1).

Production Process AA is a process for synthesizing a compound represented by the formula (1-z) having a formyl group, which belongs to the compounds represented by the formula (1), the process comprising hydrolyzing a compound represented by the formula (1-y) in the presence of a water in a solvent.

In the formula (1-y), Rxb is preferably a chlorine atom, a bromine atom, or an iodine atom.

The use of a water is an absolute necessity for the reaction. Also, to allow the reaction to proceed efficiently, silver nitrate may be used.

The amount of water used in the reaction is at least 1 equivalent amount relative to the compound represented by the formula (1-y) and is not particularly limited as long as the target reaction takes place. Also, water may be used as a solvent.

The amount of silver nitrate used in the reaction is at least 2 equivalent amounts relative to the compound represented by the formula (1-y) and is not particularly limited as long as the target reaction takes place, but is usually 2 equivalent amounts to 10 equivalent amounts.

The solvent used in the reaction is not particularly limited as long as the target reaction takes place, and examples thereof include aqueous solvents, ether solvents such as diethyl ether, diisopropyl ether, methyl-t-butyl ether, dimethoxyethane, tetrahydrofuran and dioxane, nitrile solvents such as acetonitrile, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1-y).

The temperature at which the reaction is performed is not particularly limited as long as the target reaction takes place, but is usually from −10° C. to 100° C. or is not more than the boiling point of the solvent.

As post-treatment, insoluble metals may be removed by filtration. Further, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1-z) obtained above may be dehydrated with a desiccant such as sodium sulfate or magnesium sulfate. This drying process may be omitted.

The reaction mixture including the compound represented by the formula (1-z) obtained above may be distilled under reduced pressure to remove the solvent while avoiding the decomposition of the compound.

After the distillation, the reaction mixture including the compound represented by the formula (1-z) may be purified by, for example, washing, reprecipitation, recrystallization or column chromatography using an appropriate solvent. The purification process may be selected appropriately in accordance with the desired purity.

Production Process AB

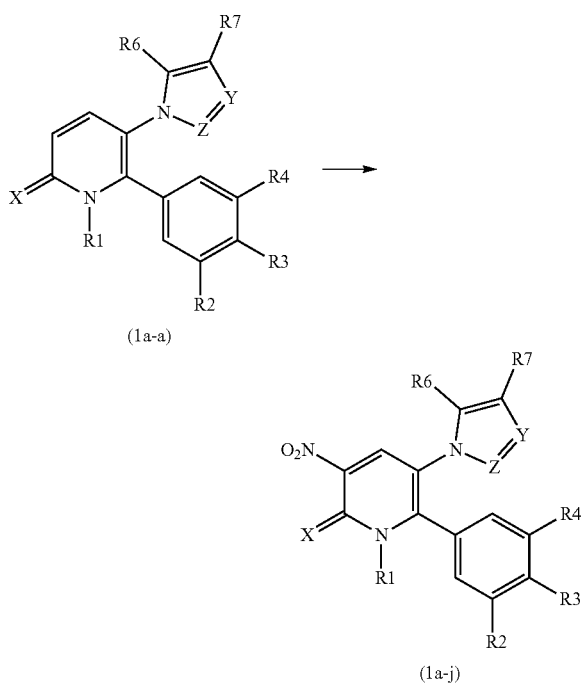

wherein R1, R2, R3, R4, R6, R7, X, Y and Z are the same as defined hereinabove.

Production Process AB is a process for synthesizing a compound represented by the formula (1a-j) having a nitro group, which belongs to the compounds represented by the formula (1a), the process comprising reacting a compound represented by the formula (1a-a) with a copper nitrate in a solvent.

As the copper nitrate used in this reaction, hydrate such as copper nitrate trihydrate can also be used.

The amount of the copper nitrate used in the reaction is not particularly limited as long as the target reaction takes place, but is preferably 1 equivalent amount to 10 equivalent amounts.

The solvent used in this reaction is preferably acetic anhydride.

The amount of the solvent used in the reaction is not particularly limited as long as the target reaction takes place, but is usually 3 to 200 times the weight of the compound represented by the formula (1a-a).

The temperature at which the reaction is performed is not particularly limited as long as the target reaction takes place, but is usually from −10° C. to the boiling point of the solvent.

As post-treatment, insoluble metals may be removed by filtration. Further, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1a-j) obtained above may be dehydrated with a desiccant such as sodium sulfate or magnesium sulfate. This drying process may be omitted.

The reaction mixture including the compound represented by the formula (1a-j) obtained above may be distilled under reduced pressure to remove the solvent while avoiding the decomposition of the compound.

After the distillation, the reaction mixture including the compound represented by the formula (1a-j) may be purified by, for example, washing, reprecipitation, recrystallization or column chromatography using an appropriate solvent. The purification process may be selected appropriately in accordance with the desired purity.

Production Process AC

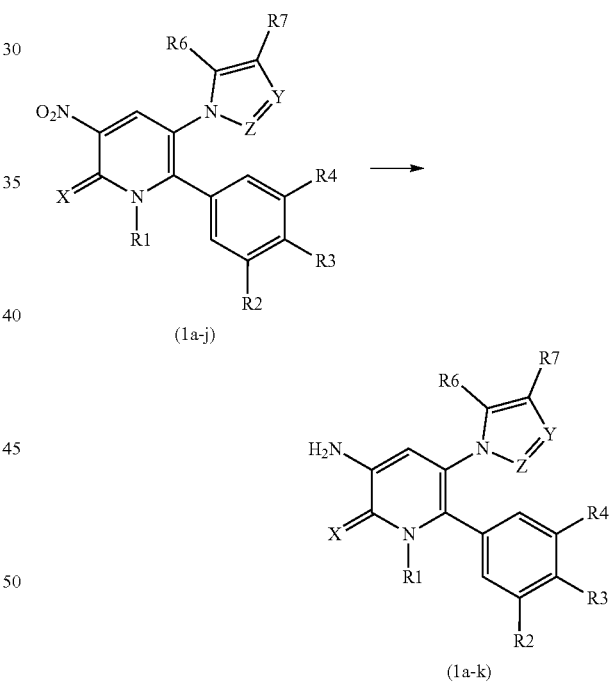

wherein R1, R2, R3, R4, R6, R7, X, Y and Z are the same as defined hereinabove.

Production Process AC is a process for synthesizing a compound represented by the formula (1a-k) having a amino group, which belongs to the compounds represented by the formula (1a), the process comprising reacting a compound represented by the formula (1a-j) with a reducing agent in a solvent.

Production Process AC may be performed in accordance with Production Process X while replacing the compound represented by the formula (1-u) in Production Process X by the compound represented by the formula (1a-j).

Production Process AD

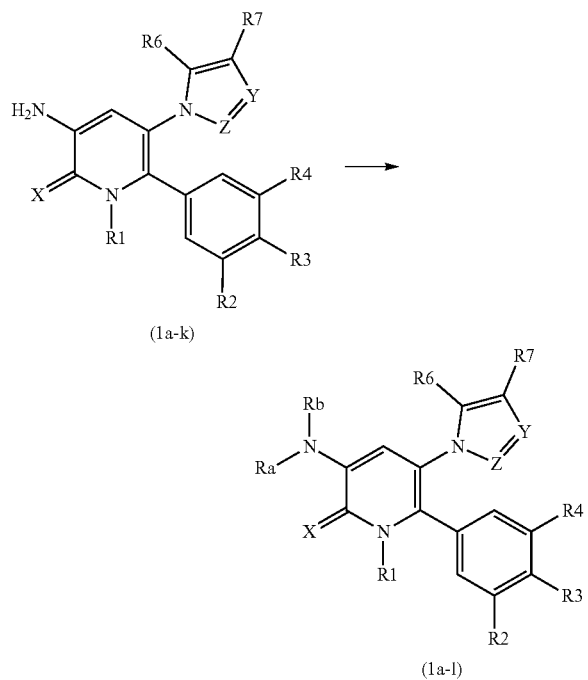

(1a-k)

(1a-l)

wherein R1, R2, R3, R4, R6, R7, Ra, Rb, X, Y and Z are the same as defined hereinabove.

Production Process AD is a process for synthesizing a compound represented by the formula (1a-1) having a amino group, which belongs to the compounds represented by the formula (1a), the process comprising reacting a compound represented by the formula (1a-k) with an alkylating agent in the presence of a base in a solvent.

The alkylating agent used in this reaction may include Ra-Lv (wherein Ra and Lv are the same as defined hereinabove) and Rb-Lv (wherein Ra and Lv are the same as defined hereinabove). In the case where Ra and Rb are taken together with the nitrogen atom to which they are bounded to form an aziridinyl group, an azetidinyl group, a pyrrolidinyl group, a piperidinyl group, a morpholinyl group, a homopiperidinyl group, or an azocanyl group, an example of an alkylating agent may include Lv-Rh-Lv (wherein Rh represents an ethylene group, a propylene group, a butylene group, a pentylene group, a hexylene group, a heptylene group, or —$CH_2CH_2OCH_2CH_2$—, and Lv is the same as defined hereinabove). These alkylating agents can be obtained as commercially available products or can be produced by known methods.

When Rb represents a hydrogen atom, the equivalent amount of the alkylating agent, Ra-Lv used in this reaction may be 1 equivalent amount or more with respect to the compound represented by the formula (1a-k), and is not particularly limited as long as the target reaction takes place, and is usually 1 equivalent amount to 1.5 equivalent amounts. In the case where Ra and Rb are taken together with the nitrogen atom to which they are bounded to form an aziridinyl group, an azetidinyl group, a pyrrolidinyl group, a piperidinyl group, a morpholinyl group, a homopiperidinyl group, or an azocanyl group, the equivalent amount of the alkylating agent, Lv-Rh-Lv may be 1 equivalent or more with respect to the compound represented by the formula (1a-k), and is not particularly limited as long as the target reaction takes place, and. is usually 1 equivalent amount to 10 equivalent amounts. In the case where Ra and Rb are the same, the equivalent amount of the alkylating agent, Ra-Lv may be 2 equivalents or more with respect to the compound represented by the formula (1a-k), and is not particularly limited as long as the target reaction takes place, and is usually 2 equivalent amount to 30 equivalent amounts.

Examples of the base used in this reaction include inorganic bases such as sodium carbonate, potassium carbonate, cesium carbonate and sodium hydride, but is not particularly limited as long as the target reaction takes place.

In the case of producing a compound represented by the formula (1a-1) having RaHN—, the amount of the base used in the reaction is at least 1 equivalent amount relative to the compound represented by the formula (1a-k) and is not particularly limited as long as the target reaction takes place, and is usually 1 equivalent amount to 10 equivalent amounts. In the case of producing a compound represented by the formula (1a-1) in which Ra and Rb are the same, or a compound represented by the formula (1a-1) in which Ra and Rb are taken together with the nitrogen atom to which they are bounded to form an aziridinyl group, an azetidinyl group, a pyrrolidinyl group, a piperidinyl group, a morpholinyl group, a homopiperidinyl group, or an azocanyl group, the amount of the base used in this reaction may be 2 equivalents or more with respect to the compound represented by formula (1a-k), and is not particularly limited as long as the target reaction takes place, and is usually 2 equivalents to 30 equivalents.

The solvent used in the reaction is not particularly limited as long as the target reaction takes place, and examples thereof include ether solvents such as diethyl ether, diisopropyl ether, methyl-t-butyl ether, dimethoxyethane, tetrahydrofuran and dioxane, alcohol solvents such as methanol, ethanol and isopropanol, benzene solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N, N-dimethylformamide and N, N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone, and the like. The solvents may be used singly, or two or more may be mixed in any proportions.

The amount of the solvent used in the reaction is not particularly limited as long as the target reaction takes place, but is usually 3 to 200 times the weight of the compound represented by the formula (1a-k).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1a-1) obtained above may be dehydrated with a desiccant such as sodium sulfate or magnesium sulfate. This drying process may be omitted.

The reaction mixture including the compound represented by the formula (1a-1) obtained above may be distilled under reduced pressure to remove the solvent while avoiding the decomposition of the compound.

After the distillation, the reaction mixture including the compound represented by the formula (1a-1) may be purified by, for example, washing, reprecipitation, recrystallization or column chromatography using an appropriate solvent. The purification process may be selected appropriately in accordance with the desired purity.

In the case of producing a compound in which Ra and Rb are different and Ra and Rb represent other than a hydrogen atom, first, a compound represented by the formula (1a-1) having RaHN— is produced by the method described above. Then, by carrying out the method again while replacing the compound represented by (1a-k) and Ra-Lv in the above method with the compound represented by formula (1a-1) having RaHN— and Rb-Lv, respectively, a compound represented by the formula (1a-1) having RaRbN— can be produced.

Production Process AE

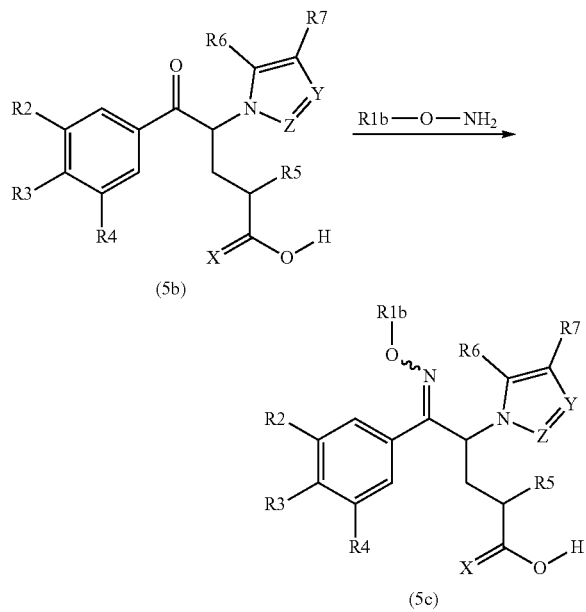

(5b)

(5c)

wherein R1b represents a C1-C6 alkyl group optionally substituted with substituent(s) A, a C1-C6 haloalkyl group, a C—C8 cycloalkyl group optionally substituted with a substituent(s) A, a C2-C6 alkenyl group optionally substituted with a substituent(s) A, a C2-C6 haloalkenyl group, a C2-C6 alkynyl group optionally substituted with a substituent(s) A, or a C2-C6 haloalkynyl group, the wavy line represents geometric isomerism, and R2, R3, R4, R5, R6, R7, X, Y and Z are the same as defined hereinabove.

Production Process AE is a process for synthesizing a intermediate for production represented by the formula (5c), the process comprising reacting a compound represented by the formula (5b) with R1b-O—NH$_2$ in a solvent.

The compound represented by the formula (5c) represents either only E form or Z form, or a mixture of E form and Z form in any ratio.

R1b-O—NH$_2$ used in this reaction can be obtained as a commercial product or can be produced by a known method. R1b-O—NH$_2$ may form a salt with an acidic compound such as hydrochloric acid or acetic acid, and is not particularly limited as long as the target reaction takes place. However, when using a salt of R1b-O—NH$_2$ and an acidic compound, desalting with a basic substance is preferable. Examples of bases used for desalting include inorganic bases such as acid sodium, potassium carbonate, cesium carbonate and sodium hydride, organic bases such as triethylamine, tributylamine, diisopropylethylamine, pyridine, 4-dimethylaminopyridine, collidine and lutidine, but is not particularly limited as long as the target reaction takes place. The amount of the base used for desalting may be at least one equivalent with respect to R1b-O—NH$_2$, and is not particularly limited as long as the target reaction takes place, and is usually 1 equivalent to 10 equivalents.

The amount of R1b-O—NH$_2$ used in this reaction may be 1 equivalent or more with respect to the compound represented by the formula (5b), and is not particularly limited as long as the target reaction takes place, and is usually from 1 equivalent to 10 equivalents.

The solvent used in the reaction is not particularly limited as long as the target reaction takes place, and examples thereof include ether solvents such as diethyl ether, diisopropyl ether, methyl-t-butyl ether, dimethoxyethane, tetrahydrofuran and dioxane, alcohol solvents such as methanol, ethanol and isopropanol, benzene solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N, N-dimethylformamide and N, N-dimethylacetamide, urea solvents such as 1,3-dimethyl-2-imidazolidinone, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone, and the like. The solvents may be used singly, or two or more may be mixed in any proportions.

The amount of the solvent used in the reaction is not particularly limited as long as the target reaction takes place, and is usually 3 to 200 times the weight of the compound represented by the formula (5b).

The temperature at which the reaction is performed is not particularly limited as long as the target reaction takes place, but is usually from 0° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (5c) obtained above may be dehydrated with a desiccant such as sodium sulfate or magnesium sulfate. This drying process may be omitted.

The reaction mixture including the compound represented by the formula (5c) obtained above may be distilled under reduced pressure to remove the solvent while avoiding the decomposition of the compound.

After the distillation, the reaction mixture including the compound represented by the formula (5c) may be purified by, for example, washing, reprecipitation, recrystallization or column chromatography using an appropriate solvent. The purification process may be selected appropriately in accordance with the desired purity.

Production Process AF

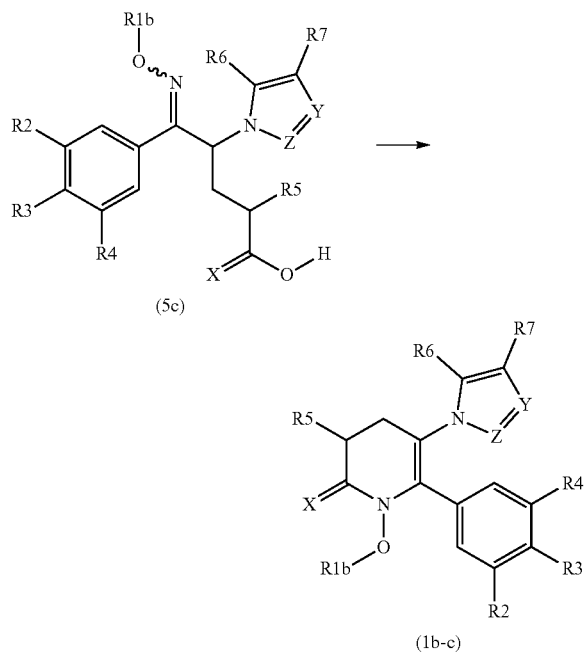

(5c)

(1b-c)

wherein R1, R2, R3, R4, R5, R6, R7, X, Y and Z are the same as defined hereinabove.

Production Process AF is a process for synthesizing a compound represented by the formula (1b-c), which belongs to the compounds represented by the formula (1b), the process comprising reacting a compound represented by the formula (5c) with an acid chloride forming agent in a solvent.

Examples of the acid chloride forming agent used in this reaction include thionyl chloride, phosphorus oxychloride, oxalyl chloride and the like.

The amount of the acid chloride forming agent used in this reaction may be at least 1 equivalent with respect to the compound represented by the formula (5c), and is not particularly limited as long as the target reaction takes place, and is usually 1 equivalent to 10 equivalents.

Although N, N-dimethylformamide can be added to facilitate the reaction, it is not essential. The amount of N, N-dimethylformamide may be a catalytic amount relative to the acid chloride forming agent, and is not particularly limited as long as the desired reaction takes place, and is usually 1 equivalent or less.

The solvent used in the reaction is not essential, and is not particularly limited as long as the target reaction takes place, and examples thereof include ether solvents such as diethyl ether, diisopropyl ether, methyl-t-butyl ether, dimethoxyethane, tetrahydrofuran and dioxane, benzene solvents such as benzene, toluene, xylene, mesitylene, chlorobenzene and dichlorobenzene, ester solvents such as ethyl acetate, isopropyl acetate and butyl acetate, nitrile solvents such as acetonitrile, halogen solvents such as dichloromethane, dichloroethane, chloroform and carbon tetrachloride, sulfur solvents such as dimethyl sulfoxide and sulfolane, ketone solvents such as acetone, methyl ethyl ketone and methyl isobutyl ketone, and the like. The solvents may be used singly, or two or more may be mixed in any proportions.

The amount of the solvent used in the reaction is not particularly limited as long as the target reaction takes place, and is usually 200 times or less by weight of the compound represented by the formula (5c).

The temperature at which the reaction is performed is not particularly limited as long as the target reaction takes place, but is usually from −10° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield.

The reaction mixture including the compound represented by the formula (1b-c) obtained above may be dehydrated with a desiccant such as sodium sulfate or magnesium sulfate. This drying process may be omitted.

The reaction mixture including the compound represented by the formula (1b-c) obtained above may be distilled under reduced pressure to remove the solvent while avoiding the decomposition of the compound.

After the distillation, the reaction mixture including the compound represented by the formula (1b-c) may be purified by, for example, washing, reprecipitation, recrystallization or column chromatography using an appropriate solvent. The purification process may be selected appropriately in accordance with the desired purity.

Production Process AG

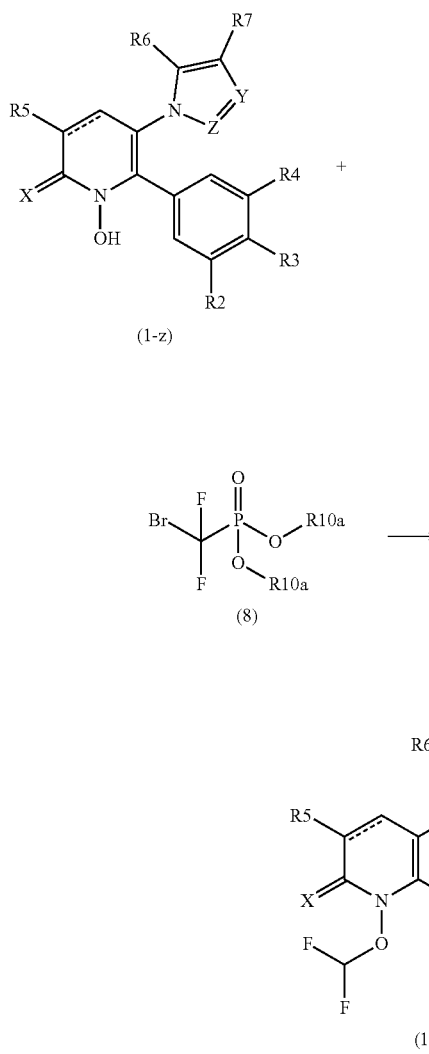

wherein R2, R3, R4, R5, R6, R7, R10a, X, Y, Z and a broken line are the same as defined hereinabove.

Production Process AG is a process for synthesizing a compound represented by the formula (1-aa) having a difluoromethoxy group, which belongs to the compounds represented by the formula (1), the process comprising reacting a compound represented by the formula (1-z) with a compound represented by the formula (8) in the presence of a base in a solvent.

The compound represented by the formula (8) used in this reaction can be obtained as a commercial product, or can be produced by a known method.

The amount of the compound represented by the formula (8) used in this reaction may be 1 equivalent or more with respect to the compound represented by the formula (1-z), and is not particularly limited as long as the target reaction takes place, and is usually 1 equivalent to 10 equivalents.

Examples of the base used in this reaction, include inorganic bases such as lithium hydroxide, sodium hydroxide and potassium hydroxide.

The amount of the base used in this reaction may be 2 equivalents or more with respect to the compound represented by the formula (1-z), and is not particularly limited as long as the target reaction takes place, and is usually 2 equivalents to 50 equivalents.

The solvent used in this reaction is not particularly limited as long as the target reaction takes place, and examples thereof include water solvents, ether solvents such as tetrahydrofuran and dioxane, nitrile solvents such as acetonitrile, and the like. The solvents may be used singly, or two or more may be mixed in any proportions.

The amount of the solvent used in the reaction is not particularly limited as long as the target reaction takes place, and is usually 3 times to 200 times the weight of the compound represented by the formula (1-z).

The temperature at which the reaction is performed is not particularly limited as long as the target reaction takes place, but is usually from −80° C. to 150° C. or is not more than the boiling point of the solvent.

As post-treatment, water or an appropriate aqueous solution may be added to the reaction mixture to perform separation. The aqueous solution that is used here may be, for example, an acidic aqueous solution such as of hydrochloric acid, sulfuric acid or ammonium chloride, an alkaline aqueous solution such as of potassium hydroxide, sodium hydroxide, sodium carbonate, potassium carbonate, sodium hydrogen carbonate or potassium hydrogen carbonate, an aqueous solution of a sulfur-containing salt such as of sodium thiosulfate or sodium sulfite, or brine. During the separation operation, a water immiscible solvent may be added as required, with examples including benzene-based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. Also, the solvents may be used singly, or two or more may be mixed in any proportions. The number of separation operations is not particularly limited and may be determined in accordance with the desired purity or yield. It is also possible, but not essential, to remove insolubles by carrying out a filtration operation.

The reaction mixture including the compound represented by the formula (1-aa) obtained above may be dehydrated with a desiccant such as sodium sulfate or magnesium sulfate. This drying process may be omitted.

The reaction mixture including the compound represented by the formula (1-aa) obtained above may be distilled under reduced pressure to remove the solvent while avoiding the decomposition of the compound.

After the distillation, the reaction mixture including the compound represented by the formula (1-aa) may be purified by, for example, washing, reprecipitation, recrystallization or column chromatography using an appropriate solvent. The purification process may be selected appropriately in accordance with the desired purity.

Production Process AH

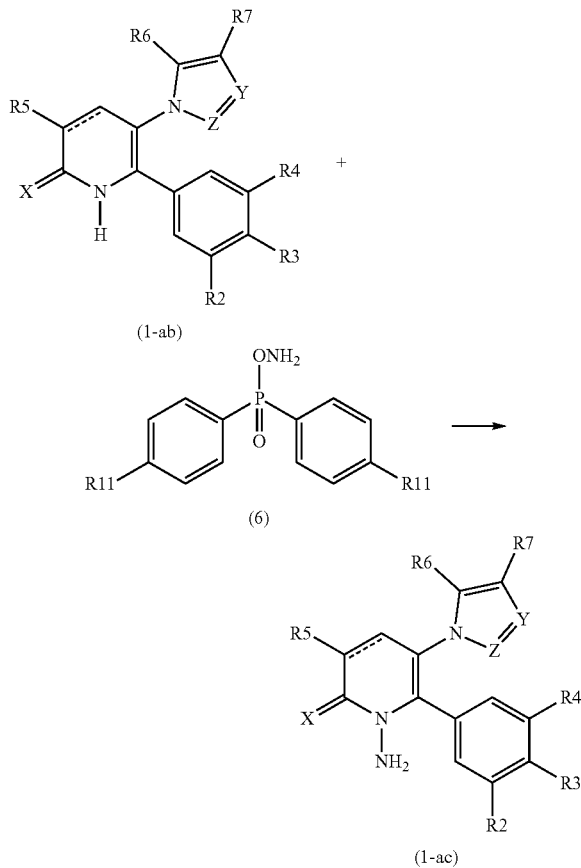

(1-ab)

(6)

(1-ac)

wherein R2, R3, R4, R5, R6, R7, R11, X, Y, Z and a broken line are the same as defined hereinabove.

Production Process AH is a process for synthesizing a compound represented by the formula (1-ac), which belongs to the compounds represented by the formula (1), the process comprising reacting a compound represented by the formula (1-ab) with a compound represented by the formula (6) in the presence of a base in a solvent.

Production Process AH can be carried out according to Production Process V by replacing the compound represented by the formula (1-s) in Production Process V with the compound represented by the formula (1-ab), Production Process AI

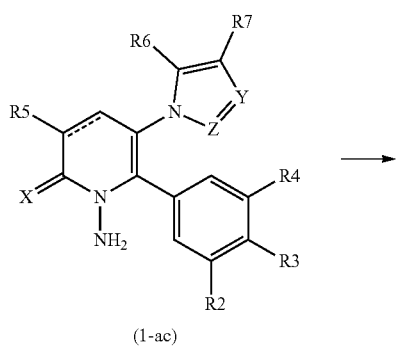

(1-ac)

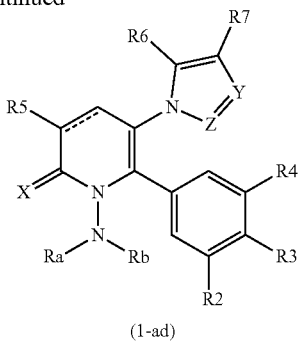

(1-ad)

wherein R2, R3, R4, R5, R6, R7, X, Y, and Z are the same as defined hereinabove.

Production Process AI is a process for synthesizing a compound represented by the formula (1-ad) having an amino group, which belongs to the compounds represented by the formula (1a), the process comprising reacting a compound represented by the formula (1-ac) with an alkylating agent in the presence of a base in a solvent.

Production Process A1 can be carried out according to Production Process AD by replacing the compound represented by the formula (1a-k) in Production Process AD with the compound represented by the formula (1-ac), The compounds represented by the formula (1) may be produced by an appropriate combination of Production Process A to Production Process A1 described hereinabove. The compounds of the formula (1) may be also produced by an appropriate combination of a known process and any of Production Process A to Production Process AI.

The inventive compounds can protect plants from harmful organisms and thus may be used as agricultural chemicals, particularly as agricultural and horticultural pest control agents. Specific examples of such use include fungicides, insecticides, herbicides, plant growth regulators, and the like, with fungicides being preferable.

The inventive compounds may be used as agricultural and horticultural fungicides in farms, paddy fields, tea gardens, orchards, meadows, grasses, forests, gardens, roadside trees, etc. for the prevention and treatment of plant diseases.

Plant diseases in the present invention mean that systemic abnormal pathological symptoms such as wilting, damping-off, yellowing, dwarfism and spindly growth, or partial pathological symptoms such as spotting, leaf blight, mosaic pattern, leaf rolling, die back, root rot, clubroot and knotting, are induced in plants such as crops, flowering plants, flowering trees and shrubs, and trees. In other words, the term means that plants become or have become ill. Some main pathogens that cause plant diseases are fungi, bacteria, spiroplasmas, phytoplasmas, viruses, viroids, parasitic higher plants and nematodes. The inventive compounds are effective against fungi, which are not limitative.

Diseases caused by fungi are mainly fungal diseases. Examples of the fungi (pathogens) that cause fungal diseases include Plasmodiophora, Oomycetes, Zygomycetes, Ascomycetes, Basidiomycetes, Deuteromycetes, and the like. Examples of the Plasmodiophora include clubroot fungus, potato powdery scab fungus, beet necrotic yellow vein virus, and the like. Examples of the Oomycetes include blight fungus, downy mildew fungus, *Pythium* species, *Aphanomyces* species, and the like. Examples of the Zygomycetes include *Rhizopus* species, and the like. Examples of the Ascomycetes include peach leaf curl fungus, corn southern leaf blight fungus, rice blast fungus, powdery mildew fungus, anthracnose fungus, *fusarium* head blight fungus, bakanae fungus, stem rot fungus, and the like. Examples of the Basidiomycetes include rust fungus, smut fungus, violet root rot fungus, blister blight fungus, rice sheath blight fungus, and the like. Examples of the Deuteromycetes include gray mold fungus, *Alternaria* species, *Fusarium* species, *Penicillium* species, *Rhizoctonia* species, southern blight fungus, and the like.

The inventive compounds are effective against various plant diseases. The following provides specific examples of disease names and pathogens thereof.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Wairea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani*, *Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seeding blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus);

wheat and barley: powdery mildew (*Blumeria graminis* f. sp. *hordei*; f. sp. *tritici*), rust (*Puccinia striiformis*, *Puccinia graminis*, *Puccinia recondita*, *Puccinia hordei*), leaf blotch (*Pyrenophora graminea*), net blotch (*Pyrenophora teres*), *Fusarium* head blight (*Gibberella zeae*, *Fusarium culmorum*, *Fusarium avenaceum*, *Monographella nivalis*), *Typhula* snow blight (*Typhula incarnata*, *Typhula ishikariensis*, *Monographella nivalis*), loose smut (*Ustilago nuda*), stinking smut (*Tilletia caries*, *Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), take-all (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*);

corn: *Fusarium* blight (*Gibberella zeae*, etc.), damping-off (*Fusarium avenaceum*, *Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe ampelina*), ripe rot (*Glomerella cingulata*, *Colletotrichum acutatum*), black rot (*Guignardia bidwellii*), *Phomopsis* leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), *Alternaria* leaf spot (*Alternaria mali*), rust (*Gymnosporangium yamadae*), blossom blight (*Monilinia mali*), apple canker (*Valsa ceratosperma*), ring spot (*Botryosphaeria berengeriana*), anthracnose (*Colletotrichum acutatum*, *Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali*, *Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*);

Japanese pears: black spot (*Alternaria kikuchiana*), pear scab (*Venturia nashicola*), rust (*Gymnosporangium asiaticum*), ring spot (*Botryosphaeria berengeriana* f. sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudomonas syringae* pv. *syringae*); European pears: blight (*Phytophthora cactorum*, *Phytophthora syringae*), bacterial shoot blight (*Erwinia* sp.); peaches: black spot (*Cladosporium carpophilum*), *Phomopsis* rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*); persimmons: anthracnose (*Glomerella cingulata*), leaf spot (*Cercospora kaki*; *Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*);

tomatoes, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce and the like: sclerotial disease (*Sclerotinia sclerotiorum*); various vegetables such as tomatoes, cucumbers, beans, Japanese radishes, watermelons, eggplants, rapeseed, green peppers, spinach and beets: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*, etc.), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus); tomatoes: ring spot (*Alternaria solan*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridiflava*), soft rot (*Erwinia carotovora* subsp. *carotovora*), bacterial leaf gall (*Crynebacterium* sp.), yellowing wilt (*Phytoplasma asteris*), yellow dwarfism (Tobacco leaf curl, subgroup III geminivirus); eggplants: powdery mildew (*Sphaerotheca fuliginea* etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysanthemi*), soft rot (*Erwinia carotovora* subsp. *carotovora*), bacterial spot (*Pseudomonas* sp.); rapeseed: black spot (*Alternaria brassicae*), black rot (*Xhanthomonas campestris* pv. *campestris*), bacterial black spot (*Pseudomonas syringae* pv. *maculicola*), soft rot (*Erwinia carotovora*); cruciferous vegetables: black spot (*Alternaria brassicae* etc.), white spot (*Cercosporella brassicae*), black leg (*Phoma lingam*), clubroot (Plasmodiophora *brassicae*), downy mildew (*Peronospora parasitica*), black rot (*Xanthomonas campestris* pv. *campestris*), bacterial black spot (*Pseudomonas syringae* pv. *maculicola*), soft rot (*Erwinia carotovora* subsp. *carotovora*);

cabbage: club foot (*Thanatephorus cucumeris*), yellowing wilt (*Fusarium oxysporum*), alternaria sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), Rhizoctonia root rot (*Rhizoctonia solani*), stem rot (*Phytophthora sojae*), downy mildew (*Peronospora manshurica*), rust (*Phakopsora pachyrhizi*), anthracnose (*Colletotrichum truncatum* etc.), leaf scald (*Xhanthomonas campestris* pv. *glycines*), bacterial spot (*Pseudomonas syringae* pv. *glycinea*); kidney beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*); peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora piss*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); sugar beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*);

carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae* etc.), anthracnose (*Glomerella cingulata*), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), Tobacco mosaic virus (Tobacco mosaic virus);

coffee: rust (*Hemileia vastatrix*); banana: black sigatoka (*Mycosphaerella fijiensis*), panama disease (*Fusarium oxysporum* f. sp *cubense*); cotton: damping-off (*Fusarium oxysporum*), frosty mildew (Ramularia areola); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa* etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), chrysanthemum virescence (*Phytoplasma aurantifolia*); grasses: brown patch disease (*Rhizoctonia solani*), dollar spot disease (*Sclerotinia homoeocarpa*), curvularia leaf blight (*Curvularia* sp.), rust (*Puccinia zoysiae*), helminthosporium leaf blight (*Cochliobolus* sp.), scald (*Rhynchosporium secalis*), take-all (*Gaeumannomyces graminis*), anthracnose (*Colletotrichum* sp.), *typhula* brown snow blight (*Typhula incarnata*), typhula black snow blight (*Typhula ishikariensis*), *Sclerotinia* (*Myriosclerotinia borealis*), fairy ring disease (*Marasmius oreades* etc.), *Pythium* blight (*Pythium aphanidermatum* etc.), blast (*Pyricularia grisea*).

The inventive compounds may be used singly, and may be preferably used as compositions such as powders, water-dispersible powders, water-dispersible granules, water-soluble powders, water-soluble granules, granules, emulsions, solutions, microemulsions, aqueous suspension preparations, aqueous emulsion preparations and suspoemulsion preparations by being mixed with solid carriers, liquid carriers, gas carriers, surfactants, binders, dispersants, stabilizers and the like. The form of use is not limited to such compositions as long as effects are obtained.

Some specific formulating examples will be described below without limiting the scope of the invention thereto.

Preparation Example 1: Flowable

The inventive compound (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 part by mass), xanthan gum (0.2 parts by mass), and ion exchanged water (78.7 parts by mass) are mixed to give a slurry. Further, the slurry is wet milled with Dyno-Mill KDL using glass beads having a diameter of 1.0 mm to give a flowable.

Preparation Example 2: Emulsion

The inventive compound (5 parts by mass) is dissolved into a mixed solution of xylene (40 parts by mass) and cyclohexane (35 parts by mass). Tween 20 (20 parts by mass) is added to the resultant solution, and the mixture is mixed to give an emulsion.

Preparation Example 3: Water-Dispersible Powder

The inventive compound (10 parts by mass), white carbon (10 parts by mass), polyvinyl alcohol (2 parts by mass), sodium dioctylsulfosuccinate (0.5 parts by mass), sodium alkylbenzenesulfonate (5 parts by mass), calcined diatomaceous earth (10 parts by mass), and kaolinite clay (62.5 parts by mass) are mixed thoroughly, and the mixture is milled with an air mill to give a water-dispersible powder.

The present invention includes a method for controlling a plant disease, including applying the agricultural and horticultural pest control agent described above to a plant, a plant seed, or a soil for plant cultivation. The present invention also includes a method for controlling a plant disease, including applying the agricultural and horticultural fungicide described above to a plant, a plant seed, or a soil for plant cultivation.

The application of compositions (such as agricultural and horticultural pest control agents, and agricultural and horticultural fungicides) including the inventive compounds will be described hereinbelow.

For example, a composition containing the inventive compound may be applied by being brought into contact with a plant body or seeds, or by being added to cultivation soil and brought into contact with the roots or underground stem of a plant. Specific examples of the manners of application include spraying of the composition onto the stem and leaves of an individual plant, injection treatment, seedling nursery box treatment, cell tray treatment, spraying of the composition to plant seeds, plant seed coating treatment, plant seed immersion treatment, plant seed dressing treatment, spraying of the composition onto the surface of soil, spraying of the composition onto the surface of soil followed by mixing into the soil, injection into soil, injection and subsequent mixing into soil, irrigation to soil, irrigation and subsequent mixing into soil, and the like. The compositions offer sufficient effects when applied by any methods usually used by a person skilled in the art.

The term "plant" used in the present invention refers to one which thrives by photosynthesis without moving. Specific examples thereof include rice, wheat, barley, corn, coffee, bananas, grapes, apples, pears, peaches, cherries, persimmons, citrus fruits, soybeans, kidney beans, cotton, strawberries, potatoes, cabbage, lettuce, tomatoes, cucumbers, eggplants, watermelons, sugar beets, spinach, field peas, squash, sugar cane, tobacco, green peppers, sweet potatoes, taro potatoes, konjak, cotton, sunflowers, roses, tulips, chrysanthemums, grasses, etc., and F1 hybrids, etc. of the above plants. Examples further include gene recombinant crops that are created by genetic or other artificial manipulation and are inherently not present in nature, with specific examples including agricultural and horticultural crops such as soybeans, corn, cotton and the like which have been imparted with resistance to herbicides, rice, tobacco and the like acclimated to cold climates, and corn, cotton and the like which have been given the ability to produce insecticidal substances. Examples further include trees such as pines, ash trees, ginkgoes, maples, evergreen oaks, poplars, and zelkova trees, and the like. The term "plant body" used in the present invention is a generic term for all portions that constitute an individual plant, for example, stems, leaves, roots, seeds, flowers, fruits and the like.

The term "seed" used in the present invention refers to one which stores nutrients for the germination of seedlings and is used for agricultural production. Specific examples thereof include seeds of corn, soybeans, cotton, rice, sugar beets, wheat, barley, sunflowers, tomatoes, cucumbers, eggplants, spinach, field peas, squash, sugar cane, tobacco, green peppers, rape, etc., seeds of F1 hybrids, etc. of the above plants, seed tubers of taro potatoes, potatoes, sweet potatoes, konjak, etc., bulbs of edible lilies, tulips, etc., seed bulbs of scallions, etc., seeds and tubers of gene recombinant crops, and the like.

The amount and concentration in which the composition containing the inventive compound is applied may vary depending on factors such as the type of target crop, the type of target disease, the degree of progression of the disease, the formulation form of the compound, the application method and various environmental conditions. In the case of spraying or irrigation, the amount applied in terms of active ingredient may be suitably 0.1 to 10,000 g per hectare, and preferably 10 to 1,000 g per hectare. In the case of seed treatment, the amount used in terms of active ingredient may be 0.0001 to 1,000 g, and preferably 0.001 to 100 g per kg of seeds. Where the composition containing the inventive compound is sprayed to the stem and leaves of an individual plant, is sprayed to the surface of soil, is injected into the soil or is irrigated to the soil, the treatment may be carried out after the composition is diluted to an appropriate concentration with a suitable carrier. When the composition containing the inventive compound is brought into contact with plant seeds, the seeds may be immersed, dressed, sprayed or coated after the composition is diluted to an appropriate concentration. In the immersion, dressing, spraying or coating treatment, the amount of the composition in terms of active ingredient is usually about 0.05 to 50% of the dry weight of the plant seeds, and is preferably 0.1 to 30%, but is not limited thereto and may be determined appropriately depending on the form of the composition and the type of plant seeds to be treated.

Where necessary, the inventive compounds may be used as mixtures with other agricultural chemicals, for example, agricultural chemicals such as fungicides, insecticides (including miticides and nematicides), herbicides, biological pesticides and plant growth regulators, disease control agents containing nucleic acids as active ingredients (WO 2014/062775), soil improvers and fertilizing substances. A mixture of the inventive compound and the other agricultural chemical may be used in such a manner that the inventive compound and the other agricultural chemical are formulated into a single preparation, that each is formulated into separate preparations and the preparations are mixed together before use, that each is formulated into separate preparations and the preparations are used concurrently, or that each is formulated into separate preparations and the preparations are used successively.

Specific examples of the ingredients contained in fungicides which may be used as mixtures with the inventive compounds include those belonging to Group b below, and salts, isomers and N-oxides thereof. The fungicides are not limited thereto, and known fungicides may be used.
Group b:
b-1: Phenylamide Fungicides
Examples of the phenylamide fungicides include [b-1.1] benalaxyl, [b-1.2] benalaxyl-M or kiralaxyl, [b-1.3] furalaxyl, [b-1.4] metalaxyl, [b-1.5] metalaxyl-M or mefenoxam, [b-1.6] oxadixyl, [b-1.7] ofurace, and the like.
b-2: Mitosis Inhibitors and Cell Division Inhibitors
Examples of the mitosis inhibitors and cell division inhibitors include [b-2.1] benomyl, [b-2.2] carbendazim, [b-2.3] fuberidazole, [b-2.4] thiabendazole, [b-2.5]thiophanate, [b-2.6] thiophanate-methyl, [b-2.7] diethofencarb, [b-2,8] zoxamide, [b-2.9] ethaboxam, [b-2.10] pencycuron, [b-2.11] fluopicolide, [b-2.12] phenamacril, and the like.
b-3: Succinic Dehydrogenase Inhibitors (SDHI)
Examples of the succinic dehydrogenase inhibitors (SDHI) include [b-3.1]benodanil, [b-3.2] benzovindiflupyr, [b-3.3] bixafen, [b-3.4] boscalid, [b-3.5] carboxin, [b-3.6] fenfuram, [b-3.7] fluopyram, [b-3.8] flutolanil, [b-3.9] fluxapyroxad, [b-3.10] furametpyr, [b-3.11] isofetamid, [b-3.12] isopyrazam, [b-3.13] mepronil, [b-3.14]oxycarboxin, [b-3.15] penthiopyrad, [b-3.16] penflufen, [b-3.17] pydiflumetofen, [b-3.18] sedaxane, [b-3.19] thifluzamide, [b-3.20] pyraziflumid, and the like.
b-4: Quinone Outside Inhibitors (QoI)
Examples of the quinone outside inhibitors (QoI) include [b-4.1] azoxystrobin, [b-4.2] coumoxystrobin, [b-4.3] dimoxystrobin, [b-4.4] enoxastrobin, [b-4.5] famoxadone, [b-4.6] fenamidone, [b-4.7] fenaminstrobin, [b-4.8] flufenoxystrobin, [b-4.9] fluoxastrobin, [b-4.10] kresoxim-methyl, [b-4.11] mandestrobin, [b-4.12] metominostrobin, [b-4.13] orysastrobin, [b-4.14] picoxystrobin, [b-4.15] pyraclostrobin, [b-4.16] pyrametostrobin, [b-4.17] pyraoxystrobin, [b-4.18] pyribencarb, [b-4.19]triclopyricarb, [b-4.20] trifloxystrobin, and the like.
b-5: Quinone Inside Inhibitors (QiI)
Examples of the quinone inside inhibitors (QiI) include [b-5.1] cyazofamid, [b-5.2] amisulbrom, and the like.
b-6: Oxidative Phosphorylation Uncoupling Inhibitors
Examples of the oxidative phosphorylation uncoupling inhibitors include [b-6.1] binapacryl, [b-6.2] meptyldinocap, [b-6.3] dinocap, [b-6.4] fluazinam, and the like.
b-7: Quinone Outside Stigmatellin Binding Subsite Inhibitors (QoSI)
Examples of the quinone outside stigmatellin binding subsite inhibitors (QoSI) include [b-7.1] ametoctradin, and the like.
b-8: Amino Acid Biosynthesis Inhibitors
Examples of the amino acid biosynthesis inhibitors include [b-8.1] cyprodinil, [b-8.2] mepanipyrim, [b-8.3] pyrimethanil, and the like.
b-9: Protein Biosynthesis Inhibitors
Examples of the protein biosynthesis inhibitors include [b-9.1] streptomycin, [b-9.2] blasticidin-S, [b-9.3] kasugamycin, [b-9.4] oxytetracycline, and the like.
b-10: Signal Transduction Inhibitors
Examples of the signal transduction inhibitors include [b-10.1] fenpiclonil, [b-10.2] fludioxonil, [b-10.3] quinoxyfen, [b-10.4] proquinazid, [b-10.5] chlozolinate, [b-10.6] dimethachlone, [b-10.7] iprodione, [b-10.8] procymidone, [b-10.9] vinclozolin, and the like.
b-11: Lipid and Cell Membrane Biosynthesis Inhibitors
Examples of the lipid and cell membrane biosynthesis inhibitors include [b-11.1] edifenphos, [b-11.2] iprobenfos, [b-11.3] pyrazophos, [b-11.4] isoprothiolane, [b-11.5] biphenyl, [b-11.6] chloroneb, [b-11.7] dicloran, [b-11.8] quintozene, [b-11.9] tecnazene, [b-11.10] tolclofos-methyl, [b-11.11] echlomezol or etridiazole, [b-11.12] iodocarb, [b-11.13] propamocarb, [b-11.14] prothiocarb, and the like.
b-12: Demethylation Inhibitors (DM1)
Examples of the demethylation inhibitors (DMI) include [b-12.1] azaconazole, [b-12.2] bitertanol, [b-12.3] bromuconazole, [b-12.4] cyproconazole, [b-12.5] difenoconazole, [b-12.6] diniconazole, [b-12.7] diniconazole-M, [b-12.8] epoxiconazole, [b-12.9] etaconazole, [b-12.10] fenarimol, [b-12.11] fenbuconazole, [b-12.12] fluquinconazole, [b-12.13] quinconazole, [b-12.14] flusilazole, [b-12.15] flutriafol, [b-12.16] hexaconazole, [b-12.17] imazalil, [b-12.18] imibenconazole, [b-12.19] ipconazole, [b-12.20] metconazole, [b-12.21] myclobutanil, [b-12.22] nuarimol, [b-12.23] oxpoconazole, [b-12.24] oxpoconazole fumarate, [b-12.25] pefurazoate, [b-12.26] penconazole, [b-12.27] prochloraz, [b-12.28] propiconazole, [b-12.29] prothioconazole, [b-12.30] pyrifenox, [b-12.31] pyrisoxazole, [b-12.32] simeconazole, [b-12.33] tebuconazole, [b-12.34] tetraconazole, [b-12.35] triadimefon, [b-12.36]triadimenol, [b-12.37] triflumizole, [b-12.38] triforine, [b-12.39] triticonazole, [b-12.40] mefentrifluconazole, [b-12.41] ipfentrifluconazole, and the like.
B-13: Amine Fungicides
Examples of the amine fungicides include [b-13.1] aldimorph, [b-13.2]dodemorph, [b-13.3] fenpropimorph, [b-13.4] tridemorph, [b-13.5] fenpropidin, [b-13.6]piperalin, [b-13.7] spiroxamine, and the like.
b-14: 3-Keto Reductase Inhibitors in C4-Demethylation in Sterol Biosynthesis
Examples of the 3-keto reductase inhibitors in C4-demethylation in sterol biosynthesis include [b-14.1] fenhexamid, [b-14.2] fenpyrazamine, and the like.
b-15: Squalene Epoxidase Inhibitors in Sterol Biosynthesis
Examples of the squalene epoxidase inhibitors in sterol biosynthesis include [b-15.1] pyributicarb, [b-15.2] naftifine, [b-15.3] terbinafine, and the like.
b-16: Cell Wall Biosynthesis Inhibitors
Examples of the cell wall biosynthesis inhibitors include [b-16.1] polyoxins, [b-16.2] dimethomorph, [b-16.3] flumorph, [b-16.4] pyrimorph, [b-16.5] benthiavalicarb, [b-16.6] benthiavalicarb-isopropyl, [b-16.7] iprovalicarb, [b-16.8] mandipropamid, [b-17.9] valifenalate, and the like.

b-17: Melanin Biosynthesis Inhibitors

Examples of the melanin biosynthesis inhibitors include [b-17.1] phthalide or fthalide, [b-17.2] pyroquilone, [b-17.3] tricyclazole, [b-17.4] carpropamid, [b-17.5] diclocymet, [b-17.6] fenoxanil, [b-17.7] tolprocarb, and the like.

b-18: Host Plant Resistance Inducers

Examples of the host plant resistance inducers include [b-18.1] acibenzolar-S-methyl, [b-18.2] probenazole, [b-18.3] tiadinil, [b-18.4] isotianil, [b-18.5] laminarin, and the like.

b-19: Dithiocarbamate Fungicides

Examples of the dithiocarbamate fungicides include [b-19.1] mancozeb or manzeb, [b-19.2] maneb, [b-19.3] metiram, [b-19.4] propineb, [b-19.5] thiram, [b-19.6] zineb, [b-19.7] ziram, [b-19.8] ferbam, and the like.

b-20: Phthalimide Fungicides

Examples of the phthalimide fungicides include [b-20.1] captan, [b-20.2] captafol, [b-20.3] folpet, [b-20.4] fluorofolpet, and the like.

b-21: Guanidine Fungicides

Examples of the guanidine fungicides include [b-21.1] guazatine, [b-21.2]iminoctadine, [b-21.3] iminoctadine albesilate, [b-21.4] iminoctadine triacetate, and the like.

b-22: Multi-Site Contact Active Fungicides

Examples of the multi-site contact active fungicides include [b-22.1] copper oxychloride, [b-22.2] copper (II) hydroxide, [b-22.3] copper hydroxide sulfate, [b-22.4] organocopper compound, [b-22.5] dodecylbenzenesulphonic acid bisethylenediamine copper [II] salt, DBEDC, [b-22.6] sulphur, [b-22.7] fluoroimide, [b-22.8] chlorothalonil, [b-22.9] dichlofluanid, [b-22.10] tolylfluanid, [b-22.11] anilazine, [b-22.12] dithianon, [b-22.13] chinomethionat or quinomethionate, [b-22.14] extract from lupine seedling cotyledons, and the like.

b-23: Other Fungicides

Examples of other fungicides include [b-23.1] dichlobentiazox, [b-23.2] fenpicoxamid, [b-23.3] dipymetitrone, [b-23.4] bupirimate, [b-23.5] dimethirimol, [b-23.6] ethirimol, [b-23.7] fentin acetate, [b-23.8] fentin chloride, [b-23.9] fentin hydroxide, [b-23.10] oxolinic acid, [b-23.11] hymexazol, [b-23.12] octhilinone, [b-23.13] fosetyl, [b-23.14] phosphorous acid, [b-23.15] sodium phosphite, [b-23.16]ammonium phosphite, [b-23.17] potassium phosphite, [b-23.18] tecloftalam, [b-23.19]triazoxide, [b-23.20] flusulfamide, [b-23.21] diclomezine, [b-23.22] silthiofam, [b-23.23] diflumetorim, [b-23.24] methasulfocarb, [b-23.25] cyflufenamid, [b-23.26] metrafenone, [b-23.27] pyriofenone, [b-23.28] dodine, [b-23.29] flutianil, [b-23.30] ferimzone, [b-23.31] oxathiapiprolin, [b-23.32] tebufloquin, [b-23.33] picarbutrazox, [b-23.34] validamycins, [b-23.35] cymoxanil, [b-23.36] quinofumelin,

[b-23.37] Compound of the Formula (s):

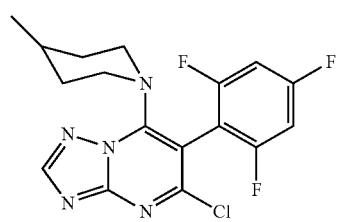

(s1)

(see WO 98/046607),

[b-23.38] compound of the formula (s2):

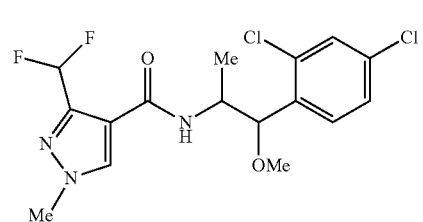

(s2)

(see WO 08/148570),

[b-23.39] compound of the formula (s3):

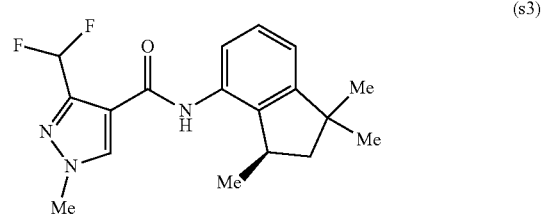 [SMILES: C[C@@H]1CC(C)(C)c2cccc(NC(=O)c3cn(C)nc3C(F)F)c21]

(s3)

(see WO 92/012970),

[b-23.40] compound of the formula (s4):

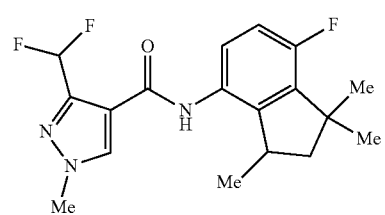

(s4)

(see WO 12/084812),

[b-23.41] compound of the formula (s5):

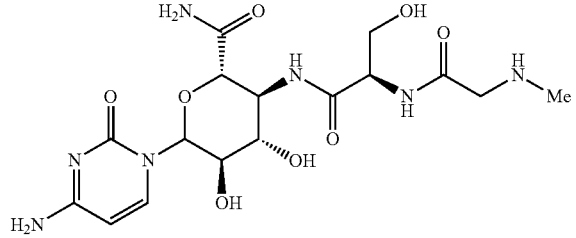

(s5)

(gougerotin),

[b-23.42] compound of the formula (s6):
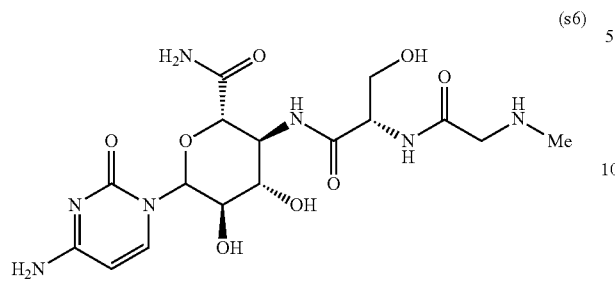
(ningnanmycin),
[b-23.43] compound of the formula (s7):
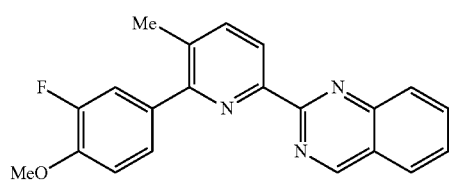
(see WO 10/136475),
[b-23.44] compound of the formula (s8):
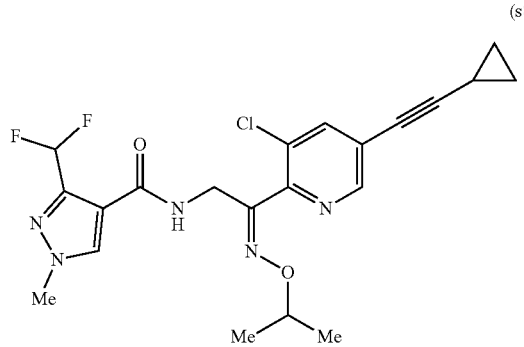
(see WO 14/010737),
[b-23.45] compound of the formula (s9):
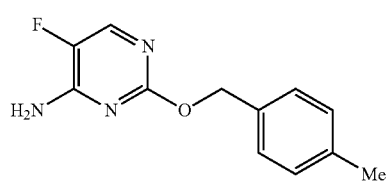
(see WO 11/085084),
[b-23.46] compound of the formula (s10):
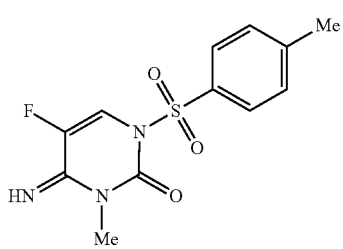
(see WO 11/137002),
[b-23.47] compound of the formula (s11):
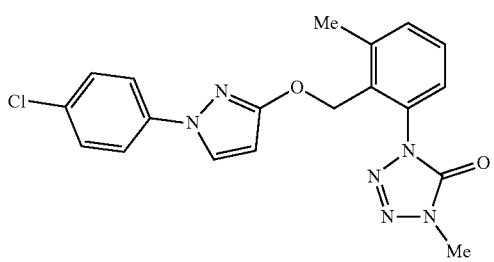
(see WO 13/162072),
[b-23.48] compound of the formula (s12):
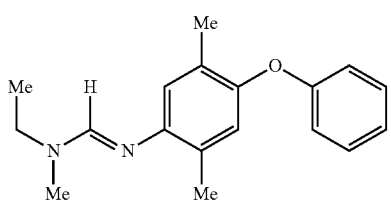
(see WO 08/110313),
[b-23.49] compound of the formula (s13):
(see WO 09/156098),

[b-23.50] compound of the formula (s14):

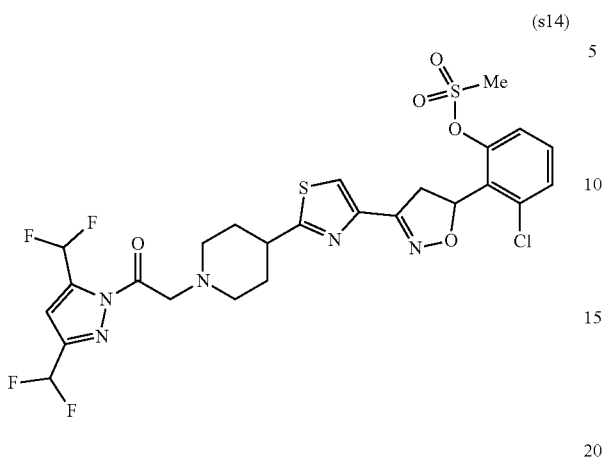

(see WO 12/025557),

[b-23.51] compound of the formula (s15):

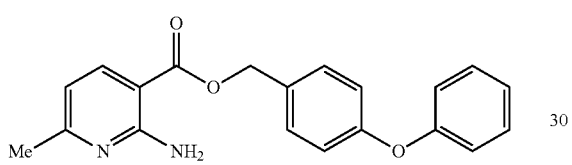

(see WO 14/006945),

[b-23.52] compounds of the formula (s16):

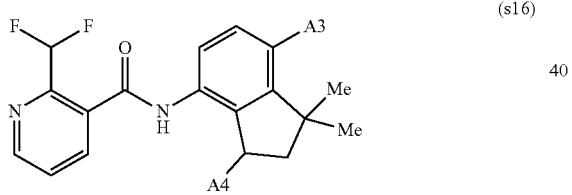

wherein A3 represents a hydrogen atom, a halogen atom, a C1-C6 alkyl group, a C1-C6 haloalkyl group or a cyano group, and A4 represents a hydrogen atom, a C1-C6 alkyl group, a C1-C6 haloalkyl group or a C3-C8 cycloalkyl group (see WO 14/095675),

[b-23.53] compounds of the formula (s17):

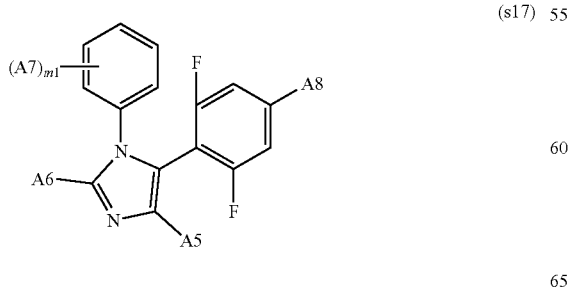

wherein m1 represents an integer of 0 to 3, A5 and A6 are independent of one another and each represent a halogen atom or a C1-C6 alkyl group, A7 and A8 are independent of one another and each represent a halogen atom or a C1-C6 alkoxy group, and when m1 is 2 or greater, the two or more substituents A7 are independent of one another and may be the same as or different from one another (see WO 09/137538 and WO 09/137651),

[b-23.54] compounds of the formula (s18):

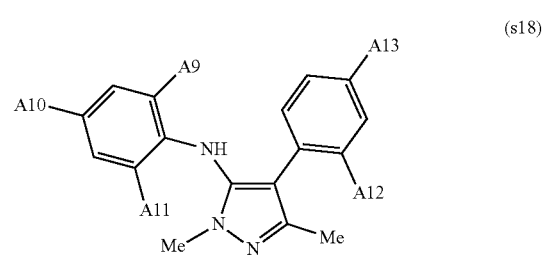

wherein A9 and A10 are independent of one another and each represent a hydrogen atom or a halogen atom, A11 represents a halogen atom, A12 represents a halogen atom or a C1-C6 alkyl group, and A13 represents a halogen atom, a cyano group, a C1-C6 alkyl group or a C1-C6 alkoxy group (see WO 12/031061),

[b-23.55] compounds of the formula (s19):

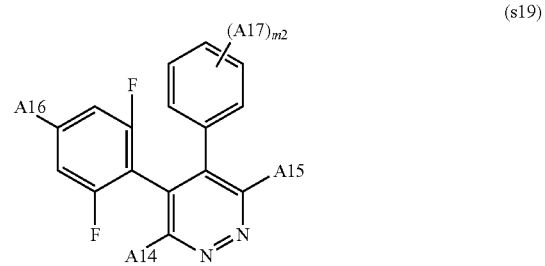

wherein m2 represents an integer of 0 to 6, A14 and A15 are independent of one another and each represent a halogen atom, a cyano group or a C1-C6 alkyl group, A16 represents a hydrogen atom, a halogen atom or a C1-C6 alkoxy group, A17 represents a halogen atom or a C1-C6 alkoxy group, and when m2 is 2 or greater, the two or more substituents A17 are independent of one another and may be the same as or different from one another (see WO 05/121104),

[b-23.56] compounds of the formula (s20):

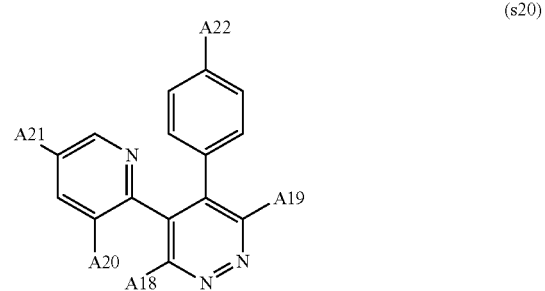

wherein A18 and A19 are independent of one another and each represent a halogen atom, a cyano group or a C1-C6 alkyl group, and A20, A21 and A22 are independent of one another and each represent a hydrogen atom, a halogen atom or a C1-C6 alkoxy group (see WO 07/066601),

[b-23.57] compounds of the formula (s21):

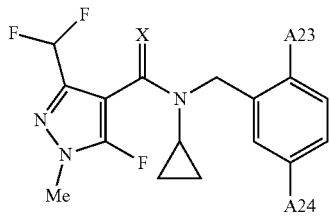

(s21)

wherein A23 and A24 are independent of one another and each represent a hydrogen atom, a halogen atom, a C1-C6 alkyl group or a C3-C8 cycloalkyl group, and X represents an oxygen atom or a sulfur atom (see WO 07/087906, WO 09/016220 and WO 10/130767),

[b-23.58] compounds of the formula (s22):

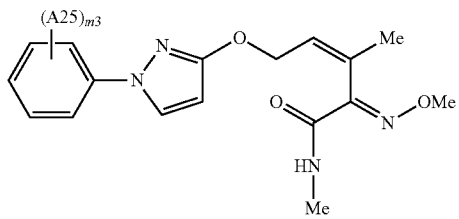

(s22)

wherein m3 represents an integer of 0 to 5, A25 represents a halogen atom, a C1-C6 alkyl group, a C1-C6 haloalkyl group, a C1-C6 alkoxy group, a C1-C6 haloalkoxy group or a C3-C8 cycloalkyl group, and when m3 is 2 or greater, the two or more substituents A25 are independent of one another and may be the same as or different from one another (see WO 13/092224),

[b-23.59] compounds of the formula (s23):

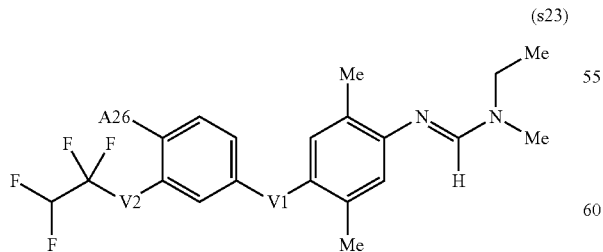

(s23)

wherein A26 represents a hydrogen atom or a halogen atom, and V1 and V2 are independent of one another and each represent an oxygen atom or a sulfur atom (see WO 12/025450),

[b-23.60] compounds of the formula (s24) or the formula (s25):

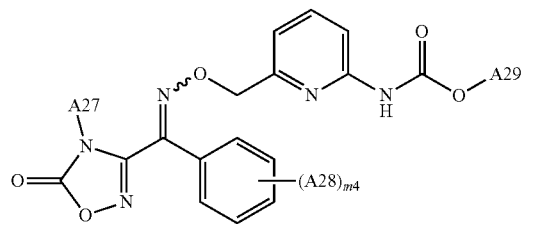

(s24)

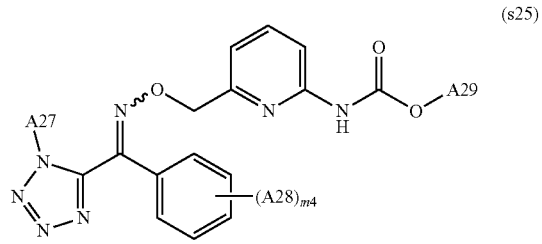

(s25)

wherein m4 represents an integer of 0 to 5, A27 represents a C1-C6 alkyl group, A28 represents a halogen atom, a cyano group, a C1-C6 alkyl group or a C1-C6 haloalkyl group wherein when m4 is 2 or greater, the two or more substituents A28 are independent of one another and may be the same as or different from one another, and A29 represents a C1-C6 alkyl group, a C2-C6 alkenyl group or a C3-C6 alkynyl group (see WO 13/037717),

[b-23.61] compounds of the formula (s26) or the formula (s27):

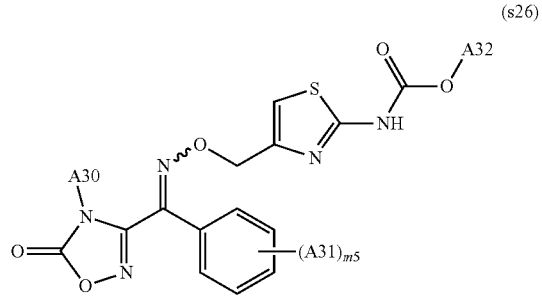

(s26)

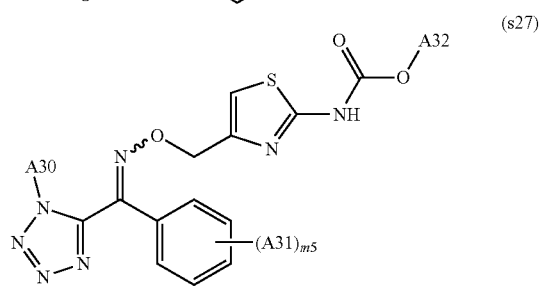

(s27)

wherein m5 represents an integer of 0 to 5, A30 represents a C1-C6 alkyl group, A31 represents a halogen atom, a cyano group, a C1-C6 alkyl group or a C1-C6 haloalkyl group wherein when m5 is 2 or greater, the two or more substituents A31 are independent of one another and may be the same as or different from one another, and A32 represents a C1-C6 alkyl group, a C2-C6 alkenyl group or a C3-C6 alkynyl group (see WO 13/037717),

[b-23.62] compounds of the formula (s28):

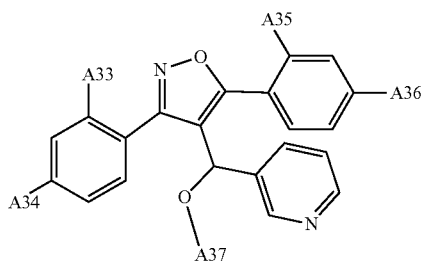

wherein A33, A34, A35 and A36 are independent of one another and each represent a hydrogen atom or a halogen atom, and A37 represents a hydrogen atom, an acetyl group or a benzoyl group (see WO 06/031631 and WO 10/069882),

[b-23.63] compounds of the formula (s29):

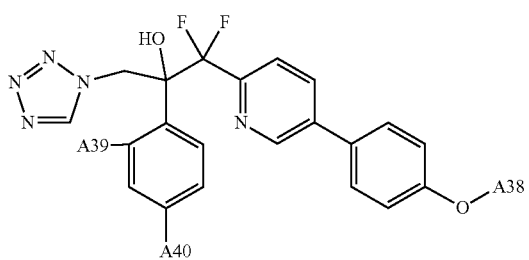

wherein A38 represents a C1-C6 alkyl group or a C1-C6 haloalkyl group, and A39 and A40 are independent of one another and each represent a hydrogen atom or a halogen atom (see WO 14/043376), [0824]

[b-23.64] compounds of the formula (s30):

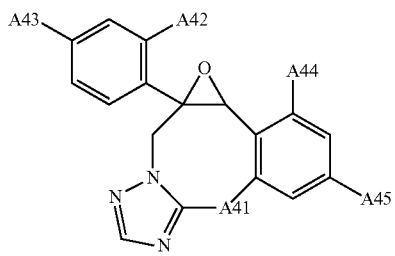

wherein A41 represents a hydrogen atom, a hydrosulfide group (—SH), a thiocyanate group (—SCN) or a C1-C6 alkylthio group, and A42, A43, A44 and A45 are independent of one another and each represent a hydrogen atom or a halogen atom (see WO 09/077443),

[b-23.65] compounds of the formula (s31) or the formula (s32):

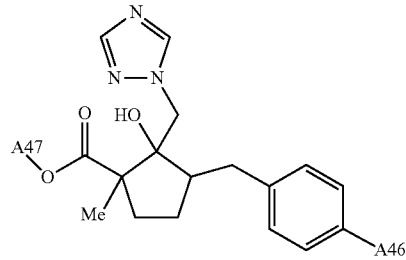

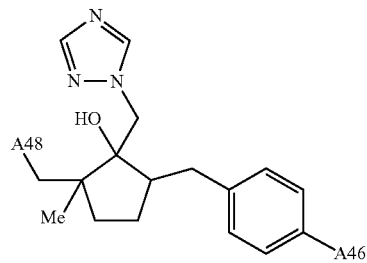

wherein A46 represents a hydrogen atom or a halogen atom, A47 represents a C1-C6 alkyl group, and A48 represents a halogen atom (see WO 11/070771),

[b-23.66] compounds of the formula (s33):

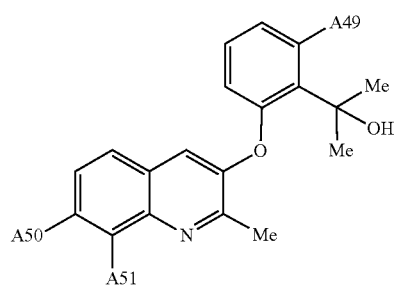

wherein A49, A50 and A51 are independent of one another and each represent a hydrogen atom or a halogen atom (see WO 11/081174), and the like.

Specific examples of the ingredients contained in insecticides which may be used as mixtures with the inventive compounds include those belonging to Group c below, and salts, isomers and N-oxides thereof. The insecticides are not limited thereto, and known insecticides may be used.

Group c:

c-1: Carbamate-Based Acetylcholinesterase (AChE) Inhibitors

Examples of the carbamate-based acetylcholinesterase (AChE) inhibitors include [c-1.1] phosphocarb, [c-1.2] alanycarb, [c-1.3] butocarboxim, [c-1.4]butoxycarboxim, [c-1.5] thiodicarb, [c-1.6] thiofanox, [c-1.7] aldicarb, [c-1.8] bendiocarb, [c-1.9] benfuracarb, [c-1.10] carbaryl, [c-1.11] carbofuran, [c-1.12]carbosulfan, [c-1.13] ethiofencarb, [c-1.14] fenobucarb, [c-1.15] formetanate, [c-1.16] furathiocarb, [c-1.17] isoprocarb, [c-1.18] methiocarb, [c-1.19] methomyl, [c-1.20]oxamyl, [c-1.21] pirimicarb, [c-1.22] propoxur, [c-1.23] trimethacarb, [c-1.24] XMC (3,5-xylyl methylcarbamate), [c-1.25] allyxycarb, [c-1.26] aldoxycarb, [c-1.27] bufencarb, [c-1.28] butacarb, [c-1.29] carbanolate, [c-1.30] metolcarb, [c-1.31] xylylcarb, [c-1.32] fenothiocarb, [c-1.33] xylylcarb, [c-1.34] bendiocarb, and the like.

c-2: Organophosphorus-Based Acetylcholinesterase (AChE) Inhibitors

Examples of the organophosphorus-based acetylcholinesterase (AChE) inhibitors include [c-2.1] acephate, [c-2.2] azamethiphos, [c-2.3] azinphos-methyl, [c-2.4] azinphos-ethyl, [c-2.5] ethephon, [c-2.6] cadusafos, [c-2.7] chlorethoxyfos, [c-2.8] chlorfenvinphos, [c-2.9] chlormephos, [c-2.10] chlorpyrifos, [c-2.11] chlorpyrifos-methyl, [c-2.12] coumaphos, [c-2.13] cyanophos, [c-2.14] demeton-S-methyl, [c-2.15] diazinon, [c-2.16] dichlofenthion, [c-2.17] dichlorvos, [c-2.18] dicrotophos, [c-2.19] dimethoate, [c-2.20] dimethylvinphos, [c-2.21] disulfoton, [c-2.22] O-ethyl O-4-nitrophenyl phenylphosphonothioate, [c-2.23] ethion, [c-2.24]ethoprophos, [c-2.25] famphur, [c-2.26] fenamiphos, [c-2.27] fenitrothion, [c-2.28]fenthion, [c-2.29] fosthiazate, [c-2.30] heptenophos, [c-2.31] isofenphos-methyl, [c-2.32] isocarbophos, [c-2.33] isoxathion, [c-2.34] malathion, [c-2.35] mecarbam, [c-2.36] methamidophos, [c-2.37] methidathion, [c-2.38] mevinphos, [c-2.39] monocrotophos, [c-2.40] naled, [c-2.41] omethoate, [c-2.42] oxydemeton-methyl, [c-2.43] parathions, [c-2.44] parathion-methyl, [c-2.45] phenthoate, [c-2.46] phorate, [c-2.47] phosalone, [c-2.48] phosmet, [c-2.49] phosphamidon, [c-2.50] phoxim, [c-2.51] pirimiphos-methyl, [c-2.52] profenofos, [c-2.53] propetamphos, [c-2.54] prothiofos, [c-2.55] pyraclofos, [c-2.56] pyridaphenthion, [c-2.57] quinalphos, [c-2.58] sulfotep, [c-2.59] tebupirimfos, [c-2.60] temephos, [c-2.61] terbufos, [c-2.62] thiometon, [c-2.63] triazophos, [c-2.64] trichlorfon, [c-2.65] vamidothion, [c-2.66] chlorothion, [c-2.67] bromfenvinfos, [c-2.68] bromophos, [c-2.69] bromophos-ethyl, [c-2.70] butathiofos, [c-2.71] carbophenothion, [c-2.72] chlorphoxim, [c-2.73] sulprofos, [c-2.74] diamidafos, [c-2.75] tetrachlorvinphos, [c-2.76] propaphos, [c-2.77] mesulfenfos, [c-2.78]dioxabenzofos, [c-2.79] etrimfos, [c-2.80] oxydeprofos, [c-2.81] formothion, [c-2.82] fensulfothion, [c-2.83] isazofos, [c-2.84] imicyafos, [c-2.85] isamidofos, [c-2.86]thionazin, [c-2.87] fosthietan, and the like.

c-3: GABA-Gated Chloride Channel Blockers

Examples of the GABA-gated chloride channel blockers include [c-3.1] chlordane, [c-3.2] endosulfan, [c-3.3] lindane, [c-3.4] dienochlor, [c-3.5] ethiprole, [c-3.6] fipronil, [c-3.7] acetoprole, and the like.

c-4: Sodium Channel Modulators

Examples of the sodium channel modulators include [c-4.1] acrinathrin, [c-4.2] allethrin[(1R)-isomer], [c-4.3] bifenthrin, [c-4.4] bioallethrin, [c-4.5] bioallethrin S-cyclopentenyl isomer, [c-4.6] bioresmethrin, [c-4.7] cyclopro-thrin, [c-4.8] cyfluthrin, [c-4.9] beta-cyfluthrin, [c-4.10] cyhalothrin, [c-4.11] gamma-cyhalothrin, [c-4.12] lambda-cyhalothrin, [c-4.13] cypermethrin, [c-4.14] alpha-cypermethrin, [c-4.15] beta-cypermethrin, [c-4.16] theta-cypermethrin, [c-4.17] zeta-cypermethrin, [c-4.18] cyphenothrin [(1R)-trans-isomer], [c-4.19] deltamethrin, [c-4.20] empenthrin[(EZ)-(1R)-isomer], [c-4.21] esfenvalerate, [c-4.22] ethofenprox, [c-4.23] fenpropathrin, [c-4.24] fenvalerate, [c-4.25] flucythrinate, [c-4.26] flumethrin, [c-4.27] tau-fluvalinate, [c-4.28] halfenprox, [c-4.29] imiprothrin, [c-4.30] methothrin, [c-4.31] metofluthrin, [c-4.32] epsilon-metofluthrin, [c-4.33] momfluorothrin, [c-4.34] epsilon-momfluorothrin, [c-4.35] permethrin, [c-4.36] phenothrin [(1R)-trans-isomer], [c-4.37] prallethrin, [c-4.38] resmethrin, [c-4.39] kadethrin, [c-4.40] silafluofen, [c-4.41] tefluthrin, [c-4.42] tetramethrin, [c-4.43] tetramethrin[(1R)-isomer], [c-4.44] tralomethrin, [c-4.45] transfluthrin, [c-4.46] ZXI8901 (3-(4-bromophenoxy)phenyl]-cyanomethyl 4-(difluoromethoxy)-α-(1-methylethyl)benzeneacetate, [c-4.47] biopermethrin, [c-4.48] furamethrin, [c-4.49] profluthrin, [c-4.50] flubrocythrinate, [c-4.51] dimefluthrin, [c-4.52] DDT (dichloro-diphenyl-trichloroethane), [c-4.53] methoxychlor, [c-4.54] phenothrin, [c-4.55] fluvalinate, and the like.

c-5: Nicotinic Acetylcholine Receptor (nAChR) Competitive Modulators

Examples of the nicotinic acetylcholine receptor (nAChR) competitive modulators include [c-5.1] acetamiprid, [c-5.2] clothianidin, [c-5.3] dinotefuran, [c-5.4] imidacloprid, [c-5.5] nitenpyram, [c-5.6] thiacloprid, [c-5.7] thiamethoxam, [c-5.8]nicotine, [c-5.9] nicotine sulfate, [c-5.10] sulfoxaflor, [c-5.11] flupyradifurone, [c-5.12]triflumezopyrim, and the like.

c-6: Nicotinic Acetylcholine Receptor (nAChR) Allosteric Modulators

Examples of the nicotinic acetylcholine receptor (nAChR) allosteric modulators include [c-6.1] spinosad, [c-6.2] spinetoram, and the like.

c-7: Glutamate-Gated Chloride Channel (GluCl) Allosteric Modulators

Examples of the glutamate-gated chloride channel (GluCl) allosteric modulators include [c-7.1] abamectin, [c-7.2] emamectin benzoate, [c-7.3] lepimectin, [c-7.4] milbemectin, and the like.

c-8: Juvenile Hormone Analogues

Examples of the juvenile hormone analogues include [c-8.1] hydroprene, [c-8.2] kinoprene, [c-8.3] methoprene, [c-8.4] fenoxycarb, [c-8.5] pyriproxyfen, and the like.

c-9: Nonspecific (Multisite) Inhibitors

Examples of the nonspecific (multisite) inhibitors include [c-9.1] methyl bromide, [c-9.2] chloropicrin, [c-9.3] cryolite, [c-9.4] sulfuryl fluoride, [c-9.5] borax, [c-9.6] boric acid, [c-9.7] disodium octaborate, [c-9.8] sodium metaborate, [c-9.9] tartar emetic, [c-9.10] dazomet, [c-9.11] metam, [c-9.12] metam sodium, and the like.

c-10: Chordotonal Organ TRPV Channel Modulators

Examples of the chordotonal organ TRPV channel modulators include [c-10.1] pymetrozine, [c-10.2] pyrifluquinazon, and the like.

C-11: Mite Growth Inhibitors

Examples of the mite growth inhibitors include [c-11.1] clofentezine, [c-11.2] diflovidazin, [c-11.3] hexythiazox, [c-11.4] etoxazole, and the like.

c-12: Mitochondria ATP Synthase Inhibitors

Examples of the mitochondria ATP synthase inhibitors include [c-12.1] diafenthiuron, [c-12.2] azocyclotin, [c-12.3] cyhexatin, [c-12.4] fenbutatin oxide, [c-12.5] propargite, [c-12.6] tetradifon, and the like.

c-13: Uncouplers of Oxidative Phosphorylation Via Disruption of Proton Gradient

Examples of the uncouplers of oxidative phosphorylation via disruption of the proton gradient include [c-13.1] chlorfenapyr, [c-13.2] DNOC (dinitro-ortho-cresol), [c-13.3] binapacryl, [c-13.4] sulfluramid, and the like.

c-14: Nicotinic Acetylcholine Receptor (nAChR) Channel Blockers

Examples of the nicotinic acetylcholine receptor (nAChR) channel blockers include [c-14.1] bensultap, [c-14.2] cartap hydrochloride, [c-14.3] thiocyclam, [c-14.4] monosultap, and the like.

c-15: Chitin Biosynthesis Inhibitors, Type 0

Examples of the chitin biosynthesis inhibitors, type 0, include [c-15.1]bistrifluron, [c-15.2] chlorfluazuron, [c-15.3] diflubenzuron, [c-15.4] flucycloxuron, [c-15.5] flufenoxuron, [c-15.6] hexaflumuron, [c-15.7] lufenuron,

[c-15.8] novaluron, [c-15.9] noviflumuron, [c-15.10] teflubenzuron, [c-15.11] triflumuron, and the like.

c-16: Chitin Biosynthesis Inhibitors, Type 1

Examples of the chitin biosynthesis inhibitors, type 1, include [c-16.1] buprofezin, and the like.

c-17: Dipteran Molting Disruptors

Examples of the dipteran molting disruptors include [c-17.1] cyromazine, and the like.

c-18: Molting Hormone (Ecdysone) Receptor Agonists

Examples of the molting hormone (ecdysone) receptor agonists include [c-18.1] chromafenozide, [c-18.2] halofenozide, [c-18.3] methoxyfenozide, [c-18.4] tebufenozide, and the like.

c-19: Octopamine Receptor Agonists

Examples of the octopamine receptor agonists include [c-19.1] amitraz, and the like.

c-20: Mitochondrial Complex III Electron Transport Inhibitors

Examples of the mitochondrial complex III electron transport inhibitors include [c-20.1] hydramethylnon, [c-20.2] acequinocyl, [c-20.3] fluacrypyrim, [c-20.4] bifenazate, and the like.

c-21: Mitochondrial Complex I Electron Transport Inhibitors (METI)

Examples of the mitochondrial complex I electron transport inhibitors (METI) include [c-21.1] fenazaquin, [c-21.2] fenpyroximate, [c-21.3] pyridaben, [c-21.4] pylimidifen, [c-21.5] tebufenpyrad, [c-21.6] tolfenpyrad, [c-21.7] rotenone, and the like.

c-22: Voltage-Dependent Sodium Channel Blockers

Examples of the voltage-dependent sodium channel blockers include [c-22.1] indoxacarb, [c-22.2] metaflumizone, and the like.

c-23: Acetyl CoA Carboxylase Inhibitors

Examples of the acetyl CoA carboxylase inhibitors include [c-23.1] spirodiclofen, [c-23.2] spiromesifen, [c-23.3] spirotetramat, and the like.

c-24: Mitochondrial Complex IV Electron Transport Inhibitors

Examples of the mitochondrial complex IV electron transport inhibitors include [c-24.1] aluminum phosphide, [c-24.2] calcium phosphide, [c-24.3] phosphine, [c-24.4] zinc phosphide, [c-24.5] calcium cyanide, [c-24.6] potassium cyanide, [c-24.7] sodium cyanide, and the like.

c-25: Mitochondrial Complex II Electron Transport Inhibitors

Examples of the mitochondrial complex II electron transport inhibitors include [c-25.1] cyenopyrafen, [c-25.2] cyflumetofen, [c-25.3] pyflubumide, and the like.

c-26: Ryanodine Receptor Modulators

Examples of the ryanodine receptor modulators include [c-26.1] chlorantraniliprole, [c-26.2] cyantraniliprole, [c-26.3] flubendiamide, and the like.

c-27: Chordotonal Organ Modulators on Undefined Target Sites

Examples of the chordotonal organ modulators on undefined target sites include [c-27.1] flonicamid, and the like.

c-28: Other Insecticides

Examples of other insecticides include [c-28.1] azadirachtin, [c-28.2]benzoximate, [c-28.3] phenisobromolate, [c-28.4] chinomethionat, [c-28.5] dicofol, [c-28.6] pyridalyl, [c-28.7] bromopropylate, [c-28.8] triazamate, [c-28.9] dicyclanil, [c-28.10] dinobuton, [c-28.11] dinocap, [c-28.12] hydrogen cyanide, [c-28.13] methyl iodide, [c-28.14] karanjin, [c-28.15] mercury chloride, [c-28.16] methyl isothiocyanate, [c-28.17] pentachlorophenol, [c-28.18] phosphine, [c-28.19] piperonyl butoxide, [c-28.20] polynactins, [c-28.21] sabadilla, [c-28.22] sulcofuron-sodium, [c-28.23]tribufos, [c-28.24] aldrin, [c-28.25] amidithion, [c-28.26] amidothioate, [c-28.27]aminocarb, [c-28.28] amiton, [c-28.29] aramite, [c-28.30] athidathion, [c-28.31]azothoate, [c-28.32] barium polysulphide, [c-28.33] benclothiaz, [c-28.34]5-(1,3-benzodioxole-5-yl)-3-hexylcyclohexa-2-enone, [c-28.35]1,1-bis(4-chlorophenyl)-2-ethoxyethanol, [c-28.36] butonate, [c-28.37] butopyronoxyl, [c-28.38] 2-(2-butoxyethoxy)ethyl thiocyanate, [c-28.39] camphechlor, [c-28.40] chlorbenside, [c-28.41] chlordecone, [c-28.42] chlordimeform, [c-28.43] chlorfenethol, [c-28.44] chlorfenson, [c-28.45] fluazuron, [c-28.46] metaldehyde, [c-28.47] bialaphos, [c-28.48] levamisol, [c-28.49] amidoflumet, [c-28.50] pyrafluprole, [c-28.51] pyriprole, [c-28.52] tralopyril, [c-28.53] flupyrazofos, [c-28.54] diofenolan, [c-28.55] chlorobenzilate, [c-28.56] flufenzine, [c-28.57] benzomate, [c-28.58] flufenerim, [c-28.59] albendazole, [c-28.60] oxibendazole, [c-28.61] fenbendazole, [c-28.62]metam-sodium, [c-28.63] 1,3-dichloropropene, [c-28.64] flometoquin, [c-28.65]cyclaniliprole, [c-28.66] tetraniliprole, [c-28.67] broflanilide, [c-28.68] dicloromezotiaz, [c-28.69] ethylene dibromide, [c-28.70] acrylonitrile, [c-28.71] bis(2-chloroethyl)ether, [c-28.72] 1-bromo-2-chloroethane, [c-28.73] 3-bromo-1-chloroprop-1-ene, [c-28.74] bromocyclen, [c-28.75] carbon disulfide, [c-28.76] tetrachloromethane, [c-28.77] nemadectin, [c-28.78] cymiazole, [c-28.79] calcium polysulfide, [c-28.80] cytokinin, [c-28.81] 2-(octylthio)ethanol, [c-28.82] potassium oleate, [c-28.83] sodium oleate, [c-28.84] machine oil, [c-28.85] tar oil, [c-28.86] anabasine, [c-28.87] morantel tartrate, [c-28.88] insect flower (pyrethrum), [c-28.89] rape seed oil, [c-28.90] soybean lecithin, [c-28.91] starch, [c-28.92] hydroxypropylstarch, [c-28.93] decanoyloctanoylglycerol, [c-28.94] propylene glycol fatty acid ester, [c-28.95] diatomite, [c-28.96] afoxolaner, [c-28.97] fluazaindolizine, [c-28.98] afidopyropen, [c-28.99] cyhalodiamide, [c-28.100] tioxazafen, [c-28.101] fluhexafon, [c-28.102] fluralaner, [c-28.103] fluxametamide, [c-28.104] tetrachlorantraniliprole, [c-28.105] sarolaner, [c-28.106] lotilaner, [c-28.107]cycloxaprid, [c-28.108] fluensulfone, [c-28.109] TPIC (tripropyl isocyanurate), [c-28.110] D-D (1,3-dichloropropene), [c-28.111] peroxocarbonate, [c-28.112] MB-599 (verbutin), [c-28.113] bis(2,3,3,3-tetrachloropropyl) ether, [c-28.114] DCIP (bis(2-chloro-1-methylethyl)ether), [c-28.115] ENT-8184 (N-2-(ethylhexyl)bicyclo[2.2.1]hept-5-ene-2,3-dicarboximide), [c-28.116] Bayer 22408 (O,O-diethyl O-naphthalimido phosphorothioate), [c-28.117] Bayer 32394 (tris(1-dodecyl-3-methyl-2-phenylbenzimidazolium)hexacyanoferrate,

[c-28.118] compound of the formula (s34):

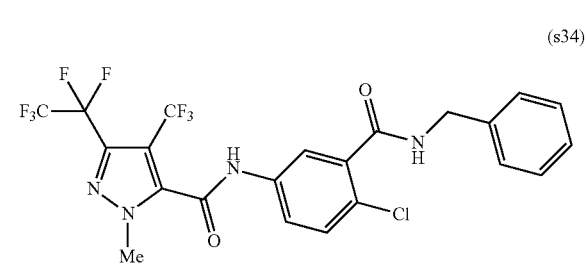 [SMILES: Cn1nc(C(F)(F)C(F)(F)F)c(C(F)(F)F)c1C(=O)Nc1ccc(Cl)c(C(=O)NCc2ccccc2)c1]

(s34)

(see WO 10/051926),

[c-28.119] compound of the formula (s35):

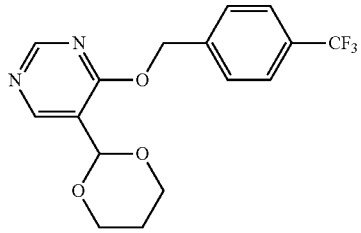

(see WO 13/115391),

[c-28.120] compound of the formula (s36):

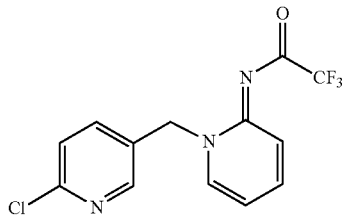

(see WO 12/029672),

[c-28.121] compound of the formula (s37):

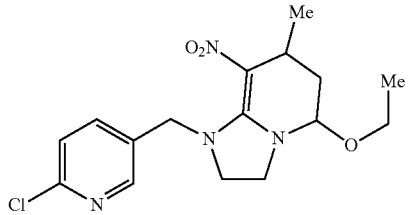

(see WO 06/056108),

[c-28.122] compound of the formula (s38):

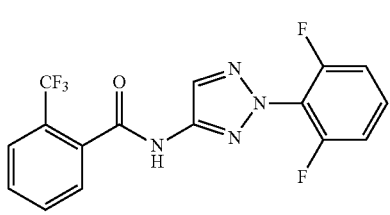

(see WO 14/053450 and WO 15/144683),

[c-28.123] compound of the formula (s39):

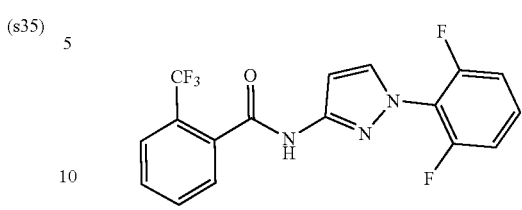

(see WO 14/053450 and WO 15/144683),

[c-28.124] compound of the formula (s40):

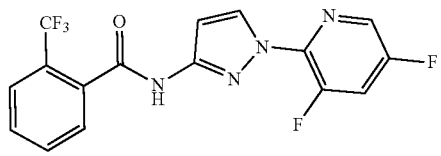

(see WO 14/053450 and WO 15/144683),

[c-28.125] compounds of the formula (s41):

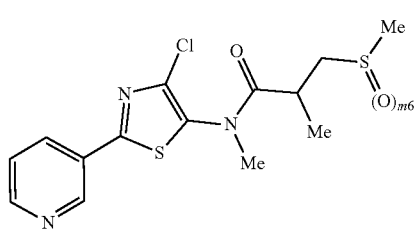

wherein m6 represents an integer of 0 to 2 (see WO 10/129497),

[c-28.126] compounds of the formula (s42):

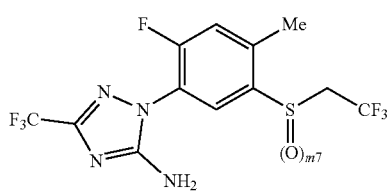

wherein m7 represents an integer of 0 to 2 (see WO 11/152320),

[c-28.127] compounds of the formula (s43):

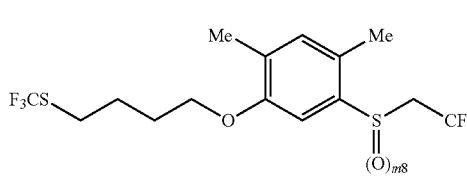

wherein m8 represents an integer of 0 to 2 (see Japanese Patent Application Kokai Publication No. H27-160813),

[c-28.128] compounds of the formula (s44):

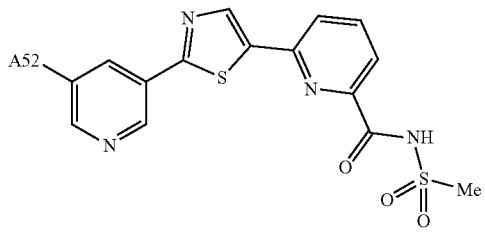
(s44)

wherein A52 represents a hydrogen atom or a fluorine atom (see WO 11/134964 and WO 14/005982),

[c-28.129] compounds of the formula (s45):

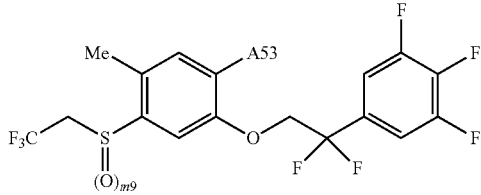
(s45)

wherein m9 represents an integer of 0 to 2, and A53 represents a fluorine atom or a chlorine atom (see WO 15/025826),

[c-28.130] compounds of the formula (s46):

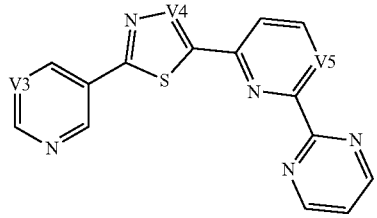
(s46)

wherein V3 represents a nitrogen atom, a carbon atom or C—F, and V4 and V5 are independent of one another and each represent a nitrogen atom or a carbon atom (see WO 11/134964 and WO 14/005982),

[c-28.131] compounds of the formula (s47):

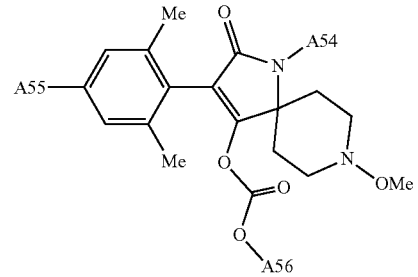
(s47)

wherein A54 represents a hydrogen atom, a methyl group, a methoxy group or an ethoxy group, A55 represents a chlorine atom or a methyl group, and A56 represents a methyl group or an ethyl group (see WO 09/049851),

[c-28.132] compounds of the formula (s48):

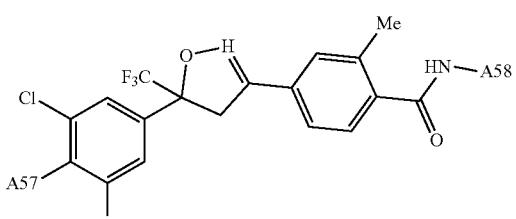
(s48)

wherein A57 represents a hydrogen atom, a fluorine atom or a chlorine atom, and A58 represents one partial structure selected from the group consisting of:

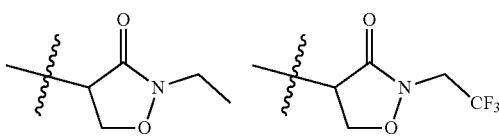

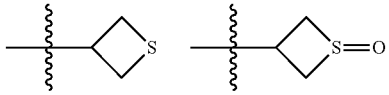

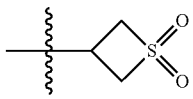

(see WO 11/067272),

[c-28.133] compounds of the formula (s49):

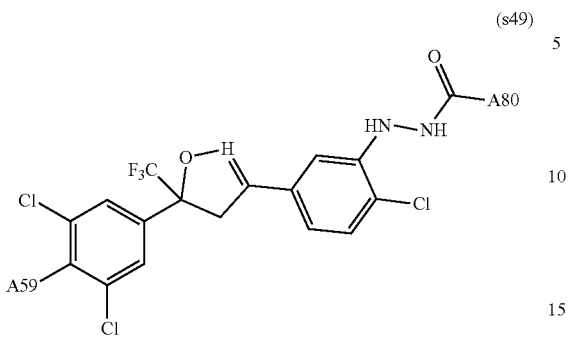

wherein A59 represents a hydrogen atom, a fluorine atom or a chlorine atom, and A60 represents a partial structure selected from the group consisting of:

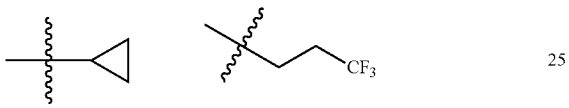

(see WO 10/090344),

[c-28.134] compounds of the formula (s50):

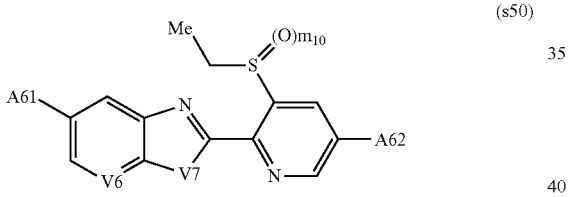

wherein m10 represents an integer of 0 to 2, A61 represents a trifluoromethyl group, a trifluoromethylthio group, a trifluoromethylsulfinyl group or a trifluoromethylsulfonyl group, A62 represents a hydrogen atom or a trifluoromethyl group, V6 represents a nitrogen atom or a carbon atom, and V7 represents an oxygen atom or a N-methyl group (see WO 14/104407),

[c-28.135] compounds of the formula (s51):

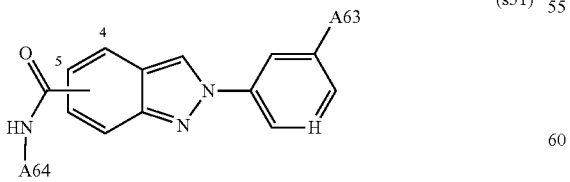

wherein A63 represents a hydrogen atom or a fluorine atom, the amide group is bonded to 4-position or 5-position, and A64 represents a partial structure selected from the group consisting of:

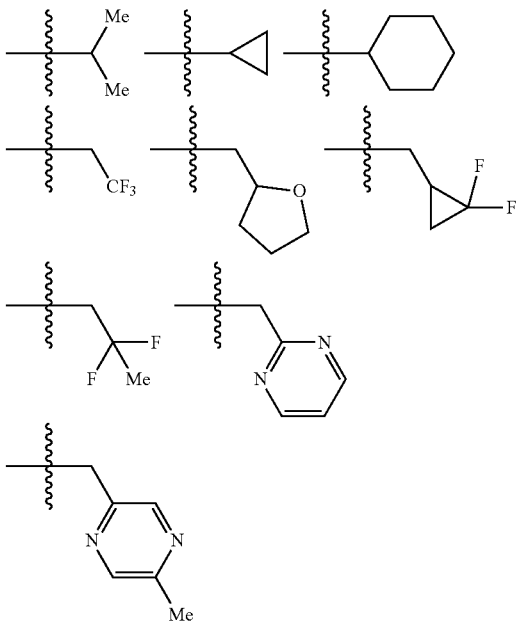

(see WO 15/038503, WO 16/144351 and WO 16/144678),

[c-28.136] compounds of the formula (s52):

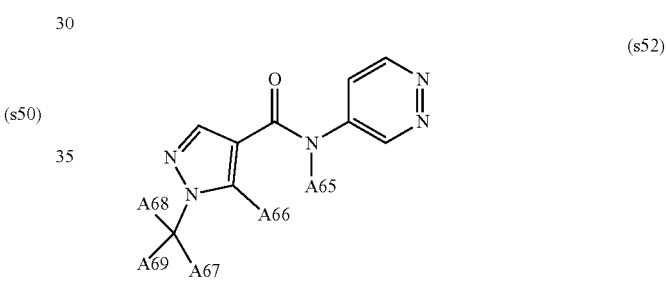

wherein A65 represents a hydrogen atom, a C1-C6 alkyl group or a C1-C6 haloalkyl group, A66 represents a hydrogen atom, a halogen atom or a C1-C6 alkyl group, A67 and A68 are independent of one another and each represent a hydrogen atom, a C1-C6 alkyl group optionally substituted with a cyano group, an alkyl group optionally substituted with a methoxy group, an alkyl group optionally substituted with an ethoxy group, or a C3-C8 cycloalkyl group, and A69 represents a hydrogen atom, a cyano group, a C1-C6 haloalkyl group optionally substituted with a cyano group, a C1-C6 alkyl group, or a C3-C8 cycloalkyl group (see WO 12/143317 and WO 16/016369),

[c-28.137] compounds of the formula (s53) or the formula (s54):

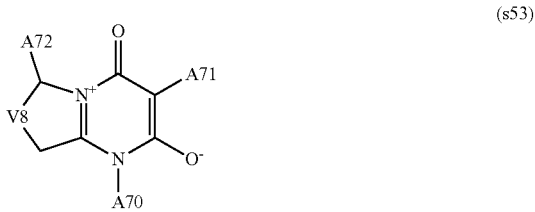

-continued (s54)

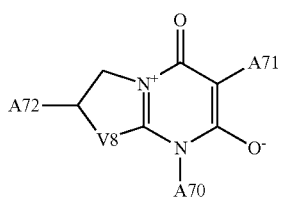

wherein A70 represents a methyl group, an ethyl group, an isopropyl group, a 2,2,2-trifluoroethyl group or a phenyl group, A71 represents a partial structure selected from the group consisting of:

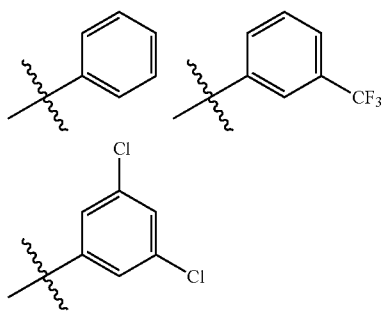

A72 represents a partial structure selected from the group consisting of:

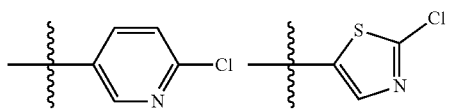

and V8 represents an oxygen atom, a sulfur atom, —CH$_2$— or —CH$_2$CH$_2$— (see WO 14/167084 and WO 16/055431),

[c-28.138] compounds of the formula (s55):

(s55)

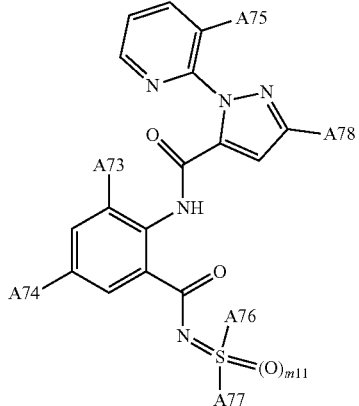

wherein m11 represents an integer of 0 to 1, A73 represents a chlorine atom, a bromine atom, a methyl group or a trifluoromethyl group, A74 represents a hydrogen atom, a chlorine atom, a bromine atom, a cyano group or a trifluoromethyl group, A75 represents a hydrogen atom, a chlorine atom or a bromine atom, A76 and A77 are independent of one another and each represent a C1-C6 alkyl group or a C3-C8 cycloalkyl group, and A78 represents a chlorine atom, a bromine atom, a cyano group, a nitro group, a difluoromethyl group or a trifluoromethyl group (see WO 13/024009),

[c-28.139] compounds of the formula (s56):

(s56)

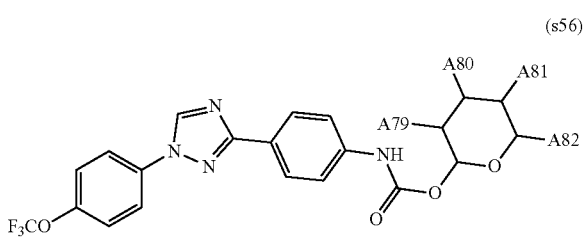

wherein A79, A80, A81 and A82 are independent of one another and each represent a hydrogen atom, a halogen atom, a C1-C6 alkyl group, a C1-C6 haloalkyl group, a C1-C6 alkoxy group or a C3-C8 cycloalkoxy group (see WO 12/027521),

[c-28.140] compounds of the formula (s57):

(s57)

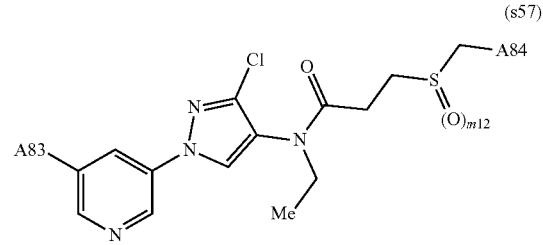

wherein m12 represents an integer of 0 to 2, A83 represents a hydrogen atom or a fluorine atom, and A84 represents a partial structure selected from the group consisting of:

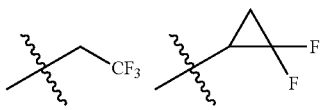 [SMILES: *CC(F)(F)F ; *C1CC1(F)F]

(see WO 13/162715),

[c-28.141] acynonapyr,

[c-28.142] compounds of the formula (s59):

(s59)

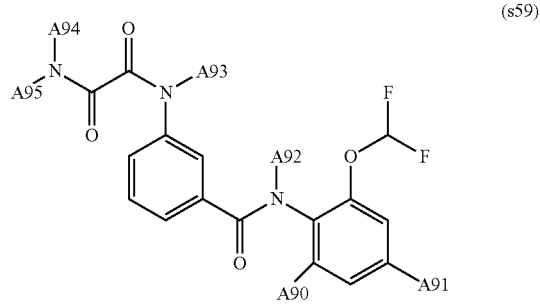

wherein A90 represents a halogen atom, a C1-C6 alkyl group or a C1-C6 haloalkyl group, A91 represents a C1-C6 haloalkyl group, A92 and A93 are independent of one another and each represent a hydrogen atom, a C1-C6 alkyl group, an acetyl group, a propionoyl group, a methanesulfonylethyl group, a methoxycarbonyl group or an ethoxycarbonyl group, and A94 and A95 are independent of one another and each represent a hydrogen atom, a C1-C6 alkyl group or a C1-C6 haloalkyl group (see WO 12/164698), and the like.

The mixing ratio of the inventive compounds and the other agricultural chemicals described above which may be mixed therewith as necessary is not particularly limited as long as effects are obtained. Usually, the weight ratio of the other agricultural chemical to the inventive compound is 0.001 to 1000, and preferably 0.01 to 100.

EXAMPLES

The present invention will be described in greater detail hereinbelow based on Synthetic Examples, Reference Examples and Test Examples. However, it should be construed that the scope of the invention is not limited thereto.

Synthesis Example 1

Synthesis of 6-(4-methoxyphenyl)-5-(4-methyl-1H-pyrazol-1-yl)-3,4-dihydropyridine-2(1H)-one

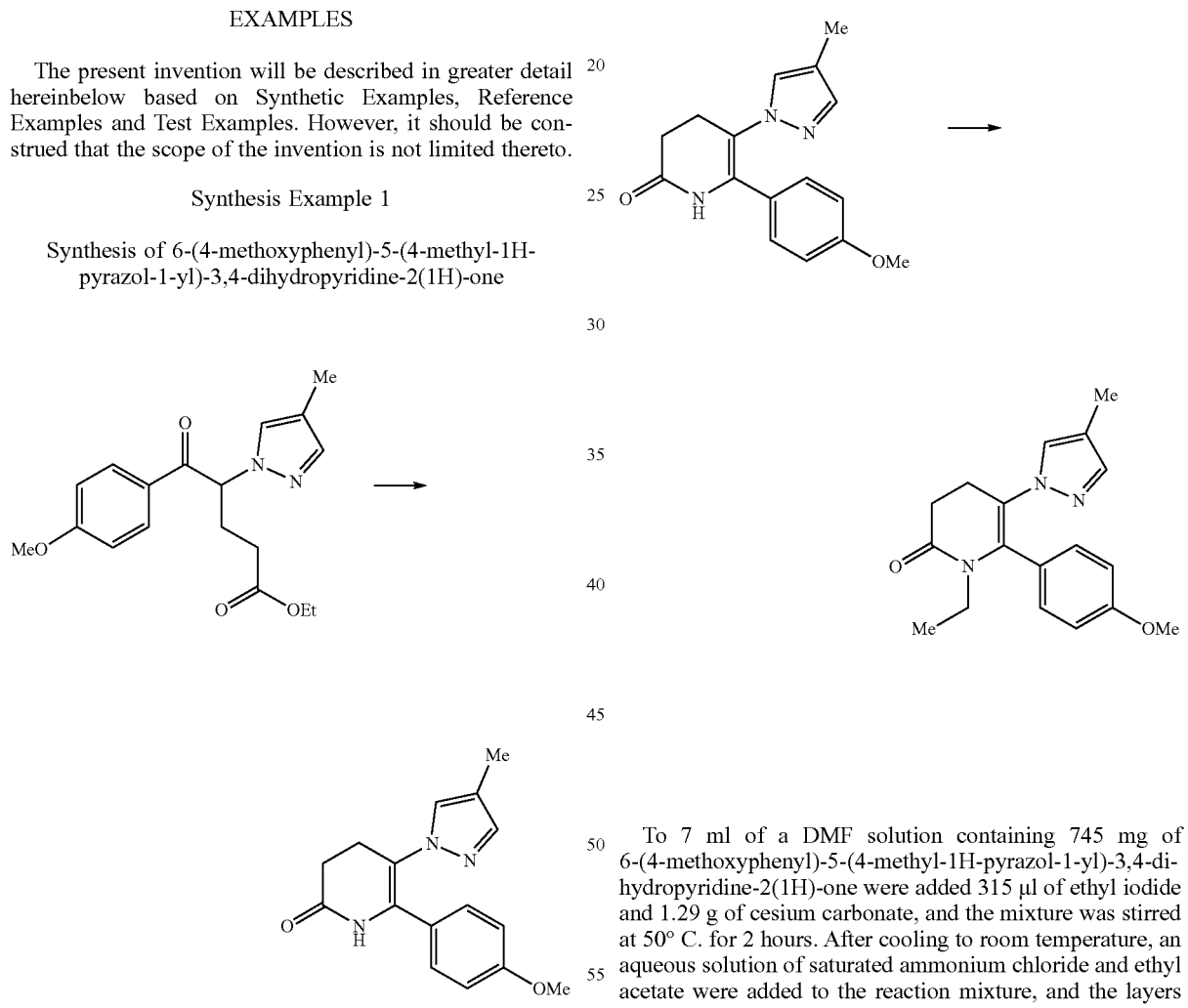

28 ml of an acetic acid solution containing 5.57 g of ethyl 5-(4-methoxyphenyl)-4-(4-methyl-1H-pyrazol-1-yl)-5-oxopentanoate obtained in Reference Example 2 and 38.9 g of ammonium acetate was stirred at 120° C. for 5 hours. After cooling to room temperature, ethyl acetate and water were added to the reaction mixture, and the layers were separated. To the resulting organic layer was added water, and potassium carbonate was further added until bubble releasing subsided, after which the resulting mixture was separated. Subsequently, the organic layer was washed with a saturated brine and then dried over sodium sulfate. After the solvent was distilled off under reduced pressure, the precipitate was washed with diisopropyl ether. The resulting brown solid was the title compound, which was 1.31 g in weight.

$^1$H-NMR (CDCl$_3$) δ: 7.39 (1H, s), 6.99 (2H, dt, J=9.4, 2.6 Hz), 6.80 (2H, dt, J=9.4, 2.6 Hz), 6.74-6.72 (2H, m), 3.79 (3H, s), 2.96-2.94 (2H, m), 2.81-2.77 (2H, m), 1.93 (3H, s).

Synthesis Example 2

Synthesis of 1-ethyl-6-(4-methoxyphenyl)-5-(4-methyl-1H-pyrazol-1-yl)-3,4-dihydropyridine-2(1H)-one To 7 ml of a DMF solution containing 745 mg of 6-(4-methoxyphenyl)-5-(4-methyl-1H-pyrazol-1-yl)-3,4-dihydropyridine-2(1H)-one were added 315 μl of ethyl iodide and 1.29 g of cesium carbonate, and the mixture was stirred at 50° C. for 2 hours. After cooling to room temperature, an aqueous solution of saturated ammonium chloride and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 596 mg of a brown solid.

$^1$H-NMR (CDCl$_3$) δ: 7.29 (1H, s), 7.05 (2H, dt, J=9.3, 2.4 Hz), 6.83 (2H, dt, J=9.3, 2.4 Hz), 6.57 (1H, s), 3.81 (3H, s), 3.45 (2H, q, J=7.0 Hz), 2.84-2.83 (2H, m), 2.77-2.75 (2H, m), 1.87 (3H, s), 0.93 (3H, t, J=7.0 Hz).

Synthesis Example 3

Synthesis of 1-ethyl-6-(4-methoxyphenyl)-5-(4-methyl-1H-pyrazol-1-yl)pyridine-2(1H)-one (Compound No:PY-036)

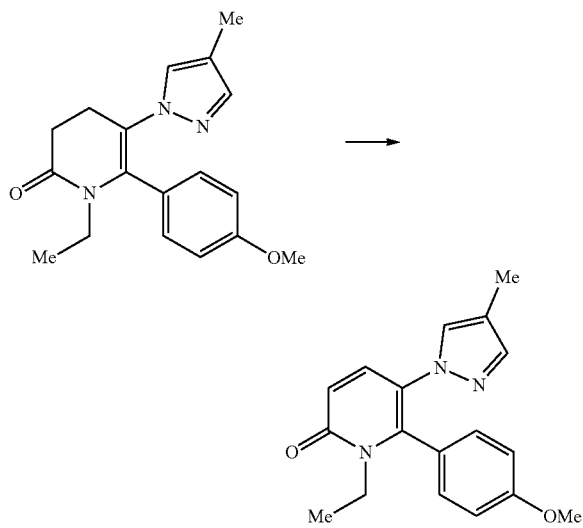

To 12 ml of a carbon tetrachloride solution containing 596 mg of 1-ethyl-6-(4-methoxyphenyl)-5-(4-methyl-1H-pyrazol-1-yl)-3,4-dihydropyridine-2(1H)-one were added 409 mg of N-bromosuccinimide and 89 mg of 2,2'-azobis(4-methoxy-2,4-dimethylvaleronitrile), and the mixture was stirred at 40° C. for 50 minutes. Further, 68 mg of N-bromosuccinimide and 30 mg of 2,2'-azobis(4-methoxy-2,4-dimethylvaleronitrile) were additionally added thereto, and the mixture was stirred for 15 minutes. After cooling to room temperature, ethyl acetate and water were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 336 mg of a colorless transparent oil.

Synthesis Example 4

Synthesis of 3-chloro-5-(5-chloro-4-methyl-1H-pyrazol-1-yl)-1-ethyl-6-(4-methoxyphenyl)pyridine-2(1H)-one (Compound No:PY-018)

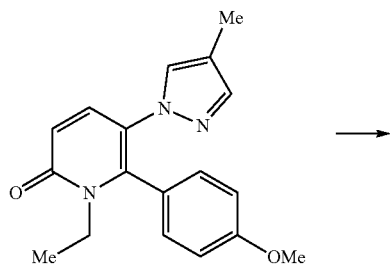

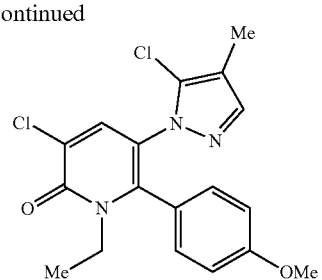

3 ml of an acetonitrile solution containing 150 mg of 1-ethyl-6-(4-methoxyphenyl)-5-(4-methyl-1H-pyrazol-1-yl)pyridine-2(1H)-one and 155 mg of N-chlorosuccinimide was stirred at 80° C. for 20 minutes. After cooling to room temperature, water and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 68 mg of a white solid.

Synthesis Example 5

Synthesis of 1-(2,2-difluoroethyl)-6-(4-methoxyphenyl)-5-(4-methyl-1H-pyrazol-1-yl)-3,4-dihydropyridine-2(1H)-one

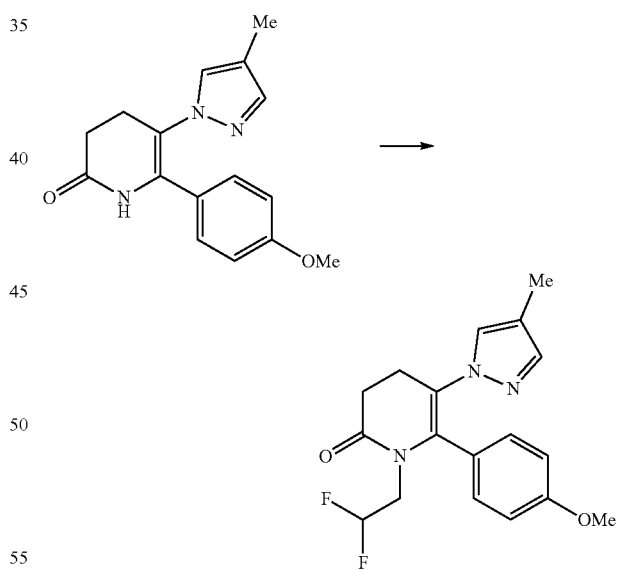

8 ml of a DMF solution containing 803 mg of 6-(4-methoxyphenyl)-5-(4-methyl-1H-pyrazol-1-yl)-3,4-dihydropyridine-2(1H)-one, 2.01 g of 2,2-difluoroethyl p-toluenesulfonate and 2.77 g of cesium carbonate was stirred at 60° C. for 1 hour. After cooling to room temperature, an aqueous solution of saturated ammonium chloride and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 528 mg of a brown solid.

$^1$H-NMR (CDCl$_3$) δ: 7.29 (1H, s), 7.04 (2H, dt, J=9.4, 2.5 Hz), 6.86 (2H, dt, J=9.4, 2.5 Hz), 6.60 (1H, s), 5.88 (1H, tt, J=56.7, 4.5 Hz), 3.82 (3H, s), 3.72 (2H, td, J=13.4, 4.5 Hz), 2.92-2.90 (2H, m), 2.85-2.80 (2H, m), 1.87 (3H, s).

Synthesis Example 6

Synthesis of 1-(2,2-difluoroethyl)-6-(4-methoxyphenyl)-5-(4-methyl-1H-pyrazol-1-yl)pyridine-2(1H)-one (Compound No: PY-031)

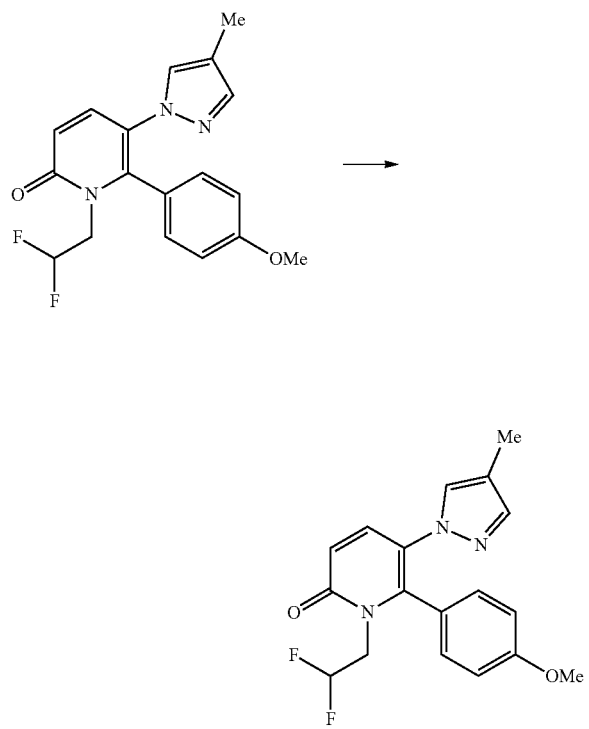

To 10 ml of a carbon tetrachloride solution containing 528 mg of 1-(2,2-difluoroethyl)-6-(4-methoxyphenyl)-5-(4-methyl-1H-pyrazol-1-yl)-3,4-dihydropyridine-2(1H)-one were added 325 mg of N-bromosuccinimide and 70 mg of 2,2'-azobis(4-methoxy-2,4-dimethylvaleronitrile), and the mixture was stirred at 40° C. for 50 minutes. After cooling to room temperature, ethyl acetate and water were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 319 mg of a colorless transparent oil.

Synthesis Example 7

Synthesis of 3-chloro-5-(5-chloro-4-methyl-1H-pyrazol-1-yl)-1-(2,2-difluoroethyl)-6-(4-methoxyphenyl)pyridine-2(1H)-one (Compound No: PY-032)

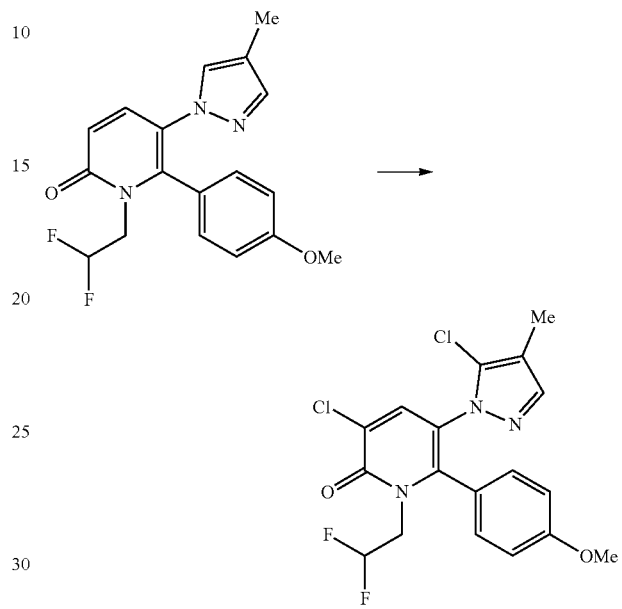

3 ml of an acetonitrile solution containing 106 mg of 1-(2,2-difluoroethyl)-6-(4-methoxyphenyl)-5-(4-methyl-1H-pyrazol-1-yl)pyridine-2(1H)-one, 90 mg of N-chlorosuccinimide and 85 µl of trimethylchlorosilane was stirred at 600 for 15 minutes. After cooling to room temperature, an aqueous solution of saturated sodium hydrogen carbonate and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 72 mg of a white amorphous substance.

Synthesis Example 8

Synthesis of 3-chloro-5-(5-chloro-4-methyl-1H-pyrazol-1-yl)-1-ethyl-6-(4-hydroxyphenyl)pyridine-2(1H)-one (Compound No: PY-041)

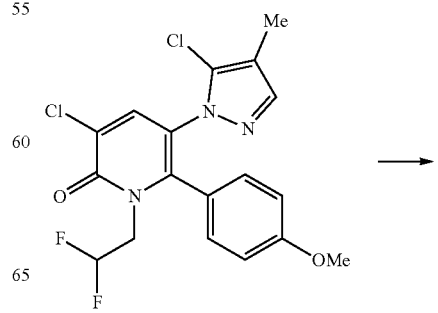

-continued

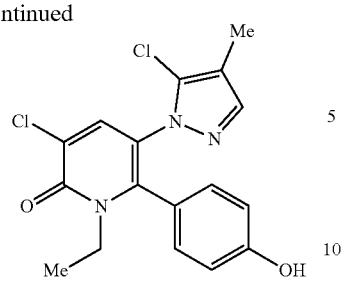

8 ml of a dichloroethane solution containing 751 mg of 3-chloro-5-(5-chloro-4-methyl-1H-pyrazol-1-yl)-1-ethyl-6-(4-methoxyphenyl)pyridine-2(1H)-one, 794 mg of aluminum chloride and 1.42 ml of 1-dodecanethiol was stirred at 700 for 15 minutes. After cooling to room temperature, water and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 720 mg of a white amorphous substance.

Synthesis Example 9

Synthesis of 3-chloro-5-(5-chloro-4-methyl-1H-pyrazol-1-yl)-6-(4-(2,2-difluoroethoxy)phenyl)-1-ethylpyridine-2(1H)-one (Compound No: PY-046)

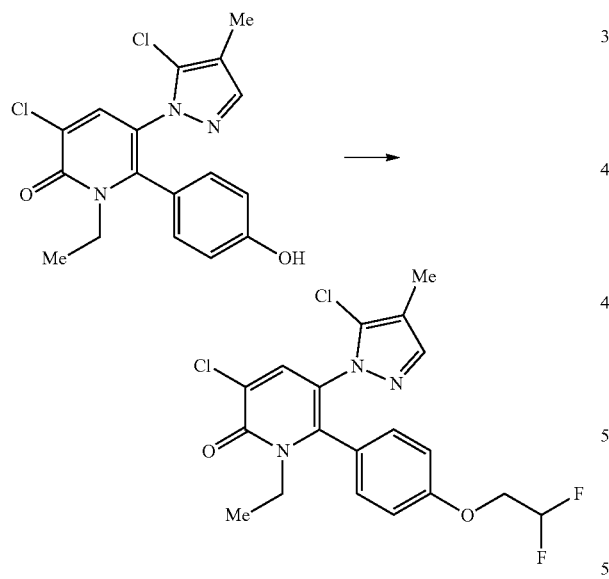

3 ml of an acetonitrile solution containing 94 mg of 3-chloro-5-(5-chloro-4-methyl-1H-pyrazol-1-yl)-1-ethyl-6-(4-hydroxyphenyl)pyridine-2(1H)-one, 122 mg of 2,2-difluoroethyl p-toluenesulfonate and 168 mg of cesium carbonate was stirred at 80° C. for 20 minutes. After cooling to room temperature, an aqueous solution of saturated ammonium chloride and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 100 mg of a white amorphous substance.

Synthesis Example 10

Synthesis of 3-chloro-1-ethyl-6-(4-fluorophenyl)-5-(5-(trifluoromethyl)-1H-pyrazol-1-yl)pyridine-2(1H)-one (Compound No: PY-90)

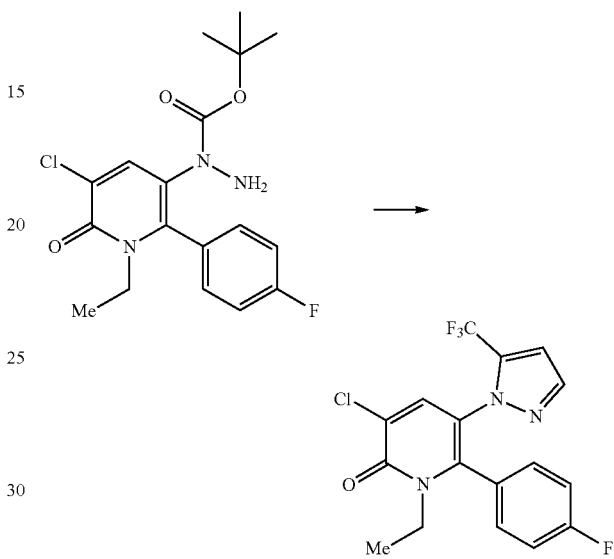

To 3 ml of an ethanol solution containing 99 mg of t-butyl 1-(5-chloro-1-ethyl-2-(4-fluorophenyl)-6-oxo-1,6-dihydropyridin-3-yl)hydrazine-1-carb oxylate and 74 µl of 4-ethoxy-1,1,1-trifluoro-3-butene-2-one was added 65 µl of 4 N hydrogen chloride solution in dioxane, and the mixture was stirred at 90° C. for 80 minutes. After cooling to room temperature, an aqueous solution of saturated sodium hydrogen carbonate and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 59 mg of a white solid.

Synthesis Example 11

Synthesis of 6-(4-fluorophenyl)-5-(4-nitro-1H-pyrazol-1-yl)-3,4-dihydropyridine-2(1H)-one

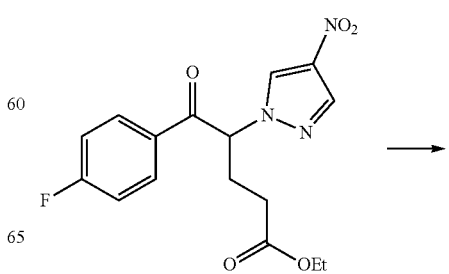

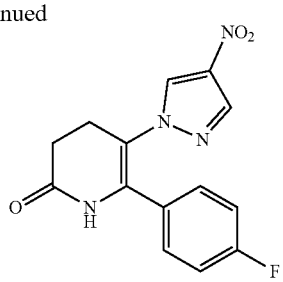

75 ml of an acetic acid solution containing 15.9 g of ethyl 5-(4-fluorophenyl)-4-(4-nitro-1H-pyrazol-1-yl)-5-oxopentanoate obtained in Reference Example 14 and 66.8 g of ammonium acetate was stirred at 120° C. for 4 hours. Further, 33.4 g of ammonium acetate was additionally added, and the mixture was stirred at 120° C. for 4 hours. After cooling to room temperature, ethyl acetate and water were added to the reaction mixture, and the layers were separated. To the resulting organic layer was added water, and potassium carbonate was further added until bubble releasing subsided, after which the resulting mixture was separated. Subsequently, the organic layer was washed with a saturated brine and then dried over sodium sulfate. After the solvent was distilled off under reduced pressure, the precipitate was washed with a mixture solvent of ethyl acetate and diisopropyl ether. The resulting brown solid was the title compound, which was 5.94 g in weight.

$^1$H-NMR (CDCl$_3$): 8.14 (1H, s), 7.69 (1H, s), 7.14-7.12 (2H, m), 7.08-7.03 (2H, m), 6.94 (1H, br s), 3.02-2.98 (2H, m), 2.87-2.84 (2H, m).

Synthesis Example 12

Synthesis of 1-ethyl-6-(4-fluorophenyl)-5-(4-nitro-1H-pyrazol-1-yl)-3,4-dihydropyridine-2(1H)-one

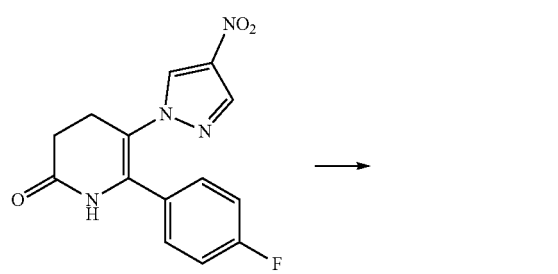

To 18 ml of a DMF solution containing 1.82 g of 6-(4-fluorophenyl)-5-(4-nitro-1H-pyrazol-1-yl)-3,4-dihydropyridine-2(1H)-one were added 963 μl of ethyl iodide and 3.92 g of cesium carbonate, and the mixture was stirred at 50° C. for 2 hours. After cooling to room temperature, an aqueous solution of saturated ammonium chloride and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 1.46 g of a yellow solid.

$^1$H-NMR (CDCl$_3$) δ: 8.03 (1H, s), 7.58 (1H, s), 7.17-7.16 (2H, m), 7.08-7.06 (2H, m), 3.44 (2H, q, J=7.0 Hz), 2.90-2.83 (4H, m), 0.95 (3H, t, J=7.0 Hz).

Synthesis Example 13

Synthesis of 1-ethyl-6-(4-fluorophenyl)-5-(4-nitro-1H-pyrazol-1-yl)pyridine-2(1H)-one

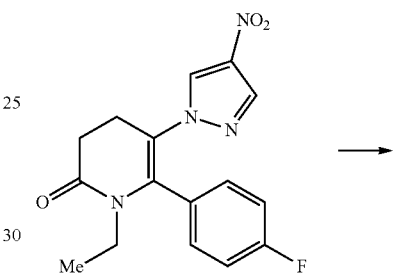

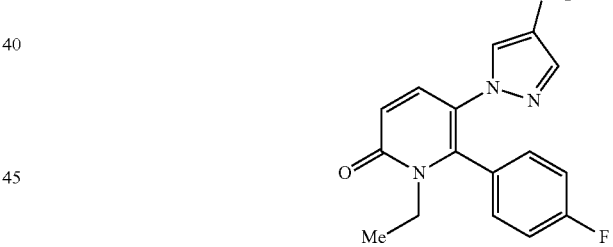

To 30 ml of a carbon tetrachloride solution containing 1.46 g of 1-ethyl-6-(4-fluorophenyl)-5-(4-nitro-1H-pyrazol-1-yl)-3,4-dihydropyridine-2(1H)-one were added 826 mg of N-bromosuccinimide and 36 mg of azobisisobutyronitrile, and the mixture was stirred at 90° C. for 1 hour. After cooling to room temperature, dichloromethane and water were added to the reaction mixture, and the layers were separated. The resulting organic layer was washed with an aqueous solution of sodium thiosulfate and then dried over sodium sulfate. After the solvent was distilled off under reduced pressure, the resulting residue was purified by silica gel column chromatography. The title compound was obtained as 0.90 g of a white solid.

$^1$H-NMR (CDCl$_3$) δ: 8.00 (1H, d, J=0.6 Hz), 7.79 (1H, d, J=0.6 Hz), 7.44 (1H, d, J=9.8 Hz), 7.27-7.24 (2H, m), 7.13-7.12 (2H, m), 6.72 (1H, d, J=9.8 Hz), 3.88 (2H, q, J=7.0 Hz), 1.16 (3H, t, J=7.0 Hz).

Synthesis Example 14

Synthesis of 3-chloro-1-ethyl-6-(4-fluoroethyl)-5-(4-nitro-1H-pyrazol-1-yl)pyridine-2(11H)-one

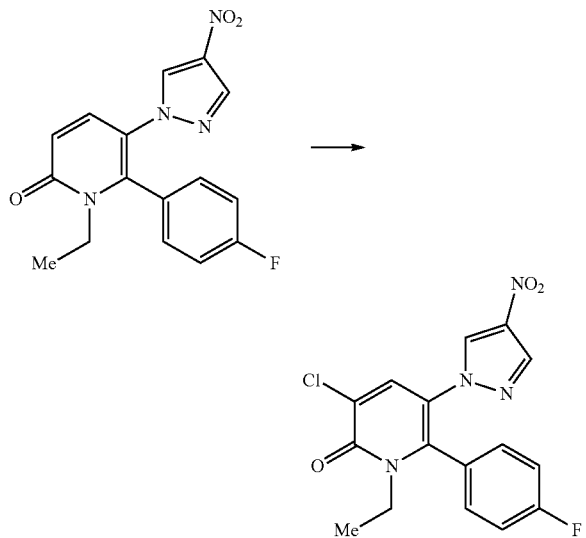

9 ml of a DMF solution containing 902 mg of 1-ethyl-6-(4-fluorophenyl)-5-(4-nitro-1H-pyrazol-1-yl)pyridine-2(1H)-one and 550 mg of N-chlorosuccinimide was stirred at 70° C. for 1 hour. After cooling to room temperature, water and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 955 mg of a white amorphous substance.

$^1$H-NMR (CDCl$_3$) δ: 8.01 (1H, s), 7.78 (1H, s), 7.70 (1H, s), 7.26-7.23 (2H, m), 7.16-7.12 (2H, m), 3.94 (2H, q, J=7.0 Hz), 1.19 (3H, t, J=7.0 Hz).

Synthesis Example 15

Synthesis of 3-chloro-5-(5-chloro-4-nitro-1H-pyrazol-1-yl)-1-ethyl-6-(4-fluorophenyl)pyridine-2(1H)-one

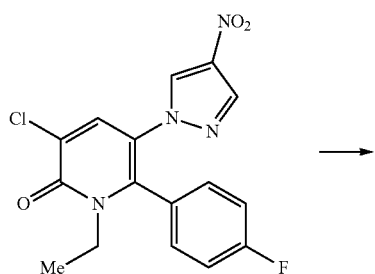

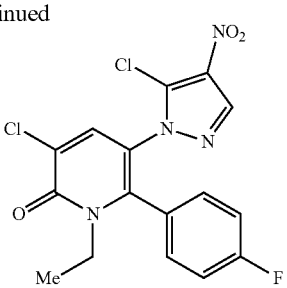

To 3 ml of a THE solution containing 311 mg of 3-chloro-1-ethyl-6-(4-fluoroethyl)-5-(4-nitro-1H-pyrazol-1-yl)pyridine-2(1H)-one was added dropwise 857 μl of 1.3 mol/L hexamethyldisilazane lithium solution in THE at −78° C., and the mixture was stirred for 10 minutes. Subsequently, 3 ml of a THE solution containing 264 mg of hexachloroethane was added dropwise at −78° C., and the mixture was stirred for 10 minutes. An aqueous solution of saturated ammonium chloride and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 279 mg of a white amorphous substance.

$^1$H-NMR (CDCl$_3$) δ: 8.07 (1H, s), 7.53 (1H, s), 7.26-7.24 (2H, m), 7.12-7.10 (2H, m), 3.95-3.93 (2H, br m), 1.20 (3H, t, J=7.0 Hz).

Synthesis Example 16

Synthesis of 5-(4-amino-5-chloro-1H-pyrazol-1-yl)-3-chloro-1-ethyl-6-(4-fluorophenyl)pyridine-2(1H)-one

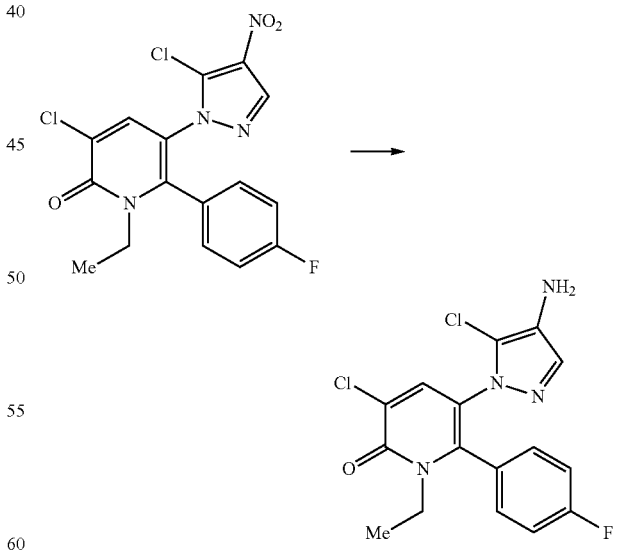

A mixture solvent of 4.5 ml of ethanol and 1.5 ml of water containing 290 mg of 3-chloro-5-(5-chloro-4-nitro-1H-pyrazol-1-yl)-1-ethyl-6-(4-fluorophenyl)pyridine-2(1H)-one, 122 mg of iron and 39 mg of ammonium chloride was stirred at 80° C. for 80 minutes. After cooling to room temperature, the reaction mixture was filtered over Celite, an aqueous solution of saturated sodium hydrogen carbonate and ethyl acetate were added thereto, and the layers were separated. The resulting organic layer was washed with a saturated brine and then dried over sodium sulfate. After the solvent was distilled off under reduced pressure, the resulting residue was purified by silica gel column chromatography. The title compound was obtained as 241 mg of a white amorphous substance.

$^1$H-NMR (CDCl$_3$) δ: 7.52 (1H, s), 7.26-7.23 (2H, m), 7.13 (1H, s), 7.05-7.03 (2H, m), 3.93 (2H, q, J=7.0 Hz). 2.80 (2H, br s), 1.17 (3H, t, J=7.0 Hz).

Synthesis Example 17

Synthesis of 3-chloro-5-(5-chloro-1H-pyrazol-1-yl)-1-ethyl-6-(4-fluorophenyl)pyridine-2(1H)-one
(Compound No: PY-104)

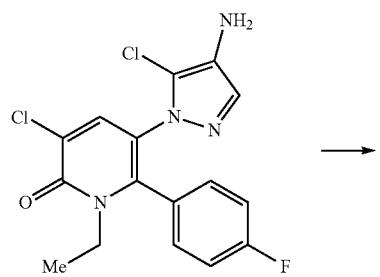

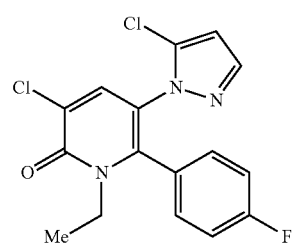

3 ml of an ethanol solution containing 241 mg of 5-(4-amino-5-chloro-1H-pyrazol-1-yl)-3-chloro-1-ethyl-6-(4-fluorophenyl)pyridine-2(1H)-one, 86 μl of t-butyl nitrite and 1.50 ml of a 50% aqueous solution of hypophosphorous acid was stirred at 40° C. for 15 minutes. After cooling to room temperature, water and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 162 mg of a white amorphous substance.

Synthesis Example 18

Synthesis of 5-(4,5-dichloro-1H-imidazol-1-yl)-6-phenyl-3,4-dihydropyridine-2(1H)-one

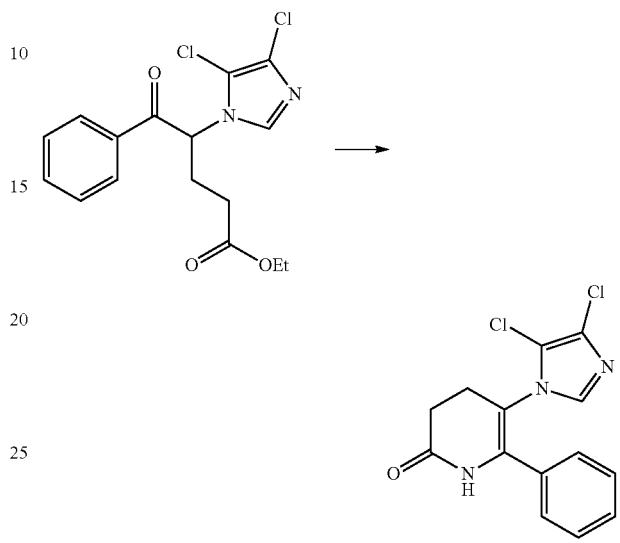

32 ml of an acetic acid solution containing 3.20 g of ethyl 4-(4,5-dichloro-1H-imidazol-1-yl)-5-oxo-5-phenylpentanoate obtained in Reference Example 16 and 13.9 g of ammonium acetate was stirred at 120° C. for 2 hours. After cooling to room temperature, ethyl acetate and water were added to the reaction mixture, and the layers were separated. To the resulting organic layer was added water, and potassium carbonate was further added until bubble releasing subsided, after which the resulting mixture was separated. Subsequently, the organic layer was washed with a saturated brine and then dried over sodium sulfate. After the solvent was distilled off under reduced pressure, the resulting residue was purified by silica gel column chromatography. The title compound was obtained as 1.93 g of a brown solid.

$^1$H-NMR (CDCl$_3$) δ: 7.36-7.31 (3H, m), 7.11-7.10 (2H, m), 7.04 (1H, s), 6.93 (1H, br s), 2.85-2.82 (4H, br m).

Synthesis Example 19

Synthesis of 5-(4,5-dichloro-1H-imidazol-1-yl)-1-ethyl-6-phenyl-3,4-dihydropyridine-2(1H)-one

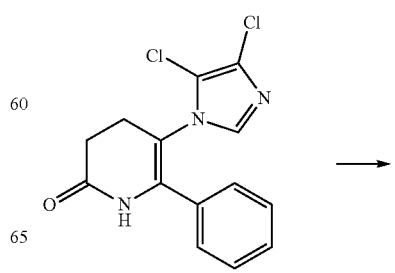

-continued

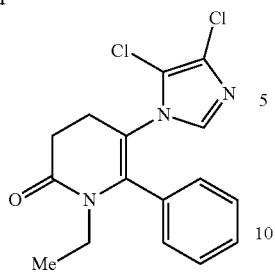

To 5 ml of a DMF solution containing 500 mg of 5-(4,5-dichloro-1H-imidazol-1-yl)-6-phenyl-3,4-dihydropyridine-2(1H)-one were added 195 µl of ethyl iodide and 793 mg of cesium carbonate, and the mixture was stirred at 50° C. for 1 hour. After cooling to room temperature, an aqueous solution of saturated ammonium chloride and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 498 mg of a brown solid.

$^1$H-NMR (CDCl$_3$) δ: 7.32-7.31 (3H, m), 7.13-7.12 (2H, m), 7.01 (1H, s), 3.43-3.41 (2H, br m), 2.86-2.84 (2H, m), 2.70-2.68 (2H, br m), 0.97 (3H, t, J=7.1 Hz).

Synthesis Example 20

Synthesis of 5-(4,5-dichloro-1H-imidazol-1-yl)-1-ethyl-6-phenylpyridine-2(1H)-one (Compound No: IM-001)

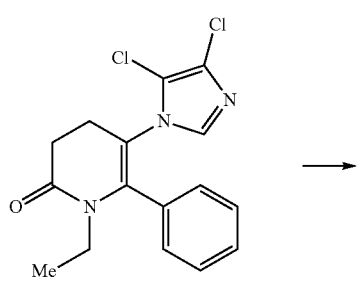

To 10 ml of a carbon tetrachloride solution containing 498 mg of 5-(4,5-dichloro-1H-imidazol-1-yl)-1-ethyl-6-phenyl-3,4-dihydropyridine-2(1H)-one were added 277 mg of N-bromosuccinimide and 24 mg of azobisisobutyronitrile, and the mixture was stirred at 90° C. for 30 minutes. After cooling to room temperature, ethyl acetate and water were added to the reaction mixture, and the layers were separated. The resulting organic layer was washed with an aqueous solution of sodium thiosulfate and then dried over sodium sulfate. After the solvent was distilled off under reduced pressure, the resulting residue was purified by silica gel column chromatography. The title compound was obtained as 380 mg of a white amorphous substance.

Synthesis Example 21

Synthesis of 3-chloro-5-(4,5-dichloro-1H-imidazol-1-yl)-1-ethyl-6-phenylpyridine-2(1H)-one (Compound No: IM-003)

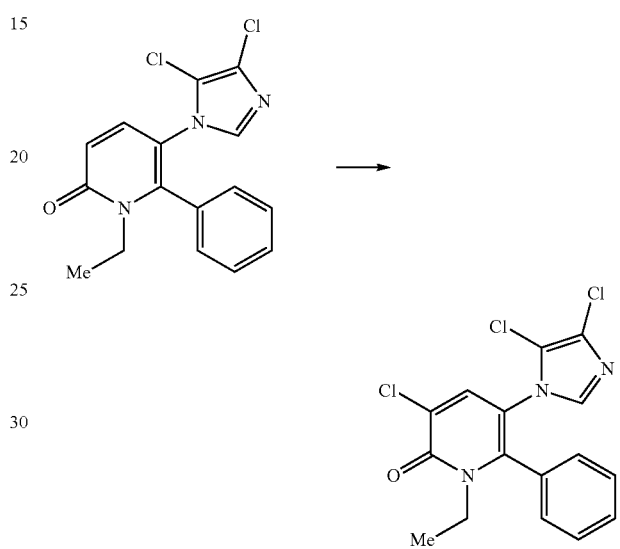

2 ml of a DMF solution containing 188 mg of 5-(4,5-dichloro-1H-imidazol-1-yl)-1-ethyl-6-phenylpyridine-2 (1H)-one and 98 mg of N-chlorosuccinimide was stirred at 70° C. for 45 minutes. After cooling to room temperature, water and ethyl acetate were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 124 mg of a white amorphous substance.

Synthesis Example 22

Synthesis of 6-(4-fluorophenyl)-1-methoxy-5-(4-methyl-1H-pyrazol-1-yl)-3,4-dihydropyridin-2(1H)-one

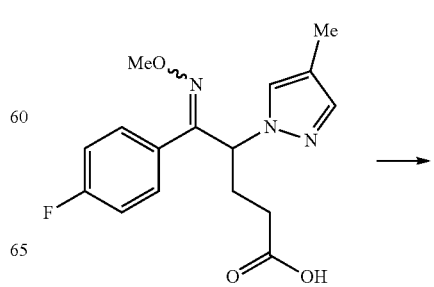

-continued

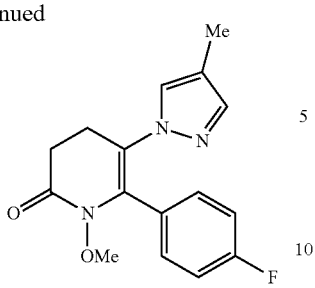

To 20 ml of a dichloromethane solvent containing 2.3 g of 5-(4-fluorophenyl)-5-(methoxyimino)-4-(4-methyl-1H-pyrazol-1-yl) pentanoic acid obtained in Reference Example 17 was added dropwise 644 μl of thionyl chloride under ice-cooling, and then the mixture was warmed to room temperature and stirred for 5 hours. The reaction mixture was carefully poured into saturated aqueous sodium hydroxide solution, and then ethyl acetate was added and layers are separated. The resulting organic layer was washed with saturated brine and dried over sodium sulfate. After the solvent was distilled off under reduced pressure, the resulting residue was purified by silica gel column chromatography. The title compound was obtained as 1.24 g of white solid.

$^1$H-NMR (CDCl$_3$) δ: 7.34 (1H, s), 7.21-7.19 (2H, m), 7.02-6.99 (2H, m), 6.59-6.57 (11, m), 3.48 (3H, s), 2.97-2.94 (2H, m), 2.87-2.83 (2H, m), 1.88 (3H, s).

Synthesis Example 23

Synthesis of 6-(4-fluorophenyl)-1-methoxy-5-(4-methyl-1H-pyrazol-1-yl)pyridin-2(1H)-one (Compound No.: PY-374)

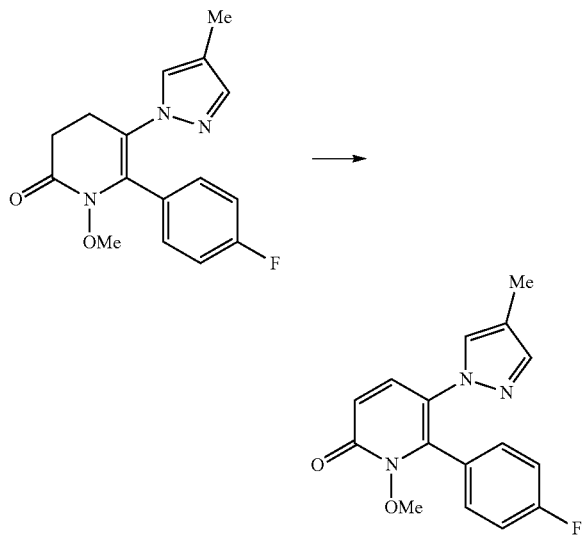

To 20 ml of a carbon tetrachloride solution of containing 1.13 g of 6-(4-fluorophenyl)-1-methoxy-5-(4-methyl-1H-pyrazol-1-yl)-3,4-dihydropyridin-2(1H)-one were added 701 mg of N-bromosuccinimide and 62 mg of azobisisobutyronitrile and the mixture was stirred at 80° C. for 2 hours. After cooling to room temperature, ethyl acetate and water were added to the reaction mixture, and the layers were separated. The resulting organic layer was washed with aqueous sodium thiosulfate solution and dried over sodium sulfate. After the solvent was distilled off under reduced pressure, the resulting residue was purified by silica gel column chromatography. The title compound was obtained as 492 mg of a white solid.

Synthesis Example 24

Synthesis of 3-bromo-6-(4-fluorophenyl)-1-methoxy-5-(4-methyl-1H-pyrazol-1-yl)pyridin-2(1H)-one (Compound No.: PY-381)

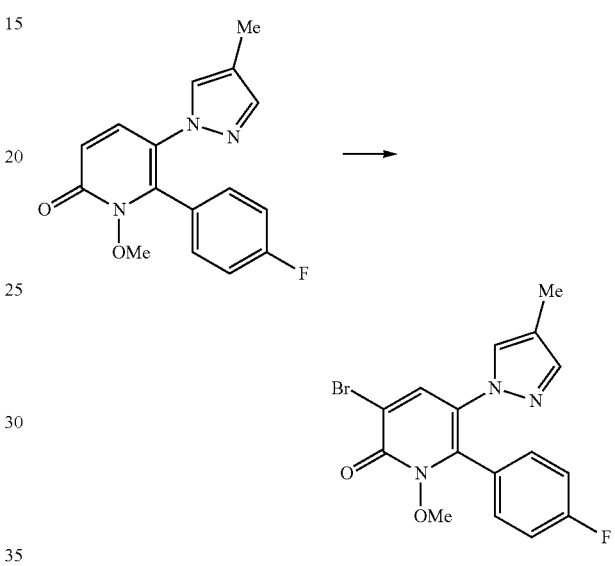

3 ml of a DMF solution containing 240 mg of 6-(4-fluorophenyl)-1-methoxy-5-(4-methyl-1H-pyrazol-1-yl) pyridin-2(1H)-one and 186 mg of N-bromosuccinimide was stirred for 1 hour at 70° C. After cooling to room temperature, water and ethyl acetate were added to the reaction mixture, and the layers were separated. The resulting organic layer was washed successively with aqueous sodium thiosulfate solution and saturated brine, and dried over sodium sulfate. After the solvent was distilled off under reduced pressure, the resulting residue was purified by silica gel column chromatography. The title compound was obtained as 241 mg of a white solid.

Synthesis Example 25

Synthesis of 3-bromo-5-(5-chloro-4-methyl-1H-pyrazol-1-yl)-6-(4-fluorophenyl)-1-methoxypyridin-2(1H)-one (Compound No.: PY-382)

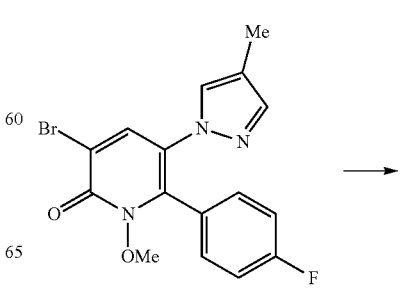

283

-continued

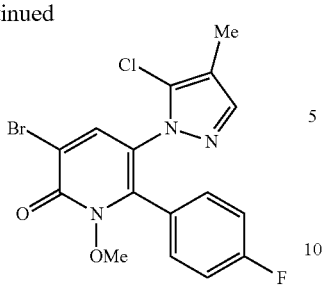

2 ml of an acetonitrile solution containing 198 mg of 3-bromo-6-(4-fluorophenyl)-1-methoxy-5 (4-methyl-1H-pyrazol-1-yl) pyridin-2(1H)-one, 75 mg of N-chlorosuccinimide and 71 s0 of trimethylchlorosilane was stirred at 40° C. for 1 hour. After cooling to room temperature, saturated aqueous sodium hydrogen carbonate solution and ethyl acetate were added to the reaction mixture, and the layers were separated. The resulting organic layer was washed successively with aqueous sodium thiosulfate solution and saturated brine, and then dried over sodium sulfate. After the solvent was distilled off under reduced pressure, the resulting residue was purified by silica gel column chromatography. The title compound was obtained as 173 mg of a white solid.

Reference Example 1

Synthesis of 1-(4-methoxyphenyl)-2-(4-methyl-1H-pyrazol-1-yl)ethane-1-one

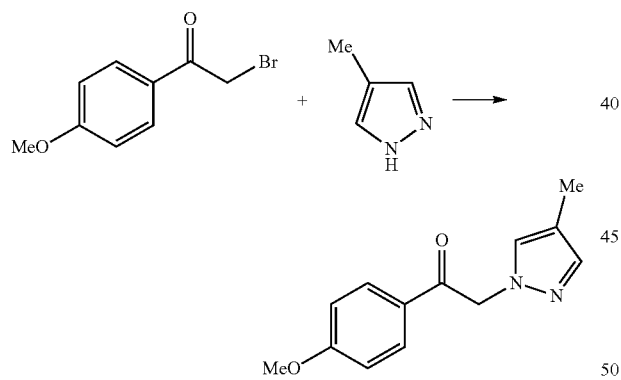

50 ml of an ethyl acetate solution containing 10.7 g of 2-bromo-1-(4-methoxyphenyl)ethane-1-one, 4.60 g of 4-methyl-1H-pyrazole and 7.88 ml of triethylamine was stirred 80° C. for 1 hour. After cooling to room temperature, 1 N hydrochloric acid and ethyl acetate were added to the reaction mixture, and the layers were separated. The resulting organic layer was sequentially washed with a solution of saturated sodium hydrogen carbonate and a saturated brine and then dried over sodium sulfate. After the solvent was distilled off under reduced pressure, the precipitate was washed with diisopropyl ether. The title compound was obtained as 3.89 g of a brown solid.

$^1$H-NMR (CDCl$_3$) δ: 7.97 (2H, dt, J=9.6, 2.4 Hz), 7.38 (1H, s), 7.27 (1H, s), 6.97 (2H, dt, J=9.6, 2.4 Hz), 5.48 (2H, s), 3.89 (3H, s), 2.11 (3H, s).

284

Reference Example 2

Synthesis of ethyl 5-(4-methoxyphenyl)-4-(4-methyl-1H-pyrazol-1-yl)-5-oxopentanoate

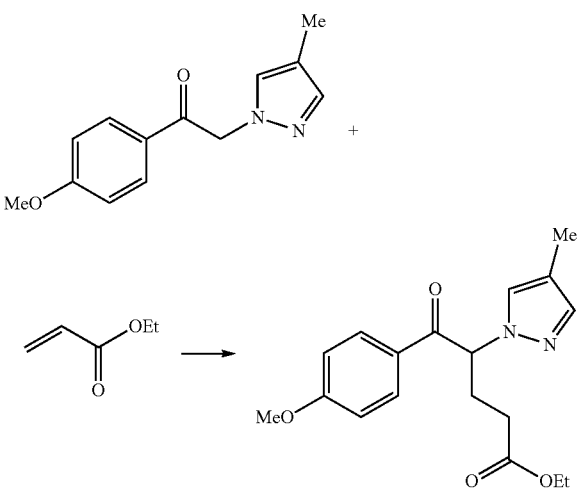

To 38 ml of a THF solution containing 3.89 g of 1-(4-methoxyphenyl)-2-(4-methyl-1H-pyrazol-1-yl)ethane-1-one were added 379 mg of potassium t-butoxide and 1.93 ml of ethyl acrylate, and the mixture was stirred at room temperature for 10 minutes. After a solution of saturated ammonium chloride and ethyl acetate were added thereto to separate the layer, the resulting organic layer was washed with a saturated brine and then dried over sodium sulfate. After the solvent was distilled off under reduced pressure, 5.57 g of a brown oil containing the title compound was obtained, which was used in the next reaction without further purification.

$^1$H-NMR (CDCl$_3$) δ: 8.05 (2H, dd, J=7.0, 2.1 Hz), 7.31 (2H, br s), 6.93 (2H, dd, J=7.0, 2.1 Hz), 5.97 (1H, dd, J=9.8, 4.9 Hz), 4.14 (2H, q, J=7.2 Hz), 3.86 (3H, s), 2.46-2.23 (4H, m), 2.05 (3H, s), 1.25 (3H, t, J=7.2 Hz).

Reference Example 3

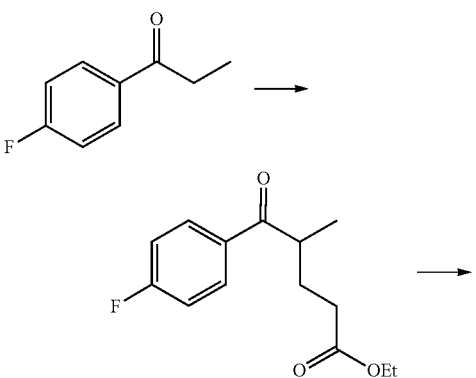

-continued

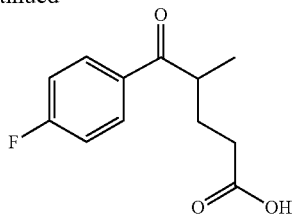

Step 1: Synthesis of ethyl 5-(4-fluorophenyl)-4-methyl-5-oxopentanoate

To 250 ml of a THF solution containing 25.0 g of 4-fluoropropiophenone were added 3.69 g of potassium t-butoxide and 17.27 g of ethyl acrylate, and the mixture was stirred under ice cooling for 3 hours. After an aqueous solution of saturated ammonium chloride and ethyl acetate were added thereto to separate the layer, the resulting organic layer was washed with a saturated brine and then dried over sodium sulfate. After the solvent was distilled off under reduced pressure, the title compound was obtained as 41.5 g of a yellow oil, which was used in the next reaction without further purification.

$^1$H-NMR (CDCl$_3$) δ: 8.01-8.00 (2H, m), 7.17-7.11 (2H, m), 4.11 (2H, q, J=7.2 Hz), 3.55-3.53 (1H, m), 2.42-2.27 (1H, m), 2.19-2.12 (1H, m), 1.78-1.74 (1H, m), 1.23 (3H, t, J=7.2 Hz), 1.21 (3H, d, J=7.0 Hz).

Step 2: Synthesis of 5-(4-fluorophenyl)-4-methyl-5-oxopentanoic acid

To 41.5 g of ethyl 5-(4-fluorophenyl)-4-methyl-5-oxopentanoate obtained in Step 1 were added 200 ml of THE and 100 ml of water, after which 20.71 g of lithium hydroxide monohydrate was added, and the mixture was stirred at 60° C. for 3 hours. After cooling to room temperature, THE contained in the reaction mixture was distilled off under reduced pressure. Water and diethyl ether were added thereto to separate the layer, and 12 N hydrochloric acid and ethyl acetate were added to the resulting aqueous layer to separate the layer. The resulting organic layer was washed with a saturated brine and then dried over sodium sulfate. After the solvent was distilled off under reduced pressure, the title compound was obtained as 34.0 g of a brown oil.

$^1$H-NMR (CDCl$_3$) δ: 8.02-7.98 (211, m), 7.16-7.13 (2H, m), 3.56-3.53 (1H, m), 2.49-2.33 (2H, m), 2.18-2.15 (1H, m), 1.79-1.77 (1H, m), 1.22 (311, d, J=7.0 Hz).

Reference Example 4

Synthesis of 6-(4-fluorophenyl)-5-methyl-3,4-dihydropyridine-2(1H)-one

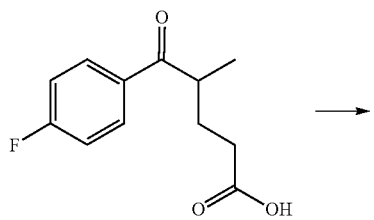

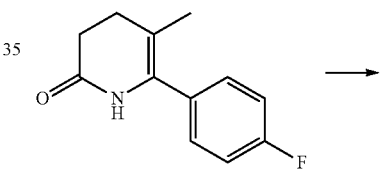

340 ml of an acetic acid solution containing 34.0 g of 5-(4-fluorophenyl)-4-methyl-5-oxopentanoic acid and 233.7 g of ammonium acetate was stirred at 90° C. for 3 hours and after another 120° C. for 5 hours. After cooling to room temperature, ethyl acetate and water were added to the reaction mixture, and the layers were separated. The resulting organic layer was washed with a saturated brine and then dried over sodium sulfate. After the solvent was distilled off under reduced pressure, the precipitate was washed with diisopropyl ether. The resulting brown solid was the title compound, which was 17.8 g in weight.

$^1$H-NMR (CDCl$_3$) δ: 7.29-7.25 (2H, m), 7.11-7.06 (2H, m), 6.77 (11, s), 2.58-2.55 (2H, m), 2.43-2.41 (2H, m), 1.73 (3H, t, J=0.9 Hz).

Reference Example 5

Synthesis of 1-ethyl-6-(4-fluorophenyl)-5-methyl-3,4-dihydropyridine-2(1H)-one

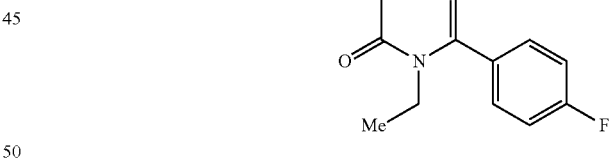

To 173 ml of a DMF solution containing 17.3 g of 6-(4-fluorophenyl)-5-methyl-3,4-dihydropyridine-2(1H)-one were added 20.17 ml of ethyl iodide and 82.16 g of cesium carbonate, and the mixture was stirred at 70° C. for 3 hours and after another 90° C. for 8 hours. After cooling to room temperature, water and ethyl acetate were added to the reaction mixture, and the layers were separated. The resulting organic layer was sequentially washed with water and a saturated brine and then dried over magnesium sulfate. After the solvent was distilled off under reduced pressure, the resulting residue was purified by silica gel column chromatography. The title compound was obtained as 8.11 g of a pale-yellow oil.

$^1$H-NMR (CDCl$_3$) δ: 7.19-7.16 (2H, m), 7.12-7.07 (2H, m), 3.33 (2H, q, J=7.0 Hz), 2.59-2.54 (2H, m), 2.33-2.30 (2H, m), 1.60 (3H, s), 0.89 (3H, t, J=7.0 Hz).

Reference Example 6

Synthesis of 1-ethyl-6-(4-fluorophenyl)-5-methylpyridine-2(1H)-one

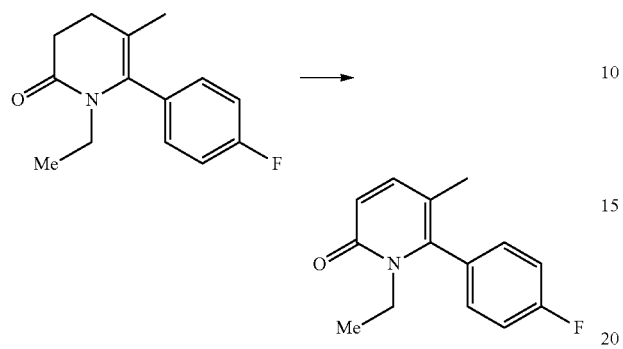

130 ml of a toluene solution containing 8.11 g of 1-ethyl-6-(4-fluorophenyl)-5-methyl-3,4-dihydropyridine-2(1H)-one and 15.79 g of 2,3-dichloro-5,6-dicyano-p-benzoquinone was stirred at 90° C. for 4 hours. After cooling to room temperature, the reaction mixture was filtered to remove any insoluble substance. After the solvent was distilled off from the filtrate under reduced pressure, the resulting residue was purified by silica gel column chromatography. The title compound was obtained as 6.30 g of a yellow solid.

$^1$H-NMR (CDCl$_3$) δ: 7.25-7.18 (5H, m), 6.58 (1H, d, J=9.3 Hz), 3.79 (2H, q, J=7.1 Hz), 1.73 (3H, s), 1.09 (3H, t, J=7.1 Hz).

Reference Example 7

Synthesis of 3-chloro-1-ethyl-6-(4-fluorophenyl)-5-methylpyridine-2(1H)-one

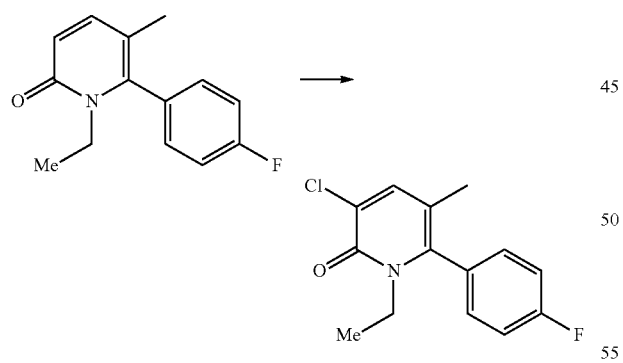

63 ml of a DMF solution containing 6.30 g of 1-ethyl-6-(4-fluorophenyl)-5-methylpyridine-2(1H)-one and 4.00 g of N-chlorosuccinimide was stirred at 70° C. for 3 hours. After cooling to room temperature, ethyl acetate and water were added to the reaction mixture, and the layers were separated. The resulting organic layer was sequentially washed with an aqueous solution of sodium thiosulfate and a saturated brine and then dried over sodium sulfate. After the solvent was distilled off under reduced pressure, the resulting residue was purified by silica gel column chromatography. The title compound was obtained as 6.25 g of a brown solid.

$^1$H-NMR (CDCl$_3$) δ: 7.47 (1H, s), 7.23-7.21 (4H, m), 3.84 (2H, q, J=7.1 Hz), 1.75 (3H, s), 1.11 (3H, t, J=7.1 Hz).

Reference Example 8

Synthesis of 3-chloro-5-(dibromomethyl)-1-ethyl-6-(4-fluorophenyl)pyridine-2(1H)-one

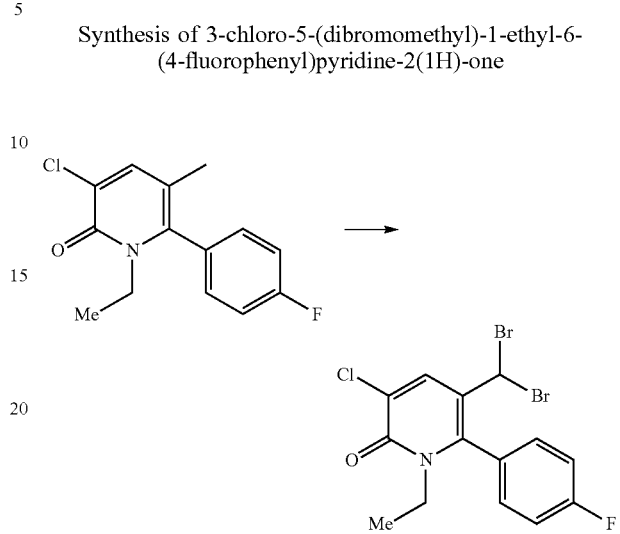

To 100 ml of a chlorobenzene solution containing 5.17 g of 3-chloro-1-ethyl-6-(4-fluorophenyl)-5-methylpyridine-2(1H)-one were added 7.25 g of N-bromosuccinimide and 318 mg of azobisisobutyronitrile, and the mixture was stirred at 90° C. for 4 hours. After cooling to room temperature, water and dichloromethane were added to the reaction mixture, and the layers were separated. The resulting organic layer was washed with an aqueous solution of sodium thiosulfate and then dried over sodium sulfate. After the solvent was distilled off under reduced pressure, the resulting solid was washed with isopropyl ether. The title compound was obtained as 7.37 g of a brown solid.

$^1$H-NMR (CDCl$_3$) δ: 8.09 (1H, s), 7.35-7.29 (4H, m), 5.86 (1H, s), 3.78 (2H, q, J=7.0 Hz), 1.11 (3H, t, J=7.0 Hz).

Reference Example 9

Synthesis of 5-chloro-1-ethyl-2-(4-fluorophenyl)-6-oxo-1,6-dihydropyridine-3-carbaldehyde

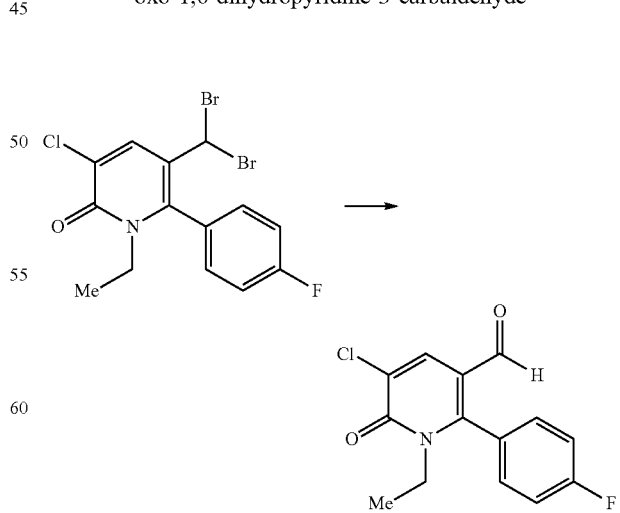

To 130 ml of acetonitrile containing 8.67 g of 3-chloro-5-(dibromomethyl)-1-ethyl-6-(4-fluorophenyl)pyridine-2

(1H)-one was added 65 ml of an aqueous solution containing 10.41 g of silver nitrate, and the mixture was stirred at room temperature for 3 hours. The resulting reaction mixture was filtered to remove any insoluble substance. After the solvent was distilled off from the filtrate under reduced pressure, water and ethyl acetate were added thereto, and the layers were separated. The resulting organic layer was washed with 1 N hydrochloric acid and a saturated brine and then dried over sodium sulfate. After the solvent was distilled off under reduced pressure, the resulting solid was washed with isopropyl ether. The title compound was obtained as 5.01 g of a yellow solid.

$^1$H-NMR (CDCl$_3$) δ: 9.09 (1H, s), 8.11 (1H, s), 7.40-7.39 (2H, m), 7.31-7.29 (2H, m), 3.90 (2H, q, J=7.1 Hz), 1.18 (3H, t, J=7.1 Hz).

Reference Example 10

Synthesis of 5-chloro-1-ethyl-2-(4-fluorophenyl)-6-oxo-1,6-dihydropyridine-3-carboxylic acid

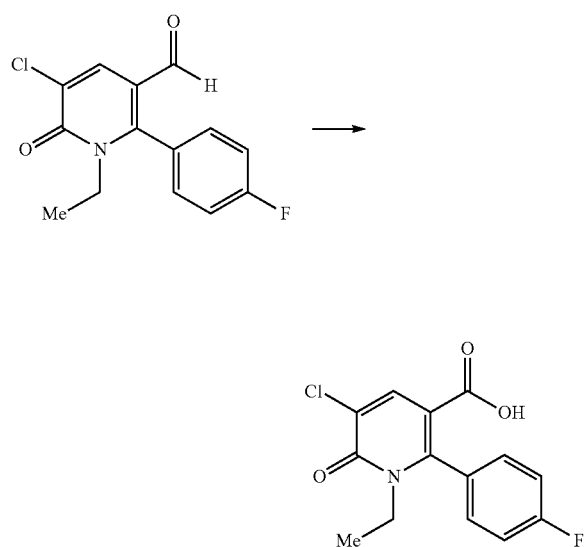

To a mixture solution of 7.5 ml of water, 22.5 ml of THF and 22.5 ml of tertiary butanol containing 1.5 g of 5-chloro-1-ethyl-2-(4-fluorophenyl)-6-oxo-1,6-dihydropyridine-3-carbaldehyde, 2.43 ml of 2-methyl-2-butene and 795 mg of sodium dihydrogenphosphate dihydrate was added 1.72 g of sodium chlorite (80% by weight), and the mixture was stirred at room temperature for 3 hours. Water and ethyl acetate were added to the reaction mixture to separate the layer, after which the resulting organic layer was sequentially washed with an aqueous solution of sodium thiosulfate and a saturated brine and then dried over sodium sulfate. After the solvent was distilled off under reduced pressure, the resulting solid was washed with isopropyl ether. The title compound was obtained as 1.00 g of a yellow solid.

$^1$H-NMR (CDCl$_3$) δ: 8.17 (1H, s), 7.25-7.17 (4H, m), 3.86 (2H, q, J=7.1 Hz), 1.13 (3H, t, J=7.1 Hz).

Reference Example 11 t-butyl (5-chloro-1-ethyl-2-(4-fluorophenyl)-6-oxo-1,6-dihydropyridin-3-carbamate

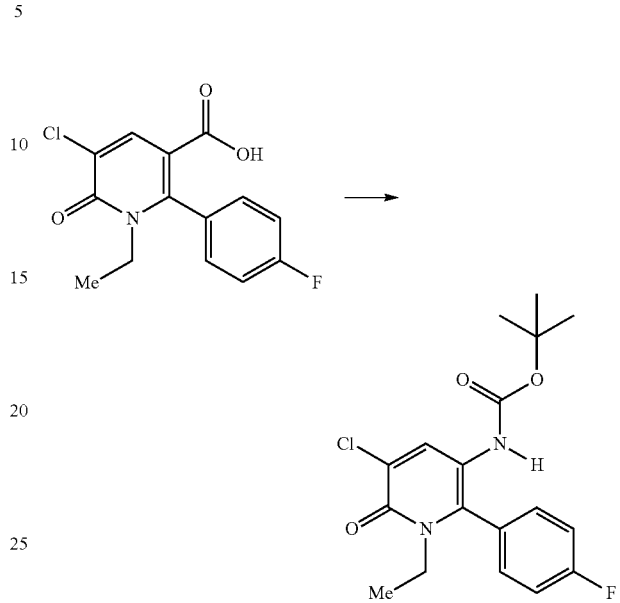

To 20 ml of tertiary butanol containing 1.64 g of 5-chloro-1-ethyl-2-(4-fluorophenyl)-6-oxo-1,6-dihydropyridine-3-carboxylic acid were added 1.82 g of diphenylphosphoryl azide and 0.92 ml of triethylamine, and the mixture was stirred at room temperature for 1 hour and after another at 80° C. for 2 hours. After cooling to room temperature, water and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 0.63 g of a pale-yellow solid.

$^1$H-NMR (CDCl$_3$) δ: 7.91 (1H, br s), 7.35-7.21 (4H, m), 5.37 (1H, br s), 3.83 (2H, q, J=7.0 Hz), 1.38 (9H, s), 1.11 (3H, t, J=7.0 Hz).

Reference Example 12

Synthesis of t-butyl 1-(5-chloro-1-ethyl-2-(4-fluorophenyl)-6-oxo-1,6-dihydropyridin-3-yl)hydrazine-1-carb oxylate

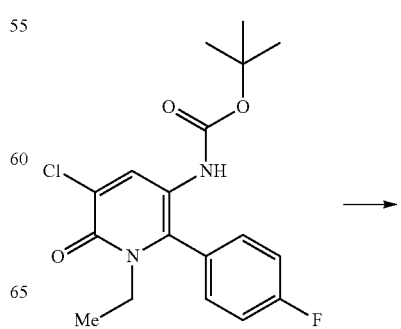

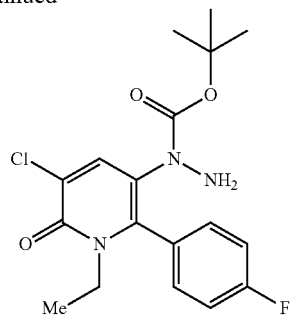

To 20 ml of a DMF solution containing 311 mg of 60% sodium hydride (in a dispersed state in liquid paraffin) was added dropwise 20 ml of a DMF solution containing 1.90 g of t-butyl (5-chloro-1-ethyl-2-(4-fluorophenyl)-6-oxo-1,6-dihydropyridin-3-yl)carbamate under ice cooling, and the mixture was stirred for 10 minutes. Subsequently, 1.57 g of O-(diphenylphosphinyl)hydroxylamine was added thereto, after which the temperature of the mixture was elevated from ice cooling to room temperature and the mixture was stirred for 20 minutes. Again, the reaction mixture was ice-cooled, and a solution of saturated ammonium chloride and ethyl acetate were thereto to separate the layer. The resulting organic layer was washed with a saturated brine and then dried over sodium sulfate. After the solvent was distilled off under reduced pressure, the resulting residue was purified by silica gel column chromatography. The title compound was obtained as 1.90 g of a white solid.

$^1$H-NMR (CDCl$_3$) δ: 7.46 (1H, s), 7.38-7.36 (2H, br m), 7.19-7.17 (2H, m), 3.97 (2H, br s), 3.84-3.82 (2H, br m), 1.37 (9H, s), 1.13 (3H, t, J=7.0 Hz).

Reference Example 13

Synthesis of 1-(4-fluorophenyl)-2-(4-nitro-1H-pyrazol-1-yl)ethane-1-one

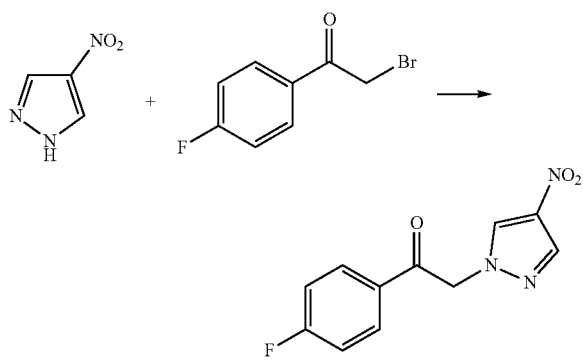

To 40 ml of a DMF solution containing 3.50 g of 60% sodium hydride (in a dispersed state in liquid paraffin) was added dropwise 20 ml of a DMF solution containing 8.25 g of 4-nitropyrazole under ice cooling, and the mixture was stirred for 15 minutes. Subsequently, 20 ml of a DMF solution containing 19.0 g of 2-bromo-4-fluoroacetophenone was added dropwise under ice cooling, and the mixture was stirred for 20 minutes. An aqueous solution of saturated ammonium chloride and ethyl acetate were added to the reaction mixture, and the layers were separated. The resulting organic layer was washed with a saturated brine and then dried over sodium sulfate. After the solvent was distilled off under reduced pressure, the resulting residue was purified by silica gel column chromatography. The title compound was obtained as 10.8 g of a yellow solid.

$^1$H-NMR (CDCl$_3$) δ: 8.29 (1H, s), 8.14 (1H, s), 8.04-8.03 (2H, m), 7.26-7.22 (2H, m), 5.63 (2H, s).

Reference Example 14

Synthesis of ethyl 5-(4-fluorphenyl)-4-(4-nitro-1H-pyrazol-1-yl)-5-oxopentanoate

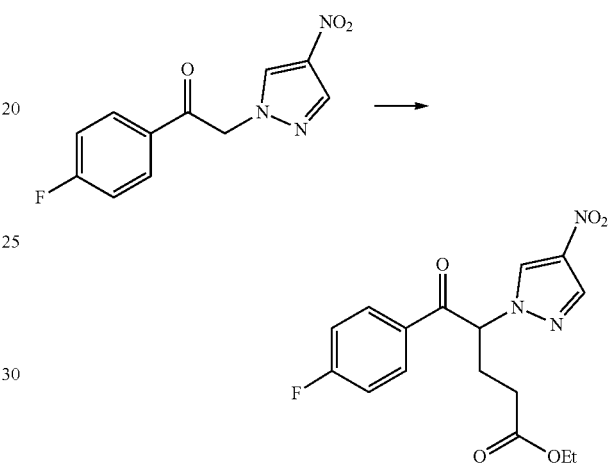

To 100 ml of THF containing 10.8 g of 1-(4-fluorophenyl)-2-(4-nitro-1H-pyrazol-1-yl)ethane-1-one were added 1.29 ml of 1,8-diazabicyclo[5.4.0]-7-undecene and 4.95 ml of ethyl acrylate, and the mixture was stirred at room temperature for 35 minutes. After a solution of saturated ammonium chloride and ethyl acetate were added thereto to separate the layer, the resulting organic layer was washed with a saturated brine and then dried over sodium sulfate. After the solvent was distilled off under reduced pressure, 15.9 g of a yellow oil containing the title compound was obtained, which was used in the next reaction without further purification.

$^1$H-NMR (CDCl$_3$) δ: 8.44 (1H, d, J=0.6 Hz), 8.20-8.18 (2H, m), 8.09 (1H, d, J=0.6 Hz), 7.25-7.20 (2H, m), 6.27-6.23 (1H, m), 4.19 (2H, q, J=7.2 Hz), 2.62-2.55 (1H, m), 2.46-2.44 (1H, m), 2.29-2.18 (2H, m), 1.28 (3H, t, J=7.2 Hz).

Reference Example 15

Synthesis of 2-(4,5-dichloro-1H-imidazol-1-yl)-1-phenylethane-1-one

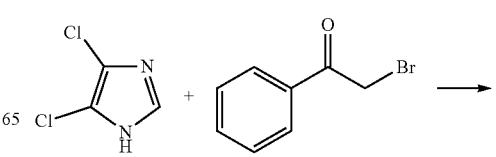

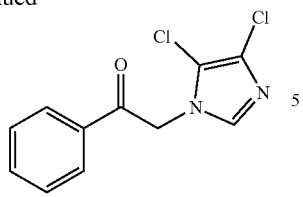

30 ml of an ethyl acetate solution containing 3.00 g of phenacyl bromide, 4.13 g of 4,5-dichloroimidazole and 2.12 ml of triethylamine was stirred under reflux for 1 hour. After cooling to room temperature, 1 N hydrochloric acid was added to the reaction mixture, and the layers were separated. The resulting organic layer was washed with a saturated brine and then dried over sodium sulfate. After the solvent was distilled off under reduced pressure, the precipitate was washed with a mixture solvent of ethyl acetate and diisopropyl ether. The resulting white solid was the title compound, which was 2.79 g in weight.

$^1$H-NMR (CDCl$_3$) δ: 8.01-8.00 (2H, m), 7.72-7.68 (1H, m), 7.58-7.56 (2H, m), 7.44 (1H, s), 5.36 (2H, s).

Reference Example 16

Synthesis of ethyl 4-(4,5-dichloro-1H-imidazol-1-yl)-5-oxo-5-phenylpentanoate

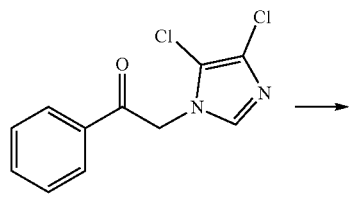

To 23 ml of a THF solution containing 2.30 g of 2-(4,5-dichloro-1H-imidazol-1-yl)-1-phenylethane-1-one were added 607 mg of potassium t-butoxide and 1.03 ml of ethyl acrylate, and the mixture was stirred at room temperature for 20 minutes. After a solution of saturated ammonium chloride and ethyl acetate were added thereto to separate the layer, the resulting organic layer was washed with a saturated brine and then dried over sodium sulfate. After the solvent was distilled off under reduced pressure, 3.20 g of a yellow oil containing the title compound was obtained, which was used in the next reaction without further purification.

$^1$H-NMR (CDCl$_3$) δ: 8.10-8.07 (2H, m), 7.68-7.64 (2H, m), 7.56-7.54 (2H, m), 6.08 (1H, dd, J=10.7, 4.3 Hz), 4.21-4.16 (2H, m), 2.65-2.56 (1H, m), 2.45-2.42 (1H, m), 2.37-2.14 (2H, m), 1.28 (3H, t, J=7.0 Hz).

Reference Example 17

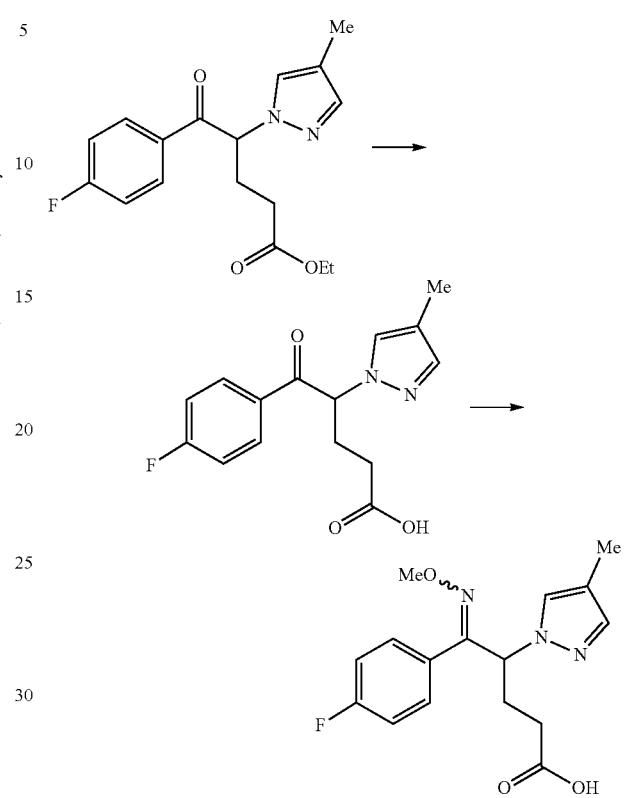

Step 1: Synthesis of 5-(4-fluorophenyl)-4-(4-methyl-1H-pyrazol-1-yl)-5-oxopentanoic acid To 2.92 g of ethyl 2-(4-fluorophenyl)-4-(4-methyl-1H-pyrazol-1-yl)-5-oxopentanoate obtained by carrying out with reference to Reference Examples 1 and 2 were added 30 ml of ethanol and 7.5 ml of water, and then 1.92 g of lithium hydroxide monohydrate was added thereto, and the mixture was stirred at 60° C. for 30 minutes. After cooling to room temperature, the solvent in the reaction mixture was distilled off under reduced pressure. Water and diethyl ether were added thereto to separate the layers, and the resulting aqueous layer was separated by adding 12 N hydrochloric acid and ethyl acetate. The resulting organic layer was washed with saturated brine and dried over sodium sulfate. After the solvent was distilled off under reduced pressure, the title compound was obtained as 2.25 g of a brown oil, which was used for the next reaction without further purification.

Step 2: Synthesis of 5-(4-fluorophenyl)-5-(methoxyimino)-4-(4-methyl-1H-pyrazol-1-yl) pentanoic acid To 23 ml of an ethanol solution containing 2.25 g of 5-(4-fluorophenyl)-4-(4-methyl-1H-pyrazol-1-yl)-5-oxopentanoic acid obtained in Step 1 were added 0.71 g of methoxyamine hydrochloride and 1.38 ml of pyridine, and the mixture was stirred at 90° C. for 2.5 hours. After cooling to room temperature and distilling off ethanol in the reaction mixture under reduced pressure, a saturated ammonium chloride solution and ethyl acetate were added to the reaction mixture, and the layers were separated. The resulting organic layer was washed with saturated brine and dried over sodium sulfate. After the solvent was distilled off under reduced pressure, the title compound was obtained as 2.30 g of a brown oil, which was used for the next reaction without further purification.

Tables 5 and 6 show compounds synthesized according to the above-described Examples, but the compounds of the present invention are not limited thereto.

In Table 5, the structure A is depicted as follows.

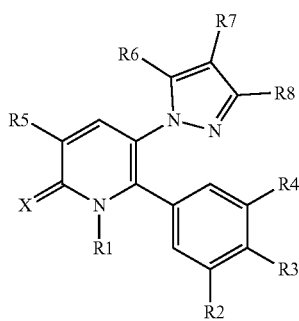

In Table 5, the structure B is depicted as follows.

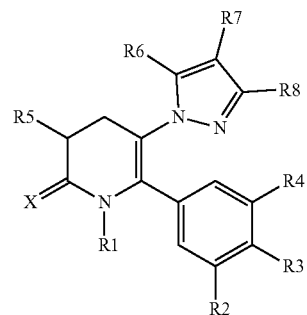

In Table 6, the structure C is depicted as follows.

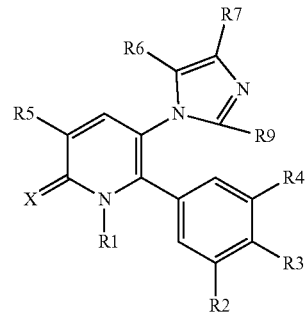

TABLE 5

| Compound No. | R1 | R2 | R3 | R4 | R5 | R6 | R7 | R8 | X | Structure |
|---|---|---|---|---|---|---|---|---|---|---|
| PY-001 | Et | H | N≡C— | H | Br | H | Cl | H | O | A |
| PY-002 | Et | H | N≡C— | H | H | H | Cl | H | O | A |
| PY-003 | Et | H | N≡C— | H | Cl | H | Cl | H | O | A |
| PY-004 | Et | H | MeO— | H | Br | H | Cl | H | O | A |
| PY-005 | Et | H | MeO— | H | Cl | H | Cl | H | O | A |
| PY-006 | Et | H | F | H | Br | H | Cl | H | O | A |
| PY-007 | Et | H | F | H | Cl | H | Cl | H | O | A |
| PY-008 | F2CHCH2— | H | F | H | Cl | H | Cl | H | O | A |
| PY-009 | Et | H | H | H | Br | H | Cl | H | O | A |
| PY-010 | Et | H | H | H | Cl | H | Cl | H | O | A |
| PY-011 | Et | H | H | H | Cl | Cl | Me | H | O | A |
| PY-012 | Et | H | F | H | Cl | Cl | Me | H | O | A |
| PY-013 | Et | H | F | H | Br | H | Me | H | O | A |
| PY-014 | Et | H | F | H | Br | Cl | Me | H | O | A |
| PY-015 | Et | H | H | H | Br | H | Me | H | O | A |
| PY-016 | Et | H | H | H | Br | Cl | Me | H | O | A |
| PY-017 | Et | H | N≡C— | H | Cl | Cl | Me | H | O | A |
| PY-018 | Et | H | MeO— | H | Cl | Cl | Me | H | O | A |
| PY-019 | Et | H | MeO— | H | Br | H | Me | H | O | A |
| PY-020 | F2CHCH2— | H | F | H | Cl | Cl | Me | H | O | A |
| PY-021 | F2CHCH2— | H | F | H | Br | H | Me | H | O | A |
| PY-022 | F2CHCH2— | H | F | H | Br | Cl | Me | H | O | A |
| PY-023 | Et | H | O2N— | H | Cl | Cl | Me | H | O | A |
| PY-024 | Et | H | H2N— | H | Cl | Cl | Me | H | O | A |
| PY-025 | Et | H | MeNH— | H | Cl | Cl | Me | H | O | A |
| PY-026 | Et | H | Me2N— | H | Cl | Cl | Me | H | O | A |
| PY-027 | F2CHCH2— | H | MeO— | H | Br | H | Cl | H | O | A |
| PY-028 | F2CHCH2— | H | MeO— | H | Cl | H | Cl | H | O | A |
| PY-029 | F2CHCH2— | H | MeO— | H | Me | H | Cl | H | O | A |
| PY-030 | Et | H | H | H | H | H | Me | H | O | A |
| PY-031 | F2CHCH2— | H | MeO— | H | H | H | Me | H | O | A |
| PY-032 | F2CHCH2— | H | MeO— | H | Cl | Cl | Me | H | O | A |
| PY-033 | F2CHCH2— | H | MeO— | H | Br | H | Me | H | O | A |
| PY-034 | F2CHCH2— | H | MeO— | H | Br | Cl | Me | H | O | A |
| PY-035 | Et | H | Br | H | H | H | Me | H | O | A |
| PY-036 | Et | H | MeO— | H | H | H | Me | H | O | A |

TABLE 5-continued

| Compound No. | R1 | R2 | R3 | R4 | R5 | R6 | R7 | R8 | X | Structure |
|---|---|---|---|---|---|---|---|---|---|---|
| PY-037 | Et | H | MeO— | H | Br | Cl | Me | H | O | A |
| PY-038 | Me | H | MeO— | H | H | H | Me | H | O | A |
| PY-039 | Me | H | MeO— | H | Cl | Cl | Me | H | O | A |
| PY-040 | Me | H | MeO— | H | Br | H | Me | H | O | A |
| PY-041 | Et | H | HO— | H | Cl | Cl | Me | H | O | A |
| PY-042 | Me | H | MeO— | H | Br | Cl | Me | H | O | A |
| PY-043 | Et | H | EtO— | H | Cl | Cl | Me | H | O | A |
| PY-044 | Et | H | MeOCH2CH2O— | H | Cl | Cl | Me | H | O | A |
| PY-045 | E | H | HC≡CCH2O— | H | Cl | Cl | Me | H | O | A |
| PY-046 | Et | H | F2CHCH2O— | H | Cl | Cl | Me | H | O | A |
| PY-047 | Et | H | F3CCH2O— | H | Cl | Cl | Me | H | O | A |
| PY-048 | Et | H | MeOCH2O— | H | Cl | Cl | Me | H | O | A |
| PY-049 | Et | H | AcO— | H | Cl | Cl | Me | H | O | A |
| PY-050 | Et | H | MeSO2-O— | H | Cl | Cl | Me | H | O | A |
| PY-051 | Et | H | MeO— | H | Cl | Me | H | H | O | A |
| PY-052 | Et | H | MeO— | H | Cl | Me | H | Me | O | A |
| PY-053 | Et | H | F3CO— | H | H | H | Me | H | O | A |
| PY-054 | Et | H | F3CO— | H | Cl | Cl | Me | H | O | A |
| PY-055 | Et | H | F3CO— | H | Br | H | Me | H | O | A |
| PY-056 | Et | H | F3CO— | H | Br | Cl | Me | H | O | A |
| PY-057 | Et | H | Br | H | H | Me | Br | Me | O | A |
| PY-058 | Et | H | Br | H | Me | Me | H | Me | O | A |
| PY-059 | Et | H | Me | H | H | H | Me | H | O | A |
| PY-060 | Et | H | F2CHO— | H | Cl | Cl | Me | H | O | A |
| PY-061 | Et | H | F2CHO— | H | Br | H | Me | H | O | A |
| PY-062 | Et | H | F2CHO— | H | Br | Cl | Me | H | O | A |
| PY-063 | Et | H | MeO— | H | Cl | Me | HC(=O)— | H | O | A |
| PY-064 | Et | H | MeO— | H | Cl | Me | Me | H | O | A |
| PY-065 | Et | H | Me | H | Cl | Cl | Me | H | O | A |
| PY-066 | Et | H | Me | H | Br | Cl | Me | H | O | A |
| PY-067 | Et | H | Et | H | Cl | Cl | Me | H | O | A |
| PY-068 | Et | H | Pr | H | Cl | Cl | Me | H | O | A |
| PY-069 | Et | H | cPr | H | Cl | Cl | Me | H | O | A |
| PY-070 | Et | H | Br | H | Cl | Cl | Me | H | O | A |
| PY-071 | Et | H | Br | H | Br | Cl | Me | H | O | A |
| PY-072 | Et | H | Me | H | Br | H | Me | H | O | A |
| PY-073 | Et | H | Et | H | H | H | Me | H | O | A |
| PY-074 | Et | H | Me | H | Me | Me | H | Me | O | A |
| PY-075 | Et | H | MeO— | H | Cl | F3C— | H | H | O | A |
| PY-076 | Et | H | 4-morpholino | H | Cl | Cl | Me | H | O | A |
| PY-077 | Et | H | piperidin-1-yl | H | Cl | Cl | Me | H | O | A |
| PY-078 | Et | H | AcNH— | H | Cl | Cl | Me | H | O | A |
| PY-079 | Et | H | MeO— | H | Cl | Me | F | H | O | A |
| PY-080 | Et | H | MeO— | H | Cl | Cl3C— | H | H | O | A |
| PY-081 | Me | H | F | H | H | H | Me | H | O | A |
| PY-082 | Me | H | F | H | Cl | Cl | Me | H | O | A |
| PY-083 | Me | H | F | H | Br | Cl | Me | H | O | A |
| PY-084 | Et | H | Cl | H | H | H | Me | H | O | A |
| PY-085 | Et | H | Cl | H | Cl | Cl | Me | H | O | A |
| PY-086 | Et | H | Cl | H | Br | Cl | Me | H | O | A |
| PY-087 | F2CHCH2— | H | Cl | H | H | H | Me | H | O | A |
| PY-088 | F2CHCH2— | H | Cl | H | Br | Cl | Me | H | O | A |
| PY-089 | F2CHCH2— | H | Cl | H | Cl | Cl | Me | H | O | A |
| PY-090 | Et | H | F | H | Cl | F3C— | H | H | O | A |
| PY-091 | Et | H | F | H | Br | Br | Me | H | O | A |
| PY-092 | Et | H | F | H | Br | H | Me | Br | O | A |
| PY-093 | Et | H | Ac(Me)N— | H | Cl | Cl | Me | H | O | A |
| PY-094 | Et | F | H | F | Cl | Cl | Me | H | O | A |
| PY-095 | Et | F | H | F | Cl | Cl | Me | H | O | A |
| PY-096 | Et | F | H | F | Br | H | Me | H | O | A |
| PY-097 | Et | H | F | F | Br | H | Me | H | O | A |
| PY-098 | Et | F | H | F | H | H | Me | H | O | A |
| PY-099 | F2CHCH2— | H | F | H | Cl | Cl | HC(=O)— | H | O | A |
| PY-100 | Et | H | H | F | Cl | Cl | Me | H | O | A |
| PY-101 | F2CHCH2— | H | F | H | Cl | Cl | MeOCH2— | H | O | A |
| PY-102 | F2CHCH2— | H | F | H | Cl | Cl | HOCH2— | H | O | A |
| PY-103 | F2CHCH2— | H | F | H | Cl | Cl | F2CH— | H | O | A |
| PY-104 | Et | H | F | H | Cl | Cl | H | H | O | A |
| PY-105 | Et | H | F | H | Cl | Br | H | H | O | A |
| PY-106 | F2CHCH2— | H | F | H | Cl | Cl | H | H | O | A |
| PY-107 | F2CHCH2— | H | F | H | Cl | Br | H | H | O | A |
| PY-108 | F2CHCH2— | H | F | H | Cl | MeO— | H | H | O | A |
| PY-109 | Et | H | Br | H | Br | H | O2N— | H | O | A |
| PY-110 | Et | H | H | H | Cl | H | O2N— | H | O | A |
| PY-111 | Et | H | H | H | Cl | Cl | O2N— | H | O | A |
| PY-112 | Et | H | H | H | Cl | Cl | H2N— | H | O | A |
| PY-113 | Et | H | H | H | Cl | Cl | H | H | O | A |
| PY-114 | F2CHCH2— | H | F | H | H | Cl | Me | H | O | A |

TABLE 5-continued

| Compound No. | R1 | R2 | R3 | R4 | R5 | R6 | R7 | R8 | X | Structure |
|---|---|---|---|---|---|---|---|---|---|---|
| PY-115 | F2CHCH2— | H | F | H | I | Cl | Me | H | O | A |
| PY-116 | Et | H | H | H | Br | H | O2N— | H | O | A |
| PY-117 | Et | H | H | H | Br | Cl | O2N— | H | O | A |
| PY-118 | Et | H | H | H | Br | Cl | H2N— | H | O | A |
| PY-119 | Et | H | H | H | Br | Cl | H | H | O | A |
| PY-120 | Et | H | H | H | Cl | Br | O2N— | H | O | A |
| PY-121 | Et | H | MeO— | H | Cl | H | O2N— | H | O | A |
| PY-122 | Et | H | MeO— | H | Cl | Cl | H | H | O | A |
| PY-123 | F2CHCH2— | H | F | H | Cl | Cl | Et | H | O | A |
| PY-124 | F2CHCH2— | H | F | H | Cl | Cl | H2C=CH— | H | O | A |
| PY-125 | F2CHCH2— | H | F | H | Cl | Cl | HC≡C— | H | O | A |
| PY-126 | F3CCH2— | H | F | H | H | H | Me | H | O | A |
| PY-127 | F2CHCH2— | H | F | H | H | H | Me | H | O | A |
| PY-128 | F2CHCH2— | H | H | H | H | H | Me | H | O | A |
| PY-129 | F2CHCH2— | H | H | H | Cl | Cl | Me | H | O | A |
| PY-130 | F2CHCH2— | H | H | H | H | Cl | Me | H | O | A |
| PY-131 | F2CHCH2— | H | H | H | Br | Cl | Me | H | O | A |
| PY-132 | F2CHCH2— | H | H | H | H | H | O2N— | H | O | A |
| PY-133 | Et | H | H | H | Cl | Br | H2N— | H | O | A |
| PY-134 | Et | H | H | H | Cl | Br | H | H | O | A |
| PY-135 | Et | H | H | H | Br | Br | O2N— | H | O | A |
| PY-136 | F2CHCH2— | H | H | H | Cl | H | O2N— | H | O | A |
| PY-137 | Et | H | H | H | Br | Br | H2N— | H | O | A |
| PY-138 | Et | H | H | H | Br | Br | H | H | O | A |
| PY-139 | Et | H | MeO— | H | Cl | Br | H | H | O | A |
| PY-140 | Et | H | MeO— | H | H | H | O2N— | H | O | A |
| PY-141 | F2CHCH2— | H | Br | H | H | H | O2N— | H | O | B |
| PY-142 | Et | H | MeO— | H | Br | H | O2N— | H | O | A |
| PY-143 | Et | H | MeO— | H | Br | Cl | O2N— | H | O | A |
| PY-144 | Et | H | MeO— | H | Br | Br | O2N— | H | O | A |
| PY-145 | Et | H | MeO— | H | Br | Cl | H2N— | H | O | A |
| PY-146 | Et | H | MeO— | H | Br | Cl | H | H | O | A |
| PY-147 | Et | H | MeO— | H | Br | Br | H2N— | H | O | A |
| PY-148 | F2CHCH2— | H | Br | H | H | H | O2N— | H | O | A |
| PY-149 | Et | H | MeO— | H | Br | Br | H | H | O | A |
| PY-150 | F2CHCH2— | H | F | H | H | H | O2N— | H | O | B |
| PY-151 | F2CHCH2— | H | F | H | H | H | O2N— | H | O | A |
| PY-152 | F2CHCH2— | H | F | H | Cl | H | O2N— | H | O | A |
| PY-153 | F2CHCH2— | H | F | H | Cl | H | H2N— | H | O | A |
| PY-154 | F2CHCH2— | H | F | H | Cl | H | H | H | O | A |
| PY-155 | F2CHCH2— | H | F | H | Br | Br | Me | H | O | A |
| PY-156 | F2CHCH2— | H | F | H | Br | H | Me | Br | O | A |
| PY-157 | F2CHCH2— | H | H | H | Cl | Cl | H | H | O | A |
| PY-158 | F2CHCH2— | H | H | H | Br | H | O2N— | H | O | A |
| PY-159 | F2CHCH2— | H | H | H | Cl | Br | H2N— | H | O | A |
| PY-160 | F2CHCH2— | H | H | H | Br | Cl | H2N— | H | O | A |
| PY-161 | F2CHCH2— | H | H | H | Cl | Br | H | H | O | A |
| PY-162 | Me | H | H | H | H | H | O2N— | H | O | B |
| PY-163 | F2CHCH2— | H | H | H | Br | Cl | H | H | O | A |
| PY-164 | F2CHCH2— | H | MeO— | H | H | H | O2N— | H | O | A |
| PY-165 | F2CHCH2— | H | MeO— | H | Cl | H | O2N— | H | O | A |
| PY-166 | F2CHCH2— | H | MeO— | H | Br | H | O2N— | H | O | A |
| PY-167 | F2CHCH2— | H | MeO— | H | Cl | Cl | O2N— | H | O | A |
| PY-168 | F2CHCH2— | H | MeO— | H | Cl | Br | O2N— | H | O | A |
| PY-169 | F2CHCH2— | H | MeO— | H | Cl | Cl | H2N— | H | O | A |
| PY-170 | F2CHCH2— | H | MeO— | H | Br | Cl | O2N— | H | O | A |
| PY-171 | F2CHCH2— | H | MeO— | H | Cl | Cl | H | H | O | A |
| PY-172 | F2CHCH2— | H | MeO— | H | Cl | Br | H2N— | H | O | A |
| PY-173 | F2CHCH2— | H | MeO— | H | Br | Cl | H2N— | H | O | A |
| PY-174 | F2CHCH2— | H | MeO— | H | Br | Br | O2N— | H | O | A |
| PY-175 | F2CHCH2— | H | MeO— | H | Br | Cl | H | H | O | A |
| PY-176 | Me | H | Br | H | H | H | O2N— | H | O | B |
| PY-177 | F2CHCH2— | H | MeO— | H | Br | Br | H2N— | H | O | A |
| PY-178 | F2CHCH2— | H | F | H | Cl | MeO— | Me | H | O | A |
| PY-179 | H2N— | H | F | H | Cl | Cl | Me | H | O | A |
| PY-180 | MeNH— | H | F | H | Cl | Cl | Me | H | O | A |
| PY-181 | F2CHCH2— | H | F | H | Cl | MeS— | Me | H | O | A |
| PY-182 | F2CHCH2— | H | F | H | Cl | MeS(O)— | Me | H | O | A |
| PY-183 | F2CHCH2— | H | F | H | Cl | MeSO2— | Me | H | O | A |
| PY-184 | F2CHCH2— | H | MeO— | H | Br | Cl | H | H | O | A |
| PY-185 | Me | H | Br | H | H | H | O2N— | H | O | A |
| PY-186 | F2CHCH2— | H | MeO— | H | Br | Br | H | H | O | A |
| PY-187 | Me | H | MeO— | H | H | H | O2N— | H | O | A |
| PY-188 | Me | H | MeO— | H | Cl | H | O2N— | H | O | A |
| PY-189 | Me | H | MeO | H | O | Cl | O2N— | H | O | A |
| PY-190 | Me | H | MeO— | H | Br | H | O2N— | H | O | A |
| PY-191 | Me | H | MeO— | H | Cl | Cl | H2N— | H | O | A |
| PY-192 | Me | H | MeO— | H | Cl | Br | O2N— | H | O | A |

TABLE 5-continued

| Compound No. | R1 | R2 | R3 | R4 | R5 | R6 | R7 | R8 | X | Structure |
|---|---|---|---|---|---|---|---|---|---|---|
| PY-193 | Me | H | MeO— | H | Cl | Cl | H | H | O | A |
| PY-194 | Me | H | MeO— | H | Br | Cl | O2N— | H | O | A |
| PY-195 | Me | H | MeO— | H | Cl | Br | H2N— | H | O | A |
| PY-196 | Me | H | H | H | H | H | O2N— | H | O | A |
| PY-197 | Me | H | H | H | Cl | H | O2N— | H | O | A |
| PY-198 | Me | H | H | H | Cl | Cl | O2N— | H | O | A |
| PY-199 | F2CHCH2— | H | H | H | Br | Br | H | H | O | A |
| PY-200 | Me | H | H | H | Cl | Br | O2N— | H | O | A |
| PY-201 | Me | H | H | H | Cl | Cl | H | H | O | A |
| PY-202 | Me | H | H | H | Cl | Br | H | H | O | A |
| PY-203 | Me | H | H | H | Br | Cl | O2N— | H | O | A |
| PY-204 | Me | H | H | H | Br | Br | O2N— | H | O | A |
| PY-205 | Me | H | H | H | Br | Cl | H2N— | H | O | A |
| PY-206 | Me | H | H | H | Br | Br | H2N— | H | O | A |
| PY-207 | Me | H | H | H | Br | Cl | H | H | O | A |
| PY-208 | Me | H | H | H | Br | Br | H | H | O | A |
| PY-209 | F2CHCH2— | H | F | H | Cl | F3C— | EtOC(=O) | H | O | A |
| PY-210 | F2CHCH2— | H | F | H | Cl | Cl | EtCH(OH)— | H | O | A |
| PY-211 | F2CHCH2— | H | F | H | Cl | Cl | Pr | H | O | A |
| PY-212 | F2CHCH2— | H | F | H | Cl | Cl | HC≡CCH(OH)— | H | O | A |
| PY-213 | F2CHCH2— | H | F | H | Cl | Cl | HC≡CCH2— | H | O | A |
| PY-214 | Me | H | MeO— | H | Br | Br | O2N— | H | O | A |
| PY-215 | Me | H | MeO— | H | Br | Cl | H2N— | H | O | A |
| PY-216 | Me | H | MeO— | H | Cl | Br | H | H | O | A |
| PY-217 | Me | H | MeO— | H | Br | Br | H2N— | H | O | A |
| PY-218 | Me | H | MeO— | H | Br | Cl | H | H | O | A |
| PY-219 | Me | H | MeO— | H | Br | Br | H | H | O | A |
| PY-220 | F2CHCH2— | H | H | F | H | H | Me | H | O | B |
| PY-221 | F2CHCH2— | H | H | F | H | H | Me | H | O | A |
| PY-222 | F2CHCH2— | H | H | F | Cl | Cl | Me | H | O | A |
| PY-223 | F2CHCH2— | H | F | H | Cl | Cl | MeCH(OH)— | H | O | A |
| PY-224 | F2CHCH2— | H | H | F | H | Cl | Me | H | O | A |
| PY-225 | F2CHCH2— | H | F | H | Cl | Cl | Ac | H | O | A |
| PY-226 | F2CHCH2— | H | F | H | Cl | Cl | Me2C(OH)— | H | O | A |
| PY-227 | F2CHCH2— | H | F | H | Cl | Cl | iPr | H | O | A |
| PY-228 | Et | H | F | H | Cl | —(CH2)3— | | H | O | A |
| PY-229 | F2CHCH2— | H | H | F | Br | Cl | Me | H | O | A |
| PY-230 | F2CHCH2— | H | F | H | Cl | H | EtOC(=O)— | H | O | A |
| PY-231 | F2CHCH2— | H | F | H | Cl | H | EtOC(=O)— | H | O | B |
| PY-232 | F2CHCH2— | H | H | H | Me | H | Me | H | O | A |
| PY-233 | F2CHCH2— | H | H | H | Cl | H | Me | H | O | A |
| PY-234 | F2CHCH2— | H | F | H | Me | Cl | Me | H | O | A |
| PY-235 | F2CHCH2— | H | F | H | Cl | H | Me | H | O | A |
| PY-236 | F2CHCH2— | H | H | H | Cl | H | Me | Br | O | A |
| PY-237 | Et | H | F | H | Cl | Me | H | H | O | A |
| PY-238 | F2CHCH2— | H | F | H | Cl | Me | H | H | O | A |
| PY-239 | F2CHCH2— | H | F | H | Cl | Et | H | Et | O | A |
| PY-240 | F2CHCH2— | H | F | H | Cl | Et | H | Me | O | A |
| PY-241 | F2CHCH2— | H | F | H | Cl | Me | H | Me | O | A |
| PY-242 | F2CHCH2— | H | F | H | Cl | tBu | H | Me | O | A |
| PY-243 | F2CHCH2— | H | F | H | Cl | iPr | H | Me | O | A |
| PY-244 | F2CHCH2— | H | F | H | Cl | —(CH2)4— | | H | O | A |
| PY-245 | Et | H | HC≡C— | H | Cl | Cl | H | H | O | A |
| PY-246 | F2CHCH2— | H | N≡C— | H | H | H | Me | H | O | B |
| PY-247 | F2CHCH2— | H | N≡C— | H | H | H | Me | H | O | A |
| PY-248 | F2CHCH2— | H | F | F | H | H | Me | H | O | B |
| PY-249 | F2CHCH2— | H | N≡C— | H | Cl | Cl | Me | H | O | A |
| PY-250 | F2CHCH2— | H | F | F | H | H | Me | H | O | A |
| PY-251 | F2CHCH2— | H | F | F | Cl | H | Me | H | O | A |
| PY-252 | F2CHCH2— | H | F | F | H | Cl | Me | H | O | A |
| PY-253 | F2CHCH2— | H | F | F | Cl | Cl | Me | H | O | A |
| PY-254 | F2CHCH2— | H | F | F | Br | Cl | Me | H | O | A |
| PY-255 | F2CHCH2— | H | H | H | Br | H | Me | Br | O | A |
| PY-256 | F2CHCH2— | H | H | H | Br | Br | Me | H | O | A |
| PY-257 | F2CHCH2— | H | F | H | Cl | Br | Me | H | O | A |
| PY-258 | F2CHCH2— | H | F | H | Cl | cPr | H | Me | O | A |
| PY-259 | F2CHCH2— | H | F | H | Cl | —(CH2)3— | | H | O | A |
| PY-260 | F2CHCH2— | H | F | H | Cl | MeOC(=O)— | Me | H | O | A |
| PY-261 | F2CHCH2— | H | F | H | Cl | F3C— | H | H | O | A |
| PY-262 | F2CHCH2— | H | F | H | Cl | F3C— | Me | H | O | A |
| PY-263 | F2CHCH2— | H | F | H | Cl | Me | EtOC(=O)— | H | O | A |
| PY-264 | F2CHCH2— | H | F | H | Cl | Et | Me | H | O | A |
| PY-265 | F2CHCH2— | H | F | H | Cl | F2CH— | Me | H | O | A |
| PY-266 | F2CHCH2— | H | F | H | Cl | F3CCF2— | Me | H | O | A |
| PY-267 | F2CHCH2— | H | F | H | Cl | H | Me | Br | O | A |
| PY-268 | F2CHCH2— | H | F | H | Cl | iPr | Me | H | O | A |
| PY-269 | F2CHCH2— | H | F | H | Ac | Cl | Me | H | O | A |
| PY-270 | F2CHCH2— | H | F | H | MeCH(OH)— | Cl | Me | H | O | A |

TABLE 5-continued

| Compound No. | R1 | R2 | R3 | R4 | R5 | R6 | R7 | R8 | X | Structure |
|---|---|---|---|---|---|---|---|---|---|---|
| PY-271 | F2CHCH2— | H | F | H | Et | Cl | Me | H | O | A |
| PY-272 | F2CHCH2— | H | F | H | H2C=CH— | Cl | Me | H | O | A |
| PY-273 | F2CHCH2— | H | F | H | O2N— | Cl | Me | H | O | A |
| PY-274 | F2CHCH2— | H | F | H | H2N— | Cl | Me | H | O | A |
| PY-275 | F2CHCH2— | H | F | H | MeO— | Cl | Me | H | O | A |
| PY-276 | F2CHCH2— | H | F | H | Cl | Me | Me | H | O | A |
| PY-277 | F2CHCH2— | H | F | H | Br | Et | Me | H | O | A |
| PY-278 | F2CHCH2— | H | F | H | Br | Me | Me | H | O | A |
| PY-279 | F2CHCH2— | H | F | H | Br | iPr | Me | H | O | A |
| PY-280 | F2CHCH2— | H | F | H | Br | F3C— | Me | H | O | A |
| PY-281 | F2CHCH2— | H | F | H | Br | H | Me | F3C— | O | A |
| PY-282 | F2CHCH2— | H | F | H | Br | F2CH— | Me | H | O | A |
| PY-283 | F2CHCH2— | H | F | H | Br | F3CCF2— | Me | H | O | A |
| PY-284 | F2CHCH2— | H | F | H | Cl | F2CHCF2— | Me | H | O | A |
| PY-285 | F2CHCH2— | H | F | H | Cl | ClCF2— | Me | H | O | A |
| PY-286 | F2CHCH2— | H | F | H | Br | F2CHCF2— | Me | H | O | A |
| PY-287 | F2CHCH2— | H | F | H | Br | ClCF2— | Me | H | O | A |
| PY-288 | F2CHCH2— | H | F | H | Cl | MeCF2— | Me | H | O | A |
| PY-289 | F2CHCH2— | H | F | H | Br | MeCF2— | Me | H | O | A |
| PY-290 | F2CHCH2— | H | H | H | Cl | Me | Me | H | O | A |
| PY-291 | F2CHCH2— | H | H | H | Cl | Et | Me | H | O | A |
| PY-292 | F2CHCH2— | H | MeO— | H | Me | Cl | Me | H | O | A |
| PY-293 | F2CHCH2— | H | F | H | Me2N— | Cl | Me | H | O | A |
| PY-294 | F2CHCH2— | H | F | H | MeNH— | Cl | Me | H | O | A |
| PY-295 | F2CHCH2— | H | F | H | Cl | BrCF2— | Me | H | O | A |
| PY-296 | F2CHCH2— | H | F | H | Br | BrCF2— | Me | H | O | A |
| PY-297 | F2CHCH2— | H | MeO— | H | Cl | F3C— | Me | H | O | A |
| PY-298 | F2CHCH2— | H | MeO— | H | Cl | F2CH— | Me | H | O | A |
| PY-299 | F2CHCH2— | H | MeO— | H | Br | F3C— | Me | H | O | A |
| PY-300 | F2CHCH2— | H | MeO— | H | Br | F2CH— | Me | H | O | A |
| PY-301 | F2CHCH2— | H | H | H | Cl | F3C— | Me | H | O | A |
| PY-302 | F2CHCH2— | H | H | H | Cl | F2CH— | Me | H | O | A |
| PY-303 | F2CHCH2— | H | F | H | Cl | tBu | Me | H | O | A |
| PY-304 | F2CHCH2— | H | F | H | Cl | cPr | Me | H | O | A |
| PY-305 | F2CHCH2— | H | F | H | Br | cPr | Me | H | O | A |
| PY-306 | Et | H | F | H | Cl | F3C— | Me | H | O | A |
| PY-307 | Et | H | F | H | Cl | ClCF2— | Me | H | O | A |
| PY-308 | F2CHCH2— | H | Br | H | H | Cl | Me | H | O | A |
| PY-309 | Et | H | F | H | Cl | F2CH— | Me | H | O | A |
| PY-310 | Et | H | F | H | Br | F3C— | Me | H | O | A |
| PY-311 | Et | H | F | H | Br | F2CH— | Me | H | O | A |
| PY-312 | E | H | F | H | Cl | Me | Me | H | O | A |
| PY-313 | Et | H | F | H | Cl | cPr | Me | H | O | A |
| PY-314 | F2CHCH2— | H | F | H | Br | tBu | Me | H | O | A |
| PY-315 | Et | H | N≡C— | H | Cl | F3C— | Me | H | O | A |
| PY-316 | E | H | N≡C— | H | Cl | F2CH— | Me | H | O | A |
| PY-317 | F2CHCH2— | H | F | Cl | Cl | Cl | Me | H | O | A |
| PY-318 | Et | H | Cl | F | Cl | Cl | Me | H | O | A |
| PY-319 | Et | H | Cl | F | Br | H | Me | H | O | A |
| PY-320 | Et | H | Cl | F | Br | Cl | Me | H | O | A |
| PY-321 | Et | H | F | Cl | Cl | Cl | Me | H | O | A |
| PY-322 | Et | H | F | Cl | Br | H | Me | H | O | A |
| PY-323 | F2CHCH2— | H | F | Cl | Br | Cl | Me | H | O | A |
| PY-324 | F2CHCH2— | H | F | H | H | Cl | Me | H | O | B |
| PY-325 | Et | H | F | Cl | Br | Cl | Me | H | O | A |
| PY-326 | Et | H | F | Br | Cl | Cl | Me | H | O | A |
| PY-327 | Et | H | F | Br | Br | Cl | Me | H | O | A |
| PY-328 | F2CHCH2— | H | F | Me | Cl | Cl | Me | H | O | A |
| PY-329 | F2CHCH2— | H | F | Me | Br | H | Me | H | O | A |
| PY-330 | F2CHCH2— | H | F | Me | Br | Cl | Me | H | O | A |
| PY-331 | Et | F | F | F | Cl | Cl | Me | H | O | A |
| PY-332 | Et | F | F | F | Br | H | Me | H | O | A |
| PY-333 | F2CHCH2— | H | H | Cl | Cl | H | Me | Cl | O | A |
| PY-334 | F2CHCH2— | H | H | Cl | Cl | Cl | Me | H | O | A |
| PY-335 | F2CHCH2— | H | F | Br | Cl | Cl | Me | H | O | A |
| PY-336 | F2CHCH2— | H | F | Br | Br | Cl | Me | H | O | A |
| PY-337 | Et | H | Cl | Cl | Cl | Cl | Me | H | O | A |
| PY-338 | Et | H | Cl | Cl | Br | Cl | Me | H | O | A |
| PY-339 | Et | H | F | HC≡C— | Cl | Cl | Me | H | O | A |
| PY-340 | Et | F | F | F | Br | Cl | Me | H | O | A |
| PY-341 | F2CHCH2— | F | F | F | Cl | Cl | Me | H | O | A |
| PY-342 | F2CHCH2— | F | F | F | Br | H | Me | H | O | A |
| PY-343 | Et | H | H | Cl | Cl | Cl | Me | H | O | A |
| PY-344 | F2CHCH2— | H | H | Cl | Br | H | Me | H | O | A |
| PY-345 | Et | H | H | Cl | Br | H | Me | H | O | A |
| PY-346 | Et | H | H | Cl | Br | Cl | Me | H | O | A |
| PY-347 | F2CHCH2— | F | F | F | Br | Cl | Me | H | O | A |
| PY-348 | F2CHCH2— | H | H | Br | Cl | Cl | Me | H | O | A |

TABLE 5-continued

| Compound No. | R1 | R2 | R3 | R4 | R5 | R6 | R7 | R8 | X | Structure |
|---|---|---|---|---|---|---|---|---|---|---|
| PY-349 | F2CHCH2— | H | H | Br | Br | Cl | Me | H | O | A |
| PY-350 | F2CHCH2— | Br | H | Br | Br | H | Me | H | O | A |
| PY-351 | Et | H | H | Br | Cl | Cl | Me | H | O | A |
| PY-352 | F2CHCH2— | H | Cl | Cl | Cl | Cl | Me | H | O | A |
| PY-353 | Et | H | F | HC≡C— | Br | Cl | Me | H | O | A |
| PY-354 | F2CHCH2— | H | Cl | Cl | Br | Cl | Me | H | O | A |
| PY-355 | Et | H | F | Me | Cl | Cl | Me | H | O | A |
| PY-356 | Et | H | F | Me | Br | H | Me | H | O | A |
| PY-357 | Et | H | H | Br | Br | H | Me | H | O | A |
| PY-358 | Et | H | H | Br | Br | Cl | Me | H | O | A |
| PY-359 | F2CHCH2— | H | F | H | Br | Cl | BrCH2— | H | O | A |
| PY-360 | F2CHCH2— | H | F | H | Br | Cl | Br2CH— | H | O | A |
| PY-361 | Et | H | F | Me | Br | Cl | Me | H | O | A |
| PY-362 | Et | H | H | HC≡C— | Cl | Cl | Me | H | O | A |
| PY-363 | Et | H | H | HC≡C— | Br | Cl | Me | H | O | A |
| PY-364 | Pr | H | F | H | Cl | Cl | Me | H | O | A |
| PY-365 | F3CCH2— | H | F | H | Cl | Cl | Me | H | O | A |
| PY-366 | Pr | H | F | H | Br | Cl | Me | H | O | A |
| PY-367 | F2CHCF2— | H | F | H | Cl | Cl | Me | H | O | A |
| PY-368 | F2CHCH2— | H | Cl | F | Cl | Cl | Me | H | O | A |
| PY-369 | F3CCH2— | H | F | H | Br | Cl | Me | H | O | A |
| PY-370 | F2CHCF2— | H | F | H | Br | Cl | Me | H | O | A |
| PY-371 | F2CHCH2— | H | Cl | F | Br | Cl | Me | H | O | A |
| PY-372 | FCH2CH2— | H | F | H | Cl | Cl | Me | H | O | A |
| PY-373 | FCH2CH2— | H | F | H | Br | Cl | Me | H | O | A |
| PY-374 | MeO— | H | F | H | H | H | Me | H | O | A |
| PY-375 | MeO— | H | F | H | Cl | H | Me | H | O | A |
| PY-376 | MeO— | H | F | H | Cl | Cl | Me | H | O | A |
| PY-377 | Et | H | H | F | Br | Cl | Me | H | O | A |
| PY-378 | Et | F | H | F | Br | Cl | Me | H | O | A |
| PY-379 | EtO— | H | F | H | Cl | Cl | Me | H | O | A |
| PY-380 | EtO— | H | F | H | Br | Cl | Me | H | O | A |
| PY-381 | MeO— | H | F | H | Br | H | Me | H | O | A |
| PY-382 | MeO— | H | F | H | Br | Cl | Me | H | O | A |
| PY-383 | F2CHCH2— | F | H | F | Cl | Cl | Me | H | O | A |
| PY-384 | F2CHCH2— | F | H | F | Br | Cl | Me | H | O | A |
| PY-385 | BnO— | H | F | H | Br | Cl | Me | H | O | A |
| PY-386 | BnO— | H | F | H | Cl | Cl | Me | H | O | A |
| PY-387 | H2C=CHCH2— | H | F | H | Cl | Cl | Me | H | O | A |
| PY-388 | H2C=CHCH2— | H | F | H | Br | Cl | Me | H | O | A |
| PY-389 | HO— | H | F | H | Cl | Cl | Me | H | O | A |
| PY-390 | H2C=CHCH2O— | H | F | H | Cl | Cl | Me | H | O | A |
| PY-391 | HO— | H | F | H | Br | Cl | Me | H | O | A |
| PY-392 | HOCH2CH2— | H | F | H | Br | Cl | Me | H | O | A |
| PY-393 | FCH2O— | H | F | H | Cl | Cl | Me | H | O | A |
| PY-394 | HOCH2CH2— | H | F | H | Cl | Cl | Me | H | O | A |
| PY-395 | FCH2O— | H | F | H | Cl | Cl | Me | H | O | A |
| PY-396 | F2CHO— | H | F | H | Cl | Cl | Me | H | O | A |
| PY-397 | F2CHO— | H | F | H | Br | Cl | Me | H | O | A |
| PY-398 | HC≡CCH2O | H | F | H | Cl | Cl | Me | H | O | A |
| PY-399 | BnO— | H | Br | H | O | Cl | Me | H | O | A |
| PY-400 | HO— | H | Br | H | Cl | Cl | Me | H | O | A |
| PY-401 | F2CHO— | H | Br | H | Cl | Cl | Me | H | O | A |
| PY-402 | FCH2O— | H | Br | H | O | Cl | Me | H | O | A |
| PY-403 | F2CHCH2— | H | F | H | Cl | Cl | ClCH2— | H | O | A |
| PY-404 | F2CHCH2— | H | F | H | Cl | Cl | BrCH2 | H | O | A |
| PY-405 | HO— | H | Br | H | Br | Cl | Me | H | O | A |
| PY-406 | HO— | H | F | H | Br | Br | Me | H | O | A |
| PY-407 | F2CHO— | H | Br | H | Br | Cl | Me | H | O | A |
| PY-408 | F2CHO— | H | F | H | Br | Br | Me | H | O | A |
| PY-409 | FCH2O— | H | F | H | Br | Br | Me | H | O | A |
| PY-410 | BnO— | H | Br | H | Br | Cl | Me | H | O | A |
| PY-411 | HO— | H | Cl | H | Cl | Cl | Me | H | O | A |
| PY-412 | FCH2O— | H | F | H | Cl | Br | Me | H | O | A |
| PY-413 | HO— | H | Cl | H | Br | Cl | Me | H | O | A |
| PY-414 | FCH2O— | H | Cl | H | Cl | Cl | Me | H | O | A |
| PY-415 | F2CHO— | H | Cl | H | Cl | Cl | Me | H | O | A |
| PY-416 | F2CHO— | H | Cl | H | Br | Cl | Me | H | O | A |

TABLE 6

| Compound No. | R1 | R2 | R3 | R4 | R5 | R6 | R7 | R9 | X | Formula |
|---|---|---|---|---|---|---|---|---|---|---|
| IM-001 | Et | H | H | H | H | Cl | Cl | H | O | C |
| IM-002 | Et | H | H | H | Cl | Cl | Cl | Cl | O | C |
| IM-003 | Et | H | H | H | Cl | Cl | Cl | H | O | C |
| IM-004 | Et | H | H | H | Br | Cl | Cl | H | O | C |

TABLE 6-continued

| Compound No. | R1 | R2 | R3 | R4 | R5 | R6 | R7 | R9 | X | Formula |
|---|---|---|---|---|---|---|---|---|---|---|
| IM-005 | Et | H | F | H | Br | Cl | Cl | H | O | C |
| IM-006 | Et | H | F | H | Cl | Cl | Cl | Cl | O | C |
| IM-007 | Et | H | F | H | Cl | Cl | Cl | H | O | C |
| IM-008 | Et | H | MeO— | H | Cl | Me | Me | H | O | C |

TABLE 7

| Compound No. | $^1$H-NMR (CDCl$_3$) |
|---|---|
| PY-001 | $^1$H-NMR (CDCl$_3$) δ: 7.85 (1H, s), 7.71-7.69 (2H, m), 7.41-7.38 (2H, m), 7.35 (1H, d, J = 0.9 Hz), 7.10 (1H, d, J = 0.9 Hz), 3.89 (2H, q, J = 7.1 Hz), 1.17 (3H, t, J = 7.1 Hz). |
| PY-002 | $^1$H-NMR (CDCl$_3$) δ: 7.71-7.68 (2H, m), 7.41-7.39 (3H, m), 7.34-7.34 (1H, br m), 7.10 (1H, d, J = 0.6 Hz), 6.70 (1H, d, J = 9.8 Hz), 3.83 (2H, q, J = 7.0 Hz), 1.15 (3H, t, J = 7.0 Hz). |
| PY-003 | $^1$H-NMR (CDCl$_3$) δ: 7.72-7.70 (2H, m), 7.65 (1H, s), 7.40-7.38 (2H, m), 7.35 (1H, d, J = 0.9 Hz), 7.10 (1H, d, J = 0.9 Hz), 3.90 (2H, q, J = 7.0 Hz), 1.18 (3H, t, J = 7.0 Hz). |
| PY-004 | $^1$H-NMR (CDCl$_3$) δ: 7.88 (1H, s), 7.39 (1H, d, J = 0.6 Hz), 7.13 (2H, dd, J = 6.7, 2.1 Hz), 6.99 (1H, d, J = 0.6 Hz), 6.90 (2H, dd, J = 6.7, 2.1 Hz), 3.96 (2H, q, J = 7.0 Hz), 3.83 (3H, s), 1.16 (3H, t, J = 7.0 Hz). |
| PY-005 | $^1$H-NMR (CDCl$_3$) δ: 7.69 (1H, $), 7.39 (1H, d, J = 0.6 Hz), 7.13 (2H, dd, J = 6.7, 2.1 Hz), 6.99 (1H, d, J = 0.6 Hz), 6.90 (2H, dd, J = 6.7, 2.1 Hz), 3.96 (2H, q, J = 7.0 Hz), 3.84 (3H, s), 1.17 (3H, t, J = 7.0 Hz). |
| PY-006 | $^1$H-NMR (CDCl$_3$) δ: 7.87 (1H, s), 7.38 (1H, d, J = 0.6 Hz), 7.24-7.21 (2H, m), 7.12-7.09 (2H, m), 7.03 (1H, d, J = 0.6 Hz), 3.93 (2H, q, J = 7.0 Hz), 1.17 (3H, t, J = 7.0 Hz). |
| PY-007 | $^1$H-NMR (CDCl$_3$) δ: 7.67 (1H, s), 7.38 (1H, d, J = 0.7 Hz), 7.23-7.22 (2H, m), 7.12-7.09 (2H, m), 7.03 (1H, d, J = 0.7 Hz), 3.94 (2H, q, J = 7.0 Hz), 1.17 (3H, t, J = 7.0 Hz). |
| PY-008 | $^1$H-NMR (CDCl$_3$) δ: 7.77 (1H, s), 7.40 (1H, d, J = 0.6 Hz), 7.23-7.21 (2H, m), 7.14-7.12 (2H, m), 7.02 (1H, d, J = 0.6 Hz), 6.37-6.22 (1H, m), 4.19-4.13 (2H, m). |
| PY-009 | $^1$H-NMR (CDCl$_3$) δ: 7.90 (1H, s), 7.45-7.39 (3H, m), 7.37 (1H, s), 7.23-7.21 (2H, m), 6.98 (1H, s), 3.95 (2H, q, J = 7.0 Hz), 1.17 (3H, t, J = 7.0 Hz). |
| PY-010 | $^1$H-NMR (CDCl$_3$) δ: 7.71 (1H, s), 7.45-7.39 (3H, m), 7.37 (1H, s), 7.23-7.21 (2H, m), 6.98 (1H, s), 3.95 (2H, q, J = 7.1 Hz), 1.17 (3H, t, J = 7.1 Hz). |
| PY-011 | $^1$H-NMR (CDCl$_3$) δ: 7.53 (1H, s), 7.37-7.31 (3H, m), 7.25-7.23 (2H, m), 7.22 (1H, s), 3.94-3.92 (2H, br m), 1.84 (3H, s), 1.18 (3H, t, J = 7.1 Hz). |
| PY-012 | $^1$H-NMR (CDCl$_3$) δ: 7.53 (1H, s), 7.26-7.24 (3H, m), 7.05-7.02 (2H, m), 3.94-3.92 (2H, br m), 1.86 (3H, s), 1.17 (3H, t, J = 7.0 Hz). |
| PY-013 | 1H-NMR (DMSO-D$_6$) δ: 8.06 (1H, s), 7.46-7.43 (2H, m), 7.25 (4H, m), 3.75 (2H, q, J = 7.0 Hz), 1.84 (3H, s), 1.03 (3H, t, J = 7.0 Hz). |
| PY-014 | $^1$H-NMR (CDCl$_3$) δ: 7.72 (1H, s), 7.25-7.24 (3H, m), 7.04-7.02 (2H, m), 3.95-3.93 (2H, br m), 1.86 (3H, s), 1.17 (3H, t, J = 7.0 Hz). |
| PY-015 | $^1$H-NMR (CDCl$_3$) δ: 7.92 (1H, s), 7.45-7.35 (3H, m), 7.24-7.22 (3H, m), 6.72 (1H, s), 3.95 (2H, q, J = 7.0 Hz), 1.86 (3H, s), 1.16 (3H, t, J = 7.0 Hz). |
| PY-016 | 1H-NMR (CDCl3) 0: 7.73 (1H, s), 7.35-7.32 (3H, m), 7.26-7.25 (2H, m), 7.22 (1H, s), 3.94-3.93 (2H, br m), 1.84 (3H, s), 1.17 (3H, t, J = 7.1 Hz). |
| PY-017 | $^1$H-NMR (CDCl$_3$) δ: 7.66-7.64 (2H, br m), 7.54 (1H, s), 7.41-7.40 (2H, br m), 7.24 (1H, s), 3.90-3.89 (2H, br m), 1.86 (3H, s), 1.18 (3H, t, J = 7.0 Hz). |
| PY-018 | $^1$H-NMR (CDCl$_3$) δ: 7.51 (1H, s), 7.25 (1H, s), 7.17-7.16 (2H, br m), 6.84-6.83 (2H, br m), 3.95-3.94 (2H, br m), 3.80 (3H, s), 1.86 (3H, s), 1.17 (3H, t, J = 7.0 Hz). |
| PY-019 | $^1$H-NMR (CDCl$_3$) δ: 7.90 (1H, s), 7.26 (1H, s), 7.14 (2H, dt, J = 9.4, 2.4 Hz), 6.88 (2H, dt, J = 9.4, 2.4 Hz), 6.75 (1H, s), 3.96 (2H, q, J = 7.0 Hz), 3.82 (3H, s), 1.89 (3H, s), 1.16 (3H, t, J = 7.0 Hz). |
| PY-020 | $^1$H-NMR (CDCl$_3$) δ: 7.60 (1H, s), 7.26-7.23 (3H, m), 7.06-7.04 (2H, m), 6.29 (1H, tt, J = 56.9, 4.6 Hz), 4.17 (2H, td, J = 12.2, 4.6 Hz), 1.86 (3H, s). |
| PY-021 | $^1$H-NMR (CDCl$_3$) δ: 7.99 (1H, s), 7.26 (1H, s), 7.25-7.21 (2H, m), 7.12-7.07 (2H, m), 6.75 (1H, s), 6.37-6.23 (1H, m), 4.17 (2H, td, J = 12.3, 4.7 Hz), 1.90 (3H, s). |
| PY-022 | $^1$H-NMR (CDCl$_3$) δ: 7.80 (1H, s), 7.26-7.23 (3H, m), 7.07-7.03 (2H, m), 6.35-6.24 (1H, m), 4.17 (2H, td, J = 12.2, 4.9 Hz), 1.86 (3H, s). |
| PY-023 | $^1$H-NMR (CDCl$_3$) δ: 8.23-8.21 (2H, m), 7.55 (1H, s), 7.50-7.47 (2H, m), 7.24 (1H, $), 3.90 (2H, q, J = 7.0 Hz), 1.86 (3H, s), 1.19 (3H, t, J = 7.0 Hz). |
| PY-024 | $^1$H-NMR (CDCl$_3$) δ: 7.49 (1H, s), 7.26 (1H, s), 7.00-6.99 (2H, m), 6.59-6.57 (2H, m), 3.99 (2H, br m), 3.81 (2H, br s), 1.87 (3H, s), 1.17 (3H, t, J = 7.0 Hz). |
| PY-025 | $^1$H-NMR (CDCl$_3$) δ: 7.49 (1H, s), 7.27 (1H, s), 7.02-7.00 (2H, m), 6.50-6.48 (2H, m), 4.00-3.98 (1H, br m), 3.92-3.90 (1H, br m), 2.83 (3H, d, J = 4.9 Hz), 1.87 (3H, s), 1.18 (3H, t, J = 7.0 Hz). |
| PY-026 | $^1$H-NMR (CDCl$_3$) δ: 7.49 (1H, s), 7.27 (1H, s), 7.06-7.04 (2H, m), 6.59-6.56 (2H, m), 4.00-3.97 (2H, br m), 2.96 (6H, s), 1.87 (3H, s), 1.18 (3H, t, J = 7.1 Hz). |

TABLE 7-continued

| Compound No. | ¹H-NMR (CDCl₃) |
|---|---|
| PY-027 | ¹H-NMR (CDCl₃) δ: 7.99 (1H, s), 7.41 (1H, d, J = 0.6 Hz), 7.13-7.11 (2H, m), 6.98 (1H, d, J = 0.6 Hz), 6.93-6.91 (2H, m), 6.30 (1H, tt, J = 57.0, 4.7 Hz), 4.20 (2H, td, J = 12.3, 4.7 Hz), 3.84 (3H, s). |
| PY-028 | ¹H-NMR (CDCl₃) δ: 7.79 (1H, s), 7.42 (1H, d, J = 0.6 Hz), 7.13-7.11 (2H, m), 6.98 (1H, d, J = 0.6 Hz), 6.94-6.92 (2H, m), 6.30 (1H, tt, J = 57.0, 4.8 Hz), 4.20 (2H, td, J = 12.3, 4.8 Hz), 3.84 (s, 3H). |
| PY-029 | ¹H-NMR (CDCl₃) δ: 7.42 (1H, q, J = 1.2 Hz), 7.40 (1H, s), 7.12-7.10 (2H, m), 6.99 (1H, s), 6.91-6.89 (2H, m), 6.28 (1H, tt, J = 57.3, 4.7 Hz), 4.15 (2H, td, J = 12.5, 4.7 Hz), 3.83 (3H, s), 2.23 (3H, d, J = 1.2 Hz). |
| PY-030 | ¹H-NMR (CDCl₃) δ: 7.46 (1H, d, J = 9.8 Hz), 7.39-7.34 (3H, m), 7.25-7.22 (3H, m), 6.75 (1H, s), 6.66 (1H, d, J = 9.8 Hz), 3.89 (2H, q, J = 7.0 Hz), 1.86 (3H, s), 1.14 (3H, t, J = 7.0 Hz). |
| PY-031 | ¹H-NMR (CDCl₃) δ: 7.56 (1H, d, J = 9.8 Hz), 7.27 (1H, s), 7.14-7.12 (2H, m), 6.90-6.88 (2H, m), 6.75 (1H, s), 6.67 (1H, d, J = 9.8 Hz), 6.28 (1H, tt, J = 57.3, 4.6 Hz), 4.15 (2H, td, J = 12.5, 4.6 Hz), 3.83 (3H, s), 1.89 (3H, s). |
| PY-032 | ¹H-NMR (CDCl₃)) δ: 7.58 (1H, s), 7.27 (1H, s), 7.16-7.14 (2H, m), 6.86-6.84 (2H, m), 6.29 (1H, tt, J = 57.0, 4.7 Hz), 4.21 (2H, td, J = 12.3, 4.7 Hz), 3.81 (3H, s), 1.87 (3H, s). |
| PY-033 | ¹H-NMR (CDCl₃)) δ: 8.01 (1H, s), 7.28 (1H, s), 7.14-7.12 (2H, m), 6.91-6.89 (2H, m), 6.73 (1H, s), 6.31 (1H, tt, J = 57.2, 4.7 Hz), 4.20 (2H, td, J = 12.3, 4.7 Hz), 3.83 (3H, s), 1.89 (3H, s). |
| PY-034 | ¹H-NMR (CDCl₃) δ: 7.78 (1H, s), 7.27 (1H, s), 7.16-7.15 (2H, m), 6.86-6.84 (2H, m), 6.29 (1H, tt, J = 57.0, 4.6 Hz), 4.21 (2H, td, J = 12.3, 4.6 Hz), 3.81 (3H, s), 1.86 (3H, s). |
| PY-035 | ¹H-NMR (CDCl₃) δ: 7.51-7.49 (2H, m), 7.41 (1H, d, J = 9.5 Hz), 7.24 (1H, s), 7.13-7.12 (2H, m), 6.80 (1H, s), 6.66 (1H, d, J = 9.5 Hz), 3.87 (2H, q, J = 7.0 Hz), 1.91 (3H, s), 1.13 (3H, t, J = 7.0 Hz). |
| PY-036 | ¹H-NMR (CDCl₃) δ: 7.44 (1H, d, J = 9.8 Hz), 7.25 (1H, s), 7.16-7.13 (2H, m), 6.88-6.86 (2H, m), 6.76 (1H, s), 6.64 (1H, d, J = 9.8 Hz), 3.90 (2H, q, J = 7.0 Hz), 1.89 (3H, s), 1.13 (3H, t, J = 7.0 Hz). |
| PY-037 | ¹H-NMR (CDCl₃) δ: 7.71 (1H, s), 7.25 (1H, s), 7.17-7.15 (2H, m), 6.84-6.82 (2H, m), 3.95 (2H, br m), 1.86 (3H, s), 1.17 (3H, t, J = 7.0 Hz). |
| PY-038 | ¹H-NMR (CDCl₃) δ: 7.44 (1H, d, J = 9.8 Hz), 7.28 (1H, s), 7.11-7.09 (2H, m), 6.89-6.87 (2H, m), 6.74 (1H, s), 6.65 (1H, d, J = 9.8 Hz), 3.82 (3H, s), 3.33 (3H, s), 1.90 (3H, s). |
| PY-039 | ¹H-NMR (CDCl₃) δ: 7.54 (1H, s), 7.29 (1H, s), 7.13-7.10 (2H, m), 6.86-6.83 (2H, m), 3.80 (3H, s), 3.40 (3H, s), 1.87 (3H, s). |
| PY-040 | ¹H-NMR (CDCl₃) δ: 7.93 (1H, s), 7.29 (1H, s), 7.11-7.08 (2H, m), 6.91-6.88 (2H, m), 6.72 (1H, s), 3.82 (3H, s), 3.40 (3H, s), 1.90 (3H, s). |
| PY-041 | ¹H-NMR (CDCl₃) δ: 7.51 (1H, s), 7.26 (1H, s), 7.12-7.11 (2H, m), 6.78-6.76 (2H, m), 5.25 (1H, br s), 3.97-3.95 (2H, br m), 1.87 (3H, s), 1.17 (3H ,t, J = 7.0 Hz). |
| PY-042 | ¹H-NMR (CDCl₃) δ: 7.74 (1H, s), 7.29 (1H, s), 7.13-7.10 (2H, m), 6.85-6.83 (2H, m), 3.80 (3H, s), 3.41 (3H, s), 1.87 (3H, s). |
| PY-043 | ¹H-NMR (CDCl₃) δ: 7.51 (1H, s), 7.25 (1H, s), 7.15-7.13 (2H, m), 6.83-6.81 (2H, m), 4.01 (2H, q, J = 6.9 Hz), 3.96-3.94 (2H, br m), 1.86 (3H, s), 1.41 (3H, t, J = 6.9 Hz), 1.17 (3H, t, J = 7.0 Hz). |
| PY-044 | ¹H-NMR (CDCl₃) δ: 7.51 (1H, s), 7.24 (1H, s), 7.16-7.14 (2H, m), 6.87-6.85 (2H, m), 4.10-4.09 (2H, m), 3.96-3.94 (2H, br m), 3.76-3.74 (2H, m), 3.45 (3H, s), 1.86 (3H, s), 1.16 (3H, t, J = 7.0 Hz). |
| PY-045 | ¹H-NMR (CDCl₃) δ: 7.52 (1H, s), 7.25 (1H, s), 7.19-7.17 (2H, m), 6.92-6.91 (2H, m), 4.68 (2H, d, J = 2.4 Hz), 3.97-3.95 (2H, br m), 2.55 (1H, t, J = 2.4 Hz), 1.86 (3H, s), 1.18 (3H, t, J = 7.0 Hz). |
| PY-046 | ¹H-NMR (CDCl₃) δ: 7.51 (1H, s), 7.25 (1H, s), 7.21-7.19 (2H, m), 6.87-6.85 (2H, m), 6.09 (1H, tt, J = 55.0, 4.0 Hz), 4.17 (2H, td, J = 13.0, 4.0 Hz), 3.95-3.93 (2H, br m), 1.86 (3H, s), 1.17 (3H, t, J = 7.1 Hz). |
| PY-047 | ¹H-NMR (CDCl₃) δ: 7.52 (1H, s), 7.25 (1H, s), 7.23-7.29 (2H, m), 6.90-6.88 (2H, m), 4.34 (2H, q, J = 8.1 Hz), 3.96-3.94 (2H, br m), 1.86 (3H, s), 1.17 (3H, t, J = 7.1 Hz). |
| PY-048 | ¹H-NMR (CDCl₃) δ: 7.51 (1H, s), 7.25 (1H, s), 7.17-7.15 (2H, m), 6.98-6.96 (2H, m), 5.16 (2H, s), 3.98-3.95 (2H, br m), 3.47 (3H, s), 1.86 (3H, s), 1.18 (3H, t, J = 7.1 Hz). |
| PY-049 | ¹H-NMR (CDCl₃) δ: 7.53 (1H, s), 7.27-7.26 (2H, m), 7.24 (1H, s), 7.10-7.08 (2H, m), 3.97-3.95 (2H, br m), 2.29 (3H, s), 1.85 (3H, s), 1.19 (3H, t, J = 7.1 Hz). |
| PY-050 | ¹H-NMR (CDCl₃) δ: 7.54 (1H, s), 7.34-7.31 (2H, m), 7.28-7.26 (2H, m), 7.24 (1H, s), 3.96-3.94 (2H, br m), 3.17 (3H, s), 1.85 (3H, s), 1.19 (3H, t, J = 7.1 Hz). |
| PY-051 | ¹H-NMR (CDCl₃) δ: 7.54 (1H, s), 7.33 (1H, s), 7.15-7.13 (2H, br m), 6.84-6.82 (2H, br m), 5.83 (1H, s), 4.00-3.98 (2H, br m), 3.79 (3H, s), 1.96 (3H, s), 1.17 (3H, t, J = 7.0 Hz). |
| PY-052 | ¹H-NMR (CDCl₃) δ : 7.54 (1H, s), 7.16-7.14 (2H, br m), 6.84-6.82 (2H, br m), 5.61 (1H, s), 3.99-3.97 (2H, br m), 3.80 (3H, s), 2.12 (3H, s), 1.88 (3H, s), 1.14 (3H, t, J = 7.1 Hz). |
| PY-053 | ¹H-NMR (CDCl₃) δ: 7.44 (1H, d, J = 9.8 Hz), 7.29-7.28 (2H, m), 7.23 (1H, s), 7.21-7.20 (2H, m), 6.75 (1H, s), 6.67 (1H, d, J = 9.8 Hz), 3.89 (2H, q, J = 7.0 Hz), 1.88 (3H, s), 1.15 (3H, t, J = 7.0 Hz). |
| PY-054 | ¹H-NMR (CDCl₃) δ: 7.54 (1H, s), 7.31-7.29 (2H, br m), 7.24 (1H, s), 7.19-7.17 (2H, br m), 3.95-3.93 (2H, br m), 1.85 (3H, s), 1.19 (3H, t, J = 7.0 Hz). |

TABLE 7-continued

| Compound No. | ¹H-NMR (CDCl₃) |
|---|---|
| PY-055 | ¹H-NMR (CDCl₃) δ: 7.90 (1H, s), 7.29-7.27 (2H, m), 7.24 (1H, s), 7.22-7.21 (2H, m), 6.74 (1H, s), 3.95 (2H, q, J = 7.0 Hz), 1.88 (3H, s), 1.18 (3H, t, J = 7.0 Hz). |
| PY-056 | ¹H-NMR (CDCl₃) δ: 7.74 (1H, s), 7.31-7.29 (2H, br m), 7.24 (1H, s), 7.19-7.17 (2H, br m), 3.96-3.94 (2H, br m), 1.85 (3H, s), 1.19 (3H, t, J = 7.0 Hz). |
| PY-057 | ¹H-NMR (CDCl₃) δ: 7.53-7.45 (2H, m), 7.23 (1H, d, J = 9.5 Hz), 7.12 (2H, br s), 6.65 (1H, d, J = 9.5 Hz), 3.87 (2H, br s), 2.11 (3H, s), 1.94 (3H, s), 1.12 (3H, t, J = 7.0 Hz). |
| PY-058 | ¹H-NMR (CDCl₃) δ: 7.48-7.43 (2H, m), 7.19 (1H, q, J = 1.2 Hz), 7.16-7.08 (2H, m), 5.61 (1H, s), 3.91 (2H, br s), 2.21 (3H, d, J = 1.2 Hz), 2.12 (3H, s), 1.89 (3H, s), 1.11 (3H, t, J = 7.1 Hz). |
| PY-059 | ¹H-NMR (CDCl₃) δ: 7.45 (1H, d, J = 9.5 Hz), 7.24 (1H, s), 7.18-7.14 (2H, m), 7.13-7.09 (2H, m), 6.76 (1H, s), 6.64 (1H, d, J = 9.5 Hz), 3.89 (2H, q, J = 7.1 Hz), 2.36 (3H, s), 1.88 (3H, s), 1.13 (3H, t, J = 7.1 Hz). |
| PY-060 | ¹H-NMR (CDCl₃) δ: 7.53 (1H, s), 7.27-7.26 (3H, m), 7.09-7.07 (2H, br m), 6.54 (1H, t, J = 73.0 Hz), 3.94-3.91 (2H, br m), 1.86 (3H, s), 1.18 (3H, t, J = 7.0 Hz). |
| PY-061 | ¹H-NMR (CDCl₃) δ: 7.89 (1H, s), 7.25-7.24 (3H, m), 7.13-7.11 (2H, m), 6.76 (1H, s), 6.55 (1H, t, J = 73.0 Hz), 3.94 (2H, q, J = 7.0 Hz), 1.89 (3H, s), 1.17 (3H, t, J = 7.0 Hz). |
| PY-062 | ¹H-NMR (CDCl₃) δ: 7.72 (1H, s), 7.27-7.25 (3H, m), 7.09-7.07 (2H, br m), 6.54 (1H, t, J = 73.1 Hz), 3.95-3.93 (2H, br m), 1.86 (3H, s), 1.18 (3H, t, J = 7.0 Hz). |
| PY-063 | ¹H-NMR (CDCl₃) δ: 9.74 (1H, s), 7.83 (1H, s), 7.53 (1H, s), 7.15-7.12 (2H, br m), 6.84-6.81 (2H, br m), 4.02-3.98 (2H, br m), 3.80 (3H, s), 2.25 (3H, s), 1.18 (3H, t, J = 7.1 Hz). |
| PY-064 | ¹H-NMR (CDCl₃) δ: 7.50 (1H, s), 7.18 (1H, s), 7.15-7.12 (2H, br m), 6.84-6.81 (2H, br m), 3.99-3.96 (2H, br m), 3.80 (3H, s), 1.85 (3H, s), 1.82 (3H, s), 1.16 (3H, t, J = 7.0 Hz). |
| PY-065 | ¹H-NMR (CDCl₃) δ: 7.51 (1H, s), 7.24 (1H, s), 7.15-7.11 (4H, m), 3.99-3.87 (2H, m), 2.34 (3H, s), 1.86 (3H, s), 1.17 (3H, t, J = 7.0 Hz). |
| PY-066 | ¹H-NMR (CDCl₃) δ: 7.71 (1H, s), 7.24 (1H, s), 7.15-7.09 (4H, m), 3.99-3.88 (2H, m), 2.33 (3H, s), 1.85 (3H, s), 1.17 (3H, t, J = 7.0 Hz). |
| PY-067 | ¹H-NMR (CDCl₃) δ: 7.52 (1H, s), 7.24 (1H, s), 7.18-7.13 (4H, br, m), 4.08-3.80 (2H, m), 2.63 (2H, q, J = 7.6 Hz), 1.84 (3H, s), 1.21 (3H, t, J = 7.6 Hz), 1.18 (3H, t, J = 6.7 Hz). |
| PY-068 | ¹H-NMR (CDCl₃) δ: 7.53 (1H, s), 7.23 (1H, s), 7.17-7.08 (4H, m), 4.05-3.84 (2H, m), 2.56 (2H, t, J = 7.5 Hz), 1.83 (3H, s), 1.61 (2H, tq, J = 7.5, 7.3 Hz), 1.17 (3H, t, J = 7.0 Hz), 0.87 (3H, t, J = 7.3 Hz). |
| PY-069 | ¹H-NMR (CDCl₃) δ: 7.50 (1H, s), 7.24 (1H, s), 7.14-7.07 (2H, m), 7.04-6.96 (2H, m), 4.05-3.80 (2H, m), 1.89-1.82 (1H, m), 1.86 (3H, s), 1.17 (3H, t, J = 7.0 Hz), 1.04-0.95 (2H, m), 0.73-0.68 (2H, m). |
| PY-070 | ¹H-NMR (CDCl₃) δ: 7.52 (1H, s), 7.51-7.47 (2H, m), 7.26 (1H, s), 7.16-7.11 (2H, m), 3.99-3.84 (2H, m), 1.88 (3H, s), 1.17 (3H, t, J = 7.0 Hz). |
| PY-071 | ¹H-NMR (CDCl₃) δ: 7.72 (1H, s), 7.51-7.47 (2H, m), 7.26 (1H, s), 7.17-7.12 (2H, m), 3.99-3.84 (2H, m), 1.88 (3H, s), 1.17 (3H, t, J = 7.1 Hz). |
| PY-072 | ¹H-NMR (CDCl₃) δ: 7.91 (1H, s), 7.25 (1H, s), 7.20-7.15 (2H, m), 7.12-7.08 (2H, m), 6.76 (1H, s), 3.94 (2H, q, J = 7.0 Hz), 2.37 (3H, s), 1.88 (3H, s), 1.16 (3H, t, J = 7.0 Hz). |
| PY-073 | ¹H-NMR (CDCl₃) δ: 7.47 (1H, d, J = 9.5 Hz), 7.24 (1H, s), 7.20-7.16 (2H, m), 7.15-7.11 (2H, m), 6.72-6.70 (1H, m), 6.64 (1H, d, J = 9.5 Hz), 3.90 (2H, q, J = 7.0 Hz), 2.66 (2H, q, J = 7.6 Hz), 1.86 (3H, s), 1.23 (3H, t, J = 7.6 Hz), 1.14 (3H, t, J = 7.0 Hz). |
| PY-074 | ¹H-NMR (CDCl₃) δ: 7.19 (1H, q, J = 1.2 Hz), 7.11 (4H, br s), 5.59 (1H, s), 4.20-3.68 (2H, br m), 2.33 (3H, s), 2.21 (3H, d, J = 1.2 Hz), 2.12 (3H, s), 1.87 (3H, s), 1.11 (3H, t, J = 7.0 Hz). |
| PY-075 | ¹H-NMR (CDCl₃) δ: 7.55 (1H, s), 7.42 (1H, d, J = 1.5 Hz), 7.05-7.03 (2H, br m), 6.83-6.81 (2H, m), 6.51 (1H, d, J = 1.5 Hz), 4.00-3.98 (1H, br m), 3.90-3.88 (1H, br m), 3.79 (3H, s), 1.17 (3H, t, J = 7.0 Hz). |
| PY-076 | ¹H-NMR (CDCl₃) δ: 7.50 (1H, s), 7.26 (1H, s), 7.15-7.09 (2H, m), 6.83-6.77 (2H, m), 4.03-3.90 (2H, br m), 3.87-3.82 (4H, m), 3.21-3.16 (4H, m), 1.87 (3H, s), 1.18 (3H, t). |
| PY-077 | ¹H-NMR (CDCl₃) δ: 7.49 (1H, s), 7.26 (1H, s), 7.08-7.04 (2H, m), 6.83-6.77 (2H, m), 4.02-3.90 (2H, br m), 3.21-3.17 (4H, m), 1.87 (3H, s), 1.74-1.65 (6H, m), 1.18 (3H, t, J = 7.0 Hz). |
| PY-078 | ¹H-NMR (CDCl₃) δ: 7.75-7.34 (1H, br s), 7.51 (1H, s), 7.26 (1H, s), 7.25-7.18 (4H, m), 4.01-3.86 (2H, br m), 2.19 (3H, s), 1.85 (3H, s), 1.16 (3H, t, J = 7.0 Hz). |
| PY-079 | ¹H-NMR (CDCl₃) δ: 7.51 (1H, s), 7.25 (1H, d, J = 4.3 Hz), 7.13-7.11 (2H, br m), 6.86-6.84 (2H, br m), 4.00-3.98 (2H, br m), 3.81 (3H, s), 1.91 (3H, d, J = 1.2 Hz), 1.17 (3H, t, J = 7.0 Hz). |
| PY-080 | ¹H-NMR (CDCl₃) δ: 7.60 (1H, s), 7.35 (1H, s), 7.25-7.22 (1H, br m), 7.09-7.07 (1H, br m), 6.85-6.84 (2H, m), 6.53 (1H, s), 4.00-3.98 (2H, br m), 3.81 (3H, s), 1.18 (3H, t, J = 7.1 Hz). |
| PY-081 | ¹H-NMR (CDCl₃) δ: 7.47 (1H, d, J = 9.5 Hz), 7.26 (1H, s), 7.20-7.17 (2H, m), 7.08-7.06 (2H, m), 6.76 (1H, s), 6.68 (1H, d, J = 9.5 Hz), 3.32 (3H, s), 1.91 (3H, s). |

TABLE 7-continued

| Compound No. | ¹H-NMR (CDCl₃) |
|---|---|
| PY-082 | ¹H-NMR (CDCl₃) δ: 7.56 (1H, s), 7.28 (1H, s), 7.22-7.19 (2H, m), 7.07-7.02 (2H, m), 3.39 (3H, s), 1.87 (3H, s). |
| PY-083 | ¹H-NMR (CDCl₃) δ: 7.75 (1H, s), 7.28 (1H, s), 7.22-7.19 (2H, m), 7.06-7.03 (2H, m), 3.39 (3H, s), 1.87 (3H, s). |
| PY-084 | ¹H-NMR (CDCl₃) δ: 7.42 (1H, d, J = 9.8 Hz), 7.36-7.33 (2H, m), 7.24 (1H, s), 7.20-7.18 (2H, m), 6.80 (1H, s), 6.66 (1H, d, J = 9.8 Hz), 3.87 (2H, q, J = 7.1 Hz), 1.91 (3H, s), 1.13 (3H, t, J = 7.1 Hz). |
| PY-085 | ¹H-NMR (CDCl₃) δ: 7.52 (1H, s), 7.34-7.32 (2H, br m), 7.25 (1H, s), 7.21-7.20 (2H, br m), 3.93-3.92 (2H, br m), 1.87 (3H, s), 1.17 (3H, t, J = 7.1 Hz). |
| PY-086 | ¹H-NMR (CDCl₃) δ: 7.72 (1H, s), 7.34-7.31 (2H, br m), 7.25 (1H, s), 7.21-7.19 (2H, br m), 3.93-3.90 (2H, br m), 1.87 (3H, s), 1.17 (3H, t, J = 7.0 Hz). |
| PY-087 | ¹H-NMR (CDCl₃) δ: 7.53 (1H, d, J = 9.8 Hz), 7.38-7.36 (2H, m), 7.26 (1H, s), 7.18-7.16 (2H, m), 6.79 (1H, s), 6.69 (1H, d, J = 9.8 Hz), 6.27 (1H, tt, J = 57.1, 4.6 Hz), 4.11 (2H, td, J = 12.3, 4.6 Hz), 1.91 (3H, s). |
| PY-088 | ¹H-NMR (CDCl₃) δ: 7.79 (1H, s), 7.35-7.33 (2H, m), 7.27 (1H, s), 7.20-7.18 (2H, m), 6.29 (1H, tt, J = 56.9, 4.6 Hz), 4.16 (2H. td, J = 12.3, 4.6 Hz), 1.87 (3H, s). |
| PY-089 | ¹H-NMR (CDCl₃) δ: 7.59 (1H, s), 7.35-7.33 (2H, m), 7.27 (1H, s), 7.20-7.18 (2H, m), 6.29 (1H, tt, J = 56.9, 4.7 Hz), 4.16 (2H. td, J = 12.3, 4.7 Hz), 1.88 (3H, s). |
| PY-090 | ¹H-NMR (CDCl₃) δ: 7.57 (1H, s), 7.42 (1H, d, J = 1.2 Hz), 7.37-7.34 (1H, br m), 7.13-7.10 (1H, br m), 7.03-7.01 (2H, br m), 6.52 (1H, d, J = 1.2 Hz), 3.96-3.86 (2H, br m), 1.17 (3H, t, J = 7.0 Hz). |
| PY-091 | ¹H-NMR (CDCl₃) δ: 7.71 (1H, s), 7.26-7.25 (3H, m), 7.05-7.02 (2H, m), 3.94-3.92 (2H, br m), 1.87 (3H, s), 1.17 (3H, t, J = 7.0 Hz). |
| PY-092 | ¹H-NMR (CDCl₃) δ: 7.88 (1H, s), 7.25-7.23 (2H, m), 7.12-7.10 (2H, m), 6.70 (1H, s), 3.93 (2H, q, J = 7.0 Hz), 1.83 (3H, s), 1.16 (3H, t, J = 7.0 Hz). |
| PY-093 | ¹H-NMR (CDCl₃) δ: 7.58 (1H, s), 7.35-7.29 (2H, m), 7.23 (1H, s), 7.20-7.14 (2H, m), 4.06-3.94 (2H, br m), 3.26 (3H, s), 1.81 (3H, s), 1.76 (3H, br s), 1.22 (3H, t, J = 7.1 Hz). |
| PY-094 | ¹H-NMR (CDCl₃) δ: 7.52 (1H, s), 7.28 (1H, s), 6.88-6.81 (3H, m), 3.94 (2H, q, J = 7.0 Hz), 1.89 (3H, s), 1.22 (3H, t, J = 7.0 Hz). |
| PY-095 | ¹H-NMR (CDCl₃) δ: 7.52 (1H, s), 7.27 (1H, s), 7.19-7.10 (2H, m), 7.05-7.00 (1H, br m), 4.00-3.87 (2H, br m), 1.89 (3H, s), 1.19 (3H, t, J = 7.0 Hz). |
| PY-096 | ¹H-NMR (CDCl₃) δ: 7.87 (1H, s), 7.28 (1H, s), 6.91-6.79 (4H, m), 3.94 (2H, q, J = 7.0 Hz), 1.93 (3H, s), 1.20 (3H, t, J = 7.0 Hz). |
| PY-097 | ¹H-NMR (CDCl₃) δ: 7.86 (1H, s), 7.26 (1H, s), 7.22-7.15 (1H, m), 7.13-7.07 (1H, m), 7.03-6.98 (1H, m), 6.83 (1H, t, J = 0.8 Hz), 3.97-3.90 (2H, br m), 1.93 (3H, s), 1.18 (3H, t, J = 7.0 Hz). |
| PY-098 | ¹H-NMR (CDCl₃) δ: 7.41 (1H, d, J = 9.5 Hz), 7.26 (1H, s), 6.89-6.78 (4H, m), 6.68 (1H, d, J = 9.5 Hz), 3.88 (2H, q, J = 7.1 Hz), 1.94 (3H, s), 1.18 (3H, t, J = 7.1 Hz). |
| PY-099 | ¹H-NMR (CDCl₃) δ: 9.70 (1H, s), 7.89 (1H, s), 7.63 (1H, s), 7.26-7.23 (2H, m), 7.12-7.06 (2H, m), 6.30 (1H, tt, J = 56.9, 4.7 Hz), 4.18 (2H, t, J = 12.2, 4.7 Hz). |
| PY-100 | ¹H-NMR (CDCl₃) δ: 7.53 (1H, s), 7.36-7.30 (1H, m), 7.25 (1H, s), 7.11-6.97 (3H, m), 3.99-3.90 (2H, br m), 1.86 (3H, s), 1.19 (3H, t, J = 7.2 Hz). |
| PY-101 | ¹H-NMR (CDCl₃) δ: 7.63 (1H, s), 7.47 (1H, s), 7.26-7.22 (2H, m), 7.08-7.03 (2H, m), 6.30 (1H, tt, J = 56.9, 4.6 Hz), 4.23-4.13 (2H, m), 4.15 (2H, s), 3.15 (3H, s). |
| PY-102 | ¹H-NMR (CDCl₃) δ: 7.62 (1H, s), 7.50 (1H, s), 7.26-7.23 (2H, m), 7.09-7.03 (2H, m), 6.30 (1H, tt, J = 56.9, 4.7 Hz), 4.39 (2H, d, J = 5.8 Hz), 4.18 (2H, td, J = 12.1, 4.7 Hz), 1.41 (1H, t, J = 5.8 Hz). |
| PY-103 | ¹H-NMR (CDCl₃) δ: 7.63 (1H, s), 7.62 (1H, s), 7.26-7.21 (2H, m), 7.11-7.05 (2H, m), 6.46 (1H, t, J = 55.0 Hz), 6.29 (1H, tt, J = 56.6, 4.6 Hz), 4.18 (2H, td, J = 12.2, 4.6 Hz). |
| PY-104 | ¹H-NMR (CDCl₃) δ: 7.57 (1H, s), 7.38 (1H, d, J = 2.0 Hz), 7.26-7.25 (2H, m), 7.06-7.02 (2H, m), 6.04 (1H, d, J = 2.0 Hz), 3.95-3.93 (2H, br m), 1.18 (3H, t, J = 7.1 Hz). |
| PY-105 | ¹H-NMR (CDCl₃) δ: 7.55 (1H, s), 7.38 (1H, d, J = 2.0 Hz), 7.28-7.27 (2H, br m), 7.04-7.02 (2H, br m), 6.14 (1H, d, J = 2.0 Hz), 3.93-3.90 (2H, br m), 1.18 (3H, t, J = 7.0 Hz). |
| PY-106 | ¹H-NMR (CDCl₃) δ: 7.64 (1H, s), 7.40 (1H, d, J = 2.0 Hz), 7.26-7.23 (2H, m), 7.06-7.04 (2H, m), 6.29 (1H, tt, J = 56.8, 4.6 Hz), 6.05 (1H, d, J = 2.0 Hz), 4.18 (2H, td, J = 12.3, 4.6 Hz). |
| PY-107 | ¹H-NMR (CDCl₃) δ: 7.63 (1H, s), 7.40 (1H, d, J = 2.0 Hz), 7.27-7.26 (2H, br m), 7.06-7.04 (2H, br m), 6.37-6.23 (2H, m), 4.20-4.18 (2H, br m). |
| PY-108 | ¹H-NMR (CDCl₃) δ: 7.68 (1H, s), 7.24 (1H, d, J = 2.1 Hz), 7.23-7.21 (2H, m), 7.06-7.04 (2H, m), 6.30 (2H,tt, J = 56.9, 4.6 Hz), 5.24 (1H, d, J = 2.1 Hz), 4.17 (2H, td, J = 12.3, 4.6 Hz), 3.65 (3H, s). |
| PY-109 | ¹H-NMR (CDCl₃) δ: 8.01 (1H, s), 7.88 (1H, s), 7.82 (1H, s), 7.58 (2H, dd, J = 6.6, 2.0 Hz), 7.13 (2H, dd, J = 6.5, 1.8 Hz), 3.93 (2H, q, J = 7.0 Hz), 1.19 (3H, t, J = 7.0 Hz). |
| PY-110 | ¹H-NMR (CDCl₃) δ: 8.00 (1H, d, J = 0.7 Hz), 7.74 (1H, s), 7.71 (1H, d, J = 0.7 Hz), 7.48-7.41 (3H, m), 7.25-7.23 (2H, m), 3.96 (2H, q, J = 7.1 Hz), 1.19 (3H, t, J = 7.1 Hz). |

TABLE 7-continued

| Compound No. | ¹H-NMR (CDCl₃) |
|---|---|
| PY-111 | ¹H-NMR (CDCl₃) δ: 8.04 (1H, s), 7.54 (1H, s), 7.45-7.37 (3H, m), 7.24 (2H, dd, J = 8.1, 1.4 Hz), 3.97-3.92 (2H, m), 1.20 (3H, t, J = 7.0 Hz). |
| PY-112 | ¹H-NMR (CDCl₃) δ: 7.52 (1H, s), 7.38-7.32 (3H, m), 7.26-7.24 (2H, m), 7.11 (1H, s), 3.94-3.93 (2H, m), 1.17 (3H, t, J = 7.0 Hz). |
| PY-113 | ¹H-NMR (CDCl₃) δ: 7.57 (1H, s), 7.37-7.32 (4H, m), 7.27-7.25 (2H, m), 6.00 (1H, d, J = 1.8 Hz), 3.96-3.94 (2H, m), 1.18 (3H, t, J = 7.0 Hz). |
| PY-114 | ¹H-NMR (CDCl₃) δ: 7.36 (1H, d, J = 9.8 Hz), 7.26-7.23 (3H, m), 7.05-7.03 (2H, m), 6.70 (1H, d, J = 9.8 Hz), 6.27 (1H, tt, J = 57.0, 4.5 Hz), 4.12 (2H, td, J = 12.3, 4.5 Hz), 1.87 (3H, s). |
| PY-115 | ¹H-NMR (CDCl₃) δ: 8.02 (1H, s), 7.26 (1H, s), 7.24-7.23 (2H, m), 7.06-7.04 (2H, m), 6.29 (1H, tt, J = 57.0, 4.8 Hz), 4.17 (2H, td, J = 12.2, 4.8 Hz), 1.86 (3H, s). |
| PY-116 | ¹H-NMR (CDCl₃) δ: 8.00 (1H, d, J = 0.6 Hz), 7.93 (1H, s), 7.71 (1H, d, J = 0.6 Hz), 7.48-7.42 (3H, m), 7.24-7.23 (2H, m), 3.96 (2H, q, J = 7.0 Hz), 1.19 (3H, t, J = 7.0 Hz). |
| PY-117 | ¹H-NMR (CDCl₃) δ: 8.04 (1H, s), 7.74 (1H, s), 7.42-7.40 (3H, m), 7.25-7.23 (2H, m), 3.97-3.92 (2H, m), 1.20 (3H, t, J = 7.0 Hz). |
| PY-118 | ¹H-NMR (CDCl₃) δ: 7.73 (1H, s), 7.37-7.35 (3H, m), 7.27-7.25 (2H, m), 7.12 (1H, s), 3.95-3.94 (2H, m), 2.78 (2H, s), 1.18 (3H, t, J = 7.0 Hz). |
| PY-119 | ¹H-NMR (CDCl₃) δ: 7.77 (1H, s), 7.36-7.33 (4H, m), 7.27-7.24 (2H, m), 6.00 (1H, d, J = 2.0 Hz), 3.96-3.94 (2H, m), 1.18 (3H, t, J = 7.0 Hz). |
| PY-120 | ¹H-NMR (CDCl₃) δ: 8.06 (1H, s), 7.53 (1H, s), 7.40-7.37 (3H, m), 7.27-7.25 (2H, m), 4.02-3.87 (2H, m), 1.20 (3H, t, J = 7.0 Hz). |
| PY-121 | ¹H-NMR (CDCl₃) δ: 8.02 (1H, s), 7.73 (2H, d, J = 3.5 Hz), 7.18-7.09 (2H, m), 6.96-6.88 (2H, m), 3.97 (2H, q, J = 7.0 Hz), 3.83 (3H, s), 1.18 (3H, t, J = 7.0 Hz). |
| PY-122 | ¹H-NMR (CDCl₃) δ: 7.56 (1H, s), 7.39 (1H, d, J = 1.8 Hz), 7.17 (2H, d, J = 8.9 Hz), 6.84 (2H, d, J = 8.0 Hz), 6.03 (1H, d, J = 2.1 Hz), 4.09-3.84 (2H, br m), 3.80 (3H, s), 1.18 (3H, t, J = 7.0 Hz). |
| PY-123 | ¹H-NMR (CDCl₃) δ: 7.64 (1H, s), 7.28 (1H, s), 7.24-7.22 (2H, m), 7.06-7.03 (2H, m), 6.29 (1H, tt, J = 56.9, 4.6 Hz), 4.18 (2H, td, J = 12.2, 4.6 Hz), 2.26 (2H, q, J = 7.6 Hz), 1.02 (3H, t, J = 7.6 Hz). |
| PY-124 | ¹H-NMR (CDCl₃) δ: 7.61 (1H, s), 7.56 (1H, s), 7.24-7.23 (2H, m), 7.07-7.05 (2H, m), 6.37-6.21 (2H, m), 5.51 (1H, dd, J = 17.7, 1.2 Hz), 5.18 (1H, dd, J = 11.2, 1.2 Hz), 4.18 (2H, td, J = 12.3, 4.6 Hz). |
| PY-125 | ¹H-NMR (CDCl₃) δ: 7.60 (1H, s), 7.52 (1H, s), 7.25-7.22 (2H, m), 7.09-7.07 (2H, m), 6.29 (1H, tt, J = 56.9, 4.6 Hz), 4.17 (2H, td, J = 12.1, 4.6 Hz), 3.16 (1H, s). |
| PY-126 | ¹H-NMR (CDCl₃) δ: 7.50 (1H, d, J = 9.8 Hz), 7.26 (1H, s), 7.22-7.20 (2H, m), 7.09-7.07 (2H, m), 6.77 (1H, s), 6.72 (1H, d, J = 9.8 Hz), 4.63-4.60 (2H, br m), 1.90 (3H, s). |
| PY-127 | ¹H-NMR (CDCl₃) δ: 7.54 (1H, d, J = 9.8 Hz), 7.26 (1H, s), 7.23-7.22 (2H, m), 7.10-7.06 (2H, m), 6.77 (1H, s), 6.69 (1H, d, J = 9.8 Hz), 6.28 (1H, tt, J = 57.0, 4.7 Hz), 4.12 (2H, td, J = 12.5, 4.7 Hz), 1.90 (3H, s). |
| PY-128 | ¹H-NMR (CDCl₃) δ: 7.66 (1H, s), 7.56 (1H, d, J = 9.8 Hz), 7.47-7.42 (5H, m), 7.19 (1H, s), 6.76 (1H, d, J = 9.8 Hz), 6.30 (1H, tt, J = 57.0, 4.8 Hz), 4.08 (2H, td, J = 12.4, 4.8 Hz), 2.03 (3H, s). |
| PY-129 | ¹H-NMR (CDCl₃) δ: 7.61 (1H, s), 7.41-7.33 (3H, m), 7.24-7.23 (3H, m), 6.29 (1H, tt, J = 56.9, 4.6 Hz), 4.19 (2H, td, J = 12.3, 4.6 Hz), 1.84 (3H, s). |
| PY-130 | ¹H-NMR (CDCl₃) δ: 7.38-7.32 (4H, m), 7.24-7.23 (3H, m), 6.69 (1H, d, J = 9.8 Hz), 6.26 (1H, tt, J = 57.0, 4.6 Hz), 4.14 (2H, td, J = 12.8, 4.6 Hz), 1.84 (3H, s). |
| PY-131 | ¹H-NMR (CDCl₃) δ: 7.80 (1H, s), 7.38-7.35 (3H, m), 7.25-7.22 (3H, m), 6.29 (1H, tt, J = 56.9, 4.6 Hz), 4.19 (2H, td, J = 12.3, 4.6 Hz), 1.84 (3H, s). |
| PY-132 | ¹H-NMR (CDCl₃) δ: 8.01 (1H, d, J = 0.6 Hz), 7.71 (1H, d, J = 0.6 Hz), 7.57 (1H, d, J = 9.8 Hz), 7.48-7.43 (3H, m), 7.24-7.22 (2H, m), 6.76 (1H, d, J = 9.8 Hz), 6.27 (1H, tt, J = 57.0, 4.7 Hz), 4.14 (2H, td, J = 12.3, 4.7 Hz). |
| PY-133 | ¹H-NMR (CDCl₃) δ: 7.50 (1H, s), 7.35-7.34 (3H, m), 7.27-7.26 (2H, m), 7.11 (1H, s), 3.94-3.93 (2H, m), 2.81 (2H, s), 1.17 (3H, t, J = 7.0 Hz). |
| PY-134 | ¹H-NMR (CDCl₃) δ: 7.56 (1H, s), 7.36-7.31 (4H, m), 7.28-7.27 (2H, m), 6.11 (1H, d, J = 2.0 Hz), 3.97-3.92 (2H, m), 1.18 (3H, t, J = 7.1 Hz). |
| PY-135 | ¹H-NMR (CDCl₃) δ: 8.06 (1H, s), 7.72 (1H, s), 7.40-7.36 (3H, m), 7.27-7.25 (2H, m), 4.02-3.87 (2H, m), 1.20 (3H, t, J = 7.1 Hz). |
| PY-136 | ¹H-NMR (CDCl₃) δ: 8.02 (1H, d, J = 0.6 Hz), 7.83 (1H, s), 7.70 (1H, d, J = 0.6 Hz), 7.52-7.45 (3H, m), 7.24-7.22 (2H, m), 6.29 (1H, tt, J = 56.9, 4.8 Hz), 4.20 (2H, td, J = 12.2, 4.8 Hz). |
| PY-137 | ¹H-NMR (CDCl₃) δ: 7.70 (1H, s), 7.36-7.33 (3H, m), 7.28-7.25 (2H, m), 7.11 (1H, s), 3.95-3.92 (2H, m), 2.81 (2H, s), 1.17 (3H, t, J = 7.0 Hz). |
| PY-138 | ¹H-NMR (CDCl₃) δ: 7.76 (1H, s), 7.36-7.32 (4H, m), 7.28-7.27 (2H, m), 6.10 (1H, d, J = 1.8 Hz), 3.99-3.91 (2H, m), 1.18 (3H, t, J = 7.0 Hz). |
| PY-139 | ¹H-NMR (CDCl₃) δ: 7.54 (1H, s), 7.39 (1H, d, J = 2.2 Hz), 7.18 (2H, d, J = 9.0 Hz), 6.83 (2H, d, J = 9.0 Hz), 6.13 (1H, d, J = 2.0 Hz), 4.11-3.84 (2H, br m), 3.79 (3H, s), 1.18 (3H, t, J = 7.1 Hz). |
| PY-140 | ¹H-NMR (CDCl₃) δ: 8.01 (1H, s), 7.75 (1H, d, J = 0.6 Hz), 7.45 (1H, d, J = 9.5 Hz), 7.15 (2H, dd, J = 6.7, 2.1 Hz), 6.91 (2H, dd, J = 6.7, 2.1 Hz), 6.69 (1H, d, J = 9.5 Hz), 3.91 (2H, q, J = 7.0 Hz), 3.83 (3H, s), 1.16 (3H, t, J = 7.0 Hz). |

TABLE 7-continued

| Compound No. | ¹H-NMR (CDCl₃) |
|---|---|
| PY-141 | ¹H-NMR (CDCl₃) δ: 8.03 (1H, s), 7.65 (1H, s), 7.54 (2H, dd, J = 6.6, 2.0 Hz), 7.03 (2H, d, J = 8.3 Hz), 5.92 (1H, tt, J = 56.4, 4.3 Hz), 3.70 (2H, td, J = 13.4, 4.4 Hz), 2.94-2.91 (4H, m). |
| PY-142 | ¹H-NMR (CDCl₃) δ: 8.02 (1H, s), 7.91 (1H, s), 7.73 (1H, s), 7.14 (2H, d, J = 8.8 Hz), 6.92 (2H, d, J = 8.8 Hz), 3.97 (2H, q, J = 7.3 Hz), 3.83 (3H, s), 1.18 (3H, t, J = 7.0 Hz). |
| PY-143 | ¹H-NMR (CDCl₃) δ: 8.07 (1H, s), 7.72 (1H, s), 7.15 (2H, d, J = 8.8 Hz), 6.85 (2H, br s), 4.07-3.85 (2H, br m), 3.81 (3H, s), 1.19 (3H, t, J = 7.1 Hz). |
| PY-144 | ¹H-NMR (CDCl₃) δ: 8.09 (1H, s), 7.71 (1H, s), 7.16 (2H, d, J = 8.9 Hz), 6.85 (2H, s), 4.08-3.86 (2H, br m), 3.81 (3H, s), 1.19 (3H, t, J = 7.0 Hz). |
| PY-145 | ¹H-NMR (CDCl₃) δ: 7.70 (1H, s), 7.16 (2H, d, J = 8.9 Hz), 7.14 (1H, s), 6.84 (2H, d, J = 8.9 Hz), 4.03-3.90 (2H, br m), 3.80 (3H, s), 2.79 (2H, s), 1.17 (3H, t, J = 7.0 Hz). |
| PY-146 | ¹H-NMR (CDCl₃) δ: 7.75 (1H, s), 7.39 (1H, d, J = 1.8 Hz), 7.17 (2H, d, J = 9.2 Hz), 6.83 (2H, d, J = 10.0 Hz), 6.82 (3H, br s), 6.03 (1H, d, J = 1.8 Hz), 3.96 (3H, br s), 3.80 (2H, s), 1.17 (3H, t, J = 7.0 Hz). |
| PY-147 | ¹H-NMR (CDCl₃) δ: 7.68 (1H, s), 7.17 (2H, d, J = 9.0 Hz), 7.14 (1H, s), 6.83 (2H, d, J = 8.8 Hz), 3.95 (2H, br s), 3.80 (3H, s), 2.83 (2H, br s), 1.17 (4H, t, J = 7.0 Hz). |
| PY-148 | ¹H-NMR (CDCl₃) δ: 8.02 (1H, s), 7.82 (1H, d, J = 0.6 Hz), 7.60-7.58 (2H, m), 7.52 (1H, d, J = 9.8 Hz), 7.12 (2H, d, J = 8.3 Hz), 6.76 (1H, d, J = 9.8 Hz), 6.26 (1H, tt, J = 5.8, 56.9 Hz), 4.14-4.06 (2H, m). |
| PY-149 | ¹H-NMR (CDCl₃) δ: 7.74 (1H, s), 7.39 (1H, d, J = 1.8 Hz), 7.18 (2H, d, J = 8.9 Hz), 6.82 (2H, s), 6.13 (1H, d, J = 1.8 Hz), 4.10-3.84 (2H, br m), 3.79 (3H, s), 1.18 (3H, t, J = 7.0 Hz). |
| PY-150 | ¹H-NMR (CDCl₃) δ: 8.03 (1H, d, J = 0.6 Hz), 7.61 (1H, d, J = 0.6 Hz), 7.17-7.13 (2H, m), 7.11-7.09 (2H, m), 5.93 (1H, tt, J = 56.4, 4.4 Hz), 3.70 (2H, td, J = 13.3, 4.4 Hz), 2.97-2.89 (4H, m). |
| PY-151 | ¹H-NMR (CDCl₃) δ: 8.02 (1H, d, J = 0.5 Hz), 7.79 (1H, d, J = 0.5 Hz), 7.54 (1H, d, J = 9.8 Hz), 7.25-7.23 (2H, m), 7.17-7.12 (2H, m), 6.76 (1H, d, J = 9.8 Hz), 6.27 (1H, tt, J = 57.0, 4.7 Hz), 4.12 (2H, td, J = 12.3, 4.7 Hz). |
| PY-152 | ¹H-NMR (CDCl₃) δ: 8.03 (1H, d, J = 0.5 Hz), 7.79 (1H, s), 7.78 (1H, d, J = 0.5 Hz), 7.25-7.23 (2H, m), 7.19-7.14 (2H, m), 6.30 (1H, tt, J = 56.9, 4.6 Hz), 4.17 (2H, td, J = 12.1, 4.6 Hz). |
| PY-153 | ¹H-NMR (CDCl₃) δ: 7.78 (1H, s), 7.24-7.22 (2H, m), 7.14 (1H, d, J = 0.7 Hz), 7.12-7.10 (2H, m), 6.59 (1H, d, J = 0.7 Hz), 6.30 (1H, tt, J = 57.0, 4.6 Hz), 4.16 (2H, td, J = 12.3, 4.6 Hz), 2.78 (2H, br s). |
| PY-154 | ¹H-NMR (CDCl₃) δ: 7.83 (1H, s), 7.48 (1H, d, J = 1.8 Hz), 7.23-7.21 (2H, m), 7.11-7.07 (2H, m), 6.99 (1H, d, J = 2.4 Hz), 6.31 (1H, tt, J = 56.9, 4.8 Hz), 6.10 (1H, td, J = 2.4, 1.8 Hz), 4.18 (2H, td, J = 12.3, 4.8 Hz). |
| PY-155 | ¹H-NMR (CDCl₃) δ: 7.78 (1H, s), 7.26-7.25 (3H, m), 7.05-7.03 (2H, m), 6.29 (1H, tt, J = 56.9, 4.7 Hz), 4.18-4.16 (2H, br m), 1.87 (3H, s). |
| PY-156 | ¹H-NMR (CDCl₃) δ: 7.99 (1H, s), 7.25-7.22 (2H, m), 7.15-7.11 (2H, m), 6.68 (1H, d, J = 0.9 Hz), 6.29 (1H, tt, J = 57.0, 4.8 Hz), 4.15 (2H, td, J = 12.3, 4.8 Hz), 1.83 (3H, d, J = 0.9 Hz). |
| PY-157 | ¹H-NMR (CDCl₃) δ: 7.65 (1H, s), 7.41-7.33 (4H, m), 7.24-7.23 (2H, m), 6.29 (1H, tt, J = 56.9, 4.6 Hz), 6.02 (1H, d, J = 2.0 Hz), 4.20 (2H, td, J = 12.3, 4.6 Hz). |
| PY-158 | ¹H-NMR (CDCl₃) δ: 8.02 (2H, s), 8.02 (2H, d, J = 0.5 Hz), 7.70 (1H, d, J = 0.5 Hz), 7.52-7.44 (3H, m), 7.24-7.22 (2H, m), 6.30 (1H, tt, J = 56.9, 4.8 Hz), 4.20 (2H, td, J = 12.2, 4.8 Hz). |
| PY-159 | ¹H-NMR (CDCl₃) δ: 7.58 (1H, s), 7.40-7.34 (3H, m), 7.26-7.24 (2H, m), 7.12 (1H, s), 6.28 (1H, tt, J = 56.9, 4.7 Hz), 4.19 (2H, td, J = 12.2, 4.7 Hz), 2.82 (2H, s). |
| PY-160 | ¹H-NMR (CDCl₃) δ: 7.79 (1H, s), 7.41-7.34 (3H, m), 7.24-7.23 (2H, m), 7.13 (1H, s), 6.28 (1H, tt, J = 56.9, 4.6 Hz), 4.18 (2H, td, J = 12.2, 4.6 Hz), 2.78 (2H, s). |
| PY-161 | ¹H-NMR (CDCl₃) δ: 7.63 (1H, s), 7.40-7.34 (4H, m), 7.27-7.25 (4H, m), 6.29 (1H, tt, J = 57.0, 4.7 Hz), 6.12-6.12 (1H, m), 4.23-4.18 (2H, m). |
| PY-162 | 1H-NMR (CDCl3) δ: 8.03 (1H, d, J = 0.5 Hz), 7.53 (1H, d, J = 0.5 Hz), 7.40-7.35 (3H, m), 7.13-7.11 (2H, m), 2.94-2.85 (7H, m). |
| PY-163 | ¹H-NMR (CDCl₃) δ: 7.86 (1H, s), 7.42-7.35 (4H, m), 7.26-7.25 (2H, m), 6.30 (1H, tt, J = 56.9, 4.6 Hz), 6.03 (1H, d, J = 2.1 Hz), 4.21 (2H, td, J = 12.2, 4.6 Hz). |
| PY-164 | ¹H-NMR (CDCl₃) δ: 8.03 (1H, d, J = 0.5 Hz), 7.74 (1H, d, J = 0.7 Hz), 7.55 (1H, d, J = 9.8 Hz), 7.14 (2H, d, J = 8.8 Hz), 6.93 (2H, d, J = 8.8 Hz), 6.73 (1H, d, J = 9.8 Hz), 6.27 (1H, tt, J = 56.6, 4.6 Hz), 4.16 (2H, td, J = 12.3, 4.7 Hz), 3.83 (3H, s). |
| PY-165 | ¹H-NMR (CDCl₃) δ: 8.04 (1H, s), 7.81 (1H, s), 7.73 (1H, d, J = 0.6 Hz), 7.13 (2H, d, J = 8.6 Hz), 6.94 (2H, d, J = 8.9 Hz), 6.30 (1H, tt, J = 56.9, 4.6 Hz), 4.21 (2H, td, J = 12.2, 4.8 Hz), 3.84 (3H, s). |
| PY-166 | ¹H-NMR (CDCl₃) δ: 8.04 (1H, d, J = 0.6 Hz), 8.00 (1H; s), 7.73 (1H, d, J = 0.6 Hz), 7.13 (2H, d, J = 8.6 Hz), 6.94 (2H, d, J = 8.9 Hz), 6.30 (1H, tt, J = 57.2, 4.6 Hz), 4.21 (2H, td, J = 12.2, 4.6 Hz), 3.84 (3H, s). |

TABLE 7-continued

| Compound No. | $^1$H-NMR (CDCl$_3$) |
|---|---|
| PY-167 | $^1$H-NMR (CDCl$_3$)) δ: 8.09 (1H, s), 7.60 (1H, s), 7.20-7.08 (2H, br m), 6.95-6.81 (2H, br m), 6.29 (1H, tt, J = 57.2, 4.3 Hz), 4.28-4.15 (2H br m), 3.82 (3H, s). |
| PY-168 | $^1$H-NMR (CDCl$_3$) δ: 8.11 (1H, s), 7.58 (1H, s), 7.15 (2H, dd, J = 14.8, 8.4 Hz), 6.87 (2H, dd, J = 20.0, 8.4 Hz), 6.30 (1H, tt, J = 57.2, 4.6 Hz), 4.29-4.14 (2H, m), 3.81 (3H, d, J = 7.0 Hz). |
| PY-169 | $^1$H-NMR (CDCl$_3$) δ: 7.57 (1H, s), 7.16 (1H, s), 7.15 (2H, d, J = 8.8 Hz), 6.85 (2H, d, J = 8.8 Hz), 6.29 (1H, tt, J = 57.1, 4.9 Hz), 4.20 (2H, td, J = 12.3, 4.6 Hz), 3.81 (3H, s), 2.80 (2H, br s). |
| PY-170 | $^1$H-NMR (CDCl$_3$) δ: 8.09 (1H, s), 7.79 (1H, s), 7.14 (2H, br s), 6.88 (2H, br s), 6.29 (1H, tt, J = 56.9, 4.7 Hz), 4.30-4.13 (2H, br m), 3.82 (3H, s). |
| PY-171 | $^1$H-NMR (CDCl$_3$) δ: 7.63 (1H, s), 7.41 (1H, d, J = 2.0 Hz), 7.15 (2H, d, J = 8.8 Hz), 6.85 (2H, d, J = 8.3 Hz), 6.29 (1H, tt, J = 56.9, 4.7 Hz), 6.04 (1H, d, J = 2.0 Hz), 4.22 (2H, td, J = 12.5, 4.6 Hz), 3.80 (3H, s). |
| PY-172 | $^1$H-NMR (CDCl$_3$) δ: 7.56 (1H, s), 7.16 (2H, d, J = 8.8 Hz), 7.15 (1H, s), 6.85 (2H, d, J = 8.8 Hz), 6.29 (1H, tt, J = 57.0, 4.6 Hz), 4.21 (2H, td, J = 12.2, 4.4 Hz), 3.81 (3H, s), 2.84 (2H, s). |
| PY-173 | $^1$H-NMR (CDCl$_3$) δ: 7.77 (1H, s), 7.16 (1H, s), 7.15 (2H, d, J = 8.9 Hz), 6.85 (2H, d, J = 8.9 Hz), 6.29 (1H, tt, J = 57.0, 4.6 Hz), 4.20 (2H, td, J = 12.4, 4.7 Hz), 3.81 (3H, s), 2.80 (2H, br s). |
| PY-174 | $^1$H-NMR (CDCl$_3$) δ: 8.10 (1H, s), 7.78 (1H, s), 7.15 (2H, dd, J = 12.3, 8.9 Hz), 6.87 (2H, dd, J = 15.5, 8.7 Hz), 6.29 (1H, tt, J = 56.9, 4.6 Hz), 4.27-4.15 (2H, m), 3.82 (3H, s). |
| PY-175 | $^1$H-NMR (CDCl$_3$) δ: 7.61 (1H, s), 7.41 (1H, d, J = 2.0 Hz), 7.17 (2H, d, J = 8.3 Hz), 6.85 (2H, br s), 6.29 (1H, tt, J = 56.9, 4.6 Hz), 6.14 (1H, d, J = 2.0 Hz), 4.33-4.10 (2H, br m), 3.80 (3H, s). |
| PY-176 | $^1$H-NMR (CDCl$_3$) δ: 8.04 (1H, d, J = 0.6 Hz), 7.64 (1H, d, J = 0.6 Hz), 7.51 (2H, d, J = 8.6 Hz), 7.01 (2H, d, J = 8.6 Hz), 2.89-2.86 (2H, m), 2.85 (3H, s). |
| PY-177 | $^1$H-NMR (CDCl$_3$) δ: 7.76 (1H, s), 7.16 (3H, d, J = 8.8 Hz), 6.85 (2H, d, J = 8.8 Hz), 6.29 (1H, tt, J = 57.0, 4.7 Hz), 4.20 (2H, td, J = 12.5, 4.9 Hz), 3.81 (3H, s). |
| PY-178 | $^1$H-NMR (CDCl$_3$) δ: 7.63 (1H, s), 7.24-7.22 (2H, m), 7.07-7.05 (3H, m), 6.29 (1H, tt, J = 56.9, 4.6 Hz), 4.17 (2H, td, J = 12.3, 4.6 Hz), 3.74 (3H, s), 1.89 (3H, s). |
| PY-179 | $^1$H-NMR (CDCl$_3$) δ: 7.59 (1H, s), 7.33 (1H, s), 7.30-7.28 (2H, m), 7.04-7.02 (2H, m), 5.32 (2H, br s), 1.88 (3H, s). |
| PY-180 | $^1$H-NMR (CDCl$_3$) δ: 7.58 (1H, s), 7.35 (1H, s), 7.31-7.29 (2H, br m), 6.99-6.98 (2H, m), 6.19 (1H, q, J =5.9 Hz), 2.39 (3H, d, J = 5.9 Hz), 1.88 (3H, s). |
| PY-181 | $^1$H-NMR (CDCl$_3$) δ: 7.59 (1H, s), 7.30 (1H, s), 7.25-7.23 (2H, m), 7.03-7.01 (2H, m), 6.30 (1H, tt, J = 56.9, 4.7 Hz), 4.18 (2H, td, J = 1 4.7 Hz), 2.09 (3H, s), 1.96 (3H, s).2.3, |
| PY-182 | $^1$H-NMR (CDCl$_3$) δ: 7.61 (1H, br s), 7.32-7.30 (3H, m), 7.08-7.06 (2H, br m), 6.28 (1H, tt, J = 56.9, 4.7 Hz), 4.18-4.16 (2H, br m), 2.78 (3H, br s), 2.17 (3H, s). |
| PY-183 | $^1$H-NMR (CDCl$_3$) δ: 7.55 (1H, s), 7.4-7.39 (1H, m), 7.36 (1H, d, J = 0.5 Hz), 7.27-7.25 (1H, m), 7.10-7.08 (1H, m), 7.03-6.98 (1H, m), 6.25 (1H, tt, J = 56.6, 4.7 Hz), 4.29-4.18 (1H, m), 4.08-4.03 (1H, m), 2.94 (3H, s), 2.17 (3H, d, J = 0.5 Hz). |
| PY-184 | $^1$H-NMR (CDCl$_3$) δ: 7.83 (1H, s), 7.40 (1H, d, J = 2.0 Hz), 7.15 (2H, d, J = 8.5 Hz), 6.85 (2H, d, J = 8.3 Hz), 6.30 (1H, tt, J = 56.9, 4.6 Hz), 6.04 (1H, d, J = 2.0 Hz), 4.22 (2H, td, J = 12.5, 4.6 Hz), 3.80 (3H, s). |
| PY-185 | $^1$H-NMR (CDCl$_3$) δ: 8.03 (1H, s), 7.81 (1H, s), 7.58 (2H, dt, J = 8.7, 2.1 Hz), 7.46 (1H, d, J = 9.8 Hz), 7.10 (2H, dt, J = 8.9, 2.1 Hz), 6.73 (1H, d, J = 9.8 Hz), 3.32 (3H, s). |
| PY-186 | $^1$H-NMR (CDCl$_3$) δ: 7.81 (1H, s), 7.41 (1H, d, J = 2.0 Hz), 7.17 (2H, d, J = 8.1 Hz), 6.85 (2H, br s), 6.29 (1H, tt, J = 57.1, 4.6 Hz), 6.14 (1H, d, J = 2.0 Hz), 4.29-4.15 (2H, br m), 3.80 (3H, s). |
| PY-187 | $^1$H-NMR (CDCl$_3$) δ: 8.04 (1H, d, J = 0.6 Hz), 7.72 (1H, d, J = 0.6 Hz), 7.49 (1H, d, J = 9.5 Hz), 7.11 (2H, dt, J = 9.4, 2.6 Hz), 6.92 (2H, dt, J = 9.5, 2.8 Hz), 6.71 (1H, d, J = 9.5 Hz), 3.83 (3H, s), 3.34 (3H, s). |
| PY-188 | $^1$H-NMR (CDCl$_3$) δ: 8.05 (1H, d, J = 0.5 Hz), 7.75 (1H, s), 7.71 (1H, d, J = 0.5 Hz), 7.10 (2H, d, J = 8.8 Hz), 6.93 (2H, d, J = 8.8 Hz), 3.83 (3H, s), 3.42 (3H, s). |
| PY-189 | $^1$H-NMR (CDCl$_3$) δ: 8.11 (1H, s), 7.55 (1H, s), 7.10 (2H, br s), 6.87 (2H, br s), 3.81 (3H, s), 3.42 (3H, s). |
| PY-190 | $^1$H-NMR (CDCl$_3$) δ: 8.05 (1H, s), 7.94 (1H, s), 7.71 (1H, s), 7.10 (2H, d, J = 9.3 Hz), 6.93 (2H, d, J = 9.0 Hz), 3.83 (3H, s), 3.42 (3H, s). |
| PY-191 | $^1$H-NMR (DMSO-D$_6$) δ: 7.89 (1H, s), 7.21 (2H, d, J = 8.1 Hz), 6.92 (2H, d, J = 8.8 Hz), 4.01 (2H, br s), 3.75 (3H, s), 3.25 (3H, s). |
| PY-192 | $^1$H-NMR (CDCl$_3$) δ: 8.13 (1H, s), 7.53 (1H, s), 7.17-7.06 (2H, br m), 6.94-6.77 (2H, br m), 3.81 (3H, s), 3.42 (3H, s). |
| PY-193 | $^1$H-NMR (CDCl$_3$) δ: 7.58 (1H, s), 7.42 (1H, d, J = 1.8 Hz), 7.12 (2H, d, J = 8.9 Hz), 6.84 (2H, d, J = 8.3 Hz), 6.05 (1H, d, J = 1.8 Hz), 3.80 (3H, s), 3.42 (3H, s). |

TABLE 7-continued

| Compound No. | ¹H-NMR (CDCl₃) |
|---|---|
| PY-194 | ¹H-NMR (CDCl₃) δ: 8.11 (1H, s), 7.75 (1H, s), 7.10 (2H, br s), 6.87 (2H, br s), 3.81 (3H, s), 3.42 (3H, s). |
| PY-195 | ¹H-NMR (CDCl₃) δ: 7.51 (1H, s), 7.17 (1H, s), 7.13 (2H, d, J = 9.0 Hz), 6.84 (2H, d, J = 8.8 Hz), 3.80 (3H, s), 3.40 (3H, s), 2.84 (2H, br s). |
| PY-196 | ¹H-NMR (CDCl₃) δ: 8.02 (1H, d, J = 0.6 Hz), 7.70 (1H, d, J = 0.6 Hz), 7.51 (1H, d, J = 9.8 Hz), 7.45-7.43 (3H, m), 7.21-7.19 (2H, m), 6.73 (1H, d, J = 9.8 Hz), 3.34 (3H, s). |
| PY-197 | ¹H-NMR (CDCl₃) δ: 8.03 (1H, d, J = 0.6 Hz), 7.77 (1H, s), 7.69 (1H, d, J = 0.6 Hz), 7.48-7.43 (3H, m), 7.21-7.18 (2H, m), 3.41 (3H, s). |
| PY-198 | ¹H-NMR (CDCl₃) δ: 8.08 (1H, s), 7.57 (1H, s), 7.46-7.38 (3H, m), 7.21-7.19 (2H, m), 3.41 (3H, s). |
| PY-199 | ¹H-NMR (CDCl₃) δ: 7.83 (1H, s), 7.40-7.33 (4H, m), 7.27-7.25 (2H, m), 6.29 (1H, tt, J = 56.9, 4.7 Hz), 6.12-6.12 (1H, m), 4.20 (2H, t, J = 13.3 Hz). |
| PY-200 | ¹H-NMR (CDCl₃) δ: 8.09 (1H, s), 7.55 (1H, s), 7.45-7.37 (3H, m), 7.22-7.20 (2H, m), 3.41 (3H, s). |
| PY-201 | ¹H-NMR (CDCl₃) δ: 7.60 (1H, s), 7.39 (1H, d, J = 2.0 Hz), 7.37-7.33 (3H, m), 7.22-7.19 (2H, m), 6.03 (1H, d, J = 2.0 Hz), 3.41 (3H, s). |
| PY-202 | ¹H-NMR (CDCl₃) δ: 7.59 (1H, s), 7.40 (1H, d, J = 2.0 Hz), 7.37-7.34 (3H, m), 7.23-7.21 (2H, m), 6.13 (1H, d, J = 2.0 Hz), 3.41 (3H, s). |
| PY-203 | ¹H-NMR (CDCl₃) δ: 8.07 (1H, s), 7.77 (1H, s), 7.45-7.40 (3H, m), 7.21-7.19 (2H, m), 3.41 (3H, s). |
| PY-204 | ¹H-NMR (CDCl₃) δ: 8.09 (1H, s), 7.75 (1H, s), 7.44-7.37 (3H, m), 7.22-7.20 (2H, m), 3.41 (3H, s). |
| PY-205 | ¹H-NMR (CDCl₃) δ: 7.75 (1H, s), 7.38-7.33 (3H, m), 7.22-7.19 (2H, m), 7.14 (1H, s), 3.39 (3H, s), 2.78 (2H, br s). |
| PY-206 | ¹H-NMR (CDCl₃) δ: 7.73 (1H, s), 7.39-7.32 (3H, m), 7.23-7.20 (2H, m), 7.14 (1H, s), 3.39 (3H, s), 2.82 (2H, br s). |
| PY-207 | ¹H-NMR (CDCl₃) δ: 7.80 (1H, s), 7.39 (1H, d, J = 2.0 Hz), 7.38-7.32 (3H, m), 7.22-7.20 (2H, m), 6.02 (1H, d, J = 2.0 Hz), 3.41 (3H, s). |
| PY-208 | ¹H-NMR (CDCl₃) δ: 7.78 (1H, s), 7.40 (1H, d, J = 2.0 Hz), 7.37-7.31 (3H, m), 7.24-7.21 (2H, m), 6.13 (1H, d, J = 2.0 Hz), 3.41 (3H, s). |
| PY-209 | ¹H-NMR (CDCl₃) δ: 7.89 (1H, s), 7.61 (1H, s), 7.24-7.23 (1H, m), 7.19-7.16 (1H, m), 7.09-7.04 (2H, m), 6.27 (1H, tt, J = 56.9, 4.6 Hz), 4.28 (2H, q, J = 7.2 Hz), 4.21-4.09 (2H, m), 1.32 (3H, t, J = 7.2 Hz). |
| PY-210 | ¹H-NMR (CDCl₃) δ: 7.64 (1H, s), 7.46 (1H, s), 7.24-7.22 (2H, m), 7.06-7.03 (2H, m), 6.29 (1H, tt, J = 56.8, 4.6 Hz), 4.43-4.42 (1H, m), 4.18 (2H, td, J = 12.3, 4.6 Hz), 1.74-1.70 (1H, m), 1.60-1.58 (1H, br m), 0.70-0.68 (3H, br m). |
| PY-211 | ¹H-NMR (CDCl₃) δ: 7.65 (1H, s), 7.26-7.21 (3H, m), 7.05-7.03 (2H, m), 6.29 (1H, tt, J = 56.9, 4.6 Hz), 4.19 (2H, td, J = 12.3, 4.6 Hz), 2.22 (2H, t, J = 7.3 Hz), 1.41-1.38 (2H, m), 0.74 (3H, t, J = 7.4 Hz). |
| PY-212 | ¹H-NMR (CDCl₃) δ: 7.63 (1H, s), 7.60 (1H, s), 7.25-7.23 (2H, m), 7.07-7.05 (2H, m), 6.29 (1H, tt, J = 56.9, 4.7 Hz), 5.24 (1H, dd, J = 12.2, 4.7 Hz), 4.18 (2H, td, J = 12.2, 4.7 Hz), 2.58 (1H, d, J = 2.2 Hz), 2.02-1.99 (1H, br m). |
| PY-213 | ¹H-NMR (CDCl₃) δ: 7.63 (1H, s), 7.46 (1H, s), 7.24-7.22 (2H, m), 7.08-7.03 (2H, m), 6.29 (1H, tt, J = 56.9, 4.6 Hz), 4.18 (2H, td, J = 12.2, 4.6 Hz), 3.19 (2H, d, J = 2.8 Hz), 2.05 (1H, t, J = 2.8 Hz). |
| PY-214 | ¹H-NMR (CDCl₃) δ: 8.13 (1H, s), 7.73 (1H, s), 7.16-7.08 (2H, m), 6.93-6.81 (2H, m), 3.81 (3H, s), 3.42 (3H, s). |
| PY-215 | ¹H-NMR (CDCl₃) δ: 7.73 (1H, s), 7.18 (1H, s), 7.12 (2H, d, J = 9.2 Hz), 6.85 (2H, d, J = 8.6 Hz), 3.80 (3H, s), 3.40 (3H, s). |
| PY-216 | ¹H-NMR (CDCl₃) δ: 7.57 (1H, s), 7.43 (1H, d, J = 2.1 Hz), 7.13 (2H, d, J = 8.3 Hz), 6.83 (2H, br s), 6.15 (1H, d, J = 2.1 Hz), 3.79 (3H, s), 3.42 (3H, s). |
| PY-217 | ¹H-NMR (CDCl₃) δ: 7.71 (1H, s), 7.18 (1H, s), 7.13 (2H, d, J = 8.9 Hz), 6.85 (2H, d, J = 8.6 Hz), 3.80 (3H, s), 3.40 (3H, s), 2.84 (2H, br s). |
| PY-218 | ¹H-NMR (CDCl₃) δ: 7.78 (1H, s), 7.43 (1H, d, J = 1.8 Hz), 7.12 (2H, d, J = 8.9 Hz), 6.85 (2H, br s), 6.05 (1H, d, J = 1.8 Hz), 3.80 (3H, s), 3.42 (3H, s). |
| PY-219 | ¹H-NMR (CDCl₃) δ: 7.77 (1H, s), 7.43 (1H, d, J = 2.0 Hz), 7.13 (2H. d, J = 8.5 Hz), 6.84 (2H, br s), 6.15 (1H, d, J = 2.0 Hz), 3.79 (3H, s), 3.42 (3H, s). |
| PY-220 | ¹H-NMR (CDCl₃) δ: 7.34-7.32 (1H, m), 7.29 (1H, s), 7.07-7.05 (1H, m), 6.94-6.92 (1H, m), 6.88-6.85 (1H, m), 6.61 (1H, s), 5.91 (1H, tt, J = 56.5, 4.4 Hz), 3.71 (2H, td, J = 13.4, 4.4 Hz), 2.94-2.90 (2H, m), 2.86-2.82 (2H, m), 1.88 (3H, s). |
| PY-221 | ¹H-NMR (CDCl₃) δ: 7.55 (1H, d, J = 9.8 Hz), 7.38-7.36 (1H, m), 7.15-7.10 (1H, m), 7.04-7.02 (1H, m), 6.97-6.96 (1H, m), 6.78 (1H, s), 6.70 (1H, d, J = 9.8 Hz), 6.70 (1H, tt, J = 57.0, 4.7 Hz), 4.12 (2H, td, J = 12.5, 4.7 Hz), 1.89 (3H, s). |
| PY-222 | ¹H-NMR (CDCl₃) δ: 7.60 (1H, s), 7.35 (1H, td, J = 7.9, 5.6 Hz), 7.27 (1H, s), 7.11-7.09 (1H, m), 7.05-7.03 (1H, m), 7.00-6.98 (1H, m), 6.78 (1H, s), 6.29 (1H, tt, J = 56.9, 4.6 Hz), 4.22-4.14 (2H, m), 1.87 (3H, s). |

TABLE 7-continued

| Compound No. | ¹H-NMR (CDCl₃) |
| --- | --- |
| PY-223 | ¹H-NMR (CDCl₃) δ: 7.63 (1H, s), 7.48 (1H, s), 7.26-7.22 (2H, m), 7.07-7.04 (2H, m), 6.29 (1H, tt, J = 56.8, 4.8 Hz), 4.74-4.69 (1H, m), 4.18 (1H, td, J = 12.1, 4.8 Hz), 1.37 (3H, d, J = 6.1 Hz). |
| PY-224 | ¹H-NMR (CDCl₃) δ: 7.36-7.33 (2H, m), 7.25 (1H, s), 7.07-7.01 (3H, m), 6.70 (1H, d, J = 9.8 Hz), 6.26 (1H, tt, J = 57.0, 4.7 Hz), 4.12 (2H, td, J = 12.2, 4.7 Hz), 1.87 (3H, s). |
| PY-225 | ¹H-NMR (CDCl₃) δ: 7.85 (1H, s), 7.60 (1H, s), 7.26-7.22 (2H, m), 7.09-7.06 (2H, m), 6.29 (1H, tt, J = 56.9, 4.7 Hz), 4.19-4.15 (2H, m), 2.39 (3H, s). |
| PY-226 | ¹H-NMR (CDCl₃) δ: 7.67 (1H, s), 7.42 (1H, s), 7.24-7.22 (2H, m), 7.06-7.03 (2H, m), 6.29 (1H, tt, J = 56.8, 4.8 Hz), 4.19 (2H, td, J = 12.2, 4.8 Hz), 1.67 (1H, br s), 1.43 (6H, s). |
| PY-227 | ¹H-NMR (CDCl₃) δ: 7.67 (1H, s), 7.28 (1H, s), 7.23-7.21 (2H, m), 7.04-7.02 (2H, m), 6.29 (1H, tt, J = 56.9, 4.6 Hz), 4.19 (2H, td, J = 12.3, 4.6 Hz), 2.68-2.61 (1H, m), 1.05 (6H, d, J = 6.3 Hz). |
| PY-228 | ¹H-NMR (CDCl₃) δ: 7.62 (1H, d, J = 0.5 Hz), 7.25-7.22 (2H, m), 7.11 (1H, s), 7.06 (2H, t, J = 8.5 Hz), 3.97 (2H, q, J = 7.0 Hz), 2.47-2.43 (2H, m), 2.37-2.24 (4H, m), 1.16 (3H, t, J = 7.0 Hz). |
| PY-229 | ¹H-NMR (CDCl₃) δ: 7.80 (1H, s), 7.35 (1H, td, J = 8.1, 5.7 Hz), 7.27 (1H, s), 7.11-7.09 (1H, m), 7.05-7.04 (1H, m), 7.00-6.98 (1H, m), 6.29 (1H, tt, J = 56.9, 4.7 Hz), 4.19-4.16 (2H, m), 1.87 (3H, s). |
| PY-230 | ¹H-NMR (CDCl₃) δ: 7.84 (1H, s), 7.78 (1H, s), 7.54 (1H, s), 7.24-7.22 (2H, m), 7.14-7.09 (2H, m), 4.15-4.14 (4H, m), 1.29 (3H, t, J = 7.1 Hz). |
| PY-231 | ¹H-NMR (CDCl₃) δ: 7.89 (1H, d, J = 0.6 Hz), 7.41 (1H, d, J = 0.6 Hz), 7.19-7.17 (2H, br m), 7.09-7.07 (2H, br m), 5.91 (1H, ddt, J = 76.3, 38.8, 14.0 Hz), 4.68-4.67 (1H, m), 4.21 (2H, q, J = 7.2 Hz), 4.17-4.10 (1H, m), 3.60 (1H, dd, J = 17.4, 4.0 Hz), 3.40-3.36 (1H, m), 2.97 (1H, dd, J = 17.4, 3.7 Hz), 1.28 (3H, t, J = 7.2 Hz). |
| PY-232 | ¹H-NMR (CDCl₃) δ: 7.43 (1H, q, J = 1.2 Hz), 7.26 (1H, s), 7.22-7.20 (2H, m), 7.09-7.06 (2H, m), 6.75 (1H, s), 6.29 (1H, tt, J = 57.1, 4.6 Hz), 4.12 (2H, td, J = 12.5, 4.6 Hz), 2.23 (3H, d, J = 1.2 Hz), 1.89 (3H, s). |
| PY-233 | ¹H-NMR (CDCl₃) δ: 7.83 (1H, s), 7.43-7.39 (3H, m), 7.27 (1H, s), 7.23-7.21 (2H, m), 6.70 (1H, s), 6.30 (1H, tt, J = 57.0, 4.6 Hz), 4.19 (2H, td, J = 12.2, 4.6 Hz), 1.86 (3H, s). |
| PY-234 | ¹H-NMR (CDCl₃) δ: 7.25-7.21 (4H, m), 7.05-7.00 (2H, m), 6.28 (1H, tt, J = 57.1, 4.6 Hz), 4.12 (1H, td, J = 12.5, 4.6 Hz), 2.23 (3H, d, J = 1.2 Hz), 1.86 (3H, s). |
| PY-235 | ¹H-NMR (CDCl₃) δ: 7.79 (1H, s), 7.27 (1H, s), 7.23-7.21 (2H, m), 7.12-7.09 (2H, m), 6.75 (1H, s), 6.30 (1H, tt, J = 57.0, 4.6 Hz), 4.17 (2H, td, J = 12.2, 4.6 Hz), 1.90 (3H, s). |
| PY-236 | ¹H-NMR (CDCl₃) δ: 7.84 (1H, s), 7.48-7.42 (3H, m), 7.23-7.22 (2H, m), 6.62 (1H, q, J = 0.9 Hz), 6.29 (1H, tt, J = 57.0, 4.6 Hz), 4.17 (2H, td, J = 12.2, 4.6 Hz), 1.79 (3H, d, J = 0.9 Hz). |
| PY-237 | ¹H-NMR (CDCl₃) δ: 7.55 (1H, s), 7.31 (1H, d, J = 1.7 Hz), 7.27-7.20 (2H, m), 7.03 (2H, t, J = 8.7 Hz), 5.84 (1H, dd, J = 1.7, 0.7 Hz), 3.98-3.95 (2H, m), 1.99 (3H, s), 1.17 (3H, t, J = 7.0 Hz). |
| PY-238 | ¹H-NMR (CDCl₃) δ: 7.63 (1H, s), 7.33 (1H, d, J = 1.8 Hz), 7.24-7.21 (2H, m), 7.05 (2H, t, J = 8.6 Hz), 6.32 (1H, tt, J = 57.0, 4.7 Hz), 5.85-5.85 (1H, m), 4.20 (2H, td, J = 12.2, 4.7 Hz), 1.99 (3H, s). |
| PY-239 | ¹H-NMR (CDCl₃) δ: 7.65 (1H, s), 7.21-7.18 (2H, m), 7.05-7.01 (2H, m), 6.29 (1H, tt, J = 57.0, 4.6 Hz), 5.67 (1H, s), 4.19 (2H, td, J = 12.2, 4.6 Hz), 2.48 (2H, q, J = 7.5 Hz), 2.26-2.18 (2H, br m), 1.12 (3H, t, J = 7.5 Hz), 1.06 (3H, t, J = 7.5 Hz). |
| PY-240 | ¹H-NMR (CDCl₃) δ: 7.62 (1H, s), 7.24-7.21 (2H, m), 7.06-7.02 (2H, m), 6.29 (1H, tt, J = 57.0, 4.6 Hz), 5.65 (1H, s), 4.19 (2H, td, J = 12.3, 4.6 Hz), 2.21-2.17 (1H, m), 2.12 (3H, s), 1.04 (2H, t, J = 7.5 Hz). |
| PY-241 | ¹H-NMR (CDCl₃) δ: 7.63 (1H, s), 7.23 (2H, dd, J = 8.9, 5.2 Hz), 7.05 (2H, t, J = 8.9 Hz), 6.30 (1H, tt, J = 57.0, 4.6 Hz), 5.63 (1H, s), 4.19 (2H, td, J = 12.2, 4.6 Hz), 2.11 (3H, s), 1.91 (3H, d, J = 0.6 Hz). |
| PY-242 | ¹H-NMR (CDCl₃) δ: 7.62 (1H, s), 7.56-7.52 (1H, m), 7.26-7.22 (1H, m), 7.09-6.99 (2H, m), 6.29 (1H, tt, J = 57.0, 4.6 Hz), 5.73 (1H, s), 4.21-4.14 (2H, m), 2.11 (3H, s), 1.12 (9H, s). |
| PY-243 | ¹H-NMR (CDCl₃) δ: 7.65 (1H, s), 7.26-7.20 (2H, br m), 7.08-7.00 (2H, br m), 6.29 (1H, tt, J = 57.0, 4.6 Hz), 5.62 (1H, s), 5.62 (1H, s), 4.22-4.16 (2H, m), 2.51-2.41 (1H, m), 2.13 (3H, s), 1.04 (3H, br s), 0.91 (3H, br s). |
| PY-244 | ¹H-NMR (CDCl₃) δ: 7.62 (1H, s), 7.23-7.20 (2H, m), 7.18 (1H, s), 7.05 (2H, t, J = 8.7 Hz), 6.31 (1H, tt, J = 57.0, 4.6 Hz), 4.19 (2H, td, J = 12.2, 4.6 Hz), 2.33 (2H, t, J = 5.9 Hz), 2.21-2.18 (2H, m), 1.65-1.60 (2H, m), 1.57-1.53 (2H, m). |
| PY-245 | ¹H-NMR (CDCl₃) δ: 7.57 (1H, s), 7.46 (2H, d, J = 8.3 Hz), 7.38 (1H, d, J = 2.1 Hz), 7.23 (2H, d, J = 8.6 Hz), 6.03 (1H, d, J = 1.8 Hz), 3.93 (2H, br s), 3.16 (1H, s), 1.18 (3H, t, J = 7.0 Hz). |
| PY-246 | ¹H-NMR (CDCl₃) δ: 7.64-7.63 (2H, m), 7.26-7.25 (3H, m), 6.63 (1H, s), 5.91 (1H, tt, J = 56.4, 4.3 Hz), 3.68 (2H, td, J = 13.5, 4.3 Hz), 2.93-2.90 (2H, m), 2.88-2.84 (2H, m), 1.89 (3H, s). |

TABLE 7-continued

| Compound No. | ¹H-NMR (CDCl₃) |
|---|---|
| PY-247 | ¹H-NMR (CDCl₃) δ: 7.69-7.66 (2H, m), 7.51 (1H, d, J = 9.8 Hz), 7.39-7.37 (2H, m), 7.23 (1H, s), 6.82 (1H, s), 6.72 (1H, d, J = 9.8 Hz), 6.26 (1H, tt, J = 57.0, 4.6 Hz), 4.07 (2H, td, J = 12.5, 4.6 Hz), 1.91 (3H, s). |
| PY-248 | ¹H-NMR (CDCl₃) δ: 7.29 (1H, s), 7.16-7.13 (1H, m), 7.01-6.97 (1H, m), 6.90-6.89 (1H, m), 6.66 (1H, s), 5.92 (1H, tt, J = 56.4, 4.4 Hz), 3.70 (2H, td, J = 13.4, 4.4 Hz), 2.91-2.88 (2H, m), 2.85-2.82 (2H, m), 1.91 (3H, s). |
| PY-249 | ¹H-NMR (CDCl₃) δ: 7.67-7.65 (2H, m), 7.62 (1H, s), 7.40-7.38 (2H, m), 7.25 (1H, s), 6.28 (1H, tt, J = 56.7, 4.6 Hz), 4.13 (2H, td, J = 12.3, 4.6 Hz), 1.87 (3H, s). |
| PY-250 | ¹H-NMR (CDCl₃) δ: 7.51 (1H, d, J = 9.8 Hz), 7.27 (1H, s), 7.21-7.17 (1H, m), 7.12-7.07 (1H, m), 7.02-6.99 (1H, m), 6.83 (1H, s), 6.70 (1H, d, J = 9.8 Hz), 6.27 (1H, tt, J = 57.1, 4.6 Hz), 4.11 (2H, td, J = 12.5, 4.6 Hz), 1.93 (3H, s). |
| PY-251 | ¹H-NMR (CDCl₃) δ: 7.76 (1H, s), 7.28 (1H, s), 7.23-7.19 (1H, m), 7.12-7.07 (1H, m), 7.01-6.99 (1H, m), 6.82 (1H, s), 6.30 (1H, tt, J = 56.9, 4.6 Hz), 4.16 (2H, td, J = 12.3, 4.6 Hz), 1.93 (3H, s). |
| PY-252 | ¹H-NMR (CDCl₃) δ: 7.36 (1H, d, J = 9.8 Hz), 7.27 (1H, s), 7.19-7.10 (2H, m), 7.03 (1H, br m), 6.71 (1H, d, J = 9.8 Hz), 6.27 (1H, tt, J = 57.0, 4.7 Hz), 4.11 (2H, td, J = 12.3, 4.7 Hz), 1.89 (3H, s). |
| PY-253 | ¹H-NMR (CDCl₃) δ: 7.60 (1H, s), 7.29 (1H, s), 7.20-7.11 (2H, m) 7.03-7.01 (1H, br m), 6.29 (1H, tt, J = 56.9, 4.6 Hz), 4.19-4.14 (2H, m), 1.89 (3H, s). |
| PY-254 | ¹H-NMR (CDCl₃) δ: 7.80 (1H, s), 7.29 (1H, s), 7.20-7.10 (2H, m) 7.04-7.02 (1H, br m), 6.29 (1H, tt, J = 56.9, 4.6 Hz), 4.17 (2H, td, J = 12.1, 4.6 Hz), 1.89 (3H, s). |
| PY-255 | ¹H-NMR (CDCl₃) δ: 8.03 (1H, s), 7.49-7.41 (3H, m) 7.24-7.22 (2H, m), 6.62 (1H, d, J = 0.7 Hz), 6.29 (1H, tt, J = 57.0, 4.6 Hz), 4.17 (2H, td, J = 12.2, 4.6 Hz), 1.79 (3H, d, J = 0.7 Hz). |
| PY-256 | ¹H-NMR (CDCl₃) δ: 7.79 (1H, s), 7.40-7.33 (3H, m) 7.26-7.25 (3H, m), 6.29 (1H, tt, J = 56.9, 4.7 Hz), 4.20-4.18 (2H, br m), 1.85 (3H, s) |
| PY-257 | ¹H-NMR (CDCl₃) δ: 7.59 (1H, s), 7.26-7.25 (3H, m), 7.05-7.03 (2H, br m), 6.29 (1H, tt, J = 56.9, 4.6 Hz), 4.19-4.17 (2H, br m), 1.87 (3H, s). |
| PY-258 | ¹H-NMR (CDCl₃) δ: 7.69 (1H, s), 7.27-7.24 (2H, m), 7.07-7.03 (2H, m), 6.30 (1H, tt, J = 57.0, 4.7 Hz), 5.32 (1H, s), 4.20 (2H, td, J = 12.3, 4.7 Hz), 2.07 (3H, s), 1.37-1.31 (1H, m), 0.86 (2H, dd, J = 8.3, 1.8 Hz), 0.44-0.43 (2H, br m). |
| PY-259 | ¹H-NMR (CDCl₃) δ: 7.71 (1H, s), 7.25-7.22 (2H, m), 7.13 (1H, s), 7.10-7.06 (2H, m), 6.31 (1H, tt, J = 57.0, 4.6 Hz), 4.19 (2H, td, J = 12.2, 4.6 Hz), 2.46-2.44 (2H, m), 2.35-2.30 (2H, m), 2.25-2.23 (2H, m). |
| PY-260 | ¹H-NMR (CDCl₃) δ: 7.59 (1H, s), 7.29 (1H, s), 7.22-7.16 (1H, m), 7.12-7.08 (1H, m), 7.03-6.97 (2H, m), 6.29 (1H, tt, J = 57.0, 4.7 Hz), 4.21-4.08 (2H, m), 3.81 (3H, s), 2.11 (3H, s). |
| PY-261 | ¹H-NMR (CDCl₃) δ: 7.64 (1H, s), 7.43-7.43 (1H, m), 7.06-7.01 (2H, m), 6.53-6.53 (1H, m), 6.28 (1H, tt, J = 56.9, 4.7 Hz), 4.21-4.11 (2H, m). |
| PY-262 | ¹H-NMR (CDCl₃) δ: 7.60 (1H, d, J = 0.5 Hz), 7.35-7.30 (1H, m), 7.25 (1H, s), 7.15-7.11 (1H, m), 7.04 (2H, t, J = 8.2 Hz), 6.27 (1H, tt, J = 56.9, 4.7 Hz), 4.20-4.09 (2H, m), 2.05 (3H, q, J = 1.8 Hz). |
| PY-263 | ¹H-NMR (CDCl₃) δ: 7.78 (1H, s), 7.59 (1H, s), 7.21 (2H, br s), 7.06 (2H, br s), 6.31 (1H, tt, J = 57.1, 4.6 Hz), 4.23 (2H, q, J = 7.1 Hz), 4.19 (2H, td, J = 12.2, 4.9 Hz), 2.25 (3H, s), 1.31 (3H, t, J = 7.1 Hz). |
| PY-264 | ¹H-NMR (CDCl₃) δ: 7.60 (1H, s), 7.21 (2H, br s), 7.17 (1H, s), 7.03 (2H, t, J = 8.3 Hz), 6.30 (1H, tt, J = 56.9, 4.6 Hz), 4.18 (2H, td, J = 12.3, 4.7 Hz), 2.29 (2H, br s), 1.85 (3H, s), 0.98 (3H, t, J = 7.6 Hz). |
| PY-265 | ¹H-NMR (CDCl₃) δ: 7.63 (1H, s), 7.32-7.13 (2H, m), 7.23 (1H, s), 7.06-7.02 (2H, m), 6.49 (1H, t, J = 53.1 Hz), 6.28 (1H, tt, J = 56.9, 4.6 Hz), 4.16 (2H, td, J = 12.2, 4.6 Hz), 2.02 (3H, t, J = 1.7 Hz). |
| PY-266 | ¹H-NMR (CDCl₃) δ: 7.58 (1H, d, J = 0.9 Hz), 7.32-7.31 (1H, m), 7.27-7.24 (4H, m), 7.20-7.18 (1H, m), 7.07 (1H, td, J = 8.3, 2.5 Hz), 7.01 (1H, td, J = 8.3, 2.5 Hz), 6.27 (1H, tt, J = 56.9, 4.6 Hz), 4.17-4.10 (2H, m), 2.01-2.00 (3H, m). |
| PY-267 | ¹H-NMR (CDCl₃) δ: 7.79 (1H, s), 7.25-7.23 (2H, m), 7.15-7.12 (2H, m), 6.68 (1H, d, J = 0.9 Hz), 6.29 (1H, tt, J = 57.0, 4.6 Hz), 4.15 (2H, td, J = 12.2, 4.6 Hz), 1.83 (3H, d, J = 0.9 Hz). |
| PY-268 | ¹H-NMR (CDCl₃) δ: 7.54 (1H, s), 7.34-7.29 (1H, m), 7.19-7.15 (1H, m), 7.14 (1H, s), 7.08 (1H, td, J = 8.1, 2.7 Hz), 7.02 (1H, td, J = 8.8, 2.4 Hz), 6.30 (1H, tt, J = 57.1, 5.1 Hz), 4.18 (2H, tdd, J = 12.2, 4.6, 2.7 Hz), 2.71-2.59 (1H, m), 1.94 (3H, s), 1.14 (3H, d, J = 7.1 Hz), 0.98 (3H, d, J = 7.1 Hz). |
| PY-269 | ¹H-NMR (CDCl₃) δ: 8.16 (1H, s), 7.25-7.24 (3H, m), 7.08-7.06 (2H, m), 6.30 (1H, tt, J = 57.0, 4.6 Hz), 4.20 (2H, td, J = 12.4, 4.6 Hz), 2.75 (3H, s), 1.87 (3H, s). |
| PY-270 | ¹H-NMR (CDCl₃) δ: 7.37 (1H, s), 7.26-7.22 (3H, m), 7.05-7.03 (2H, m), 6.27 (1H, tt, J = 57.0, 4.7 Hz), 4.96-4.94 (1H, br m), 4.15 (2H, td, J = 12.5, 4.7 Hz), 3.96 (1H, br m), 1.87 (3H, s), 1.55 (3H, d, J = 6.4 Hz). |

TABLE 7-continued

| Compound No. | ¹H-NMR (CDCl₃) |
|---|---|
| PY-271 | ¹H-NMR (CDCl₃) δ: 7.25-7.22 (3H, m), 7.20 (1H, t, J = 1.2 Hz), 7.04-7.01 (2H, m), 6.28 (1H, tt, J = 57.1, 4.6 Hz), 4.13 (2H, td, J = 12.5, 4.6 Hz), 2.65 (2H, dq, J = 7.4, 1.2 Hz), 1.87 (3H, s), 1.24 (3H, d, J = 7.4 Hz). |
| PY-272 | ¹H-NMR (CDCl₃) δ: 7.46 (1H, s), 7.26-7.23 (3H, m), 7.05-7.02 (2H, m), 6.84 (1H, dd, J = 17.6, 11.4 Hz), 6.30 (1H, tt, J = 57.2, 4.6 Hz), 6.12 (1H, dd, J = 17.6, 1.2 Hz), 5.48 (1H, dd, J = 11.4, 1.2 Hz) 4.16 (2H, td, J = 12.5, 4.6 Hz), 1.87 (3H, s). |
| PY-273 | ¹H-NMR (CDCl₃)δ: 8.41 (1H, s), 7.30 (1H, s), 7.27-7.25 (2H, m), 7.11-7.10 (2H, m), 6.34 (1H, tt, J = 56.9, 4.6 Hz), 4.26 (2H, td, J = 12.1, 4.6 Hz), 1.88 (3H, s). |
| PY-274 | ¹H-NMR (CDCl₃) δ: 7.24 (1H, s), 7.22-7.20 (2H, m), 7.01-6.99 (2H, m), 6.52 (1H, s), 6.26 (1H, tt, J = 57.0, 4.7 Hz), 4.44 (2H, br s), 4.16 (2H, td, J = 12.5, 4.7 Hz), 1.85 (3H, s). |
| PY-275 | ¹H-NMR (CDCl₃) δ: 7.27 (1H, s), 7.24-7.22 (2H, m), 7.04-7.00 (2H, m), 6.63 (1H, s), 6.28 (1H, tt, J = 56.9, 4.6 Hz), 4.16 (2H, td, J = 12.5, 4.6 Hz), 3.88 (3H, s), 1.87 (3H, s). |
| PY-276 | ¹H-NMR (CDCl₃) δ: 7.59 (1H, s), 7.21 (2H, s), 7.18 (1H, s), 7.04 (2H, t, J = 8.7 Hz), 6.31 (1H, tt, J = 57.1, 4.6 Hz), 4.19 (3H, td, J = 12.3, 4.6 Hz), 1.88 (3H, s), 1.82 (3H, s). |
| PY-277 | ¹H-NMR (CDCl₃)) δ: 7.80 (1H, s), 7.22 (2H, br s), 7.17 (1H, s), 7.03 (2H, t, J = 8.5 Hz), 6.30 (1H, tt, J = 57.1, 4.6 Hz), 4.18 (2H, td, J = 12.3, 4.6 Hz), 2.29 (2H, q, J = 7.3 Hz), 1.85 (3H, s), 0.98 (3H, t, J = 7.3 Hz). |
| PY-278 | ¹H-NMR (CDCl₃) δ: 7.79 (1H, s), 7.25-7.17 (2H, br m), 7.18 (1H, s), 7.04 (2H, t, J = 8.7 Hz), 6.31 (1H, tt, J = 56.9, 4.6 Hz), 4.19 (3H, td, J = 12.3, 4.6 Hz), 1.88 (3H, s), 1.59 (3H, s). |
| PY-279 | ¹H-NMR (CDCl₃) δ: 7.74 (1H, s), 7.35-7.28 (1H, m), 7.19-7.15 (1H, m), 7.15 (1H, s), 7.08 (1H, td, J = 8.5, 2.4 Hz), 7.02 (1H, td, J = 8.5, 2.7 Hz), 6.31 (1H, tt, J = 56.9, 4.6 Hz), 4.18 (2H, tdd, J = 12.2, 4.4, 1.7 Hz), 2.71-2.59 (1H, m), 1.94 (3H, s), 1.14 (3H, d, J = 7.1 Hz), 0.98 (3H, d, J = 7.1 Hz). |
| PY-280 | ¹H-NMR (CDCl₃) δ: 7.80 (1H, d, J = 0.5 Hz), 7.35-7.30 (1H, m), 7.25 (1H, s), 7.16-7.11 (1H, m), 7.07-7.01 (2H, m), 6.27 (1H, tt, J = 56.9, 4.6 Hz), 4.14 (2H, ddd, J = 23.8, 12.0, 4.6 Hz), 2.05 (3H, q, J = 1.8 Hz). |
| PY-281 | ¹H-NMR (CDCl₃) δ: 7.98 (1H, s), 7.25-7.21 (2H, m), 7.15-7.09 (2H, m), 6.84 (1H, t, J = 1.0 Hz), 6.29 (1H, tt, J = 56.9, 4.6 Hz), 4.16 ( 2H, td, J = 12.2, 4.6 Hz), 1.97 (3H, t, J = 1.0 Hz). |
| PY-282 | ¹H-NMR (CDCl₃) δ: 7.83 (1H, s), 7.31-7.19 (2H, m), 7.23 (1H, s), 7.06-7.01 (2H, m), 6.49 (1H, t, J = 53.1 Hz), 6.28 (1H, tt, J = 56.9, 4.6 Hz), 4.15 (2H, td, J = 12.0, 4.6 Hz), 2.02 (3H, t, J = 1.7 Hz). |
| PY-283 | ¹H-NMR (CDCl₃) δ: 7.77 (1H, d, J = 0.9 Hz), 7.31 (1H, s), 7.28-7.24 (3H, m), 7.21-7.18 (1H, m), 7.07 (1H, td, J = 8.6, 2.8 Hz), 7.01 (1H, td, J = 8.6, 2.8 Hz), 6.27 (1H, tt, J = 56.9, 4.7 Hz), 4.13 (2H, td J = 12.2, 4.7 Hz), 2.00 (3H, s). |
| PY-284 | ¹H-NMR (CDCl₃) δ: 7.60 (1H, s), 7.29-7.27 (2H, m), 7.20-7.17 (1H, m), 7.05 (1H, td, J = 8.6, 2.7 Hz), 7.01 (1H, td, J = 8.6, 2.7 Hz), 6.26 (1H, tt, J = 56.9, 4.7 Hz), 5.85 (1H, td, J = 54.1, 2.8 Hz), 4.13 (2H, td, J = 12.3, 4.7 Hz), 2.00 (3H, s). |
| PY-285 | ¹H-NMR (CDCl₃) δ: 7.64 (1H, s), 7.34-7.32 (1H, m), 7.24 (1H, s), 7.19-7.15 (1H, m), 7.07-7.02 (2H, m), 6.27 (1H, tt, J = 56.9, 4.6 Hz), 4.22-4.08 (2H, m), 2.06 (3H, t, J = 1.7 Hz). |
| PY-286 | ¹H-NMR (CDCl₃) δ: 7.80 (1H, s), 7.30-7.27 (2H, m), 7.21-7.18 (1H, m), 7.08-6.99 (2H, m), 6.26 (1H, tt, J = 56.9, 4.6 Hz), 5.85 (1H, td, J = 54.1, 2.9 Hz), 4.13 (2H, td, J = 12.2, 4.6 Hz), 2.00 (3H, s). |
| PY-287 | ¹H-NMR (CDCl₃) δ: 7.84 (1H, s), 7.35-7.31 (1H, m), 7.23 (1H, s), 7.19-7.15 (1H, m), 7.07-7.00 (2H, m), 6.27 (1H, tt, J = 56.9, 4.7 Hz), 4.22-4.07 (2H, m), 2.06 (3H, t, J = 2.0 Hz). |
| PY-288 | ¹H-NMR (CDCl₃) δ: 7.59 (1H, s), 7.36-7.32 (1H, m), 7.20-7.16 (2H, m), 7.06-7.00 (2H, m), 6.27 (1H, tt, J = 56.9, 4.6 Hz), 4.23-4.06 (2H, m), 2.00 (3H, t, J = 1.7 Hz), 1.82 (3H, t, J = 18.7 Hz). |
| PY-289 | ¹H-NMR (CDCl₃) δ: 7.79 (1H, s), 7.36-7.32 (1H, m), 7.20-7.17 (2H, m), 7.06-7.00 (2H, m), 6.27 (1H, tt, J = 56.9, 4.6 Hz), 4.21-4.07 (2H, m), 2.00 (3H, t, J = 1.8 Hz), 1.82 (3H, t, J = 18.8 Hz). |
| PY-290 | ¹H-NMR (CDCl₃) δ: 7.60 (1H, s), 7.39-7.31 (3H, m), 7.25-7.18 (2H, m), 7.18 (1H, s), 6.30 (1H, tt, J = 56.6, 4.9 Hz), 4.21 (2H, td, J = 12.2, 4.6 Hz), 1.87 (3H, s), 1.79 (3H, s). |
| PY-291 | ¹H-NMR (CDCl₃) δ: 7.61 (1H, s), 7.41-7.28 (2H, br m), 7.28-7.14 (2H, br m), 7.17 (1H, s), 6.30 (1H, tt, J = 57.2, 4.6 Hz), 4.20 (2H, td, J = 12.2, 4.6 Hz), 2.29 (2H, q, J = 7.6 Hz), 1.83 (3H, s), 0.97 (3H, t, J = 7.6 Hz). |
| PY-292 | ¹H-NMR (CDCl₃) δ: 7.25 (1H, s), 7.23 (1H, q, J = 1.2 Hz), 7.15-7.14 (2H, m), 6.84-6.82 (2H, m), 6.28 (1H, tt, J = 57.2, 4.6 Hz), 4.16 (2H, td, J = 12.5, 4.6 Hz), 3.80 (3H, s), 2.22 (3H, d, J = 1.2 Hz), 1.86 (3H, s). |
| PY-293 | ¹H-NMR (CDCl₃) δ: 7.26 (1H, s), 7.23-7.21 (2H, m), 7.02-6.99 (2H, m), 6.50 (1H, s), 6.28 (1H, tt, J = 57.3, 4.6 Hz), 4.14 (2H, td, J = 12.5, 4.6 Hz), 2.95 (6H, s), 1.87 (3H, s). |

TABLE 7-continued

| Compound No. | ¹H-NMR (CDCl₃) |
|---|---|
| PY-294 | ¹H-NMR (CDCl₃) δ: 7.26 (1H, s), 7.22-7.21 (2H, m), 7.00-6.98 (2H, m), 6.23 (1H, tt, J = 57.5, 4.5 Hz), 6.14 (1H, s), 5.19-5.18 (1H, br m), 4.16 (2H, td, J = 12.3, 4.5 Hz), 2.87 (3H, d, J = 5.2 Hz), 1.87 (3H, s). |
| PY-295 | ¹H-NMR (CDCl₃) δ: 7.64 (1H, s), 7.35-7.31 (1H, m), 7.23 (1H, s), 7.19-7.15 (1H, m), 7.08-7.01 (2H, m), 6.27 (1H, tt, J = 56.9, 4.7 Hz), 4.20-4.10 (2H, m), 2.07-2.04 (3H, m). |
| PY-296 | ¹H-NMR (CDCl₃) δ: 7.84 (1H, s), 7.34-7.31 (1H, m), 7.23 (1H, s), 7.20-7.15 (1H, m), 7.07-7.00 (2H, m), 6.27 (1H, tt, J = 56.9, 4.6 Hz), 4.20-4.10 (2H, m), 2.06 (3H, t, J = 1.8 Hz). |
| PY-297 | ¹H-NMR (CDCl₃) δ: 7.58 (1H, d, J = 0.5 Hz), 7.25 (1H, s), 7.22 (1H, d, J = 7.8 Hz), 7.04 (1H, d, J = 7.6 Hz), 6.85-6.82 (2H, m), 6.26 (1H, tt, J = 57.0, 4.7 Hz), 4.23-4.13 (2H, m), 3.80 (3H, s), 2.05-2.04 (3H, m). |
| PY-298 | ¹H-NMR (CDCl₃) δ: 7.61 (1H, s), 7.24 (1H, s), 7.22-7.03 (2H, m), 6.86-6.83 (2H, m), 6.45 (1H, t, J = 53.2 Hz), 6.28 (1H, tt, J = 56.9, 4.7 Hz), 4.23-4.16 (2H, m), 3.80 (3H, s), 2.02 (3H, t, J = 1.7 Hz). |
| PY-299 | ¹H-NMR (CDCl₃) δ: 7.78 (1H, d, J = 0.6 Hz), 7.25 (1H, s), 7.22 (1H, d, J = 8.6 Hz), 7.05 (1H, d, J = 8.3 Hz), 6.86-6.82 (2H, m), 6.27 (1H, tt, J = 56.9, 4.6 Hz), 4.24-4.16 (2H, m), 3.80 (3H, s), 2.05-2.04 (3H, m). |
| PY-300 | ¹H-NMR (CDCl₃) δ: 7.81 (1H, s), 7.24 (1H, s), 7.22-7.04 (2H, m), 6.84 (2H, d, J = 8.9 Hz), 6.45 (1H, t, J = 53.2 Hz), 6.28 (1H, tt, J = 57.0, 4.7 Hz), 4.23-4.16 (2H, m), 3.80 (3H, s), 2.02 (3H, t, J = 1.7 Hz). |
| PY-301 | ¹H-NMR (CDCl₃) δ: 7.60 (1H, s), 7.39-7.30 (4H, m), 7.23 (1H, s), 7.15-7.11 (1H, m), 6.26 (1H, tt, J = 56.9, 4.6 Hz), 4.21-4.10 (3H, m), 2.03-2.02 (3H, m). |
| PY-302 | ¹H-NMR (CDCl₃) δ: 7.64 (1H, s), 7.41-7.32 (3H, m), 7.29-7.10 (2H, m), 7.21 (1H, s), 6.47 (1H, t, J = 53.2 Hz), 6.28 (1H, tt, J = 56.9, 4.6 Hz), 4.18 (2H, td, J = 12.3, 4.6 Hz), 2.00 (3H, t, J = 1.8 Hz). |
| PY-303 | ¹H-NMR (CDCl₃) δ: 7.56 (1H, s), 7.41 (1H, ddd, J = 8.8, 5.1, 2.2 Hz), 7.30-7.25 (1H, m), 7.17 (1H, td, J = 10.0, 5.0 Hz), 7.09 (1H, td, J = 8.4, 2.7 Hz), 7.01 (1H, td, J = 8.4, 2.7 Hz), 6.29 (1H, tt, J = 57.1, 4.9 Hz), 4.23-4.10 (1H, m), 2.02 (3H, s), 1.14 (9H, s). |
| PY-304 | ¹H-NMR (CDCl₃) δ: 7.63 (1H, s), 7.24 (3H, dd, J = 8.4, 5.8 Hz), 7.15 (1H, s), 7.05 (2H, t, J = 8.4 Hz), 6.32 (1H, tt, J = 56.9, 4.6 Hz), 4.21 (2H, td, J = 12.2, 4.6 Hz), 1.85 (3H, s), 1.18-1.11 (1H, m), 0.82-0.75 (2H, m), 0.55-0.48 (2H, m). |
| PY-305 | ¹H-NMR (CDCl₃) δ: 7.82 (1H, s), 7.24 (2H, dd, J = 8.8, 5.4 Hz), 7.15 (1H, s), 7.05 (2H, t, J = 8.8 Hz), 6.32 (1H, tt, J = 57.1, 4.8 Hz), 4.20 (2H, td, J = 12.3, 4.8 Hz), 1.84 (3H, s), 1.20-1.09 (1H, m), 0.82-0.75 (2H, m), 0.55-0.48 (2H, m). |
| PY-306 | ¹H-NMR (CDCl₃) δ: 7.52 (1H, s), 7.37-7.32 (1H, m), 7.23 (1H, s), 7.16-7.11 (1H, m), 7.03 (2H, t, J = 8.8 Hz), 4.02-3.93 (1H, m), 3.88-3.80 (1H, m), 2.05-2.04 (3H, m), 1.16 (3H, t, J = 7.1 Hz). |
| PY-307 | ¹H-NMR (CDCl₃) δ: 7.57 (1H, s), 7.37-7.33 (1H, m), 7.22 (1H, s), 7.19-7.15 (1H, m), 7.05-7.00 (2H, m), 4.02-3.95 (1H, m), 3.87-3.81 (1H, m), 2.05 (3H, t, J = 1.8 Hz), 1.16 (3H, t, J = 7.0 Hz). |
| PY-308 | ¹H-NMR (CDCl₃) δ: 7.50-7.48 (2H, m), 7.35 (1H, d, J = 9.8 Hz), 7.26 (1H, s), 7.14-7.12 (2H, m), 6.70 (1H, d, J = 9.8 Hz), 6.37-6.14 (1H, m), 4.13-4.09 (2H, m), 1.88 (3H, s). |
| PY-309 | ¹H-NMR (CDCl₃) δ: 7.56 (1H, s), 7.38-7.13 (2H, m), 7.21 (1H, s), 7.04-7.01 (2H, m), 6.48 (1H, t, J = 53.1 Hz), 4.02-3.82 (2H, m), 2.02 (3H, t, J = 1.7 Hz), 1.17 (3H, t, J = 7.0 Hz). |
| PY-310 | ¹H-NMR (CDCl₃) δ: 7.73-7.72 (1H, m), 7.36-7.31 (1H, m), 7.23 (1H, s), 7.15-7.12 (1H, m), 7.03 (2H, t, J = 8.4 Hz), 4.00-3.93 (1H, m), 3.88-3.81 (1H, m), 2.04 (3H, q, J = 1.8 Hz), 1.16 (3H, t, J = 7.1 Hz) |
| PY-311 | ¹H-NMR (CDCl₃) δ: 7.76 (1H, s), 7.39-7.12 (2H, m), 7.21 (1H, s), 7.04-7.00 (2H, m), 6.48 (1H, t, J = 53.1 Hz), 3.99-3.85 (2H, m), 2.02 (3H, t, J = 1.7 Hz), 1.16 (3H, t, J = 7.1 Hz). |
| PY-312 | ¹H-NMR (CDCl₃) δ: 7.51 (1H, d, J = 0.6 Hz), 7.28-7.18 (2H, br m), 7.17 (1H, s), 7.03 (2H, t, J = 8.6 Hz), 4.02-3.88 (2H, br m), 1.88 (3H, s), 1.82 (3H, s), 1.17 (3H, t, J = 6.7 Hz). |
| PY-313 | ¹H-NMR (CDCl₃) δ: 7.55 (1H, s), 7.28-7.20 (2H, br m), 7.13 (1H, s), 7.03 (2H, t, J = 8.6 Hz), 3.98 (2H, br s), 1.84 (2H, s), 1.20-1.12 (4H, m), 0.81-0.72 (2H, m), 0.57-0.49 (2H, m). |
| PY-314 | ¹H-NMR (CDCl₃) δ: 7.76 (1H, s), 7.44-7.38 (1H, m), 7.29 (1H, s), 7.17 (1H, s), 7.09 (1H, td, J = 8.5, 2.9 Hz), 7.01 (1H, td, J = 8.6, 2.8 Hz), 6.30 (1H, tt, J = 56.6, 4.6 Hz), 4.27-4.05 (2H, m), 2.02 (3H, s), 1.14 (9H, s). |
| PY-315 | 1H-NMR (CDCl3) δ: 7.64 (2H, dd, J = 7.3, 1.5 Hz), 7.55-7.50 (1H, m), 7.54-7.54 (1H, m), 7.31-7.25 (1H, m), 7.23 (1H, s), 4.01-3.88 (1H, m), 3.85-3.74 (1H, m), 2.06-2.04 (3H, m), 1.17 (3H, t, J = 7.0 Hz): |
| PY-316 | ¹H-NMR (CDCl₃) δ: 7.63 (2H, dd, J = 7.3, 1.5 Hz), 7.57 (1H, s), 7.47-7.35 (2H, m), 7.19 (1H, s), 6.52 (1H, t, J = 53.0 Hz), 3.93-3.82 (2H, m), 2.02 (3H, t, J = 1.5 Hz), 1.17 (3H, t, J = 7.1 Hz). |

TABLE 7-continued

| Compound No. | ¹H-NMR (CDCl₃) |
|---|---|
| PY-317 | ¹H-NMR (CDCl₃) δ: 7.60 (1H, s), 7.33 (1H, d, J = 6.1 Hz), 7.29 (1H, s), 7.18-7.10 (2H, m), 6.29 (1H, tt, J = 56.7, 4.9 Hz), 4.26-4.09 (2H, m), 1.89 (3H, s). |
| PY-318 | ¹H-NMR (CDCl₃) δ: 7.52 (1H, s), 7.39 (1H, t, J = 7.8 Hz), 7.28 (1H, s), 7.09 (1H, d, J = 8.1 Hz), 7.01 (1H, d, J = 8.1 Hz), 3.96-3.89 (2H, m), 1.89 (3H, s), 1.19 (3H, t, J = 7.0 Hz). |
| PY-319 | ¹H-NMR (CDCl₃) δ: 7.86 (1H, s), 7.42 (1H, t, J = 7.8 Hz), 7.26-7.26 (1H, m), 7.07 (1H, dd, J = 8.9, 1.8 Hz), 7.01-6.99 (1H, m), 6.85-6.85 (1H, m), 3.93 (2H, q, J = 7.0 Hz), 1.93 (3H, s), 1.18 (3H, t, J = 7.0 Hz). |
| PY-320 | ¹H-NMR (CDCl₃) δ: 7.72 (1H, s), 7.39 (1H, dd, J = 8.2, 7.4 Hz), 7.27 (1H, s), 7.11-7.08 (1H, m), 7.03-7.00 (1H, m), 3.92 (2H, q, J = 7.0 Hz), 1.89 (3H, s), 1.19 (3H, t, J = 7.0 Hz). |
| PY-321 | ¹H-NMR (CDCl₃) δ: 7.52 (1H, s), 7.34 (1H, d, J = 6.6 Hz), 7.27 (1H, s), 7.18-7.09 (2H, m), 3.98-3.87 (2H, br m), 1.88 (3H, s), 1.18 (3H, t, J = 7.0 Hz). |
| PY-322 | ¹H-NMR (CDCl₃) δ: 7.86 (1H, s), 7.33 (1H, dt, J = 6.7, 1.2 Hz), 7.26 (1H, s), 7.15 (2H, dd, J = 6.1, 1.5 Hz), 6.85 (1H, s), 3.93 (2H, dq, J = 21.9, 6.8 Hz), 1.93 (3H, s), 1.18 (3H, t, J = 7.0 Hz). |
| PY-323 | ¹H-NMR (CDCl₃) δ: 7.80 (1H, s), 7.33 (1H, d, J = 6.4 Hz), 7.29 (1H, s), 7.19-7.11 (2H, m), 6.29 (1H, tt, J = 56.9, 4.6 Hz), 4.27-4.04 (2H, m), 1.89 (3H, s). |
| PY-324 | ¹H-NMR (CDCl₃) δ: 7.27 (1H, s), 7.18-7.15 (2H, m), 6.99-6.96 (2H, m), 5.91 (1H, tt, J = 56.6, 4.3 Hz), 3.73-3.71 (2H, br m), 2.91-2.90 (2H, m), 2.72-2.70 (2H, br m), 1.87 (3H, s). |
| PY-325 | ¹H-NMR (CDCl₃) δ: 7.73 (1H, s), 7.35 (1H, d, J = 6.1 Hz), 7.27 (1H, s), 7.20-7.08 (2H, m), 4.01-3.84 (2H, br m), 1.89 (3H, s), 1.19 (3H, t, J = 7.1 Hz). |
| PY-326 | ¹H-NMR (CDCl₃) δ: 7.53 (1H, s), 7.50 (1H, dd, J = 6.3, 2.0 Hz), 7.27 (1H, s), 7.23-7.18 (1H, br m), 7.09 (1H, t, J = 8.2 Hz), 3.98-3.89 (2H, br m), 1.89 (3H, s), 1.19 (3H, t, J = 7.1 Hz). |
| PY-327 | ¹H-NMR (CDCl₃) δ: 7.73 (1H, s), 7.50 (1H, dd, J = 6.3, 2.2 Hz), 7.27 (1H, s), 7.23-7.18 (1H, br m), 7.09 (1H, t, J = 8.3 Hz), 3.99-3.89 (2H, br m), 1.88 (3H, s), 1.19 (3H, t, J = 7.0 Hz). |
| PY-328 | ¹H-NMR (CDCl₃) δ: 7.59 (1H, s), 7.27-7.26 (1H, m), 7.08-7.03 (2H, m), 6.97 (1H, t, J = 8.8 Hz), 6.29 (1H, tt, J = 56.9, 4.7 Hz), 4.22-4.14 (2H, m), 2.23 (3H, d, J = 1.7 Hz), 1.87 (3H, s). |
| PY-329 | ¹H-NMR (CDCl₃) δ: 7.99 (1H, s), 7.28 (1H, s), 7.06-7.02 (3H, m), 6.75 (1H, d, J = 0.9 Hz), 6.30 (1H, tt, J = 57.0, 4.7 Hz), 4.21-4.13 (2H, m), 2.25 (3H, d, J = 1.5 Hz), 1.90 (3H, s). |
| PY-330 | ¹H-NMR (CDCl₃) δ: 7.79 (1H, s), 7.27-7.25 (1H, m), 7.09-7.02 (2H, m), 6.97 (1H, t, J = 8.8 Hz), 6.29 (1H, tt, J = 57.0, 4.6 Hz), 4.18 (2H, td, J = 12.5, 4.6 Hz), 2.23 (3H, d, J = 1.5 Hz), 1.87 (3H, s). |
| PY-331 | ¹H-NMR (CDCl₃) δ: 7.52 (1H, s), 7.30 (1H, s), 6.95 (2H, t, J = 6.7 Hz), 3.93 (2H, q, J = 7.0 Hz), 1.92 (3H, s), 1.21 (3H, t, J = 7.0 Hz). |
| PY-332 | ¹H-NMR (CDCl₃) δ: 7.84 (1H, s), 7.28 (1H, s), 6.93 (2H, t, J = 6.7 Hz), 6.89 (1H, s), 3.93 (2H, q, J = 7.0 Hz), 1.96 (3H, s), 1.20 (3H, t, J = 7.0 Hz). |
| PY-333 | ¹H-NMR (CDCl₃) δ: 7.79 (1H, s), 7.47-7.45 (1H, m), 7.39-7.37 (1H, m), 7.26-7.25 (1H, m), 7.15-7.13 (1H, m), 6.74 (1H, d, J = 0.7 Hz), 6.28 (1H, tt, J = 56.9, 4.7 Hz), 4.21-4.10 (2H, m), 1.85 (3H, d, J = 0.7 Hz). |
| PY-334 | ¹H-NMR (CDCl₃) δ: 7.61 (1H, s), 7.38-7.36 (1H, m), 7.31-7.29 (1H, m), 7.27 (1H, s), 7.26-7.24 (1H, m), 7.16-7.14 (1H, m), 6.29 (1H, tt, J = 56.8, 4.6 Hz), 4.23-4.10 (2H, m), 1.87 (3H, s). |
| PY-335 | ¹H-NMR (CDCl₃) δ: 7.60 (1H, s), 7.48 (1H, dd, J = 6.3, 2.0 Hz), 7.29 (1H, s), 7.24-7.17 (1H, m), 7.11 (1H, t, J = 8.3 Hz), 6.29 (1H, tt, J = 56.8, 4.6 Hz), 4.29-4.07 (2H, m), 1.89 (3H, s). |
| PY-336 | ¹H-NMR (CDCl₃) δ: 7.80 (1H, s), 7.48 (1H, dd, J = 6.1, 2.1 Hz), 7.29 (1H, s), 7.23-7.18 (1H, m), 7.11 (1H, t, J = 8.3 Hz), 6.29 (1H, tt, J = 56.9, 5.2 Hz), 4.26-4.04 (2H, m), 1.89 (3H, s). |
| PY-337 | ¹H-NMR (CDCl₃) δ: 7.52 (1H, s), 7.43 (1H, d, J = 8.3 Hz), 7.38 (1H, d, J = 1.7 Hz), 7.28 (1H, s), 7.11 (1H, dd, J = 8.4, 2.1 Hz), 3.99-3.87 (2H, br m), 1.89 (3H, s), 1.20 (3H, t, J = 7.1 Hz). |
| PY-338 | ¹H-NMR (CDCl₃) δ: 7.72 (1H, s), 7.43 (1H, d, J = 8.3 Hz), 7.38 (1H, s), 7.28 (1H, s), 7.12 (1H, d, J = 8.3 Hz), 4.00-3.85 (2H, br m), 1.89 (3H, s), 1.19 (3H, t, J = 7.0 Hz). |
| PY-339 | ¹H-NMR (CDCl₃) δ: 7.53 (1H, s), 7.40 (1H, dd, J = 6.3, 2.2 Hz), 7.27 (1H, s), 7.26-7.19 (1H, m), 7.07 (1H, t, J = 8.7 Hz), 3.94 (2H, q, J = 7.0 Hz), 3.35 (1H, s), 1.88 (3H, s), 1.18 (3H, t, J = 7.0 Hz). |
| PY-340 | ¹H-NMR (CDCl₃) δ: 7.72 (1H, s), 7.30 (1H, s), 6.95 (2H, t, J = 7.0 Hz), 3.92 (2H, q, J = 7.0 Hz), 1.91 (3H, s), 1.21 (3H, t, J = 7.0 Hz). |
| PY-341 | ¹H-NMR (CDCl₃) δ: 7.59 (1H, s), 7.32 (1H, s), 6.95 (2H, t, J = 6.7 Hz), 6.29 (1H, tt, J = 56.8, 4.6 Hz), 4.16 (2H, td, J = 12.3, 4.6 Hz), 1.92 (3H, s). |
| PY-342 | ¹H-NMR (CDCl₃) δ: 7.94 (1H, s), 7.30 (1H, s), 6.93 (2H, t, J = 6.7 Hz), 6.88 (1H, t, J = 0.7 Hz), 6.29 (1H, tt, J = 56.9, 4.6 Hz), 4.15 (2H, td, J = 12.1, 4.6 Hz), 1.96 (3H, s). |

TABLE 7-continued

| Compound No. | ¹H-NMR (CDCl₃) |
|---|---|
| PY-343 | ¹H-NMR (CDCl₃) δ: 7:53 (1H, s), 7.35 (1H, dq, J = 8.2, 1.1 Hz), 7.30-7.28 (1H, m), 7.27-7.26 (2H, m), 7.16-7.14 (1H, m), 3.94-3.92 (2H, m), 1.87 (4H, s), 1.19 (3H, t, J = 7.1 Hz). |
| PY-344 | ¹H-NMR (CDCl₃) δ: 7.99 (1H, s), 7.43-7.41 (1H, m), 7.34 (1H, t, J = 7.6 Hz), 7.28 (1H, s), 7.23 (1H, t, J = 1.7 Hz), 7.13 (1H, d, J = 7.6 Hz), 6.78-6.78 (1H, m), 6.29 (1H, tt, J = 56.9, 4.7 Hz), 4.20-4.14 (2H, m), 1.90 (3H, s). |
| PY-345 | ¹H-NMR (CDCl₃) δ: 7.89 (1H, s), 7.40-7.38 (1H, m), 7.31 (1H, t, J = 7.8 Hz), 7.25-7.25 (2H, m), 7.14-7.12 (1H, m), 6.80-6.80 (1H, m), 3.95-3.92 (2H, m), 1.90 (3H, s), 1.18 (3H, t, J = 7.1 Hz). |
| PY-346 | ¹H-NMR (CDCl₃) δ: 7.73 (1H, s), 7.36-7.34 (1H, m), 7.29 (1H, d, J = 7.6 Hz), 7.27-7.26 (2H, m), 7.16-7.15 (1H, m), 3.93-3.92 (2H, m), 1.87 (3H, s), 1.19 (3H, t, J = 7.0 Hz). |
| PY-347 | ¹H-NMR (CDCl₃) δ: 7.79 (1H, s), 7.32 (1H, d, J = 0.5 Hz), 6.95 (2H, t, J = 7.0 Hz), 6.29 (1H, tt, J = 56.9, 4.6 Hz), 4.16 (2H, td, J = 1 2.2, 4.6 Hz), 1.92 (3H, d, J = 0.5 Hz). |
| PY-348 | ¹H-NMR (CDCl₃) δ: 7.61 (1H, s), 7.53 (1H, dt, J = 7.5, 1.6 Hz), 7.41-7.39 (1H, m), 7.27 (1H, s), 7.24-7.22 (1H, m), 7.21-7.19 (1H, m), 6.29 (1H, tt, J = 56.8, 4.6 Hz), 4.21-4.14 (2H, m), 1.87 (3H, s). |
| PY-349 | ¹H-NMR (CDCl₃) δ: 7.81 (1H, s), 7.54-7.52 (1H, m), 7.41-7.39 (1H, br m), 7.27-7.26 (1H, m), 7.23 (1H, d, J = 7.6 Hz), 7.21-7.19 (1H, m), 6.29 (1H, tt, J = 56.9, 4.6 Hz), 4.24-4.11 (2H, m), 1.87 (3H, s). |
| PY-350 | ¹H-NMR (CDCl₃) δ: 7.99 (1H, s), 7.58-7.56 (1H, m), 7.39 (1H, t, J = 1.7 Hz), 7.30-7.26 (2H, m), 7.18 (1H, d, J = 8.1 Hz), 6.78-6.78 (1H, m), 6.29 (1H, tt, J = 56.9, 4.7 Hz), 4.23-4.11 (2H, m), 1.91 (3H, s). |
| PY-351 | ¹H-NMR (CDCl₃) δ: 7.53 (1H, s), 7.52-7.50 (1H, m), 7.43 (1H, br s), 7.25 (1H, d, J = 6.8 Hz), 7.21-7.20 (2H, m), 3.95-3.93 (2H, m), 1.87 (3H, s), 1.19 (3H, t, J = 7.0 Hz). |
| PY-352 | ¹H-NMR (CDCl₃) δ: 7.60 (1H, s), 7.45 (1H, d, J = 8.3 Hz), 7.36 (1H, d, J = 1.8 Hz), 7.29 (1H, s), 7.11 (1H, dd, J = 8.3, 1.8 Hz), 6.28 (1H, tt, J = 56.9, 4.9 Hz), 4.25-4.08 (2H, m), 1.90 (3H, s). |
| PY-353 | ¹H-NMR (CDCl₃) δ: 7.73 (1H, s), 7.40 (1H, dd, J = 5.9, 2.1 Hz), 7.27 (1H, s), 7.26-7.20 (1H, m), 7.06 (1H, t, J = 8.7 Hz), 3.99-3.84 (2H, br m), 3.35 (1H, s), 1.88 (3H, s), 1.18 (3H, t, J = 7.1 Hz). |
| PY-354 | ¹H-NMR (CDCl₃) δ: 7.80 (1H, s), 7.45 (1H, d, J = 8.3 Hz), 7.36 (1H, d, J = 1.8 Hz), 7.29 (1H, s), 7.11 (1H, d, J = 6.1 Hz), 6.29 (1H, tt, J = 56.6, 4.3 Hz), 4.25-4.08 (2H, m), 1.90 (3H, s). |
| PY-355 | ¹H-NMR (CDCl₃) δ: 7.51 (1H, s), 7.25 (1H, d, J = 0.5 Hz), 7.09-7.04 (2H, m), 6.96 (1H, t, J = 8.9 Hz), 4.01-3.86 (2H, m), 2.23 (3H, d, J = 1.7 Hz), 1.87 (3H, s), 1.17 (3H, t, J = 7.1 Hz). |
| PY-356 | ¹H-NMR (CDCl₃) δ: 7.88 (1H, d, J = 2.8 Hz), 7.25 (1H, s), 7.06-6.98 (3H, m), 6.77 (1H, t, J = 0.8 Hz), 4.00-3.88 (2H, m), 2.25 (3H, d, J = 1.8 Hz), 1.90 (3H, s), 1.16 (3H, t, J = 7.0 Hz). |
| PY-357 | ¹H-NMR (CDCl₃) δ: 7.89 (1H, s), 7.54 (1H, dq, J = 8.0, 1.0 Hz), 7.41-7.41 (1H, m), 7.25-7.24 (2H, m), 7.19-7.18 (1H, m), 6.81-6.80 (1H, m), 3.98-3.90 (2H, m), 1.91-1.91 (3H, m), 1.18 (3H, t, J = 7.0 Hz). |
| PY-358 | ¹H-NMR (CDCl₃) δ: 7.73 (1H, s), 7.53-7.49 (1H, m), 7.43 (1H, br s), 7.25 (1H, d, J = 6.3 Hz), 7.22-7.20 (2H, m), 3.93-3.92 (2H, m), 1.87 (3H, s), 1.19 (3H, t, J = 7.0 Hz). |
| PY-359 | ¹H-NMR (CDCl₃) δ: 7.86 (1H, s), 7.48 (1H, s), 7.23-7.21 (2H, m), 7.07-7.04 (2H, m), 6.29 (1H, tt, J = 56.8, 4.6 Hz), 4.21-4.17 (4H, m). |
| PY-360 | ¹H-NMR (CDCl₃) δ: 7.87 (1H, s), 7.70 (1H, s), 7.22-7.19 (2H, m), 7.07-7.05 (2H, m), 6.35-6.24 (2H, m), 4.20 (2H, td, J = 12.3, 4.7 Hz). |
| PY-361 | ¹H-NMR (CDCl₃) δ: 7.71 (1H, s), 7.25 (1H, d, J = 0.5 Hz), 7.09-7.04 (2H, m), 6.96 (1H, t, J = 8.8 Hz), 4.02-3.85 (2H, m), 2.23 (3H, d, J = 1.5 Hz), 1.87 (3H, s), 1.17 (3H, t, J = 7.0 Hz). |
| PY-362 | ¹H-NMR (CDCl₃) δ: 7.53 (1H, s), 7.48 (1H, dt, J = 7.7, 1.4 Hz), 7.39 (1H, s), 7.32-7.29 (1H, m), 7.25-7.22 (2H, m), 3.94-3.92 (2H, m), 3.12 (1H, d, J = 3.9 Hz), 1.86 (3H, s), 1.18 (3H, t, J = 7.1 Hz). |
| PY-363 | ¹H-NMR (CDCl₃) δ: 7.73 (1H, s), 7.49-7.47 (1H, m), 7.40-7.38 (1H, br m), 7.30 (1H, t, J = 7.7 Hz), 7.25-7.22 (2H, m), 3.95-3.92 (2H, br m), 3.12 (1H, s), 1.85 (3H, s), 1.18 (3H, t, J = 7.0 Hz). |
| PY-364 | ¹H-NMR (CDCl₃) δ: 7.52 (1H, s), 7.26-7.19 (1H, m), 7.25 (2H, s), 7.03 (2H, t, J = 8.7 Hz), 3.81 (2H, br s), 1.86 (3H, s), 1.63-1.56 (2H, m), 0.74 (3H, t, J = 7.5 Hz). |
| PY-365 | ¹H-NMR (CDCl₃) δ: 7.57 (1H, s), 7.27 (1H, s), 7.26-7.20 (2H, br m), 7.05 (2H, t, J = 8.7 Hz), 4.66 (2H, br s), 1.87 (3H, s). |
| PY-366 | ¹H-NMR (CDCl₃) δ: 7.72 (1H, s), 7.25 (1H, s), 7.24 (2H, dd, J = 8.7, 5.4 Hz), 7.03 (2H, t, J = 8.7 Hz), 3.80 (2H, br s), 1.86 (3H, s), 1.67-1.52 (2H, m), 0.74 (3H, t, J = 7.4 Hz). |
| PY-367 | ¹H-NMR (CDCl₃) δ: 7.61 (1H, s), 7.27 (1H, s), 7.24 (2H, dd, J = 8.5, 5.4 Hz), 7.06 (2H, t, J = 8.7 Hz), 6.06 (1H, tt, J = 53.2, 4.9 Hz), 4.50 (2H, t, J = 12.6 Hz), 1.87 (3H, s). |
| PY-368 | ¹H-NMR (CDCl₃) δ: 7.59 (1H, s), 7.41 (1H, dd, J = 8.3, 7.3 Hz), 7.29 (1H, s), 7.08 (1H, dd, J = 9.0, 1.7 Hz), 7.01 (1H, d, J = 8.6 Hz), 6.29 (1H, tt, J = 56.7, 4.6 Hz), 4.16 (2H, tdd, J = 12.2, 4.6, 1.3 Hz), 1.90 (3H, d, J = 0.6 Hz). |

TABLE 7-continued

| Compound No. | $^1$H-NMR (CDCl$_3$) |
|---|---|
| PY-369 | $^1$H-NMR (CDCl$_3$) δ: 7.77 (1H, s), 7.27 (1H, s), 7.23 (2H, dd, J = 8.7, 5.6 Hz), 7.05 (2H, t, J = 8.7 Hz), 4.67 (2H, br s), 1.87 (3H, s). |
| PY-370 | $^1$H-NMR (CDCl$_3$) δ: 7.81 (1H, s), 7.27 (1H, s), 7.25 (2H, dd, J = 8.7, 5.1 Hz), 7.05 (2H, t, J = 8.7 Hz), 6.07 (1H, tt, J = 53.0, 4.9 Hz), 4.50 (2H, t, J = 12.3 Hz), 1.87 (3H, s). |
| PY-371 | $^1$H-NMR (CDCl$_3$) δ: 7.79 (1H, s), 7.41 (1H, dd, J = 8.2, 7.4 Hz), 7.29 (1H, s), 7.08 (1H, dd, J = 8.9, 1.8 Hz), 7.01 (1H, d, J = 8.2 Hz), 6.29 (1H, tt, J = 56.8, 4.6 Hz), 4.16 (2H, td, J = 12.3, 4.6 Hz), 1.89 (3H, s). |
| PY-372 | $^1$H-NMR (CDCl$_3$) δ: 7.59 (1H, s), 7.26-7.23 (2H, m), 7.25 (1H, s), 7.02 (2H, t, J = 8.6 Hz), 4.69 (2H, dt, J = 47.4, 4.9 Hz), 4.19 (2H, dt, J = 24.2, 4.3 Hz), 1.86 (3H, s). |
| PY-373 | $^1$H-NMR (CDCl$_3$) δ: 7.78 (1H, s), 7.25 (1H, br s), 7.25 (2H, t, J = 6.4 Hz), 7.02 (2H, t, J = 8.7 Hz), 4.68 (2H, dt, J = 47.1, 5.5 Hz), 4.19 (2H, dt, J = 24.2, 4.6 Hz), 1.86 (3H, s). |
| PY-374 | $^1$H-NMR (CDCl$_3$) δ: 7.52 (1H, d, J = 9.8 Hz), 7.35 (1H, s), 7.30 (2H, dd, J = 8.6, 5.2 Hz), 7.05 (2H, t, J = 8.6 Hz), 6.76 (1H, d, J = 9.8 Hz), 6.71 (1H, s), 3.67 (3H, s), 1.92 (3H, s). |
| PY-375 | $^1$H-NMR (CDCl$_3$) δ: 7.77 (1H, s), 7.37 (1H, s), 7.29 (2H, dd, J = 8.9, 5.2 Hz), 7.07 (2H, t, J = 8.7 Hz), 6.69 (1H, s), 3.70 (3H, s), 1.92 (3H, s). |
| PY-376 | $^1$H-NMR (CDCl$_3$) δ: 7.58 (1H, s), 7.39 (1H, s), 7.31 (2H, br s), 7.03 (2H, t, J = 8.6 Hz), 3.72 (3H, s), 1.89 (3H, s). |
| PY-377 | $^1$H-NMR (CDCl$_3$) δ: 7.73 (1H, s), 7.33 (1H, td, J = 8.0, 5.6 Hz), 7.25 (1H, s), 7.11-7.05 (2H, m), 7.02-6.99 (1H, m), 3.97-3.90 (2H, m), 1.86 (3H, s), 1.19 (3H, t, J = 7.0 Hz). |
| PY-378 | $^1$H-NMR (CDCl$_3$) δ: 7.72 (1H, s), 7.28 (1H, s), 6.87-6.83 (3H, m), 3.93 (2H, q, J = 7.0 Hz), 1.89 (3H, s), 1.21 (3H, t, J = 7.0 Hz). |
| PY-379 | $^1$H-NMR (CDCl$_3$) δ: 7.58 (1H, s), 7.39 (1H, s), 7.31 (2H, br s), 7.02 (2H, t, J = 8.4 Hz), 3.97 (2H, br s), 1.89 (3H, s), 1.00 (3H, t, J = 7.0 Hz). |
| PY-380 | $^1$H-NMR (CDCl$_3$) δ: 7.77 (1H, s), 7.39 (1H, s), 7.31 (2H, br s), 7.02 (2H, t, J = 8.4 Hz), 3.97 (2H, br s), 1.89 (3H, s), 1.00 (3H, t, J = 7.0 Hz). |
| PY-381 | $^1$H-NMR (CDCl$_3$) δ: 7.97 (1H, s), 7.36 (1H, s), 7.29 (2H, dd, J = 8.7, 5.2 Hz), 7.06 (2H, t, J = 8.7 Hz), 6.70 (1H, s), 3.69 (3H, s), 1.92 (3H, s). |
| PY-382 | $^1$H-NMR (CDCl$_3$) δ: 7.78 (1H, s), 7.38 (1H, s), 7.31 (2H, br s), 7.02 (2H, t, J = 8.4 Hz), 3.71 (3H, s), 1.89 (3H, s). |
| PY-383 | $^1$H-NMR (CDCl$_3$) δ: 7.60 (1H, s), 7.30 (1H, s), 6.89-6.82 (3H, m), 6.29 (1H, tt, J = 56.7, 4.6 Hz), 4.17 (2H, td, J = 12.2, 4.6 Hz), 1.90 (3H, s). |
| PY-384 | $^1$H-NMR (CDCl$_3$) δ: 7.80 (1H, d, J = 0.6 Hz), 7.30 (1H, s), 6.89-6.82 (3H, m), 6.29 (1H, tt, J = 56.7, 4.6 Hz), 4.17 (2H, td, J = 12.2, 4.6 Hz), 1.90 (3H, s). |
| PY-385 | $^1$H-NMR (CDCl$_3$) δ: 7.80 (1H, s), 7.37 (1H, s), 7.33-7.27 (1H, m), 7.23 (2H, t, J = 7.4 Hz), 7.16 (2H, br s), 7.00-6.90 (4H, m), 4.92 (2H, br s), 1.88 (3H, s). |
| PY-386 | $^1$H-NMR (CDCl$_3$) δ: 7.60 (1H, s), 7.37 (1H, s), 7.34-7.28 (1H, m), 7.23 (2H, t, J = 7.4 Hz), 7.15 (2H, br s), 7.00-6.90 (4H, m), 4.92 (2H, br s), 1.88 (3H, s). |
| PY-387 | $^1$H-NMR (CDCl$_3$) δ: 7.56 (1H, s), 7.26 (1H, s), 7.23 (2H, dd, J = 8.9, 5.2 Hz), 7.00 (2H, t, J = 8.5 Hz), 5.86-5.76 (1H, m), 5.17 (1H, dd, J = 10.3, 1.2 Hz), 4.88 (1H, dd, J = 17.3, 1.2 Hz), 4.49 (2H, d, J = 5.4 Hz), 1.86 (3H, s). |
| PY-388 | $^1$H-NMR (CDCl$_3$) δ: 7.79 (1H, s), 7.40-7.33 (1H, m), 7.28 (1H, s), 7.23-7.16 (1H, br m), 7.10-6.98 (2H, m), 4.85-4.76 (1H, br m), 4.65 (1H, br s), 4.13 (1H, br s), 3.76 (1H, dd, J = 10.7, 4.3 Hz), 3.52 (1H, dd, J = 11.3, 8.6 Hz), 1.87 (3H, s). |
| PY-389 | $^1$H-NMR (CDCl$_3$) δ: 7.65 (1H, s), 7.41 (1H, s), 7.32 (2H, dd, J = 8.9, 5.2 Hz), 7.04 (2H, t, J = 8.7 Hz), 1.91 (3H, s). |
| PY-390 | $^1$H-NMR (CDCl$_3$) δ: 7.58 (1H, s), 7.39 (1H, s), 7.29 (2H, br s), 7.02 (2H, t, J = 8.6 Hz), 5.55-5.46 (1H, m), 5.19-5.17 (1H, m), 5.14-5.09 (1H, m), 4.43 (2H, br s), 1.89 (3H, s). |
| PY-391 | $^1$H-NMR (CDCl$_3$) δ: 7.83 (1H, s), 7.41 (1H, s), 7.32 (2H, dd, J = 8.9, 5.2 Hz), 7.04 (2H, t, J = 8.7 Hz), 1.91 (3H, s). |
| PY-392 | $^1$H-NMR (CDCl$_3$) δ: 7.78 (1H, s), 7.26-7.22 (2H, br m), 7.25 (1H, s), 7.03 (2H, t, J = 8.7 Hz), 4.12 (2H, t, J = 5.2 Hz), 3.81 (2H, q, J = 5.1 Hz), 2.74 (1H, t, J = 5.1 Hz), 1.86 (3H, s). |
| PY-393 | $^1$H-NMR (CDCl$_3$) δ: 7.83 (1H, s), 7.37 (1H, s), 7.28-7.21 (2H, br m), 7.00 (2H, t, J = 8.3 Hz), 5.63 (2H, d, J = 53.5 Hz), 1.89 (3H, s). |
| PY-394 | $^1$H-NMR (CDCl$_3$) δ: 7.59 (1H, s), 7.27-7.21 (3H, m), 7.03 (2H, t, J = 8.5 Hz), 4.11 (2H, t, J = 5.3 Hz), 3.81 (2H, q, J = 5.2 Hz), 2.77 (1H, t, J = 5.3 Hz), 1.86 (3H, s). |
| PY-395 | $^1$H-NMR (CDCl$_3$) δ: 7.63 (1H, s), 7.37 (1H, s), 7.28-7.21 (2H, br m), 7.00 (2H, t, J = 8.6 Hz), 5.64 (2H, d, J = 53.5 Hz), 1.89 (3H, s). |
| PY-396 | $^1$H-NMR (CDCl$_3$) δ: 7.65 (1H, s), 7.39 (1H, s), 7.29-7.21 (2H, br m), 7.02 (2H, t, J = 8.6 Hz), 6.82 (1H, t, J = 73.2 Hz), 1.89 (3H, s). |

TABLE 7-continued

| Compound No. | $^1$H-NMR (CDCl$_3$) |
|---|---|
| PY-397 | $^1$H-NMR (CDCl$_3$) : 7.85 (1H, s), 7.39 (1H, s), 7.28-7.21 (2H, br m), 7.02 (2H, t, J = 6.8 Hz), 6.83 (1H, t, J = 73.2 Hz), 1.89 (3H, s). |
| PY-398 | $^1$H-NMR (CDCl$_3$) δ: 7.61 (1H, s), 7.39 (1H, s), 7.28 (2H, br s), 7.00 (2H, t, J = 8.7 Hz), 4.82 (2H, s), 2.41 (1H, t, J = 2.4 Hz), 1.89 (3H, s). |
| PY-399 | $^1$H-NMR (CDCl$_3$) δ: 7.59 (1H, s), 7.40 (2H, d, J = 8.6 Hz), 7.37 (1H, s), 7.31 (1H, tt, J = 7.3, 1.5 Hz), 7.23 (2H, t, J = 7.5 Hz), 7.01 (2H, br s), 6.91 (2H, d, J = 7.0 Hz), 4.93 (2H, br s), 1.89 (3H, s). |
| PY-400 | $^1$H-NMR (CDCl$_3$) δ: 7.64 (1H, s), 7.49 (2H, d, J = 8.8 Hz), 7.41 (1H, s), 7.19 (2H, d, J = 8.5 Hz), 1.92 (3H, s). |
| PY-401 | $^1$H-NMR (CDCl$_3$) δ: 7.64 (1H, s), 7.47 (2H, d, J = 8.6 Hz), 7.39 (1H, s), 7.12 (2H, d, J = 8.6 Hz), 6.82 (1H, t, J = 73.2 Hz), 1.90 (3H, s). |
| PY-402 | $^1$H-NMR (CDCl$_3$) δ: 7.62 (1H, s), 7.45 (2H, d, J = 8.6 Hz), 7.38 (1H, s), 7.13 (2H, d, J = 8.6 Hz), 5.63 (2H, d, J = 53.2 Hz), 1.91 (3H, s). |
| PY-403 | $^1$H-NMR (CDCl$_3$) δ: 7.65 (1H, s), 7.49 (1H, s), 7.23-7.21 (2H, m), 7.07-7.05 (2H, m), 6.41-6.18 (1H, m), 4.29 (2H, s), 4.19 (2H, td, J = 12.2, 4.7 Hz). |
| PY-404 | $^1$H-NMR (CDCl$_3$) δ: 7.66 (1H, s), 7.48 (1H, s), 7.23-7.21 (2H, m), 7.07-7.05 (2H, m), 6.39-6.20 (1H, m), 4.21-4.17 (4H, m). |
| PY-405 | $^1$H-NMR (CDCl$_3$) δ: 7.80 (1H, s), 7.46 (2H, d, J = 8.5 Hz), 7.40 (1H, s), 7.17 (2H, d, J = 8.1 Hz), 1.92 (3H, s). |
| PY-406 | $^1$H-NMR (CDCl$_3$) δ: 7.81 (1H, d, J = 8.3 Hz), 7.41 (1H, d, J = 3.7 Hz), 7.34-7.27 (2H, br m), 7.05-6.97 (2H, br m), 1.91 (3H, d, J = 4.3 Hz). |
| PY-407 | $^1$H-NMR (CDCl$_3$) δ: 7.83 (1H, s), 7.47 (2H, d, J = 8.5 Hz), 7.39 (1H, s), 7.12 (2H, d, J = 8.1 Hz), 6.82 (1H, t, J = 73.2 Hz), 1.90 (3H, s). |
| PY-408 | $^1$H-NMR (CDCl$_3$) δ: 7.84 (1H, d, J = 7.1 Hz), 7.39 (1H, d, J = 2.9 Hz), 7.31-7.21 (2H, br m), 7.06-6.95 (2H, br m), 6.82 (1H, t, J = 74.2 Hz), 1.89 (3H, d, J = 3.4 Hz). |
| PY-409 | $^1$H-NMR (CDCl$_3$) δ: 7.82 (1H, d, J = 7.1 Hz), 7.38 (1H, d, J = 3.2 Hz), 7.30-7.20 (2H, br m), 7.04-6.94 (2H, br m), 5.63 (2H, d, J = 53.5 Hz), 1.89 (3H, d, J = 3.2 Hz). |
| PY-410 | $^1$H-NMR (CDCl$_3$) δ: 7.78 (1H, s), 7.39 (2H, d, J = 7.1 Hz), 7.37 (1H, s), 7.31 (1H, t, J = 7.1 Hz), 7.23 (2H, t, J = 7.1 Hz), 7.02 (2H, d, J = 7.1 Hz), 6.91 (2H, d, J = 7.1 Hz), 4.92 (2H, br s), 1.89 (3H, s). |
| PY-411 | $^1$H-NMR (CDCl$_3$) δ: 7.63 (1H, s), 7.40 (1H, s), 7.30 (2H, d, J = 8.2 Hz), 7.23 (2H, d, J = 8.2 Hz), 1.91 (3H, s). |
| PY-412 | $^1$H-NMR (CDCl$_3$) δ: 7.63 (1H, d, J = 7.1 Hz), 7.38 (1H, d, J = 3.2 Hz), 7.32-7.18 (2H, br m), 7.00 (2H, t, J = 10.0 Hz), 5.64 (2H, d, J = 53.5 Hz), 1.89 (3H, d, J = 3.2 Hz). |
| PY-413 | $^1$H-NMR (CDCl$_3$) δ: 7.78 (1H, s), 7.39 (1H, s), 7.26 (2H, d, J = 8.3 Hz), 7.20 (2H, d, J = 8.3 Hz), 1.90 (3H, s). |
| PY-414 | $^1$H-NMR (CDCl$_3$) δ: 7.64 (1H, s), 7.39 (1H, s), 7.30 (2H, d, J = 8.9 Hz), 7.20 (2H, d, J = 8.0 Hz), 5.65 (2H, d, J = 53.5 Hz), 1.91 (3H, s). |
| PY-415 | $^1$H-NMR (CDCl$_3$) δ: 7.64 (1H, s), 7.39 (1H, s), 7.31 (2H, d, J = 8.6 Hz), 7.19 (2H, d, J = 8.6 Hz), 6.82 (1H, t, J = 73.1 Hz), 1.90 (3H, s). |
| PY-416 | $^1$H-NMR (CDCl$_3$) δ: 7.84 (1H, s), 7.39 (1H, s), 7.31 (2H, d, J = 8.6 Hz), 7.19 (2H, d, J = 8.6 Hz), 6.82 (1H, t, J = 73.2 Hz), 1.90 (3H, s). |
| IM-001 | $^1$H-NMR (CDCl$_3$) δ: 7.42-7.41 (3H, m), 7.25 (1H, d, J = 9.5 Hz), 7.20-7.18 (2H, m), 7.09 (1H, s), 6.69 (1H, d, J = 9.5 Hz), 3.88-3.86 (2H, br m), 1.17 (3H, t, J = 7.0 Hz). |
| IM-002 | $^1$H-NMR (CDCl$_3$) δ: 7.47-7.42 (4H, m), 7.28-7.23 (2H, m), 3.92 (2H, q, J = 7.0 Hz), 1.20 (3H, t, J = 7.0 Hz). |
| IM-003 | $^1$H-NMR (CDCl$_3$) δ: 7.51 (1H, s), 7.44-7.42 (3H, m), 7.19-7.17 (2H, m), 7.10 (1H, s), 3.94-3.92 (2H, br m), 1.20 (3H, t, J = 7.2 Hz). |
| IM-004 | $^1$H-NMR (CDCl$_3$) δ: 7.71 (1H, s), 7.44-7.42 (3H, m), 7.21-7.19 (2H, m), 7.10 (1H, s), 3.94-3.92 (2H, br m), 1.29 (3H, t, J = 7.0 Hz). |
| IM-005 | $^1$H-NMR (CDCl$_3$) δ: 7.71 (1H, s), 7.20-7.17 (2H, br m), 7.13-7.11 (3H, m), 3.93-3.90 (2H, br m), 1.19 (3H, t, J = 7.1 Hz). |
| IM-006 | $^1$H-NMR (CDCl$_3$) δ: 7.44 (1H, s), 7.31-7.22 (2H, m), 7.16-7.13 (2H, m), 3.91 (2H, q, J = 7.2 Hz), 1.20 (3H, t, J = 7.2 Hz). |
| IM-007 | $^1$H-NMR (CDCl$_3$) δ: 7.51 (1H, s), 7.17-7.12 (5H, m), 3.93-3.91 (2H, br m), 1.20 (3H, t, J = 7.1 Hz). |
| IM-008 | $^1$H-NMR (CDCl$_3$)) δ: 7.45 (1H, s), 7.08-7.03 (3H, br m), 6.86-6.84 (2H, br m), 3.96-3.94 (2H, br m), 3.80 (3H, s), 2.02 (3H, s), 1.94 (3H, s), 1.18 (3H, t, J = 7.1 Hz). |

The following specifically illustrates the effectiveness of the inventive compounds on plant diseases without limiting the scope of the invention to such examples.

Disease development in Test Examples described below was evaluated in increments of 0.05 by setting 0 as no incidence of disease and 3 as disease development in a plant of untreated group. Further, control values were calculated using the following equation based on disease development.
<Control Value>

Control value=100{1−(n/3)} n=Disease development of each treated group

[Test Example A] Blast on Rice

Seeds of a test plant (rice variety: Sachikaze) were planted and cultivated until the second leaves appeared. In the test, the inventive compounds were dissolved into a dimethyl sulfoxide-methanol mixture solution (volume ratio: 9/1), and the resultant solutions were diluted with well water to a concentration of 250 ppm. The dilutions thus obtained were sprayed to the test plant (2.5 ml/pot). After the dilutions dried, a conidial suspension (1-2×10$^5$ conidia/ml) of *Magnaporthe grisea* was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

As the result, the following compounds showed more than 50% of control values.

Compound No: PY-001, PY-005, PY-011, PY-012, PY-013, PY-014, PY-016, PY-017, PY-018, PY-020, PY-021, PY-022, PY-023, PY-028, PY-032, PY-034, PY-035, PY-039, PY-041, PY-042, PY-043, PY-044, PY-046, PY-047, PY-048, PY-052, PY-054, PY-056, PY-061, PY-062, PY-063, PY-064, PY-070, PY-071, PY-073, PY-074, PY-075, PY-079, PY-082, PY-083, PY-085, PY-088, PY-089, PY-090, PY-091, PY-094, PY-097, PY-099, PY-100, PY-101, PY-102, PY-103, PY-104, PY-105, PY-106, PY-107, PY-111, PY-113, PY-114, PY-119, PY-122, PY-124, PY-125, PY-129, PY-130, PY-131, PY-138, PY-139, PY-154, PY-155, PY-156, PY-157, PY-158, PY-161, PY-163, PY-164, PY-167, PY-168, PY-170, PY-171, PY-174, PY-175, PY-180, PY-181, PY-194, PY-197, PY-199, PY-210, PY-212, PY-213, PY-220, PY-222, PY-223, PY-224, PY-225, PY-227, PY-229, PY-230, PY-231, PY-232, PY-233, PY-234, PY-235, PY-236, PY-238, PY-239, PY-240, PY-243, PY-249, PY-251, PY-253, PY-256, PY-257, PY-261, PY-262, PY-264, PY-265, PY-267, PY-276, PY-278, PY-282, PY-288, PY-289, PY-290, PY-296, PY-296, PY-297, PY-298, PY-299, PY-301, PY-306, PY-308, PY-310, PY-311, PY-312, PY-316, PY-317, PY-318, PY-320, PY-321, PY-324, PY-325, PY-326, PY-327, PY-328, PY-330, PY-331, PY-334, PY-335, PY-336, PY-337, PY-339, PY-343, PY-348, PY-349, PY-351, PY-352, PY-353, PY-354, PY-355, PY-359, PY-360, PY-361, PY-362, PY-363, PY-364, PY-373, PY-376, PY-377, PY-382, PY-383, PY-387, PY-393, PY-396, PY-404, PY-412, PY-415, IM-001, IM-002, IM-003, IM-004, IM-005, IM-006, and IM-007.

[Test Example B] Gray Mold on Tomato

Seeds of a test plant (tomato variety: Oogata Fukuju) were planted and cultivated until three to five first leaves (true leaves) appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (4-8×10$^5$ conidia/ml) of *Botrytis cinerea* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

As the result, the following compounds showed more than 50% of control values.

Compound No: PY-005, PY-010, PY-011, PY-012, PY-014, PY-016, PY-018, PY-019, PY-020, PY-021, PY-022, PY-023, PY-025, PY-027, PY-028, PY-029, PY-032, PY-033, PY-034, PY-037, PY-039, PY-041, PY-042, PY-043, PY-044, PY-046, PY-047, PY-048, PY-049, PY-065, PY-066, PY-070, PY-071, PY-075, PY-082, PY-083, PY-085, PY-086, PY-088, PY-089, PY-090, PY-091, PY-094, PY-095, PY-100, PY-103, PY-105, PY-106, PY-107, PY-109, PY-110, PY-111, PY-112, PY-113, PY-114, PY-115, PY-119, PY-122, PY-123, PY-124, PY-125, PY-129, PY-130, PY-131, PY-134, PY-136, PY-137, PY-138, PY-139, PY-146, PY-148, PY-149, PY-155, PY-157, PY-161, PY-163, PY-171, PY-175, PY-179, PY-180, PY-186, PY-188, PY-193, PY-198, PY-199, PY-200, PY-201, PY-202, PY-203, PY-204, PY-208, PY-213, PY-216, PY-218, PY-221, PY-222, PY-224, PY-229, PY-232, PY-234, PY-242, PY-244, PY-251, PY-252, PY-254, PY-256, PY-257, PY-260, PY-262, PY-263, PY-265, PY-270, PY-276, PY-280, PY-282, PY-283, PY-284, PY-285, PY-292, PY-305, PY-308, PY-309, PY-317, PY-318, PY-321, PY-322, PY-325, PY-326, PY-327, PY-328, PY-329, PY-331, PY-334, PY-335, PY-336, PY-339, PY-340, PY-343, PY-345, PY-346, PY-348, PY-349, PY-351, PY-352, PY-353, PY-354, PY-355, PY-356, PY-358, PY-361, PY-362, PY-363, PY-368, PY-372, PY-373, PY-376, PY-377, PY-378, PY-383, PY-384, PY-387, PY-397, PY-400, PY-406, PY-408, PY-409, PY-411, PY-413, IM-001, IM-002, IM-003, IM-004, IM-005, and IM-007.

[Test Example C] *Alternaria* Sooty Spot on Cabbage

Seeds of a test plant (cabbage variety: Shikidori) were planted and cultivated until the cotyledons extended. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (4-8×10$^5$ conidia/ml) of *Alternaia brassicicola* was inoculated to the plant by spraying. After the inoculation, the plant was kept in a mist chamber at room temperature of 20 to 23° C. for about 48 hours to promote the onset of disease. The disease development was investigated 2 to 3 days after the inoculation, and the effectiveness of the dilutions was evaluated.

As the result, the following compounds showed more than 50% of control values.

Compound No: PY-001, PY-002, PY-003, PY-004, PY-005, PY-006, PY-007, PY-010, PY-011, PY-012, PY-013, PY-014, PY-015, PY-016, PY-017, PY-018, PY-019, PY-020, PY-021, PY-022, PY-023, PY-024, PY-025, PY-027, PY-028, PY-029, PY-030, PY-031, PY-032, PY-033, PY-034, PY-036, PY-037, PY-039, PY-041, PY-042, PY-043, PY-044, PY-045, PY-046, PY-047, PY-048, PY-049, PY-051, PY-052, PY-053, PY-055, PY-057, PY-059, PY-060, PY-064, PY-065, PY-066, PY-067, PY-070, PY-071, PY-072, PY-074, PY-075, PY-076, PY-079, PY-082, PY-083, PY-084, PY-085, PY-086, PY-087, PY-088, PY-089, PY-090, PY-091, PY-094, PY-095, PY-096, PY-097, PY-099, PY-100, PY-102, PY-103, PY-104, PY-105, PY-106, PY-107, PY-113, PY-114, PY-115, PY-116, PY-117, PY-118, PY-119, PY-120, PY-121, PY-122, PY-123, PY-124, PY-125, PY-127, PY-128, PY-129, PY-130, PY-131, PY-132, PY-133, PY-135, PY-137, PY-138, PY-139, PY-140, PY-141, PY-142, PY-144, PY-145, PY-146, PY-147, PY-148, PY-149, PY-151, PY-152, PY-153, PY-154, PY-155, PY-157, PY-159, PY-160, PY-161, PY-164, PY-165, PY-168, PY-169, PY-171, PY-172, PY-173, PY-175, PY-177, PY-178, PY-179, PY-180, PY-181, PY-184, PY-186, PY-187, PY-189, PY-191, PY-192, PY-193, PY-194, PY-195, PY-199, PY-205, PY-206, PY-207, PY-212, PY-214, PY-215, PY-216, PY-217, PY-221, PY-222, PY-224, PY-229, PY-232, PY-233, PY-234, PY-235, PY-237, PY-238, PY-244, PY-246, PY-247, PY-248, PY-249, PY-250, PY-251, PY-252, PY-254, PY-255, PY-256, PY-257, PY-259, PY-262, PY-264, PY-265, PY-269, PY-273, PY-274, PY-275, PY-276, PY-277, PY-278, PY-279, PY-280, PY-282, PY-285, PY-286, PY-287, PY-288, PY-289, PY-290, PY-291, PY-292, PY-295, PY-296, PY-297, PY-298, PY-299, PY-300, PY-301, PY-302, PY-304, PY-306, PY-307, PY-308, PY-310, PY-312, PY-313, PY-314, PY-315, PY-318, PY-319, PY-320, PY-321, PY-322, PY-325, PY-328, PY-329, PY-332, PY-335, PY-339, PY-342, PY-343, PY-344, PY-345, PY-346, PY-348, PY-349, PY-350, PY-351, PY-352, PY-353, PY-354, PY-355, PY-356, PY-357, PY-358, PY-359, PY-360, PY-361, PY-362, PY-363, PY-364, PY-368, PY-370, PY-372, PY-373, PY-374, PY-375, PY-376, PY-377, PY-378, PY-379, PY-381, PY-382, PY-383, PY-384, PY-385, PY-386, PY-387, PY-388, PY-389, PY-390, PY-393, PY-395, PY-396, PY-397, PY-398, PY-399, PY-402, PY-403, PY-404, PY-405, PY-406, PY-407, PY-408, PY-409, PY-410, PY-411, PY-412, PY-413, PY-414, PY-416, IM-001, IM-003, IM-004, IM-005, and IM-007.

[Test Example D] Powdery Mildew on Barley

Seeds of a test plant (barley variety: Akashinriki) were planted and cultivated until the first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, conidia of *Blumeria graminis* f. sp. *hordei* were inoculated to the plant by shaking off. The disease development was investigated 6 to 10 days after the inoculation, and the effectiveness of the dilutions was evaluated.

As the result, the following compounds showed more than 50% of control values.

Compound No: PY-011, PY-012, PY-013, PY-014, PY-015, PY-016, PY-018, PY-020, PY-021, PY-022, PY-028, PY-029, PY-030, PY-031, PY-032, PY-033, PY-034, PY-037, PY-039, PY-043, PY-053, PY-059, PY-075, PY-082, PY-083, PY-085, PY-086, PY-087, PY-088, PY-089, PY-090, PY-091, PY-094, PY-098, PY-100, PY-101, PY-104, PY-105, PY-106, PY-107, PY-108, PY-114, PY-115, PY-124, PY-125, PY-126, PY-127, PY-128, PY-129, PY-130, PY-131, PY-154, PY-155, PY-180, PY-186, PY-199, PY-221, PY-222, PY-224, PY-229, PY-232, PY-233, PY-234, PY-235, PY-238, PY-241, PY-248, PY-250, PY-251, PY-252, PY-254, PY-256, PY-262, PY-265, PY-271, PY-272, PY-275, PY-277, PY-280, PY-281, PY-282, PY-285, PY-287, PY-290, PY-291, PY-292, PY-295, PY-296, PY-297, PY-299, PY-301, PY-302, PY-308, PY-324, PY-326, PY-328, PY-329, PY-334, PY-335, PY-336, PY-338, PY-339, PY-343, PY-348, PY-349, PY-351, PY-352, PY-353, PY-358, PY-362, PY-369, PY-371, PY-372, PY-373, PY-377, PY-378, PY-379, PY-383, PY-384, PY-387, PY-394, PY-395 and IM-007.

[Test Example E] Brown Rust on Wheat

Seeds of a test plant (wheat variety: Norin 61) were planted and cultivated until the first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a urediniospore suspension ($1-2\times10^5$ urediniospores/ml) of *Puccinia recondita* was inoculated to the plant by spraying. After the inoculation, the plant was kept in a mist chamber at room temperature of 20 to 23° C. for about 24 hours to promote the onset of disease. The disease development was investigated 7 to 10 days after the inoculation, and the effectiveness of the dilutions was evaluated.

As the result, the following compounds showed more than 50% of control values.

Compound No: PY-004, PY-005, PY-010, PY-011, PY-012, PY-013, PY-014, PY-015, PY-016, PY-017, PY-018, PY-019, PY-020, PY-021, PY-022, PY-023, PY-024, PY-025, PY-027, PY-028, PY-029, PY-032, PY-033, PY-034, PY-037, PY-039, PY-040, PY-041, PY-042, PY-043, PY-044, PY-046, PY-048, PY-049, PY-067, PY-069, PY-070, PY-071, PY-075, PY-076, PY-078, PY-082, PY-083, PY-085, PY-086, PY-087, PY-088, PY-089, PY-090, PY-091, PY-094, PY-095, PY-097, PY-099, PY-100, PY-101, PY-102, PY-103, PY-104, PY-105, PY-106, PY-107, PY-109, PY-113, PY-114, PY-115, PY-119, PY-123, PY-124, PY-125, PY-127, PY-129, PY-130, PY-134, PY-138, PY-139, PY-142, PY-143, PY-149, PY-154, PY-155, PY-170, PY-171, PY-175, PY-180, PY-186, PY-193, PY-199, PY-202, PY-211, PY-212, PY-213, PY-216, PY-219, PY-222, PY-223, PY-224, PY-228, PY-229, PY-232, PY-233, PY-234, PY-235, PY-238, PY-251, PY-252, PY-262, PY-276, PY-277, PY-278, PY-280, PY-282, PY-285, PY-287, PY-292, PY-295, PY-296, PY-297, PY-299, PY-301, PY-306, PY-308, PY-310, PY-321, PY-324, PY-325, PY-326, PY-328, PY-329, PY-331, PY-334, PY-335, PY-336, PY-337, PY-339, PY-341, PY-343, PY-346, PY-348, PY-351, PY-352, PY-353, PY-354, PY-356, PY-358, PY-360, PY-362, PY-363, PY-368, PY-371, PY-372, PY-373, PY-376, PY-377, PY-382, PY-383, PY-384, PY-387, PY-391, PY-392, PY-393, PY-399, PY-401, PY-408, PY-409, IM-001, IM-003, IM-004, IM-005, IM-006, and IM-007.

[Test Example F] Late Blight on Tomato

Seeds of a test plant (tomato variety: Oogata Fukuju) were planted and cultivated until three to five first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension ($4-8\times10^3$ zoosporangia/ml) of *Phytophthora infestans* was inoculated to the plant by spraying. After the inoculation, the plant was kept in a mist chamber at room temperature of 20° C. for about 24 hours to promote the onset of disease. The disease development was investigated 5 to 10 days after the inoculation, and the effectiveness of the dilutions was evaluated.

As the result, the following compounds showed more than 50% of control values.

Compound No: PY-067, PY-068, PY-123, PY-125, PY-127, PY-130, PY-132, PY-135, PY-180, PY-185, PY-192, PY-194, PY-220, PY-222, PY-266, and PY-268.

[Test Example G] Downy Mildew on Vine

Seeds of a test plant (grape variety: Neomuscat) were planted and cultivated until three to four first leaves appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a zoosporangia suspension (1-2× $10^4$ zoosporangia/ml) of Plasmopara viticola was inoculated to the plant by spraying. After the inoculation, the plant was kept in a mist chamber at room temperature of 20° C. for about 24 hours to promote the onset of disease. The disease development was investigated 7 to 10 days after the inoculation, and the effectiveness of the dilutions was evaluated.

As the result, the following compounds showed more than 50% of control values.

Compound No: PY-001, PY-008, PY-031, PY-032, PY-034, PY-035, PY-036, PY-037, PY-038, PY-039, PY-040, PY-041, PY-042, PY-043, PY-044, PY-045, PY-046, PY-047, PY-065, PY-077, PY-080, PY-082, PY-104, PY-114, PY-120, PY-180, PY-181, PY-187, PY-189, PY-192, PY-193, PY-194, PY-195, PY-201, PY-202, PY-222, PY-229, PY-237, PY-256, PY-292, PY-297, PY-299, PY-329, PY-334, PY-342, PY-354, PY-358, PY-360, PY-367, PY-368, PY-400, IM-003, and IM-008.

[Test Example H] Anthracnose on Cucumber

Seeds of a test plant (cucumber variety: Sagami Hanjiro) were planted and cultivated until the first leaf appeared. In the test, the inventive compounds were dissolved into a dimethyl sulfoxide-methanol mixture solution (volume ratio: 9/1), and the resultant solutions were diluted with well water to a concentration of 250 ppm. The thus-obtained dilutions were sprayed to the test plant (2.5 ml/pot). After the dilutions dried, a conidial suspension (2-4×$10^5$ conidia/ml) of Colletotrichum orbiculare was inoculated to the plant by spraying. After the inoculation, the plant was kept in a mist chamber at room temperature of 20 to 23° C. for about 24 hours to promote the onset of disease. The disease development was investigated 6 to 10 days after the inoculation, and the effectiveness of the dilutions was evaluated.

As the result, the following compounds showed more than 50% of control values.

Compound No: PY-003, PY-009, PY-011, PY-012, PY-013, PY-014, PY-016, PY-017, PY-018, PY-020, PY-022, PY-023, PY-026, PY-028, PY-030, PY-032, PY-034, PY-035, PY-036, PY-037, PY-038, PY-039, PY-040, PY-042, PY-043, PY-044, PY-047, PY-050, PY-055, PY-058, PY-061, PY-062, PY-065, PY-070, PY-071, PY-073, PY-074, PY-075, PY-078, PY-079, PY-081, PY-082, PY-083, PY-085, PY-086, PY-088, PY-089, PY-090, PY-091, PY-092, PY-093, PY-094, PY-095, PY-099, PY-100, PY-103, PY-104, PY-105, PY-106, PY-107, PY-108, PY-112, PY-113, PY-114, PY-122, PY-124, PY-129, PY-130, PY-131, PY-139, PY-144, PY-149, PY-150, PY-154, PY-155, PY-157, PY-158, PY-159, PY-160, PY-161, PY-162, PY-163, PY-165, PY-166, PY-169, PY-171, PY-172, PY-175, PY-176, PY-180, PY-182, PY-183, PY-184, PY-190, PY-191, PY-192, PY-193, PY-194, PY-195, PY-196, PY-199, PY-200, PY-202, PY-203, PY-204, PY-207, PY-208, PY-209, PY-211, PY-214, PY-215, PY-216, PY-217, PY-218, PY-220, PY-222, PY-223, PY-224, PY-225, PY-226, PY-227, PY-229, PY-232, PY-234, PY-237, PY-239, PY-245, PY-250, PY-251, PY-254, PY-256, PY-257, PY-258, PY-260, PY-266, PY-274, PY-278, PY-290, PY-291, PY-292, PY-293, PY-294, PY-296, PY-297, PY-299, PY-300, PY-301, PY-303, PY-310, PY-315, PY-318, PY-321, PY-323, PY-325, PY-326, PY-328, PY-333, PY-335, PY-336, PY-339, PY-343, PY-346, PY-347, PY-348, PY-349, PY-351, PY-352, PY-353, PY-354, PY-355, PY-358, PY-360, PY-361, PY-362, PY-363, PY-365, PY-366, PY-368, PY-368, PY-370, PY-372, PY-373, PY-376, PY-377, PY-378, PY-380, PY-381, PY-382, PY-383, PY-384, PY-387, PY-390, PY-393, PY-396, PY-415, IM-001, IM-003, IM-004, IM-005, and IM-007.

INDUSTRIAL APPLICABILITY

The inventive compounds are novel compounds capable of preventing and treating plant diseases, and are therefore valuable as agricultural chemicals, for example, agricultural and horticultural pest control agents, in particular, agricultural and horticultural fungicides.

The disclosure of Japanese Patent Application No. 2018-139462 (filing date: Jul. 25, 2018) is incorporated herein by reference in its entirety.

All documents, patent applications, and technical standards described herein are incorporated herein by reference to the extent that the fact that the individual documents, patent applications and technical standards are incorporated by reference is described specifically and individually.

What is claimed is:

1. A compound represented by the formula (1), or a salt thereof:

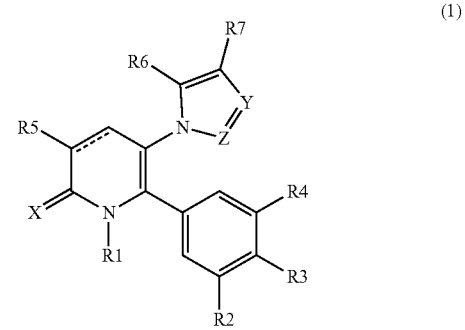

(1)

wherein R1 represents
hydroxy,
cyano,
C1-C6 alkyl optionally substituted with at least one substituent A,
C1-C6 haloalkyl,
C3-C8 cycloalkyl optionally substituted with at least one substituent A,
C2-C6 alkenyl optionally substituted with at least one substituent A,
C2-C6 haloalkenyl,
C2-C6 alkynyl optionally substituted with at least one substituent A,
C2-C6 haloalkynyl,
C1-C6 alkoxy optionally substituted with at least one substituent A,
C1-C6 haloalkoxy,
C3-C8 cycloalkoxy optionally substituted with at least one substituent A, C2-C6 alkenyloxy optionally substituted with at least one substituent A,
C2-C6 haloalkenyloxy,
C3-C6 alkynyloxy optionally substituted with at least one substituent A,
C3-C6 haloalkynyloxy,
or
RaRbN— wherein Ra and Rb are independent of one another and each represent hydrogen, C1-C6 alkyl optionally substituted with at least one substituent B, C1-C6 haloalkyl, or a C3-C8 cycloalkyl, or Ra and Rb are taken together with the nitrogen atom to which they are bonded to form aziridinyl, azetidinyl, pyrrolidinyl, piperidinyl, morpholyl, homopiperidinyl, or an azocanyl;
R2, R3 and R4 are independent of one another and each represent
hydrogen,
halogen,
hydroxy,
cyano,
nitro,
C1-C6 alkyl optionally substituted with at least one substituent C,
C1-C6 haloalkyl,
C3-C8 cycloalkyl optionally substituted with at least one substituent C,
C2-C6 alkenyl optionally substituted with at least one substituent C,
C2-C6 haloalkenyl,
C2-C6 alkynyl optionally substituted with at least one substituent C,
C2-C6 haloalkynyl,
C1-C6 alkoxy optionally substituted with at least one substituent C,
C1-C6 haloalkoxy,
C3-C8 cycloalkoxy optionally substituted with at least one substituent C,
C2-C6 alkenyloxy optionally substituted with at least one substituent C,
C2-C6 haloalkenyloxy,
C3-C6 alkynyloxy optionally substituted with at least one substituent C,
C3-C6 haloalkynyloxy,
RdC(=O)— wherein Rd represents hydrogen, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove,
RdC(=O)O— wherein Rd is the same as defined hereinabove,
Rc-L- wherein Rc represents C1-C6 alkyl or C1-C6 haloalkyl, and L represents S, SO, or SO$_2$,
Rc-SO$_2$—O— wherein Rc is the same as defined hereinabove,
RaRbN— wherein Ra and Rb are the same as defined hereinabove, or
ReC(=O)N(Rf)— wherein Re represents hydrogen, a C1-C6 alkyl group optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove, and Rf represents hydrogen, C1-C6 alkyl optionally substituted with at least one substituent B, C1-C6 haloalkyl, or C3-C8 cycloalkyl);

R5 represents
hydrogen,
halogen,
cyano,
nitro,
C1-C6 alkyl optionally substituted with at least one substituent A,
C1-C6 haloalkyl,
C3-C8 cycloalkyl optionally substituted with at least one substituent A,
C2-C6 alkenyl optionally substituted with at least one substituent A,
C2-C6 haloalkenyl,
C2-C6 alkynyl optionally substituted with at least one substituent A,
C2-C6 haloalkynyl,
C1-C6 alkoxy optionally substituted with at least one substituent A,
C1-C6 haloalkoxy,
C3-C8 cycloalkoxy optionally substituted with at least one substituent A,
C2-C6 alkenyloxy optionally substituted with at least one substituent A,
C2-C6 haloalkenyloxy,
C3-C6 alkynyloxy optionally substituted with at least one substituent A,
C3-C6 haloalkynyloxy,
Rc-L- wherein Rc and L are the same as defined hereinabove,
RaRbN— wherein Ra and Rb are the same as defined hereinabove, or
RgC(=O)— wherein Rg represents hydrogen, hydroxy, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove;
X represents oxygen or sulfur;
Y represents R8-C or nitrogen;
Z represents R9-C or nitrogen;
R6, R7, R8 and R9 are independent of one another and each represent hydrogen,
halogen,
hydroxy,
cyano,
nitro,
C1-C6 alkyl optionally substituted with at least one substituent C,
C1-C6 haloalkyl,
C3-C8 cycloalkyl optionally substituted with at least one substituent C,
C2-C6 alkenyl optionally substituted with at least one substituent C,
C2-C6 haloalkenyl,
C2-C6 alkynyl optionally substituted with at least one substituent C,
C2-C6 haloalkynyl,
C1-C6 alkoxy optionally substituted with at least one substituent C,
C1-C6 haloalkoxy,
C3-C8 cycloalkoxy optionally substituted with at least one substituent C,
C2-C6 alkenyloxy optionally substituted with at least one substituent C,
C2-C6 haloalkenyloxy,
C3-C6 alkynyloxy optionally substituted with at least one substituent C, C3-C6 haloalkynyloxy, RdC(=O)— wherein Rd is the same as defined hereinabove, RdC(=O)O— wherein Rd is the same as defined hereinabove, Rc-L- wherein Rc and L are the same as defined hereinabove, RaRbN— wherein Ra and Rb are the same as defined hereinabove, or ReC(=O)N(Rf)— wherein Re and Rf are the same as defined hereinabove, or R6 and R7 are taken together to form C2-C6 alkylene, and, R8 and R9 represent those as defined hereinabove; and the at least one substituent A is at least one selected from the consisting of hydroxy, cyano, C3-C8 cycloalkyl, C1-C6 alkoxy, C1-C6 haloalkoxy, C3-C8 cycloalkoxy, RaRbN— wherein Ra and Rb are the same as defined hereinabove and Rc-L- wherein Rc and L are the same as defined hereinabove;

the at least one substituent B is at least one selected from the consisting of a cyano, C1-C6 alkoxy, C1-C6 haloalkoxy and C3-C8 cycloalkoxy; and the at least one substituent C is at least one selected from the consisting of hydroxy, cyano, C3-C8 cycloalkyl, C1-C6 alkoxy, C1-C6 haloalkoxy, C3-C8 cycloalkoxy, C2-C6 alkoxyalkoxy, RaRbN— wherein Ra and Rb are the same as defined hereinabove, Rc-L- wherein Rc and L are the same as defined hereinabove, RdC(=O)— wherein Rd is the same as defined hereinabove and 3 to 6-membered ring containing 1 to 2 oxygen.

2. The compound according to claim 1, or salt thereof, wherein

R1 represents hydroxyl,

C1-C6 alkyl optionally substituted with at least one substituent A,

C1-C6 haloalkyl,

C2-C6 alkenyl optionally substituted with at least one substituent A,

C2-C6 haloalkenyl,

C2-C6 alkynyl optionally substituted with at least one substituent A,

C1-C6 alkoxy optionally substituted with at least one substituent A,

C1-C6 haloalkoxy,

C2-C6 alkenyloxy optionally substituted with at least one substituent A,

C3-C6 alkynyloxy optionally substituted with at least one substituent A, or

RaRbN— wherein Ra and Rb are independent of one another and each represent a hydrogen, C1-C6 alkyl optionally substituted with at least one substituent B, C1-C6 haloalkyl, or C3-C8 cycloalkyl, or Ra and Rb are taken together with the nitrogen atom to which they are bonded to form an aziridinyl, an azetidinyl, pyrrolidinyl, piperidinyl, morpholyl, homopiperidinyl, or azocanyl;

R2, R3 and R4 are independent of one another and each represent hydrogen, halogen, hydroxy, cyano, nitro, C1-C6 alkyl optionally substituted with at least one substituent C, C1-C6 haloalkyl, C3-C8 cycloalkyl optionally substituted with at least one substituent C, C2-C6 alkenyl optionally substituted with at least one substituent C, C2-C6 alkynyl optionally substituted with at least one substituent C, C1-C6 alkoxy optionally substituted with at least one substituent C, C1-C6 haloalkoxy, C3-C8 cycloalkoxy optionally substituted with at least one substituent C, C2-C6 alkenyloxy optionally substituted with at least one substituent C, C3-C6 alkynyloxy optionally substituted with at least one substituent C, RdC(=O)O— wherein Rd represents hydrogen, C1-C6 alkyl optionally substituted with at least one substituent B, C1-C6 haloalkyl, a C3-C8 cycloalkyl, C1-C6 alkoxy, C1-C6 haloalkoxy, C3-C8 cycloalkoxy, or RaRbN— wherein Ra and Rb are the same as defined hereinabove, Rc-L- wherein Rc represents C1-C6 alkyl or C1-C6 haloalkyl, and L represents S, SO, or $SO_2$, Rc-$SO_2$—O— wherein Rc is the same as defined hereinabove, RaRbN— wherein Ra and Rb are the same as defined hereinabove, or ReC(=O)N(Rf)— wherein Re represents hydrogen, C1-C6 alkyl optionally substituted with at least one substituent B, C1-C6 haloalkyl, a C3-C8 cycloalkyl, C1-C6 alkoxy, C1-C6 haloalkoxy, C3-C8 cycloalkoxy, or RaRbN— wherein Ra and Rb are the same as defined hereinabove, and Rf represents hydrogen, C1-C6 alkyl optionally substituted with at least one substituent B, C1-C6 haloalkyl, or C3-C8 cycloalkyl;

R5 represents hydrogen, halogen, nitro,

C1-C6 alkyl optionally substituted with at least one substituent A,

C1-C6 haloalkyl,

C2-C6 alkenyl optionally substituted with at least one substituent A,

C2-C6 alkynyl optionally substituted with at least one substituent A,

C1-C6 alkoxy optionally substituted with at least one substituent A,

RaRbN— wherein Ra and Rb are the same as defined hereinabove, or

RgC(=O)— wherein Rg represents hydrogen, hydroxy, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove;

R6, R7, R8 and R9 are independent of one another and each represent hydrogen, halogen, cyano, nitro, C1-C6 alkyl optionally substituted with at least one substituent C, C1-C6 haloalkyl,
C3-C8 cycloalkyl optionally substituted with at least one substituent C,
C2-C6 alkenyl optionally substituted with at least one substituent C,
C2-C6 alkynyl optionally substituted with at least one substituent C,
C1-C6 alkoxy optionally substituted with at least one substituent C,
C2-C6 alkenyloxy optionally substituted with at least one substituent C,
C3-C6 alkynyloxy optionally substituted with at least one substituent C,
RdC(=O)— wherein Rd is the same as defined hereinabove,
Rc-L- wherein Rc and L are the same as defined hereinabove,
RaRbN— wherein Ra and Rb are the same as defined hereinabove, or
ReC(=O)N(Rf)— wherein Re and Rf are the same as defined hereinabove, or
R6 and R7 are taken together to form C2-C6 alkylene, and, R8 and R9 represent those as defined hereinabove.

3. The compound according to claim 2, or salt thereof, wherein
R1 represents
hydroxyl,
C1-C6 alkyl optionally substituted with at least one substituent A,
C1-C6 haloalkyl,
C2-C6 alkenyl optionally substituted with at least one substituent A,
C1-C6 alkoxy optionally substituted with at least one substituent A,
C1-C6 haloalkoxy,
C2-C6 alkenyloxy optionally substituted with at least one substituent A,
C3-C6 alkynyloxy optionally substituted with at least one substituent A,
or
RaRbN— wherein Ra and Rb are independent of one another and each represent a hydrogen, C1-C6 alkyl optionally substituted with at least one substituent B, C1-C6 haloalkyl, or C3-C8 cycloalkyl, or Ra and Rb are taken together with the nitrogen atom to which they are bonded to form aziridinyl, azetidinyl, pyrrolidinyl, piperidinyl, morpholyl, homopiperidinyl, or azocanyl;
R2, R3 and R4 are independent of one another and each represent
hydrogen,
halogen,
hydroxy,
cyano,
nitro,
C1-C6 alkyl optionally substituted with at least one substituent C,
C3-C8 cycloalkyl optionally substituted with at least one substituent C,
C2-C6 alkynyl optionally substituted with at least one substituent C,
C1-C6 alkoxy optionally substituted with at least one substituent C,
C1-C6 haloalkoxy,
C3-C6 alkynyloxy optionally substituted with at least one substituent C,
RdC(=O)O— wherein Rd represents hydrogen, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are independent of one another and each represent hydrogen, C1-C6 alkyl optionally substituted with at least one substituent B, C1-C6 haloalkyl, or C3-C8 cycloalkyl, or Ra and Rb are taken together with the nitrogen atom to which they are bonded to form aziridinyl, azetidinyl, pyrrolidinyl, piperidinyl, morpholyl, a homopiperidinyl, or azocanyl,
Rc-SO$_2$—O— wherein Rc represents C1-C6 alkyl or C1-C6 haloalkyl, and L represents S, SO, or SO$_2$,
RaRbN— wherein Ra and Rb are the same as defined hereinabove), or
ReC(=O)N(Rf)— wherein Re represents hydrogen, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove, and Rf represents hydrogen, C1-C6 alkyl optionally substituted with at least one substituent B, C1-C6 haloalkyl, or C3-C8 cycloalkyl;
R5 represents
hydrogen,
halogen,
nitro,
C1-C6 alkyl optionally substituted with at least one substituent A,
C2-C6 alkenyl optionally substituted with at least one substituent A,
C1-C6 alkoxy optionally substituted with at least one substituent A,
RaRbN— wherein Ra and R b are the same as defined hereinabove, or
RgC(=O)— wherein Rg represents hydrogen, hydroxy, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove;
X represents oxygen;
when Y is R8-C, Z represents nitrogen, or, when Y is nitrogen, Z represents R9-C;
R6, R7, R8 and R9 are independent of one another and each represent
hydrogen,
halogen,
nitro,
C1-C6 alkyl optionally substituted with at least one substituent C,
C1-C6 haloalkyl,
C3-C8 cycloalkyl optionally substituted with at least one substituent C,
C2-C6 alkenyl optionally substituted with at least one substituent C,
C2-C6 alkynyl optionally substituted with at least one substituent C,
C1-C6 alkoxy optionally substituted with at least one substituent C,
RdC(=O)— wherein Rd is the same as defined hereinabove,
Rc-L- wherein Rc and L are the same as defined hereinabove, or
RaRbN— wherein Ra and Rb are the same as defined hereinabove, or
R6 and R7 are taken together to form C2-C6 alkylene, and R8 and R9 represent those as defined hereinabove.

4. A compound represented by the formula (2), or salt thereof:

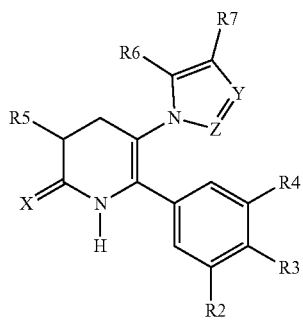

wherein
R2, R3 and R4 are independent of one another and each represent
hydrogen,
halogen,
hydroxy,
cyano,
nitro,
C1-C6 alkyl optionally substituted with at least one substituent C,
C1-C6 haloalkyl,
C3-C8 cycloalkyl optionally substituted with at least one substituent C,
C2-C6 alkenyl optionally substituted with at least one substituent C,
C2-C6 haloalkenyl,
C2-C6 alkynyl optionally substituted with at least one substituent C,
C2-C6 haloalkynyl,
C1-C6 alkoxy optionally substituted with at least one substituent C,
C1-C6 haloalkoxy,
C3-C8 cycloalkoxy optionally substituted with at least one substituent C,
C2-C6 alkenyloxy optionally substituted with at least one substituent C,
C2-C6 haloalkenyloxy,
C3-C6 alkynyloxy optionally substituted with at least one substituent C,
C3-C6 haloalkynyloxy,
RdC(=O)— wherein Rd represents hydrogen, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are independent of one another and each represent hydrogen, C1-C6 alkyl optionally substituted with at least one substituent B, C1-C6 haloalkyl, or C3-C8 cycloalkyl, or Ra and Rb are taken together with the nitrogen atom to which they are bonded to form aziridinyl, azetidinyl, pyrrolidinyl, piperidinyl, morpholyl, homopiperidinyl, or azocanyl,
RdC(=O)O— wherein Rd is the same as hereinabove,
Rc-L- wherein Rc represents C1-C6 alkyl or C1-C6 haloalkyl, and L represents S, SO, or SO₂,
Rc-SO₂—O— wherein Rc is the same as hereinabove,
RaRbN— wherein Ra and Rb are the same as defined hereinabove, or
ReC(=O)N(Rf)— wherein Re represents hydrogen, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove, and Rf represents hydrogen, C1-C6 alkyl optionally substituted with at least one substituent B, C1-C6 haloalkyl, or C3-C8 cycloalkyl;
R5 represents
hydrogen,
halogen,
cyano,
nitro,
C1-C6 alkyl optionally substituted with at least one substituent A,
C1-C6 haloalkyl,
C3-C8 cycloalkyl optionally substituted with at least one substituent A,
C2-C6 alkenyl optionally substituted with at least one substituent A,
C2-C6 haloalkenyl,
C2-C6 alkynyl optionally substituted with at least one substituent A,
C2-C6 haloalkynyl,
C1-C6 alkoxy optionally substituted with at least one substituent A,
C1-C6 haloalkoxy,
C3-C8 cycloalkoxy optionally substituted with at least one substituent A,
C2-C6 alkenyloxy optionally substituted with at least one substituent A,
C2-C6 haloalkenyloxy,
C3-C6 alkynyloxy optionally substituted with at least one substituent A,
C3-C6 haloalkynyloxy,
Rc-L- wherein Rc and L are the same as defined hereinabove,
RaRbN— wherein Ra and Rb are the same as defined hereinabove, or
RgC(=O)— wherein Rg represents hydrogen, hydroxy, C1-C6 alkyl optionally substituted with at least one substituent B, C1-C6 haloalkyl, C3-C8 cycloalkyl, C1-C6 alkoxy, C1-C6 haloalkoxy, C3-C8 cycloalkoxy, or RaRbN— wherein Ra and Rb are the same as defined hereinabove;
X represents oxygen or sulfur;
Y represents R8-C or nitrogen;
Z represents R9-C or nitrogen;
R6, R7, R8 and R9 are independent of one another and each represent
hydrogen,
halogen,
hydroxy,
cyano,
nitro,
C1-C6 alkyl optionally substituted with at least one substituent C,
C1-C6 haloalkyl,
C3-C8 cycloalkyl optionally substituted with at least one substituent C,
C2-C6 alkenyl optionally substituted with at least one substituent C,
C2-C6 haloalkenyl,
C2-C6 alkynyl optionally substituted with at least one substituent C,
C2-C6 haloalkynyl, C1-C6 alkoxy optionally substituted with at least one substituent C,
C1-C6 haloalkoxy,
C3-C8 cycloalkoxy optionally substituted with at least one substituent C,
C2-C6 alkenyloxy optionally substituted with at least one substituent C,
C2-C6 haloalkenyloxy,
C3-C6 alkynyloxy optionally substituted with at least one substituent C,
C3-C6 haloalkynyloxy,
RdC(=O)— wherein Rd is the same as defined hereinabove,
RdC(=O)O— wherein Rd is the same as defined hereinabove,
Rc-L- wherein Rc and L are the same as defined hereinabove,
RaRbN— wherein Ra and Rb are the same as defined hereinabove, or
ReC(=O)N(Rf)— wherein Re and Rf are the same as defined hereinabove, or
R6 and R7 are taken together to form C2-C6 alkylene, and, R8 and R9 represent those as defined hereinabove; and
the at least one substituent A is at least one selected from the consisting of hydroxy, cyano, C3-C8 cycloalkyl, C1-C6 alkoxy, C1-C6 haloalkoxy, C3-C8 cycloalkoxy, RaRbN— wherein Ra and Rb are the same as defined hereinabove and Rc-L- wherein Rc and L are the same as defined hereinabove;

the at least one substituent B is at least one selected from the consisting of cyano, C1-C6 alkoxy, C1-C6 haloalkoxy and C3-C8 cycloalkoxy; and the at least one substituent C is at least one selected from the consisting of hydroxy, cyano, C3-C8 cycloalkyl, C1-C6 alkoxy, C1-C6 haloalkoxy, C3-C8 cycloalkoxy, C2-C6 alkoxyalkoxy, RaRbN— wherein Ra and Rb are the same as defined hereinabove, Rc-L- wherein Rc and L are the same as defined hereinabove, RdC(=O)— wherein Rd is the same as defined hereinabove and a-3 to 6-membered ring containing 1 to 2 oxygen atoms.

5. An agricultural and horticultural pest control agent comprising the compound described in claim 1, or salt thereof, as an active ingredient.

6. An agricultural and horticultural fungicide comprising the compound described in claim 1, or salt thereof, as an active ingredient.

7. A method for controlling a plant disease caused by a pathogen, comprising applying the agricultural and horticultural pest control agent described in claim 5 to a plant, a plant seed or soil for plant cultivation.

8. A method for controlling a plant disease caused by a pathogen, comprising applying the agricultural and horticultural fungicide described in claim 6 to a plant, a plant seed or soil for plant cultivation.

9. The method described in claim 7, wherein the plant disease is caused by a fungal pathogen.

10. The method described in claim 8, wherein the plant disease is caused by a fungal pathogen.

* * * * *